US007767393B2

(12) United States Patent
Chinnaiyan et al.

(10) Patent No.: US 7,767,393 B2

(45) Date of Patent: Aug. 3, 2010

(54) EXPRESSION PROFILE OF PROSTATE CANCER

(75) Inventors: Arul M. Chinnaiyan, Plymouth, MI (US); Mark A. Rubin, Ann Arbor, MI (US); Arun Sreekumar, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 312 days.

(21) Appl. No.: 11/343,797

(22) Filed: Jan. 31, 2006

(65) Prior Publication Data

US 2006/0211017 A1 Sep. 21, 2006

Related U.S. Application Data

(62) Division of application No. 10/210,120, filed on Aug. 1, 2002, now Pat. No. 7,229,774.

(60) Provisional application No. 60/309,581, filed on Aug. 2, 2001, provisional application No. 60/334,468, filed on Nov. 15, 2001.

(51) Int. Cl.
*C12Q 1/68* (2006.01)
*G01N 33/53* (2006.01)

(52) U.S. Cl. ........................... 435/6; 436/811; 436/813

(58) Field of Classification Search ....................... None
See application file for complete search history.

(56) References Cited

U.S. PATENT DOCUMENTS 6,518,028 B1 * 2/2003 O'Brien ........................ 435/6

OTHER PUBLICATIONS

Magee et al., "Expresson Profiling Reveals Hepsin Overexpression in Prostate Cancer," Cancer Research, Aug. 1, 2001, vol. 61, pp. 5692-5696.*

Bostwick et al., "Prostate Specific Membrane Antigen Expression in Prostatic Intraepithelial Neoplasia and Adenocarcinoma," Cancer, 1997, vol. 82, No. 11, pp. 2256-2261.*

Nelson et al., "Preoperative parameters for predicting early prostate cancer recurrence after radical prostatectomy.," Urology 59:740-5; discussion 745-6 [2002].

Rogers, CG, "Prostate Cancer Detection on Urinalysis for α-Methylacyl Coenzyme a Racemase Protein," The Journal of Urology, vol. 172, pp. 1502-1503, Oct. 2004.

Rubin et al., "alpha-Methylacyl coenzyme A racemase as a tissue biomarker for prostate cancer," JAMA 287 (13):1662-70 [2002].

Rubin, et al., Quantiative Determination of Expression of the Prostate Cancer Protein π-Methylacyl CoA Racemase; Am. J. Pathol. Mar. 3, 2004, vol. 164, No. 3, pp. 831-840.

Satijn et al., "Polycomb group protein complexes: do different complexes regulate distinct target genes?," Biochim. Biophys. Acta. 1447:1 [1999].

Scheurle et al., "HER-2/neu expression in archival non-small cell lung carcinomas using FDA-approved Hercep test," Anticancer Res. 20:2091 (2000).

Sinclair et al., "Enhancer of Polycomb is a suppressor of position-effect variegation in Drosophila melanogaster," Genetics 148:211 [1998].

Sreekumar et al, "Humoral Immune Response to α-Methylacyl-CoA Racemase and Prostate Cancer," The Journal of Cancer Institute, vol. 96, No. 11, Jun. 2, 2004.

Stamey et al., "Molecular genetic profiling of Gleason grade 4/5 prostate cancers compared to benign prostatic hyperplasia," J. Virology 166:2171 (2001).

Zhou, et al., Expression and Diagnostic Utility of Alpha-Methylacyl-CoA-Racemase (P504S) in Foamy Gland and Pseudohyperplastic; Am. J. Syrg. Pathol., (2003), vol. 27, No. 6.

Zielie, PJ, "A Novel Diagnostic Test for Prostate Cancer Emerges from the Determination of α-Methylacyl-Coenzyme a Racemase in Prostatic Secretions," The Journal of Urology, vol. 172, pp. 1130-1133, Sep. 2004.

Alizadeh et al., "Distinct types of diffuse large B-cell lymphoma identified by gene expression profiling," Nature 403:503 [2000].

Breuer et al., "Very high frequency of lymphoma induction by a chemical carcinogen in pim-1 transgenic mice," Nature 340:61 [1989].

Brichory et al., "An immune response manifested by the common occurrence of annexins I and II autoantibodies and high circulating levels of IL-6 in lung cancer," PNAS 98:9824-9829 (2001).

Brock et al., "The Polycomb group—no longer an exclusive club?," Curr. Opin. Genet. Dev. 11:175 [2001].

Brown and Botstein, "Exploring the new world of the genome with DNA microarrays," Nat. Gent., 21:33 [1999].

Chan et al., "Annexin IV inhibits calmodulin-dependent protein kinase II-activated chloride conductance. A novel mechanism for ion channel regulation," J. Biol. Chem. 269:32464 [1994].

Chen et al., "Cloning of a human homolog of the Drosophila enhancer of zeste gebe (EZH2) that maps to chromosome 21q22.2," Genomics 38:30 (1996).

Chinnadurai, "CtBP, an unconventional transcriptional corepressor in development and oncogenesis," Mol Cell. 9: 213 [2002].

Clayton et al., "Clincial consequences of defects in peroxisomal beta-oxidation," Biochem. Soc. Trans. 29:298 [2001].

Cuypers et al., "Murine leukemia virus-induced T-cell lymphomagenesis: integration of proviruses in a distinct chromosomal region," Cell 37:141 [1984].

De Marzo et al., "Proliferative inflammatory atrophy of the prostate: implications for prostatic carcinogenesis," Am J Pathol 155:1985 [1999].

Debril et al., "The pleiotropic functions of peroxisome proliferator-activated receptor gamma," J. Mol. Med. 79:30 [2001].

Dhanasekaran et al., "Delineation of prognostic biomarkers in prostate cancer," Nature 412: 822 [2001].

(Continued)

*Primary Examiner*—Young J Kim
(74) *Attorney, Agent, or Firm*—Casimir Jones, S.C.

(57) ABSTRACT

The present invention relates to compositions and methods for cancer diagnostics, including but not limited to, cancer markers. In particular, the present invention provides gene expression profiles associated with prostate cancers. Genes identified as cancer markers using the methods of the present invention find use in the diagnosis and characterization of prostate cancer. In addition, the genes provide targets for cancer drug screens and therapeutic applications.

4 Claims, 129 Drawing Sheets

OTHER PUBLICATIONS

Emmert Buck et al., "Molecular profiling of clinical tissue specimens: feasibility and applications," Am. J. Pathol., 156:1109 [2000].

Epstein and Potter, "The pathological interpretation and significance of prostate needle biopsy findings: implications and current controversies," J. Urol., 166:402 [2001].

Etzioni et al., "Cancer surveillance series: interpreting trends in prostate cancer—part III: Quantifying the link between population prostate-specific antigen testing and recent declines in prostate cancer mortality," J. Natl. Cancer Inst., 91:1033 [1999].

Ferdinandusse et al., "Mutations in the gene encoding peroxisomal alpha-methylacyl-CoA racemase cause adult-onset sensory motor neuropathy," Nat. Genet., 24:188 [2000].

Ferdinandusse et al., Plasma analysis of di- and trihydroxycholestanoic acid diastereoisomers in peroxisomal alpha-methylacyl-CoA racemase deficienc J Lipid Res 42:137 [2001].

Ferdinandusse et al., "Subcellular localization and physiological role of alpha-methylacyl-CoA racemase," J. Lipid Res., 41:1890 [2000].

Fox Chase Center, Publication Online, Apr. 20, 2000, 2 pages at http://:www.sciencedaily.com/releases/2000/04/000406090853.htm.

Francis et al., "In vitro studies on L-771,688 (SNAP 6383), a new potent and selective alpha1A-adrenoceptor antagonist," Eur J Pharmacol 2:409 [2001].

Gunster eta I., "Differential expression of human Polycomb group proteins in various tissues and cell types," J. Cell Biochem. Supl. 36:129 (2001).

Hammond et al., "An RNA-directed nuclease mediates post-transcriptional gene silencing in Drosophila cells," Nature 404:293 [2000].

Hinoi et al., "Loss of CDX2 expression and microsatellite instability are prominent features of large cell minimally differentiated carcinomas of the colon," Am. J. Pathol. 159:2239 [2001.

Hisatake et al., "Down-Regulation of prostate-specific antigen expression by ligands for peroxisome proliferator-activated receptor gamma in human prostate cancer," Cancer Res. 60:5494 [2000].

Hubaishy et al., "Modulation of annexin II tetramer by tyrosine phosphorylation," Biochemistry 34:14527 [1995].

Jacobs et al., "The oncogene and Polycomb-group gene bmi-1 regulates cell proliferation and senescence through the ink4a locus.," Nature 397:164 [1999].

Jacobsen et al., "Incidence of prostate cancer diagnosis in the eras before and after serum prostate-specific antigen testing," JAMA 274:1445 [1995].

Kazama et al., "Hepsin, a putative membrane-associated serine protease, activates human factor VII and initiates a pathway of blood coagulation on the cell surface leading to thrombin formation," J. Biol. Chem., 270:66 [1995].

Kotti et al., "In mouse alpha -methylacyl-CoA racemase, the same gene product is simultaneously located in mitochondria and peroxisomes," J. Biol.Chem., 275:20887 [2000].

Kubota et al., "Ligand for peroxisome proliferator-activated receptor gamma (troglitazone) has potent antitumor effect against human prostate cancer both in vitro and in vivo," Cancer Res. 58:3344 [1998].

Kumar Smith et al., "Base excess and lactate as prognostic indicators for patients admitted to intensive care.," J. Biol. Chem. 276(24)21039-45 [2001].

Kurachi et al., "Hepsin," Methods Enzymol., 244:100 [1994].

Luo et al., "Human prostate cancer and benign prostatic hyperplasia: molecular dissection by gene expression pro," Cancer Res. 61:4683 [2001].

Maattanen et al., "European randomized study of prostate cancer screening: first-year results of the Finnish trial", Br. J. Cancer 79:1210 [1999].

Macejak et al., "Inhibition of hepatitis C virus (HCV)-RNA-dependent translation and replication of a chimeric HCV poliovirus using synthetic stabilized ribozymes," Hepatology 31:769 [2000].

Magee et al., "Expression profiling reveals hepsin overexpression in prostate cancer," Cancer Res. 61:5692 [2001].

* cited by examiner

Figure 4
a
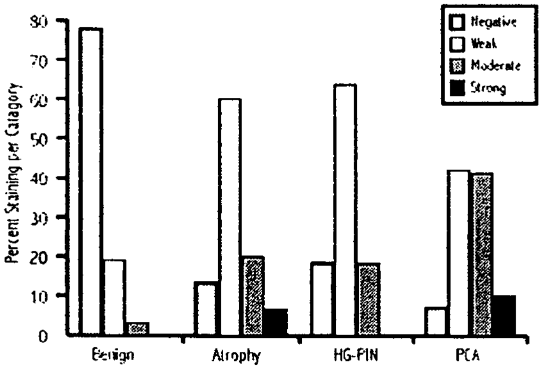
b
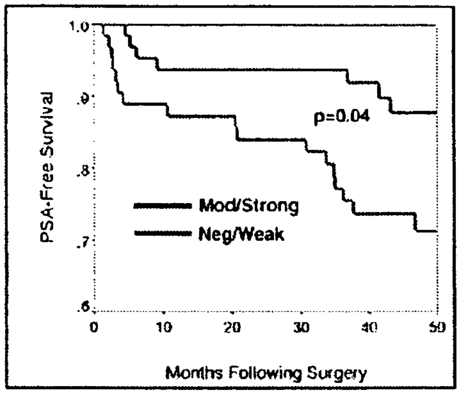

Figure 7
a
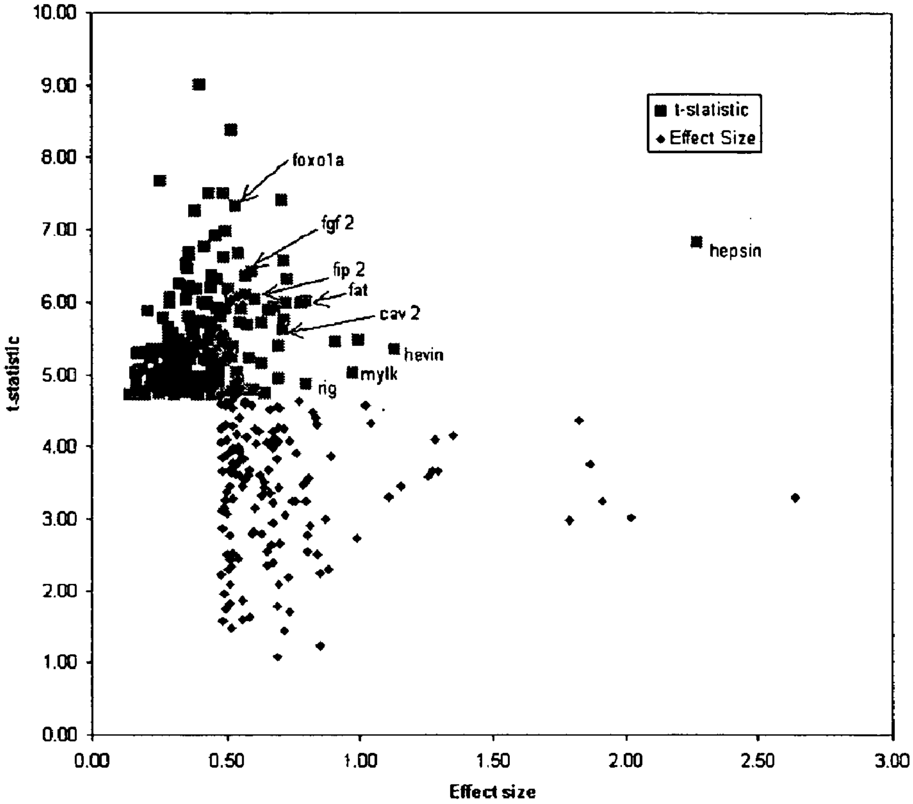
b
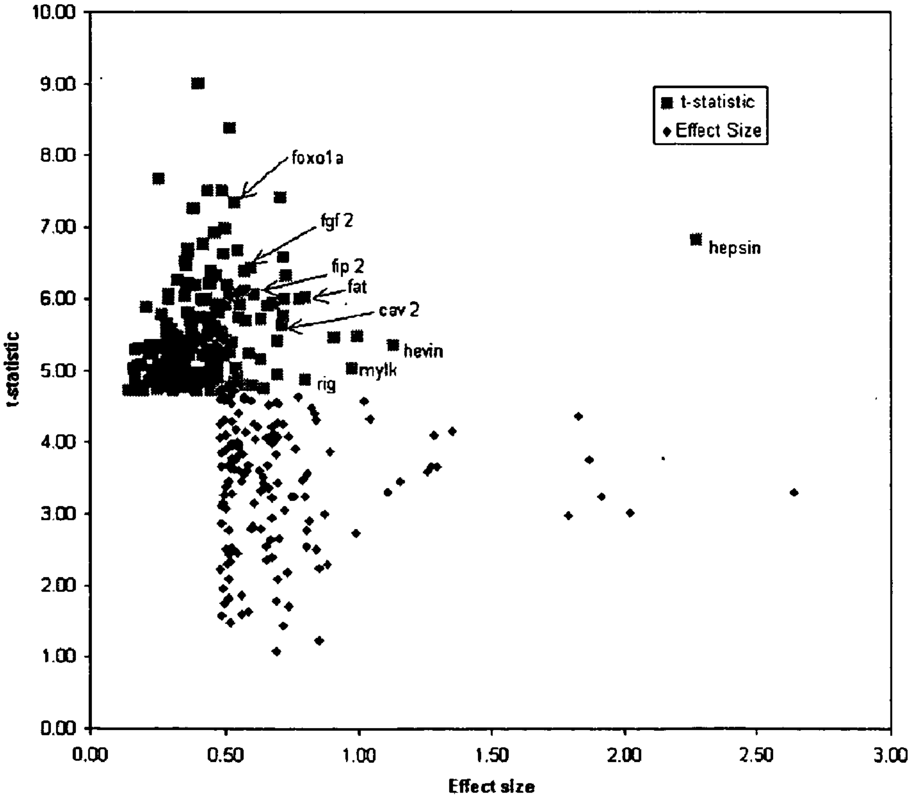

Figure 9

| SEQ ID NO | Name | Accession Number |
|---|---|---|
| 1 | Hepsin | M18930 |
| 2 | pim-1 | M54915 |
| 3 | FKBP5 | XM_004288 |
| 4 | FASN | NM_004104 |
| 5 | FOLH1 | M99487 |
| 6 | TNFSF10 | XM_045049 |
| 7 | PCM1 | XM_044711 |
| 8 | S100A11 | XM_047223 |
| 9 | IGFBP3 | XM_004689 |
| 10 | SLUG | XM_011634 |
| 11 | GSTM3 | J05459 |
| 12 | IL1R2 | X59770 |
| 13 | ITGB4 | X53587 |
| 14 | CCND2 | XM_034568 |
| 15 | EDNRB | S57283 |
| 16 | APP | X06989 |
| 17 | THROMBOSPONDIN 1 | X04665 |
| 18 | ANNEXIN A1 | XM_005665 |
| 19 | EPHA1 | M18391 |
| 20 | NCK1 | XM_051968 |
| 21 | MAPK6 | XM_017662 |
| 22 | SGK | XM_037045 |
| 23 | HEVIN | XM_011533 |
| 24 | MEIS2 | XM_012430 |
| 25 | MYLK | XM_042191 |
| 26 | FZD7 | NM_003507 |
| 27 | CAVEOLIN 2 | XM_004966 |
| 28 | TACC1 | XM_049505 |
| 29 | ARHB | XM_002689 |
| 30 | PSG9 | NM_002784 |
| 31 | GSTM1 | NM_000561 |
| 32 | Keratin 5 | XM_006847 |
| 33 | TIMP2 | XM_027036 |
| 34 | GELSOLIN | XM_016545 |
| 35 | ITM2C | AA034213 |
| 36 | GSTM5 | XM_002154 |
| 37 | VINCULIN | XM_011883 |
| 38 | FHL1 | XM_042931 |

Figure 9 (cont.)

| | | |
|---|---|---|
| 39 | GSTP1 | XM_040116 |
| 40 | MEIS1 | XM_010880 |
| 41 | ETS2 | XM_009766 |
| 42 | PPP2CB | XM_005121 |
| 43 | CATHEPSIN B | XM_005133 |
| 44 | COL1A2 | XM_029246 |
| 45 | RIG | XM_006029 |
| 46 | VIMENTIN | XM_042952 |
| 47 | MOESIN | XM_013042 |
| 48 | MCAM | XM_006077 |
| 49 | FIBRONECTIN 1 | XM_030549 |
| 50 | NBL1 | XM_001434 |
| 51 | ANNEXIN A4 | XM_031594 |
| 52 | ANNEXIN A11 | XM_035906 |
| 53 | IL1R1 | XM_002686 |
| 54 | IGFBP5 | XM_046731 |
| 55 | CYSTATIN C | XM_009599 |
| 56 | COL15A1 | XM_005592 |
| 57 | ADAMTS1 | XM_047796 |
| 58 | SKI | XM_001535 |
| 59 | EGR1 | XM_033546 |
| 60 | FOSB | NM_006732 |
| 61 | CFLAR | XM_027980 |
| 62 | JUN | XM_001472 |
| 63 | YWHAB | XM_009519 |
| 64 | NRAS | XM_001317 |
| 65 | C7 | J03507 |
| 66 | SCYA2 | XM_038982 |
| 67 | ITGA1 | XM_032902 |
| 68 | LUMICAN | XM_006900 |
| 69 | C1S | XM_032536 |
| 70 | C4BPA | XM_052053 |
| 71 | COL3A1 | XM_044878 |
| 72 | FAT | XM_003477 |
| 73 | MMECD10 | XM_030168 |
| 74 | CLUSTERIN | XM_005113 |
| 75 | PLA2G2A | XM_027887 |
| 76 | MADH4 | XM_030100 |
| 77 | SEPP1 | XM_011306 |
| 78 | RAB2 | XM_037653 |
| 79 | PP1CB | NM_002709 |
| 80 | MPDZ | XM_051281 |

Figure 9 (cont.)

| | | |
|---|---|---|
| 81 | PRKCL2 | XM_001880 |
| 82 | ATF2 | XM_027217 |
| 83 | RAB5A | NM_004162 |
| 84 | Cathepsin H | XM_007633 |
| 85 | CTBP1 | XM_003445 |
| 86 | MAP3K10 | XM_042665 |
| 87 | TBXA2R | XM_047633 |
| 88 | MTA1 | NM_004689 |
| 89 | RAP2 | NM_002886 |
| 90 | TRAP1 | XM_036666 |
| 91 | TFCP2 | XM_051171 |
| 92 | E2-EPF | XM_012615 |
| 93 | UBCH10 | XM_009488 |
| 94 | TASTIN | XM_006826 |
| 95 | EZH2 | XM_004774; NM004456 |
| 96 | FLS353 | AB024704 |
| 97 | MYBL2 | XM_009492 |
| 98 | LIMK1 | XM_051836 |
| 99 | TRAF4 | XM_031428 |
| 104 | AMACR | XM_043772; NM01324 |
| 114 | GP73 | AF236056 |
| 115 | CTBP2 | AF016507 |
| 116 | Annexin A2 | NM_004039 |
| 117 | Annexin A4 | XM_031596 |
| 118 | Annexin A11 | NM_001157 |
| 119 | ABCC5 (MDR5) | XM_002914 |
| 120 | ASNS | M27396 |
| 121 | TOP2A | NM_001067 |
| 122 | VaV2 | XM_005638 |

Figure 10

SEQ ID NO:1

```
1     tcgagcccgc tttccaggga ccctacctga gggcccacag gtgaggcagc ctggcctagc
61    aggccccacg ccaccgcctc tgcctccagg ccgcccgctg ctgcggggcc accatgctcc
121   tgcccaggcc tggagactga cccgaccccg gcactacctc gaggctccgc cccccacctgc
181   tggaccccag ggtcccaccc tggcccagga ggtcagccag ggaatcatta acaagaggca
241   gtgacatggc gcagaaggag ggtggccgga ctgtgccatg ctgctccaga cccaaggtgg
301   cagctctcac tgcggggacc ctgctacttc tgacagccat cggggcggca tcctgggcca
361   ttgtggctgt tctcctcagg agtgaccagg agccgctgta cccagtgcag gtcagctctg
421   cggacgctcg gctcatggtc tttgacaaga cggaagggac gtggcggctg ctgtgctcct
481   cgcgctccaa cgccagggta gccggactca gctgcgagga gatgggcttc ctcagggcac
541   tgacccactc cgagctggac gtgcgaacgg cgggcgccaa tggcacgtcg ggcttcttct
601   gtgtggacga ggggaggctg ccccacaccc agaggctgct ggaggtcatc tccgtgtgtg
661   attgccccag aggccgtttc ttggccgcca tctgccaaga ctgtggccgc aggaagctgc
721   ccgtggaccg catcgtggga ggccgggaca ccagcttggg ccggtggccg tggcaagtca
781   gccttcgcta tgatggagca cacctctgtg gggatccct gctctccggg gactgggtgc
841   tgacagccgc ccactgcttc ccggagcgga accgggtcct gtcccgatgg cgagtgtttg
901   ccggtgccgt ggcccaggcc tctccccacg gtctgcagct gggggtgcag gctgtggtct
961   accacggggg ctatcttccc tttcgggacc ccaacagcga ggagaacagc aacgatattg
1021  ccctggtcca cctctccagt cccctgcccc tcacagaata catccagcct gtgtgcctcc
1081  cagctgccgg ccaggccctg gtggatggca agatctgtac cgtgacgggc tggggcaaca
1141  cgcagtacta tggccaacag gccggggtac tccaggaggc tcgagtcccc ataatcagca
1201  atgatgtctg caatggcgct gacttctatg gaaaccagat caagcccaag atgttctgtg
1261  ctggctaccc cgagggtggc attgatgcct gccagggcga cagcggtggt ccctttgtgt
1321  gtgaggacag catctctcgg acgccacgtt ggcggctgtg tggcattgtg agttggggca
1381  ctggctgtgc cctggcccag aagccaggcg tctacaccaa agtcagtgac ttccgggagt
1441  ggatcttcca ggccataaag actcactccg aagccagcgg catggtgacc cagctctgac
1501  cggtggcttc tcgctgcgca gcctccaggg cccgaggtga tcccggtggt gggatccacg
1561  ctgggccgag gatgggacgt tttcttcttt gggcccggtc cacaggtcca aggacaccct
1621  ccctccaggg tcctctcttc cacagtggcg ggcccactca gccccgagac cacccaacct
1681  caccctcctg acccccatgt aaatattgtt ctgctgtctg ggactcctgt ctaggtgccc
1741  ctgatgatgg gatgctcttt aaataataaa gatggttttg att
```

SEQ ID NO:2

```
1     gaggaggccc gagaggagtc ggtggcagcg gcggcggcgg gaccggcagc agcagcagca
61    gcagcagcag caaccactag cctcctgccc cgcggcgttg cgacgagccc cacgagccgc
121   tcaccccgcc gttctcagcg ctgcccgacc ccgctggcgc gcctcccgcc gcagtcccgg
181   cagcgcctca gttgtcctcc gactcgccct cggccttcgc gcagcgcagc acagccgcac
241   gcaccgcagc acagcacagc acagcccagg catagcttcg gcacagcccc ggctccggct
301   cctgcggcag ctcctctggc acgtccctgc gccgacattc tggaggttgg atgctcttgt
361   ccaaaatcaa ctcgcttgcc cacctgcgcg ccgcgccctg caacgacctg cacgccacca
421   agctggcgcc cggcaaggag aaggagcccc tggagtcgca gtaccaggtg ggcccgctac
481   tgggcagcgg cggcttcggc tcggtctact caggcatccg cgtctccgac aacttgccgg
541   tggccatcaa acacgtggag aaggaccgga tttccgactg ggagagctg cctaatggca
601   ctcgagtgcc catggaagtg gtcctgctga agaaggtgag ctcgggtttc tccggcgtca
661   ttaggctcct ggactggttc gagaggcccg acagtttcgt cctgatcctg gagaggcccg
721   agccggtgca agatctcttc gacttcatca cggaaagggg agccctgcaa gaggagctgg
781   cccgcagctt cttctggcag gtgctggagg ccgtgcggca ctgccacaac tgcggggtgc
```

Figure 10 (cont.)

```
841   tacaccgcga catcaaggac gaaaacatcc ttatcgacct caatcgcggc gagctcaagc
901   tcatcgactt cgggtcgggg gcgctgctca aggacaccgt ctacacggac ttcgatggga
961   cccgagtgta tagccctcca gagtggatcc gctaccatcg ctaccatggc aggtcggcgg
1021  cagtctggtc cctggggatc ctgctgtatg atatggtgtg tggagatatt cctttcgagc
1081  atgacgaaga gatcatcagg ggccaggttt tcttcaggca gagggtctct tcagaatgtc
1141  agcatctcat tagatggtgc ttggccctga gaccatcaga taggccaacc ttcgaagaaa
1201  tccagaacca tccatggatg caagatgttc tcctgcccca ggaaactgct gagatccacc
1261  tccacagcct gtcgccgggg cccagcaaat agcagccttt ctggcaggtc ctcccctctc
1321  ttgtcagatg cccgagggag ggaagcttc tgtctccagc ttcccgagta ccagtgacac
1381  gtctcgccaa gcaggacagt gcttgataca ggaacaacat ttacaactca ttccagatcc
1441  caggcccctg gaggctgcct cccaacagtg ggaagagtg actctccagg ggtcctaggc
1501  ctcaactcct cccatagata ctctcttctt ctcataggtg tccagcattg ctggactctg
1561  aaatatcccg gggtgggg gtgggggtgg gcagaaccct gccaatggaa ctctttcttc
1621  atcatgagtt ctgctgaatg ccgcgatggg tcaggtaggg gggaaacagg ttgggatggg
1681  ataggactag cacattttaa gtccctgtca cctcttccga ctctttctga gtgccttctg
1741  tggggactcc ggctgtgctg ggagaaatac ttgaacttgc ctcttttacc tgctgcttct
1801  ccaaaaatct gcctgggttt tgttccctat ttttctctcc tgtcctccct cacccccctcc
1861  ttcatatgaa aggtgccatg gaagaggcta cagggccaaa cgctgagcca cctgcccttt
1921  tttctgcctc ctttagtaaa actccgagtg aactggtctt ccttttttggt ttttacttaa
1981  ctgtttcaaa gccaagacct cacacacaca aaaaaatgca caaaccaagc aatcaacaga
2041  aaagctgtaa atgtgtgtac agttggcatg gtagtataca aaaagattgt agtggatcta
2101  atttttaaga aattttgcct ttaagttatt ttacctgttt ttgtttcttg ttttgaaaga
2161  tgcgcattct aacctggagg tcaatgttat gtatttattt atttatttat ttggttccct
2221  tcctattcca agcttccata gctgctgccc tagttttctt tcctcctttc ctcctctgac
2281  ttggggacct tttgggggag ggctgcgacg cttgctctgt ttgtggggtg acgggactca
2341  ggcgggacag tgctgcagct ccctggcttc tgtggggccc ctcacctact tacccaggtg
2401  ggtcccggct ctgtgggtga tgggaggggc cattgctgac tgtgtatata ggataattat
2461  gaaacacagt tctggatggt gtgccttcca gatcctctct ggggctgtgt tttgagcagc
2521  aggtagcctg ctggttttat ctgagtgaaa tactgtacag ggaataaaa gagatcttat
2581  ttttttttta tacttgcgtt tggaataaaa accctttggc ttt
```

SEQ ID NO:3

```
1     gaacaatgaa gaaagcccca cagccactgt tgctgagcag ggagaggata ttacctccaa
61    aaaagacagg ggagtattaa agattgtcaa aagagtgggg aatggtgagg aaacgccgat
121   gattggagac aaagtttatg tccattacaa aggaaaattg tcaaatggaa agaagtttga
181   ttccagtcat gatagaaatg aaccatttgt ctttagtctt ggcaaaggcc aagtcatcaa
241   ggcatgggac attggggtgg ctaccatgaa gaaaggagag atatgccatt tactgtgcaa
301   accagaatat gcatatggct cggctggcag tctccctaaa attccctcga atgcaactct
361   ctttttttgag attgagctcc ttgatttcaa aggagaggat ttatttgaag atggaggcat
421   tatccggaga accaaacgga aaggagaggg atattcaaat ccaaacgaag gagcaacagt
481   agaaatccac ctggaaggcc gctgtggtgg aaggatgttt gactgcagag atgtggcatt
541   cactgtgggc gaaggagaag accacgacat tccaattgga attgacaaag ctctggagaa
601   aatgcagcgg gaagaacaat gtattttata tcttggacca agatatggtt ttggagaggc
661   agggaagcct aaatttggca ttgaacctaa tgctgagctt atatatgaag ttacacttaa
721   gagcttcgaa aaggccaaag aatcctggga gatggatacc aaagaaaaat tggagcaggc
781   tgccattgtc aaagagaagg gaaccgtata cttcaaggga ggcaaataca tgcaggcggt
841   gattcagtat gggaagatag tgtcctggtt agagatggaa tatggtttat cagaaaagga
901   atcgaaagct tctgaatcat ttctccttgc tgcctttctg aacctggcca tgtgctacct
961   gaagcttaga gaatacacca aagctgttga atgctgtgac aaggcccttg gactggacag
1021  tgccaatgag aaaggcttgt ataggagggg tgaagcccag ctgctcatga acgagtttga
1081  gtcagccaag ggtgactttg agaaagtgct ggaagtaaac ccccagaata aggctgcaag
1141  actgcagatc tccatgtgcc agaaaaaggc caaggagcac aacgagcggg accgcaggat
1201  atacgccaac atgttcaaga agtttgcaga gcaggatgcc aaggaagagg ccaataaagc
1261  aatgggcaag aagacttcag aaggggtcac taatgaaaaa ggaacagaca gtcaagcaat
```

Figure 10 (cont.)

```
1321  ggaagaagag aaacctgagg gccacgtatg acgccacgcc aaggagggaa gagtcccagt
1381  gaactcggcc cctcctcaat gggctttccc ccaactcagg acagaacagt gtttaatgta
1441  aagtttgtta tagtctatgt gattctggaa gcaaatggca aaaccagtag cttcccaaaa
1501  acagcccccc tgctgctgcc cggagggttc actgaggggt ggcacgggac cactccaggt
1561  ggaacaaaca gaaatgactg tggtgtggag ggagtgagcc agcagcttaa gtccagctca
1621  tttcagtttc tatcaacctt caagtatcca attcagggtc cctggagatc atcctaacaa
1681  tgtggggctg ttaggtttta cctttgaact ttcatagcac tgcagaaacc tttaaaaaaa
1741  aaatgcttca tgaatttctc ctttcctaca gttgggtagg gtaggggaag gaggataagc
1801  ttttgttttt taaatgactg aagtgctata aatgtagtct gttgcatttt taaccaacag
1861  aacccacagt agaggggtct catgtctccc cagttccaca gcagtgtcac agacgtgaaa
1921  gccagaacct cagaggccac ttgcttgctg acttagcctc ctcccaaagt ccccctcctc
1981  agccagcctc cttgtgagag tggctttcta ccacacacag cctgtccctg gggagtaat
2041  tctgtcattc ctaaaacacc cttcagcaat gataatgagc agatgagagt ttctggatta
2101  gcttttccta ttttcgatga agttctgaga tactgaaatg tgaaaagagc aatcagaatt
2161  gtgctttttc tcccctcctc tattcctttt agggaataat attcaataca cagtacttcc
2221  tcccag
```

SEQ ID NO:4

```
1     atggaggagg tggtgattgc cggcatgttc gggaagctgc cagagtcgga gaacttgcag
61    gagttctggg acaacctcat cggcggtgtg gacatggtca cggacgatga ccgtcgctgg
121   aaggctgggc tctacggcct gccccggcgg tccggcaagc tgaaggacct gtctaggttt
181   gatgcctcct tcttcggagt ccaccccaag caggcacaca cgatggaccc tcagctgcgg
241   ctgctgctgg aagctaccta tgaagccatc gtggacggag gcatcaaccc agattcactc
301   cgaggaacac acactggcgt ctgggtgggc gtgagcggct ctgagacctc ggaggccctg
361   agccgagacc ccgagacact cgtgggctac agcatggtgg gctgccagcg agcgatgatg
421   gccaaccggc tctccttctt cttcgacttc agagggccca gcatcgcact ggacacagcc
481   tgctcctcca gcctgatggc cctgcagaac gcctaccagg ccatccacag cgggcagtgc
541   cctgccgcca tcgtgggggg catcaacgtc ctgctgaagc ccaacacctc cgtgcagttc
601   ttgaggctgg ggatgctcag ccccgagggc acctgcaagg ccttcgacac agcggggaat
661   gggtactgcc gctcggaggg tgtggtggct gtcctgctga ccaagaagtc cctggcccgg
721   aaggtctaca ccaccatcct gaacaaaggc accaatacag atggcttcaa ggagcaaggc
781   gtgaccttcc ctcaggatat ccaggagcag cctatccgct cgttgtacca gtcggccgga
841   gtggcccctg agtcatttga atacatcgaa gcccacggac caggcaccaa ggtgggcgac
901   ccccaggagc gtaatggcat cacccgagcc ctgtgcgcca cccgccagga gccgctgctc
961   atcggctcca ccaagtccaa catggggcac ccggagccag cctcggggct cgacgccctg
1021  gccaaggtgc tgctgtccct ggagcacggg ctctgggccc ccaacctgca cttccatagc
1081  cccaaccctg agatcccagc gctgttggat gggcggctgc aggtggtgga ccagcccctg
1141  cccgtccgtg gcggcaacgt gggcatcaac tcctttggct tcgggggctc caacatgcac
1201  atcatcctga ggcccaacac gcagtccgcc cccgcacccg ccccacatgc caccctgccc
1261  cgtctgctgc gggccagcgg acgcacccct gaggccgtgc agaagctgct ggagcagggc
1321  ctccggcaca gccagggcct ggctttcctg agcatgctga acgacatcgc ggctgtcccc
1381  gccaccgcca tgcccttccg tggctacgct gtgctgggtg gtgagacgcg gtggcccaga
1441  gtgcagcagg tgcccgctgg cgagcgcccg ctctggttca tctgctctgg gatgggcaca
1501  cagtggcgtg gaatggggct gagccttatg cgcctggacc gcttccgaga ttccatccta
1561  cgctccgatg aggctgtgaa ccgattcggc ctgaaggtgt cacagctgct gctgagcaca
1621  gacgagagca cctttgatga catcgtccat tcgtttgtga gcctgactgc catccagata
1681  ggcctcatag acctgctgag ctgcatggga cctgaggcag atggcatcgt cggccactcc
1741  ctgggggagt ggctgtcggt acgcgacggc tgcctgtccc aggaggaggc cgtcctcgct
1801  gcctactgga ggggacagtg catcaaagaa gccccacttc ccgccggcgc catggcagcc
1861  gtgggcttgt cctgggagga gtgtaaacag cgctgccccc ctgcggtggt gcccgcctgc
1921  cacaactcca aggacacagt caccatctcg ggacctcagg ccccggtgtt tgagttcgtg
1981  gagcagctga ggaaggaggg tgtgtttgcc aaggaggtgc ggaccggcgg tatggccttc
2041  cactcctact tcatggaggc catcgcaccc ccactgctgc aggagctcaa gaaggtgatc
2101  cgggagccga agccacgttc agcccgctgg ctcagcacct ctatccccga ggcccagtgg
```

Figure 10 (cont.)

```
2161  cacagcagcc tggcacgcac gtcttccgcc gagtacaatg tcaacaacct ggtgagccct
2221  gtgctgttcc aggaggccct gtggcacgtg cctgagcacg cggtggtgct ggagatcgcc
2281  ccgaccccgt gccctcaggc tgtcctgaag cgggtccgta agccgagctg caccatcatc
2341  ccccgtatga agaaggatca cagggacaac ctggagttct tcctggccgg catcggcagg
2401  ctgcacctct caggcatcga cgccaacccc aatgccttgt tcccacctgt ggagtcccca
2461  gctccccgag gaactcccct catctcccca ctcatcaagt gggaccacag cctggcctgg
2521  gacgcgccgg ccgccgagga cttccccaac ggttcaggtt ccccctcagc caccatctac
2581  acatgcacac caagctccga gtctcctgac cgctacctgg tggaccacac catcgacggt
2641  cgcgtcctct tccccgccac tggctacctg agcatagtgt ggaagacgct ggcccgcgcc
2701  tgggctgggc tcgagcagct gcctgtggtg tttgaggatg tggtgcagca ccaggccacc
2761  atcctgccca agactgggac agtgtccttg gaggtacggc tcctggaggc caccggtgcc
2821  ttcgaggtgt cagagaacgg caacctggta gtgagtggga aggtgtacca gtgggatgac
2881  cctgacccca ggctcttcga ccacccggaa agtccccacc ccaattcccc acggagtccc
2941  ctcttcctgg cccaggcaga agtttacaag gagctgcgtc tgcgtggcta cgactacggc
3001  cctcatttcc agggcatcct ggaggccagc ctggaaggtg actcggggag gctgctgtgg
3061  aaggataact gggtgagctt catggacacc atgctgcaga tgtccatcct gggctcggcc
3121  aagcacggcc tgtacctacc cacccgtgtc accgccatcc acatcgaccc tgccacccac
3181  aggcagaagc tgtacacact gcaggacaag gcccaagtgg ctgacgtggt ggtgagcagg
3241  tggccgaggg tcacagtggc gggaggcgtc cacatctccg ggctccacac tgagtcggcc
3301  ccgcggcggc acgaggagca gcaggtgccc atcctggaga agttttgctt cactccccac
3361  acggaggagg ggtgcctgtc tgagcacgct gccctcgagg aggagctgca actgtgcaag
3421  gggctggtcg aggcactcga gaccaaggtg acccagcagg ggctgaagat ggtggtgccg
3481  gactggacgg ggcccagatc cccccgggac ccctcacagc aggaactgcc ccggctgttg
3541  tcggctgcct gcaggcttca gctcaacggg aacctgcagc tggagctggc gcaggtgctg
3601  gcccaggaga ggcccaagct gccagaggac cctctgctca gcggcctcct ggactccccg
3661  gcactcaagg cctgcctgga cactgccgtg gagaacatgc ccagcctgaa gatgaaggtg
3721  gtggaggtgc tggccggcca cggtcacctg tattcccgca tcccaggcct gctcagcccc
3781  catcccctgc tgcagctgag ctacacggcc accgaccgcc acccccaggc cctggaggct
3841  gcccaggccg agctgcagca gcacgacgtt gcccagggcc agtgggatcc cgcagaccct
3901  gcccccagcg ccctgggcag cgcggacctc ctggtgtgca actgtgctgt ggctgccctc
3961  ggggacccgg cctcagctct cagcaacatg gtggctgccc tgagagaagg gggctttctg
4021  ctcctgcaca cactgctccg gggggcaccct cgggacatcg tggccttcct cacctccact
4081  gagccgcagt atggccaggg catcctgagc caggacgcgt gggagagcct cttctccagg
4141  gtgtcgctgc gcctggtggg cctgaagaag tccttctacg gcgccacgct cttcctgtgc
4201  cgccggccca ccccgcagga cagccccatc ttcctgccgg tggacgatac cagcttccgc
4261  tgggtggagt ctctgaaggg catcctggct gacgaagact cttcccggcc tgtgtggctg
4321  aaggccatca actgtgccac ctcgggcgtg gtgggcttgg tgaactgtct ccgccgagag
4381  cccggcggaa ccgtccggtg tgtgctgctc tccaacctca gcagcacctc ccacgtcccg
4441  gaggtggacc cgggctccgc agaactgcag aaggtgttgc agggagacct ggtgatgaac
4501  gtctaccgcg acggggcctg gggggttttc cgccacttcc tgctggagga caagcctgag
4561  gagccgacgg cacatgcctt tgtgagcacc ctcacccggg gggacctgtc ctccatccgc
4621  tgggtctgct cctcgctgcg ccatgcccag cccacctgcc ctggcgccca gctctgcacg
4681  gtctactacg cctccctcaa cttccgcgac atcatgctgg ccactggcaa gctgtcccct
4741  gatgccatcc cagggaagtg gacctcccag gacagcctgc taggtatgga gttctcgggc
4801  cgagacgcca gcggcaagcg tgtgatggga ctggtgcctg ccaagggcct ggccacctct
4861  gtcctgctgt caccggactt cctctgggat gtgccttcca actggacgct ggaggaggcg
4921  gcctcggtgc ctgtcgtcta cagcacggcc tactacgcgc tggtggtgcg tgggcgggtg
4981  cgccccgggg agacgctgct catccactcg ggctcgggcg gcgtgggcca ggccgccatc
5041  gccatcgccc tcagtctggg ctgccgcgtc ttcaccaccg tggggtcggc tgagaagcgg
5101  gcgtacctcc aggccaggtt cccccagctc gacagcacca gcttcgccaa ctcccgggac
5161  acatccttcg agcagcatgt gctgtggcac acgggcggga agggcgttga cctggtcttg
5221  aactccttgg cggaagagaa gctgcaggcc agcgtgaggt gcttcggtac gcacggtcgc
5281  ttcctggaaa ttggcaaatt cgacctttct cagaaccacc cgctcggcat ggctatcttc
5341  ctgaagaacg tgacattcca cggggtccta ctggatgcgt tcttcaacga gagcagtgct
```

Figure 10 (cont.)

```
5401  gactggcggg aggtgtgggc gcttgtcgag gccgccatcc gggatggggt ggtacggccc
5461  ctcaagtgca cggtgttcca tggggcccag gtggaggacg ccttccgcta catggcccaa
5521  gggaagcaca ttggcaaagt cgtcgtgcag gtgcttgcgg aggagccggc agtgctgaag
5581  ggggccaaac ccaagctgat gtcggccatc tccaagacct tctgcccggc ccacaagagc
5641  tacatcatcg ctggtggtct gggtggcttc ggcctggagt tggcgcagtg gctgatacag
5701  cgtggggtgc agaagctcgt gttgacttct cgctccggga tccggacagg ctaccaggcc
5761  aagcaggtcc gccggtggag gcgccagggg ctacaggtgc aggtgtccac cagcaacatc
5821  agctcactgg agggggcccg ggcctcatt gccgaggcgg cgcagcttgg gcccgtgggg
5881  ggcgtcttca acctggccgt ggtcttgaga gatggcttgc tggagaacca gaccccagag
5941  ttcttccagg acgtctgcaa gcccaagtac agcggcaccc tgaacctgga cagggtgacc
6001  cgagaggcgt gccctgagct ggactacttt gtggtcttct cctctgtgag ctgcgggcgt
6061  ggcaatgcgg gacagagcaa ctacggcttt gccaattccg ccatggagcg tatctgtgag
6121  aaacgccggc acgaaggcct cccaggcctg gccgtgcagt ggggcgccat cggcaccgtg
6181  ggcattttgg tggagacgat gagcaccaac gacacgatcg tcagtggcac gctgcccacg
6241  cgcattggcg tccttggcct ggaggtgctg gacctcttcc tgaaccagcc ccacatggtc
6301  ctgagcagct ttgtgctggc tgagaaggct gcggcctata gggacaggga cagccagcgg
6361  gacctggtgg aggccgtggc acacatcctg ggcatccgcg acttggctgc tgtcaacctg
6421  ggcggctcac tggcggacct gggcctggac tcgctcatga gcgcgccggt gcgccagacg
6481  ctggagcgtg agctcaacct ggtgctgtcc gtgcgcgagg tgcggcaact cacgctccgg
6541  aaactgcagg agctgtcctc aaaggcggat gaagccagcg agctggcatg ccccacgccc
6601  aaggaggatg gtctggccca gcagcagact cagctgaacc tgcgctccct gctggtgaaa
6661  ccggagggcc ccaccctgat gcggctcaac tccgtgcaga gctcggagcg gcccctgttc
6721  ctggtgcacc caatcgaggc taccaccgtg ttccacagcc tcggtcccgg tctcagcatc
6781  cccacctatg gcctgcagtg caccccggct gcgccccttg acagcatcca cagcctggct
6841  gcctactaca tcgactgcat caggcaggtg cagcccgagg gcccctaccg cgtggccggc
6901  tactcctacg gggcctgcgt ggcctttgaa atgtgctccc agctgcaggc ccagcagagc
6961  ccagccccca cccacaacag cctcttcctg ttcgacggct cgcccaccta cgtactggcc
7021  tacacccaga gctaccgggc aaagctgacc ccaggctgta aggctgaggc tgagacggag
7081  gccatatgct tcttcgtgca gcagttcacg gacatggagc acaacagggt gctggaggcg
7141  ctgctgccgc tgaagggcct agaggagcgt gtggcagccg ccgtggacct gatcatcaag
7201  agccaccagg gcctggaccg ccaggagctg agctttgcgg cccggtcctt ctactacagg
7261  ctgcgtgccg ctgaccagta tacacccaag gccaagtaca gtggcaacgt gatgctactg
7321  cgggccaaga cgggtggccg ctacggcgag gacctgggcg cggactacaa cctctcccag
7381  gtatgcgacg ggaaagtatc cgtccatatc atcgagggtg accaccgcac gctgctggag
7441  ggcagcggcc tggagtccat catcagcatc atccacagct ccctggctga gccacgtgtg
7501  agtcgggagg gctag
```

SEQ ID NO:5

```
1    ctcaaaaggg gccggatttc cttctcctgg aggcagatgt tgcctctctc tctcgctcgg
61   attggttcag tgcactctag aaacactgct gtggtggaga aactggaccc caggtctgga
121  gcgaattcca gcctgcaggg ctgataagcg aggcattagt gagattgaga gagactttac
181  cccgccgtgg tggttggagg gcgcgcagta gagcagcagc acaggcgcgg gtcccgggag
241  gccggctctg ctcgcgccga gatgtggaat ctccttcacg aaaccgactc ggctgtggcc
301  accgcgcgcc gcccgcgctg gctgtgcgct ggggcgctgg tgctggcggg tggcttcttt
361  ctcctcggct tcctcttcgg gtggtttata aaatcctcca atgaagctac taacattact
421  ccaaagcata atatgaaagc atttttggat gaattgaaag ctgagaacat caagaagttc
481  ttatataatt ttacacagat accacattta gcaggaacag aacaaaactt tcagcttgca
541  aagcaaattc aatcccagtg gaaagaattt ggcctggatt ctgttgagct agcacattat
601  gatgtcctgt tgtcctaccc aaataagact catcccaact acatctcaat aattaatgaa
661  gatggaaatg agattttcaa cacatcatta tttgaaccac ctcctccagg atatgaaaat
721  gtttcggata ttgtaccacc tttcagtgct ttctctcctc aaggaatgcc agagggcgat
781  ctagtgtatg ttaactatgc acgaactgaa gacttcttta aattggaacg ggacatgaaa
841  atcaattgct ctgggaaaat tgtaattgcc agatatggga aagttttcag aggaaataag
901  gttaaaaatg cccagctggc aggggccaaa ggagtcattc tctactccga ccctgctgac
```

Figure 10 (cont.)

```
961   tactttgctc ctggggtgaa gtcctatcca gatggttgga atcttcctgg aggtggtgtc
1021  cagcgtggaa atatcctaaa tctgaatggt gcaggagacc ctctcacacc aggttaccca
1081  gcaaatgaat atgcttatag gcgtggaatt gcagaggctg ttggtcttcc aagtattcct
1141  gttcatccaa ttggatacta tgatgcacag aagctcctag aaaaaatggg tggctcagca
1201  ccaccagata gcagctggag aggaagtctc aaagtgccct acaatgttgg acctggcttt
1261  actggaaact ttctacaca aaaagtcaag atgcacatcc actctaccaa tgaagtgaca
1321  agaatttaca atgtgatagg tactctcaga ggagcagtgg aaccagacag atatgtcatt
1381  ctgggaggtc accgggactc atgggtgttt ggtggtattg accctcagag tggagcagct
1441  gttgttcatg aaattgtgag gagctttgga acactgaaaa aggaagggtg gagacctaga
1501  agaacaattt tgtttgcaag ctgggatgca gaagaatttg gtcttcttgg ttctactgag
1561  tgggcagagg agaattcaag actccttcaa gagcgtggcg tggcttatat taatgctgac
1621  tcatctatag aaggaaacta cactctgaga gttgattgta caccgctgat gtacagcttg
1681  gtacacaacc taacaaaaga gctgaaaagc cctgatgaag gctttgaagg caaatctctt
1741  tatgaaagtt ggactaaaaa aagtccttcc ccagagttca gtggcatgcc caggataagc
1801  aaattgggat ctggaaatga ttttgaggtg ttcttccaac gacttggaat tgcttcaggc
1861  agagcacggt atactaaaaa ttgggaaaca aacaaattca gcggctatcc actgtatcac
1921  agtgtctatg aaacatatga gttggtggaa aagttttatg atccaatgtt taaatatcac
1981  ctcactgtgg cccaggttcg aggagggatg gtgtttgagc tagccaattc catagtgctc
2041  ccttttgatt gtcgagatta tgctgtagtt ttaagaaagt atgctgacaa aatctacagt
2101  atttctatga aacatccaca ggaaatgaag acatacagtg tatcatttga ttcacttttt
2161  tctgcagtaa agaattttac agaaattgct tccaagttca gtgagagact ccaggacttt
2221  gacaaaagca acccaatagt attaagaatg atgaatgatc aactcatgtt tctggaaaga
2281  gcatttattg atccattagg gttaccagac aggccttttt ataggcatgt catctatgct
2341  ccaagcagcc acaacaagta tgcaggggag tcattcccag gaatttatga tgctctgttt
2401  gatattgaaa gcaaagtgga cccttccaag gcctggggag aagtgaagag acagatttat
2461  gttgcagcct tcacagtgca ggcagctgca gagactttga gtgaagtagc ctaagaggat
2521  tctttagaga atccgtattg aatttgtgtg gtatgtcact cagaaagaat cgtaatgggt
2581  atattgataa attttaaaat tggtatattt gaaataaagt tgaatattat atataaaaaa
2641  aaaaaaaaaa aaa
```

SEQ ID NO:6

```
1 cctcactgac tataaaagaa tagagaagga agggcttcag tgaccggctg cctggctgac
61 ttacagcagt cagactctga caggatcatg gctatgatgg aggtccaggg gggacccagc
121 ctgggacaga cctgcgtgct gatcgtgatc ttcacagtgc tcctgcagtc tctctgtgtg
181 gctgtaactt acgtgtactt taccaacgag ctgaagcaga tgcaggacaa gtactccaaa
241 agtggcattg cttgtttctt aaaagaagat gacagttatt gggaccccaa tgacgaagag
301 agtatgaaca gcccctgctg gcaagtcaag tggcaactcc gtcagctcgt tagaaagatg
361 attttgagaa cctctgagga aaccatttct acagttcaag aaaagcaaca aaatatttct
421 cccctagtga gagaaagagg tcctcagaga gtagcagctc acataactgg gaccagagga
481 agaagcaaca cattgtcttc tccaaactcc aagaatgaaa aggctctggg ccgcaaaata
541 aactcctggg aatcatcaag gagtgggcat tcattcctga gcaacttgca cttgaggaat
601 ggtgaactgg tcatccatga aaaagggttt tactacatct attcccaaac atactttcga
661 tttcaggagg aaataaaaga aaacacaaag aacgacaaac aaatggtcca atatatttac
721 aaatacacaa gttatcctga ccctatattg ttgatgaaaa gtgctagaaa tagttgttgg
781 tctaaagatg cagaatatgg actctattcc atctatcaag gggaatattt tgagcttaag
841 gaaaatgaca gaatttttgt ttctgtaaca aatgagcact tgatagacat ggaccatgaa
901 gccagttttt ttggggcctt tttagttggc taactgacct ggaaagaaaa agcaataacc
961 tcaaagtgac tattcagttt tcaggatgat acactatgaa gatgtttcaa aaaatctgac
1021 caaaacaaac aaacagaaaa cagaaaacaa aaaaacctct atgcaatctg agtagagcag
1081 ccacaaccaa aaaattctac aacacacact gttctgaaag tgactcactt atcccaagag
1141 aatgaaattg ctgaaagatc tttcaggact ctacctcata tcagtttgct agcagaaatc
1201 tagaagactg tcagcttcca aacattaatg caatggttaa catcttctgt ctttataatc
1261 tactccttgt aaagactgta gaagaaagag caacaatcca tctctcaagt agtgtatcac
1321 agtagtagcc tccaggtttc cttaagggac aacatcctta agtcaaaaga gagaagaggc
```

Figure 10 (cont.)

```
1381 accactaaaa gatcgcagtt tgcctggtgc agtggctcac acctgtaatc ccaacatttt
1441 gggaacccaa ggtgggtaga tcacgagatc aagagatcaa gaccatagtg accaacatag
1501 tgaaacccca tctctactga aagtacaaaa attagctggg tgtgttggca catgcctgta
1561 gtcccagcta cttgagaggc tgaggcaaga gaattgtttg aacccgggag gcagaggttg
1621 cagtgtggtg agatcatgcc actacactcc agcctggcga cagagcgaga cttggtttca
1681 aaaaaaaaaa aaaaaaaaac ttcagtaagt acgtgttatt tttttcaata aaattctatt
1741 acagtatgtc
```

SEQ ID NO:7

```
   1 ggtcacatga ctccagtcta gctcgcattg cggctcccgc ccgggcgagt tctcgccccc
  61 gcgcggccgt tgccgaggag acggcgcatg tcccgccgcg cgttgccccc tctgcagtac
 121 ccccgcccct cttctcccac cacaatgaga tcctaagatg gcggtggctg cggcggttgg
 181 cgctgcgtag ctgaggtcga aaaggcggcc actggggccg aggcagccag gaaacgtgtg
 241 ggcctctctg ctgcggtctc cgagggccga ccgctgccgg cggcgggtcg tgggggctga
 301 ctgtcgctct gcctttgaca ggagaggctg cttcttgtag aggaaacagc tttgaagtgt
 361 ggagcgggaa aggagcagtt tctgagctgc aaaaactagt ttctaaacag agagttaatt
 421 gttaaatcca gtatggccac aggaggaggt ccctttgaag atggcatgaa tgatcaggat
 481 ttaccaaact ggagtaatga gaatgttgat gacaggctca acaatatgga ttggggtgcc
 541 caacagaaga aagcaaatag atcatcagaa aagaataaga aaaagtttgg tgtagaaagt
 601 gataaaagag taaccaatga tatttctccg gagtcgtcac caggagttgg aaggcgaaga
 661 acaaagactc cacatacgtt cccacacagt agatacatga gtcagatgtc tgtcccagag
 721 caggcagaat tagagaaact gaaacagcgg ataaacttca gtgatttaga tcagagaagc
 781 attggaagtg attcccaagg tagagcaaca gctgctaaca acaaacgtca gcttagtgaa
 841 aaccgaaagc ccttcaactt tttgcctatg cagattaata ctaacaagag caaagatgca
 901 tctacaagtc ccccaaacag agaaacgatt ggatcagcac agtgtaaaga gttgtttgct
 961 tctgctttaa gtaatgacct cttgcaaaac tgtcaggtgt ctgaagaaga tgggaggggga
1021 gaacctgcaa tggagagcag ccagattgta agcaggcttg ttcaaattcg cgattatatt
1081 actaaagcta gttccatgcg ggaagatctt gtagagaaaa atgagagatc tgctaatgtt
1141 gagcgcctta ctcatctaat agatcacctt aaagaacaag agaagtcata tatgaaattt
1201 cttaaaaaaa tccttgccag agatcctcag caggagccta tggaagagat agaaaatttg
1261 aagaaacaac atgatttatt aaaaagaatg ttacaacagc aggagcaact aagagctcta
1321 cagggacggc aggctgcact tctagctctg caacataaag cagagcaagc tattgcagtg
1381 atggatgatt ctgttgttgc agaaactgca ggtagcttat ctggcgtcag tatcacatct
1441 gaactaaatg aagaattgaa tgacttaatt cagcgttttc ataatcagct tcgtgattct
1501 cagcctccag ctgttccaga caatagaaga caggcagaaa gtctttcatt aactagggag
1561 gtttcccaga gcaggaaacc atcagcttca gaacgtttac ctgatgagaa agtcgaactt
1621 tttagcaaaa tgagagtgct acaggaaaag aaacaaaaaa tggacaaatt gcttggagaa
1681 cttcatacac ttcgagatca gcatcttaac aattcatcat cctctccaca aaggagtgtc
1741 gatcagagaa gtacttcagc tccctctgct tctgtaggct tggcaccggt tgtcaatgga
1801 gaatccaata gcctcacatc atctgttcct tatcctactg cttctctagt atctcagaat
1861 gagagtgaaa acgaaggcca cctcaatcca tctgaaaaac tccagaagtt aaatgaagtt
1921 cgaaagagat tgaatgagct aagagaatta gttcattatt atgaacaaac gtcagacatg
1981 atgacagatg ctgtgaatga aaacaggaaa gatgaagaaa ctgaagagtc agaatatgat
2041 tctgagcatg aaaattccga gcctgttact aacattcgaa atccacaagt agcttccact
2101 tggaatgaag taaatagtca tagtaatgca cagtgtgttt ctaataatag agatgggcga
2161 acagttaatt ctaattgtga aattaacaac agatctgctg ccaacataag ggctctaaac
2221 gtgcctcctt ctttagattg tcgatataat agagaagggg aacaggagat tcatgttgca
2281 caaggtgaag atgatgagga ggaggaggaa gaagcagaag aggagggagt cagtggagct
2341 tcattatcta gtcacaggag cagtctggtt gatgagcatc cagaagatgc tgaatttgaa
2401 cagaagatca accgacttat ggctgcaaaa cagaaactta gacagttaca agatcttgtt
2461 gctatggtac aggatgatga tgcagctcaa ggagttatct ctgccagtgc atcaaatttg
2521 gatgatttct acccagcaga agaagacacc aagcaaaatt caaataacac tagaggaaat
2581 gccaataaaa cacagaaaga tactggagta aatgaaaagg caagagagaa attttatgag
2641 gctaaactac agcagcaaca gagagagcta aaacaattgc aggaagaaag aaagaaactg
```

Figure 10 (cont.)

```
2701 attgacattc aggagaaaat tcaagcattg caaacggcat gccctgactt acagctgtca
2761 gctgctagtg tgggtaactg tcccaccaaa aaatatatgc cagctgttac ttcaacccca
2821 actgttaatc aacacgagac cagtacaagc aaatctgttt ttgagcctga agattcttca
2881 atagtagata atgagttgtg gtcagaaatg agaagacatg aaatgttgag ggaggagctg
2941 cgacagagaa gaaagcagct tgaagctctg atggctgaac atcagaggag gcaaggtcta
3001 gctgaaactg catctccagt ggctgtgtca ttgagaagtg atggatctga gaacctatgt
3061 actcctcagc aaagtagaac agaaaaaacg atggcaactt ggggagggtc tacccagtgt
3121 gcactagatg aagaaggaga tgaagacggt tacctttctg aaggaattgt tcggacagat
3181 gaagaggagg aagaagagca agatgccagt tccaatgata acttttctgt gtgtccttct
3241 racagtgtga atcataactc ctacaatgga aaggaaacta aaaataggtg gaagaacaat
3301 tgcccttttt cggcagatga aaattatcgt cctttagcca agacaaggca acagaatatc
3361 agcatgcaac ggcaagaaaa ccttcgttgg gtgtcagagc tctcttacgt agaagagaaa
3421 gaacaatggc aagaacaaat caatcagcta aagaaacagc ttgattttag tgtcagtatt
3481 tgtcagactt tgatgcaaga ccagcagact ctatcttgtc tgctacaaac tcttctcacg
3541 ggtccttaca gtgttatgcc cagcaatgtt gcatctcctc aagtacactt cataatgcac
3601 cagttgaacc agtgctatac tcagctaaca tggcaacaga ataatgttca gaggttgaaa
3661 caaatgctaa atgaacttat gcgccagcaa aatcagcatc cagaaaaacc tggaggcaag
3721 gaaagaggca gtagtgcatc gcaccctcct tctcccagtt tattttgtcc tttcagcttt
3781 ccaacacagc ctgtaaatct cttcaatata cctggattta ctaacttttc atcatttgca
3841 ccaggtatga atttcagccc tttatttcct tctaatttg gagatttttc tcagaatatc
3901 tctacaccca gtgaacagca gcaaccctta gcccagaatt cttcaggaaa aacagaatat
3961 atggcttttc caaaaccttt tgaaagcagt tcctctattg gagcagagaa accaaggaat
4021 aaaaaactgc ctgaagagga ggtggaaagc agtaggacac catggttata tgaacaagaa
4081 ggtgaagtag agaaaccatt tatcaagact ggattttcag tgtctgtaga aaaatctaca
4141 agtagtaacc gcaaaaatca attagataca aacggaagaa gacgccagtt tgatgaagaa
4201 tcactggaaa gctttagcag tatgcctgat ccagtagatc caacaacagt gactaaaaca
4261 ttcaagacaa gaaaagcgtc tgcacaggcc agcctggcat ctaaagataa aactcccaag
4321 tcaaaaagta agaagaggaa ttctactcag ctgaaaagca gagttaaaaa catcaggtat
4381 gaaagtgcca gtatgtctag cacatgtgaa ccttgcaaaa gtaggaacag acattcagcc
4441 cagactgaag agcctgttca agcaaaagta ttcagcagaa agaatcatga gcaactggaa
4501 aaaataataa aatgtaatag gtctacagaa atatcttcag aaactgggag tgatttttcc
4561 atgtttgaag ctttgcgaga tactatttat tctgaagtag ctacattaat ttctcaaaat
4621 gaatctcgtc cacattttct tattgaactc ttccatgagc tgcagctact aaacacagac
4681 tacttgagac agagggcttt atatgcattg caggacatag tatccagaca tatttctgag
4741 agccatgaaa aaggagaaaa tgtaaagtca gtaaactctg gtacttggat agcatcaaac
4801 tcagaactta ctcctagtga gagccttgct actactgatg atgaaacttt tgagaagaac
4861 tttgaaagag aaacccataa aataagtgag caaaatgatg ctgataatgc tagtgtcctg
4921 tctgtatcat caaattttga gcctttttgca acagatgatc taggtaacac cgtgattcac
4981 ttagatcaag cattagccag aatgagagaa tatgagcgta tgaagactga ggctgaaagt
5041 aactcaaata tgagatgcat ctgcaggatt attgaggatg gagatggtgc tggtgcaggt
5101 actacagtta ataatttaga agaaactccc gttattgaaa atcgtagttc acaacaacct
5161 gtaagtgaag tttctaccat cccatgtcct agaattgata ctcagcagct ggaccggcaa
5221 attaaagcaa ttatgaaaga agtcattcct tttttgaagg agcacatgga tgaagtatgc
5281 tcctcgcagc ttctaacttc agtaaggcgc atggttttga cccttaccca gcaaaatgat
5341 gagagcaaag agtttgtaaa gttctttcat aaacaacttg gaagtatatt acaggattca
5401 ctggcaaaat ttgctggcag aaaactgaaa gactgtggag aagatcttct tgtagagata
5461 tctgaagtgt tgttcaatga attggctttc tttaagctta tgcaagattt ggataataat
5521 agtataactg ttaaacagag atgcaaaagg aaaatagaag caactggagt gatacaatct
5581 tgtgccaaag agctaaaagg attcttgaag atcatggctc acctgctgga gagattgatg
5641 atgaagacaa agacaaggat gaaactgaaa cagttaagca gactcaaaca tctgaggtgt
5701 atgatggtcc caaaaatgta agatctgata tttctgatca agaggaagat gaagaaagtg
5761 aaggatgtcc agtgtctatt aatttgtcta aagctgaaac tcaggcttta actaattatg
5821 gaagtggaga agatgaaaat gaggatgaag aaatggaaga atttgaagaa ggccctgtgg
5881 atgtccagac ttccctccag gctaacactg aagctactga agaaaatgaa catgatgaac
```

Figure 10 (cont.)

```
5941 aggtcctaca acgtgacttt aaaaagacag cagaaagcaa aaatgtccca ttggaacgag
6001 aagccactag taaaaatgac caaaataact gtcctgtgaa accctgttac ctcaatatct
6061 tggaagatga gcaaccttta aatagtgctg cccataagga gtcacctcct actgttgatt
6121 caactcaaca gcctaaccct ttgccgttac gtttacctga aatggaaccc ttagtgccta
6181 gagtcaaaga agttaaatct gctcaggaaa ctcctgaaag ctctctggct ggaagtcctg
6241 atactgaatc tccagtgtta gtgaatgact atgaagcaga atctggtaat ataagtcaaa
6301 agtctgatga agaagatttt gtaaaagttg aagatttacc actgaaactg acaatatatt
6361 cagaggcaga tctaagaaag aaaatggtag aagaagaaca gaaaaaccat ttatctggtg
6421 aaatatgtga aatgcagacc gaagaattag ctggaaattc tgagacacta aaagaacctg
6481 aaacggtggg agcccagagt atatgagatg tcttcagagg ctcatctaac tctgtcctta
6541 catactcaat gcatatatga aaacaatact aaataaacat ctgatctgta taaaaat
```

SEQ ID NO:8

```
  1 ctccaaaggc aaaaatctcc agccctacag agactgagcg gtgcatcgag tccctgattg
 61 ctgtcttcca gaagtatgct ggaaaggatg gttataacta cactctctcc aagacagagt
121 tcgtaagctt catgaataca gaactagctg ccttcacaaa gaaccagaag gaccctggtg
181 tccttgaccg catgatgaag aaactggaca ccaacagtga tggtcagcta gatttctcag
241 aatttcttaa tctgattggt ggcctagcta tggcttgcca tgactccttc ctcaaggctg
301 tcccttccca gaagcggacc tgaggacccc ttggccctgg ccttcaaacc caccccctttt
361 ccttccagcc tttctgtcat catctccaca gcccacccat cccctgagca cactaaccac
421 ctcatgcagg ccccacctgc caatagtaat aaagcaatgt cacttttta aaacatgaa
```

SEQ ID NO:9

```
1 gccgcttcct gcctggattc cacagcttcg cgccgtgtac tgtcgcccca tccctgcgcg
61 cccagcctgc caagcagcgt gccccggttg caggcgtcat gcagcgggcg cgacccacgc
121 tctgggccgc tgcgctgact ctgctggtgc tgctccgcgg gccgccggtg gcgcgggctg
181 gcgcgagctc ggcgggcttg ggtcccgtgg tgcgctgcga gccgtgcgac gcgcgtgcac
241 tggcccagtg cgcgcctccg cccgccgtgt gcgcggagct ggtgcgcgag ccgggctgcg
301 gctgctgcct gacgtgcgca ctgagcgagg gccagccgtg cggcatctac accgagcgct
361 gtggctccgg ccttcgctgc cagccgtcgc ccgacgaggc gcgaccgctg caggcgctgc
421 tggacggccg cgggctctgc gtcaacgcta gtgccgtcag ccgcctgcgc gcctacctgc
481 tgccagcgcc gccagctcca ggaaatgcta gtgagtcgga ggaagaccgc agcgccggca
541 gtgtggagag cccgtccgtc tccagcacgc accgggtgtc tgatcccaag ttccaccccc
601 tccattcaaa gataatcatc atcaagaaag ggcatgctaa agacagccag cgctacaaag
661 ttgactacga gtctcagagc acagataccc agaacttctc ctccgagtcc aagcgggaga
721 cagaatatgg tccctgccgt agagaaatgg aagacacact gaatcacctg aagttcctca
781 atgtgctgag tcccaggggt gtacacattc ccaactgtga caagaaggga ttttataaga
841 aaaagcagtg tcgcccttcc aaaggcagga agcggggctt ctgctggtgt gtggataagt
901 atgggcagcc tctcccaggc tacaccacca aggggaagga ggacgtgcac tgctacagca
961 tgcagagcaa gtagacgcct gccgcaaggt taatgtggag ctcaaatatg ccttattttg
1021 cacaaaagac tgccaaggac atgaccagca gctggctaca gcctcgattt atatttctgt
1081 ttgtggtgaa ctgatttttt ttaaaccaaa gtttagaaag aggtttttga aatgcctatg
1141 gtttctttga atggtaaact tgagcatctt ttcactttcc agtagtcagc aaagagcagt
1201 ttgaattttc ttgtcgcttc ctatcaaaat attcagagac tcgagcacag cacccagact
1261 tcatgcgccc gtggaatgct caccacatgt tggtcgaagc ggccgaccac tgactttgtg
1321 acttaggcgg ctgtgttgcc tatgtagaga acacgcttca cccccactcc ccgtacagtg
1381 cgcacaggct ttatcgagaa taggaaaacc tttaaacccc ggtcatccgg acatcccaac
1441 gcatgctcct ggagctcaca gccttctgtg gtgtcatttc tgaaacaagg gcgtggatcc
1501 ctcaaccaag aagaatgttt atgtcttcaa gtgacctgta ctgcttgggg actattggag
1561 aaaataaggt ggagtcctac ttgtttaaaa aatatgtatc taagaatgtt ctagggcact
1621 ctgggaacct ataaaggcag gtatttcggg ccctcctctt caggaatctt cctgaagaca
1681 tggcccagtc gaaggcccag gatggctttt gctgcggccc cgtggggtag gagggacaga
1741 gagacaggga gagtcagcct ccacattcag aggcatcaca agtaatggca caattcttcg
1801 gatgactgca gaaaatagtg ttttgtagtt caacaactca agacgaagct tatttctgag
```

Figure 10 (cont.)

```
1861 gataagctct ttaaaggcaa agctttattt tcatctctca tcttttgtcc tccttagcac
1921 aatgtaaaaa agaatagtaa tatcagaaca ggaaggagga atggcttgct ggggagccca
1981 tccaggacac tgggagcaca tagagattca cccatgtttg ttgaacttag agtcattctc
2041 atgcttttct ttataattca cacatatatg cagagaagat atgttcttgt taacattgta
2101 tacaacatag ccccaaatat agtaagatct atactagata atcctagatg aaatgttaga
2161 gatgctattt gatacaactg tggccatgac tgaggaaagg agctcacgcc cagagactgg
2221 gctgctctcc cggaggccaa acccaagaag gtctggcaaa gtcaggctca gggagactct
2281 gccctgctgc agacctcggt gtggacacac gctgcataga gctctccttg aaaacagagg
2341 ggtctcaaga cattctgcct acctattagc ttttctttat ttttttaact ttttgggggg
2401 aaaagtattt ttgagaagtt tgtcttgcaa tgtatttata aatagtaaat aaagttttta
2461 ccatt
```

SEQ ID NO:10

```
   1 atgccgcgct ccttcctggt caagaagcat ttcaacgcct ccaaaaagcc aaactacagc
  61 gaactggaca cacatacagt gattatttcc ccgtatctct atgagagtta ctccatgcct
 121 gtcataccac aaccagagat cctcagctca ggagcataca gccccatcac tgtgtggact
 181 accgctgctc cattccacgc ccagctaccc aatggcctct ctcctctttc cggatactcc
 241 tcatctttgg ggcgagtgag tccccctcct ccatctgaca cctcctccaa ggaccacagt
 301 ggctcagaaa gccccattag tgatgaagag gaaagactac agtccaagct ttcagacccc
 361 catgccattg aagctgaaaa gtttcagtgc aatttatgca ataagaccta ttcaactttt
 421 tctgggctgg ccaaacataa gcagctgcac tgcgatgccc agtctagaaa atctttcagc
 481 tgtaaatact gtgacaagga atatgtgagc ctgggcgccc tgaagatgca tattcggacc
 541 cacacattac cttgtgtttg caagatctgc ggcaaggcgt ttccagacc ctggttgctt
 601 caaggacaca ttagaactca cacgggggag aagccttttt cttgccctca ctgcaacaga
 661 gcatttgcag acaggtcaaa tctgagggct catctgcaga cccattctga tgtaaagaaa
 721 taccagtgca aaaactgctc caaaaccttc tccagaatgt ctctcctgca caaacatgag
 781 gaatctggct gctgtgtagc acactga
```

SEQ ID NO:11

```
   1 ctcggaagcc cgtcaccatg tcgtgcgagt cgtctatggt tctcgggtac tgggatattc
  61 gtgggctggc gcacgccatc cgcctgctcc tggagttcac ggatacctct tatgaggaga
 121 aacggtacac gtgcggggaa gctcctgact atgatcgaag ccaatggctg gatgtgaaat
 181 tcaagctaga cctggacttt cctaatctgc cctacctcct ggatgggaag aacaagatca
 241 cccagagcaa tgccatcttg cgctacatcg ctcgcaagca caacatgtgt ggtgagactg
 301 aagaagaaaa gattcgagtg gacatcatag agaaccaagt aatggatttc cgcacacaac
 361 tgataaggct ctgttacagc tctgaccacg aaaaactgaa gcctcagtac ttggaagagc
 421 tacctggaca actgaaacaa ttctccatgt ttctgtggaa attctcatgg tttgccgggg
 481 aaaagctcac ctttgtggat tttctcacct atgatatctt ggatcagaac cgtatatttg
 541 accccaagtg cctggatgag ttcccaaacc tgaaggcttt catgtgccgt tttgaggctt
 601 tggagaaaat cgctgcctac ttacagtctg atcagttctg caagatgccc atcaacaaca
 661 agatggccca gtggggcaac aagcctgtat gctgagcagg aggcagactt gcagagcttg
 721 ttttgtttca tcctgtccgt aaggggtcag cgctcttgct ttgctctttt caatgaatag
 781 cacttatgtt actggtgtcc agctgagttt ctcttgggta taaaggctaa aagggaaaaa
 841 ggatatgtgg agaatcatca agatatgaat tgaatcgctg cgatactgtg gcatttccct
 901 actccccaac tgagttcaag ggctgtaggt tcatgcccaa gccctgagag tgggtactag
 961 aaaaaacgag attgcacagt tggagagagc aggtgtgtta aatggactgg agtccctgtg
1021 aagactgggt gaggataaca caagtaaaac tgtggtactg atggacttaa ccggagttcg
1081 gaaaccgtcc tgtgtacaca tgggagttta gtgtgataaa ggcagtattt cagactggtg
1141 ggctagccaa tagagttggc aattgcttat tgaaactcat taaaaataat agagccccac
1201 ttgacactat tcactaaaat taatctggaa tttaaggccc aacattaaac acaaagctgt
1261 attgat
```

SEQ ID NO:12

```
   1 gccacgtgct gctgggtctc agtcctccac ttcccgtgtc ctctggaagt tgtcaggagc
```

Figure 10 (cont.)

61 aatgttgcgc ttgtacgtgt tggtaatggg agtttctgcc ttcacccttc agcctgcggc
121 acacacaggg gctgccagaa gctgccggtt tcgtgggagg cattacaagc gggagttcag
181 gctggaaggg gagcctgtag ccctgaggtg cccccaggtg ccctactggt tgtgggcctc
241 tgtcagcccc cgcatcaacc tgacatggca taaaaatgac tctgctagga cggtcccagg
301 agaagaagag acacggatgt gggcccagga cggtgctctg tggcttctgc cagccttgca
361 ggaggactct ggcacctacg tctgcactac tagaaatgct tcttactgtg acaaaatgtc
421 cattgagctc agagtttttg agaatacaga tgctttcctg ccgttcatct catacccgca
481 aattttaacc ttgtcaacct ctggggtatt agtatgccct gacctgagtg aattcacccg
541 tgacaaaact gacgtgaaga ttcaatggta caaggattct cttcttttgg ataaagacaa
601 tgagaaattt ctaagtgtga gggggaccac tcacttactc gtacacgatg tggccctgga
661 agatgctggc tattaccgct gtgtcctgac atttgcccat gaaggccagc aatacaacat
721 cactaggagt attgagctac gcatcaagaa aaaaaaagaa gagaccattc ctgtgatcat
781 ttccccctc aagaccatat cagcttctct ggggtcaaga ctgacaatcc cgtgtaaggt
841 gtttctggga accggcacac ccttaaccac catgctgtgg tggacggcca atgacaccca
901 catagagagc gcctacccgg gaggccgcgt gaccgagggg ccacgccagg aatattcaga
961 aaataatgag aactacattg aagtgccatt gatttttgat cctgtcacaa gagaggattt
1021 gcacatggat tttaaatgtg ttgtccataa taccctgagt tttcagacac tacgcaccac
1081 agtcaaggaa gcctcctcca cgttctcctg gggcattgtg ctggccccac tttcactggc
1141 cttcttggtt ttggggggaa tatggatgca cagacggtgc aaacacagaa ctggaaaagc
1201 agatggtctg actgtgctat ggcctcatca tcaagacttt caatcctatc ccaagtgaaa
1261 taaatggaat gaaataattc aaacacaaaa aaaaaaaaaa aaaaaaaa SEQ ID NO:13
1 gcgctgcccg cctcgtcccc naccccaac cccccgcgcc cgccctcgga cagtccctgc
61 tcgcccgcgc gctgcagccc catctcctag cggcagccca ggcgcggagg gagcgagtcc
121 gccccgaggt aggtccagga cgggcgcaca gcagcagccg aggctggccg ggagagggag
181 gaagaggatg gcagggccac gccccagccc atgggccagg ctgctcctgg cagccttgat
241 cagcgtcagc ctctctggga ccttggcaaa ccgctgcaag aaggccccag tgaagagctg
301 cacggagtgt gtccgtgtgg ataaggactg cgcctactgc acagacgaga tgttcaggga
361 ccggcgctgc aacacccagg cggagctgct ggccgcgggc tgccagcggg agagcatcgt
421 ggtcatggag agcagcttcc aaatcacaga ggagacccag attgacacca ccctgcggcg
481 cagccagatg tccccccaag gcctgcgggt ccgtctgcgg cccggtgagg agcggcattt
541 tgagctggag gtgtttgagc cactggagag ccccgtggac ctgtacatcc tcatggactt
601 ctccaactcc atgtccgatg atctggacaa cctcaagaag atggggcaga acctggctcg
661 ggtcctgagc cagctcacca gcgactacac tattggattt ggcaagtttg tggacaaagt
721 cagcgtcccg cagacggaca tgaggcctga gaagctgaag gagccctggc ccaacagtga
781 ccccccttc tccttcaaga acgtcatcag cctgacagaa gatgtggatg agttccggaa
841 taaactgcag ggagagcgga tctcaggcaa cctggatgct cctgagggcg gcttcgatgc
901 catcctgcag acagctgtgt gcacgaggga cattggctgg cgccccggaca gcacccacct
961 gctggtcttc tccaccgagt cagccttcca ctatgaggct gatggcgcca acgtgctggc
1021 tggcatcatg agccgcaacg atgaacggtg ccacctggac accacgggca cctacaccca
1081 gtacaggaca caggactacc cgtcggtgcc caccctggtg cgcctgctcg ccaagcacaa
1141 catcatcccc atctttgctg tcaccaacta ctcctatagc tactacgaga agcttcacac
1201 ctatttccct gtctcctcac tgggggtgct gcaggaggac tcgtccaaca tcgtggagct
1261 gctggaggag gccttcaatc ggatccgctc caacctggac atccgggccc tagacagccc
1321 ccgaggcctt cggacagagg tcacctccaa gatgttccag aagacgagga ctgggtcctt
1381 tcacatccgg cggggggaag tgggtatata ccaggtgcag ctgcgggccc ttgagcacgt
1441 ggatgggacg cacgtgtgcc agctgccgga ggaccagaag ggcaacatcc atctgaaacc
1501 ttccttctcc gacggcctca agatggacgc gggcatcatc tgtgatgtgt gcacctgcga
1561 gctgcaaaaa gaggtgcggt cagctcgctg cagcttcaac ggagacttcg tgtgcggaca
1621 gtgtgtgtgc agcgagggct ggagtggcca gacctgcaac tgctccaccg gctctctgag
1681 tgacattcag ccctgcctgc gggagggcga ggacaagccg tgctccggcc gtggggagtg
1741 ccagtgcggg cactgtgtgt gctacggcga aggccgctac gagggtcagt tctgcgagta
1801 tgacaacttc cagtgtcccc gcacttccgg gttcctgtgc aatgaccgag gacgctgctc

Figure 10 (cont.)

```
1861 catgggccag tgtgtgtgtg agcctggttg gacaggccca agctgtgact gtcccctcag
1921 caatgccacc tgcatcgaca gcaatggggg catctgtaat ggacgtggcc actgtgagtg
1981 tggccgctgc cactgccacc agcagtcgct ctacacggac accatctgcg agatcaacta
2041 ctcggcgatc cacccgggcc tctgcgagga cctacgctcc tgcgtgcagt gccaggcgtg
2101 gggcaccggc gagaagaagg ggcgcacgtg tgaggaatgc aacttcaagg tcaagatggt
2161 ggacgagctt aagagagccg aggaggtggt ggtgcgctgc tccttccggg acgaggatga
2221 cgactgcacc tacagctaca ccatggaagg tgacggcgcc cctgggccca acagcactgt
2281 cctggtgcac aagaagaagg actgccctcc gggctccttc tggtggctca tcccccctgct
2341 cctcctcctc ctgccgctcc tggccctgct actgctgcta tgctggaagt actgtgcctg
2401 ctgcaaggcc tgcctggcac ttctcccgtg ctgcaaccga ggtcacatgg tgggctttaa
2461 ggaagaccac tacatgctgc gggagaacct gatggcctct gaccacttgg acacgcccat
2521 gctgcgcagc gggaacctca agggccgtga cgtggtccgc tggaaggtca ccaacaacat
2581 gcagcggcct ggctttgcca ctcatgccgc cagcatcaac cccacagagc tggtgcccta
2641 cgggctgtcc ttgcgcctgg cccgcctttg caccgagaac ctgctgaagc ctgacactcg
2701 ggagtgcgcc cagctgcgcc aggaggtgga ggagaacctg aacgaggtct acaggcagat
2761 ctccggtgta cacaagctcc agcagaccaa gttccggcag cagcccaatg ccgggaaaaa
2821 gcaagaccac accattgtgg acacagtgct gatggcgccc cgctcggcca agccggccct
2881 gctgaagctt acagagaagc aggtggaaca gagggccttc cacgacctca aggtggcccc
2941 cggctactac accctcactg cagaccagga cgcccggggc atggtggagt tccaggaggg
3001 cgtggagctg gtggacgtac gggtgcccct ctttatccgg cctgaggatg acgacgagaa
3061 gcagctgctg gtggaggcca tcgacgtgcc cgcaggcact gccaccctcg gccgccgcct
3121 ggtaaacatc accatcatca aggagcaagc cagagacgtg gtgtcctttg agcagcctga
3181 gttctcggtc agccgcgggg accaggtggc ccgcatccct gtcatccggc gtgtcctgga
3241 cggcgggaag tcccaggtct cctaccgcac acaggatggc accgcgcagg gcaaccggga
3301 ctacatcccc gtggagggtg agctgctgtt ccagcctggg gaggcctgga aagagctgca
3361 ggtgaagctc ctggagctgc aagaagttga ctccctcctg cggggccgcc aggtccgccg
3421 tttccacgtc cagctcagca accctaagtt tggggcccac ctgggccagc cccactccac
3481 caccatcatc atcagggacc cagatgaact ggaccggagc ttcacgagtc agatgttgtc
3541 atcacagcca ccccctcacg gcgacctggg cgcccccgcag aaccccaatg ctaaggccgc
3601 tgggtccagg aagatccatt tcaactggct gccccccttct ggcaagccaa tggggtacag
3661 ggtaaagtac tggattcagg gcgactccga atccgaagcc cacctgctcg acagcaaggt
3721 gccctcagtg gagctcacca acctgtaccc gtattgcgac tatgagatga aggtgtgcgc
3781 ctacggggct cagggcgagg gaccctacag ctccctggtg tcctgccgca cccaccagga
3841 agtgcccagc gagccagggc gtctggcctt caatgtcgtc tcctccacgg tgacccagct
3901 gagctgggct gagccggctg agaccaacgg tgagatcaca gcctacgagg tctgctatgg
3961 cctggtcaac gatgacaacc gacctattgg gcccatgaag aaagtgctgg ttgacaaccc
4021 taagaaccgg atgctgctta ttgagaacct tcgggagtcc cagccctacc gctacacggt
4081 gaaggcgcgc aacggggccg gctgggggcc tgagcgggag gccatcatca acctggccac
4141 ccagcccaag aggcccatgt ccatccccat catccctgac atccctatcg tggacgccca
4201 gagcggggag gactacgaca gcttccttat gtacagcgat gacgttctac gctctccatc
4261 gggcagccag aggcccagcg tctccgatga cactggctgc ggctggaagt tcgagcccct
4321 gctgggggag gagctggacc tgcggcgcgt cacgtggcgg ctgcccccgg agctcatccc
4381 gcgcctgtcg gccagcagcg ggcgctcctc cgacgccgag gcccccacgg cccccggac
4441 gacggcggcg cgggcgggaa gggcggcagc cgtgccccgc agtgcgacac ccgggccccc
4501 cggagagcac ctggtgaatg gccggatgga ctttgccttc ccgggcagca ccaactccct
4561 gcacaggatg accacgacca gtgctgctgc ctatggcacc cacctgagcc cacacgtgcc
4621 ccaccgcgtg ctaagcacat cctccaccct cacacgggac tacaactcac tgacccgctc
4681 agaacactca cactcgacca cactgcccag ggactactcc accctcacct ccgtctcctc
4741 ccacgactct cgcctgactg ctggtgtgcc cgacacgccc acccgcctgg tgttctctgc
4801 cctggggccc acatctctca gagtgagctg gcaggagccg cggtgcgagc ggccgctgca
4861 gggctacagt gtggagtacc agctgctgaa cggcggtgag ctgcatcggc tcaacatccc
4921 caaccctgcc cagacctcgg tggtggtgga agacctcctg cccaaccact cctacgtgtt
4981 ccgcgtgcgg gcccagagcc aggaaggctg ggggccgagag cgtgagggtg tcatcaccat
5041 tgaatcccag gtgcacccgc agagcccact gtgtcccctg ccaggctccg ccttcacttt
```

Figure 10 (cont.)

5101 gagcactccc agtgccccag gcccgctggt gttcactgcc ctgagcccag actcgctgca
5161 gctgagctgg gagcggccac ggaggcccaa tggggatatc gtcggctacc tggtgacctg
5221 tgagatggcc caaggaggag ggccagccac cgcattccgg gtggatggag acagccccga
5281 gagccggctg accgtgccgg gcctcagcga gaacgtgccc tacaagttca aggtgcaggc
5341 caggaccact gagggcttcg ggccagagcg cgagggcatc atcaccatag agtcccagga
5401 tggaggaccc ttcccgcagc tgggcagccg tgccgggctc ttccagcacc cgctgcaaag
5461 cgagtacagc agcatcacca ccacccacac cagcgccacc gagcccttcc tagtggatgg
5521 gctgaccctg gggggcccagc acctggaggc aggcggctcc ctcacccggc atgtgaccca
5581 ggagtttgtg agccggacac tgaccaccag cggaaccctt agcacccaca tggaccaaca
5641 gttcttccaa acttgaccgc accctgcccc accccgcca tgtcccacta ggcgtcctcc
5701 cgactcctct cccggagcct cctcagctac tccatccttg cacccctggg ggcccagccc
5761 acccgcatgc acagagcagg ggctaggtgt ctcctgggag gcatgaaggg ggcaaggtcc
5821 gtcctctgtg ggcccaaacc tatttgtaac caaagagctg ggagcagcac aaggacccag
5881 cctttgttct gcacttaata aatggttttg ctactgctaa aaaaaaaaaa aaaaaaaaaa
5941 aaaaaaaaaa aaaaaaaaaa aaaaaaaaaa aaaaaaaaaa aaaaaaaaaa aaaa SEQ ID NO:14
1 ccgccgggct ggccatggag ctgctgtgcc acgaggtgga cccggtccgc agggccgtgc
61 gggaccgcaa cctgctccga gacgaccgcg tcctgcagaa cctgctcacc atcgaggagc
121 gctaccttcc gcagtgctcc tacttcaagt gcgtgcagaa ggacatccaa ccctacatgc
181 gcagaatggt ggccacctgg atgctggagg tctgtgagga acagaagtgc gaagaagagg
241 tcttccctct ggccatgaat tacctggacc gtttcttggc tggggtcccg actccgaagt
301 cccatctgca actcctgggt gctgtctgca tgttcctggc ctccaaactc aaagagacca
361 gcccgctgac cgcggagaag ctgtgcattt acaccgacaa ctccatcaag cctcaggagc
421 tgctggagtg ggaactggtg gtgctgggga agttgaagtg gaacctggca gctgtcactc
481 ctcatgactt cattgagcac atcttgcgca agctgcccca gcagcgggag aagctgtctc
541 tgatccgcaa gcatgctcag accttcattg ctctgtgtgc caccgacttt aagtttgcca
601 tgtacccacc gtcgatgatc gcaactggaa gtgtgggagc agccatctgt gggctccagc
661 aggatgagga agtgagctcg ctcacttgtg atgccctgac tgagctgctg gctaagatca
721 ccaacacaga cgtggattgt ctcaaagctt gccaggagca gattgaggcg gtgctcctca
781 atagcctgca gcagtaccgt caggaccaac gtgacggatc caagtcggag gatgaactgg
841 accaagccag caccccctaca gacgtgcggg atatcgacct gtgaggatgc cagttgggcc
901 gaaagagaga gacgcgtcca taatctggtc tcttcttctt tctggttgtt tttgttcttt
961 gtgttttagg gtgaaactta aaaaaaaaat tctgccccca cctagatcat atttaaagat
1021 cttttagaag tgagagaaaa aggtcctacg aaaacggaat aataaaaagc atttggtgcc
1081 tatttgaagt acagcataag ggaatccctt gtatatgcga acagttattg tttgattatg
1141 taaaagtaat agtaaaatgc ttacaggaaa acctgcagag tagttagaga atatgtatgc
1201 ctgcaatatg ggaacaaatt agaggagact tttttttttc atgttatgag ctagcacata
1261 caccccccttg tagtataatt tcaaggaact gtgtacgcca tttatggcat gattagattg
1321 caaagcaatg aactcaagaa ggaattgaaa taaggaggga catgatgggg aaggagtaca
1381 aaacaatctc tcaacatgat tgaaccattt gggatggaga agcacctttg ctctcagcca
1441 cctgttacta agtcaggagt gtagttggat ctctacatta atgtcctctt gctgtctaca
1501 gtagctgcta cctaaaaaaa gatgttttat tttgccagtt ggacacaggt gattggctcc
1561 tgggtttcat gttctgtgac atcctgcttc ttcttccaaa tgcagttcat tgcagacacc
1621 accatattgc tatctaatgg ggaaatgtag ctatgggcca taaccaaaac tcacatgaaa
1681 cggaggcaga tggagaccaa gggtgggatc cagaatggag tcttttctgt tattgtattt
1741 aaaagggtaa tgtggccttg gcatttcttc ttagaaaaaa actaattttt ggtgctgatt
1801 ggcatgtctg gttcacagtt tagcattgtt ataaaccatt ccattcgaaa agcactttga
1861 aaaattgttc ccgagcgata gatgggatgg tttatgca SEQ ID NO:15
1 gagacattcc ggtgggggac tctggccagc ccgagcaacg tggatcctga gagcactccc
61 aggtaggcat ttgccccggt gggacgcctt gccagagcag tgtgtggcag gcccccgtgg
121 aggatcaaca cagtggctga acactgggaa ggaactggta cttggagtct ggacatctga

Figure 10 (cont.)

```
181 aacttggctc tgaaactgcg cagcggccac cggacgcctt ctggagcagg tagcagcatg
241 cagccgcctc caagtctgtg cggacgcgcc ctggttgcgc tggttcttgc ctgcggcctg
301 tcgcggatct ggggagagga gagaggcttc ccgcctgaca gggccactcc gcttttgcaa
361 accgcagaga taatgacgcc acccactaag accttatggc ccaagggttc caacgccagt
421 ctggcgcggt cgttggcacc tgcggaggtg cctaaaggag acaggacggc aggatctccg
481 ccacgcacca tctcccctcc cccgtgccaa ggacccatcg agatcaagga gactttcaaa
541 tacatcaaca cggttgtgtc ctgccttgtg ttcgtgctgg ggatcatcgg gaactccaca
601 cttctgagaa ttatctacaa gaacaagtgc atgcgaaacg gtcccaatat cttgatcgcc
661 agcttggctc tgggagacct gctgcacatc gtcattgaca tccctatcaa tgtctacaag
721 ctgctggcag aggactggcc atttggagct gagatgtgta agctggtgcc tttcatacag
781 aaagcctccg tgggaatcac tgtgctgagt ctatgtgctc tgagtattga cagatatcga
841 gctgttgctt cttggagtag aattaaagga attggggttc caaaatggac agcagtagaa
901 attgttttga tttgggtggt ctctgtggtt ctggctgtcc ctgaagccat aggttttgat
961 ataattacga tggactacaa aggaagttat ctgcgaatct gcttgcttca tcccgttcag
1021 aagacagctt tcatgcagtt ttacaagaca gcaaaagatt ggtggctgtt cagtttctat
1081 ttctgcttgc cattggccat cactgcattt ttttatacac taatgacctg tgaaatgttg
1141 agaaagaaaa gtggcatgca gattgcttta aatgatcacc taaagcagag acgggaagtg
1201 gccaaaaccg tcttttgcct ggtccttgtc tttgccctct gctggcttcc ccttcacctc
1261 agcaggattc tgaagctcac tctttataat cagaatgatc ccaatagatg tgaacttttg
1321 agctttctgt tggtattgga ctatattggt atcaacatgg cttcactgaa ttcctgcatt
1381 aacccaattg ctctgtattt ggtgagcaaa agattcaaaa actgctttaa gtcatgctta
1441 tgctgctggt gccagtcatt tgaagaaaaa cagtccttgg aggaaaagca gtcgtgctta
1501 aagttcaaag ctaatgatca cggatatgac aacttccgtt ccagtaataa atacagctca
1561 tcttgaaaga agaactattc actgtatttc attttcttta tattggaccg aagtcattaa
1621 aacaaaatga aacatttgcc aaaacaaaac aaaaaactat gtatttgcac agcacactat
1681 taaaatatta agtgtaatta ttttaacact cacagctaca tatgacattt tatgagctgt
1741 ttacggcatg gaaagaaaat cagtgggaat taagaaagcc tcgtcgtgaa agcacttaat
1801 tttttacagt tagcacttca acatagctct taacaacttc caggatattc acacaacact
1861 taggcttaaa aatgagctca ctcagaattt ctattctttc taaaaagaga tttatttta
1921 aatcaatggg actctgatat aaaggaagaa taagtcactg taaaacagaa cttttaaatg
1981 aagcttaaat tactcaattt aaaattttaa aatcctttaa aacaactttt caattaatat
2041 tatcacacta ttatcagatt gtaattagat gcaaatgaga gagcagttta gttgttgcat
2101 ttttcggaca ctggaaacat ttaaatgatc aggagggagt aacagaaaga gcaaggctgt
2161 ttttgaaaat cattacactt tcactagaag cccaaacctc agcattctgc aatatgtaac
2221 caacatgtca caaacaagca gcatgtaaca gactggcaca tgtgccagct gaatttaaaa
2281 tataatactt ttaaaaagaa aattattaca tcctttacat tcagttaaga tcaaacctca
2341 caaagagaaa tagaatgttt gaaaggctat cccaaaagac ttttttgaat ctgtcattca
2401 catacctgt gaagacaata ctatctacaa ttttttcagg attattaaaa tcttcttttt
2461 tcactatcgt agcttaaact ctgtttggtt ttgtcatctg taaatactta cctacataca
2521 ctgcatgtag atgattaaat gagggcaggc cctgtgctca tagctttacg atggagagat
2581 gccagtgacc tcataataaa gactgtgaac tgcctggtgc agtgtccaca tgacaaaggg
2641 gcaggtagca ccctctctca cccatgctgt ggttaaaatg gtttctagca tatgtataat
2701 gctatagtta aaatactatt tttcaaaatc atacagatta gtacatttaa cagctacctg
2761 taaagcttat tactaatttt tgtattattt ttgtaaatag ccaatagaaa agtttgcttg
2821 acatggtgct tttctttcat ctagaggcaa aactgctttt tgagaccgta agaacctctt
2881 agctttgtgc gttcctgcct aatttttata tcttctaagc aaagtgcctt aggatagctt
2941 gggatgagat gtgtgtgaaa gtatgtacaa gagaaaacgg aagagagagg aaatgaggtg
3001 gggttggagg aaacccatgg ggacagattc ccattcttag cctaacgttc gtcattgcct
3061 cgtcacatca atgcaaaagg tcctgatttt gttccagcaa aacacagtgc aatgttctca
3121 gagtgacttt cgaaataaat tgggcccaag agctttaact cggtcttaaa atatgcccaa
3181 atttttactt tgtttttctt ttaataggct gggccacatg ttggaaataa gctagtaatg
3241 ttgttttctg tcaatattga atgtgatggt acagtaaacc aaaacccaac aatgtggcca
3301 gaaagaaaga gcaataataa ttaattcaca caccatatgg attctattta taaatcaccc
3361 acaaacttgt tctttaattt catcccaatc actttttcag aggcctgtta tcatagaagt
```

Figure 10 (cont.)

```
3421 cattttagac tctcaatttt aaattaattt tgaatcacta atattttcac agtttattaa
3481 tatatttaat ttctatttaa attttagatt atttttatta ccatgtactg aatttttaca
3541 tcctgatacc ctttccttct ccatgtcagt atcatgttct ctaattatct tgccaaattt
3601 tgaaactaca cacaaaaagc atacttgcat tatttataat aaaattgcat tcagtggctt
3661 tttaaaaaaa atgtttgatt caaaacttta acatactgat aagtaagaaa caattataat
3721 ttctttacat actcaaaacc aagatagaaa aaggtgctat cgttcaactt caaaacatgt
3781 ttcctagtat taaggacttt aatatagcaa cagacaaaat tattgttaac atggatgtta
3841 cagctcaaaa gatttataaa agattttaac ctattttctc ccttattatc cactgctaat
3901 gtggatgtat gttcaaacac cttttagtat tgatagctta catatggcca aaggaataca
3961 gtttatagca aaacatgggt atgctgtagc taactttata aaagtgtaat ataacaatgt
4021 aaaaaattat atatctggga ggatttttg gttgcctaaa gtggctatag ttactgattt
4081 tttattatgt aagcaaaacc aataaaaatt taagtttttt taacaactac cttatttttc
4141 actgtacaga cactaattca ttaaatacta attgattgtt taaaagaaat ataaatgtga
4201 caagtggaca ttatttatgt taaatataca attatcaagc aagtatgaag ttattcaatt
4261 aaaatgccac atttctggtc tctggg
```

SEQ ID NO:16

```
   1 gaattcccgc ggagcagcgt gcgcggggcc ccgggagacg gcggcggtag cggcgcgggc
  61 agagcaagga cgcggcggat cccactcgca cagcagcgca ctcggtgccc cgcgcagggt
 121 cgcgatgctg cccggtttgg cactgctcct gctggccgcc tggacggctc gggcgctgga
 181 ggtacccact gatggtaatg ctggcctgct ggctgaaccc cagattgcca tgttctgtgg
 241 cagactgaac atgcacatga atgtccagaa tgggaagtgg gattcagatc catcagggac
 301 caaaacctgc attgatacca aggaaggcat cctgcagtat tgccaagaag tctaccctga
 361 actgcagatc accaatgtgg tagaagccaa ccaaccagtg accatccaga actggtgcaa
 421 gcggggccgc aagcagtgca agacccatcc ccactttgtg attccctacc gctgcttagt
 481 tggtgagttt gtaagtgatg cccttctcgt tcctgacaag tgcaaattct tacaccagga
 541 gaggatggat gtttgcgaaa ctcatcttca ctggcacacc gtcgccaaag agacatgcag
 601 tgagaagagt accaacttgc atgactacgg catgttgctg ccctgcggaa ttgacaagtt
 661 ccgaggggta gagtttgtgt gttgcccact ggctgaagaa agtgacaatg tggattctgc
 721 tgatgcggag gaggatgact cggatgtctg gtggggcgga gcagacacag actatgcaga
 781 tgggagtgaa gacaaagtag tagaagtagc agaggaggaa gaagtggctg aggtggaaga
 841 agaagaagcc gatgatgacg aggacgatga ggatggtgat gaggtagagg aagaggctga
 901 ggaaccctac gaagaagcca cagagagaac caccagcatt gccaccacca ccaccaccac
 961 cacagagtct gtggaagagg tggttcgaga ggtgtgctct gaacaagccg agacggggcc
1021 gtgccgagca atgatctccc gctggtactt tgatgtgact gaagggaagt gtgccccatt
1081 cttttacggc ggatgtggcg gcaaccggaa caactttgac acagaagagt actgcatggc
1141 cgtgtgtggc agcgccattc ctacaacagc agccagtacc cctgatgccg ttgacaagta
1201 tctcgagaca cctggggatg agaatgaaca tgcccatttc cagaaagcca aagagaggct
1261 tgaggccaag caccgagaga gaatgtccca ggtcatgaga gaatgggaag aggcagaacg
1321 tcaagcaaag aacttgccta aagctgataa gaaggcagtt atccagcatt tccaggagaa
1381 agtggaatct ttggaacagg aagcagccaa cgagagacag cagctggtgg agacacacat
1441 ggccagagtg gaagccatgc tcaatgaccg ccgccgcctg gccctggaga actacatcac
1501 cgctctgcag gctgttcctc ctcggcctcg tcacgtgttc aatatgctaa agaagtatgt
1561 ccgcgcagaa cagaaggaca gacagcacac cctaaagcat ttcgagcatg tgcgcatggt
1621 ggatcccaag aaagccgctc agatccggtc ccaggttatg acacacctcc gtgtgattta
1681 tgagcgcatg aatcagtctc tctccctgct ctacaacgtg cctgcagtgg ccgaggagat
1741 tcaggatgaa gttgatgagc tgcttcagaa agagcaaaac tattcagatg acgtcttggc
1801 caacatgatt agtgaaccaa ggatcagtta cggaaacgat gctctcatgc catctttgac
1861 cgaaacgaaa accaccgtgg agctccttcc cgtgaatgga gagttcagcc tggacgatct
1921 ccagccgtgg cattcttttg ggctgactc tgtgccagcc aacacagaaa acgaagttga
1981 gcctgttgat gcccgccctg ctgccgaccg aggactgacc actcgaccag gttctgggtt
2041 gacaaatatc aagacggagg agatctctga agtgaagatg gatgcagaat tccgacatga
2101 ctcaggatat gaagttcatc atcaaaaatt ggtgttcttt gcagaagatg tgggttcaaa
2161 caaaggtgca atcattggac tcatggtggg cggtgttgtc atagcgacag tgatcgtcat
```

Figure 10 (cont.)

```
2221 caccttggtg atgctgaaga agaaacagta cacatccatt catcatggtg tggtggaggt
2281 tgacgccgct gtcaccccag aggagcgcca cctgtccaag atgcagcaga acggctacga
2341 aaatccaacc tacaagttct ttgagcagat gcagaactag acccccgcca cagcagcctc
2401 tgaagttgga cagcaaaacc attgcttcac tacccatcgg tgtccattta tagaataatg
2461 tgggaagaaa caaacccgtt ttatgattta ctcattatcg ccttttgaca gctgtgctgt
2521 aacacaagta gatgcctgaa cttgaattaa tccacacatc agtaatgtat tctatctctc
2581 tttacatttt ggtctctata ctacattatt aatgggtttt gtgtactgta aagaatttag
2641 ctgtatcaaa ctagtgcatg aatagattct ctcctgatta tttatcacat agccccttag
2701 ccagttgtat attattcttg tggtttgtga cccaattaag tcctacttta catatgcttt
2761 aagaatcgat gggggatgct tcatgtgaac gtgggagttc agctgcttct cttgcctaag
2821 tattcctttc ctgatcacta tgcattttaa agttaaacat ttttaagtat ttcagatgct
2881 ttagagagat tttttttcca tgactgcatt ttactgtaca gattgctgct tctgctatat
2941 ttgtgatata ggaattaaga ggatacacac gtttgtttct tcgtgcctgt tttatgtgca
3001 cacattaggc attgagactt caagcttttc tttttttgtc cacgtatctt tgggtctttg
3061 ataaagaaaa gaatccctgt tcattgtaag cacttttacg gggcgggtgg ggaggggtgc
3121 tctgctggtc ttcaattacc aagaattc
```

SEQ ID NO:17

```
   1 gccgccctcg ccaccgctcc cggccgccgc gctccggtac acacaggatc cctgctgggc
  61 accaacagct ccaccatggg gctggcctgg ggactaggcg tcctgttcct gatgcatgtg
 121 tgtggcacca accgcattcc agagtctggc ggagacaaca gcgtgtttga catctttgaa
 181 ctcaccgggg ccgccccgcaa ggggtctggg cgccgactgg tgaagggccc cgacccttcc
 241 agcccagctt tccgcatcga ggatgccaac ctgatccccc ctgtgcctga tgacaagttc
 301 caagacctgg tggatgctgt gcggacagaa aagggtttcc tccttctggc atccctgagg
 361 cagatgaaga agacccgggg cacgctgctg gccctggagc ggaaagacca ctctggccag
 421 gtcttcagcg tggtgtccaa tggcaaggcg ggcaccctgg acctcagcct gaccgtccaa
 481 ggaaagcagc acgtggtgtc tgtggaagaa gctctcctgg caaccggcca gtggaagagc
 541 atcaccctgt ttgtgcagga agacagggcc cagctgtaca tcgactgtga aaagatggag
 601 aatgctgagt tggacgtccc catccaaagc gtcttcacca gagacctggc cagcatcgcc
 661 agactccgca tcgcaaaggg gggcgtcaat gacaatttcc aggggggtgct gcagaatgtg
 721 aggtttgtct ttggaaccac accagaagac atcctcagga acaaaggctg ctccagctct
 781 accagtgtcc tcctcaccct tgacaacaac gtggtgaatg gttccagccc tgccatccgc
 841 actaactaca ttggccacaa gacaaaggac ttgcaagcca tctgcggcat ctcctgtgat
 901 gagctgtcca gcatggtcct ggaactcagg ggcctgcgca ccattgtgac cacgctgcag
 961 gacagcatcc gcaaagtgac tgaagagaac aaagagttgg ccaatgagct gaggcggcct
1021 cccctatgct atcacaacgg agttcagtac agaaataacg aggaatggac tgttgatagc
1081 tgcactgagt gtcactgtca gaactcagtt accatctgca aaaaggtgtc ctgccccatc
1141 atgccctgct ccaatgccac agttcctgat ggagaatgct gtcctcgctg ttggcccagc
1201 gactctgcgg acgatggctg gtctccatgg tccgagtgga cctcctgttc tacgagctgt
1261 ggcaatggaa ttcagcagcg cggccgctcc tgcgatagcc tcaacaaccg atgtgagggc
1321 tcctcggtcc agacacggac ctgccacatt caggagtgtg acaagagatt taaacaggat
1381 ggtggctgga gccactggtc cccgtggtca tcttgttctg tgacatgtgg tgatggtgtg
1441 atcacaagga tccggctctg caactctccc agcccccaga tgaacgggaa accctgtgaa
1501 ggcgaagcgc gggagaccaa agcctgcaag aaagacgcct gccccatcaa tggaggctgg
1561 ggtccttggt caccatggga catctgttct gtcacctgtg gaggaggggt acagaaacgt
1621 agtcgtctct gcaacaaccc cacaccccag tttggaggca aggactgcgt tggtgatgta
1681 acagaaaacc agatctgcaa caagcaggac tgtccaattg atggatgcct gtccaatccc
1741 tgctttgccg gcgtgaagtg tactagctac cctgatggca gctggaaatg tggtgcttgt
1801 ccccctggtt acagtggaaa tggcatccag tgcacagatg ttgatgagtg caaagaagtg
1861 cctgatgcct gcttcaacca caatggagag caccggtgtg agaacacgga ccccggctac
1921 aactgcctgc cctgcccccc acgcttcacc ggctcacagc ccttcggcca gggtgtcgaa
1981 catgccacgg ccaacaaaca ggtgtgcaag ccccgtaacc cctgcacgga tgggacccac
2041 gactgcaaca agaacgccaa gtgcaactac ctgggccact atagcgaccc catgtaccgc
2101 tgcgagtgca agcctggcta cgctggcaat ggcatcatct gcggggagga cacagacctg
```

Figure 10 (cont.)

```
2161 gatggctggc ccaatgagaa cctggtgtgc gtggccaatg cgacttacca ctgcaaaaag
2221 gataattgcc ccaaccttcc caactcaggg caggaagact atgacaagga tggaattggt
2281 gatgcctgtg atgatgacga tgacaatgat aaaattccag atgacaggga caactgtcca
2341 ttccattaca acccagctca gtatgactat gacagagatg atgtgggaga ccgctgtgac
2401 aactgtccct acaaccacaa cccagatcag gcagacacag acaacaatgg ggaaggagac
2461 gcctgtgctg cagacattga tggagacggt atcctcaatg aacgggacaa ctgccagtac
2521 gtctacaatg tggaccagag agacactgat atggatgggg ttggagatca gtgtgacaat
2581 tgccccttgg aacacaatcc ggatcagctg gactctgact cagaccgcat tggagatacc
2641 tgtgacaaca atcaggatat tgatgaagat ggccaccaga acaatctgga caactgtccc
2701 tatgtgccca atgccaacca ggctgaccat gacaaagatg gcaagggaga tgcctgtgac
2761 cacgatgatg acaacgatgg cattcctgat gacaaggaca actgcagact cgtgcccaat
2821 cccgaccaga aggactctga cggcgatggt cgaggtgatg cctgcaaaga tgattttgac
2881 catgacagtg tgccagacat cgatgacatc tgtcctgaga atgttgacat cagtgagacc
2941 gatttccgcc gattccagat gattcctctg gaccccaaag ggacatccca aaatgaccct
3001 aactgggttg tacgccatca gggtaaagaa ctcgtccaga ctgtcaactg tgatcctgga
3061 ctcgctgtag gttatgatga gtttaatgct gtggacttca gtggcacctt cttcatcaac
3121 accgaaaggg acgatgacta tgctggattt gtctttggct accagtccag cagccgcttt
3181 tatgttgtga tgtggaagca agtcacccag tcctactggg acaccaaccc cacgagggct
3241 cagggatact cgggcctttc tgtgaaagtt gtaaactcca ccacagggcc tggcgagcac
3301 ctgcggaacg ccctgtggca cacaggaaac acccctggcc aggtgcgcac cctgtggcat
3361 gaccctcgtc acataggctg gaaagatttc accgcctaca gatggcgtct cagccacagg
3421 ccaaagacgg gtttcattag agtggtgatg tatgaaggga agaaaatcat ggctgactca
3481 ggacccatct atgataaaac ctatgctggt ggtagactag ggttgtttgt cttctctcaa
3541 gaaatggtgt tcttctctga cctgaaatac gaatgtagag atccctaatc atcaaattgt
3601 tgattgaaag actgatcata aaccaatgct ggtattgcac cttctggaac tatgggcttg
3661 agaaaacccc caggatcact tctccttggc ttccttcttt tctgtgcttg catcagtgtg
3721 gactcctaga acgtgcgacc tgcctcaaga aaatgcagtt ttcaaaaaca gactcagcat
3781 tcagcctcca atgaataaga catcttccaa gcatataaac aattgctttg gtttcctttt
3841 gaaaaagcat ctacttgctt cagttgggaa ggtgcccatt ccactctgcc tttgtcacag
3901 agcagggtgc tattgtgagg ccatctctga gcagtggact caaaagcatt ttcaggcatg
3961 tcagagaagg gaggactcac tagaattagc aaacaaaacc accctgacat cctccttcag
4021 gaacacgggg agcagaggcc aaagcactaa ggggagggcg catacccgag acgattgtat
4081 gaagaaaata tggaggaact gttacatgtt cggtactaag tcattttcag ggattgaaa
4141 gactattgct ggatttcatg atgctgactg gcgttagctg attaacccat gtaaataggc
4201 acttaaatag aagcaggaaa gggagacaaa gactggcttc tggacttcct ccctgatccc
4261 caccccttact catcacctgc agtggccaga attagggaat cagaatcgaa accagtgtaa
4321 ggcagtgctg gctgccattg cctggtcaca ttgaaattgg tggcttcatt ctagatgtag
4381 cttgtgcaga tgtagcagga aaataggaaa acctaccatc tcagtgagca ccag
```

SEQ ID NO:18

```
  1 atttctcttt agttctttgc aagaaggtag agataaagac actttttcaa aaatggcaat
 61 ggtatcagaa ttcctcaagc aggcctggtt tattgaaaat gaagagcagg aatatgttca
121 aactgtgaag tcatccaaag gtggtcccgg atcagcggtg agcccctatc ctaccttcaa
181 tccatcctcg gatgtcgctg ccttgcataa ggccataatg gttaaaggtg tggatgaagc
241 aaccatcatt gacattctaa ctaagcgaaa caatgcacag cgtcaacaga tcaaagcagc
301 atatctccag gaaacaggaa agcccctgga tgaaacactg aagaaagccc ttacaggtca
361 ccttgaggag gttgttttag ctctgctaaa aactccagcg caatttgatg ctgatgaact
421 tcgtgctgcc atgaagggcc ttggaactga tgaagatact ctaattgaga ttttggcatc
481 aagaactaac aaagaaatca gagacattaa cagggtctac agagaggaac tgaagagaga
541 tctggccaaa gacataacct cagacacatc tggagatttt cggaacgctt tgctttctct
601 tgctaagggt gaccgatctg aggactttgg tgtgaatgaa gacttggctg attcagatgc
661 cagggccttg tatgaagcag gagaaaggag aaaggggaca gacgtaaacg tgttcaatac
721 catccttacc accagaagct atccacaact tcgcagagtg tttcagaaat acaccaagta
781 cagtaagcat gacatgaaca aagttctgga cctggagttg aaaggtgaca ttgagaaatg
```

Figure 10 (cont.)

```
 841 cctcacagct atcgtgaagt gcgccacaag caaaccagct ttctttgcag agaagcttca
 901 tcaagccatg aaaggtgttg gaactcgcca taaggcattg atcaggatta tggtttcccg
 961 ttctgaaatt gacatgaatg atatcaaagc attctatcag aagatgtatg gtatctccct
1021 ttgccaagcc atcctggatg aaaccaaagg agattatgag aaaatcctgg tggctctttg
1081 tggaggaaac taaacattcc cttgatggtc tcaagctatg atcagaagac tttaattata
1141 tattttcatc ctataagctt aaataggaaa gtttcttcaa caggattaca gtgtagctac
1201 ctacatgctg aaaaatatag cctttaaatc atttttatat tataactctg tataatagag
1261 ataagtccat tttttaaaaa tgttttcccc aaaccataaa accctataca agttgttcta
1321 gtaacaatac atgagaaaga tgtctatgta gctgaaaata aaatgacgtc acaagac
```

SEQ ID NO:19

```
   1 gcccccgccc ggcccgcccc gctctcctag tcccttgcaa cctggcgctg catccgggcc
  61 actgtcccag gtcccaggtc ccggcccgga gctatggagc ggcgctggcc cctggggcta
 121 gggctggtgc tgctgctctg cgccccgctg cccccggggg cgcgcgccaa ggaagttact
 181 ctgatggaca caagcaaggc acagggagag ctgggctggc tgctggatcc cccaaaagat
 241 gggtggagtg aacagcaaca gatactgaat gggacacccc tctacatgta ccaggactgc
 301 ccaatgcaag gacgcagaga cactgaccac tggcttcgct ccaattggat ctaccgcggg
 361 gaggaggctt cccgcgtcca cgtggagctg cagttcaccg tgcgggactg caagagtttc
 421 cctgggggag ccgggcctct gggctgcaag gagaccttca accttctgta catggagagt
 481 gaccaggatg tgggcattca gctccgacgg cccttgttcc agaaggtaac cacggtggct
 541 gcagaccaga gcttcaccat tcgagacctt gcgtctggct ccgtgaagct gaatgtggag
 601 cgctgctctc tgggccgcct gacccgccgt ggcctctacc tcgctttcca caacccgggt
 661 gcctgtgtgg ccctggtgtc tgtccgggtc ttctaccagc gctgtcctga gaccctgaat
 721 ggcttggccc aattcccaga cactctgcct ggccccgctg ggttggtgga agtggcgggc
 781 acctgcttgc cccacgcgcg ggccagcccc aggccctcag gtgcaccccg catgcactgc
 841 agccctgatg gcgagtggct ggtgcctgta ggacggtgcc actgtgagcc tggctatgag
 901 gaaggtggca gtggcgaagc atgtgttgcc tgccctagcg gctcctaccg gatggacatg
 961 gacacacccc attgtctcac gtgcccccag cagagcactg ctgagtctga gggggccacc
1021 atctgtacct gtgagagcgg ccattacaga gctcccgggg agggccccca ggtggcatgc
1081 acaggtcccc cctcggcccc ccgaaacctg agcttctctg cctcagggac tcagctctcc
1141 ctgcgttggg aacccccagc agatacgggg ggacgccagg atgtcagata cagtgtgagg
1201 tgttcccagt gtcagggcac agcacaggac gggggggcct gccagccctg tggggtgggc
1261 gtgcacttct cgccgggggc ccgggcgctc accacacctg cagtgcatgt caatggcctt
1321 gaaccttatg ccaactacac ctttaatgtg gaagcccaaa atggagtgtc agggctgggc
1381 agctctggcc atgccagcac ctcagtcagc atcagcatgg ggcatgcaga gtcactgtca
1441 ggcctgtctc tgagactggt gaagaaagaa ccgaggcaac tagagctgac ctgggcgggg
1501 tcccggcccc gaagccctgg ggcgaacctg acctatgagc tgcacgtgct gaaccaggat
1561 gaagaacggt accagatggt tctagaaccc agggtcttgc tgacagagct gcagcctgac
1621 accacataca tcgtcagagt ccgaatgctg accccactgg gtcctggccc tttctcccct
1681 gatcatgagt ttcggaccag cccaccagtg tccaggggcc tgactggagg agagattgta
1741 gccgtcatct ttgggctgct gcttggtgca gccttgctgc ttgggattct cgttttccgg
1801 tccaggagag cccagcggca gaggcagcag aggcacgtga ccgcgccacc gatgtggatc
1861 gagaggacaa gctgtgctga agccttatgt ggtacctcca ggcatacgag gaccctgcac
1921 agggagcctt ggactttacc cggaggctgg tctaattttc cttcccggga gcttgatcca
1981 gcgtggctga tggtggacac tgtcatagga gaaggagagt ttggggaagt gtatcgaggg
2041 accctcaggc tccccagcca ggactgcaag actgtggcca ttaagacctt aaaagacaca
2101 tccccaggtg gccagtggtg gaacttcctt cgagaggcaa ctatcatggg ccagtttagc
2161 cacccgcata ttctgcatct ggaaggcgtc gtcacaaagc gaaagccgat catgatcatc
2221 acagaattta tggagaatgc agccctggat gccttcctga gggagcggga ggaccagctg
2281 gtccctgggc agctagtggc catgctgcag ggcatagcat ctggcatgaa ctacctcagt
2341 aatcacaatt atgtccaccg ggacctggct gccagaaaca tcttggtgaa tcaaaacctg
2401 tgctgcaagg tgtctgactt tggcctgact cgcctcctgg atgactttga tggcacatac
2461 gaaacccagg gaggaaagat ccctatccgt tggacagccc ctgaagccat tgcccatcgg
2521 atcttcacca cagccagcga tgtgtggagc tttgggattg tgatgtggga ggtgctgagc
```

Figure 10 (cont.)

```
2581 tttggggaca agccttatgg ggagatgagc aatcaggagg ttatgaagag cattgaggat
2641 gggtaccggt tgccccctcc tgtggactgc cctgcccctc tgtatgagct catgaagaac
2701 tgctgggcat atgaccgtgc ccgccggcca cacttccaga agcttcaggc acatctggag
2761 caactgcttg ccaacccccca ctccctgcgg accattgcca actttgaccc cagggtgact
2821 cttcgcctgc ccagcctgag tggctcagat gggatcccgt atcgaaccgt ctctgagtgg
2881 ctcgagtcca tacgcatgaa acgctacatc ctgcacttcc actcggctgg gctggacacc
2941 atggagtgtg tgctggagct gaccgctgag gacctgacgc agatgggaat cacactgccc
3001 gggcaccaga agcgcattct ttgcagtatt cagggattca aggactgatc cctcctctca
3061 ccccatgccc aatcagggtg caaggagcaa ggacggggcc aaggtcgctc atggtcactc
3121 cctgcgcccc ttcccacaac ctgccagact aggctatcgg tgctgcttct gcccgcttta
3181 aggagaaccc tgctctgcac cccagaaaac ctctttgttt taaaagggag gtgggggtag
3241 aagtaaaagg atgatcatgg gagggagctc aggggttaat atatatacat acatacacat
3301 atatatattg ttgtaaataa acaggaaatg atttctgcc tccatcccac ccatcagggc
3361 tgcaggcact
```

SEQ ID NO:20

```
   1 ccaagagcta cgcggcggcg gcggagcgca ggcctcgtgc cgttacggcc atcacggcgg
  61 ccgcagtggc gtcctggagc cctcctcagt gctgaagctg ctgaaagatg gcagaagaag
 121 tggtggtagt agccaaattt gattatgtgg cccaacaaga acaagagttg gacatcaaga
 181 agaatgagag attatggctt ctggatgatt ctaagtcctg gtggcgagtt cgaaattcca
 241 tgaataaaac aggttttgtg ccttctaact atgtggaaag gaaaaacagt gctcggaaag
 301 catctattgt gaaaaaccta aaggatacct taggcattgg aaaagtgaaa agaaaaccta
 361 gtgtgccaga ttctgcatct cctgctgatg atagttttgt tgacccaggg gaacgtctct
 421 atgacctcaa catgcccgct tatgtgaaat ttaactacat ggctgagaga gaggatgaat
 481 tatcattgat aaaggggaca aaggtgatcg tcatggagaa atgcagtgat gggtggtggc
 541 gtggtagcta caatggacaa gttggatggt tcccttcaaa ctatgtaact gaagaaggtg
 601 acagtccttt gggtgaccat gtgggttctc tgtcagagaa attagcagca gtcgtcaata
 661 acctaaatac tgggcaagtg ttgcatgtgg tacaggctct ttacccattc agctcatcta
 721 atgatgaaga acttaatttc gagaaaggag atgtaatgga tgttattgaa aaacctgaaa
 781 atgacccaga gtggtggaaa tgcaggaaga tcaatggtat ggttggtcta gtaccaaaaa
 841 actatgttac cgttatgcag aataatccat taacttcagg tttggaacca tcacctccac
 901 agtgtgatta cattaggcct tcactcactg gaaagtttgc tggcaatcct tggtattatg
 961 gcaaagtcac caggcatcaa gcagaaatgg cattaaatga aagaggacat gaaggggatt
1021 tcctcattcg tgatagtgaa tcttcgccaa atgatttctc agtatcacta aaagcacaag
1081 ggaaaaacaa gcattttaaa gtccaactaa aagagactgt ctactgcatt gggcagcgta
1141 aattcagcac catggaagaa cttgtagaac attacaaaaa ggcaccaatt tttacaagtg
1201 aacaaggaga aaaattatat cttgtcaagc atttatcatg atactgctga ccagaagtga
1261 ctgctgtgta gctgtaattt gtcatgtaat tgaagactga gaaaatgttg ggtccagtcg
1321 tgcttgattg gaaattgttg tttctaaatc tatatgagaa ttgacaataa gtatttttat
1381 tataactcag cccatacata tatactatgt atgcagtgca tctgcataga acagttcctt
1441 atccttggcc ttctgtttta ttgttttttt ctttgctgtt ttccctttgc ttctaatatt
1501 acagttttgt attttgtaaa caaaaatcaa ataatgcata tcagaatctt tatatggaag
1561 aaatccttta ttgcctttcc tttgtttcct tgtaaaggca ccctgttctg ttatggtttt
1621 tcattatata aaattattat atctatatat gacatatgct aaaatttctt ggagagtgtt
1681 aatcttttct gtgactaaat agcaataata agtggaaaat tagaaattat ttccaggtat
1741 tatatttgtc acaggccatt gtaaatacca agtatattgt gtctgccata atttttaaaa
1801 atacattcat tgtcttcagt catacagcaa gacacatgag acatagatta gaaaacatgt
1861 tgtacaattt taatttacaa ctgttggaaa taaaaatcac ttaatttttt tcc
```

SEQ ID NO:21

```
   1 catggcggcg actgcggcaa agcgagagcc tcggagacgc cgctgccgcc agcacagccg
  61 gagacctgag ccgacactgg gggcagtccg cgagccccgc actctctcga tgagtcggag
 121 aagtcccgtt gtatcagagt aagatggacg gtagctttga ttgtgattgt ggtgagctgg
 181 agccacctga tcactaacaa aagacatctt ctgttaacca acagccgcca gggcttcctg
```

Figure 10 (cont.)

```
 241 ttgaaataaa tatatagcaa caaaggaaaa aaagaagcaa aacggaaata gtgcttacca
 301 gcaccttaga atgatgctgc tcaggaccag tccaacactg aatgtatctg cactgtgagg
 361 agaatgttca tagaagcctg ttgtgtgcat atttattcac atttttgtta aatgttaaat
 421 cgtttagcac ggtaatctga gtgcacagta tgtcatttca ttccgtttga gtttcttgtt
 481 ttcgttaaat gtctgcagag ttgctgcccc tttcttgaac tatgagtact gcaatctttt
 541 taattctcaa tatgaataga gctttttgag ctttaaatct aaggggaact cgacaggcct
 601 gtttggcata tgcaatgaac atcaagaaac catcttgctg tggaagcata attatttttc
 661 ttctcccttt ttgaaagatc tttccttttg atgccagttt tcttccttgt ttacacaagt
 721 tcaatttgaa aggaaaaggc aatagtaagg gtttcaaaat ggcagagaaa tttgaaagtc
 781 tcatgaacat tcatggtttt gatctgggtt ctaggtatat ggacttaaaa ccattgggtt
 841 gtggaggcaa tggcttggtt ttttctgctg tagacaatga ctgtgacaaa agagtagcca
 901 tcaagaaaat tgtccttact gatccccaga gtgtcaaaca tgctctacgt gaaatcaaaa
 961 ttattagaag acttgaccat gataacattg tgaaagtgtt tgagattctt ggtcccagtg
1021 gaagccaatt aacagacgat gtgggctctc ttacggaact gaacagtgtt tacattgttc
1081 aggagtacat ggagacagac ttggctaatg tgctggagca gggcccttta ctggaagagc
1141 atgccaggct tttcatgtat cagctgctac gggggctcaa gtatattcac tctgcaaatg
1201 tactgcacag agatctcaaa ccagctaatc ttttcattaa tacggaagac ttggtgctga
1261 agataggtga ctttggtctt gcacggatca tggatcctca ttattcccat aagggtcatc
1321 tttctgaagg attggttact aaatggtaca gatctccacg tcttttactt tctcctaata
1381 attatactaa agccattgac atgtgggctg caggctgcat ctttgctgaa atgctgactg
1441 gtaaaaccct tttgcaggt gcacatgaac ttgaacagat gcagctgatt ttagaatcta
1501 ttcctgttgt acatgaggaa gatcgtcagg agcttctcag cgtaattcca gtttacatta
1561 gaaatgacat gactgagcca cacaaacctt taactcagct gcttccagga attagtcgag
1621 aagcactgga tttcctggaa caaattttga catttagccc catggatcgg ttaacagcag
1681 aagaagcact ctcccatcct tacatgagca tatattcttt tccaatggat gagccaattt
1741 caagccatcc ttttcatatt gaagatgaag ttgatgatat tttgcttatg gatgaaactc
1801 acagtcacat ttataactgg gaaaggtatc atgattgtca gttttcagag catgattggc
1861 ctgtacataa caactttgat attgatgaag ttcagcttga tccaagagct ctgtccgatg
1921 tcactgatga agaagaagta caagttgatc cccgaaaata tttggatgga gatcgggaaa
1981 agtatctgga ggatcctgct tttgatacca attactctac tgagccttgt tggcaatact
2041 cagatcatca tgaaaacaaa tattgtgatc tggagtgtag ccatacttgt aactacaaaa
2101 cgaggtcatc atcatattta gataacttag tttggagaga gagtgaagtt aaccattact
2161 atgaacccaa gcttattata gatctttcca attggaaaga acaaagcaaa gaaaaatctg
2221 ataagaaagg caaatcaaaa tgtgaaagga atggattggt taaagcccag atagcgctag
2281 aggaagcatc acagcaactg gctggaaaag aaagggaaaa gaatcaggga tttgattttg
2341 attcctttat tgcaggaact attcagctta gttcccagca tgagcctact gatgttgttg
2401 ataaattaaa tgacttgaat agctcagtgt cccaactaga attgaaaagt ttgatatcaa
2461 agtcagtaag ccaagaaaaa caggaaaaag gaatggcaaa tctggctcaa ttagaagcct
2521 tgtaccagtc ttcttgggac agccagtttg tgagtggtgg ggaggactgt tttttcataa
2581 atcagttttg tgaggtaagg aaggatgaac aagttgagaa ggaaaacact tacactagtt
2641 acttggacaa gttctttagc aggaaagaag atactgaaat gctagaaact gagccagtag
2701 aggatgggaa gcttggggag agaggacatg aggaaggatt tctgaacaac agtggggagt
2761 tcctctttaa caagcagctc gagtccatag gcatcccaca gtttcacagt ccagttgggt
2821 caccacttaa gtcaatacag gccacattaa caccttctgc tatgaaatct tcccctcaaa
2881 ttcctcatca aacatacagc agcattctga aacatctgaa ctaaaacact cagcagacat
2941 ttatctttgt attcttcatg aaatgtgttt tgtctttttt tattactagt gtttaagtca
3001 tttttttactt gaatcagatg gtgtcattta gtaaggattt tatgagttct tgttttttaa
3061 aatccagact ttcttttttct acatgtgaga tagttttcat tttaactggc atgtcatttg
3121 cacacaaaaa taaagactag agcaaaataa tgcaacgcag gaggagaaaa gaaatgcact
3181 aagacaagaa cattctctca tagaacattg atctgtttta caggaaacaa accttgcctt
3241 gaaatttaca cagtgag
```

SEQ ID NO:22

```
   1 ggtctttgag cgctaacgtc tttctgtctc cccgcggtgg tgatgacggt gaaaactgag
```

Figure 10 (cont.)

```
  61 gctgctaagg gcaccctcac ttactccagg atgaggggca tggtggcaat tctcatcgct
 121 ttcatgaagc agaggaggat gggtctgaac gactttattc agaagattgc caataactcc
 181 tatgcatgca aacaccctga agttcagtcc atcttgaaga tctcccaacc tcaggagcct
 241 gagcttatga atgccaaccc ttctcctcca ccaagtcctt ctcagcaaat caaccttggc
 301 ccgtcgtcca atcctcatgc taaaccatct gactttcact tcttgaaagt gatcggaaag
 361 ggcagttttg gaaaggttct tctagcaaga cacaaggcag aagaagtgtt ctatgcagtc
 421 aaagttttac agaagaaagc aatcctgaaa aagaaagagg agaagcatat tatgtcggag
 481 cggaatgttc tgttgaagaa tgtgaagcac cctttcctgg tgggccttca cttctctttc
 541 cagactgctg acaaattgta ctttgtccta gactacatta atggtggaga gttgttctac
 601 catctccaga gggaacgctg cttcctggaa ccacgggctc gtttctatgc tgctgaaata
 661 gccagtgcct tgggctacct gcattcactg aacatcgttt atagagactt aaaaccagag
 721 aatatttgc tagattcaca gggacacatt gtccttactg acttcggact ctgcaaggag
 781 aacattgaac acaacagcac aacatccacc ttctgtggca cgccggagta tctcgcacct
 841 gaggtgcttc ataagcagcc ttatgacagg actgtggact ggtggtgcct gggagctgtc
 901 ttgtatgaga tgctgtatgg cctgccgcct ttttatagcc gaaacacagc tgaaatgtac
 961 gacaacattc tgaacaagcc tctccagctg aaaccaaata ttacaaattc cgcaagacac
1021 ctcctggagg gcctcctgca gaaggacagg acaaagcggc tcggggccaa ggatgacttc
1081 atggagatta agagtcatgt cttcttctcc ttaattaact gggatgatct cattaataag
1141 aagattactc ccccttttaa cccaaatgtg agtgggccca acgacctacg gcactttgac
1201 cccgagttta ccgaagagcc tgtccccaac tccattggca agtcccctga cagcgtcctc
1261 gtcacagcca gcgtcaagga agctgccgag gctttcctag gcttttccta tgcgcctccc
1321 acggactctt tcctctgaac cctgttaggg cttggtttta aaggatttta tgtgtgtttc
1381 cgaatgtttt agttagcctt ttggtggagc cgccagctga caggacatct tacaagagaa
1441 tttgcacatc tctggaagct tagcaatctt attgcacact gttcgctgga agctttttga
1501 agagcacatt ctcctcagtg agctcatgag gttttcattt ttattcttcc ttccaacgtg
1561 gtgctatctc tgaaacgagc gttagagtgc cgccttagac ggaggcagga gtttcgttag
1621 aaagcggacg ctgttctaaa aaaggtctcc tgcagatctg tctgggctgt gatgacgaat
1681 attatgaaat gtgccttttc tgaagagatt gtgttagctc caaagctttt cctatcgcag
1741 tgtttcagtt ctttattttc ccttgtggat atgctgtgtg aaccgtcgtg tgagtgtggt
1801 atgcctgatc acagatggat tttgttataa gcatcaatgt gacacttgca ggacactaca
1861 acgtgggaca ttgtttgttt cttccatatt tggaagataa atttatgtgt agactttttt
1921 gtaagatacg gttaataact aaaatttatt gaaatggtct tgcaatgact cgtattcaga
1981 tgcttaaaga aagcattgct gctacaaata tttctatttt tagaaagggt ttttatggac
2041 caatgcccca gttgtcagtc agagccgttg gtgtttttca ttgtttaaaa tgtcacctgt
2101 aaaatgggca ttatttatgt tttttttttt gcattcctga taattgtatg tattgtataa
2161 agaacgtctg tacattgggt tataacacta gtatatttaa acttacaggc ttatttgtaa
2221 tgtaaaccac cattttaatg tactgtaatt aacatggtta taatacgtac aatccttccc
2281 tcatcccatc acacaacttt ttttgtgtgt gataaactga ttttggtttg caataaaacc
2341 ttgaaaaata ttta
```

SEQ ID NO:23

```
1 gagcagcaga atttcaactc cagtagactt gaatatgcct ctgggcaaag aagcagagct
  61 aacgaggaaa gggatttaaa gagtttttct tgggtgtttg tcaaactttt attccctgtc
 121 tgtgtgcaga ggggattcaa cttcaatttt tctgcagtgg ctctgggtcc agccccttac
 181 ttaaagatct ggaaagcatg aagactgggc tttttttcct atgtctcttg ggaactgcag
 241 ctgcaatccc gacaaatgca agattattat ctgatcattc caaaccaact gctgaaacgg
 301 tagcacctga caacactgca atccccagtt taagggctga agctgaagaa aatgaaaaag
 361 aaacagcagt atccacagaa gacgattccc accataaggc tgaaaaatca tcagtactaa
 421 agtcaaaaga ggaaagccat gaacagtcag cagaacaggg caagagttct agccaagagc
 481 tgggattgaa ggatcaagag gacagtgatg gtcacttaag tgtgaatttg gagtatgcac
 541 caactgaagg tacattggac ataaaagaag atatgagtga gcctcaggag aaaaaactct
 601 cagagaacac tgattttttg gctcctggtg ttagttcctt cacagattct aaccaacaag
 661 aaagtatcac aaagagagag gaaaaccaag aacaacctag aaattattca catcatcagt
 721 tgaacaggag cagtaaacat agccaaggcc taaggatca aggaaaccaa gagcaggatc
```

Figure 10 (cont.)

781 caaatatttc caatggagaa gaggaagaag aaaaagagcc aggtgaagtt ggtacccaca
841 atgataacca agaaagaaag acagaattgc ccagggagca tgctaacagc aagcaggagg
901 aagacaatac ccaatctgat gatattttgg aagagtctga tcaaccaact caagtaagca
961 agatgcagga ggatgaattt gatcagggta accaagaaca agaagataac tccaatgcag
1021 aaatggaaga ggaaaatgca tcgaacgtca ataagcacat tcaagaaact gaatggcaga
1081 gtcaagaggg taaaactggc ctagaagcta tcagcaacca caaagagaca gaagaaaaga
1141 ctgtttctga ggctctgctc atggaaccta ctgatgatgg taataccacg cccagaaatc
1201 atggagttga tgatgatggc gatgatgatg gcgatgatgg cggcactgat ggccccaggc
1261 acagtgcaag tgatgactac ttcatcccaa gccaggcctt tctggaggcc gagagagctc
1321 aatccattgc ctatcacctc aaaattgagg agcaaagaga aaaagtacat gaaaatgaaa
1381 atataggtac cactgagcct ggagagcacc aagaggccaa gaaagcagag aactcatcaa
1441 atgaggagga aacgtcaagt gaaggcaaca tgagggtgca tgctgtggat tcttgcatga
1501 gcttccagtg taaaagaggc cacatctgta aggcagacca acagggaaaa cctcactgtg
1561 tctgccagga tccagtgact tgtcctccaa caaaacccct tgatcaagtt tgtggcactg
1621 acaatcagac ctatgctagt tcctgtcatc tattcgctac taaatgcaga ctggagggga
1681 ccaaaaaggg gcatcaactc cagctggatt attttggagc ctgcaaat SEQ ID NO:24
1 cggataagga caaaaaacgc cagaagaaaa gaggcatttt ccccaaagta gcaacaaata
61 tcatgagagc atggctcttc cagcatctca cacatccgta cccttccgaa gagcagaaga
121 aacagttagc gcaagacaca ggacttacaa ttctccaagt aaacaactgg tttattaatg
181 ccagaagaag aatagtacag cccatgattg accagtcaaa tcgagcagtg agccaaggag
241 cagcatatag tccagagggt cagcccatgg ggagctttgt gttggatggt cagcaacaca
301 tggggatccg gcctgcagga cctatgagtg gaatgggcat gaatatgggc atggatgggc
361 aatggcacta catgtaacct tcatcatgta aagcaatcgc aaagcaaggg ggaagtttgc
421 agagcatgcc aggggactac gtttctcagg gtggtcctat gggaatgagt atggcacagc
481 caagttacac tcctccccag atgaccccac accctactca attaagacat ggacccccaa
541 tgcattcata tttgccaagc catccccacc acccagccat gatgatgcac ggaggacccc
601 ctacccaccc tggaatgact atgtcagcac agagccccac aatgttaaat tctgtagatc
661 ccaatgttgg cggacaggtt atggacattc atgcccaata gtataaggga actcaaggga
721 aaaggaaaca cacgcaaaaa ctattttaag actttctgaa ctttgaccag atgttgacac
781 ttaatatgaa attccagaca gctgtgatta ttttttactt ttgtcatttt tcatcaagca
841 acagaggacc aatgcaacaa gaacacaaat gtgaaatcat gggctgactg agacaattct
901 gtccatgtaa agatcctctg gaaaaagact ccgagagtta taactactgt agtataaata
961 taggaactaa gttaaacttg tacatttctg ttgatcacgc cgttatgttg cctcaaatag
1021 ttttagaaga gaaaaaaaaa tatatccttg ttttccacac tatgtgtgtt gttcccaaaa
1081 gaatgactgt tttggttcat cagtgaattc accatccagg agagactgtg gtatatattt
1141 taaacctgtt gggccaatga gaaaagaacc acactggaga tcatgatgaa cttttggctg
1201 aacctcatca ctcgaactcc agcttcaaga atgtgttttc atgcccggcc tttgttcctc
1261 cataaatgtg tcctttagtt tcaaacagat ctttatagtt cgtgcttcat aagccaattc
1321 ttattattat ttttggggga ctcttcttca aagagcttgc caatgaagat ttaaagacag
1381 agcaggagct tcttccagga gttctgagcc ttggttgtgg acaaaacaat cttaagttgg
1441 gcagctttcc tcaacacaaa aaaaagttat taatggtcat tgaaccataa ctaggacttt
1501 atcagaaact caaagcttgg gggataaaaa ggagcaagag aatactgtaa caaacttcgt
1561 acagagttcg gtctattaat tgtttcatgt tagatattct atgtgtttac ctcaattgaa
1621 aaaaaaaaga atgtttttgc tagtatcaga tctgctgtgg aattggtatt gtatgtccat
1681 gaattcttct tttctcagca cgtgttcctc actagaagaa aatgctgtta cctttaagct
1741 ttgtcaaatt tacattaaaa tacttgtatg aggactgtga cgttatgtta aaaaaaaaaa
1801 ggtgttaagt cacaaaaagc ggtaataaat atttcatttt tgattttt SEQ ID NO:25
1 agcacactga ggaggcgatc cgccagcagg aggtggagca gctggacttc cgagacctcc
61 tggggaagaa ggtgagtaca aagaccctat cggaagacga cctgaaggag atcccagccg
121 agcagatgga tttccgtgcc aacctgcagc ggcaagtgaa gccaaagact gtgtctgagg

Figure 10 (cont.)

```
 181 aagagaggaa ggtgcacagc ccccagcagg tcgattttcg ctctgtcctg gccaagaagg
 241 ggacttccaa gacccccgtg cctgagaagg tgccaccgcc aaaacctgcc accccggatt
 301 ttcgctcagt gctgggtggc aagaagaaat taccagcaga gaatggcagc agcagtgccg
 361 agaccctgaa tgccaaggca gtggagagtt ccaagcccct gagcaatgca cagccttcag
 421 ggcccttgaa acccgtgggc aacgccaagc ctgctgagac cctgaagcca atgggcaacg
 481 ccaagcctgc cgagaccctg aagcccatgg gcaatgccaa gcctgatgag aacctgaaat
 541 ccgctagcaa agaagaactc aagaaagacg ttaagaatga tgtgaactgc aagagaggcc
 601 atgcagggac cacagataat gaaaagagat cagagagcca ggggacagcc ccagccttca
 661 agcagaagct gcaagatgtt catgtggcag agggcaagaa gctgctgctc cagtgccagg
 721 tgtcttctga ccccccagcc accatcatct ggacgctgaa cggaaagacc atcaagacca
 781 ccaagttcat catcctctcc caggaaggct cactctgctc cgtctccatc gagaaggcac
 841 tgcctgagga cagaggctta tacaagtgtg tagccaagaa tgacgctggc caggcggagt
 901 gctcctgcca agtcaccgtg gatgatgctc cagccagtga gaacaccaag gccccagaga
 961 tgaaatcccg gaggcccaag agctctcttc ctcccgtgct aggaactgag agtgatgcga
1021 ctgtgaaaaa gaaacctgcc cccaagacac ctccgaaggc agcaatgccc cctcagatca
1081 tccagttccc tgaggaccag aaggtacgcg caggagagtc agtggagctg tttggcaaag
1141 tgacaggcac tcagcccatc acctgtacct ggatgaagtt ccgaaagcag atccaggaaa
1201 gcgagcacat gaaggtggag aacagcgaga atggcagcaa gctcaccatc ctggccgcgc
1261 gccaggagca ctgcggctgc tacacactgc tggtggagaa caagctgggc agcaggcagg
1321 cccaggtcaa cctcactgtc gtggataagc cagacccccc agctggcaca ccttgtgcct
1381 ctgacattcg gagctcctca ctgaccctgt cctggtatgg ctcctcatat gatgggggca
1441 gtgctgtaca gtcctacagc atcgagatct gggactcagc caacaagacg tggaaggaac
1501 tagccacatg ccgcagcacc tctttcaacg tccaggacct gctgcctgac cacgaatata
1561 agttccgtgt acgtgcaatc aacgtgtatg gaaccagtga gccaagccag gagtctgaac
1621 tcacaacggt aggagagaaa cctgaagagc cgaaggatga agtggaggtg tcagacgatg
1681 atgagaagga gcccgaggtt gattaccgga cagtgacaat caatactgaa caaaaagtat
1741 ctgacttcta cgacattgag gagagattag gatctgggaa atttggacag gtctttcgac
1801 ttgtagaaaa gaaaactcga aaagtctggg cagggaagtt cttcaaggca tattcagcaa
1861 aagagaaaga gaatatccgg caggagatta gcatcatgaa ctgcctccac caccctaagc
1921 tggtccagtg tgtggatgcc tttgaagaaa aggccaacat cgtcatggtc ctggagatcg
1981 tgtcaggagg ggagctgttt gagcgcatca ttgacgagga ctttgagctg acggagcgtg
2041 agtgcatcaa gtacatgcgg cagatctcgg agggagtgga gtacatccac aagcagggca
2101 tcgtgcacct ggacctcaag ccggagaaca tcatgtgtgt caacaagacg ggcaccagga
2161 tcaagctcat cgactttggt ctggccagga ggctggagaa cgcggggtct ctgaaggtcc
2221 tctttggcac cccagaattt gtggctcctg aagtgatcaa ctatgagccc atcggctacg
2281 ccacagacat gtggagcatc ggggtcatct gctacatcct agtcagtggc ctttccccct
2341 tcatgggaga caacgataac gaaaccttgg ccaacgttac ctcagccacc tgggacttcg
2401 acgacgaggc attcgatgag atctccgacg atgccaagga tttcatcagc aatctgctga
2461 agaaagatat gaaaaaccgc ctggactgca cgcagtgcct tcagcatcca tggctaatga
2521 aagataccaa gaacatggag gccaagaaac tctccaagga ccggatgaag aagtacatgg
2581 caagaaggaa atggcagaaa acgggcaatg ctgtgagagc cattggaaga ctgtcctcta
2641 tggcaatgat ctcagggctc agtggcagga aatcctcaac agggtcacca accagcccgc
2701 tcaatgcaga aaaactagaa tctgaagaag atgtgtccca agctttcctt gaggctgttg
2761 ctgaggaaaa gcctcatgta aaaccctatt tctctaagac cattcgcgat ttagaagttg
2821 tggagggaag tgctgctaga tttgactgca agattgaagg atacccagac cccgaggttg
2881 tctggttcaa agatgaccag tcaatcaggg agtcccgcca cttccagata gactacgatg
2941 aggacgggaa ctgctcttta attattagtg atgtttgcgg ggatgacgat gccaagtaca
3001 cctgcaaggc tgtcaacagt cttggagaag ccacctgcac agcagagctc attgtggaaa
3061 cgatggagga aggtgaaggg gaaggggaag aggaagaaga gtgaaacaaa gccagagaaa
3121 agcagtttct aagtcatatt aaaaggacta tttctctaaa actc
```

SEQ ID NO:26

```
   1 ctctcccaac cgcctcgtcg cactcctcag gctgagagca ccgctgcact cgcggccggc
  61 gatgcgggac cccggcgcgg ccgctccgct ttcgtccctg ggcctctgtg ccctggtgct
```

Figure 10 (cont.)

121 ggcgctgctg ggcgcactgt ccgcgggcgc cggggcgcag ccgtaccacg gagagaaggg
181 catctccgtg ccggaccacg gcttctgcca gcccatctcc atcccgctgt gcacggacat
241 cgcctacaac cagaccatcc tgcccaacct gctgggccac acgaaccaag aggacgcggg
301 cctcgaggtg caccagttct acccgctggt gaaggtgcag tgttctcccg aactccgctt
361 tttcttatgc tccatgtatg cgcccgtgtg caccgtgctc gatcaggcca tcccgccgtg
421 tcgttctctg tgcgagcgcg cccgccaggg ctgcgaggcg ctcatgaaca agttcggctt
481 ccagtggccc gagcggctgc gctgcgagaa cttcccggtg cacggtgcgg gcgagatctg
541 cgtgggccag aacacgtcgg acggctccgg gggcccaggc ggcggcccca ctgcctaccc
601 taccgcgccc tacctgccgg acctgccctt caccgcgctg cccccggggg cctcagatgg
661 cagggggcgt cccgccttcc ccttctcatg cccccgtcag ctcaaggtgc cccgtacct
721 gggctaccgc ttcctgggtg agcgcgattg tggcgccccg tgcgaaccgg gccgtgccaa
781 cggcctgatg tactttaagg aggaggagag gcgcttcgcc cgcctctggg tgggcgtgtg
841 gtccgtgctg tgctgcgcct cgacgctctt taccgttctc acctacctgg tggacatgcg
901 gcgcttcagc tacccagagc ggcccatcat cttcctgtcg ggctgctact tcatggtggc
961 cgtggcgcac gtggccggct tccttctaga ggaccgcgcc gtgtgcgtgg agcgcttctc
1021 ggacgatggc taccgcacgg tggcgcaggg caccaagaag gagggctgca ccatcctctt
1081 catggtgctc tacttcttcg gcatggccag ctccatctgg tgggtcattc tgtctctcac
1141 ttggttcctg gcggccggca tgaagtgggg ccacgaggcc atcgaggcca actcgcagta
1201 cttccacctg gccgcgtggg ccgtgcccgc cgtcaagacc atcactatcc tggccatggg
1261 ccaggtagac ggggacctgc tgagcggggt gtgctacgtt ggcctctcca gtgtggacgc
1321 gctgcggggc ttcgtgctgg cgcctctgtt cgtctacctc ttcataggca cgtccttctt
1381 gctggccggc ttcgtgtccc tcttccgtat ccgcaccatc atgaaacacg acggcaccaa
1441 gaccgagaag ctggagaagc tcatggtgcg catcggcgtc ttcagcgtgc tctacacagt
1501 gcccgccacc atcgtcctgg cctgctactt ctacgagcag gccttccgcg agcactggga
1561 gcgcacctgg ctcctgcaga cgtgcaagag ctatgccgtg ccctgcccgc ccggccactt
1621 cccgcccatg agccccgact tcaccgtctt catgatcaag tacctgatga ccatgatcgt
1681 cggcatcacc actggcttct ggatctggtc gggcaagacc ctgcagtcgt ggcgccgctt
1741 ctaccacaga cttagccaca gcagcaaggg ggagactgcg gtatgagccc cggcccctcc
1801 ccacctttcc caccccagcc ctcttgcaag aggagaggca cggtagggaa aagaactgct
1861 gggtgggggc ctgtttctgt aactttctcc ccctctactg agaagtgacc tggaagtgag
1921 aagttctttg cagatttggg gcgaggggtg atttggaaaa gaagacctgg gtggaaagcg
1981 gtttggatga aaagatttca ggcaaagact tgcaggaaga tgatgataac ggcgatgtga
2041 atcgtcaaag gtacgggcca gcttgtgcct aatagaaggt tgagaccagc agagactgct
2101 gtgagtttct cccggctccg aggctgaacg gggactgtga gcgatccccc tgctgcaggg
2161 cgagtggcct gtccagaccc ctgtgaggcc ccgggaaagg tacagccctg tctgcggtgg
2221 ctgctttgtt ggaaagaggg agggcctcct gcggtgtgct tgtcaagcag tggtcaaacc
2281 ataatctctt ttcactgggg ccaaactgga gcccagatgg gttaatttcc agggtcagac
2341 attacggtct ctcctcccct gcccccctccc gcctgttttt cctcccgtac tgctttcagg
2401 tcttgtaaaa taagcatttg gaagtcttgg gaggcctgcc tgctagaatc ctaatgtgag
2461 gatgcaaaag aaatgatgat aacattttga gataaggcca aggagacgtg gagtaggtat
2521 ttttgctact ttttcatttt ctggggaagg caggaggcag aaagacgggt gttttatttg
2581 gtctaatacc ctgaaaagaa gtgatgactt gttgcttttc aaaacaggaa tgcatttttc
2641 cccttgtctt tgttgtaaga gacaaaagag gaaacaaaag tgtctccctg tggaaaggca
2701 taactgtgac gaaagcaact tttataggca aagcagcgca aatctgaggt ttcccgttgg
2761 ttgttaattt ggttgagata aacattcctt tttaaggaaa agtgaagagc agtgtgctgt
2821 cacacaccgt taagccagag gttctgactt cgctaaagga aatgtaagag gttttgttgt
2881 ctgttttaaa taaatttaat tcggaacaca tgatccaaca gactatgtta aaatattcag
2941 ggaaatctct cccttcattt actttttctt gctataagcc tatatttagg tttcttttct
3001 atttttttct cccatttgga tcctttgagg taaaaaaaca taatgtcttc agcctcataa
3061 taaaggaaag ttaattaaaa aaaaaaagca aagagccatt ttgtcctgtt ttcttggttc
3121 catcaatctg tttattaaac atcatccata tgctgaccct gtctctgtgt ggttgggttg
3181 ggaggcgatc agcagatacc atagtgaacg aagaggaagg tttgaaccat gggccccatc
3241 tttaaagaaa gtcattaaaa gaaggtaaac ttcaaagtga ttctggagtt ctttgaaatg
3301 tgctggaaga cttaaattta ttaatcttaa atcatgtact ttttttctgt aatagaactc

Figure 10 (cont.)

3361 ggattctttt gcatgatggg gtaaagctta gcagagaatc atgggagcta acctttatcc
3421 cacctttgac actaccctcc aatcttgcaa cactatcctg tttctcagaa cagtttttaa
3481 atgccaatca tagagggtac tgtaaagtgt acaagttact ttatatatgt aatgttcact
3541 tgagtggaac tgctttttac attaaagtta aaatcgatct tgtgtttctt caaccttcaa
3601 aactatctca tctgtcagat ttttaaaact ccaacacagg ttttggcatc ttttgtgctg
3661 tatcttttaa gtgcatgtga aatttgtaaa atagagataa gtacagtatg tatattttgt
3721 aaatctccca tttttgtaag aaaatatata ttgtatttat acatttttac tttggatttt
3781 tgttttgttg gctttaaagg tctaccccac tttatcacat gtacagatca caaataaatt
3841 tttttaaata c

SEQ ID NO:27

1 ggggctcggg acggccgggc tgggagctgg agcccacagc gggaagcggc cgccgcccgg
61 gcctcgcagg gctaggcgag gcgagggggg gcggggccgg gcgctacggg aaggggaggc
121 cgcgcggacc gggagccgca ccgcgccagc cgggctgcag cggccgcgca ccaaggctgc
181 gatggggctg gagacggaga aggcggacgt acagctcttc atggacgacg actcctacag
241 ccaccacagc ggcctcgagt acgccgaccc cgagaagttc gcggactcgg accaggaccg
301 ggatccccac cggctcaact cgcatctcaa gctgggcttc gaggatgtga tcgcagagcc
361 ggtgactacg cactcctttg acaaagtgtg gatctgcagc catgccctct ttgaaatcag
421 caaatacgta atgtacaagt tcctgacggt gttcctggcc attcccctgg ccttcattgc
481 gggaattctc tttgccaccc tcagctgtct gcacatctgg attttaatgc cttttgtaaa
541 gacctgccta atggttctgc cttcagtgca gacaatatgg aagagtgtga cagatgttat
601 cattgctcca ttgtgtacga gcgtaggacg atgcttctct tctgtcagcc tgcaactgag
661 ccaggattga atacttggac cccaggtctg gagattggga tactgtaata cttctttgtt
721 attataacat aaaagcacca ctgttctgtt catttcctag ctgttctaat taagaaaact
781 attaagatga gcaaccacat ttagaaatgt ttattgacag gtcttttcaa ataatgcttt
841 tctaattaat agccaaagat ttcatatcta actttgtaac cagaattata cagtaagttg
901 acaccactta gatttaaagg cagacagttt tgctttagta caatagtata cattttataa
961 tgatgaactt ataatgatta agggacattt ctataaaaat actacaatag ttttatgcac
1021 aacttcccat taaaaatgag atttcttatt tgtttgtctg tttttactct gggagtaata
1081 ctttttaaat tacctttaca tatatagtca ctggcatact gagaatatac aatgatcctg
1141 gaaattgcag taacaaaagc acacaacgat tatagtaact ataagataca ataaaacaaa
1201 taaatatgaa agtagattca tgaaaatgta ttcctttaaa atattgtttt cctacaggcc
1261 tatttaacaa gatgtttcat tttactgtat attttgtagt taatataaat gttgctctaa
1321 tcagattgct taaaagcatt tttattatat ttatgttgtt gaactaatat atgaaataag
1381 taaatgtagc tcccacaagg taaacttcat tggtaagatt gcactgttct gattatgtaa
1441 gcatttgtac atcttctttg gaaataaaag ataaaa

SEQ ID NO:28

1 gtttagaaca gcctacagac ccagtggcac gagacgggcc tctctcccaa acatcttcca
61 agccagatcc tagtcagtgg gaaagcccca gcttcaaccc ctttgggagc cactctgttc
121 tgcagaactc cccacccctc tcttctgagg gctcctacca ctttgaccca gataactttg
181 acgaatccat ggatcccttt aaaccaacta cgaccttaac aagcagtgac ttttgttctc
241 ccactggtaa tcacgttaat gaaatcttag aatcacccaa gaaggcaaag tcgcgtttaa
301 taacgactac tgaacaagtg aaatttctct gttttctgtt gagtggctgt aaggtgaaga
361 agcatgaaac tcagtctctc gccctggatg catgttctcg ggatgaaggg gcagtgatct
421 cccagatttc agacatttct aatagggatg gccatgctac tgatgaggag aaactggcat
481 ccacgtcatg tggtcagaaa tcagctggtg ccgaggtgaa aggtgagcca gaggaagacc
541 tggagtactt tgaatgttcc aatgttcctg tgtctaccat aaatcatgcg ttttcatcct
601 cagaagcagg catagagaag gagacgtgcc agaagatgga agaagacggg tccactgtgc
661 ttgggctgct ggagtcctct gcagagaagg cccctgtgtc ggtgtcctgt ggaggtgaga
721 gccccctgga tgggatctgc ctcagcgaat cagacaagac agccgtgctc accttaataa
781 gagaagagat aattactaaa gagattgaag caaatgaatg gaagaagaaa tacgaagaga
841 cccggcaaga agttttggag atgaggaaaa ttgtagctga atatgaaaag actattgctc
901 aaatgattga tgaacaaagg acaagtatga cctctcagaa gagcttccag caactgacca

Figure 10 (cont.)

```
 961 tggagaagga acaggccctg gctgacctta actctgtgga aaggtccctt tctgatctct
1021 tcaggagata tgagaacctg aaaggtgttc tggaagggtt caagaagaat gaagaagcct
1081 tgaagaaatg tgctcaggat tacttagcca gagttaaaca agaggagcag cgataccagg
1141 ccctgaaaat ccacgcagaa gagaaactgg acaaagccaa tgaagagatt gctcaggttc
1201 gaacaaaagc aaaggctgag agtgcagctc tccatgctgg actccgcaaa gagcagatga
1261 aggtggagtc cctggaaagg gccctgcagc agaagaacca agaaattgaa gaactgacaa
1321 aaatctgtga tgagctgatt gcaaagctgg gaaagactga ctgagacact ccccctgtta
1381 gctcaacaga tctgcatttg gctgcttctc ttgtgaccac aattatcttg ccttatccag
1441 gaataattgc ccctttgcag agaaaaaaaa aaacttaaaa aaagcacatg cctactgctg
1501 cctgtcccgc tttgctgcca atgcaacagc cctggaagaa accctagagg gttgcatagt
1561 ctagaaagga gtgtgacctg acagtgctgg agcctcctag tttcccccta tgaaggttcc
1621 cttaggctgc tgagtttggg tttgtgattt atctttagtt tgttttaaag tcatctttac
1681 tttcccaaat gtgttaaatt tgtaactcct ctttggggtc ttctccacca cctgtctgat
1741 tttttgtga tctgtttaat cttttaattt tttagtatca gtggttttat ttaaggagac
1801 agtttggcct attgttactt ccaatttata atcaagaagg ggctctggat cccctttttaa
1861 attacacaca ctctcacaca catacatgta tgtttataga tgctgctgct cttttccctg
1921 aagcatagtc aagtaagaac tgctctacag aaggacatat ttccttggat gtgagaccct
1981 attttgaaat agagtcctga ctcagaacac caacttaaga atttggggga ttaaagatgt
2041 gaagaccaca gtcttgggtt ttcatatctg gagaagacta tttgccatga cgttttgttg
2101 ccctggtatt tggacactcc tcagctttaa tgggtgtggc ccctttaggg ttagtcctca
2161 gactaatgat agtgtctgct ttctgcatga acggcaatat gggactccct ccaagctagg
2221 gtttggcaag tctgccctag agtcatttac tctcctctgc ctccatttgt taatacagaa
2281 tcaacattta gtcttcatta tctttttttt tttttttgag acagagtttc gatctatttt
2341 aagtatgtga agaaaatcta cttgtaaaag gctcagatct taattaaaag gtaattgtag
2401 cacattacca attataaggt gaagaaatgt tttttcccca agtgtgatgc attgttcttc
2461 agatgttgaa aagaaagcaa aaaatacctt ctaacttaag acagaatttt taacaaaatg
2521 agcagtaaaa gtcacatgaa ccactccaaa aatcagtgca ttttgcatat ttttaaacaa
2581 agacagcttg ttgaatactg agaagaggag tgcaaggaga aggtctgtac taacaaagcc
2641 aaattcctca agctcttact ggactcagtt cagagtggtg ggccattaac cccaacatgg
2701 aatttttcca tataaatctc aatgaattcc ctttcatttg aataggcaaa cccaaatcca
2761 tgcaagtgtt ttaaagcact gtcctgtctt aatcttacat gctgaaagtc ttcatggtga
2821 tatgcactat attcagtata cgtatgtttt cctacttctc ttgtaaaact gttgcatgat
2881 ccaacttcag caatgaattg tgcctagtgg agaacctcta tagatcttaa aaaatgaatt
2941 attctttagc agtgtattac tcacatgggt gcaatcttta gccccaggga ggtcaataat
3001 gtcttttaaa gccagaagtc acattttacc aatatgcatt tatcataatt ggtgcttagg
3061 ctgtatattc aagcctgttg tcttaacatt ttgtataaaa aagaacaaca gaaattatct
3121 gtcatttgag aagtggcttg acaatcattt gagctttgaa agcagtcact gtggtgtaat
3181 atgaatgctg tcctagtggt catagtacca agggcacgtg tctccccttg gtataactga
3241 tttccttttt agtcctctac tgctaaataa gttaattttg cattttgcag aaagaaacat
3301 tgattgctaa atctttttgc tgctgtgttt tggtgttttc atgtttactt gttttatatt
3361 gatctgtttt aagtatgaga ggcttatagt gccctccatt gtaaatccat agtcatcttt
3421 ttaagcttat tgtgtttaag aaagtagcta tgtgttaaac agaggtgatg gcagcccttc
3481 cctagcacac tggtggaaga gaccccttaa gaacctgacc ccagtgaatg aagctgatgc
3541 acagggagca ccaaaggacc ttcgttaagt gataattgtc ctggcctctc agccatgacc
3601 gttatgagga aatatccccc attcgaactt aacagatgcc tcctctccaa agagaattaa
3661 aatcgtagct tgtacagatc aagagaatat actgggcaga atgaagtatg tttgtttatt
3721 tttctttaaa aataaaggat tttggaactc tggagagtaa gaatatagta tagagtttgc
3781 ctcaacacat gtgagggcca aataacctgc tagctaggca gtaataaact ctgttacaga
3841 agagaaaaag ggccgggcac agtggcttat tcctgtaatc ccaacactgt ggaaggccga
3901 ggcaggagga tcacttgagt ccaggagttt gaaacctacc taggcaacat ggtgaaacct
3961 tgtctctacc aaaataaaaa ttagctgggc atggtggcac gtgcctgtgg tcccagctac
4021 ttgggaggct gaggtgggag cctgggaggt caaggctgca gtgagccatg atcatgccac
4081 tgcactccat cctgggtgac agcaagatct tgtctc
```

Figure 10 (cont.)

SEQ ID NO:29

```
   1 cgagttcccc gaggtgtacg tgcccaccgt cttcgagaac tatgtggccg acattgaggt
  61 ggacggcaag caggtggagc tggcgctgtg ggacacggcg ggccaggagg actacgaccg
 121 cctgcggccg ctctcctacc cggacaccga cgtcattctc atgtgcttct cggtggacag
 181 cccggactcg ctggagaaca tccccgagaa gtgggtcccc gaggtgaagc acttctgtcc
 241 caatgtgccc atcatcctgg tggccaacaa aaaagacctg cgcagcgacg agcatgtccg
 301 cacagagctg gcccgcatga agcaggaacc cgtgcgcacg gatgacggcc gcgccatggc
 361 cgtgcgcatc caagcctacg actacctcga gtgctctgcc aagaccaagg aaggcgtgcg
 421 cgaggtcttc gagacggcca cgcgcgccgc gctgcagaag cgctacggct cccagaacgg
 481 ctgcatcaac tgctgcaagg tgctatgagg gccgcgcccg tcgcgcctgc ccctgccggc
```

SEQ ID NO:30

```
   1 cggggagacc atggggcccc tctcagcccc ttcctgcaca cacctcatca cttggaaggg
  61 ggtcctgctc acagcatcac ttttaaactt ctggaatccg cccaccactg ccgaagtcac
 121 gattgaagcc cagccaccca aagtttctga ggggaaggat gttcttctac ttgttcacaa
 181 tttgccccag aatcttcctg gctacttctg gtacaaaggg gaaatgacgg acctctacca
 241 ttacattata tcgtatatag ttgatggtaa aataattata tatgggcctg catacagtgg
 301 aagagaaaca gtatattcca acgcatccct gctgatccag aatgtcaccc ggaaggatgc
 361 aggaacctac accttacaca tcataaagcg aggtgatgag actagagaag aaattcgaca
 421 tttcaccttc accttatact atggtccaga cctccccaga atttaccctt cattcaccta
 481 ttacggttca ggagaaaacc tcgacttgtc ctgcttcacg gaatctaacc caccggcaga
 541 gtatttttgg acaattaatg ggaagtttca gcaatcagga caaaagctct ttatccccca
 601 aattactaga aatcatagcg ggctctatgt ttgctctgtt cataactcag ccactggcaa
 661 ggaaatctcc aaatccatga cagtcaaagt ctctggtccc tgccatggag acctgacaga
 721 gtttcagtca tgactgcaac aactgagaca ctgagaaaaa gaacaggctg ataccttcat
 781 gaaattcaag acaaagaaga aaaaaactca atgttattgg actaaataat caaaaggata
 841 atgttttcat aattttttat tggaaaatgt gctgattctt tgaatgtttt attctccaga
 901 tttatgaact ttttttcttc agcaattggt aaagtatact tttgtaaaca aaaattgaaa
 961 tatttgcttt tgctgtctat ctgaatgccc cagaattgtg aaactactca tgagtactca
1021 taggtttatg gtaataaagt tatttgcaca tgttccgtag ttt
```

SEQ ID NO:31

```
   1 gcaccaacca gcaccatgcc catgatactg ggtactggg acatccgcgg gctggcccac
  61 gccatccgcc tgctcctgga atacacagac tcaagctatg aggaaaagaa gtacacgatg
 121 ggggacgctc ctgattatga cagaagccag tggctgaatg aaaaattcaa gctgggcctg
 181 gactttccca atctgcccta cttgattgat ggggctcaca agatcaccca gagcaacgcc
 241 atcttgtgct acattgcccg caagcacaac ctgtgtgggg agacagaaga ggagaagatt
 301 cgtgtggaca ttttggagaa ccagaccatg gacaaccata tgcagctggg catgatctgc
 361 tacaatccag aatttgagaa actgaagcca aagtacttgg aggaactccc tgaaaagcta
 421 aagctctact cagagtttct ggggaagcgg ccatggtttg caggaaacaa gatcactttt
 481 gtagattttc tcgtctatga tgtccttgac ctccaccgta tatttgagcc caactgcttg
 541 gacgccttcc caaatctgaa ggacttcatc tcccgctttg agggcttgga gaagatctct
 601 gcctacatga agtccagccg cttcctccca agacctgtgt tctcaaagat ggctgtctgg
 661 ggcaacaagt agggccttga aggcaggagg tgggagtgag gagcccatac tcagcctgct
 721 gcccaggctg tgcagcgcag ctggactctg catcccagca cctgcctcct cgttcctttc
 781 tcctgtttat tcccatcttt actcccaaga cttcattgtc cctcttcact cccccctaaac
 841 ccctgtccca tgcaggccct ttgaagcctc agctacccac tatccttcgt gaacatcccc
 901 tcccatcatt acccttccct gcactaaagc cagcctgacc ttccttcctg ttagtggttg
 961 tgtctgcttt aaagcctgcc tggcccctcg cctgtggagc tcagccccga gctgtccccg
1021 tgttgcatga aggagcagca ttgactggtt tacaggccct gctcctgcag catggtccct
1081 gcctaggcct acctgatgga agtaaagcct caaccac
```

SEQ ID NO:32

```
   1 ttcaggaacc ggtttggtgc tggtgctgga ggcggctatg gctttggagg tggtgccggt
```

Figure 10 (cont.)

```
  61 agtggatttg gtttcggcgg tggagctggt ggtggctttg ggctcggtgg cggagctggc
 121 tttggaggtg gcttcggtgg ccctggcttt cctgtctgcc ctcctggagg tatccaagag
 181 gtcactgtca accagagtct cctgactccc ctcaacctgc aaatcgaccc cagcatccag
 241 agggtgagga ccgaggagcg cgagcagatc aagaccctca acaataagtt tgcctccttc
 301 atcgacaagg tgcggttcct ggagcagcag aacaaggttc tggacaccaa gtggaccctg
 361 ctgcaggagc agggcaccaa gactgtgagg cagaacctgg agccgttgtt cgagcagtac
 421 atcaacaacc tcaggaggca gctggacagc atcgtggggg aacggggccg cctggactca
 481 gagctgagaa acatgcagga cctggtggaa gacttcaaga acaagtatga ggatgaaatc
 541 aacaagcgta ccactgctga gaatgagttt gtgatgctga agaaggatgt agatgctgcc
 601 tacatgaaca aggtggagct ggaggccaag gttgatgcac tgatggatga gattaacttc
 661 atgaagatgt tctttgatgc ggagctgtcc cagatgcaga cgcatgtctc tgacacctca
 721 gtggtcctct ccatggacaa caaccgcaac ctggacctgg atagcatcat cgctgaggtc
 781 aaggcccagt atgaggagat tgccaaccgc agccggacag aagccgagtc ctggtatcag
 841 accaagtatg aggagctgca gcagacagct ggccggcatg gcgatgacct ccgcaacacc
 901 aagcatgaga tctctgagat gaaccggatg atccagaggc tgagagccga gattgacaat
 961 gtcaagaaac agtgcgccaa tctgcagaac gccattgcgg atgccgagca gcgtggggag
1021 ctggccctca aggatgccag gaacaagctg gccgagctgg aggaggccct gcagaaggcc
1081 aagcaggaca tggcccggct gctgcgtgag taccaggagc tcatgaacac caagctggcc
1141 ctggacgtgg agatcgccac ttaccgcaag ctgctggagg gcgaggaatg cagactcagt
1201 ggagaaggag ttggaccagt caacatctct gttgtcacaa gcagtgtttc ctctggatat
1261 ggcagtggca gtggctatgg cggtggcctc ggtggaggtc ttggcggcgg cctcggtgga
1321 ggtcttgccg gaggtagcag tggaagctac tactccagca gcagtggggg tgtcggccta
1381 ggtggtgggc tcagtgtggg gggctctggc ttcagtgcaa gcagtggccg agggctgggg
1441 gtgggctttg gcagtggcgg gggtagcagc tccagcgtca aatttgtctc caccacctcc
1501 tcctcccgga agagcttcaa gagctaagaa cctgctgcaa gtcactgcct tccaagtgca
1561 gcaacccagc ccatggagat tgcctcttct aggcagttgc tcaagccatg ttttatcctt
1621 ttctggagag tagtctagac caagccaatt gcagaaccac attctttggt tcccaggaga
1681 gccccattcc cagcccctgg tctcccgtgc cgcagttcta tattctgctt caaatcagcc
1741 ttcaggtttc ccacagcatg gcccctgctg acacgagaac ccaaagtttt cccaaatcta
1801 aatcatcaaa acagaatccc caccccaatc ccaaattttg ttttggttct aactacctcc
1861 agaatgtgt
```

SEQ ID NO:33

```
   1 agtgatcagg gccaaagcgg tcagtgagaa ggaagtggac tctggaaacg acatttatgg
  61 caaccctatc aagaggatcc agtatgagat caagcagata aagatgttca aagggcctga
 121 gaaggatata gagtttatct acacggcccc ctcctcggca gtgtgtgggg tctcgctgga
 181 cgttggagga aagaaggaat atctcattgc aggaaaggcc gagggggacg gcaagatgca
 241 catcaccctc tgtgacttca tcgtgccctg ggacaccctg agcaccaccc agaagaagag
 301 cctgaaccac aggtaccaga tgggctgcga gtgcaagatc acgcgctgcc ccatgatccc
 361 gtgctacatc tcctccccgg acgagtgcct ctggatggac tgggtcacag agaagaacat
 421 caacgggcac caggccaagt tcttcgcctg catcaagaga agtgacggct cctgtgcgtg
 481 gtaccgcggc gcggcgcccc ccaagcagga gtttctcgac atcgaggacc cataagcagg
 541 cctccaacgc ccctgtggcc aactgcaaaa aaagcctcca agggtttcga ctggtccagc
 601 tctgacatcc cttcctggaa acagcatgaa taaaacactc atcccatggg tccaaattaa
 661 tatg
```

SEQ ID NO:34

```
   1 tgtcgccacc atggctccgc accgccccgc gcccgcgctg ctttgcgcgc tgtccctggc
  61 gctgtgcgcg ctgtcgctgc ccgtccgcgc ggccactgcg tcgcgggggg cgtcccaggc
 121 gggggcgccc caggggcggg tgcccgaggc gcggcccaac agcatggtgg tggaacaccc
 181 cgagttcctc aaggcaggga aggagcctgg cctgcagatc tggcgtgtgg agaagttcga
 241 tctggtgccc gtgcccacca acctttatgg agacttcttc acgggcgacg cctacgtcat
 301 cctgaagaca gtgcagctga ggaacggaaa tctgcagtat gacctccact actggctggg
 361 caatgagtgc agccaggatg agagcggggc ggccgccatc tttaccgtgc agctggatga
```

Figure 10 (cont.)

```
 421 ctacctgaac ggccgggccg tgcagcaccg tgaggtccag ggcttcgagt cggccacctt
 481 cctaggctac ttcaagtctg gcctgaagta caagaaagga ggtgtggcat caggattcaa
 541 gcacgtggta cccaacgagg tggtggtgca gagactcttc caggtcaaag ggcggcgtgt
 601 ggtccgtgcc accgaggtac ctgtgtcctg ggagagcttc aacaatggcg actgcttcat
 661 cctggacctg ggcaacaaca tccaccagtg gtgtggttcc aacagcaatc ggtatgaaag
 721 actgaaggcc acacaggtgt ccaagggcat ccgggacaac gagcggagtg gccgggcccg
 781 agtgcacgtg tctgaggagg gcactgagcc cgaggcgatg ctccaggtgc tgggccccaa
 841 gccggctctg cctgcaggta ccgaggacac cgccaaggag gatgcggcca accgcaagct
 901 ggccaagctc tacaaggtct ccaatggtgc agggaccatg tccgtctccc tcgtggctga
 961 tgagaacccc ttcgcccagg gggccctgaa gtcagaggac tgcttcatcc tggaccacgg
1021 caaagatggg aaaatctttg tctggaaagg caagcaggca aacacggagg agaggaaggc
1081 tgccctcaaa acagcctctg acttcatcac caagatggac taccccaagc agactcaggt
1141 ctcggtcctt cctgagggcg gtgagacccc actgttcaag cagttcttca agaactggcg
1201 ggacccagac cagacagatg gcctgggctt gtcctacctt tccagccata tcgccaacgt
1261 ggagcgggtg cccttcgacg ccgccaccct gcacacctcc actgccatgg ccgcccagca
1321 cggcatggat gacgatggca caggccagaa acagatctgg agaatcgaag gttccaacaa
1381 ggtgcccgtg gaccctgcca catatggaca gttctatgga ggcgacagct acatcattct
1441 gtacaactac cgccatggtg gccgccaggg gcagataatc tataactggc agggtgccca
1501 gtctacccag gatgaggtcg ctgcatctgc catcctgact gctcagctgg atgaggagct
1561 gggaggtacc cctgtccaga gccgtgtggt ccaaggcaag gagcccgccc acctcatgag
1621 cctgtttggt gggaagccca tgatcatcta caagggcggc acctcccgcg agggcggca
1681 gacagcccct gccagcaccc gcctcttcca ggtccgcgcc aacagcgctg gagccacccg
1741 ggctgttgag gtattgccta aggctggtgc actgaactcc aacgatgcct ttgttctgaa
1801 aacccccctca gccgcctacc tgtgggtggg tacaggagcc agcgaggcag agaagacggg
1861 ggcccaggag ctgctcaggg tgctgcgggc ccaacctgtg caggtggcag aaggcagcga
1921 gccagatggc ttctgggagg ccctgggcgg gaaggctgcc taccgcacat ccccacggct
1981 gaaggacaag aagatggatg cccatcctcc tcgcctcttt gcctgctcca acaagattgg
2041 acgttttgtg atcgaagagg ttcctggtga gctcatgcag gaagacctgg caacggatga
2101 cgtcatgctt ctggacacct gggaccaggt ctttgtctgg gttggaaagg attctcaaga
2161 agaagaaaag acagaagcct tgacttctgc taagcggtac atcgagacgg acccagccaa
2221 tcgggatcgg cggacgccca tcaccgtggt gaagcaaggc tttgagcctc cctcctttgt
2281 gggctggttc cttggctggg atgatgatta ctggtctgtg gaccccttgg acagggccat
2341 ggctgagctg gctgcctgag gaggggcagg gcccacccat gtcaccggtc agtgcctttt
2401 ggaactgtcc ttccctcaaa gaggccttag agcgagcaga gcagctctgc tatgagtgtg
2461 tgtgtgtgtg tgtgttgttt cttttttttt tttttacagt atccaaaaat agccctgcaa
2521 aaattcagag tccttgcaaa attgtctaaa atgtcagtgt ttgggaaatt aaatccaata
2581 aaaacatttt gaagtgtg
```

SEQ ID NO:35

```
gaagtaaaagatttttattgttctatagacacttctgaaaagagatctaattgagaaaat
atacaaagcatttaagagtttcatccccagagactgactgaaggcgttacagccctcctc
tccaaggctcagggctgagaacggttagcatatcgaatgatcagtaaaaacatgcaaaag
tgagaaggaaagggaaaaaggtgcattcccctaagctgaggggggatggaatttcagaaca
gaggangcagggtggacaagtaccaaggtggctctccctttccctctgtgtnatctttca
aaaccanttccaagcntggatnaaagcaa
```

SEQ ID NO:36

```
  1 caaagtctga gccccgctcc gctgatgcct gtctgcagaa tccgcaccaa ccagcaccat
 61 gcccatgact ctggggtact gggacatccg tggctggcc cacgccatcc gcttgctcct
121 ggaatacaca gactcaagct atgtggaaaa gaagtacacg ctgggggacg ctcctgacta
181 tgacagaagc cagtggctga atgaaaaatt caagctgggc ctggactttc ccaatctgcc
241 ctacttgatt gatggggctc acaagatcac ccagagcaat gccatcctgc gctacattgc
301 ccgcaagcac aacctgtgtg gggagacaga agaggagaag attcgtgtgg acattttgga
361 gaaccaggtt atggataacc acatggagct ggtcagactg tgctatgacc cagattttga
```

Figure 10 (cont.)

```
 421 gaaactgaag ccaaaatact tggaggaact ccctgaaaag ctaaagctct actcagagtt
 481 tctggggaag cggccatggt ttgcaggaga caagatcacc tttgtggatt tccttgccta
 541 tgatgtcctt gacatgaagc gtatatttga gcccaagtgc ttggacgcct tcctaaactt
 601 gaaggacttc atctcccgct ttgagggttt gaagaagatc tctgcctaca tgaagtccag
 661 ccaattcctc cgaggtcttt tgtttggaaa gtcagctaca tggaacagca aatagggccc
 721 agtgatgcca gaagatggga gggaggagcc aaccttgctg cctgcgaccc tggaggacag
 781 cctgactccc tggacctgcc ttcttccttt ttccttcttt ctactctctt ctcttcccca
 841 aggcctcatt ggcttccttt cttctaacat catccctccc cgcatcgagg ctctttaaag
 901 cttcagctcc ccactgtcct ccatcaaagt ccccctccta acgtcttcct ttccctgcac
 961 taacgccaac ctgactgctt ttcctgtcag tgcttttctc ttctttgaga agccagactg
1021 atctctgagc tccctagcac tgtcctcaaa gaccatctgt atgccctgct ccctttgctg
1081 ggtccctacc ccagctccgt gtgatgccca gtaaagcctg aaccatgcct gccatgtctt
1141 gtcttattcc ctgaggctcc cttgactcag gactgtgctc gaattgtggg tggttttttg
1201 tcttctgttg tccacagcca gagcttagtg gatgggtgtg tgtgtgtgtg tgttgggggt
1261 ggtgatcagg caggttcata aatttccttg gtcatttctg ccctctagcc acatccctct
1321 gttcctcact gtggggatta ctacagaaag gtgctctgtg ccaagttcct cactcattcg
1381 cgctcctgta ggccgtctag aactggcatg gttcaaagag gggctaggct gatggggaag
1441 ggggctgagc agctcccagg cagactgcct tctttcaccc tgtcctgata gacttccctg
1501 atctagatat ccttcgtcat gacacttctc aataaaacgt atcccaccgt attgt
```

SEQ ID NO:37

```
   1 ggttgagaat gcttgcacca agcttgtcca ggcagctcag atgcttcagt cagaccctta
  61 ctcagtgcct gctcgagatt atctaattga tgggtcaagg ggcatcctct ctggaacatc
 121 agacctgctc cttaccttcg atgaggctga ggtccgtaaa attattagag tttgcaaagg
 181 aattttggaa tatcttacag tggcagaggt ggtggagact atggaagatt tggtcactta
 241 cacaaagaat cttgggccag gaatgactaa gatggccaag atgattgacg agagacagca
 301 ggagctcact caccaggagc accgagtgat gttggtgaac tcgatgaaca ccgtgaaaga
 361 gttgctgcca gttctcattt cagctatgaa gatttttgta acaactaaaa actcaaaaaa
 421 ccaaggcata gaggaagctt taaaaaatcg caattttact gtagaaaaaa tgagtgctga
 481 aattaatgag ataattcgtg tgttacaact cacctcttgg gatgaagatg cctgggccag
 541 caaggacact gaagccatga agagagcatt ggcctccata gactccaaac tgaaccaggc
 601 caaaggttgg ctccgtgacc ctagtgcctc cccaggggat gctggtgagc aggccatcag
 661 acagatctta gatgaagctg gaaaagttgg tgaactctgt gcaggcaaag aacgcaggga
 721 gattctggga acttgcaaaa tgctagggca gatgactgat caagtggctg acctccgtgc
 781 cagnnnnnnn nnnnnnnnnn nnnnnnnnnn nnnnnnnnnn nnnnnnnnnn nnnnnnnnnn
 841 nnnnnnnnnn nnnnnnnnnn nnnnnnnnnn nnnnnnnnnn nnnnnnnnnn nnnnnnnnnn
 901 nnnnnnnnnn nnnnnnnnnn nnnnnnnnnn nnnnnnnnnn nnnnnnnnnn nnnnnnnnnn
 961 nnnnnnnnnn nnnnnnnnnn nnnnnnnnnn nnnnnnnnnn nnnnnnnnnn nnnnnnnnnn
1021 nnnnnnnnnn nnnnnnnnnn nnnnnnnnnn nnnnnnnnnn nnnnnnnnnn nnnnnnnnnn
1081 nnnnnnnnnn nnnnnnnnnn nnnnnnnnnn nnnnnnnnnn nnnnnnnnnn nnnaggctcg
1141 agccttggcc aaacaggtgg ccacggccct gcagaacctg cagaccaaaa ccaaccgggc
1201 tgtggccaac agcagaccgg ccaaagcagc tgtacacctt gagggcaaga ttgagcaagc
1261 acagcggtgg attgataatc ccacagtgga tgaccgtgga gtcggtcagg ctgccatccg
1321 ggggcttgtg gccgaagggc atcgtctggc taatgttatg atggggcctt atcggcaaga
1381 tcttctcgcc aagtgtgacc gagtggacca gctgacagcc cagctggctg acctggctgc
1441 cagaggggaa ggggagagtc ctcaggcacg agcacttgca tctcagctcc aagactcctt
1501 aaaggatcta aaagctcgga tgcaggaggc catgactcag gaagtgtcag atgttttcag
1561 cgataccaca actcccatca agctgttggc agtggcagcc acggcgcctc ctgatgcgcc
1621 taacagggaa gaggtatttg atgagagggc agctaacttt gaaaaccatt caggaaagct
1681 tggtgctacg gccgagaagg cggctgcggt tggtactgct aataaatcaa cagtggaagg
1741 cattcaggcc tcagtgaaga cggcccgaga actcacaccc caggtggtct cggctgctcg
1801 tatcttactt aggaaccctg gaaatcaagc tgcttatgaa cattttgaga ccatgaagaa
1861 ccagtggatc gataatgttg aaaaaatgac agggctggtg gacgaagcca ttgataccaa
```

Figure 10 (cont.)

```
1921 atctctgttg gatgcttcag aagaagcaat taaaaaagac ctggacaagt gcaaggtagc
1981 tatggccaac attcagcctc agatgctggt tgctggggca accagtattg ctcgtcgggc
2041 caaccggatc ctgctggtgg ctaagaggga ggtggagaat tccgaggatc ccaagttccg
2101 tgaggctgtg aaagctgcct ctgatgaatt gagcaaaacc atctccccga tggtgatgga
2161 tgcaaaagct gtggctggaa acatttccga ccctggactg caaaagagct tcctggactc
2221 aggatatcgg atcctgggag ctgtggccaa ggtcagagaa gccttccaac ctcaggagcc
2281 tgacttcccg ccgcctccac cagaccttga acaactccga ctaacagatg agcttgctcc
2341 tcccaaacca cctctgcctg aaggtgaggt ccctccacct aggcctccac caccagagga
2401 aaaggatgaa gagttccctg agcagaaggc cggggaggtg attaaccagc caatgatgat
2461 ggctgccaga cagctccatg atgaagctcg caaatggtcc agcaagggca atgacatcat
2521 tgcagcagcc aagcgcatgg ctctgctgat ggctgagatg tctcggctgg taagaggggg
2581 cagtggtacc aagcgggcac tcattcagtg tgccaaggac atcgccaagg cctcagatga
2641 ggtgactcgg ttggccaagg aggttgccaa gcagtgcaca gataaacgga ttagaaccaa
2701 cctcttacag gtatgtgagc gaatcccaac cataagcacc cagctcaaaa tcctgtccac
2761 agtgaaggcc accatgctgg gccggaccaa catcagtgat gaggagtctg agcaggccac
2821 agagatgctg gttcacaatg cccagaacct catgcagtct gtgaaggaga ctgtgcggga
2881 agctgaagct gcttcaatca aaattcgaac agatgctgga tttacactgc gctgggttag
2941 aaagactccc tggtaccagt aggcacctgg ctgagcctgg ctggcacaga aacctctact
3001 aaaaagaagg aaaatgatct gagtcccagg agctgcccag agttgctggg agctgaaaaa
3061 tcacatcctg gcctggcaca tcagaaagga atgggggcct cttcaaatta gaagacattt
3121 atactctttt ttcatggaca ctttgaaatg tgtttctgta taaagcctgt attctcaaac
3181 acagttacac ttgtgcaccc tctatcccaa taggcagact gggtttctag cccatggact
3241 tcacataagc tcagaatcca agtgaacact agccagacac tctgctctgc ccttgttccc
3301 taggggacac ttccctctgt ttctctttcc ttggctccca ttcactcttc cagaatccca
3361 agacccaggg cccaggcaaa tcagttacta agaagaaaat tgctgtgcct cccaaaattg
3421 ttttgagctt tccatgttgc tgccaaccat accttccttc cctgggctgt gctacctggg
3481 tccttttcag aagtgagctt tgctgctaca ggggaaggtg gcctctgtgg agccccagca
3541 tatgggggcc tggattcatt tcctgccctt cctcagttta atccttctag tttcccacaa
3601 tataaaactg tacttcactg tcaggaagaa atcacagaat catatgattc tgcttttacc
3661 atgcccctga gcaatgtctg tgctagggaa acttcccgtc ccatatcctg cctcagcccg
3721 ccaaggtagc catcccatga acacactgtg tcctggtgct ctctgccact ggaagggcag
3781 agtagccagg gtgtggccct gccatcttcc cagcagggcc actcccggca ctccatgctt
3841 agtcactgcc tgcagaggtc tgtgctgagg ccttatcatt cattcttagc tcttaattgt
3901 tcattttgag ctgaaatgct gcattttaat tttaaccaaa acatgtctcc tatcctggtt
3961 tttgtagcct tcctccacat cctttctaaa caagatttta aagacatgta ggtgtttgtt
4021 catctgtaac tctaaaagat cctttttaaa ttcagtccta agaaagagga gtgcttgtcc
4081 cctaagagtg tttaatggca aggcagccct gtctgaagga cacttcctgc ctaagggaga
4141 gtggtatttg cagactagaa ttctagtgct gctgaagatg aatcaatggg aaatactact
4201 cctgtaattc ctacctccct gcaaccaact acaaccaagc tctctgcatc tactcccaag
4261 tatggggttc aagagagtaa tgggtttcat atttcttatc accacagtaa gttcctacta
4321 ggcaaaatga gagggcagtg tttccttttt ggtacttatt actgctaagt atttcccagc
4381 acatgaaacc ttattttttc ccaaagccag aaccagatga gtaaaggagt aagaaccttg
4441 cctgaacatc cttccttccc acccatcgct gtgtgttagt tcccaacatc gaatgtgtac
4501 aacttaagtt ggtcctttac actcaggctt tcactatttc ctttataatg aggatgatta
4561 ttttcaaggc cctcagcata tttgtatagt tgcttgcctg atataaatgc aatattaatg
4621 cctttaaagt atgaatctat gccaaagatc acttgttgtt ttactaaaga aagattactt
4681 agaggaaata agaaaaatca tgtttgctct cccggttctt ccagtggttt gagacactgg
4741 tttacacttt atgccggatg tgcttttctc caatatcagt gctcgagaca cagtgaagca
4801 aattaaaaaa aa
```

SEQ ID NO:38

```
  1 atatccagcc tttgccgaat acatcctatc tgccacacat ccagcgtgag gtccctccag
 61 ctacaaggtg ggcaccatgg cggagaagtt tgactgccac tactgcaggg atcccttgca
121 ggggaagaag tatgtgcaaa aggatggcca ccactgctgc ctgaaatgct ttgacaagtt
```

Figure 10 (cont.)

```
 181 ctgtgccaac acctgtgtgg aatgccgcaa gcccatcggt gcggactcca aggaggtgca
 241 ctataagaac cgcttctggc atgacacctg cttccgctgt gccaagtgcc ttcacccctt
 301 ggccaatgag acctttgtgg ccaaggacaa caagatcctg tgcaacaagt gcaccactcg
 361 ggaggactcc cccaagtgca aggggtgctt caaggccatt gtggcaggag atcaaaacgt
 421 ggagtacaag gggaccgtct ggcacaaaga ctgcttcacc tgtagtaact gcaagcaagt
 481 catcgggact ggaagcttct tccctaaagg ggaggacttc tactgcgtga cttgccatga
 541 gaccaagttt gccaagcatt gcgtgaagtg caacaaggcc atcacatctg gaggaatcac
 601 ttaccaggat cagccctggc atgccgattg ctttgtgtgt gttacctgct ctaagaagct
 661 ggctgggcag cgtttcaccg ctgtggagga ccagtattac tgcgtggatt gctacaagaa
 721 ctttgtggcc aagaagtgtg ctggatgcaa gaaccccatc actgggaaaa ggactgtgtc
 781 aagagtgagc cacccagtct ctaaagctag gaagcccccca gtgtgccacg ggaaacgctt
 841 gcctctcacc ctgtttccca gcgccaacct ccggggcagg catccgggtg gagagaggac
 901 ttgtccctcg tgggtggtgg ttctttatag aaaaaatcga agcttagcag ctcctcgagg
 961 cccgggtttg gtaaaggctc cagtgtggtg gcctatgaag gacaatcctg gcacgactac
1021 tgcttccact gcaaaaaatg ctcccgtgaat ctggccaaca agcgctttgt tttccaccag
1081 gagcaagtgt attgtcccga ctgtgccaaa aagctgtaaa ctgacagggg ctcctgtcct
1141 gtaaaatggc atttgaatct cgttctttgt gtccttactt tctgccctat accatcaata
1201 ggggaagagt ggtccttccc ttctttaaag ttctccttcc gtcttttctc ccattttaca
1261 gtattactca aataagggca cacagtgatc atattagcat ttagcaaaaa gcaaccctgc
1321 agcaaagtga atttctgtcc ggctgcaatt taaaaatgaa aacttaggta gattgactct
1381 tctgcatgtt tctcatagag cagaaaagtg ctaatcattt agccacttag tgatgtaagc
1441 aagaagcata ggagataaaa cccccactga gatgcctctc atgcctcagc tgggacccac
1501 cgtgtagaca cacgacatgc aagagttgca gcggctgctc caactcactg ctcaccctct
1561 tctgtgagca ggaaaagaac cctactgaca tgcatggttt aacttcctca tcagaactct
1621 gcccttcctt ctgttctttt gtgctttcaa ataactaaca cgaacttcca gaaaattaac
1681 atttgaactt agctgtaatt ctaaactgac ctttccccgt actaacgttt ggtttccccg
1741 tgtggcatgt tttctgagcg ttcctacttt aaagcatgga acatgcaggt gatttgggaa
1801 gtgtagaaag acctgagaaa acgagcctgt ttcagaggaa catcgtcaca acgaatactt
1861 ctggaagctt aacaaaacta accctgctgt ccttttttatt gtttttaatt aatatttttg
1921 ttttaattga tagcaaaata gtttatgggt ttggaaactt gcatgaaaat attttagccc
1981 cctcagatgt tcctgcagtg ctgaaattca tcctacggaa gtaaccgcaa aactctag
```

SEQ ID NO:39

```
   1 tgccgcccta caccgtggtc tatttcccag ttcgagnnnn nnnnnnnnnn nnnnnnnnnn
  61 nnnnnnnnnn nnnnnnnngc tgctggcaga tcagggccag agctggaagg aggaggtggt
 121 gaccgtggag acgtggcagg agggctcact caaagcctcc tgcctatacg ggcagctccc
 181 caagttccag gacggagacc tcaccctgta ccagtccaat accatcctgc gtcacctggn
 241 nnnnnnnnnn nnnnnnnnnn nnnnnnnngg ctctatggga aggaccagca ggaggcagcc
 301 ctggtggaca tggtgaatga cggcgtggag gacctccgct gcaaatacat ctccctcatc
 361 tacaccaact atgaggcggg caaggatgac tatgtgaagg cactgcccgg gcaactgaag
 421 ccttttgaga ccctgctgtc ccagaaccag ggaggcaaga ccttcattgt gggagaccag
 481 atctccttcg ctgactacaa cctgctggac ttgctgctga tccatgaggt cctagcccct
 541 ggctgcctgg atgcgttccc cctgctctca gcatatgtgg ggcgcctcag tgcccggccc
 601 aagctcaagg ccttcctggc ctcccctgag tacgtgaacc tccccatcaa tggcaacggg
 661 aaacagtgag ggttgggggg actctgagcg g
```

SEQ ID NO:40

```
   1 cttttcacac tggccttaaa gaggatatat tagaagttga agtaggaagg gagccagaga
  61 ggccgatggc gcaaaggtac gacgatctac cccattacgg gggcatggat ggagtaggca
 121 tcccctccac gatgtatggg gacccgcatg cagccaggtc catgcagccg gtccaccacc
 181 tgaaccacgg gcctcctctg cactcgcatc agtacccgca cacagctcat accaacgcca
 241 tggcccccag catgggctcc tctgtcaatg acgctttaaa gagagataaa gatgccattt
 301 atggacaccc cctcttccct ctcttagcac tgatttttga gaaatgtgaa ttagctactt
```

Figure 10 (cont.)

```
 361 gtacccccccg cgagccgggg gtggcgggcg gggacgtctg ctcgtcagag tcattcaatg
 421 aagatatagc cgtgttcgcc aaacagattc gcgcagaaaa acctctattt tcttctaatc
 481 cagaactgga taacttgatg attcaagcca tacaagtatt aaggtttcat ctattggaat
 541 tagagaaggt acacgaatta tgtgacaatt tctgccaccg gtatattagc tgtttgaaag
 601 ggaaaatgcc tatcgatttg gtgatagacg atagagaagg aggatcaaaa tcagacagtg
 661 aagatataac aagatcagca aatctaactg accagccctc ttggaacaga gatcatgatg
 721 acacggcatc tactcgttca ggaggaaccc caggcccttc cagcggtggc cacacgtcac
 781 acagtgggga caacagcann nnnnnnnnnn nnnnnnnnnn nnnnnnnnnn nnnnnnnnnn
 841 nnnnnnnnnn nnnnnnnnnn nnnnnnnnnn nnnnnnnnnn nnnnnnnnnn nnnnnnnnnn
 901 nnnnnnnnnn nnnnnnnnnn nnnnnnnnnn nnnnnnnnnn nnnnnnnnnn nnncacccctt
 961 acccttctga agaacagaaa aagcagttgg cacaagacac gggactcacc atccttcaag
1021 tgaacaattg gtttattaat gcccggagaa gaatagtgca gcccatgata gaccagtcca
1081 accgagcagt aagtcaagga acaccttata atcctgatgg acagcccatg ggaggtttcg
1141 taatggacgg tcagcaacat atgggaatta gagcaccagg acctatgagt ggaatgggca
1201 tgaatatggg catggagggg cagtggcact acatgtaacc ttcatctagt taaccaatcg
1261 caaagcaagg gggaaggctg caaagtatgc caggggagta tgtagcccgg ggtggtccaa
1321 tgggtgtgag tatgggacag ccaagttata cccaacccca gatgcccccc catcctgctc
1381 agctgcgtca tgggcccccc atgcatacgt acattcctgg acaccctcac cacccaacag
1441 tgatgatgca tggaggaccg ccccaccctg gaatgccaat gtcagcatca agccccacag
1501 ttcttaatac aggagaccca acaatgagtg gacaagtcat ggacattcat gctcagtagc
1561 ttaagggaat atgcattgtc tgcaatggtg actgatttca aatcatgttt tttctgcaat
1621 gactgtggag ttccattctt ggcatctact ctggaccaag gagcatccct aattcttcat
1681 agggaccttt aaaaagcagg aaataccaac tgaagtcaat ttgggggaca tgctaaataa
1741 ctatataaga cattaagaga acaaagagtg aaatattgta aatgctatta tactgttatc
1801 catattacgt tgtttcttat agatttttta aaaaaaatgt gaaatttttc cacactatgt
1861 gtgttgtttc catagctctt cacttcctcc agaagcctcc ttacattaaa aagccttaca
1921 gttatcctgc aagggacagg aaggtctgat ttgcaggatt tttagagcat taaaataact
1981 atcaggcaga agaatctttc ttctcgccta ggatttcagc catgcgcgcg ctctctctct
2041 ttctctctct tttcctctct ctccctcttt ctagcctggg gcttgaattt gcatgtctaa
2101 ttcatttact caccatattt gaattggcct gaacagatgt aaatcgggaa ggatgggaaa
2161 aactgcagtc atcaacaatg attaatcagc tgttgcaggc agtgtcttaa ggagactggt
2221 aggaggaggc atggaaacca aaaggccgtg tgtttagaag cctaattgtc acatcaagca
2281 tcattgtccc catgcaacaa ccaccacctt atacatcact tcctgtttta agcagctcta
2341 aaacatagac tgaagattta tttttaatat gttgacttta tttctgagca aagcatcggt
2401 catgtgtgta ttttttcata gtcccacctt ggagcattta tgtagacatt gtaaataaat
2461 tttgtgcaaa aaggactgga aaaatgaact gtattattgc aatttttttt t
```

SEQ ID NO:41

```
   1 ctcaataagc caaccatgtc tttcaaggat tacatccaag agaggagtga cccagtggag
  61 caaggcaaac cagttatacc tgcagctgtg ctggccggct tcacaggaag tggacctatt
 121 cagctgtggc agtttctcct ggagctgcta tcagacaaat cctgccagtc attcatcagc
 181 tggactggag acggatggga gtttaagctc gccgaccccg atgaggtggc ccgccggtgg
 241 ggaaagagga aaaataagcc caagatgaac tacgagaagc tgagccgggg cttacgctac
 301 tattacgaca agaacatcat ccacaagacg tcggggaagc gctacgtgta ccgcttcgtg
 361 tgcgacctcc agaacttgct ggggttcacg cccgaggaac tgcacgccat cctgggcgtc
 421 cagcccgaca cggaggactg a
```

SEQ ID NO:42

```
   1 ggacgacaag gcgttcacca aggagctgga ccagtgggtc gagcagctga acgagtgtaa
  61 gcagctgaac gagaaccaag tgcggacgct gtgcgagaag gcaaaggaaa ttttaacaaa
 121 agaatcaaat gtgcaagagg ttcgttgccc tgttactgtc tgtggagatg tgcatggtca
 181 atttcatgat cttatggaac tctttagaat tggtggaaaa tcaccggata caaactactt
 241 attcatgggt gactatgtag acagaggata ttattcagtg gagactgtga ctcttcttgt
 301 agcattaaag gtgcgttatc cagaacgcat tacaatattg agaggaaatc acgaaagccg
```

Figure 10 (cont.)

```
 361 acaaattacc caagtatatg gcttttatga tgaatgtctg cgaaagtatg ggaatgccaa
 421 cgtttggaaa tattttacag atctctttga ttatcttcca cttacagctt tagtagatgg
 481 acagatattc tgcctccatg gtggcctctc tccatccata gacacactgg atcatataag
 541 agccctggat cgtttacagg aagttccaca tgagggccca atgtgtgatc tgttatggtc
 601 agatccagat gatcgtggtg gatggggtat ttcaccacgt ggtgctggct acacatttgg
 661 acaagacatt tctgaaacct ttaaccatgc caatggtctc acactggttt ctcgtgccca
 721 ccagcttgta atggagggat acaattggtg tcatgatcgg aatgtggtta ccattttcag
 781 tgcacccaat tactgttatc gttgtgggaa ccaggctgct atcatggaat tagatgacac
 841 tttaaaatat tccttccttc aatttgaccc agcgcctcgt cgtggtgagc ctcatgttac
 901 acggcgcacc ccagactact tcctataaat ttctcctggg aaacctgcct ttgtatgtgg
 961 aagtatacct ggctttttaa aatatatgta tttaaaaaca aaaagcaaca gtaatctatg
1021 tgtttctgta acaaattggg atctgtcttg gcattaaacc acatcatgga ccaaatgtgc
1081 catactaatg atgagcattt agcacaattt gagactgaaa tttagtacac tatgttctag
1141 gtcagtctaa cagtttgcct gctgtattta tagtaaccat tttcctttgg actgttcaag
1201 caaaaaaggt aactaactgc ttcatctcct tttgcgctta tttggaaatt ttagttatag
1261 tgtttaactg gcatggatta atagagttgg agttttattt ttaagaaaaa ttcacaagct
1321 aacttccact aatccattat cctttatttt attgaaatgt ataattaact taactgaaga
1381 aaaggttctt cttgggagta tgttgtcata acatttaaag agatttccct tcatttaaac
1441 taaattactg ttttatgttg atctgcatat ttctgtatat ttgtcatgac agtgcttgca
1501 tcctatttgg tgtactcagc aaataaactt t
```

SEQ ID NO:43

```
   1 cctgtgagca ccacgtcaac ggctcccggc ccccatgcac gggggaggga gataccccca
  61 agtgtagcaa gatctgtgag cctggctaca gcccgaccta caaacaggac aagcactacg
 121 gatacaattc ctacagcgtc tccaatagcg agaaggacat catggccgag atctacaaaa
 181 acggccccgt ggagggagct ttctctgtgt attcggactt cctgctctac aagtcaggag
 241 tgtaccaaca cgtcaccgga gagatgatgg gtggccatgc catccgcatc ctgggctggg
 301 gagtggagaa tggcacaccc tactggctgg ttgccaactc ctggaacact gactggggtg
 361 acaatggctt ctttaaaata ctcagaggac aggatcactg tggaatcgaa tcagaagtgg
 421 tggctggaat tccacgcacc gatcagtact gggaaaagat ctaatctgcc gtgggcctgt
 481 cgtgccagtc ctgggggcga gatgggggta gaaatgcatt ttattcttta agttcacgta
 541 agatacaagt ttcagacagg gtctgaagga ctggattggc caaacatcag acctgtcttc
 601 caaggagacc aagtcctggc tacatcccag cctgtggtta cagtgcagac aggccatgtg
 661 agccaccgct gccagcacag agcgtccttc cccctgtaga ctagtgccgt agggagtacc
 721 tgttgcccca gctgactgtg gccccctccg tgatccatcc atctccaggg agcaagacag
 781 agacccagga atggaaagcg gagttcctaa caggatgaaa gttcccccat cagttccccc
 841 agtacctcca agcaagtagc tttccacatt tgtcacagaa atcagaggag agatggtgtt
 901 gggagcccct tggagaacgc cagtctccca ggccccctgc atctatcgag tttgcaatgt
 961 cacaacctct ctgatcttgt gctcagcatg attctttaat agaagtttta ttttttcgtg
1021 cactctgcta atcatgtggg tgagccagtg gaacagcggg agacctgtgc tagttttaca
1081 gattgcctcc ttatgacgcg gctcaaaagg aaaccaagtg gtcaggagtt gtttctgacc
1141 cactgatctc tactaccaca aggagaatag tttaggagaa accagctttt actgtttttg
1201 aaaaattaca gcttcaccct gtcaagttaa caaggaatgc ctgtgccaat aaaaggtttc
```

SEQ ID NO:44

```
   1 gtgtcccata gtgtttccaa acttggaaag ggcgggggag ggcgggagga tgcggagggc
  61 ggaggtatgc agacaacgag tcagagtttc cccttgaaag cctcaaaagt gtccacgtcc
 121 tcaaaaagaa tggaaccaat ttaagaagcc agccccgtgg ccacgtccct tcccccattc
 181 gctccctcct ctgcgccccc gcaggctcct cccagctgtg gctgcccggg cccccagccc
 241 cagccctccc attggtggag gcccttttgg aggcacccta gggccaggga aacttttgcc
 301 gtataaatag ggcagatccg ggctttatta ttttagcacc acggcagcag gaggtttcgg
 361 ctaagttgga ggtactggcc acgactgcat gccccgcgccc gccaggtgat acctccgccg
 421 gtgacccagg ggctctgcga cacaaggagt ctgcatgtct aagtgctaga catgctcagc
 481 tttgtggata cgcggacttt gttgctgctt gcagtaacct tatgcctagc aacatgccaa
```

Figure 10 (cont.)

```
 541 tctttacaag aggaaactgt aagaaagggc ccagccggag atagaggacc acgtggagaa
 601 aggggtccac caggcccccc aggcagagat ggtgaagatg gtcccacagg ccctcctggt
 661 ccacctggtc ctcctggccc ccctggtctc ggtgggaact ttgctgctca gtatgatgga
 721 aaaggagttg gacttggccc tggaccaatg ggcttaatgg gacctagagg cccacctggt
 781 gcagctggag ccccaggccc tcaaggtttc caaggacctg ctggtgagcc tggtgaacct
 841 ggtcaaactg gtcctgcagg tgctcgtggt ccagctggcc ctcctggcaa ggctggtgaa
 901 gatggtcacc ctggaaaacc cggacgacct ggtgagagag gagttgttgg accacagggt
 961 gctcgtggtt tccctggaac tcctggactt cctggcttca aaggcattag ggacacacat
1021 ggtctggatg gattgaaggg acagcccggt gctcctggtg tgaagggtga acctggtgcc
1081 cctggtgaaa atggaactcc aggtcaaaca ggagcccgtg ggcttcctgg tgagagagga
1141 cgtgttggtg cccctggccc agctggtgcc cgtggcagtg atggaagtgt gggtcccgtg
1201 ggtcctgctn nnnnnnnnng gtctgctggc cctccaggct tcccaggtgc ccctggcccc
1261 aagggtgaaa ttggagctat tggtaacgct ggtcctgctg gtcccgccgg tccccgtggt
1321 gaagtgggtc ttccaggcct ctccggcccc gttggacctc ctggtaatcc tggagcaaac
1381 ggccttactg gtgccaaggg tgctgctggc cttcccggcg ttgctggggc tcccggcctc
1441 cctggacccc gcggtattcc tggccctgtt ggtgctgccg gtgctactgg tgccagagga
1501 cttgttggtg agcctggtcc agctggctcc aaaggagaga gcggtaacaa gggtgagccc
1561 ggctctgctg ggccccaagg tcctcctggt cccagtggtg aagaaggaaa gagaggccct
1621 aatggggaag ctggatctgc cggccctcca ggacctcctg ggctgagagg tagtcctggt
1681 tctcgtggtc ttcctggagc tgatggcaga gctggcgtca tgggccctcc tggtagtcgt
1741 ggtgcaagtg gccctgctgg agtccgagga cctaatggag atgctggtcg ccctggggag
1801 cctggtctca tgggacccag aggtcttcct ggttcccctg gaaatatcgg ccccgctgga
1861 aaagaaggtc ctgtcggcct ccctggcatc gacggcaggc ctggcccaat tggccccgtt
1921 ggagcaagag gagagcctgg caacattgga ttccctggac ccaaaggccc cactggtgac
1981 cctggcaaaa acggtgataa aggtcatgct ggtcttgctg gtgctcgggg tgctccaggt
2041 cctgatggaa acaatggtgc tcagggacct cctggaccac agggtgttca aggtggaaaa
2101 ggtgaacagg gtcccgctgg tcctccaggc ttccagggtc tgcctggccc ctcaggtccc
2161 gctggtgaag ttggcaaacc aggagaaagg ggtctccatg gtgagtttgg tctccctggt
2221 cctgctggtc caagagggga acgcggtccc ccaggtgaga gtggtgctgc cggtcctact
2281 ggtcctattg gaagccgagg tccttctgga cccccagggc ctgatggaaa caagggtgaa
2341 cctggtgtgg ttggtgctgt gggcactgct ggtccatctg gtcctagtgg actcccagga
2401 gagaggggtg ctgctggcat acctggaggc aagggagaaa agggtgaacc tggtctcaga
2461 ggtgaaattg gtaaccctgg cagagatggt gctcgtggtg ctcatggtgc tgtaggtgcc
2521 cctggtcctg ctggagccac aggtgaccgg ggcgaagctg gggctgctgg tcctgctggt
2581 cctgctggtc ctcggggaag ccctggtgaa cgtggcgagg tcggtcctgc tggccccaac
2641 ggatttgctg gtccggctgg tgctgctggt caaccgggtg ctaaaggaga aagaggaggc
2701 aaagggccta agggtgaaaa cggtgttgtt ggtcccacag gccccgttgg agctgctggc
2761 ccagctggtc caaatggtcc ccccggtcct gctggaagtc gtggtgatgg aggcccccct
2821 ggtatgactg gtttccctgg tgctgctgga cggactggtc ccccaggacc ctctggtatt
2881 tctggccctc ctggtccccc tggtcctgct gggaaagaag ggcttcgtgg tcctcgtggt
2941 gaccaaggtc cagttggccg aactggagaa gtaggtgcag ttggtccccc tggcttcgct
3001 ggtgagaagg gtccctctgg agaggctggt actgctggac ctcctggcac tccaggtcct
3061 cagggtcttc ttggtgctcc tggtattctg ggtctccctg gctcgagagg tgaacgtggt
3121 ctacctggtg ttgctggtgc tgtgggtgaa cctggtcctc ttggcattgc cggccctcct
3181 ggggcccgtg gtcctcctgg tgctgtgggt agtcctggag tcaacggtgc tcctggtgaa
3241 gctggtcgtg atggcaaccc tgggaacgat ggtcccccag gtcgcgatgg tcaacccgga
3301 cacaagggag agcgcggtta ccctggcaat attggtcccg ttggtgctgc aggtgcacct
3361 ggtcctcatg gccccgtggg tcctgctggc aaacatggaa accgtggtga aactggtcct
3421 tctggtcctg ttggtcctgc tggtgctgtt ggcccaagag gtcctagtgg cccacaaggc
3481 attcgtggcg ataagggaga gcccggtgaa aaggggccca gaggtcttcc tggcttcaag
3541 ggacacaatg gattgcaagg tctgcctggt atcgctggtc accatggtga tcaaggtgct
3601 cctggctccg tgggtcctgc tggtcctagg ggccctgctg gtccttctgg ccctgctgga
3661 aaagatggtc gcactggaca tcctggtacg gttggacctg ctggcattcg aggccctcag
3721 ggtcaccaag gccctgctgg ccccccctggt cccccctggcc ctcctggacc tccaggtgta
```

Figure 10 (cont.)

```
3781 agcggtggtg gttatgactt tggttacgat ggagacttct acagggctga ccagcctcgc
3841 tcagcacctt ctctcagacc caaggactat gaagttgatg ctactctgaa gtctctcaac
3901 aaccagattg agacccttct tactcctgaa ggctctagaa agaacccagc tcgcacatgc
3961 cgtgacttga gactcagcca cccagagtgg agcagtggtt actactggat tgaccccaac
4021 caaggatgca ctatggaagc catcaaagta tactgtgatt tccctaccgg cgaaacctgt
4081 atccgggccc aacctgaaaa catcccagcc aagaactggt ataggagctc caaggacaag
4141 aaacacgtct ggctaggaga aactatcaat gctggcagcc agtttgaata taatgttgaa
4201 ggagtgactt ccaaggaaat ggctacccaa cttgccttca tgcgcctgct ggccaactat
4261 gcctctcaga acatcaccta ccactgcaag aacagcattg catacatgga tgaggagact
4321 ggcaacctga aaaaggctgt cattctacag ggctctaatg atgttgaact tgttgctgag
4381 ggcaacagca ggttcactta cactgttctt gtagatggct gctctaaaaa gacaaatgaa
4441 tggggaaaga caatcattga atacaaaaca aataagccat cacgcctgcc cttccttgat
4501 attgcacctt tggacatcgg tggtgctgac catgaattct ttgtggacat tggcccagtc
4561 tgtttcaaat aaatgaactc aatctaaatt aaaaaagaaa gaaatttgaa aaaactttct
4621 ctttgccatt tcttcttctt cttttttaac tgaaagctga atccttccat ttcttctgca
4681 catctacttg cttaaattgt gggcaaaaga gaaaaagaag gattgatcag agcattgtgc
4741 aatacagttt cattaactcc ttcccccgct cccccaaaaa tttgaatttt tttttcaaca
4801 ctcttacacc tgttatggaa aatgtcaacc tttgtaagaa aaccaaaata aaaattgaaa
4861 aataaaaacc ataaacattt gcaccacttg tggcttttga atatcttcca cagagggaag
4921 tttaaaaccc aaacttccaa aggtttaaac tacctcaaaa cactttccca tgagtgtgat
4981 ccacattgtt aggtgctgac ctagacagag atgaactgag gtccttgttt tgttttgttc
5041 ataatacaaa ggtgctaatt aatagtattt cagatacttg aagaatgttg atggtgctag
5101 aagaatttga gaagaaatac tcctgtattg agttgtatcg tgtggtgtat tttttaaaaa
5161 atttgattta gcattcatat tttccatctt attcccaatt aaaagtatgc agattatttg
5221 cccaaagttg tcctcttctt cagattcagc atttgttctt tgccagtctc attttcatct
5281 tcttccatgg ttccacagaa gctttgtttc ttgggcaagc agaaaaatta aattgtacct
5341 attttgtata tgtgagatgt ttaaataaat tgtgaaaaaa atgaaataaa gcatgtttgg
5401 ttttccaaaa gaacatat
```

SEQ Id NO:45

```
   1 cagaccacag gaatacctaa tgcctttttt ctcttcctgt ctttgtccct cacactacag
  61 caggcccctc ccttccctct tcaacctcat cctccctccc cacaggccca gagaaccagt
 121 tgggctttgt tctcctgcag gctatggttc atcatgcaaa tagctcctgt gtcagaaatg
 181 ctttttggct tcaaataaca gaaaagctaa caccagcttt atcaataata atatcggtgg
 241 tttacttaag gtgtccagag atggtggaga acaggattgg tttcctcctc aatgtcaagg
 301 actcaaagac tctttctgtg gtagggccac atcctaaacc ctgtatcctg tgattattta
 361 cctgacaggg caaaagagat tttgcagatg caattaaggt taaggacctt gacgtgggaa
 421 gattgtgatt atttacctga cagggcaaaa gagattttgc agatgcaatt aaggttaagg
 481 accttgacgt gggaagatta ttctggatta tctaggtggg cgcaatttga tcacatgggt
 541 ccccagaagt ggagaacctt tcccacctgt agaaagccag agagctggca cctgagaagg
 601 acagaactgt cactgcagga tttgaagatg aaggggccca tgagccaagg aatgccagtg
 661 acctatagag gctaaaaaac agcaaggaaa tggactctcc ccagagcctc cagaggaatg
 721 cagccctgtt gatcacatga tcaccagatg gctgccccag agccaaatgt cgcttcctga
 781 gcaccatact caaaggcagg ggaagtggat ggagggcagg agctccattc ttgtttgcca
 841 ctctcctttt gtcaattggg aaaaaattcc agaaactctg ggagccctcc ccttacattt
 901 cctgggtcat ggggccagcc ctagctgctg gagggactga gaactgctgt tgagcagttt
 961 acctgacggc atctgccatg gcttggcagg aactctggct ttgggagaga gcagcagcaa
1021 ggtattcaag caccacctcc acccagcccc tcccacattt cactcaggac tgagtaaagg
1081 agacactcag atgctactca gatgctggct tcagctaagt attttgcaaa gcctctcgtg
1141 ttcttacaag tttgtggcta tcatgacaaa atggagcagc ctactatatc tacatataca
1201 actatggggg acctagtttt atctcattta ccacaatgtt ttcaatcatt ttttggatga
1261 cataattttt agcctcttct ctaaatgctt cctcaagctt tccttgcctt ccagccactg
1321 caaatgactt gcagtttccc ctacatggca cctgaccctt gtgcctccct ccctctgccc
1381 atggcccaga aagccctttc ctgtgccctc tggcttcctg ataaactcct atcatcttca
```

Figure 10 (cont.)

```
1441 agagccagtt cccatgccag ctctccccaa gtgctccact gaggcttccg taacacctct
1501 gttcccacat cgggttgact gtctttgttt tgtcattgct tgctctggct gtgtctccct
1561 cattagactg ggatgccttc aaggtaggga ccctatctgg gtcagcttgg caccccaaag
1621 cgtaccacag cacctgattc tgaggaggct ctcagtagat atctgttgag taaccagaat
1681 gtagggtggt cctgatggtt tctgacattg aatagaaaac agctccctat ttgatcttaa
1741 aataatcact ataacctgga catactgtac tagatgctgt ttttgtctga cttctactct
1801 gtcaatctct ttgcacctcc atttgttcat ctgtgaaatg aagaaaatgc tcatggagtt
1861 cagtgaagat taaatgaatg aatataggta gactgcctaa tctggcactt gccacgcagc
1921 tgacttcaat atagtagctc taatattatg gtccttgagg atcttactgt cttatggccc
1981 agaactgcat ttgattaaag aaggctcccc taaaaaaaga gtcatacata ttccatttgt
2041 cctttcagaa ggccgtgaag catttacact ctttaagaca aattcccatc caaaaatagt
2101 taagatttct aaaatatttt gatgctgaaa gaggtgtgct tcagttgggt ggcaaatttg
2161 cttctatgga agatttttaa tacaggttgt ttctatttta ctttttctgg ctgaaaggat
2221 tttacattta ttcaaagtca aaagggaaaa gaaatccaag aactacagaa gagcagttga
2281 agtgatttat gcttgatttc taaatgcaac ttatgtttat acataattta aaactcaaag
2341 aaagcatgct tatacaatca tgtgcaactt taaactttaa gaactctgga tgaatacatg
2401 gtggcaacag tccatgacac ctgaaaacat catttgtgga gtggcgtaga gttcagtgtt
2461 cgcagtcgca tattacaacc atgtttcaca cagccctgct cggtttgatt ttctccacgt
2521 ggttgataat tgtcttcagt tgctgctaag tgattttgca aatttc
```

SEQ ID NO:46

```
   1 gtccccgcgc cagagacgca gccgcgctcc caccacccac acccaccgcg ccctcgttcg
  61 cctcttctcc gggagccagt ccgcgccacc gccgccgccc aggccatcgc caccctccgc
 121 agccatgtcc accaggtccg tgtcctcgtc ctcctaccgc aggatgttcg gcggcccggg
 181 caccgcgagc cggccgagct ccagccggag ctacgtgact acgtccaccc gcacctacag
 241 cctgggcagc gcgctgcgcc ccagcaccag ccgcagcctc tacgcctcgt ccccgggcgg
 301 cgtgtatgcc acgcgctcct ctgccgtgcg cctgcggagc agcgtgcccg ggtgcggct
 361 cctgcaggac tcggtggact tctcgctggc cgacgccatc aacaccgagt tcaagaacac
 421 ccgcaccaac gagaaggtgg agctgcagga gctgaatgac cgcttcgcca actacatcga
 481 caaggtgcgc ttcctggagc agcagaataa gatcctgctg gccgagctcg agcagctcaa
 541 gggccaaggc aagtcgcgcc tgggggacct ctacgaggag gagatgcggg agctgcgccg
 601 gcaggtggac cagctaacca acgacaaagc ccgcgtcgag gtggagcgcg acaacctggc
 661 cgaggacatc atgcgcctcc gggagaaatt gcaggaggag atgcttcaga gagaggaagc
 721 cgaaaacacc ctgcaatctt tcagacagga tgttgacaat gcgtctctgg cacgtcttga
 781 ccttgaacgc aaagtggaat ctttgcaaga agagattgcc tttttgaaga aactccacga
 841 agaggaaatc caggagctgc aggctcagat tcaggaacag catgtccaaa tcgatgtgga
 901 tgtttccaag cctgacctca cggctgccct gcgtgacgta cgtcagcaat atgaaagtgt
 961 ggctgccaag aacctgcagg aggcagaaga atggtacaaa tccaagtttg ctgacctctc
1021 tgaggctgcc aaccggaaca atgacgccct gcgccaggca aagcaggagt ccactgagta
1081 ccggagacag gtgcagtccc tcacctgtga agtggatgcc cttaaaggaa ccaatgagtc
1141 cctggaacgc cagatgcgtg aaatggaaga gaactttgcc gttgaagctg ctaactacca
1201 agacactatt ggccgcctgc aggatgagat tcagaatatg aaggaggaaa tggctcgtca
1261 ccttcgtgaa taccaagacc tgctcaatgt taagatggcc cttgacattg agattgccac
1321 ctacaggaag ctgctggaag gcgaggagag caggatttct ctgcctcttc caaacttttc
1381 ctccctgaac ctgagggaaa ctaatctgga ttcactccct ctggttgata cccactcaaa
1441 aaggacactt ctgattaaga cggttgaaac tagagatgga caggttatca acgaaacttc
1501 tcagcatcac gatgaccttg aataaaaatt gcacacactc agtgcagcaa tatattacca
1561 gcaagaataa aaaagaaatc catatcttaa agaaacagct ttcaagtgcc tttctgcagt
1621 ttttcaggag cgcaagatag atttggaata ggaataagct ctagttctta acaaccgaca
1681 ctcctacaag atttagaaaa aagtttacaa cataatctag tttacagaaa aatcttgtgc
1741 tagaatactt tttaaaaggt attttgaata ccattaaaac tgcttttttt tttccagcaa
1801 gtatccaacc aacttggttc tgcttcaata aatctttgga aaaactc
```

SEQ ID NO:47

Figure 10 (cont.)

1 ggccagccga atccaagccg tgtgtactgc gtgctcagca ctgcccgaca gtcctagcta
61 aacttcgcca actccgctgc ctttgccgcc accatgccca aaacgatcag tgtgcgtgtg
121 accaccatgg atgcagagct ggagtttgcc atccagccca acaccaccgg gaagcagcta
181 tttgaccagg tggtgaaaac tattggcttg agggaagttt ggttctttgg tctgcagtac
241 caggacacta aaggtttctc cacctggctg aaactcaata agaaggtgac tgcccaggat
301 gtgcggaagg aaagccccct gctctttaag ttccgtgcca agttctaccc tgaggatgtg
361 tccgaggaat tgattcagga catcactcag cgcctgttct ttctgcaagt gaaagagggc
421 attctcaatg atgatattta ctgcccgcct gagaccgctg tgctgctggc ctcgtatgct
481 gtccagtcta agtatggcga cttcaataag gaagtgcata agtctggcta cctggccgga
541 gacaagttgc tcccgcagag agtcctggaa cagcacaaac tcaacaagga ccagtgggag
601 gagcggatcc aggtgtggca tgaggaacac cgtggcatgc tcagggagga tgctgtcctg
661 gaatatctga agattgctca agatctggag atgtatggtg tgaactactt cagcatcaag
721 aacaagaaag gctcagagct gtggctgggg gtggatgccc tgggtctcaa catctatgag
781 cagaatgaca gactaactcc caagataggc ttcccctgga gtgaaatcag gaacatctct
841 ttcaatgata agaaatttgt catcaagccc attgacaaaa aagccccgga cttcgtcttc
901 tatgctcccc ggctgcggat taacaagcgg atcttggcct tgtgcatggg gaaccatgaa
961 ctatacatgc gccgtcgcaa gcctgatacc attgaggtgc agcagatgaa ggcacaggcc
1021 cgggaggaga agcaccagaa gcagatggag cgtgctatgc tggaaaatga gaagaagaag
1081 cgtgaaatgg cagagaagga gaaagagaag attgaacggg agaaggagga gctgatggag
1141 aggctgaagc agatcgagga acagactaag aaggctcagc aagaactgga agaacagacc
1201 cgtagggctc tggaacttga gcaggaacgg aagcgtgccc agagcgaggc tgaaaagctg
1261 gccaaggagc gtcaagaagc tgaagaggcc aaggaggcct tgctgcaggc ctcccgggac
1321 cagaaaaaga ctcaggaaca gctggccttg gaaatggcag agctgacagc tcgaatctcc
1381 cagctggaga tggcccgaca gaagaaggag agtgaggctg tggagtggca gcagaaggcc
1441 cagatggtac aggaagactt ggagaagacc cgtgctgagc tgaagactgc catgagtaca
1501 cctcatgtgg cagagcctgc tgagaatgag caggatgagc aggatgagaa tggggcagag
1561 gctagtgctg acctacgggc tgatgctatg gccaaggacc gcagtgagga ggaacgtacc
1621 actgaggcag agaagaatga gcgtgtgcag aagcacctga aggccctcac ttcggagctg
1681 gccaatgcca gagatgagtc caagaagact gccaatgaca tgatccatgc tgagaacatg
1741 cgactgggcc gagacaaata caagaccctg cgccagatcc ggcagggcaa caccaagcag
1801 cgcattgacg aatttgagtc tatgtaatgg gcacccagcc tctagggacc cctcctccct
1861 ttttccttgt ccccacactc ctacacctaa ctcacctaac tcatactgtg ctggagccac
1921 taactagagc agccctggag tcatgccaag catttaatgt agccatggga ccaaacctag
1981 ccccttagcc cccacccact tccctgggca aatgaatggc tcactatggt gccaatggaa
2041 cctcctttct cttctctgtt ccattgaatc tgtatggcta gaatatccta cttctccagc
2101 ctagaggtac tttccacttg atttgcaaa tgcccttaca cttactgttg tcctatggga
2161 gtcaagtgtg gagtaggttg gaagctagct cccctcctct cccctaccac tgtcttcttc
2221 agggtcctga gatttacacg gttggagtgt tatgcggtct agggaatgag acaggaccta
2281 ggatatcttc tccaggatgt caactgacct aaaatttgcc ctcccatccc gtttagagtt
2341 atttaggctt tgtaacgatt gggggataaa aagatgttca gtcatttttg tttctacctc
2401 ccagatcgga tctgttgcaa actcagcctc aataagcctt gtcgttgact ttagggactc
2461 aatttctccc cagggtggat gggggaaatg gtgccttcaa gaccttcacc aaacatacta
2521 gaagggcatt ggccattcta ttgtggcaag gctgagtaga agatcctacc ccaattcctt
2581 gtaggagtat aggccggtct aaagtgagct ctatgggcag atctacccct tacttattat
2641 tccagatctg cagtcacttc gtgggatctg cccctccctg cttcaatacc caaatcctct
2701 ccagctataa cagtagggat gagtacccaa aagctcagcc agccccatca ggactcttgt
2761 gaaaagagag gatatgttca cacctagcgt cagtattttc cctgctaggg gttttaggtc
2821 tcttcccctc tcagagctac ttgggccata gctcctgctc cacagccatc ccagccttgg
2881 catctagagc ttgatgccag taggctcaac tagggagtga gtgcaaaaag ctgagtatgg
2941 tgagagaagc ctgtgccctg atccaagttt actcaaccct ctcaggtgac caaaatcccc
3001 ttctcatcac tcccctccaa agaggtgact gggccctgcc tctgtttgac aaacctctaa
3061 cccaggtctt gacaccagct gttctgtccc ttggagctgt aaaccagaga gctgctgggg
3121 attctggcct agtcccttcc acaccccac cccttgctct caacccagga gcatccacct
3181 ccttctctgt ctcatgtgtg ctcttcttct ttctacagta ttatgtactc tactgatatc

Figure 10 (cont.)

```
3241 taaatattga tttctgcctt ccttgctaat gcaccattag aagatattag tcttggggca
3301 ggatgatttt ggcctcatta ctttaccacc cccacacctg gaaagcatat actatattac
3361 aaaatgacat tttgccaaaa ttattaatat aagaagcttt cagtattagt gatgtcatct
3421 gtcactatag gtcatacaat ccattcttaa agtacttgtt atttgttttt attattactg
3481 tttgtcttct ccccagggtt cagtcctcaa ggggccatcc tgtcccacca tgcagtgccc
3541 ctagcttaga gcctccctca attccccctg gccaccaccc cccactctgt gcctgacctt
3601 gaggagtctt gtgtgcattg ctgtgaatta gctcacttgg tgatatgtcc tatattggct
3661 aaattgaaac ctggaattgt ggggcaatct attaatagct gccttaaagt cagtaactta
3721 cccttaggga ggctggggga aaaggttaga ttttgtattc aggggttttt tgtgtacttt
3781 ttgggttttt taaaaattgt ttttggaggg gtttatgctc aatccatgtt ctatttcagt
3841 gccaataaaa tttaggaaga cttc
```

SEQ ID NO:48

```
   1 ggtgtgcccg gagaggctga gcagcctgcg cctgagctgg tggaggtgga agtgggcagc
  61 acagcccttc tgaagtgcgg cctctcccag tcccaaggca acctcagcca tgtcgactgg
 121 ttttctgtcc acaaggagaa gcggacgctc atcttccgtg tgcgccaggg ccagggccag
 181 agcgaacctg ggagtacgga gcagcggctc agcctccagg acagaggggc tactctggcc
 241 ctgactcaag tcacccccca agacgagcgc atcttcttgt gccagggcaa gcgccctcgg
 301 tcccaggagt accgcatcca gctccgcgtc tacaaagctc cggaggagcc aaacatccag
 361 gtcaaccccc tgggcatccc tgtgaacagt aaggagcctg aggaggtcgc tacctgtgta
 421 gggaggaacg ggtaccccat tcctcaagtc atctggtaca agaatggccg gcctctgaag
 481 gaggagaaga accgggtcca cattcagtcg tcccagactg tggagtcgag tggtttgtac
 541 accttgcaga gtattctgaa ggcacagctg gttaaagaag acaaagatgc ccagttttac
 601 tgtgagctca actaccggct gcccagtggg aaccacatga aggagtccag ggaagtcacc
 661 gtccctgttt tctacccgac agaaaaagtg tggctggaag tggagcccgt gggaatgctg
 721 aaggaagggg accgcgtgga aatcaggtgt ttggctgatg gcaaccctcc accacacttc
 781 agcatcagca agcagaaccc cagcaccagg gaggcagagg aagagacaac caacgacaac
 841 ggggtcctgg tgctggagcc tgcccggaag gaacacagtg ggcgctatga atgtcagggc
 901 ctggacttgg acaccatgat atcgctgctg agtgaaccac aggaactact ggtgaactat
 961 gtgtctgacg tccgagtgag tcccgcagca cactgagaga caggaaggca gcagcctcac
1021 cctgacctgt gaggcagaga gtagccagga cctcgagttc cagtggctga gagaagagac
1081 aggccaggtg ctggaaaggg ggcctgtgct tcagttgcat gacctgaaac gggaggcagg
1141 aggcggctat cgctgcgtgg cgtctgtgcc cagcataccc ggcctgaacc gcacacagct
1201 ggtcaacgtg gccatttttg gcccccccttg gatggcattc aaggagagga aggtgtgggt
1261 gaaagagaat atggtgttga atctgtcttg tgaagcgtca gggcaccccc ggcccaccat
1321 ctcctggaac gtcaacggca cggcaagtga acaagaccaa gatccacagc gagtcctgag
1381 caccctgaat gtcctcgtga ccccggagct gttggagaca ggtgttgaat gcacggcctc
1441 caacgacctg ggcaaaaaca ccagcatcct cttcctggag ctggtcaatt taaccacccct
1501 cacaccagac tccaacacaa ccactggcct cagcacttcc actgccagtc ctcataccag
1561 agccaacagc acctccacag agagaaagct gccggagccg gagagccggg gcgtggtcat
1621 cgtggctgtg attgtgtgca tcctggtcct ggcggtgctg ggcgctgtcc tctatttcct
1681 ctataagaag ggcaagctgc cgtgcaggcg ctcagggaag caggagatca cgctgccccc
1741 gtctcgtaag agcgaacttg tagttgaagt taagtcagat aagctcccag aagagatggg
1801 cctcctgcag ggcagcagcg gtgacaagag ggctccggga gaccagggag agaaatacat
1861 cgatctgagg cattagcccc gaatcacttc agctcccttc cctgcctgga ccattcccag
1921 ctccctgctc actcttctct cagccaaagc ctccaaaggg actagagaga agcctcctgc
1981 tcccctcgcc tgcacacccc ctttcagagg gccactgggt taggacctga ggacctcact
2041 tggccctgca aggcccgctt ttcagggacc agtccaccac catctccacg ttgagtgaag
2101 ctcatcccaa gcaaggagcc ccagtctccc gagcgggtag gagagtttct tgtagaacgt
2161 gtttttttctt tacacacatt atggctgtaa atacctggct cctgccagca gctgagctgg
2221 gtagcctctc tgagctggga ttacaggtgt gagccactgc gcccagccaa
```

SEQ ID NO:49

```
   1 caaacttggt ggcaacttgc ctcccggtgc gggcgtctct cccccaccgt ctcaacatgc
```

Figure 10 (cont.)

```
  61 ttaggggtcc ggggcccggg ctgctgctgc tggccgtcct gtgcctgggg acagcggtgc
 121 cctccacggg agcctcgaag agcaagaggc aggctcagca aatggttcag ccccagtccc
 181 cggtggctgt cagtcaaagc aagcccggtt gttatgacaa tggaaaacac tatcagataa
 241 atcaacagtg ggagcggacc tacctaggca atgcgttggt ttgtacttgt tatggaggaa
 301 gccgaggttt taactgcgag agtaaacctg aagctgaaga gacttgcttt gacaagtaca
 361 ctgggaacac ttaccgagtg ggtgacactt atgagcgtcc taaagactcc atgatctggg
 421 actgtacctg catcggggct gggcgaggga gaataagctg taccatcgca aaccgctgcc
 481 atgaaggggg tcagtcctac aagattggtg acacctggag gagaccacat gagactggtg
 541 gttacatgtt agagtgtgtg tgtcttggta atggaaaagg agaatggacc tgcaagccca
 601 tagctgagaa gtgttttgat catgctgctg ggacttccta tgtggtcgga gaaacgtggg
 661 agaagcccta ccaaggctgg atgatggtag attgtacttg cctgggagaa ggcagcggac
 721 gcatcacttg cacttctaga aatagatgca acgatcagga cacaaggaca tcctatagaa
 781 ttggagacac ctggagcaag aaggataatc gaggaaacct gctccagtgc atctgcacag
 841 gcaacggccg aggagagtgg aagtgtgaga ggcacacctc tgtgcagacc acatcgagcg
 901 gatctggccc cttcaccgat gttcgtgcag ctgtttacca accgcagcct cacccccagc
 961 ctcctcccta tggccactgt gtcacagaca gtggtgtggt ctactctgtg gggatgcagt
1021 ggctgaagac acaaggaaat aagcaaatgc tttgcacgtg cctgggcaac ggagtcagct
1081 gccaagagac agctgtaacc cagacttacg gtggcaactc aaatggagag ccatgtgtct
1141 taccattcac ctacaatggc aggacgtgca gcacaacttc gaattatgag caggaccaga
1201 aatactcttt ctgcacagac cacactgttt tggttcagac tcgaggagga aattccaatg
1261 gtgccttgtg ccacttcccc ttcctataca acaaccacaa ttacactgat tgcacttctg
1321 agggcagaag agacaacatg aagtggtgtg ggaccacaca gaactatgat gccgaccaga
1381 agtttgggtt ctgccccatg gctgcccacg aggaaatctg cacaaccaat gaaggggtca
1441 tgtaccgcat tggagatcag tgggataagc agcatgacat gggtcacatg atgaggtgca
1501 cgtgtgttgg gaatggtcgt ggggaatgga catgcattgc ctactcgcag cttcgagatc
1561 agtgcattgt tgatgacatc acttacaatg tgaacgacac attccacaag cgtcatgaag
1621 aggggcacat gctgaactgt acatgcttcg gtcagggtcg ggcaggtgg aagtgtgatc
1681 ccgtcgacca atgccaggat tcagagactg ggacgtttta tcaaattgga gattcatggg
1741 agaagtatgt gcatggtgtc agataccagt gctactgcta tggccgtggc attggggagt
1801 ggcattgcca acctttacag acctatccaa gctcaagtgg tcctgtcgaa gtatttatca
1861 ctgagactcc gagtcagccc aactcccacc ccatccagtg gaatgcacca cagccatctc
1921 acatttccaa gtacattctc aggtggagac ctgtgagtat cccacccaga aaccttggat
1981 actgagtctc ctaatcttat caattctgat ggtttctttt tttcccagct tttgagccaa
2041 caactctgat taactattcc tatagcattt actatatttg tttagtgaac aaacaatatg
2101 tggtcaatta aattgacttg tagactg
```

SEQ ID NO:50

```
   1 acccccgcac ccagctccgc aggaccggcg ggcgcgcgcg ggctctggag gccacgggca
  61 tgatgcttcg ggtcctggtg ggggctgtcc tccctgccat gctactggct gccccaccac
 121 ccatcaacaa gctggcactg ttcccagata agagtgcctg gtgcgaagcc aagaacatca
 181 cccagatcgt gggccacagc ggctgtgagg ccaagtccat ccagaacagg gcgtgcctag
 241 gacagtgctt cagctacagc gtccccaaca ccttcccaca gtccacagag tccctggttc
 301 actgtgactc ctgcatgcca gcccagtcca tgtgggagat tgtgacgctg gagtgcccgg
 361 gccacgagga ggtgcccagg gtggacaagc tggtggagaa gatcctgcac tgtagctgcc
 421 aggcctgcgg caaggagcct agtcacgagg ggctgagcgt ctatgtgcag ggcgaggacg
 481 ggccgggatc ccagcccggc acccaccctc acccccatcc ccacccccat cctggcgggc
 541 agacccctga gcccgaggac ccccctgggg ccccccacac agaggaagag gggggctgagg
 601 actgaggccc ccccaactct tcctcccctc tcatcccccct gtggaatgtt gggtctcact
 661 ctctggggaa gtcaggggag aagctgaagc ccccctttgg cactggatgg acttggcttc
 721 agactcggac ttgaatgctg cccggttgcc atggagatct gaaggggcgg ggttagagcc
 781 aagctgcaca atttaatata ttcaagagtg gggggaggaa gcagaggtct tcagggctct
 841 tttttgggg ggggtggtct cttcctgtct ggcttctaga gatgtgcctg tgggaggggg
 901 aggaagttgg ctgagccatt gagtgctggg ggaggccatc caagatggca tgaatcgggc
 961 taaggtccct gggggtgcag atggtactgc tgaggtcccg ggcttagtgt gagcatcttg
```

Figure 10 (cont.)

```
1021 ccagcctcag gcttgaggga gggctgggct agaaagacca ctggcagaaa caggaggctc
1081 cggcccacag gtttccccaa ggcctctcac cccacttccc atctccaggg aagcgtcgcc
1141 ccagtggcac tgaagtggcc ctccctcagc ggaggggttt gggagtcagg cctgggcagg
1201 accctgctga ctcgtggcgc gggagctggg agccaggctc tccgggcctt tctctggctt
1261 ccttggcttg cctggtgggg gaaggggagg aggggaagaa ggaaagggaa gagtcttcca
1321 aggccagaag gagggggaca accccccaag accatccctg aagacgagca tccccctcct
1381 ctccctgtta gaaatgttag tgccccgcac tgtgccccaa gttctaggcc ccccagaaag
1441 ctgccagagc cggccgcctt ctcccctctc ccagggatgc tctttgtaaa tatcggatgg
1501 gtgtgggagt gaggggttac ctccctcgcc ccaaggttcc agaggcccta ggcgggatgg
1561 gctcgctgaa cctcgaggaa ctccaggacg aggaggacat gggacttgcg tggacagtca
1621 gggttcactt gggctctctc tagctcccca attctgcctg cctcctccct cccagctgca
1681 ctttaaccct agaaggtggg gacctggggg gagggacagg gcaggcgggc ccatgaagaa
1741 agcccctcgt tgcccagcac tgtctgcgtc tgctcttctg tgcccagggt ggctgccagc
1801 ccactgcctc ctgcctgggg tggcctggcc ctcctggctg ttgcgacgcg ggcttctgga
1861 gcttgtcacc attggacagt ctccctgatg gaccctcagt cttctcatga ataaattc
```

SEQ ID NO:51

```
   1 atccgtcccg gataagaccc gctgtctggc cctgagtagg gtgtgacctc cgcagccgca
  61 gaggaggagc gcagcccggc ctcgaagaac ttctgcttgg gtggctgaac tctgatcttg
 121 acctagagtc atggccatgg caaccaaagg aggtactgtc aaagctgctt caggattcaa
 181 tgccatggaa gatgcccaga ccctgaggaa ggccatgaaa gggctcggca ccgatgaaga
 241 cgccattatt agcgtccttg cctaccgcaa caccgcccag cgccaggaga tcaggacagc
 301 ctacaagagc accatcggca gggacttgat agacgacctg aagtcagaac tgagtggcaa
 361 cttcgagcag gtgattgtgg ggatgatgac gcccacggtg ctgtatgacg tgcaagagct
 421 gcgaagggcc atgaagggag ccggcactga tgagggctgc ctaattgaga tcctggcctc
 481 ccggacccct gaggagatcc ggcgcataag ccaaacctac cagcagcaat atggacggag
 541 ccttgaagat gacattcgct ctgacacatc gttcatgttc cagcgagtgc tggtgtctct
 601 gtcagctggt gggagggatg aaggaaatta tctggacgat gctctcgtga gacaggatgc
 661 ccaggacctg tatgaggctg gagagaagaa atgggggaca gatgaggtga aatttctaac
 721 tgttctctgt tcccggaacc gaaatcacct gttgcatggt ttgatgaata caaaaggata
 781 tcacagaagg atattgaaca gagtattaaa tctgaaacat ctggtagctt tgaagatgct
 841 ctgctggcta tagtaaagtg catgaggaac aaatctgcat atttgctgga aaagctctat
 901 aaatcgatga agggcttggg caccgatgat aacaccctca tcagagtgat ggtttctcga
 961 gcagaaattg acatgttgga tatccgggca cacttcaaga gactctatgg aaagtctctg
1021 tactcgttca tcaagggtga cacatctgga gactacagga aagtactgct tgttctctgt
1081 ggaggagatg attaaaataa aaatcccaga aggacaggag gattctcaac actttgaatt
1141 tttttaactt catttttcta cactgctatt atcattatct cagaatgctt atttccaatt
1201 aaaacgccta cagctgcctc ct
```

SEQ ID NO:52

```
   1 tggggcagcc gcgcccgcgg tgttttccgc ccggcgctgg cggctgctgc gcccgcggct
  61 ccccagtgcc ccgagtgccc cgcgggcccc gcgagcggga gtgggaccca gcccctaggc
 121 agaacccagg cgccgcgccc gggacgcccg cggagagagc cactcccgcc cacgtcccat
 181 ttcgcccctc gcgtccggag tcctcgtggc cagatctaac catgagctac cctggctatc
 241 ccccgccccc aggtggctac ccaccagctg caccaggtgg tggtccctgg ggaggtgctg
 301 cctaccctcc tccgcccagc atgcccccca tcgggctgga taacgtggcc acctatgcgg
 361 ggcagttcaa ccaggactat ctctcgggaa tggcggccaa catgtctggg acatttggag
 421 gagccaacat gcccaacctg taccctgggg cccctggggc tggctaccca ccagtgcccc
 481 ctggcggctt tgggcagccc ccctctgccc agcagcctgt tcctccctat gggatgtatc
 541 cacccccagg aggaaaccca ccctccagga tgccctcata tccgccatac ccaggggccc
 601 ctgtgccggg ccagcccatg ccaccccccg gacagcagcc cccaggggcc taccctgggc
 661 agccaccagt gacctaccct ggtcagcctc cagtgccact ccctgggcag cagcagccag
 721 tgccgagcta cccaggatac ccggggtctg ggactgtcac ccccgctgtg cccccaaccc
 781 agtttggaag ccgaggcacc atcactgatg ctcccggctt tgacccccctg cgagatgccg
```

Figure 10 (cont.)

```
 841 aggtcctgcg gaaggccatg aaaggcttcg ggacggatga gcaggccatc attgactgcc
 901 tggggagtcg ctccaacaag cagcggcagc agatcctact ttccttcaag acggcttacg
 961 gcaaggattt gatcaaagat ctgaaatctg aactgtcagg aaactttgag aagacaatct
1021 tggctctgat gaagacccca gtcctctttg acatttatga gataaaggaa gccatcaagg
1081 gggttggcac tgatgaagcc tgcctgattg agatcctcgc ttcccgcagc aatgagcaca
1141 tccgagaatt aaacagagcc tacaaagcag aattcaaaaa gaccctggaa gaggccattc
1201 gaagcgacac atcagggcac ttccagcggc tcctcatctc tctctctcag ggaaaccgtg
1261 atgaaagcac aaacgtggac atgtcactcg cccagagaga tgcccaggag ctgtatgcgg
1321 ccggggagaa ccgcctggga acagacgagt ccaagttcaa tgcggttctg tgctcccgga
1381 gccgggccca cctggtagca gttttcaatg agtaccagag aatgacaggc cgggacattg
1441 agaagagcat ctgccgggag atgtccgggg acctggagga gggcatgctg gccgtggtga
1501 aatgtctcaa gaatacccca gccttctttg cggagaggct caacaaggcc atgagggggg
1561 caggaacaaa ggaccggacc ctgattcgca tcatggtgtc tcgcagcgag accgacctcc
1621 tggacatcag atcagagtat aagcggatgt acggcaagtc gctgtaccac gacatctcgg
1681 gagatacttc aggggattac cggaagattc tgctgaagat ctgtggtggc aatgactgaa
1741 cagtgactgg tggctcactt ctgcccacct gccggcaaca ccagtgccag gaaaaggcca
1801 aaagaatgtc tgtttctaac aaatccacaa atagccccga gattcaccgt cctagagctt
1861 aggcctgtct tccacccctc ctgacccgta tagtgtgcca caggacctgg gtcggtctag
1921 aactctctca ggatgccttt tctaccccat ccctcacagc ctcttgctgc taaaatagat
1981 gtttcatttt tctgactcat gcaatcattc ccctttgcct gtggctaaga cttggcttca
2041 tttcgtcatg taattgtata tttttatttg gaggcatatt ttcttttctt acagtcattg
2101 ccagacagag gcatacaagt ctgtttgctg catacacatt tctggtgagg gcgactgggt
2161 gggtgaagca ccgtgtcctc gctgaggaga gaaagggagg cgtgcctgag aaggtagcct
2221 gtgcatctgg tgagtgtgtc acgagctttg ttactgccaa actcactcct ttttagaaaa
2281 aacaaaaaaa aagggccaga aagtcattcc ttccatcttc cttgcagaaa ccacgagaac
2341 aaagccagtt ccctgtcagt gacagggctt cttgtaattt gtggtatgtg ccttaaacct
2401 gaatgtctgt agccaaaact tgtttccaca ttaagagtca gccagctctg gaatggtctg
2461 gaaatgtc
```

SEQ ID NO:53

```
   1 tagacgcacc ctctgaagat ggtgactccc tcctgagaag ctggacccct tggtaaaaga
  61 caaggccttc tccaagaaga atatgaaagt gttactcaga cttatttgtt tcatagctct
 121 actgatttct tctctggagg ctgataaatg caaggaacgt gaagaaaaaa taattttagt
 181 gtcatctgca aatgaaattg atgttcgtcc ctgtcctctt aacccaaatg aacacaaagg
 241 cactataact tggtataaag atgacagcaa gacacctgta tctacagaac aagcctccag
 301 gattcatcaa cacaaagaga aactttggtt tgttcctgct aaggtggagg attcaggaca
 361 ttactattgc gtggtaagaa attcatctta ctgcctcaga attaaaataa gtgcaaaatt
 421 tgtggagaat gagcctaact tatgttataa tgcacaagcc atatttaagc agaaactacc
 481 cgttgcagga gacggaggac ttgtgtgccc ttatatggag ttttttaaaa atgaaaataa
 541 tgagttacct aaattacagt ggtataagga ttgcaaacct ctacttcttg acaatataca
 601 ctttagtgga gtcaaagata ggctcatcgt gatgaatgtg gctgaaaagc atagagggaa
 661 ctatacttgt catgcatcct acacatactt gggcaagcaa tatcctatta cccgggtaat
 721 agaatttatt actctagagg aaaacaaacc cacaaggcct gtgattgtga gcccagctaa
 781 tgagacaatg gaagtagact tgggatccca gatacaattg atctgtaatg tcaccggcca
 841 gttgagtgac attgcttact ggaagtggaa tgggtcagta attgatgaag atgacccagt
 901 gctaggggaa gactattaca gtgtggaaaa tcctgcaaac aaaagaagga gtaccctcat
 961 cacagtgctt aatatatcgg aaattgaaag tagattttat aaacatccat ttacctgttt
1021 tgccaagaat acacatggta tagatgcagc atatatccag ttaatatatc cagtcactaa
1081 tttccagaag cacatgattg gtatatgtgt cacgttgaca gtcataattg tgtgttctgt
1141 tttcatctat aaaatcttca agattgacat tgtgctttgg tacagggatt cctgctatga
1201 ttttctccca ataaaagctt cagatggaaa gacctatgac gcatatatac tgtatccaaa
1261 gactgttggg gaagggtcta cctctgactg tgatattttt gtgtttaaag tcttgcctga
1321 ggtcttggaa aaacagtgtg gatataagct gttcatttat ggaagggatg actacgttgg
```

Figure 10 (cont.)

```
1381 ggaagacatt gttgaggtca ttaatgaaaa cgtaaagaaa agcagaagac tgattatcat
1441 tttagtcaga gaaacatcag gcttcagctg gctgggtggt tcatctgaag agcaaatagc
1501 catgtataat gctcttgttc aggatggaat taaagttgtc ctgcttgagc tggagaaaat
1561 ccaagactat gagaaaatgc cagaatcgat taaattcatt aagcagaaac atggggctat
1621 ccgctggtca ggggacttta cacagggacc acagtctgca aagacaaggt tctggaagaa
1681 tgtcaggtac cacatgccag tccagcgacg gtcaccttca tctaaacacc agttactgtc
1741 accagccact aaggagaaac tgcaaagaga ggctcacgtg cctctcgggt agcatggaga
1801 agttgccaag agttctttag gtgcctcctg tcttatggcg ttgcaggcca ggttatgcct
1861 catgctgact tgcagagttc atggaatgta actatatcat cctttatccc tgaggtcacc
1921 tggaatcaga ttattaaggg aataagccat gacgtcaata gcagcccagg gcacttcaga
1981 gtagagggct tgggaagatc ttttaaaaag gcagtaggcc cggtgtggtg gctcacgcct
2041 ataatcccag cactttggga ggctgaagtg ggtggatcac cagaggtcag gagttcgaga
2101 ccagcccagc caacatggca aaaccccatc tctactaaaa atacaaaaat gagctaggca
2161 tggtggcaca cgcctgtaat cccagctaca cctgaggctg aggcaggaga attgcttgaa
2221 ccggggagac ggaggttgca gtgagccgag tttgggccac tgcactctag cctggcaaca
2281 gagcaagact ccgtctcaaa aaaagggcaa taaatgccct ctctgaatgt ttgaactgcc
2341 aagaaaaggc atggagacag cgaactagaa gaaagggcaa gaaggaaata gccaccgtct
2401 acagatggct tagttaagtc atccacagcc caagggcggg gctatgcctt gtctggggac
2461 cctgtagagt cactgaccct ggagcggctc tcctgagagg tgctgcaggc aaagtgagac
2521 tgacacctca ctgaggaagg gagacatatt cttggagaac tttccatctg cttgtatttt
2581 ccatacacat ccccagccag aagttagtgt ccgaagaccg aattttattt tacagagctt
2641 gaaaactcac ttcaatgaac aaagggattc tccaggattc caaagttttg aagtcatctt
2701 agctttccac aggagggaga gaacttaaaa aagcaacagt agcagggaat tgatccactt
2761 cttaatgctt tcctccctgg catgaccatc ctgtcctttg ttattatcct gcattttacg
2821 tctttggagg aacagctccc tagtggcttc ctccgtctgc aatgtccctt gcacagccca
2881 cacatgaacc atccttccca tgatgccgct cttctgtcat cccgctcctg ctgaaacacc
2941 tcccaggggc tccacctgtt caggagctga agcccatgct ttcccaccag catgtcactc
3001 ccagaccacc tccctgccct gtcctccagc ttcccctcgc tgtcctgctg tgtgaattcc
3061 caggttggcc tggtggccat gtcgcctgcc cccagcactc ctctgtctct gctcttgcct
3121 gcacccttcc tcctcctttg cctaggaggc cttctcgcat ttctctagc tgatcagaat
3181 tttaccaaaa ttcagaacat cctccaattc cacagtctct gggagacttt ccctaagagg
3241 cgacttcctc tccagccttc tctctctggt caggcccact gcagagatgg tggtgagcac
3301 atctgggagg ctggtctccc tccagctgga attgctgctc tctgagggag aggctgtggt
3361 ggctgtctct gtccctcact gccttccagg agcaatttgc acatgtaaca tagatttatg
3421 taatgcttta tgtttaaaaa cattccccaa ttatcttatt taatttttgc aattattcta
3481 attttatata tagagaaagt gacctatttt ttaaaaaaat cacactctaa gttctattga
3541 acctaggact tgagcctcca tttctggctt ctagtctggt gttctgagta cttgatttca
3601 ggtcaataac ggtcccccct cactccacac tggcacgttt gtgagaagaa atgacatttt
3661 gctaggaagt gaccgagtct aggaatgctt ttattcaaga caccaaattc caaacttcta
3721 aatgttggaa ttttcaaaaa ttgtgtttag attttatgaa aaactcttct actttcatct
3781 attctttccc tagaggcaaa catttcttaa aatgtttcat tttcattaaa aatgaaagcc
3841 aaatttatat gccaccgatt gcaggacaca agcacagttt taagagttgt atgaacatgg
3901 agaggacttt tggtttttat atttctcgta tttaatatgg gtgaacacca acttttattt
3961 ggaataataa ttttcctcct aaacaaaaac acattgagtt taagtctctg actcttgcct
4021 ttccacctgc tttctcctgg gcccgctttg cctgcttgaa ggaacagtgc tgttctggag
4081 ctgctgttcc aacagacagg gcctagcttt catttgacac acagactaca gccagaagcc
4141 catggagcag ggatgtcacg tcttgaaaag cctattagat gttttacaaa tttaattttg
4201 cagattattt tagtctgtca tccagaaaat gtgtcagcat gcatagtgct aagaaagcaa
4261 gccaatttgg aaacttaggt tagtgacaaa attggccaga gagtgggggt gatgatgacc
4321 aagaattaca agtagaatgg cagctggaat ttaaggaggg acaagaatca atggataagc
4381 gtgggtggag gaagatccaa acagaaaagt gcaaagttat tccccatctt ccaagggttg
4441 aattctggag gaagaagaca cattcctagt tccccgtgaa cttcctttga cttattgtcc
4501 ccactaaaac aaaacaaaaa acttttaatg ccttccacat taattagatt ttcttgcagt
4561 ttttttatgg cattttttta aagatgccct aagtgttgaa gaagagtttg caaatgcaac
```

Figure 10 (cont.)

```
4621 aaaatattta attaccggtt gttaaaactg gtttagcaca atttatattt tccctctctt
4681 gcctttctta tttgcaataa aaggtattga gccatttttt aaatgacatt tttgataaat
4741 tatgtttgta ctagttgatg aaggagtttt ttttaacctg tttatataat tttgcagcag
4801 aagccaaatt ttttgtatat taaagcacca aattcatgta cagcatgcat cacggatcaa
4861 tagactgtac ttattttcca ataaaatttt caaactttgt actgtta
```

SEQ ID NO:54

```
  1 ccctgcactc tcgctctcct gccccacccc gaggtaaagg gggcgactaa gagaagatgg
 61 tgttgctcac cgcggtcctc ctgctgctgg ccgcctatgc ggggccggcc cagagcctgg
121 gctccttcgt gcactgcgag ccctgcgacg agaaagccct ctccatgtgc ccccccagcc
181 ccctgggctg cgagctggtc aaggagccgg gctgcggctg ctgcatgacc tgcgccctgg
241 ccgaggggca gtcgtgcggc gtctacaccg agcgctgcgc ccaggggctg cgctgcctcc
301 cccggcagga cgaggagaag ccgctgcacg ccctgctgca cggccgcggg gtttgcctca
361 acgaaaagag ctaccgcgag caagtcaaga tcgagagaga ctcccgtgag cacgaggagc
421 ccaccacctc tgagatggcc gaggagacct actcccccaa gatcttccgg cccaaacaca
481 cccgcatctc cgagctgaag gctgaagcag tgaagaagga ccgcagaaag aagctgaccc
541 agtccaagtt tgtcggggga gccgagaaca ctgcccaccc ccggatcatc tctgcacctg
601 agatgagaca ggagtctgag cagggcccct gccgcagaca catggaggct tccctgcagg
661 agctcaaagc cagcccacgc atggtgcccc gtgctgtgta cctgcccaat tgtgaccgca
721 aaggattcta caagagaaag cagtgcaaac cttcccgtgg ccgcaaacgt ggcatctgct
781 ggtgcgtgga caagtacggg atgaagctgc caggcatgga gtacgttgac ggggactttc
841 agtgccacac cttcgacagc agcaacgttg agtgatgcgt cccccccaa cctttccctc
901 accccctccc acccccagcc ccgactccag ccagcgcctc cctccacccc aggacgccac
961 tcatttcatc tcatttaagg gaaaaatata tatctatcta tttg
```

SEQ ID NO:55

```
  1 cgcagcgggt cctctctatc tagctccagc ctctcgcctg cgccccactc cccgcgtccc
 61 gcgtcctagc cgaccatggc cgggcccctg cgcgccccgc tgctcctgct ggccatcctg
121 gccgtggccc tggccgtgag ccccgcggcc ggctccagtc ccggcaagcc gccgcgccta
181 gtgggaggcc ccatggacgc cagcgtggag gaggagggtg tgcggcgtgc actggacttt
241 gccgtcggcg agtacaacaa agccagcaac gacatgtacc acagccgcgc gctgcaggtg
301 gtgcgcgccc gcaagcagat cgtagctggg gtgaactact tcttggacgt ggagctgggc
361 cgaaccacgt gtaccaagac ccagcccaac ttggacaact gccccttcca tgaccagcca
421 catctgaaaa ggaaagcatt ctgctctttc cagatctacg ctgtgccttg gcagggcaca
481 atgaccttgt cgaaatccac ctgtcaggac gcctaggggt ctgtaccggg ctggcctgtg
541 cctatcacct cttatgcaca cctcccaccc cctgtattcc cacccctgga ctggtggccc
601 ctgccttggg gaaggtctcc ccatgtgcct gcaccaggag acagacagag aaggcagcag
661 gcggcctttg ttgctcagca aggggctctg ccctccctcc ttccttcttg cttctcatag
721 ccccggtgtg cggtgcatac acccccacct cctgcaataa aatagtagca tc
```

SEQ ID NO:56

```
  1 gaaagatgga tcactccagc tcaaagagaa catgtgggaa tgaaaggaca ggctgggccc
 61 aaaggagaaa agggtgatgc tggggaggag cttcctggcc ctcctgaacc ttctgggcct
121 gttggaccca cggcaggagc agaagcagag ggctctggcc taggctgggg ctcggacgtc
181 ggctctggct ctggtgacct ggtgggcagt gagcagctgc tgagaggtcc tccaggaccc
241 ccagggccac ctggcttacc tgggattcca ggaaaaccag gaactgatgt tttcatggga
301 ccccctggat ctcctggaga ggatggacct gctggtgaac ctgggccccc gggccctgag
361 ggacagcctg gagttgatgg agccaccggc cttcccggga tgaaagggga gaagggagca
421 agagggccta atggctcagt tggtgaaaag ggtgaccctg gcaacagagg cttacctgga
481 cccccgggga aaaagggaca agctggccct cctggggtca tgggaccccc agggcctcct
541 ggacccccctg ggcccccagg ccctggatgc acaatgggac ttggattcga ggataccgaa
601 ggctctggaa gcacccagct attgaatgaa cccaaactct ccagaccaac ggctgcaatt
```

Figure 10 (cont.)

```
661  ggtctcaaag gagagaaagg agaccgggga cccaagggag aaagggggat ggatggagcc
721  agtattgtgg gaccccctgg gccgagaggg ccacctgggc acatcaaggt cttgtctaat
781  tccttgatca atatcaccca tggattcatg aatttctcgg acattcctga gctggtgggg
841  cctccggggc cggacgggtt gcctgggctg ccaggatttc cagggtccta gaggaccaaa
901  aggtgacact ggtttacctg gctttccagg actaaaagga gaacagggcg agaagggaga
961  gccgggtgcc atcctgacag aggacattcc tctggaaagg ctgatgggga aaaagggtga
1021 acctggaatg catggagccc caggaccaat ggggcccaaa ggaccaccag gacataaagg
1081 agaatttggc cttcccgggc gacctggtcg cccaggactg aatggcctca agggtaccaa
1141 aggagatcca ggggtcatta tgcagggccc acctggctta cctggccctc caggcccccc
1201 tgggccacct ggagctgtga ttaacatcaa aggagccatt ttcccaatac ccgtccgacc
1261 acactgcaaa atgccagttg atactgctca tcctgggagt ccagagctca tcacttttca
1321 cggtgttaaa ggagagaaag gatcctgggg tcttcctggc tcaaagggag aaaaaggcga
1381 ccagggagcc cagggaccac caggtcctcc acttgatcta gcttacctga gacactttct
1441 gaacaacttg aagggggaga atggagacaa ggggttcaaa ggtgaaaaag gagaaaaagg
1501 agacattaat ggcagcttcc ttatgtctgg gcctccaggc ctgcccggaa atccaggccc
1561 ggctggccaa aaaggggaga cagtcgttgg gccccaagga cccccaggtg ctcctggtct
1621 gcctgggcca cctggctttg gaagacctgg tgatcctggg ccaccggggc ccccggggcc
1681 accaggacct ccagctatcc tgggagcagc tgtggccctt ccaggtcccc ctggccctcc
1741 aggacagcca gggcttcccg gatccagaaa cctggtcaca gcattcagca acatggatga
1801 catgctgcag aaagcgcatt tggttataga aggaacattc atctacctga gggacagcac
1861 tgagtttttc attcgtgtta gagatggctg gaaaaaatta cagctgggag aactgatccc
1921 cattcctgcc gacagccctc cacccccctgc gctttccagc aacccacatc agcttctgcc
1981 tccaccaaac cctatttcaa gtgccaatta tgagaagcct gctctgcatt tggctgctct
2041 gaacatgcca ttttctgggg acattcgagc tgattttcag tgcttcaagc aggccagagc
2101 tgcaggactg ttgtccacct accgagca
```

SEQ ID NO:57

```
1    tagaaattgt taattttaac aatccagagc aggccaacga ggctttgctc tcccgacccg
61   aactaaaggt ccctcgctcc gtgcgctgct acgagcggtg tctcctgggg ctccaatgca
121  gcgagctgtg cccgaggggt tcggaaggcg caagctgggc agcgacatgg ggaacgcgga
181  gcgggctccg gggtctcgga gctttgggcc agtacccacg ctgctgctgc tcgccgcggc
241  gctactggcc gtgtcggacg cactcgggcg cccctccgag gaggacgagg agctagtggt
301  gccggagctg gagcgcgccc cgggacacgg gaccacgcgc ctccgcctgc acgcctttga
361  ccagcagctg gatctggagc tgcggcccga cagcagcttt ttggcgcccg gcttcacgct
421  ccagaacgtg gggcgcaaat ccgggtccga gacgccgctt ccggaaaccg acctggcgca
481  ctgcttctac tccggcaccg tgaatggcga tcccagctcg gctgccgccc tcagcctctg
541  cgagggcgtg cgcggcgcct tctacctgct gggggaggcg tatttcatcc agccgctgcc
601  cgccgccagc gagcgcctcg ccaccgccgc cccaggggag aagccgccgg caccactaca
661  gttccacctc ctgcggcgga atcggcaggg cgacgtcggc ggcacgtgcg gggtcgtgga
721  cgacgagccc cggccgactg ggaaagcgga gaccgaagac gaggacgaag ggactgaggg
781  cgaggacgaa ggggctcagt ggtcgccgca ggacccggca ctgcaaggcg taggacagcc
841  cacaggaact ggaagcataa gaaagaagcg atttgtgtcc agtcaccgct atgtggaaac
901  catgcttgtg gcagaccagt cgatggcaga attccacggc agtggtctaa agcattacct
961  tctcacgttg ttttcggtgg cagccagatt gtacaaacac cccagcattc gtaattcagt
1021 tagcctggtg gtggtgaaga tcttggtcat ccacgatgaa cagaaggggc cggaagtgac
1081 ctccaatgct gccctcactc tgcggaactt ttgcaactgg cagaagcagc acaacccacc
1141 cagtgaccgg gatgcagagc actatgacac agcaattctt ttcaccagac aggacttgtg
1201 tgggtcccag acatgtgata ctcttgggat ggctgatgtt ggaactgtgt gtgatccgag
1261 cagaagctgc tccgtcatag aagatgatgg tttacaagct gccttcacca cagcccatga
1321 attaggccac gtgtttaaca tgccacatga tgatgcaaag cagtgtgcca gccttaatgg
1381 tgtgaaccag gattcccaca tgatggcgtc aatgctttcc aacctggacc acagccagcc
1441 ttggtctcct tgcagtgcct acatgattac atcatttctg gataatggtc atggggaatg
1501 tttgatggac aagcctcaga atcccataca gctcccaggc gatctccctg gcacctcgta
1561 cgatgccaac cggcagtgcc agtttacatt tggggaggac tccaaacact gccccgatgc
```

Figure 10 (cont.)

```
1621 agccagcaca tgtagcacct tgtggtgtac cggcacctct ggtggggtgc tggtgtgtca
1681 aaccaaacac ttcccgtggg cggatggcac cagctgtgga gaagggaaat ggtgtatcaa
1741 cggcaagtgt gtgaacaaaa ccgacagaaa gcattttgat acgccttttc atggaagctg
1801 gggaatgtgg gggccttggg gagactgttc gagaacgtgc ggtggaggag tccagtacac
1861 gatgagggaa tgtgacaacc cagtcccaaa gaatggaggg aagtactgtg aaggcaaacg
1921 agtgcgctac agatcctgta accttgagga ctgtccagac aataatggaa aaacctttag
1981 agaggaacaa tgtgaagcac acaacgagtt ttcaaaagct tcctttggga gtgggcctgc
2041 ggtggaatgg attcccaagt acgctggcgt ctcaccaaag gacaggtgca agctcatctg
2101 ccaagccaaa ggcattggct acttcttcgt tttgcagccc aaggttgtag atggtactcc
2161 atgtagccca gattccacct ctgtctgtgt gcaaggacag tgtgtaaaag ctggttgtga
2221 tcgcatcata gactccaaaa agaagtttga taaatgtggt gtttgcgggg gaaatggatc
2281 tacttgtaaa aaaatatcag gatcagttac tagtgcaaaa cctggatatc atgatatcat
2341 cacaattcca actggagcca ccaacatcga agtgaaacag cggaaccaga ggggatccag
2401 gaacaatggc agctttcttg ccatcaaagc tgctgatggc acatatattc ttaatggtga
2461 ctacactttg tccaccttag agcaagacat tatgtacaaa ggtgttgtct tgaggtacag
2521 cggctcctct gcggcattgg aaagaattcg cagctttagc cctctcaaag agcccttgac
2581 catccaggtt cttactgtgg gcaatgccct tcgacctaaa attaaataca cctacttcgt
2641 aaagaagaag aaggaatctt tcaatgctat ccccactttt tcagcatggg tcattgaaga
2701 gtggggcgaa tgttctaagt catgtgaatt gggttggcag agaagactgg tagaatgccg
2761 agacattaat ggacagcctg cttccgagtg tgcaaaggaa gtgaagccag ccagcaccag
2821 accttgtgca gaccatccct gcccccagtg gcagctgggg gagtggtcat catgttctaa
2881 gacctgtggg aagggttaca aaaaaagaag cttgaagtgt ctgtcccatg atggaggggt
2941 gttatctcat gagagctgtg atcctttaaa gaaacctaaa catttcatag acttttgcac
3001 aatggcagaa tgcagttaag tggtttaagt ggtgttagct ttgagggcaa ggcaaagtga
3061 ggaagggctg gtgcagggaa agcaagaagg ctggagggat ccagcgtatc ttgccagtaa
3121 ccagtgaggt gtatcagtaa ggtgggatta tgggggtaga tagaaaagga gttgaatcat
3181 cagagtaaac tgccagttgc aaatttgata ggatagttag tgaggattat taacctctga
3241 gcagtgatat agcataataa agccccgggc attattatta ttatttcttt tgttacatct
3301 attacaagtt tagaaaaaac aaagcaattg tcaaaaaaag ttagaactat tacaacccct
3361 gtttcctggt acttatcaaa tacttagtat catgggggtt gggaaatgaa aagtaggaga
3421 aaagtgagat tttactaaga cctgttttac tttacctcac taacaatggg gggagaaagg
3481 agtacaaata ggatctttga ccagcactgt ttatggctgc tatggtttca gagaatgttt
3541 atacattatt tctaccgaga attaaaactt cagattgttc aacatgagag aaaggctcag
3601 caacgtgaaa taacgcaaat ggcttcctct ttcctttttt ggaccatctc agtctttatt
3661 tgtgtaattc attttgagga aaaaacaact ccatgtattt attcaagtgc attaaagtct
3721 acaatggaaa aaaagcagtg aagcattaga tgctggtaaa agctagagga gacacaatga
3781 gcttagtacc tccaacttcc tttctttcct accatgtaac cctgctttgg gaatatggat
3841 gtaaagaagt aacttgtgtc tcatgaaaat cagtacaatc acacaaggag gatgaaacgc
3901 cggaacaaaa atgaggtgtg tagaacaggg tcccacaggt ttggggacat tgagatcact
3961 tgtcttgtgg tggggaggct gctgaggggt agcaggtcca tctccagcag ctggtccaac
4021 agtcgtatcc tggtgaatgt ctgttcagct cttctgtgag aatatgattt tttccatatg
4081 tatatagtaa aatatgttac tataaattac atgtacttta taagtattgg tttgggtgtt
4141 ccttccaaga aggactatag ttagtaataa atgcctataa taacatattt atttttatac
4201 atttatttct aatgaaaaaa acttttaaat tatatcgctt ttgtggaagt gcatataaaa
4261 tagagtattt atacaatata tgttactaga aataaaagaa cacttttgg
```

SEQ ID NO:58

```
  1 gggcccgggc gcgcgggagc gggagcggcc gggggagccg gagcgcacca tggaggcggc
 61 ggcaggcggc cgcggctgtt tccagccgca cccggggctg cagaagacgc tggagcagtt
121 ccacctgagc tccatgagct cgctgggcgg cccggccgct ttctcggcgc gctgggcgca
181 ggaggcctac aagaaggaga gcgccaagga ggcgggcgcg gccgcggtgc cggcgccggt
241 gcccgcagcc accgagccgc cgcccgtgct gcacctgccc gccatccagc cgccgccgcc
301 cgtgctgccc gggcccttct tcatgccgtc cgaccgctcc accgagcgct gcgagaccgt
361 actggaaggc gagaccatct cgtgcttcgt ggtgggaggc gagaagcgcc tgtgtctgcc
```

Figure 10 (cont.)

```
 421 gcagattctc aactcggtgc tgcgcgactt ctcgctgcag cagatcaacg cggtgtgcga
 481 cgagctccac atctactgct cgcgctgcac ggccgaccag ctggagatcc tcaaagtcat
 541 gggcatcctg cccttctcgg cgccctcgtg cgggctcatc accaagacgg acgccgagcg
 601 cctgtgcaac gcgctgctct acggcggcgc ctacccgccg ccctgcaaga aggagctggc
 661 cgccagcctg gcgctgggcc tggagctcag cgagcgcagc gtccgcgtgt accacgagtg
 721 cttcggcaag tgtaaggggc tgctggtgcc cgagctctac agcagcccga gcgccgcctg
 781 catccagtgc ctggactgcc gcctcatgta cccgccgcac aagttcgtgg tgcactcgca
 841 caaggccctg gagaaccgga cctgccactg ggcttcgac tcggccaact ggcgggccta
 901 catcctgctg agccaggatt acacgggcaa ggaggagcag gcgcgcctcg gccgctgcct
 961 ggacgacgtg aaggagaaat tcgactatgg caacaagtac aagcggcggg tgccccgggt
1021 ctcctctgag cctccggcct ccataagacc caaaacagat gacacctctt cccagtcccc
1081 cgcgccttcc gaaaaggaca agccgtccag ctggctgcgg accttggccg gctcttccaa
1141 taagagcctg ggctgtgttc accctcgcca gcgcctctct gctttccgac cctggtcccc
1201 cgcagtgtca gcgagtgaga aagagctctc cccacacctc ccggccctca tccgagacag
1261 cttctactcc tacaagagct ttgagacagc cgtggcgccc aacgtggccc tcgcaccgcc
1321 ggcccagcag aaggttgtga gcagccctcc gtgtgccgcc gccgtctccc gggcccccga
1381 gcctctcgcc acttgcaccc agcctcggaa gcggaagctg actgtggaca ccccaggagc
1441 cccagagacg ctggcgcccg tggctgcccc agaggaggac aaggactcgg aggcggaggt
1501 ggaagttgaa agcagggagg aattcacctc ctccttgtcc tcgctctctt ccccgtcctt
1561 tacctcatcc agctccgcca aggacctggg ctccccgggt gcgcgtgccc tgccctcggc
1621 cgtccctgat gctgcggccc ctgccgacgc cccccagtggg ctggaggcgg agctggagca
1681 cctgcggcag gcactggagg gcggcctgga caccaaggaa gccaaagaga agttcctgca
1741 tgaggtggtc aagatgcgcg tgaagcagga ggagaagctc agcgcagccc tgcaggccaa
1801 gcgcagcctc caccaggagc tggagttcct acgcgtggcc aagaaggaga agctgcggga
1861 ggccacggag gccaagcgta acctgcggaa ggagatcgag cgtctccgcg ccgagaacga
1921 gaagaagatg aaagaggcca acgagtcacg gctgcgcctg aagcgggagc tggagcaggc
1981 gcggcaggcc cgggtgtgcg acaagggctg cgaggcgggc cgcctgcgcg ccaagtactc
2041 ggcccagatc gaagacctgc aggtgaagct gcagcacgcg gaggcggacc gggagcagct
2101 gcgggccgac ctgctgcggg agcgcgaggc ccgggagcac ctggagaagg tggtgaagga
2161 gctgcaggaa cagctgtggc cgcgggcccg ccccgaggct gcgggcagcg agggcgctgc
2221 ggagctggag ccgtagattc cgtgcctgcc gccgcagcgc cgccgacaac gcgggtgcag
2281 gggggcgcgg ctgggcggtg cagctccgcc cggctccgcc cctgcagccc acacagcaca
2341 acgtcttacc gtgcctatta ccaagcgagt gtttgtaacc atgtagtttt ggaacccact
2401 gcaaaatttt ctactggcca agttcaagtg agtaagccgc gtcccccaac tacagctgga
2461 gacggggcca gctcggcggc ctgctggtcc tctgcttgct ggaacattct aacatttaca
2521 cttttgttat aagctattta aaaccagtaa ggagacttga aattcagaaa atcaacacat
2581 ttttaaatga ctaacttcta aaagccccaa cacatgacgc catctgaaga cccgcaacgg
2641 agtgggggtg gcggccgccc caccctcccc acccggggaa gccatcacag ctcatctgcc
2701 cgcggctgcg tgaggacagc aggggttttt cttcagagtc tatttttca gcgacaagga
2761 cccaggtctt cctgctgctg ccagggagag cagggacagt gccgcgtgcg agatgagctc
2821 gaacactgcc cgccttactg ccgcctaccc cgcccgccac gccgccgtcg atgccagcgc
2881 tgtccccacg ggtaccagga agtgcagagc cgcacaggag ctgccccgga gctgagggga
2941 cggtcttcgg ctcctctgca ccccgtgatt ctgcccacgc tcctccacca cgaggcactg
3001 acctgcgtcg ggtggtgacc gtggctggcg gtcacgccct cagcccctcc gggcacacgt
3061 gccgcctgac cgggcgaccc ttttcagttc ggcaaacgtc gctcccttca ttttgggact
3121 gaggctgcag cattggaaca aaagagcatt atttcaattt ttctttcttt ttttttgttc
3181 gttcatttaa acgtatattt agaactgcac tttgtccaca accttcccctt ctctttctat
3241 tccccagtga actgaggttt ttaccgattt atagagcagt caaatccgaa gtgctcgagt
3301 gcttagaaac cccctctggt gcttggttga acaagggaat cacaagaaaa cgaaaatgca
3361 aaaactgaac ttcgggggtc gttctgtgcc ttccagcatc ttgtacagca aatcctgact
3421 cgtgtctttt tacccccaag atatctgtct tcagtagcga ctgaatctgc cactctcaga
3481 ataagttc
```

SEQ Id NO:59

Figure 10 (cont.)

```
   1 gccgccgccg ccatccgccg ccgcagccag cttccgccgc cgcaggaccg gcccctgccc
  61 cagcctccgc agccgcggcg cgtccacgcc cgcccgcgcc cagggcgagt cggggtcgcc
 121 gcctgcacgc ttctcagtgt tccccgcgcc ccgcatgtaa cccggccagg cccccgcaac
 181 tgtgtcccct gcagctccag ccccgggctg catccccccg ccccgacacc agctctccag
 241 cctgctcgtc caggatggcc gcggccaagg ccgagatgca gctgatgtcc ccgctgcaga
 301 tctctgaccc gttcggatcc tttcctcact cgcccaccat ggacaactac cctaagctgg
 361 aggagatgat gctgctgagc aacggggctc cccagttcct cggcgccgcc ggggccccag
 421 agggcagcgg cagcaacagc agcagcagca gcagcggggg cggtggaggc ggcgggggcg
 481 gcagcaacag cagcagcagc agcagcacct tcaaccctca ggcggacacg ggcgagcagc
 541 cctacgagca cctgaccgca gagtcttttc ctgacatctc tctgaacaac gagaaggtgc
 601 tggtggagac cagttacccc agccaaacca ctcgactgcc ccccatcacc tatactggcc
 661 gcttttccct ggagcctgca cccaacagtg gcaacacctt gtggcccgag cccctcttca
 721 gcttggtcag tggcctagtg agcatgacca acccaccggc ctcctcgtcc tcagcaccat
 781 ctccagcggc ctcctccgcc tccgcctccc agagcccacc cctgagctgc gcagtgccat
 841 ccaacgacag cagtcccatt tactcagcgg cacccacctt ccccacgccg aacactgaca
 901 ttttccctga gccacaaagc caggccttcc cgggctcggc agggacagcg ctccagtacc
 961 cgcctcctgc ctaccctgcc gccaagggtg gcttccaggt tcccatgatc cccgactacc
1021 tgtttccaca gcagcagggg gatctgggcc tgggcacccc agaccagaag cccttccagg
1081 gcctggagag ccgcacccag cagccttcgc taacccctct gtctactatt aaggcctttg
1141 ccactcagtc gggctcccag gacctgaagg ccctcaatac cagctaccag tcccagctca
1201 tcaaacccag ccgcatgcgc aagtacccca accggcccag caagacgccc ccccacgaac
1261 gcccttacgc ttgcccagtg gagtcctgtg atcgccgctt ctcccgctcc gacgagctca
1321 cccgccacat ccgcatccac acaggccaga agcccttcca gtgccgcatc tgcatgcgca
1381 acttcagccg cagcgaccac ctcaccaccc acatccgcac ccacacaggc gaaaagccct
1441 tcgcctgcga catctgtgga agaaagtttg ccaggagcga tgaacgcaag aggcatacca
1501 agatccactt gcggcagaag gacaagaaag cagacaaaag tgttgtggcc tcttcggcca
1561 cctcctctct ctcttcctac ccgtccccgg ttgctacctc ttacccgtcc ccggttacta
1621 cctcttatcc atccccggcc accacctcat acccatcccc tgtgcccacc tccttctcct
1681 ctcccggctc ctcgacctac ccatcccctg tgcacagtgg cttcccctcc ccgtcggtgg
1741 ccaccacgta ctcctctgtt ccccctgctt tcccggccca ggtcagcagc ttcccttcct
1801 cagctgtcac caactccttc agcgcctcca cagggctttc ggacatgaca gcaacctttt
1861 ctcccaggac aattgaaatt tgctaaaggg aaaggggaaa gaaagggaaa agggagaaaa
1921 agaaacacaa gagacttaaa ggacaggagg aggagatggc cataggagag gagggttcct
1981 cttaggtcag atggaggttc tcagagccaa gtcctccctc tctactggag tggaaggtct
2041 attggccaac aatcctttct gcccacttcc ccttccccaa ttactattcc ctttgacttc
2101 agctgcctga aacagccatg tccaagttct tcacctctat ccaaagaact tgatttgcat
2161 ggattttgga taaatcattt cagtatcatc tccatcatat gcctgacccc ttgctccctt
2221 caatgctaga aaatcgagtt ggcaaaatgg ggtttgggcc cctcagagcc ctgccctgca
2281 cccttgtaca gtgtctgtgc catggatttc gtttttcttg ggtactctt gatgtgaaga
2341 taatttgcat attctattgt attatttgga gttaggtcct cacttggggg aaaaaaaaaa
2401 aagaaaagcc aagcaaacca atggtgatcc tctattttgt gatgatgctg tgacaataag
2461 tttgaacctt ttttttgaa acagcagtcc cagtattctc agagcatgtg tcagagtgtt
2521 gttccgttaa cctttttgta aatactgctt gaccgtactc tcacatgtgg caaaatatgg
2581 tttggttttt cttttttttt tttttgaaa gtgtttttc ttcgtccttt tggtttaaaa
2641 agtttcacgt cttggtgcct tttgtgtgat gcgccttgct gatggcttga catgtgcaat
2701 tgtgagggac atgctcacct ctagccttaa gggggcagg gagtgatgat ttgggggagg
2761 ctttgggagc aaaataagga agagggctga gctgagcttc ggttctccag aatgtaagaa
2821 aacaaaatct aaaacaaaat ctgaactctc aaaagtctat ttttttaact gaaaatgtaa
2881 atttataaat atattcagga gttggaatgt tgtagttacc tactgagtag gcggcgattt
2941 ttgtatgtta tgaacatgca gttcattatt ttgtggttct attttacttt gtacttgtgt
3001 ttgcttaaac aaagtgactg tttggcttat aaacacattg aatgcgcttt attgcccatg
3061 ggatatgtgg tgtatatcct tccaaaaaat taaaacgaaa ataaagta
```

SEQ ID NO:60

Figure 10 (cont.)

```
   1 cattcataag actcagagct acggccacgg cagggacacg cggaaccaag acttggaaac
  61 ttgattgttg tggttcttct tgggggttat gaaatttcat taatcttttt tttttccggg
 121 gagaaagttt ttggaaagat tcttccagat atttcttcat tttcttttgg aggaccgact
 181 tacttttttt ggtcttcttt attactcccc tcccccgtg ggacccgccg gacgcgtgga
 241 ggagaccgta gctgaagctg attctgtaca gcgggacagc gctttctgcc cctgggggag
 301 caacccctcc ctcgcccctg ggtcctacgg agcctgcact ttcaagaggt acagcggcat
 361 cctgtggggg cctgggcacc gcaggaagac tgcacagaaa ctttgccatt gttggaacgg
 421 gacgttgctc cttccccgag cttccccgga cagcgtactt tgaggactcg ctcagctcac
 481 cggggactcc cacggctcac cccggacttg caccttactt ccccaacccg gccatagcct
 541 tggcttcccg gcgacctcag cgtggtcaca ggggcccccc tgtgcccagg gaaatgtttc
 601 aggctttccc cggagactac gactccggct cccggtgcag ctcctcaccc tctgccgagt
 661 ctcaatatct gtcttcggtg gactccttcg gcagtccacc caccgccgcg gcctcccagg
 721 agtgcgccgg tctcggggaa atgcccggtt ccttcgtgcc cacggtcacc gcgatcacaa
 781 ccagccagga cctccagtgg cttgtgcaac ccaccctcat ctcttccatg gcccagtccc
 841 aggggcagcc actggcctcc cagcccccgg tcgtcgaccc ctacgacatg ccgggaacca
 901 gctactccac accaggcatg agtggctaca gcagtggcgg agcgagtggc agtggtgggc
 961 cttccaccag cggaactacc agtgggcctg ggcctgcccg cccagcccga gcccggccta
1021 ggagaccccg agaggagacg ctcaccccag aggaagagga gaagcgaagg gtgcgccggg
1081 aacgaaataa actagcagca gctaaatgca ggaaccggcg gagggagctg accgaccgac
1141 tccaggcgga gacagatcag ttggaggaag aaaaagcaga gctggagtcg gagatcgccg
1201 agctccaaaa ggagaaggaa cgtctggagt ttgtgctggt ggcccacaaa ccgggctgca
1261 agatccccta cgaagagggg cccgggccgg gcccgctggc ggaggtgaga gatttgccgg
1321 gctcagcacc ggctaaggaa gatggcttca gctggctgct gccgcccccg ccaccaccgc
1381 ccctgccctt ccagaccagc caagacgcac cccccaacct gacggcttct ctctttacac
1441 acagtgaagt tcaagtcctc ggcgacccct tccccgttgt taacccttcg tacacttctt
1501 cgtttgtcct cacctgcccg gaggtctccg cgttcgccgg cgcccaacgc accagcggca
1561 gtgaccagcc ttccgatccc ctgaactcgc cctccctcct cgctcggtga actctttaga
1621 cacacaaaac aaacaaacac atgggggaga gagacttgga agaggaggag gaggaggaga
1681 aggaggagag agaggggaag agacaaagtg ggtgtgtggc ctccctggct cctccgtctg
1741 accctctgcg gccactgcgc cactgccatc ggacaggagg attccttgtg ttttgtcctg
1801 cctcttgttt ctgtgccccg gcgaggccgg agagctggtg actttgggga caggggggtgg
1861 gaaggggatg gacaccccca gctgactgtt ggctctctga cgtcaaccca agctctgggg
1921 atgggtgggg agggggggcgg gtgacgccca ccttcgggca gtcctgtgtg aggatgaagg
1981 gacgggggtg ggaggtaggc tgtggggtgg gctggagtcc tctccagaga ggctcaacaa
2041 ggaaaaatgc cactccctac ccaatgtctc ccacacccac cctttttttg gggtgcccag
2101 gttggtttcc cctgcactcc cgaccttagc ttattgatcc cacatttcca tggtgtgaga
2161 tcctctttac tctgggcaga agtgagcccc cccttaaagg gaattcgatg ccccccctaga
2221 ataatctcat ccccccaccc gacttctttt gaaatgtgaa cgtccttcct tgactgtcta
2281 gccactccct cccagaaaaa ctggctctga ttggaatttc tggcctccta aggctcccca
2341 ccccgaaatc agcccccagc cttgtttctg atgacagtgt tatcccaaga ccctgccccc
2401 tgccagccga ccctcctggc cttcctcgtt gggccgctct gatttcaggc agcaggggct
2461 gctgtgatgc cgtcctgctg gagtgattta tactgtgaaa tgagttggcc agattgtggg
2521 gtgcagctgg gtggggcagc acacctctgg ggggataatg tccccactcc cgaaagcctt
2581 tcctcggtct cccttccgtc catcccccctt cttcctcccc tcaacagtga gttagactca
2641 agggggtgac agaaccgaga agggggtgac agtcctccat ccacgtggcc tctctctctc
2701 tcctcaggac cctcagccct ggcctttttc tttaaggtcc cccgaccaat ccccagccta
2761 ggacgccaac ttctcccacc ccttggcccc tcacatcctc tccaggaagg cagtgagggg
2821 ctgtgacatt tttccggaga agatttcaga gctgaggctt tggtaccccc aaacccccaa
2881 tatttttgga ctggcagact caaggggctg gaatctcatg attccatgcc cgagtccgcc
2941 catccctgac catggttttg gctctcccac cccgccgttc cctgcgcttc atctcatgag
3001 gatttcttta tgaggcaaat ttatattttt taatatcggg gggtggacca cgccgccctc
3061 catccgtgct gcatgaaaaa cattccacgt gccccttgtc gcgcgtctcc catcctgatc
3121 ccagacccat tccttagcta tttatccctt tcctggtttc cgaaaggcaa ttatatctat
3181 tatgtataag taaatatatt atatatggat gtgtgtgtgt gcgtgcgcgt gagtgtgtga
```

Figure 10 (cont.)

```
3241 gcgcttctgc agcctcggcc taggtcacgt tggccctcaa agcgagccgt tgaattggaa
3301 actgcttcta gaaactctgg ctcagcctgt ctcgggctga cccttttctg atcgtctcgg
3361 cccctctgat tgttcccgat ggtctctctc cctctgtctt ttctcctccg cctgtgtcca
3421 tctgaccgtt ttcacttgtc tcctttctga ctgtccctgc caatgctcca gctgtcgtct
3481 gactctgggt tcgttgggga catgagattt tattttttgt gagtgagact gagggatcgt
3541 agatttttac aatctgtatc tttgacaatt ctgggtgcga gtgtgagagt gtgagcaggg
3601 cttgctcctg ccaaccacaa ttcaatgaat ccccgacccc cctaccccat gctgtacttg
3661 tggttctctt tttgtatttt gcatctgacc ccgggggggct gggacagatt ggcaatgggc
3721 cgtcccctct ccccttggtt ctgcactgtt gccaataaaa agctcttaaa aacgc
```

SEQ ID NO:61

```
   1 agcgagcttg cagcctcacc gacgagtctc aactaaaagg gactcccgga gctaggggtg
  61 gggactcggc ctcacacagt gagtgccggc tattggactt ttgtccagtg acagctgaga
 121 caacaaggac cacgggagga ggtgtaggag agaagcgccg cgaacagcga tcgcccagca
 181 ccaagtccgc ttccaggctt tcggtttctt tgcctccatc ttgggtgcgc cttcccggcg
 241 tctaggggag cgaaggctga ggtggcagcg gcaggagagt ccggccgcga caggacgaac
 301 tcccccactg gaaaggattc tgaaagaaat gaagtcagcc ctcagaaatg aagttgactg
 361 cctgctggct ttctgttgac tggcccggag ctgtactgca agacccttgt gagcttccct
 421 agtctaagag taggatgtct gctgaagtca tccatcaggt tgaagaagca cttgatacag
 481 atgagaagga gatgctgctc tttttgtgcc gggatgttgc tatagatgtg gttccaccta
 541 atgtcaggga ccttctggat attttacggg aaagaggtaa gctgtctgtc ggggacttgg
 601 ctgaactgct ctacagagtg aggcgatttg acctgctcaa acgtatcttg aagatggaca
 661 gaaaagctgt ggagacccac ctgctcagga accctcacct tgtttcggac tatagagtgc
 721 tgatggcaga gattggtgag gatttggata aatctgatgt gtcctcatta atttcctca
 781 tgaaggatta catgggccga ggcaagataa gcaaggagaa ggtttcttgg accttgtggt
 841 tgagttggag aaactaaatc tggttgcccc agatcaactg gatttattag aaaaatgcct
 901 aaagaacatc cacagaatag acctgaagac aaaaatccag aagtacaagc agtctgttca
 961 aggagcaggg acaagttaca ggaatgttct ccaagcagca atccaaaaga gtctcaagga
1021 tccttcaaat aacttcaggc tccataatgg gagaagtaaa gaacaaagac ttaaggaaca
1081 gcttggcgct caacaagaac cagtgaagaa atccattcag gaatcagaag ctttttgcc
1141 tcagagcata cctgaagaga gatacaagat gaagagcaag cccctaggaa tctgcctgat
1201 aatcgattgc attggcaatg agacagagct tcttcgagac accttcactt ccctgggcta
1261 tgaagtccag aaattcttgc atctcagtat gcatggtata tcccagattc ttggccaatt
1321 tgcctgtatg cccgagcacc gagactacga cagctttgtg tgtgtcctgg tgagccgagg
1381 aggctcccag agtgtgtatg gtgtggatca gactcactca gggctccccc tgcatcacat
1441 caggaggatg ttcatgggag attcatgccc ttatctagca gggaagccaa agatgttttt
1501 tattcagaac tatgtggtgt cagagggcca gctggaggac agcagcctct tggaggtgga
1561 tgggccagcg atgaagaatg tggaattcaa ggctcagaag cgagggctgt gcacagttca
1621 ccgagaagct gacttcttct ggagcctgtg tactgcggac atgtccctgc tggagcagtc
1681 tcacagctca ccatccctgt acctgcagtg cctctcccag aaactgagac aagaaagaaa
1741 acgcccactc ctggatcttc acattgaact caatggctac atgtatgatt ggaacagcag
1801 agtttctgcc aaggagaaat attatgtctg gctgcagcac actctgagaa agaaacttat
1861 cctctcctac acataagaaa ccaaaaggct gggcgtagtg gctcacacct gtaatcccag
1921 cactttggga ggccaaggag ggcagatcac ttcaggtcag gagttcgaga ccagcctggc
1981 caacatggta aacgctgtcc ctagtaaaaa tacaaaaatt a
```

SEQ ID NO:62

```
   1 agagttgcac tgagtgtggc tgaagcagcg aggcgggagt ggaggtgcgc ggagtcaggc
  61 agacagacag acacagccag ccagccaggt cggcagtata gtccgaactg caaatcttat
 121 tttcttttca ccttctctct aactgcccag agctagcgcc tgtggctccc gggctggtgt
 181 ttcgggagtg tccagagagc ctggtctcca gccgcccccg ggaggagagc cctgctgccc
 241 aggcgctgtt gacagcggcg gaaagcagcg gtacccacgc gcccgccggg ggaagtcggc
 301 gagcggctgc agcagcaaag aactttcccg gctgggagga ccggagacaa gtggcagagt
 361 cccggagcca acttttgcaa gcctttcctg cgtcttaggc ttctccacgg cggtaaagac
```

Figure 10 (cont.)

```
 421 cagaaggcgg cggagagcca cgcaagagaa gaaggacgtg cgctcagctt cgctcgcacc
 481 ggttgttgaa cttgggcgag cgcgagccgc ggctgccggg cgccccctcc ccctagcagc
 541 ggaggagggg acaagtcgtc ggagtccggg cggccaagac ccgccgccgg ccggccactg
 601 cagggtccgc actgatccgc tccgcgggga gagccgctgc tctgggaagt gagttcgcct
 661 gcggactccg aggaaccgct gcgcacgaag agcgctcagt gagtgaccgc gacttttcaa
 721 agccgggtag cgcgcgcgag tcgacaagta agagtgcggg aggcatctta attaaccctg
 781 cgctccctgg agcgagctgg tgaggagggc gcagcgggga cgacagccag cgggtgcgtg
 841 cgctcttaga gaaactttcc ctgtcaaagg ctccgggggg cgcgggtgtc cccgcttgc
 901 cacagccctg ttgcggcccc gaaacttgtg cgcgcagccc aaactaacct cacgtgaagt
 961 gacggactgt tctatgactg caaagatgga aacgaccttc tatgacgatg ccctcaacgc
1021 ctcgttcctc ccgtccgaga gcggacctta tggctacagt aaccccaaga tcctgaaaca
1081 gagcatgacc ctgaacctgg ccgacccagt ggggagcctg aagccgcacc tccgcgccaa
1141 gaactcggac ctcctcacct cgcccgacgt ggggctgctc aagctggcgt cgcccgagct
1201 ggagcgcctg ataatccagt ccagcaacgg gcacatcacc accacgccga cccccaccca
1261 gttcctgtgc cccaagaacg tgacagatga gcaggagggc ttcgccgagg gcttcgtgcg
1321 cgccctggcc gaactgcaca gccagaacac gctgcccagc gtcacgtcgg cggcgcagcc
1381 ggtcaacggg gcaggcatgg tggctcccgc ggtagcctcg gtggcagggg gcagcggcag
1441 cggcggcttc agcgccagcc tgcacagcga gccgccggtc tacgcaaacc tcagcaactt
1501 caacccaggc gcgctgagca gcggcggcgg ggcgccctcc tacggcgcgg ccggcctggc
1561 ctttcccgcg caaccccagc agcagcagca gccgccgcac cacctgcccc agcagatgcc
1621 cgtgcagcac ccgcggctgc aggccctgaa ggaggagcct cagacagtgc ccgagatgcc
1681 cggcgagaca ccgcccctgt cccccatcga catggagtcc caggagcgga tcaaggcgga
1741 gaggaagcgc atgaggaacc gcatcgctgc ctccaagtgc cgaaaaagga agctggagag
1801 aatcgcccgg ctggaggaaa aagtgaaaac cttgaaagct cagaactcgg agctggcgtc
1861 cacggccaac atgctcaggg aacaggtggc acagcttaaa cagaaagtca tgaaccacgt
1921 taacagtggg tgccaactca tgctaacgca gcagttgcaa acattttgaa gagagaccgt
1981 cgggggctga ggggcaacga agaaaaaaaa taacacagag agacagactt gagaacttga
2041 caagttgcga cggagagaaa aaagaagtgt ccgagaacta aagccaaggg tatccaagtt
2101 ggactgggtt gcgtcctgac ggcgccccca gtgtgcacga gtgggaagga cttggcgcgc
2161 cctcccttgg cgtggagcca gggagcggcc gcctgcgggc tgccccgctt tgcggacggg
2221 ctgtccccgc gcgaacggaa cgttggactt ttcgttaaca ttgaccaaga actgcatgga
2281 cctaacattc gatctcattc agtattaaag gggggagggg gagggggtta caaactgcaa
2341 tagagactgt agattgcttc tgtagtactc cttaagaaca caaagcgggg ggagggttgg
2401 ggagggggcgg caggagggag gtttgtgaga gcgaggctga gcctacagat gaactctttc
2461 tggcctgcct tcgttaactg tgtatgtaca tatatatatt ttttaatttg atgaaagctg
2521 attactgtca ataaacagct tcatgccttt gtaagttatt tcttgtttgt ttgtttgggt
2581 atcctgccca gtgttgtttg taaataagag atttggagca ctctgagttt accatttgta
2641 ataaagtata taattttttt atgttttgtt tctgaaaatt ccagaaagga tatttaagaa
2701 aatacaataa actattggaa agtactcccc taacctcttt tctgcatcat ctgtagatac
2761 tagctatcta ggtggagttg aaagagttaa gaatgtcgat taaaatcact ctcagtgctt
2821 cttactatta agcagtaaaa actgttctct attagacttt agaaataaat gtacctgatg
2881 tacctgatgc tatggtcagg ttatactcct cctcccccag ctatctatat ggaattgctt
2941 accaaaggat agtgcgatgt ttcaggaggc tggaggaagg ggggttgcag tggagaggga
3001 cagcccactg agaagtcaaa catttcaaag tttggattgt atcaagtggc atgtgctgtg
3061 accatttata atgttagtag aaattttaca ataggtgctt attctcaaag caggaattgg
3121 tggcagattt tacaaaagat gtatccttcc aatttggaat cttctctttg acaattccta
3181 gataaaaaga tggcctttgc ttatgaatat ttataacagc attcttgtca caataaatgt
3241 attcaaatac caat
```

SEQ ID NO:63

```
   1 gtggagctac cgccaccgcc gccgccgatt ccggagccgg ggtagtcgcc gccgccgccg
  61 ccgctgcagc cactgcaggc accgctgccg ccgcctgagt agtgggctta ggaaggaaga
 121 ggtcatctcg ctcggagctt cgctcggaag ggtctttgtt ccctgcagcc ctcccacggg
 181 aatgacaatg gataaaagtg agctggtaca gaaagccaaa ctcgctgagc aggctgagcg
```

Figure 10 (cont.)

```
 241 atatgatgat atggctgcag ccatgaaggc agtcacagaa caggggcatg aactctccaa
 301 cgaagagaga aatctgctct ctgttgccta caagaatgtg gtaggcgccc gccgctcttc
 361 ctggcgtgtc atctccagca ttgagcagaa aacagagagg aatgagaaga agcagcagat
 421 gggcaaagag taccgtgaga agatagaggc agaactgcag gacatctgca atgatgttct
 481 ggagctgttg gacaaatatc ttattcccaa tgctacacaa ccagaaagta aggtgttcta
 541 cttgaaaatg aaaggagatt attttaggta tctttctgaa gtggcatctg gagacaacaa
 601 acaaaccact gtgtcgaact cccagcaggc ttaccaggaa gcatttgaaa ttagtaagaa
 661 agaaatgcag cctacacacc caattcgtct tggtctggca ctaaatttct cagtctttta
 721 ctatgagatt ctaaactctc ctgaaaaggc ctgtagcctg gcaaaaacgg catttgatga
 781 agcaattgct gaattggata cgctgaatga agagtcttat aaagacagca ctctgatcat
 841 gcagttactt agggacaatc tcactctgtg gacatcggaa aaccagggag acgaaggaga
 901 cgctggggag ggagagaact aatgtttctc gtgctttgtg atctgttcag tgtcactctg
 961 taccctcaac atatatccct tgtgcgat
```

SEQ ID NO:64

```
   1 gtgccgctcc ttggtggggg ctgttcatgg cggttccggg gtctccaaca tttttcccgg
  61 ctgtggtcct aaatctgtcc aaagcagagg cagtggagct tgaggttctt gctggtgtga
 121 aatgactgag tacaaactgg tggtggttgg agcaggtggt gttgggaaaa gcgcactgac
 181 aatccagcta atccagaacc actttgtaga tgaatatgat cccaccatag aggattctta
 241 cagaaaacaa gtggttatag atggtgaaac ctgtttgttg gacatactgg atacagctgg
 301 acaagaagag tacagtgcca tgagagacca atacatgagg acaggcgaag gcttcctctg
 361 tgtatttgcc atcaataata gcaagtcatt tgcggatatt aacctctaca gggagcagat
 421 taagcgagta aaagactcgg atgatgtacc tatggtgcta gtgggaaaca agtgtgattt
 481 gccaacaagg acagttgata caaaacaagc ccacgaactg gccaagagtt acgggattcc
 541 attcattgaa acctcagcca agaccagaca gggtgttgaa gatgcttttt acacactggt
 601 aagagaaata cgccagtacc gaatgaaaaa actcaacagc agtgatgatg ggactcaggg
 661 ttgtatggga ttgccatgtg tggtgatgta acaagatact tttaaagttt tgtcagaaaa
 721 gagccacttt caagctgcac tgacaccctg gtcctgactt ccctggagga gaagtattcc
 781 tgttgctgtc ttcagtctca cagagaagct cctgctactt ccccagctct cagtagttta
 841 gtacaataat ctctatttga gaagttctca gaataactac ctcctcactt ggctgtctga
 901 ccagagaatg cacctcttgt tactccctgt tatttttctg ccctgggttc ttccacagca
 961 caaacacacc tctgccaccc caggtttttc atctgaaaag cagttcatgt ctgaaacaga
1021 gaaccaaacc gcaaacgtga aattctattg aaaacagtgt cttgagctct aaagtagcaa
1081 ctgctggtga ttttttttt ctttttactg ttgaacttag aactatgcta atttttggag
1141 aaatgtcata aattactgtt ttgccaagaa tatagttatt attgctgttt ggtttgttta
1201 taatgttatc ggctctattc tctaaactgg catctgctct agattcataa atacaaaaat
1261 gaatactgaa ttttgagtct atcctagtct tcacaacttt gacgtaatta aatccaactt
1321 tcacagtgaa gtgccttttt cctagaagtg gtttgtagac ttcctttata atatttcagt
1381 ggaatagatg tctcaaaaat ccttatgcat gaaatgaatg tctgagatac gtctgtgact
1441 tatctaccat tgaaggaaag ctatatctat ttgagagcag atgccatttt gtacatgtat
1501 gaaattggtt ttccagaggc ctgttttggg gctttcccag gagaaagatg aaactgaaag
1561 cacatgaata atttcactta ataattttta cctaatctcc actttttttca taggttacta
1621 cctatacaat gtatgtaatt tgtttcccct agcttactga taaacctaat attcaatgaa
1681 cttccatttg tattcaaatt tgtgtcatac cagaaagctc tacatttgca gatgttcaaa
1741 tattgtaaaa ctttggtgca ttgttattta atagctgtga tcagtgattt tcaaacctca
1801 aatatagtat attaacaaat tacattttca ct
```

SEQ ID NO:65

```
   1 atgaaggtga taagcttatt cattttggtg ggatttatag gagagttcca aagtttttca
  61 agtgcctcct ctccagtcaa ctgccagtgg gacttctatg ccccttggtc agaatgcaat
 121 ggctgtacca agactcagac tcgcaggcgg tcagttgctg tgtatgggca gtatggaggc
 181 cagccttgtg ttggaaatgc ttttgaaaca cagtcctgtg aacctacaag aggatgtcca
 241 acagaggagg gatgtggaga gcgtttcagg tgcttttcag gtcagtgcat cagcaaatca
 301 ttggtttgca atggggattc tgactgtgat gaagacagtg ctgatgaaga cagatgtgag
```

Figure 10 (cont.)

```
361 gactcagaaa ggagaccttc ctgtgatatc gataaacctc ctcctaacat agaacttact
421 ggaaatggtt acaatgaact cactggccag tttaggaaca gagtcatcaa taccaaaagt
481 tttggtggtc aatgtagaaa ggtgtttagt ggggatggaa aagatttcta caggctgagt
541 ggaaatgtcc tgtcctatac attccaggtg aaaataaata atgattttaa ttatgaattt
601 tacaatagta cttggtctta tgtaaaacat acgtcgacag aacacacatc atctagtcgg
661 aagcgctcct tttttagatc ttcatcatct tcttcacgca gttatacttc acataccaat
721 gaaatccata aaggaaagag ttaccaactg ctggttgttg agaacactgt tgaagtggct
781 cagttcatta ataacaatcc agaattttta caacttgctg agccattctg gaaggagctt
841 tcccacctcc cctctctgta tgactacagt gcctaccgaa gattaatcga ccagtacggg
901 acacattatc tgcaatctgg gtcgttagga ggagaataca gagttctatt ttatgtggac
961 tcagaaaaat taaaacaaaa tgattttaat tcagtcgaag aaaagaaatg taaatcctca
1021 ggttggcatt ttgtcgttaa attttcaagt catggatgca aggaactgga aaacgcttta
1081 aaagctgctt caggaaccca gaacaatgta ttgcgaggag aaccgttcat cagaggggga
1141 ggtgcaggct tcatatctgg ccttagttac ctagagctgg acaatcctgc tggaaacaaa
1201 aggcgatatt ctgcctgggc agaatctgtg actaatcttc ctcaagtcat aaaacaaaag
1261 ctgacacctt tatatgagct ggtaaaggaa gtaccttgtg cctctgtgaa aaaactatac
1321 ctgaaatggg ctcttgaaga gtatctggat gaatttgacc cctgtcattg ccggccttgt
1381 caaaatggtg gtttggctac tgttgagggg acccattgtc tgtgccattg caaaccgtac
1441 acatttggtg cggcgtgtga gcaaggagtc ctcgtaggga atcaagcagg aggggttgat
1501 ggaggttgga gttgctggtc ctcttggagc cctgtgtcc aagggaagaa aacaagaagc
1561 cgtgaatgca ataacccacc tcccagtggg ggtgggagat cctgcgttgg agaaacgaca
1621 gaaagcacac aatgcgaaga tgaggagctg gagcacttga ggttgcttga accacattgc
1681 tttcctttgt ctttggttcc aacagaattc tgtccatcac ctcctgcctt gaaagatgga
1741 tttgttcaag atgaaggtcc aatgtttcct gtggggaaaa atgtagtgta cacttgcaat
1801 gaaggatact ctcttattgg aaacccagtg gccagatgtg gagaagattt acggtggctt
1861 gttggggaaa tgcattgtca gaaaattgcc tgtgttctac ctgtactgat ggatggcata
1921 cagagtcacc cccaaaaacc tttctacaca gttggtgaga aggtgactgt ttcctgttca
1981 ggtggcatgt ccttagaagg tccttcagca tttctctgtg gctccagcct taagtggagt
2041 cctgagatga agaatgcccg ctgtgtacaa aaagaaaatc cgttaacaca ggcagtgcct
2101 aaatgtcagc gctgggagaa actgcagaat tcaagatgtg tttgtaaaat gccctacgaa
2161 tgtggacctt ccttggatgt atgtgctcaa gatgagagaa gcaaaaggat actgcctctg
2221 acagtttgca agatgcatgt tctccactgt cagggtagaa attacaccct tactggtagg
2281 gacagctgta ctctgcctgc ctcagctgag aaagcttgtg gtgcctgccc actgtgggga
2341 aaatgtgatg ctgagagcag caaatgtgtc tgccgagaag catcggagtg cgaggaagaa
2401 gggtttagca tttgtgtgga agtgaacggc aaggagcaga cgatgtctga gtgtgaggcg
2461 ggcgctctga gatgcagagg gcagagcatc tctgtcacca gcataaggcc ttgtgctgcg
2521 gaaacccagt aggctcctgg aggccatggt cagcttgctt ggaatccagc aggcagctgg
2581 ggctgagtga aaacatctgc acaactgggc actggacagc ttttccttct tctccagtgt
2641 ctaccttcct cctcaactcc cagccatctg tataaacaca atcctttgtt ctcccaaatc
2701 tgaatcgaat tactcttttg cctccttttt aatgtcagta aggatatgag cctttgcaca
2761 ggctggctgc gtgttcttga aataggtgtt accttctctg ggccttggtt ttttaaaatc
2821 tgtaaaatta gaggattgca ctagagaaac ttgaatgctc cattcaggcc tatcatttta
2881 ttaagtatga ttgacacagc ccatgggcca gaacacactc tacaaaatga ctaggataac
2941 agaaagaacg tgatctcctg attagagagg gtggtttcc tcaatggaac caaatataaa
3001 gaggacttga acaaaaatga cagatacaaa ctatttctat cctgagtagt aatctcacac
3061 ttcatcctat agagtcaacc accacagata ggaattcctt attcttttt taattttttt
3121 aagacagagt ctcactttgt tgcccaggct ggagcgcagt ggggtgatct catctccctg
3181 caacctccgc ctcctgggtt gaagcgattc ttgtgcctca gcttcccaag cagctgggat
3241 tacaggtgcc cgccaccacg cccagctaat tttgcattt ttagtagaga tgggtttcac
3301 catgttggcc atgctcgtct ccaactcctg acctcaggta atccgtctgc cttggcctcc
3361 caaatgctgg gattacagac atgaaccacc acgcctggct ggaatactta ctcttgtcgg
3421 gagattgaac cactaaaatg ttagagcaga attcattatg ctgtggtcac aggggtgtct
3481 tgtctgagaa caaatacaat tcagtcttct ctttggggtt ttagtatgtg tcaaacatag
3541 gactggaagt ttgcccctgt tctttttct tttgaaagaa catcagttca tgcctgaggc
```

Figure 10 (cont.)

```
3601 atgagtgact gtgcatttga gatagttttc cctattctgt ggatacagtc ccagagtttt
3661 cagggagtac acaggtagat tagtttgaag cattgacctt ttatttattc cttatttctc
3721 tttcatcaaa acaaaacagc agctgtggga ggagaaatga gagggcttaa atgaaattta
3781 aaataagcta tattatacaa atactatctc tgtattgttc tgaccctggt aaatatattt
3841 caaaacttca gatgacaagg attagaacac tcattaagat gctattcttc

SEQ ID NO:66
   1 ctaacccaga aacatccaat tctcaaactg aagctcgcac tctcgcctcc agcatgaaag
  61 tctctgccgc ccttctgtgc ctgctgctca tagcagccac cttcattccc caagggctcg
 121 ctcagccaga tgcaatcaat gccccagtca cctgctgtta taacttcacc aataggaaga
 181 tctcagtgca gaggctcgcg agctatagaa gaatcaccag cagcaagtgt cccaaagaag
 241 ctgtgatctt caagaccatt gtggccaagg agatctgtgc tgaccccaag cagaagtggg
 301 ttcaggattc catggaccac ctggacaagc aaacccaaac tccgaagact tgaacactca
 361 ctccacaacc caagaatctg cagctaactt attttcccct agctttcccc agacaccctg
 421 ttttatttta ttataatgaa ttttgtttgt tgatgtgaaa cattatgcct taagtaatgt
 481 taattcttat ttaagttatt gatgttttaa gtttatcttt catggtacta gtgtttttta
 541 gatacagaga cttggggaaa ttgcttttcc tcttgaacca cagttctacc cctgggatgt
 601 tttgagggtc tttgcaagaa tcattaatac aaagaatttt ttttaacatt ccaatgcatt
 661 gctaaaatat tattgtggaa atgaatattt tgtaactatt acaccaaata aatatatttt
 721 tgtac

SEQ ID NO:67
   1 ttcaatgttg atgtgaaaaa ttcaatgact ttcagcggcc cggtggaaga catgtttgga
  61 tatactgttc aacaatatga aaatgaagaa ggaaaatggg tgcttattgg ttctccgtta
 121 gttggccaac ccaaaaacag aactggagat gtctataagt gtccagttgg gagaggtgaa
 181 tcattacctt gcgtaaagtt ggatctacca gttaatacat caattcccaa tgtcacagaa
 241 gtaaaggaga acatgacatt tggatcaact ttagtcacca acccaaatgg aggatttctg
 301 gcttgtgggc ccttatatgc ctatagatgt ggacatttgc attacacaac tggaatctgt
 361 tctgacgtca gccccacatt tcaagtcgtg aattccattg cccctgtaca agaatgcagc
 421 actcaactgg acatagtcat agtgctggat ggttccaaca gtatttaccc atgggacagt
 481 gttacagctt ttttaaatga ccttcttgaa agaatggata ttggtcctaa acagacacag
 541 gttggaattg tacagtatgg agaaaacgtg acccatgagt tcaacctcaa taagtattct
 601 tccaccgaag aggtacttgt tgcagcaaag aaaatagtcc agagaggtgg ccgccagact
 661 atgacagctc ttggaataga cacagcaaga aaggaggcat tcacggaagc ccggggtgcc
 721 cgaagaggag ttaaaaaagt catggttatt gtgacagatg gagagtctca tgacaatcat
 781 cgactgaaga aggtcatcca agactgtgaa gatgaaaaca ttcaacggtt ttccatagct
 841 nnnnnnnnnn nnnnnnnnnn nnnnnnnnnn nnnnnnnnnn nnnnnnnnnn nnnnnnnnnn
 901 nnnnnnnnnn nnnnnnnnnn nnnnnnnnnn nnnnnnnnnn nnnnnnnnnn nnnnnnnnnn
 961 nnnnnnnnnn nnnnnnnnnn nnnnnnnnnn nnnnnnnnnn nnnnnnnnnn nnnnnnnnnn
1021 nnnnnnnctt catatgaaat ggaaatgtct cagactggct tcagtgctca ttattcacag
1081 nnnnnnnnnn nnnnnnnnnn nnnnnnnnnn nnnnnnnnnn nnnnnnnnnn nnnnnnnnnn
1141 nnnnnnnnnn nnnnnnnnnn nnnnnnnnnn nnnnnnnnnn nnnnnnnnnn nnnnnnnnnn
1201 nnnnnnnnnn nnnnnnnnnn nnnnngttac actgtaaact ctgctactgc ttcttctgga
1261 gatgtgctct atattgctgg acagcctcgg tacaatcata caggccaggt cattatctac
1321 aggatggaag atggaaacat caaaattctc cagacgctca gtggagaaca gattggttcc
1381 tactttggca gtattttaac aacaactgac attgacaagg attctaatac tgacattctt
1441 ctagtcggag cccctatgta catgggaaca gagaaggagg agcaaggaaa agtgtatgtg
1501 tatgctctca atcagacaag gtttgaatat caaatgagcc tggaacctat taagcagacg
1561 tgctgttcat ctcggcagca caattcatgc acaacagaaa acaaaaatga gccatgcggg
1621 gctcgttttg gaactgcaat tgctgctgta aaagacctca atcttgatgg atttaatgac
1681 atcgtgatag gagctccgct ggagatgatc acgggggagc tgtgtacatt tatcatggaa
1741 gtggcaagac tataaggaaa gagtatgcac aacgtattcc atcaggtggg gatggtaaga
1801 cactgaaatt ttttggccag tctatccacg gagaaatgga tttaaatggt gacggtctga
1861 cagatgtgac tattgggggc cttggtggtg ctgccctctt ctggtcccga gatgtggccg
```

Figure 10 (cont.)

```
1921 tagttaaagt gaccatgaat tttgagccaa ataaagtgaa tattcaaaag aaaaactgcc
1981 atatggaggg aaaggaaaca gtatgcataa atgctacagt gtgttttgat gtgaaattaa
2041 agtctaaaga agacacgatt tatgaagctg atttgcagta ccgtgtcacc ctagattcac
2101 taagacaaat atcacgaagt tttttctctg gaactcaaga gagaaaggtt caaaggaaca
2161 tcacagttcg aaaatcagaa tgcactaagc actccttcta catgttgaca agcatgactt
2221 tcaggactct gtgagaataa cgttggactt taatcttacc gatccagaaa atgggcctgt
2281 tcttgatgat tctctaccaa actcagtaca tgaatatatt ccctttgcca aagattgtgg
2341 aaataaggaa aaatgtatct cagacctcag cctgcatgtc gccaccactg aaaaggacct
2401 gctgattgtc cgatcccaga atgataagtt caacgttagc ctcacagtca aaaatacaaa
2461 ggacagtgcc tataacacca ggacaatagt gcattattct ccaaatctag ttttttcagg
2521 aattgaggct atccaaaaag acagttgtga atctaatcat aatatcacat gtaaagttgg
2581 atatcccttc ctgagaagag gagagatggt aactttcaaa atattgtttc agtttaacac
2641 atcctatctc atggaaaatg tgaccattta tttaagtgca acaagtgaca gcgaagaacc
2701 tcctgaaacc ctttctgata atgtagtaaa catttctatc ccggtaaaat atgaagttgg
2761 actacagttt tacagctctg caagtgaata ccacatttca attgctgcca atgagacagt
2821 ccctgaagtt attaattcta ctgaggacat tggaaatgaa attaatatct tctacttgat
2881 tagaaaaagt ggatcttttc caatgccaga gcttaagctg tcaatttcat tccccaatat
2941 gacatcaaat ggttaccctg tgctgtaccc aactggattg tcatcttctg agaatgcaaa
3001 ctgcagaccc catatctttg aggatccttt cagtatcaac tctggaaaga aaatgactac
3061 atcaactgac catctcaaac gaggcacaat tctggactgc aatacatgta aatttgctac
3121 catcacatgt aatctcactt cttctgacat cagccaagtc aatgtttcgc ttatcttgtg
3181 gaaaccaact tttataaaat catatttttc cagcttaaat cttactataa ggggagaact
3241 tcggagtgaa aatgcatctc tggttttaag tagcagcaat caaaaaagag agcttgctat
3301 tcaaatatcc aaagatgggc taccgggcag agtgccatta tgggtcatcc tgctgagtgc
3361 ttttgccgga ttgttgctgt taatgctgct cattttagca ctgtggaaga ttggattctt
3421 caaaagacca ctgaaaaaga aaatggagaa a
```

SEQ ID NO:68

```
   1 gtatcactca gaatctggca gccagttccg tcctgacaga gttcacagca tatattggtg
  61 gattcttgtc catagtgcat ctgctttaag aattaacgaa agcagtgtca agacagtaag
 121 gattcaaacc atttgccaaa aatgagtcta agtgcattta ctctcttcct ggcattgatt
 181 ggtggtacca gtggccagta ctatgattat gattttcccc tatcaattta tgggcaatca
 241 tcaccaaact gtgcaccaga atgtaactgc cctgaaagct acccaagtgc catgtactgt
 301 gatgagctga aattgaaaag tgtaccaatg gtgcctcctg gaatcaagta tctttacctt
 361 aggaataacc agattgacca tattgatgaa aaggcctttg agaatgtaac tgatctgcag
 421 tggctcattc tagatcacaa ccttctagaa aactccaaga taaaagggag agttttctct
 481 aaattgaaac aactgaagaa gctgcatata aaccacaaca acctgacaga gtctgtgggc
 541 ccacttccca aatctctgga ggatctgcag cttactcata acaagatcac aaagctgggc
 601 tcttttgaag gattggtaaa cctgaccttc atccatctcc agcacaatcg gctgaaagag
 661 gatgctgttt cagctgcttt taaaggtctt aaatcactcg aataccttga cttgagcttc
 721 aatcagatag ccagactgcc ttctggtctc cctgtctctc ttctaactct ctacttagac
 781 aacaataaga tcagcaacat ccctgatgag tatttcaagc gttttaatgc attgcagtat
 841 ctgcgtttat ctcacaacga actggctgat agtggaatac ctggaaattc tttcaatgtg
 901 tcatccctgg ttgagctgga tctgtcctat aacaagctta aaaacatacc aactgtcaat
 961 gaaaaccttg aaaactatta cctggaggtc aatcaacttg agaagtttga cataaagagc
1021 ttctgcaaga tcctggggcc attatcctac tccaagatca agcatttgcg tttggatggc
1081 aatcgcatct cagaaaccag tcttccaccg gatatgtatg aatgtctacg tgttgctaac
1141 gaagtcactc ttaattaata tctgtatcct ggaacaatat tttatggtta tgtttttctg
1201 tgtgtcagtt ttcatagtat ccatatttta ttactgttta ttacttccat gaattttaaa
1261 atctgaggga aatgttttgt aaacatttat ttttttttaaa gaaaagatga aaggcaggcc
1321 tatttcatca caagaacaca cacatataca cgaatagaca tcaaactcaa tgctttattt
1381 gtaaatttag tgttttttta tttctactgt caaatgatgt gcaaaacctt ttactggttg
1441 catggaaatc agccaagttt tataatcctt aaatcttaat gttcctcaaa gcttggatta
1501 aatacatatg gatgttactc tcttgcacca aattatcttg atacattcaa atttgtctgg
```

Figure 10 (cont.)

```
1561 ttaaaaaata ggtggtagat attgaggcca agaatattgc aaaatacatg aagcttcatg
1621 cacttaaaga agtattttta gaataagaat ttgcatactt acctagtgaa acttttctag
1681 aattattttt cactctaagt catgtatgtt tctctttgat tatttgcatg ttatgtttaa
1741 taagctacta gcaaaataaa acatagcaaa tg
```

SEQ ID NO:69

```
   1 tggacagagg agcagtaaca atccccactc tccaattgtg gaagagttcc aagtcccata
  61 caacaaactc caggtgatct ttaagtcaga cttttccaat gaagagcgtt ttacggggtt
 121 tgctgcatac tatgttgcca cagacataaa tgaatgcaca gattttgtag atgtcccttg
 181 tagccacttc tgcaacaatt tcattggtgg ttacttctgc tcctgccccc cggaatattt
 241 cctccatgat gacatgaaga attgcggagt taattgcagt ggggatgtat tcactgcact
 301 gattggggag attgcaagtc ccaattatcc caaaccatat ccagagaact caaggtgtga
 361 ataccagatc cggttggaga aagggttcca agtggtggtg accttgcgga gagaagattt
 421 tgatgtggaa gcagctgact cagcgggaaa ctgccttgac agtttagttt ttgttgcagg
 481 agatcggcaa tttggtcctt actgtggtca tggattccct gggcctctaa atattgaaac
 541 caagagtaat gctcttgata tcatcttcca aactgatcta acagggcaaa aaaagggctg
 601 gaaacttcgc tatcatggag atccaatgcc ctgccctaag gaagacactc ccaattctgt
 661 ttgggagcct gcgaaggcaa aatatgtctt tagagatgtg gtgcagataa cctgtctgga
 721 tgggtttgaa gttgtggagg gacgtgttgg tgcaacatct ttctattcga cttgtcaaag
 781 caatggaaag tggagtaatt ccaaactgaa atgtcaacct gtggactgtg gcattcctga
 841 atccattgag aatggtaaag ttgaagaccc agagagcact ttgtttggtt ctgtcatccg
 901 ctacacttgt gaggagccat attactacat ggaaaatgga ggaggtgggg agtatcactg
 961 tgctggtaac gggagctggg tgaatgaggt gctgggcccg gagctgccga aatgtgttcc
1021 aggtctgtgg agtccccaga gaaccctttg aagaaaaaca gaggataatt ggaggatccg
1081 atgcagatat taaaaacttc ccctggcaag tcttctttga caacccatgg gctggtggag
1141 cgctcattaa tgagtactgg gtgctgacgg ctgctcatgt tgtggaggga aacagggagc
1201 caacaatgta tgttgggtcc acctcagtgc agacctcacg gctggcaaaa tccaagatgc
1261 tcactcctga gcatgtgttt attcatccgg gatggaagct gctggaagtc ccagaaggac
1321 gaaccaattt tgataatgac attgcactgg tgcggctgaa agacccagtg aaaatgggac
1381 ccaccgtctc tcccatctgc ctaccaggca cctcttccga ctacaacctc atggatgggg
1441 acctgggact gatctcaggc tggggccgaa cagagaagag agatcgtgct gttcgcctca
1501 aggcggcaag gttacctgta gctcctttaa gaaaatgcaa agaagtgaaa gtggagaaac
1561 ccacagcaga tgcagaggcc tatgttttca ctcctaacat gatctgtgct ggaggagaga
1621 agggcatgga tagctgtaaa ggggacagtg gtggggcctt tgctgtacag gatcccaatg
1681 acaagaccaa attctacgca gctggcctgg tgtcctgggg gccccagtgt gggacctatg
1741 ggctctacac acgggtaaag aactatgttg actggataat gaagactatg caggaaaata
1801 gcaccccccg tgaggactaa tccagataca tcccaccagc ctctccaagg gtggtgacca
1861 atgcattacc ttctgttcct tatgatattc tcattatttc atcatgactg aaagaagaca
1921 cgagcgaatg atttaaatag aacttgattg ttgagacgcc ttgctagagg tagagtttga
1981 tcatagaatt gtgctggtca tacatttgtg gtctgactcc ttggggtcct ttccccggag
2041 tacctattgt agataacact atgggtgggg cactcctttc ttgcactatt ccacagggat
2101 accttaattc tttgtttcct ctttacctgt tcaaaattcc atttacttga tcattctcag
2161 tatccactgt ctatgtacaa taaaggatgt ttataagc
```

SEQ ID NO:70

```
   1 aaactctgat ctggggagga accaggacta catagatcaa ggcagttttc ttctttgaga
  61 aactatccca gatatcatca tagagtcttc tgctcttcct caactaccaa agaaaaacat
 121 cagcgaagca gcaggccatg caccccccaa aaactccatc tggggctctt catagaaaaa
 181 ggaaaatggc agcctggccc ttctccaggc tgtggaaagt ctctgatcca attctcttcc
 241 aaatgacctt gatcgctgct ctgttgcctg ctgttcttgg caattgtggt cctccaccca
 301 ctttatcatt tgctgccccg atggatatta cgttgactga gacacgcttc aaaactggaa
 361 ctactctgaa atacacctgc ctccctggct acgtcagatc ccattcaact cagacgctta
 421 cctgtaattc tgatggcgaa tgggtgtata acaccttctg tatctacaaa cgatgcagac
 481 acccaggaga gttacgtaat gggcaagtag agattaagac agatttatct tttggatcac
```

Figure 10 (cont.)

```
 541 aaatagaatt cagctgttca gaaggatttt tcttaattgg ctcaaccact agtcgttgtg
 601 aagtccaaga tagaggagtt ggctggagtc atcctctccc acaatgtgaa attgtcaagt
 661 gtaagcctcc tccagacatc aggaatggaa ggcacagcgg tgaagaaaat ttctacgcat
 721 acggcttttc tgtcacctac agctgtgacc cccgcttctc actcttgggc catgcctcca
 781 tttcttgcac tgtggagaat gaaacaatag gtgtttggag accaagccct cctacctgtg
 841 aaaaaatcac ctgtcgcaag ccagatgttt cacatgggga aatggtctct ggatttggac
 901 ccatctataa ttacaaagac actattgtgt ttaagtgcca aaaaggtttt gttctcagag
 961 gcagcagtgt aattcattgt gatgctgata gcaaatggaa tccttctcct cctgcttgtg
1021 agcccaatag ttgtattaat ttaccagaca ttccacatgc ttcctgggaa acatatccta
1081 ggccgacaaa agaggatgtg tatgttgttg ggactgtgtt aaggtaccgc tgtcatcctg
1141 gctacaaacc cactacagat gagcctacga ctgtgatttg tcagaaaaat ttgagatgga
1201 ccccatacca aggatgtgag gcgttatgtt gccctgaacc aaagctaaat aatggtgaaa
1261 tcactcaaca caggaaaagt cgtcctgcca atcactgtgt ttatttctat ggagatgaga
1321 tttcattttc atgtcatgag accagtaggt tttcagctat atgccaagga gatggcacgt
1381 ggagtccccg aacaccatca tgtggagaca tttgcaattt tcctcctaaa attgcccatg
1441 ggcattataa acaatctagt tcatacagct ttttcaaaga agagattata tatgaatgtg
1501 ataaaggcta cattctggtc ggacaggcga aactctcctg cagttattca cactggtcag
1561 ctccagcccc tcaatgtaaa gctctgtgtc ggaaaccaga attagtgaat ggaaggttgt
1621 ctgtggataa ggatcagtat gttgagcctg aaaatgtcac catccaatgt gattctggct
1681 atggtgtggt tggtccccaa agtatcactt gctctgggaa cagaacctgg tacccagagg
1741 tgcccaagtg tgagtgggag acccccgaag gctgtgaaca agtgctcaca ggcaaaagac
1801 tcatgcagtg tctcccaaac ccagaggatg tgaaaatggc cctggaggta tataagctgt
1861 ctctggaaat tgaacaactg gaactacaga gagacagcgc aagacaatcc actttggata
1921 aagaactata atttttctca aaagaaggag gaaaaggtgt cttgctggct tgcctcttgc
1981 aattcaatac agatcagttt agcaaatcta ctgtcaattt ggcagtgata ttcatcataa
2041 taaatatcta gaaatgataa tttgctaaag tttagtgctt tgagattgtg aaattattaa
2101 tcatcctctg tgtggctcat gtttttgctt ttcaacacac aaagcacaaa tttttttttcg
2161 attaaaaatg tatgtat
```

SEQ Id NO:71

```
   1 gccctgctgg ccctgctggt gctcccnnnn nnnnnnnnnn nnnnnnnnnn nnnggtcctc
  61 aaggcccacg tggtgacaaa ggtgaaacag gtgaacgtgg agctgctggc atcaaaggac
 121 atcgaggatt ccctggtaat ccaggtgccc caggttctcc agggccctgc tggtcagcag
 181 ggtgcaatcg gcagtccagg acctgcaggc cccagaggac ctgttggacc cagtggacct
 241 cctggcaaag atggaaccag tggacatcca ggtcccattg gaccaccagg gcctcgaggt
 301 aacagaggtg aaagaggatc tgagggctcc ccaggccacc cagggcaacc aggccctcct
 361 ggacctcctg gtgcccctgg tccttgc
```

SEQ Id NO:72

```
   1 gggcgcgggg agagggcgcg ggagcggctc gcgcggcagg taccatgcgg acgcgcgagc
  61 ccggcgaggg ccccggcagg cccggtccct gctcgggggc gcgctgagac ggcgggtgag
 121 ctccacgaga gcgccgtcgc cacttcgggc caactttgcg attcccgaca gttaagcaat
 181 ggggagacat ttggctttgc tcctgcttct gctccttctc ttccaacatt ttggagacag
 241 tgatggcagc caacgacttg aacagactcc tctgcagttt acacacctcg agtacaacgt
 301 caccgtgcag gagaactctg cagctaagac ttatgtgggg catcctgtca agatgggtgt
 361 ttacattaca catccagcgt gggaagtaag gtacaaaatt gtttccggag acagtgaaaa
 421 cctgttcaaa gctgaagagt acattctcgg agacttttgc tttctaagaa taaggaccaa
 481 aggaggaaat acagctattc ttaatagaga agtgaaggat cactacacat tgatagtgaa
 541 agcacttgaa aaaaatacta atgtggaggc gcgaacaaag gtcagggtgc aggtgctgga
 601 tacaaatgac ttgagaccgt tattctcacc cacctcatac agcgtttctt tacctgaaaa
 661 cacagctata aggaccagta tcgcaagagt cagcgccacg gatgcagaca taggaaccaa
 721 cggggaattt tactacagtt ttaaagatcg aacagatatg tttgctattc acccaaccag
 781 tggtgtgata gtgttaactg gtagacttga ttacctagag accaagctct atgagatgga
 841 aatcctcgct gcggaccgtg gcatgaagtt gtatgggagc agtggcatca gcagcatggc
```

Figure 10 (cont.)

```
 901 caagctaacg gtgcacatcg aacaggccaa tgaatgtgct ccggtgataa cagcagtgac
 961 attgtcacca tcagaactgg acagggaccc agcatatgca attgtgacag tggatgactg
1021 cgatcagggt gccaatggtg acatagcatc tttaagcatc gtggcaggtg accttctcca
1081 gcagtttaga acagtgaggt cctttccagg gagtaaggag tataaagtca aagccatcgg
1141 tggcattgat tgggacagtc atcctttcgg ctacaatctc acactacagg ctaaagataa
1201 aggaactccg ccccagttct cttctgttaa agtcattcac gtgacttctc cacagttcaa
1261 agccgggcca gtcaagtttg aaaaggatgt ttacagagca gaaataagtg aatttgctcc
1321 tcccaacaca cctgtggtca tggtaaaggc cattcctgct tattcccatt tgaggtatgt
1381 ttttaaaagt acacctggaa aagctaaatt cagtttaaat tacaacactg gtctcatttc
1441 tatttagaa ccagttaaaa gacagcaggc agcccatttt gaacttgaag taacaacaag
1501 tgacagaaaa gcgtccacca aggtcttggt gaaagtctta ggtgcaaata gcaatccccc
1561 tgaatttacc cagacagcgt acaaagctgc ttttgatgag aacgtgccca ttggtactac
1621 tgtcatgagc ctgagtgccg tagaccctga tgagggtgag aacgggtacg tgacatacag
1681 tatcgcaaat ttaaatcatg tgccgtttgc gattgaccat ttcactggtg ccgtgagtac
1741 gtcagaaaac ctggactacg aactgatgcc tcgggtttat actctgagga ttcgtgcatc
1801 agactggggc ttgccgtacc gccgggaagt cgaagtcctt gctacaatta ctctcaataa
1861 cttgaatgac aacacacctt tgtttgagaa aataaattgt gaagggacaa ttcccagaga
1921 tctaggcgtg ggagagcaaa taaccactgt ttctgctatt gatgcagatg aacttcagtt
1981 ggtacagtat cagattgaag ctggaaatga actggatttc tttagtttaa accccaactc
2041 gggggtattg tcattaaagc gatcgctaat ggatggctta ggtgcaaagg tgtctttcac
2101 agtctgagaa tcacagctac agatggagaa aatttgcca caccattata tatcaacata
2161 acagtggctg ccagtcacaa gctggtaaac ttgcagtgtg aagagactgg tgttgccaaa
2221 atgctggcag agaagctcct gcaggcaaat aaattacaca accagggaga ggtggaggat
2281 atttcttcg attctcactc tgtcaatgct cacataccgc agtttagaag cactcttccg
2341 actggtattc aggtaaagga aaaccagcct gtgggttcca gtgtaatttt catgaactcc
2401 actgaccttg acactggctt caatggaaaa ctggtctatg ctgtttctgg aggaaatgag
2461 gatagttgct tcatgattga tatggaaaca ggaatgctga aaattttatc tcctcttgac
2521 cgtgaaacaa cagacaaata caccctgaat attaccgtct atgaccttgg gataccccag
2581 aaggctgcgt ggcgtcttct acatgtcgtg gttgtcgatg ccaatgataa tccacccgag
2641 tttttacagg agagctattt tgtggaagtg agtgaagaca aggaggtaca tagtgaaatc
2701 atccaggttg aagccacaga taaagacctg ggcccaacg gacacgtgac gtactcaatt
2761 gttacagaca cagacacatt ttcaattgac agcgtgacgg gtgttgttaa catcgcacgc
2821 cctctggatc gagagctgca gcatgagcac tccttaaaga ttgaggccag ggaccaagcc
2881 agagaagagc ctcagctgtt ctccactgtc gttgtgaaag tatcactaga agatgttaat
2941 gacaacccac ctacatttat tccacctaat tatcgtgtga aagtccgaga ggatcttcca
3001 gaaggaaccg tcatcatgtg gttagaagcc cacgatcctg atttaggtca gtctggtcag
3061 gtcagcacac agccttctgg accacggaga aggaaacttc gatgtggata aactcagtgg
3121 agcagttagg atcgtccagc agttggactt tgagaagaag caagtgtata atctcactgt
3181 gagggccaaa gacaagggaa agccagtttc tctgtcttct acttgctatg ttgaagttga
3241 ggtggttgat gtgaatgaga acctgcaccc acccgtgttt tccagctttg tggaaaaggg
3301 gacagtgaaa gaagatgcac ctgttggttc attggtaatg acggtgtcgg ctcatgatga
3361 ggacgccaga agagatgggg agatccgata ctccattaga gatggctctg gcgttggtgt
3421 tttcaaaata ggtgaagaga caggtgtcat agagacgtca gatcgactgg accgtgaatc
3481 gacctcccat tattggctaa cagtctttgc aaccgatcag ggtgtcgtgc ctctttcatc
3541 gttcatagag atctacatag aggttgagga tgtcaatgac aatgcaccac agacatcaga
3601 gcctgtttat tacccagaaa tcatggaaaa ttctcctaaa gatgtatctg tggtccagat
3661 cgaggcattt gatccagatt cgagctctaa tgacaagctc atgtacaaaa ttacaagtgg
3721 aaatccacaa ggattctttt caatacatcc taaaacaggt ctcatcacaa ctacgtcaag
3781 gaagctagac cgagaacagc aagatgaaca catattagag gttactgtga cagacaatgg
3841 tagtcccccc aaatcaacca ttgcaagagt cattgtgaaa atccttgatg aaaatgacaa
3901 caaacctcag tttctgcaaa agttctacaa aatcagactc cctgagcggg aaaagccaga
3961 ccgagaaaga aatgccagac gggagccgct ctatcgcgtc atagccaccg acaaggatga
4021 gggccccaat gcagaaatct cctacagcat cgaagacggg aatgagcatg gcaaattttt
4081 catcgaaccg aaaactggag tggtttcgtc caagaggttt tcagcagctg gagaatatga
```

Figure 10 (cont.)

```
4141 tattctttca attaaggcag ttgacaatgg tcgccctcaa aagtcatcaa ccaccagact
4201 ccatattgaa tggatctcca agcccaaacc gtccctggag cccatttcat ttgaagaatc
4261 atttttttacc tttactgtga tggaaagtga ccccgttgct cacatgattg gagtaatatc
4321 tgtggagcct cctggcatac ccctttggtt tgacatcact ggtggcaact acgacagtca
4381 cttcgatgtg gacaagggaa ctggaaccat cattgttgcc aaacctcttg atgcagaaca
4441 gaagtcaaac tacaacctca cagtcgaggc tacagatgga accaccacta tcctcactca
4501 ggtattcatc aaagtaatag acacaaatga ccatcgtcct cagttttcta catcaaagta
4561 tgaagttgtt attcctgaag atacagcgcc agaaacagaa atttgcaaa tcagtgctgt
4621 ggatcaggat gagaaaaaca aactaatcta cactctgcag agcagtagag atccactgag
4681 tctcaagaaa tttcgtcttg atcctgcaac cggctctctc tatacttctg agaaactgga
4741 tcatgaagct gttcaccagc acaccctcac ggtcatggta cgagatcaag atgtgcctgt
4801 aaaacgcaac tttgcaagga ttgtggtcaa tgtcagcgac acgaatgacc acgccccgtg
4861 gttcaccgct tcctcctaca aagggcgggt ttatgaatcg gcagccgttg gctcagttgt
4921 gttgcaggtg acggctctgg acaaggacaa agggaaaaat gctgaagtgc tgtactcgat
4981 cgagtcagnn nnnnnnngaa atattggaaa ttcttttatg attgatcctg tcttgggctc
5041 tattaaaact gccaaagaat tagatcgaag taaccaagcg gagtatgatt taatggtaaa
5101 agctacagat aagggcagtc caccaatgag tgaaataact tctgtgcgta tctttgtcac
5161 aattgctgac aacgcctctc cgaagtttac atcaaaagaa tattctgttg aacttagtga
5221 aactgtcagc attgggagtt tcgttgggat ggttacagcc catagtcaat catcagtggt
5281 gtatgaaata aaagatggaa atacaggtga tgcttttgat attaatccac attctggaac
5341 tatcatcact cagaaagccc tggactttga aactttgccc atttacacat tgataataca
5401 aggaactaac atggctggtt tgtccactaa tacaacggtt ctagttcact tgcaggatga
5461 gaatgacaac gcgccagttt ttatgcaggc agaatataca ggactcatta gtgaatcagc
5521 ctcaattaac agcgtggtcc taacagacag gaatgtccca ctggtgattc gagcagctga
5581 tgctgataaa gactcaaatg ctttgcttgt atatcacatt gttgaaccat ctgtacacac
5641 atattttgct attgattcta gcactggtgc tattcataca gtactaagtc tggactatga
5701 agaaacaagt attttttcact ttaccgtcca agtgcatgac atgggaaccc cacgtttatt
5761 tgctgagtat gcagcgaatg taacagtaca tgtaattgac attaatgact gccccccctgt
5821 gtttgccaag ccattatatg aagcatctct tttgttacca acatacaaag gagtaaaagt
5881 catcacagta aatgctacag atgctgattc aagtgcattc tcacagttga tttactccat
5941 caccgaaggc aacatcgggg agaagttttc tatggactac aagactggtg ctctcactgt
6001 ccaaaacaca actcagttaa gaagccgcta cgagctaacc gttagagctt ccgatggcag
6061 atttgccggc cttacctctg tcaaaattaa tgtgaaagaa agcaaagaaa gtcacctaaa
6121 gtttacccag gatgtctact ctgcggtagt gaaagagaat tccaccgagg ccgaaacatt
6181 agctgtcatt actgctattg ggaatccaat caatgagcct ttgttttatc acatcctcaa
6241 cccagatcgc agatttaaaa taagccgcac ttcaggagtt ctgtcaacca ctggcacgcc
6301 cttcgatcgt gagcagcagg aggcgtttga tgtggttgta gaagtgacag aggaacataa
6361 gccttctgca gtggcccacg ttgtcgtgaa ggtcattgta gaagaccaaa atgataatgc
6421 gccggtgttt gtcaaccttc cctactacgc cgttgttaaa gtggacactg aggtgggcca
6481 tgtcattcgc tatgtcactg ctgtagacag agacagtggc agaaacgggg aagtgcatta
6541 ctacctcaag gaacatcatg aacactttca aattggaccc ttgggtgaaa tttcactgaa
6601 aaagcaattt gagcttgaca ccttaaataa agaatatctt gttacagtgg ttgcaaaaga
6661 tggagggaac ccggcctttt cagcggaagt tatcgttccg atcactgtca tgaataaagc
6721 catgcctgtg tttgaaaaac ctttctacag tgcagagatt gcagagagca tccaggtgca
6781 cagccctgtg gtccacgtgc aggctaacag cccggaaggc ctgaaagtgt tctacagcat
6841 cacagacgga gaccctttca gccagttcac tattaacttc aatactggag ttatcaatgt
6901 catagctcct ctggactttg aggcccaccc ggcatataag ctgagcatac gcgcaactga
6961 ctccttgacg ggcgctcatg ctgaagtatt tgtggacatc atagtagacg acatcaatga
7021 taaccctcct gtgtttgctc agcagtctta tgcggtgacc ctgtctgagg catctgtaat
7081 tggaacgtct gttgttcaag ttagagccac cgattctgat tcagaaccaa atagaggaat
7141 ctcataccag atgtttggga atcacagcaa gagtcatgat catttttcatg tagacagcag
7201 cactggcctc atctcactac tcagaaccct ggattacgag cagtcccggc agcacacgat
7261 ttttgtgagg gcagttgatg gtggtatgcc cacgctgagc agtgatgtga ttgtcacggt
7321 ggacgttacc gacctcaatg ataatccacc actctttgaa caacagattt atgaagccag
```

Figure 10 (cont.)

```
 7381 aattagcgag cacgcccctc atgggcattt cgtgacctgt gtaaaagcct atgatgcaga
 7441 cagttcagac atagacaagt tgcagtattc cattctgtct ggcaatgatc ataaacattt
 7501 tgtcattgac agtgcaacag ggattatcac cctctcaaac ctgcaccggc acgccctgaa
 7561 gccattttac agtcttaacc tgtcagtgtc tgatggagtt tttagaagtt ccacccaggt
 7621 tcatgtaact gtaattggag gcaatttgca cagtcctgct ttccttcaga acgaatatga
 7681 agtggaacta gctgaaaacg ctcccctaca taccctggtg atggaggtga aaactacgga
 7741 tggggattct ggtatttatg gtcacgttac ttaccatatt gtaaatgact ttgccaaaga
 7801 cagattttac ataaatgaga gaggacagat atttactttg gaaaaacttg atcgagaaac
 7861 cccggcggag aaagtgatct cagtccgttt aatggctaag gatgctggag gaaaagttgc
 7921 tttctgcacc gtgaatgtca tccttacaga tgacaatgac aatgcaccac aatttcgagc
 7981 aaccaaatac gaagtgaata tcgggtccag tgctgctaaa gggacttcag tcgttaaagt
 8041 tcttgcaagt gatgccgatg agggctccaa tgccgacatc acctatgcca ttgaagcaga
 8101 ctctgaaagt gtaaaagaga atttggaaat taacaaactg tccggcgtaa tcactacaaa
 8161 ggagagcctc attggcttgg aaaatgaatt cttcactttc tttgttagag ctgtggataa
 8221 tgggtctcca tcaaaagaat ctgttgttct tgtctatgtt aaaatccttc caccggaaat
 8281 gcagcttcca aaattttcag aacctttcta tacctttaca gtgtcagagg acgtgcctat
 8341 tggaacagag atagatctca tccgagcaga acatagtggg actgttcttt acagcctggt
 8401 caaagggaat actccagaaa gcaataggga tgagtccttt gtgattgaca gacagagcgg
 8461 gagactgaag ttggagaaga gtcttgatca tgagacaact aagtggtatc agttttccat
 8521 actggccagg tgcactcaag atgaccatga gatggtggct tctgtagatg ttagtatcca
 8581 agtgaaagat gcaaatgaca acagcccggt ctttgaatct agtccatatg aggcattcat
 8641 tgttgaaaac ctgccagggg gaagtagagt aattcagatc agggcatctg atgctgactc
 8701 aggaaccaac ggccaagtta tgtatagcct ggatcagtca caaagtgtgg aagtcattga
 8761 atcctttgcc attaacatgg aaacaggctg gattacaact ttaaaggaac ttgaccatga
 8821 aaagagagac aattaccaga ttaaagtggt tgcatcagat catggtgaaa agatccagct
 8881 atcctccaca gccattgtgg atgttaccgt caccgatgtc aacgatagtc caccacgatt
 8941 cacggccgag atctataaag ggactgtgag tgaggatgac ccccaaggtg gggtgattgc
 9001 catcttaagt accacggatg ctgattctga agagatcaac agacaagtta catatttcat
 9061 aacaggaggg gatcctttag gacagtttgc cgttgaaact atacagaatg aatggaaggt
 9121 atatgtgaag aaacctctag acagggaaaa aagggacaat taccttctta ctatcacggc
 9181 aactgatggc accttctcat caaaagcgat agttgaagtg aaagttctgg atgcaaatga
 9241 caacagtcca gtttgtgaaa agactttata ttcagacact attcctgaag acgtccttcc
 9301 tggaaaattg atcatgcaga tctctgctac agacgcagac atccgctcta acgctgaaat
 9361 tacttacacg ttattgggtt caggtgcaga aaaattcaaa ctaaatccag acacaggtga
 9421 actgaaaacg tcaacccccc ttgatcgtga ggagcaagct gtttatcatc ttctcgtcag
 9481 ggccacagat ggaggaggaa gattctgcca agccagtatt gtgctcacgc tagaagatgt
 9541 gaacgataac gcccccgaat tctctgccga tccttatgcc atcaccgtgt ttgaaaacac
 9601 agagccggga acgctgctga caagagtgca ggccacagat gccgacgcag gattaaatcg
 9661 gaagatttta tactcactga ttgactctgc tgatgggcag ttctccatta acgaattatc
 9721 tggaattatt cagttagaaa aacctttgga cagagaactc caggcagtat acaccctctc
 9781 tttgaaagct gtggatcaag gcttgccaag gaggctgact gccactggca ctgtgattgt
 9841 atcagttctt gacataaatg acaacccccc tgtgtttgag taccgtgaat atggtgccac
 9901 cgtgtctgag gacattcttg ttggaactga agttcttcaa gtgtatgcag caagtcggga
 9961 tattgaagca aatgcagaaa tcacctactc aataataagt ggaaatgaac atgggaaatt
10021 cagcatagat tctaaaacag nnnnnnnnnn nnnnnnnnnn nnnnnnnnnn nnnnnnnnnn
10081 nnnnnnnnnn nnnnnnnnnn nnnnnnnnnn nnnnnnnnnn nnnnnnnnnn nnnnnnnnnn
10141 nnnnnnnnnn nnnnnnnnnn nnnnnnnnnn nnnnnnnnnn nnnnnnnnnn nnnnnnnnnn
10201 nnnnnnnnnn nnnnnnnnnn nnnnnnnnnn nnnnnnnnnn nnnnnnnnnn nnnnnnnnnn
10261 nnnnnnnnnn nnnnnnnnnn nnnnnnnnnn nnnnnnnnnn nnnnnnnnnn nnnnnnnnnn
10321 nnnnnnnnnn nnnnnnnnnn nnnnnnnnnn nnnnnnnnnn nnnnnnnnnn nnnnnnnnnn
10381 nnnnnnnnnn nnnnnnnnnn nnnnnnnnnn nnnnnnnnnn nnnnnnnnnn nnnnnnnnnn
10441 nnnnnnnnnn nnnnnnnnnn nnnnnnnnnn nnnnnnnnnn nnnnnnnnnn nnnnnnnnnn
10501 nnnnnnnnnn nnnnnnnnnn nnnnnnnnnn nnnnnnngaa aataagccag tgggcttcag
10561 cgtgctgcag ctggtagtaa cagatgagga ttcttcccat aacggtccac ccttcttctt
```

Figure 10 (cont.)

```
10621 tactattgta actggaaatg atgagaaggc ttttgaagtt aacccgcaag gagtcctcct
10681 gacatcatct gccatcaaga ggaaggagaa agatcattac ttactgcagg tgaaggtggc
10741 agataatgga aagcctcagt tgtcatcttt gacatacatt gacattaggg taattgagga
10801 gagcatctat ccgcctgcga ttttgcccct ggagattttc atcacctctt ctggagaaga
10861 atactcaggt ggcgtcattg ggaagatcca tgccacagac caggacgtgt atgatactct
10921 aacctacagt ctcgaccctc agatggacaa cctgttctct gtttccagca caggggggcaa
10981 gctgatagca cacaaaaagc tagacatagg gcaatacctt ctcaatgtca gcgtaacaga
11041 tgggaagttc acgacggtgg ccgacatcac agtgcatatc agacaagtca cacaggagat
11101 gttgaaccac accatcgcga tccgctttgc caacctcact ccggaagaat tcgttggtga
11161 ctactggcgc aacttccagc gagctttacg gaacatcctg ggtgtgagga ggaacgacat
11221 acagattgtt agtttgcagt cctctgaacc tcacccacat ctggacgtct tactttttgt
11281 agagaaacca ggtagtgctc agatctcaac aaaacaactt ctgcacaaga ttaactcttc
11341 cgtgactgac attgaggaaa tcattggagt taggatactg aatgtattcc agaaactctg
11401 cgcgggactg gactgcccct ggaagttctg cgatgaaaag gtgtctgtgg atgaaagtgt
11461 gatgtcaaca cacagcacag ccagactgag ttttgtgact ccccgccacc acagggcagc
11521 ggtgtgtctc tgcaaagagg gaaggtgccc acctgtccac catggctgtg aagatgatcc
11581 gtgccctgag ggatccgaat gtgtgtctga tccctgggag gagaaacaca cctgtgtctg
11641 tcccagcggc aggtttggtc agtgcccagg gagttcatct atgacactga ctggaaacag
11701 ctacgtgaaa taccgtctga cggaaaatga aaacaaatta gagatgaaac tgaccatgag
11761 gctcagaaca tattccacgc atgcggttgt catgtatgct cgaggaactg actatagcat
11821 cttggagatt catcatggaa ggtgcagtca annnnnnnnn nnnnnnnnnn nnnnnnnnnn
11881 nnnnnnnnnn nnncattcag gtcaatgatg ggcagtggca cgcagtggcc ctggaagtga
11941 atggaaacta tgctcgcttg gttctagacc aagttcatac tgcatcgggc acagccccag
12001 ggactctgaa aaccctgaac ctggataact atgtgttttt tggtggccac atccgtcagc
12061 agggaacaag gcatggaaga agtcctcaag ttggtaatgg tttcaggggt tgtatggact
12121 ccatttattt gaatgggcag gagctccctt taaacagcaa acccagaagc tatgcacaca
12181 tcgaagagtc ggtggatgta tctccaggct gcttcctgac ggccacggaa gactgcgcca
12241 gcaacccttg ccagaatgga ggcgtttgca atccgtcacc tgctggaggt tattactgca
12301 aatgcagtgc cttgtacata gggacccact gtgagataag cgtcaatccg tgttcctcca
12361 agccatgcct ctatgggggc acgtgtgttg tcgacaacgg aggctttgtt tgccagtgta
12421 gaggattata tactggtcag aggtgtcagc ttagtccata ctgcaaagat gaaccctgta
12481 agaatggcgg aacatgcttt gacagtttgg atggcgccgt ttgtcagtgt gattcgggtt
12541 ttaggggaga aaggtgtcag agtgatatcg acgagtgctc tggaaaccct tgcctgcacg
12601 gggccctctg tgagaacacg cacggctcct atcactgcaa ctgcagccac gagtacaggg
12661 gacgtcactg cgaggatgct gcgcccaacc agtatgtgtc cacgccgtgg aacattgggt
12721 tggcggaagg aattggaatc gttgtgtttg ttgcagggat atttttactg gtggtggtgt
12781 ttgttctctg ccgtaagatg attagtcgga aaaagaagca tcaggctgaa cctaaagaca
12841 agcacctggg acccgctacg gctttcttgc aaagaccgta ttttgattcc aagctaaata
12901 agaacattta ctcagacata ccaccccagg tgcctgtccg gcctatttcc tacaccccga
12961 gtattccaag tgactcaaga aacaatctgg accgaaattc cttcgaagga tctgctatcc
13021 cagagcatcc cgaattcagc acttttaacc ccgagtctgt gcacgggcac cgaaaagcag
13081 tggcggtctg cagcgtggcg ccaaacctgc ctcccccacc cccttcaaac tccccttctg
13141 acagcgactc catccagaag cctagctggg actttgacta tgacacaaaa gtggtggatc
13201 ttgatccctg tctttccaag aagcctctag aggaaaagcc ttcccagcca tacagtgccc
13261 gggaaagcct gtctgaagtg cagtctctga gctccttcca gtccgaatcg tgcgatgaca
13321 atgggtatca ctgggataca tcagattgga tgccaagcgt tcctctgccg gacatacaag
13381 agttccccaa ctatgaggtg attgatgagc agacacccct gtactcagca gatccaaacg
13441 ccatcgatac ggactattac cctggaggct acgacatcga aagtgatttt cctccacccc
13501 cagaagactt ccccgcagct gatgagctac caccgttacc gcccgaattc agcaatcagt
13561 ttgaatccat ccaccctcct agagacatgc ctgccgcggg tagcttgggt tcttcatcaa
13621 gaaaccggca gaggttcaac ttgaatcagt atttgcccaa tttttatccc ctcgatatgt
13681 ctgaacctca aacaaaaggc actggtgaga atagtacttg tagagaaccc catgcccctt
13741 acccgccagg gtatcaaaga cacttcgagg cgcccgctgt cgagagcatg cccatgtctg
13801 tgtacgcctc caccgcctcc tgctctgacg tgtcagcctg ctgcgaagtg gagtccgagg
```

Figure 10 (cont.)

```
13861 tcatgatgag tgactatgag agcggggacg acggccactt cgaagaggtg acgatcccgc
13921 ccctggattc ccagcagcac acggaagtct gactctcaac tccccccaaa gtgcctgact
13981 ttagtgaacc tagaggtgat gtgagtaatc cgcgctgttc tttgcagcag tgcttccaag
14041 cttttttgg tgagccgaat gggcatggct gcgctggatc ctgcgcctct ggacgtgcta
14101 gccatttcca gtgtcccaac tactgtcatc gtgaggtttt catcggctgt gccatttccc
14161 aacgtctttt gggatttaca tctgtctgtg ttaaaataat caaacgaaaa atcagtcctg
14221 tgttgtcagc atgattcatg tatttatata gatttgatta ttttaatttt cctgtctctt
14281 tttttgtaa attttatgta cagatttgat ttttcatagt tttaactaga tttccaagat
14341 attttgtgca tttgtttcaa ctgaatttg gtggtgtcag tgccattatc tagcacccctg
14401 atttttttt ttttactata accagggttt cattctgtct ttttccactg aagtgtgaca
14461 ttttgttagt acatttcagt gtagtcattc atttctagct gtacatagga tgaaggagag
14521 atcagataca tgaacatgtc ttacatgggt tgctgtattt agaattataa acatttttca
14581 ttattggaaa gtgtaacggg gaccttctgc atacctgttt agaaccaaaa ccaccatgac
14641 acagttttta tagtgtctgt atatttgtga tgcaatggtc ttgtaaaggt ttttaatgaa
14701 aactaccatt agccagtctt tcttactgac aataaattat taataaaat
```

SEQ Id NO:73

```
   1 gattttaggt gatgggcaag tcagaaagtc agatggatat aactgatatc aacactccaa
  61 agccaaagaa gaaacagcga tggactccac tggagatcag cctctcggtc cttgtcctgc
 121 tcctcaccat catagctgtg acaatgatcg cactctatgc aacctacgat gatggtattt
 181 gcaagtcatc agactgcata aaatcagctg ctcgactgat ccaaaacatg gatgccacca
 241 ctgagccttg tacagacttt ttcaaatatg cttgcggagg ctggttgaaa cgtaatgtca
 301 ttcccgagac cagctcccgt tacggcaact ttgacatttt aagagatgaa ctagaagtcg
 361 ttttgaaaga tgtccttcaa gaacccaaaa ctgaagatat agtagcagtg cagaaagcaa
 421 aagcattgta caggtcttgt ataaatgaat ctgctattga tagcagaggt ggagaacctc
 481 tactcaaact gttaccagac atatatgggt ggccagtagc aacagaaaac tgggagcaaa
 541 aatatggtgc ttcttggaca gctgaaaaag ctattgcaca actgaattct aaatatggga
 601 aaaaagtcct tattaatttg tttgttggca ctgatgataa gaattctgtg aatcatgtaa
 661 ttcatattga ccaacctcga cttggcctcc cttctagaga ttactatgaa tgcactggaa
 721 tctataaaga ggcttgtaca gcatatgtgg attttatgat ttctgtggcc agattgattc
 781 gtcaggaaga aagattgccc atcgatgaaa accagcttgc tttggaaatg aataaagtta
 841 tggaattgga aaaagaaatt gccaatgcta cggctaaacc tgaagatcga aatgatccaa
 901 tgcttctgta taacaagatg acattggccc agatccaaaa taacttttca ctagagatca
 961 atgggaagcc attcagctgg ttgaatttca caaatgaaat catgtcaact gtgaatatta
1021 gtattacaaa tgaggaagat gtggttgttt atgctccaga atatttaacc aaacttaagc
1081 ccattcttac caaatattct gccagagatc ttcaaaattt aatgtcctgg agattcataa
1141 tggatcttgt aagcagcctc agccgaacct acaaggagtc cagaaatgct ttccgcaagg
1201 ccctttatgg tacaacctca gaaacagcaa cttggagacg ttgtgcaaac tatgtcaatg
1261 ggaatatgga aaatgctgtg gggaggcttt atgtggaagc agcatttgct ggagagagta
1321 aacatgtggt cgaggatttg attgcacaga tccgagaagt ttttattcag actttagatg
1381 acctcacttg gatggatgcc gagacaaaaa agagagctga agaaaaggcc ttagcaatta
1441 aagaaaggat cggctatcct gatgacattg tttcaaatga taacaaactg aataatgagt
1501 acctcgagtt gaactacaaa gaagatgaat acttcgagaa cataattcaa aatttgaaat
1561 tcagccaaag taaacaactg aagaagctcc gagaaaaggt ggacaaagat gagtggataa
1621 gtggagcagc tgtagtcaat gcattttact cttcaggaag aaatcagata gtcttcccag
1681 ccggcattct gcagcccccc ttctttagtg cccagcagtc caactcattg aactatgggg
1741 gcatcggcat ggtcatagga cacgaaatca cccatggctt cgatgacaat ggcagaaact
1801 ttaacaaaga tggagacctc gttgactggt ggactcaaca gtctgcaagt aactttaagg
1861 agcaatccca gtgcatggtg tatcagtatg gaaacttttc ctgggacctg gcaggtggac
1921 agcaccttaa tggaattaat acactgggag aaaacattgc tgataatgga ggtcttggtc
1981 aagcatacag agcctatcag aattatatta aaaagaatgg cgaagaaaaa ttacttcctg
2041 gacttgacct aaatcacaaa caactatttt tcttgaactt tgcacaggtg tggtgtggaa
2101 cctataggcc agagtatgcg gttaactcca ttaaaacaga tgtgcacagt ccaggcaatt
2161 tcaggattat tgggactttg cagaactctg cagagttttc agaagccttt cactgccgca
```

Figure 10 (cont.)

```
2221 agaattcata catgaatcca gaaaagaagt gccgggtttg gtgatcttca aaagaagcat
2281 tgcagccctt ggctagactt gccaacacca cagaaatggg gaattctcta atcgaaagaa
2341 aatgggccct aggggtcact gtactgactt gagggtgatt aacagagagg gcaccatcac
2401 aatacagata acattaggtt gtcctagaaa gggtgtggag ggaggaaggg ggtctaaggt
2461 ctatcaagtc aatcatttct cactgtgtac ataatgctta atttctaaag ataatattac
2521 tgtttatttc tgtttctcat atggtctacc agtttgctga tgtccctaga aaacaatgca
2581 aaacctttga ggtagaccag gatttctaat caaaagggaa aagaagatgt tgaagaatac
2641 agttaggcac cagaagaaca gtaggtgaca ctatagttta aaacacattg cctaactact
2701 agtttttact tttatttgca acatttacag tccttcaaaa tccttccaaa gaattcttat
2761 acacattggg gccttggagc ttacatagtt ttaaactcat ttttgccata catcagttat
2821 tcattctgtg atcatttatt ttaagcactc ttaaagcaaa aaatgaatgt ctaaaattgt
2881 tttttgttgt acctgctttg actgatgctg agattcttca ggcttcctgc aattttctaa
2941 gcaatttctt gctctatctc tcaaaacttg gtatttttca gagatttata taaatgtaaa
3001 aataataatt tttatattta attattaact acatttatga gtaactatta ttataggtaa
3061 tcaatgaata ttgaagtttc agcttaaaat aaacagttgt gaaccaagat ctataaagcg
3121 atatacagat gaaaatttga gactatttaa acttataaat catattgatg aaaagattta
3181 agcacaaact ttagggtaaa aattgccatt ggacagttgt ctagagatat atatacttgt
3241 ggttttcaaa ttggactttc aaaattaaat ctgtccctga gagtgtctct gataaaaggg
3301 caaatctgca cctatgtagc tctgcatctc ctgtcttttc aggtttgtca tcagatggaa
3361 atatttgat aataaattga aattgtgaac tcattgctcc ctaagactgt gacaactgtc
3421 taactttaga agtgcatttc tgaatagaaa tgggaggcct ctgatggacc ttctagaatt
3481 ataagtcaca aagagttctg gaaaagaact gtttactgct tgataggaat tcatcttttg
3541 aggcttctgt tcctctcttt tcctgttgta ttgactattt tcgttcatta cttgattaag
3601 attttacaaa agaggagcac ttccaaaatt cttattttc ctaacaaaag atgaaagcag
3661 ggaatttcta tctaaatgat gagtattagt tccctgtctc ttgaaaaatg cccatttgcc
3721 tttaaaaaaa aaagttacag aaatactata acatatgtac ataaattgca taaagcataa
3781 gtatacagtt caataaactt aactttaact gaacaatggc cctgtagcca gcacctgtaa
3841 gaaacagagc agtaccagcg ctctaaaagc acctccttgt cactttatta ctcccagaac
3901 aacaactatc ctgacttcta atatcattca ctagctttgc ctggttttgt cttttatgca
3961 gatagaatca atcagtatgt attcttttgt gcctggcttc tttctctcag ccttacattt
4021 gtgagattcc tctgtattgt gctgattgtg gatcttttca ttctcattgc agaataatgt
4081 tctattgtgg gacttattac aatttgttca tcctattgtt gatgggcact tgagaacttt
4141 ccattttggc gctattacaa atagtgcaac tatgaatgta ctgcatgtta ccatcttact
4201 tgagccttta atggacttat ttcttcaaat ccttccaaaa attattataa gcattgaaat
4261 tatagtttca agccaactgt ggataccctt accctttcct cctttatcac aaccaccgtt
4321 acaagtatac ttatatttcc ctaaaataca tttaaaactt acctaagtga catttgtagt
4381 tggagtaata ggagcttcca gctctaataa aacagctgtc tctaacttat tttatttcca
4441 tcatgtcaga gcaggtgaag agccagaagt gaagagtgac tagtacaaat tataaaaagc
4501 cactagactc ttcactgtta gctttttaaa acattaggct cccatcccta tggaggaaca
4561 actctccagt gcctggatcc cctctgtcta caaatataag atttctgggg cctaaaggat
4621 agatcaaagt caaaaatagc aatgcctccc tatccctcac acatccagac atcatgaatt
4681 ttacatggta ctcttgttga gttctgtaga gccttctgat gtctctaaag cactaccgat
4741 tctttggagt tgtcacatca gataagacat atctctaatt ccatccataa atccagttct
4801 actatggctg agttctggtc aaagaaagaa agtttagaag ctgagacaca aagggttggg
4861 agctgatgaa actcacaaat gatggtagga agaagctctc gacaataccc gttggcaagg
4921 agtctgcctc catgctgcag tgttcgagtg gattgtaggt gcaagatgga aaggattgta
4981 ggtgcaagct gtccagagaa aagagtcctt gttccagccc tattctgcca ctcctgacag
5041 ggtgaccttg ggtatttgca atattccttt gggcctctgc ttctctcacc taaaaaaaga
5101 gaattagatt atattggtgg ttctcagcaa gagaaggagt atgtgtccaa tgctgccttc
5161 ccatgaatct gtctcccagt tatgaatcag tgggcaggat aaactgaaaa ctcccattta
5221 cgtgtctgaa tcgagtgaga caaaatttta gtccaaataa caagtaccaa agttttatca
5281 agtttgggtc tgtgctgctg ttactgttaa ccatttaagt ggggcaaaac cttgctaatt
5341 ttctcaaaag catttatcat tcttgttgcc acagctggag ctctcaaact aaaagacatt
5401 tgttattttg gaaagaagaa agactctatt ctcaaagttt cctaatcaga aatttttatc
```

Figure 10 (cont.)

5461 agtttccagt ctcaaaaata caaaataaaa acaaacgttt ttaatact

SEQ ID NO:74

1 atgtccaatc agggaagtaa gtacgtcaat aaggaaattc aaaatgctgt caacggggtg
61 aaacagataa agactctcat agaaaaaaca aacgaagagc gcaagacact gctcagcaac
121 ctagaagaag ccaagaagaa gaaagaggat gccctaaatg agaccaggga atcagagaca
181 aagctgaagg agctcccagg agtgtgcaat gagaccatga tggccctctg ggaagagtgt
241 aagccctgcc tgaaacagac ctgcatgaag ttctacgcac gcgtctgcag aagtggctca
301 ggcctggttg gccgccagct tgaggagttc ctgaaccaga gctcgccctt ctacttctgg
361 atgaatggtg accgcatcga ctccctgctg gagaacgacc ggcagcagac gcacatgctg
421 gatgtcatgc aggaccactt cagccgcgcg tccagcatca tagacgagct cttccaggac
481 aggttcttca cccgggagcc ccaggatacc taccactacc tgcccttcag cctgccccac
541 cggaggcctc acttcttctt tcccaagtcc cgcatcgtcc gcagcttgat gcccttctct
601 ccgtacgagc cctgaactt ccacgccatg ttccagccct tccttgagat gatacacgag
661 gctcagcagg ccatggacat ccacttccat agcccggcct tccagcaccc gccaacagaa
721 ttcatacgag aaggcgacga tgaccggact gtgtgccggg agatccgcca caactccacg
781 ggctgcctgc ggatgaagga ccagtgtgac aagtgccggg agatcttgtc tgtggactgt
841 tccaccaaca acccctccca ggctaagctg cggcgggagc tcgacgaatc cctccaggtc
901 gctgagaggt tgaccaggaa atacaacgag ctgctaaagt cctaccagtg gaagatgctc
961 aacacctcct ccttgctgga gcagctgaac gagcagttta actgggtgtc ccggctggca
1021 aacctcacgc aaggcgaaga ccagtactat ctgcgggtca ccacggtggc ttcccacact
1081 tctgactcgg acgttccttc cggtgtcact gaggtggtcg tgaagctctt tgactctgat
1141 cccatcactg tgacggtccc tgtagaagtc tccaggaaga accctaaatt tatggagacc
1201 gtggcggaga aagcgctgca ggaataccgc aaaaagcacc gggaggagtg agatgtggat
1261 gttgcttttg cacctacggg ggcatctgag tccagctccc cccaagatga gctgcagccc
1321 cccagagaga gctctgcacg tcaccaagta accaggcccc agcctccagg cccccaactc
1381 cgcccagcct ctccccgctc tggatcctgc actctaacac tcgactctgc tgctcatggg
1441 aagaacagaa ttgctcctgc atgcaactaa ttcaataaaa ctgtcttgtg agctg

SEQ ID NO:75

1 gaaggaaaaa gagcaacaga tccagggagc attcacctgc cctgtctcca aacagccttg
61 tgcctcacct acccccaacc tcccagaggg agcagctatt taaggggagc aggagtgcag
121 aacaaacaag acggcctggg gatacaactc tggagtcctc tgagagagcc accaaggagg
181 agcaggggag cgacggccgg ggcagaagtt gagaccaccc agcagaggag ctaggccagt
241 ccatctgcat ttgtcaccca agaactctta ccatgaagac cctcctactg ttggcagtga
301 tcatgatctt tggcctactg caggcccatg ggaatttggt gaatttccac agaatgatca
361 agttgacgac aggaaaggaa gccgcactca gttatggctt ctacggctgc cactgtggcg
421 tgggtggcag aggatccccc aaggatgcaa cggatcgctg ctgtgtcact catgactgtt
481 gctacaaacg tctggagaaa cgtggatgtg gcaccaaatt tctgagctac aagtttagca
541 actcggggag cagaatcacc tgtgcaaaac aggactcctg cagaagtcaa ctgtgtgagt
601 gtgataaggc tgctgccacc tgttttgcta gaaacaagac gacctacaat aaaaagtacc
661 agtactattc caataaacac tgcagaggga gcacccctcg ttgctgagtc ccctcttccc
721 tggaaacctt ccacccagtg ctgaatttcc ctctctcata ccctccctcc ctaccctaac
781 caagttcctt ggccatgcag aaagcatccc tcacccatcc tagaggccag gcaggagccc
841 ttctataccc acccagaatg agacatccag cagatttcca gccttctact gctctcctcc
901 acctcaactc cgtgcttaac caaagaagct gtactccggg gggtctcttc tgaataaagc
961 aattagc

SEQ ID NO:76

1 gctccatcaa gtatgatggt gaaggatgaa tatgtgcatg actttgaggg acagccatcg
61 ttgtccactg aaggacattc aattcaaacc atccagcatc caccaagtaa tcgtgcatcg
121 acagagacat acagcacccc agctctgtta gccccatctg agtctaatgc taccagcact

Figure 10 (cont.)

```
 181 gccaactttc ccaacattcc tgtggcttcc acaagtcagc ctgccagtat actggggggc
 241 agccatagtg aaggactgtt gcagatagca tcagggcctc agccaggaca gcagcagaat
 301 ggatttactg gtcagccagc tacttaccat cataacagca ctaccacctg gactggaagt
 361 aggactgcac catacacacc taatttgcct caccaccaaa acggccatct tcagcaccac
 421 ccgcctatgc cgccccatcc cggacattac tggcctgttc acaatgagct tgcattccag
 481 cctcccattt ccaatcatcc tgctcctgag tattggtgtt ccattgctta ctttgaaatg
 541 gatgttcagg taggagagac atttaaggtt ccttcaagct gccctattgt tactgttgat
 601 ggatacgtgg acccttctgg aggagatcgc ttttgtttgg gtcaactctc caatgtccac
 661 aggacagaag ccattgagag agcaaggttg cacataggca aaggtgtgca gttggaatgt
 721 aaaggtgaag gtgatgtttg ggtcaggtgc cttagtgacc acgcggtctt tgtacagagt
 781 tactacttag acagagaagc tgggcgtgca cctggagatg ctgttcataa gatctaccca
 841 agtgcatata taaaggtctt tgatttgcgt cagtgtcatc gacagatgca gcagcaggcg
 901 gctactgcac aagctgcagc agctgcccag gcagcagccg tggcaggaaa catccctggc
 961 ccaggatcag taggtggaat agctccagct atcagtctgt cagctgctgc tggaattggt
1021 gttgatgacc ttcgtcgctt atgcatactc aggatgagtt ttgtgaaagg ctggggaccg
1081 gattacccaa gacagagcat caaagaaaca ccttgctgga ttgaaattca cttacaccgg
1141 gccctccagc tcctagacga agtacttcat accatgccga ttgcagaccc acaacccttta
1201 gactgaggtc ttttaccgtt ggggccctta accttatcag gatggtggac tacaaaatac
1261 aatcctgttt ataatctgaa gatatatttc acttttgttc tgctttatct tttcataaag
1321 ggttgaaaat gtgtttgctg ccttgctcct agcagacaga aactggatta aaacaatttt
1381 tttttcctc ttcagaactt gtcaggcatg gctcagagct tgaagattag gagaaacaca
1441 ttcttattaa ttcttcacct gttatgtatg aaggaatcat tccagtgcta gaaaatttag
1501 ccctttaaaa cgtcttagag ccttttatct gcagaacatc gatatgtata tcattctaca
1561 gaataatcca gtattgctga ttttaaaggc agagaagttc tcaaagttaa ttcacctatg
1621 ttattttgtg tacaagttgt tattgttgaa catacttcaa aaataatgtg ccatgtgggt
1681 gagttaattt taccaagagt aactttactc tgtgtttaaa aagtaagtta ataatgtatt
1741 gtaatctttc atccaaaata tttttgcaa gttatattag tgaagatggt ttcaattcag
1801 attgtcttgc aacttcagtt ttattttgc caaggcaaaa aactcttaat ctgtgtgtat
1861 attgagaatc ccttaaaatt accagacaaa aaaatttaaa attacgtttg ttattcctag
1921 tggatgactg ttgatgaagt atactttcc cctgttaaac agtagttgta ttcttctgta
1981 tttctaggca caaggttggt tgctaagaag cctataagag gaatttcttt tccttcattc
2041 atagggaaag gttttgtatt ttttaaaaca ctaaaagcag cgtcactcta cctaatgtct
2101 cactgttctg caaaggtggc aatgcttaaa ctaaataatg aataaactga atattttgga
2161 aactgctaaa ttctatgtta aatactgtgc agaataatgg aaacattaca gttcataata
2221 ggtagtttgg atatttttgt acttgatttg atgtgacttt ttttggtata atgtttaaat
2281 catgtatgtt atgatattgt ttaaaattca gtttttgtat cttggggcaa gactgcaaac
2341 ttttttatat cttttggtta ttctaagccc tttgccatca atgatcatat caattggcag
2401 tgactttgta tagagaattt aagtagaaaa gttgcagatg tattgactgt accacagaca
2461 caatatgtat gctttttacc tagctggtag cataaataaa actgaatctc aacat
```

SEQ ID NO:77

```
   1 gcaggcccgt tggaagtggt tgtgacaacc ccagcaatgt ggagaagcct ggggcttgcc
  61 ctggctctct gtctcctccc atcgggagga acagagagcc aggaccaaag ctccttatgt
 121 aagcaacccc cagcctggag cataagagat caagatccaa tgctaaactc caatggttca
 181 gtgactgtgg ttgctcttct tcaagccagc tgatacctgt gcatactgca ggcatctaaa
 241 ttagaagacc tgcgagtaaa actgaagaaa gaaggatatt ctaatatttc ttatattgtt
 301 gttaatcatc aaggaatctc ttctcgatta aaatacacac atcttaagaa taaggtttca
 361 gagcatattc ctgtttatca acaagaagaa aaccaaacag atgtctggac tcttttaaat
 421 ggaagcaaag atgacttcct catatatgat agatgtggcc gtcttgtata tcatcttggt
 481 ttgccttttt ccttcctaac tttcccatat gtagaagaag ccattaagat tgcttactgt
 541 gaaaagaaat gtggaaactg ctctctcacg actctcaaag atgaagactt ttgtaaacgt
 601 gtatctttgg ctactgtgga taaaacagtt gaaactccat cgcctcatta ccatcatgag
 661 catcatcaca atcatggaca tcagcacctt ggcagcagtg agctttcaga gaatcagcaa
 721 ccaggagcac caaatgctcc tactcatcct gctcctccag gccttcatca ccaccataag
```

Figure 10 (cont.)

```
 781 cacaagggtc agcataggca gggtcaccca gagaaccgag atatgccagc aagtgaagat
 841 ttacaagatt tacaaaagaa gctctgtcga aagagatgta taaatcaatt actctgtaaa
 901 ttgcccacag attcagagtt ggctcctagg agctgatgct gccattgtcg acatctgata
 961 tttgaaaaaa cagggtctgc aatcacctga cagtgtaaag aaaacctccc atctttatgt
1021 agctgacagg gacttcgggc agaggagaac ataactgaat cttgtcagtg acgtttgcct
1081 ccagctgcct gacaaataag tcagcagctt atacccacag aagccagtgc cagttgacgc
1141 tgaaagaatc aggcaaaaaa gtgagaatga ccttcaaact aaatatttaa aataggacat
1201 actccccaat ttagtctaga cacaatttca tttccagcat ttttataaac taccaaatta
1261 gtgaaccaaa aatagaaatt agatttgtgc aaacatggag aaatctactg aattggcttc
1321 cagattttaa attttatgtc atagaaatat tgactcaaac catatttttt atgatggagc
1381 aactgaaagg tgattgcagc ttttggttaa tatgtctttt tttttctttt tccagtgttc
1441 tatttgcttt aatgagaata gaaacgtaaa ctatgaccta ggggtttctg ttggataatt
1501 agcagtttag aatggaggaa gaacaacaaa gacatgcttt ccattttttt ctttacttat
1561 ctctcaaaac aatattactt tgtcttttca atcttctact tttaactaat aaaataagtg
1621 gattttgtat tttaagatcc agaaatactt aacacgtgaa tattttgcta aaaaagcata
1681 tataactatt ttaaatatcc atttatcttt tgtatatcta agactcatcc tgatttttac
1741 tatcacacat gaataaagcc tttgtatctt tctttctcta atgttgtatc atactcttct
1801 aaaacttgag tggctgtctt aaaagatata aggggaaaga taatattgtc tgtctctata
1861 ttgcttagta agtatttcca tagtcaatga tggtttaata ggtaaaccaa accctataaa
1921 cctgacctcc tttatggtta atactattaa gcaagaatgc agtacagaat tggatacagt
1981 acggatttgt ccaaataaat tcaataaaaa ccttaaa
```

SEQ ID NO:78

```
   1 caaccacttg acaacctggt tagaagatgc ccgccagcat tccaattcca acatggtcat
  61 tatgcttatt ggaaataaaa gtgatttaga atctagaaga gaagtaaaaa aagaagaagg
 121 tgaagctttt gcacgagaac atggactcat cttcatggaa acgtctgcta agactgcttc
 181 caatgtagaa gaggcattta ttaatacagc aaaagaaatt tatgaaaaaa ttcaagaagg
 241 agtctttgac attaataatg aggcaaatgg cattaaaatt ggccctcagc atgctgctac
 301 caatgcaaca catgcaggca atcagggagg acagcaggct gggggcggct gctgttgagt
 361 ctgtttttac tgtctagctg cccaacgggg cctactcact tattctttca ccccctctcc
 421 tcctgctcag ctgagacatg aaactatttg aaatggcttt atgtcacaga agactttaat
 481 ccgtcaaatt cttgtataac tttgaataaa tggttaatgt tcacttaaaa gacagatttt
 541 ggagattgta ttcatatcta tttgcatttg atttctaggt caattgatgt gattattttt
 601 gttaaatgtt gtcttgtgcc cttaactacg aactgaattg tattaaacac tacaaagtca
 661 tcttgagtat tttaaatcgg tttgtgtagt taggtttccc aacatctgtg gttacctaat
 721 gtttaatatt atagaactgt cctcagaaac tttgtcaatt ttcacggcta taaggaaaca
 781 gaaggactct tttaattctg tatttatcat ttactttctg tatatatagt ttaataacct
 841 gcttgggtgt aatttgccaa gcttgaattc tttaatgcat ttgcataaat tctatactgt
 901 ttagagctta aagctacaga agcattgtta ggaattgctt ggacactgaa ttttaaactt
 961 tttgacattg ttaacaagca tgttcatctt ttcttgtcac tagtccaaga aaaatatgct
1021 taatgtatat tacaaaggct ttgtatatgt taacctgttt taatgccaaa agtttgcttt
1081 gtccacaatt tccttaagac ctcttcagaa agggatttgt ttgccttaat gaatactgtt
1141 gggaaaaaac acagtataat gagtgaaaag ggcagaagca agaaatttct acatcttagc
1201 gactccaaga agaatgagta tccacattta gatggcacat tatgaggact ttaatctttc
1261 cttaaacaca ataatgtttt cttttttctt ttattcacat gatttctaag tatatttttc
1321 atgcaggaca gtttttcaac cttgatgtac agtgactgtg taaaattttt ctttcagtgg
1381 caacctctat aatctttaaa atatggtgag catcttgtct gttttgaagg ggatatgaca
1441 ataaatctat cagatggaaa atcctgtt
```

SEQ ID NO:79

```
   1 cctgggtctg acgcggccct gttcgagggg gcctctcttg tttatttatt tattttccgt
  61 gggtgcctcc gagtgtgcgc gcgctctcgc tacccggcgg ggaggggggtg gggggagggc
 121 ccgggaaaag ggggagttgg agccggggtc gaaacgccgc gtgacttgta ggtgagagaa
```

Figure 10 (cont.)

```
181 cgccgagccg tcgccgcagc ctccgccgcc gagaagccct tgttcccgct gctgggaagg
241 agagtctgtg ccgacaagat ggcggacggg gagctgaacg tggacagcct catcacccgg
301 ctgctggagg tacgaggatg tcgtccagga aagattgtgc agatgactga agcagaagtt
361 cgaggcttat gtatcaagtc tcgggagatc tttctcagcc agcctattct tttggaattg
421 gaagcaccgc tgaaaatttg tggagatatt catggacaat atacagattt actgagatta
481 tttgaatatg gaggtttccc accagaagcc aactatcttt tcttaggaga ttatgtggac
541 agaggaaagc agtctttgga aaccatttgt ttgctattgg cttataaaat caaatatcca
601 gagaacttct ttctcttaag aggaaaccat gagtgtgcta gcatcaatcg catttatgga
661 ttctatgatg aatgcaaacg aagatttaat attaaattgt ggaagacctt cactgattgt
721 tttaactgtc tgcctatagc agccattgtg gatgagaaga tcttctgttg tcatggagga
781 ttgtcaccag acctgcaatc tatggagcag attcggagaa ttatgagacc tactgatgtc
841 cctgatacag gtttgctctg tgatttgcta tggtctgatc cagataagga tgtgcaaggc
901 tggggagaaa atgatcgtgg tgtttccttt acttttggag ctgatgtagt cagtaaattt
961 ctgaatcgtc atgatttaga tttgatttgt cgagctcatc aggtggtgga agatggatat
1021 gaatttttttg ctaaacgaca gttggtaacc ttattttcag ccccaaatta ctgtggcgag
1081 tttgataatg ctggtggaat gatgagtgtg gatgaaactt tgatgtgttc atttcagata
1141 ttgaaaccat ctgaaaagaa agctaaatac cagtatggtg gactgaattc tggacgtcct
1201 gtcactccac ctcgaacagc taatccgccg aagaaaaggt gaagaaagga attctgtaaa
1261 gaaaccatca gatttgttaa ggacatactt cataatatat aagtgtgcac tgtaaaacca
1321 tccagccatt tgacacccctt tatgatgtca cacctttaac ttaaggagac gggtaaagga
1381 tcttaaattt ttttctaata gaaagatgtg ctacactgta ttgtaataag tatactctgt
1441 tatagtcaac aaagttaaat ccaaattcaa aattatccat taaagttaca tcttcatgta
1501 tcacaatttt taaagttgaa aagcatccca gttaaactag atgtgatagt taaaccagat
1561 gaaagcatga tgatccatct gtgtaatgtg gtttagtgt tgcttggttg tttaattatt
1621 ttgagcttgt tttgtttttg tttgttttca ctagaataat ggcaaatact tctaattttt
1681 ttccctaaac atttttaaaa gtgaaatatg ggaagagctt tacagacatt caccaactat
1741 tattttccct tgtttatcta cttagatatc tgtttaatct tactaagaaa actttcgcct
1801 cattacatta aaaaggaatt ttagagattg attgttttaa aaaaaaatac gcacattgtc
1861 caatccagtg attttaatca tacagtttga ctgggcaaac tttacagctg atagtgaata
1921 ttttgcttta tacaggaatt gacactgatt tggatttgtg cactctaatt tttaacttat
1981 tgatgctcta ttgtgcagta gcatttcatt taagataagg ctcatatagt attacccaac
2041 tagttggtaa tgtgattatg tggtaccttg gctttaggtt ttcattcgca cggaacacct
2101 tttggcatgc ttaacttcct ggtaacacct tcacctgcat tggttttctt tttcttttt
2161 ctttcttttt ttttttttt tttttttga gttgttgttt gtttttagat ccacagtaca
2221 tgagaatcct tttttgacaa gccttggaaa gctgacactg tctctttttc ctccctctat
2281 acgaaggatg tatttaaatg aatgctggtc agtgggacat tttgtcaact atgggtattg
2341 ggtgcttaac tgtctaatat tgccatgtga atgttgtata cgattgtaag gcttatgtca
2401 ctaaagattt ttattctgat tttttcataa tcaaaggtca tatgatactg tatagacaag
2461 ctttgtagtg aagtatagta gcaataattt ctgtacctga tcaagtttat tgcagccttt
2521 cttttcctat ttctttttt taagggttag tattaacaaa tggcaatgag tagaaaagtt
2581 aacatgaaga ttttagaagg agagaactta caggacacag atttgtgatt ctttgactgt
2641 gacactattg gatgtgattc taaaagcttt tattgagcat tgtcaaattt gtaagcttca
2701 tagggatgga catcatatct ataatgccct tctatatgtg ctaccataga tgtgacattt
2761 ttgaccttaa tatcgtcttt gaaaatgtta aattgagaaa cctgttaact tacattttat
2821 gaattggcac attgtattac ttactgcaag agatatttca ttttcagcac agtgcaaaag
2881 ttctttaaaa tgcatatgtc tttttttcta attccgtttt gttttaaagc acatttaaa
2941 tgtagttttc tcatttagta aaagttgtct aattgatatg aagcctgact gatttttttt
3001 ttccttacag tgagacattt aagcacacat tttattcaca tagatactat gtccttgaca
3061 tattgaaatg attcttttct gaaagtattc atgatctgca tatgatgtat taggttaggt
3121 cacaaaggtt ttatctgagg tgatttaaat aacttcctga ttggagtgtg taagctgagc
3181 gatttctaat aaaattttag ttgtacactt ttagtagtca tagtgaagca ggtctagaaa
3241 ataagccttt ggcagggaaa aagggcaatg ttgattaatc tcagtattaa accacattaa
3301 tctgtatccc attgtctggc ttttgtaaat tcatccaggt caagactaag tatgttggtt
3361 aataggaatc cttttttttt tttaaagact aaatgtgaaa aaataatcac tacttaagct
```

Figure 10 (cont.)

```
3421 aattaatatt ggtcattaaa tttaaaggat ggaaatttat catgtttaaa aattattcaa
3481 gcactcttaa aaccacttaa acagcctcca gtcataaaaa tgtgttcttt acaaatattt
3541 gcttggcaac acgacttgaa ataaataaaa ctttgtttct taggagaaaa
```

SEQ ID NO:80

```
   1 gcaacctgcc ccattatccc tggctgcgaa acaaccatcg agatttccaa agggcgaaca
  61 gggctgggcc tgagcatcgt tgggggttca gacacgctgc tgggtgccat tattatccat
 121 gaagtttatg aagaaggagc agcatgtaaa gatggaagac tctgggctgg agatcagatc
 181 ttagaggtga atggaattga cttgagaaag gccacacatg atgaagcaat caatgtcctg
 241 agacagacgc cacagagagt gcgcctgaca ctctacagag atgaggcccc atacaaagag
 301 gaggaagtgt gtgacaccct cactattgag ctgcagaaga agccgggaaa aggcctagga
 361 ttaagtattg ttggtaaaag aaacgatact ggagtatttg tgtcagacat tgtcaaagga
 421 ggaattgcag atgccgatgg aagactgatg cagggagacc agatattaat ggtgaatggg
 481 gaagacgttc gtaatgccac ccaagaagcg gttgccgctt tgctaaagtg ttccctaggc
 541 acagtaacct tggaagttgg aagaatcaaa gctggtccat tccattcaga gaggaggcca
 601 tctcaaagca gccaggtgag tgaaggcagc ctgtcatctt tcacttttcc actctctgga
 661 tccagtacat ctgagtcact ggaaagtagc tcaaagaaga atgcattggc atctgaaata
 721 cagggattaa gaacagtcga aatgaaaaag ggccctactg actcactggg aatcagcatt
 781 gctggaggag taggcagccc acttggtgat gtgcctatat ttattgcaat gatgcaccca
 841 actggagttg cagcacagac ccaaaaactc agagttgggg ataggattgt caccatctgt
 901 ggcacatcca ctgagggcat gactcacacc caagcagtta acctactgaa aaatgcatct
 961 ggctccattg aaatgcaggt ggttgctgga ggagacgtga gtgtggtcac aggtcatcag
1021 caggagcctg caagttccag tctttctttc actgggctga cgtcaagcag tatatttcag
1081 gatgatttag gacctcctca atgtaagtct attacactag agcgaggacc agatggctta
1141 ggcttcagta tagttggagg atatggcagc cctcatggag acttacccat ttatgttaaa
1201 acagtgtttg caaagggagc agcctctgaa gacggacgtc tgaaaagggg cgatcagatc
1261 attgctgtca atgggcagag tctagaagga gtcacccatg aagaagctgt tgccatcctt
1321 aaacggacaa aaggcactgt cactttgatg gttctctctt gaattggctg ccagaattga
1381 accaacccaa cccctagctc acctcctact gtaaagagaa tgcactggtc ctgacaattt
1441 ttatgctgtg ttcagccggg tcttcaaaac tgtagggggg aaataacact taagtttctt
1501 tttctcatct agaaatgctt tccttactga caacctaaca tcatttttct tttcttcttg
1561 cattttgtga acttaaagag aaggaatatt tgtgtaggtg aatctcgttt ttatttgtgg
1621 agatatctaa tgttttgtag tcacatgggc aagaattatt acatgctaag ctggttagta
1681 taaagaaaga taattctaaa gctaaccaaa gaaaatggct tcagtaaatt aggatgaaaa
1741 atgaaaatat
```

SEQ ID NO:81

```
   1 ggagcgcaat ggcgtccaac cccgaacggg gggagattct gctcacggaa ctgcaggggg
  61 attcccgaag tcttccgttt tctgagaatg tgagtgctgt tcaaaaatta gacttttcag
 121 atacaatggt gcagcagaaa ttggatgata tcaaggatcg aattaagaga gaaataagga
 181 aagaactgaa aatcaaagaa ggagctgaaa atctgaggaa agtcacaaca gataaaaaaa
 241 gtttggctta tgtagacaac atttgaaaaa aatcaaataa aaaattagaa gaactacatc
 301 acaagctgca ggaattaaat gcacatattg ttgtatcaga tccagaagat attacagatt
 361 gcccaaggac tccagatact ccaaataatg accctcgttg ttctactagc aacaatagat
 421 tgaaggcctt acaaaaacaa ttggatatag aacttaaagt aaaacaaggt gcagagaata
 481 tgatacagat gtattcaaat ggatcttcaa aggatcggaa actccatggt acagctcagc
 541 aactgctcca ggacagcaag acaaaaatag aagtcatacg aatgcagatt cttcaggcag
 601 tccagactaa tgaattggct tttgataatg caaaacctgt gataagtcct cttgaacttc
 661 ggatggaaga attaaggcat cattttagga tagagtttgc agtagcagaa ggtgcaaaga
 721 atgtaatgaa attacttggc tcaggaaaag taacagacag aaaagcactt tcagaagctc
 781 aagcaagatt taatgaatca agtcagaagt tggacctttt aaagtattca ttagagcaaa
 841 gattaaacga agtccccaag aatcatccca aaagcaggat tattattgaa gaactttcac
 901 ttgttgctgc atcaccaaca ctaagtccac gtcaaagtat gatatctacg caaaatcaat
 961 atagtacact atccaaacca gcagcactaa caggtacttt ggaagttcgt cttatgggct
```

Figure 10 (cont.)

```
1021 gccaagatat cctagagaat gtccctggac ggtcaaaagc aacatcagtt gcactgcctg
1081 gttggagtcc aagtgaaacc agatcatctt tcatgagcag aacgagtaaa agtaaaagcg
1141 gaagtagtcg aaatcttcta aaaaccgatg acttgtccaa tgatgtctgt gctgttttga
1201 agctcgataa tactgtggtt ggccaaacta gctggaaacc catttccaat cagtcatggg
1261 accagaagtt tacactggaa ctggacaggt cacgtgaact ggaaatttca gtttattggc
1321 gtgattggcg gtctctgtgt gctgtaaaat ttctgaggtt agaagatttt ttagacaacc
1381 aacggcatgg catgtgtctc tatttggaac cacagggtac tttatttgca gaggttacct
1441 tttttaatcc agttattgaa agaagaccaa aacttcaaag acaaaagaaa attttttcaa
1501 agcaacaagg caaaacattt ctcagagctc ctcaaatgaa tattaatatt gccacttggg
1561 gaaggctagt aagaagagct attcctacag taaatcattc tggcaccttc agccctcaag
1621 ctcctgtgcc tactacagtg ccagtggttg atgtacgcat ccctcaacta gcacctccag
1681 ctagtgattc tacagtaacc aaattggact ttgatcttga gcctgaacct cctccagccc
1741 caccacgagc ttcttctctt ggagaaatag atgaatcttc tgaattaaga gttttggata
1801 taccaggaca ggattcagag actgttttg atattcagaa tgacagaaat agtatacttc
1861 caaaatctca atctgaatac aagcctgata ctcctcagtc aggcctagaa tatagtggta
1921 ttcaagaact tgaggacaga agatctcagc aaaggtttca gtttaatcta caagatttca
1981 ggtgttgtgc tgtcttggga agaggacatt ttggaaaggt gcttttagct gaatataaaa
2041 acacaaatga gatgtttgct ataaaagcct taaagaaagg agatattgtg gctcgagatg
2101 aagtagacag cctgatgtgt gaaaaaagaa tttttgaaac tgtgaatagt gtaaggcatc
2161 cctttttggt gaaccttttt gcatgtttcc aaaccaaaga gcatgtttgc tttgtaatgg
2221 aatatgctgc cggtggggac ctaatgatgc acattcatac tgatgtcttt tctgaaccaa
2281 gagctgtatt ttatgctgct tgtgtagttc ttgggttgca gtatttacat gaacacaaaa
2341 ttgtttatag agatttgaaa ttggataact tattgctaga tacagagggc tttgtgaaaa
2401 ttgctgattt tggtctttgc aaagaaggaa tgggatatgg agatagaaca agcacatttt
2461 gtggcactcc tgaatttctt gccccagaag tattaacaga aacttcttat acaagggctg
2521 tagattggtg gggccttggc gtgcttatat atgaaatgct tgttggtgag tctccctttc
2581 ctggtgatga tgaagaggaa gtttttgaca gtattgtaaa tgatgaagta aggtatccaa
2641 ggttcttatc tacagaagcc atttctataa tgagaaggct gttaagaaga aatcctgaac
2701 ggcgccttgg ggctagcgag aaagatgcag aggatgtaaa aaagcaccca tttttccggc
2761 taattgattg gagcgctctg atggacaaaa aagtaaagcc accatttata cctaccataa
2821 gaggacgaga agatgttagt aattttgatg atgaatttac ctcagaagca cctattctga
2881 ctccacctcg agaaccaagg atactttcgg aagaggagca ggaaatgttc agagatttg
2941 actacattgc tgattggtgt taagttgcta gacactgcga aaccaagctg actcacaaga
3001 agacctctta aaaatagcaa cccttcattt gctctctgtg ccaccaatag cttctgagtt
3061 tttgttgtt gttgtttta ttgaaacacg tgaagatttg tttaaaagta ccattctaat
3121 acttcttcaa aagtggctcc tcattgtact tcagcgtaaa tatgagcact ggaaacagtt
3181 tcatggagtt taagttgagt gaacatcggc catgaaaatc catcacgaat acttttggat
3241 caatagtcta tttt
```

SEQ ID NO:82

```
  1 atgaaattca agttacatgt gaattctgcc aggcaataca aggacctgtg gaatatgagt
 61 gatgacaaac cctttctatg tactgcgcct ggatgtggcc agagtgaagt caccctgctg
121 agaaatgaag tggcacagct gaaacagctt cttctggctc ataaagattg ccctgtaacc
181 gccatgcaga agaaatctgg ctatcatact gctgataaag atgatagttc agaagacatt
241 tcagtgccga gtagtccaca tacagaagct atacagcata gttcggtcag cacatccaat
301 ggagtcagtt caacctccaa ggcagaagct gtagccactt cagtcctcac ccagatggcg
361 gaccagagta cagagcctgc tctttcacag atcgttatgg ctccttcctc ccagtcacag
421 ccctcaggaa gttgattaaa aacctgcagt acaacagttt tagatactca ttagtgactt
481 caaagggaaa tcaaggaaag accagtttc
```

SEQ ID NO:83

```
  1 gaattctgga agttcattga agagtctgaa attagggact tatttcaaat ttggacatgg
 61 ctagtcgagg cgcaacaaga cccaacggcc caaatactgg aaataaaata tgccagttca
121 aactagtact tctgggagag tccgctgttg gcaaatcaag cctagtgctt cgttttgtga
```

Figure 10 (cont.)

```
181 aaggccaatt tcatgaattt caagagagta ccattggggc tgcttttcta acccaaactg
241 tatgtcttga tgacactaca gtaaagtttg aaatctggga tacagctggt caagaaggat
301 accatagcct agcaccaatg tactacagag gagcacaagc agccatagtt gtatatgata
361 tcacaaatga ggagtccttt gcaagagcaa aaaattgggt taaagaactt cagaggcaag
421 caagtcctaa cattgtaata gctttatcgg gaaacaaggc cgacctagca aataaaagag
481 cagtagattt ccaggaagca cagtcctatg cagatgacaa tagtttatta ttcatggaga
541 catccgctaa aacatcaatg aatgtaaatg aaatattcat ggcaatagct aaaaaattgc
601 caaagaatga accacaaaat ccaggagcaa attctgccag aggaggagga gtagacctta
661 ccgaacccac acaaccaacc aggaatcagt gttgtagtaa ctaaacctct agtttgaac
```

SEQ Id NO:84

```
   1 gacgctctgg gccgccacct ccgcggaccc tgagcgcaag agccaagccg ccagcgctgc
  61 gatgtgggcc acgctgccgc tgctctgcgc cggggcctgg ctcctgggag tccccgtctg
 121 cggtgccgcc gaactgtgcg tgaactcctt agagaagttt cacttcaagt catggatgtc
 181 taagcaccgt aagacctaca gtacggagga gtaccaccac aggctgcaga cgtttgccag
 241 caactggagg aagataaacg cccacaacaa tgggaaccac acatttaaaa tggcactgaa
 301 ccaattttca gacatgagct ttgctgaaat aaaacacaag tatctctggt cagagcctca
 361 gaattgctca gccaccaaaa gtaactacct tcgaggtact ggtccctacc cacccttccgt
 421 ggactggcgg aaaaaaggaa attttgtctc acctgtgaaa aatcagggtg cctgcggcag
 481 ttgctggact ttctccacca ctggggccct ggagtctgcg atcgccatcg caaccggaaa
 541 gatgctgtcc ttggcggaac agcagctggt ggactgcgcc caggacttca ataatcacgg
 601 ctgccaaggg ggtctcccca gccaggcttt cgagtatatc ctgtacaaca aggggatcat
 661 gggtgaagac acctacccct accagggcaa ggatggttat tgcaagttcc aacctggaaa
 721 ggccatcggc tttgtcaagg atgtagccaa catcacaatc tatgacgagg aagcgatggt
 781 ggaggctgtg gccctctaca accctgtgag ctttgccttt gaggtgactc aggacttcat
 841 gatgtataga accggcatct actccagtac ttcctgccat aaaactccag ataaagtaaa
 901 ccatgcagta ctggctgttg ggtatggaga aaaaaatggg atcccttact ggatcgtgaa
 961 aaactcttgg ggtccccagt ggggaatgaa cgggtacttc ctcatcgagc gcggaaagaa
1021 catgtgtggc ctggctgcct gcgcctccta ccccatccct ctggtgtgag ccgtggcagc
1081 cgcagcgcag actggcggag aaggagagga acgggcagcc tgggcctggg tggaaatcct
1141 gccctggagg aagttgtggg gagatccact gggacccccca acattctgcc ctcacctctg
1201 tgcccagcct ggaaacctac agacaaggag gagttccacc atgagctcac ccgtgtctat
1261 gacgcaaaga tcaccagcca tgtgccttag tgtccttctt aacagactca aaccacatgg
1321 accacgaata ttctttctgt ccagaagggc tactttccac atatagagct ccagggactg
1381 tcttttctgt attcgctgtt caataaacat tgagtgagca cctccccaga tgg
```

SEQ ID NO:85

```
   1 ggtcggggcc cgcggccgct cgcgcctctc gatgggcagc tcgcacttgc tcaacaaggg
  61 cctgccgctt ggcgtccgac ctccgatcat gaacgggccc ctgcacccgc ggcccctggt
 121 ggcattgctg gatggccggg actgcacagt ggagatgccc atcctgaagg acgtggccac
 181 tgtggccttc tgcgacgcgc agtccacgca ggagatccat gagaaggtcc tgaacgaggc
 241 tgtgggggcc ctgatgtacc acaccatcac tctcaccagg gaggacctgg agaagttcaa
 301 agccctccgc atcatcgtcc ggattggcag tggttttgac aacatcgaca tcaagtcggc
 361 cggggattta ggcattgccg tctgcaacgt gcccgcggcg tctgtggagg agacggccga
 421 ctcgacgctg tgccacatcc tgaacctgta ccggcgggcc acctggctgc accaggcgct
 481 gcgggagggc acacgagtcc agagcgtcga gcagatccgc gaggtggcgt ccggcgctgc
 541 caggatccgc ggggagacct tgggcatcat cggacttgtc gcgtggggca ggcagtggcg
 601 ctgcgggcca aggccttcgg cttcaacgtg ctcttctacg acccttactt gtcggatggc
 661 gtggagcggg cgctggggct gcagcgtgtc agcaccctgc aggacctgct cttccacagc
 721 gactgcgtga ccctgcactg cggcctcaac gagcacaacc accacctcat caacgacttc
 781 accgtcaagc agatgagaca aggggccttc ctggtgaaca cagcccgggg tggcctggtg
 841 gatgagaagg cgctggccca ggccctgaag gagggccgga tccgcggcgc ggccctggat
 901 gtgcacgagt cggaaccctt cagctttagc cagggccctc tgaaggatgc acccaacctc
 961 atctgcaccc cccatgctgc atggtacagc gagcaggcat ccatcgagat gcgagaggag
```

Figure 10 (cont.)

```
1021 gcggcacggg agatccgcag agccatcaca ggccggatcc cagacagcct gaagaactgt
1081 gtcaacaagg accatctgac agccgccacc cactgggcca gcatggaccc cgccgtcgtg
1141 caccctgagc tcaatggggc tgcctatagg taccctccgg gcgtggtggg cgtggccccc
1201 actggcatcc cagctgctgt ggaaggtatc gtccccagcg ccatgtccct gtcccacggc
1261 ctgccccctg tggcccaccc gccccacgcc ccttctcctg gccaaaccgt caagcccgag
1321 gcggatagag accacgccag tgaccagttg tagcccggga ggagctctcc agcctcggcg
1381 cctgggcaga gggcccggaa accctcggac cagagtgtgt ggaggaggca tctgtgtggt
1441 ggccctggca ctgcagagac tggtccgggc tgtcaggagg cgggaggggg cagcgctggg
1501 cctcgtgtcg cttgtcgtcg tccgtcctgt gggcgctctg ccctgtgtcc ttcgcgttcc
1561 tcgttaagca gaagaagtca gtagttattc tcccatgaac gttcttgtct gtgtacagtt
1621 tttagaacat tacaaaggat ctgtttgctt agctgtcaac aaaaagaaaa cctgaaggag
1681 catttggaag tcaatttgag gttttttttt ttgttttttt tttttttgta tgttggaacg
1741 tgccccagaa tgaggcagtt ggcaaacttc tcaggacaat gaatccttcc cgtttttctt
1801 tttatgccac acagtgcatt gtttttttcta cctgcttgtc ttatttttag aataatttag
1861 aaaaacaaaa caaaggctgt ttttcctaat tttggcatga acccccccctt gttccaaatg
1921 aagacggcat cacgaagcag ctccaaaagg aaaagcttgg gcggtgccca gcgtgcccgc
1981 tgcccatcga cgtctgtcct ggggacgtgg agggtggcag cgtccccgcc tgcaccagtg
2041 ccgtcctgct gatgtggtag gctagcaata ttttggttaa aatcatgttt gtg

SEQ ID NO:86
   1 cgcgcggcca ggccctctta gccctctgcc gtttgggggg cacgggtgaa cctgccgccc
  61 cactcccacc ccgccccgcc ccgcccgtac agccaaatcg gaagggacga gcctgcccctt
 121 tgaaagggtt tttttcttg ctcctgcgga gggcgcccca gccatggccc tcaggagctc
 181 cctagacccc gcagggactg ccctccatcc cggccgccgg ggcccgccct ctgcatcccg
 241 cgggcagcct gtgtgaagcg gcctcccgca gcccccggcc cctcccccat ggaggaggag
 301 gagggggcgg tggccaagga gtggggcacg acccccgcgg ggcccgtctg gaccgcggtg
 361 ttcgactacg aggcggcggg cgacgaggag ctgaccctgc ggaggggcga tcgcgtccag
 421 gtgctttccc aagactgtgc ggtgtccggc gacgagggct ggtggaccgg gcagctcccc
 481 agcggccgcg tgggcgtctt ccccagcaac tacgtggccc ccggcgcccc cgctgcaccc
 541 gcgggcctcc agctgcccca ggagatcccc ttccacgagc tgcagctaga ggagatcatc
 601 ggtgtggggg gctttggcaa ggtctatcgg gccctgtggc gtggcgagga ggtggcagtc
 661 aaggccgccc ggctggaccc tgagaaggac ccggcagtga cagcggagca ggtgtgccag
 721 gaagcccggc tctttggagc cctgcagcac cccaacataa ttgcccttag ggcgcctgc
 781 ctcaaccccc cacacctctg cctagtgatg gagtatgccc ggggtggtgc actgagcagg
 841 gtgctggcag gtcgccgggt gccacctcac gtgctggtca actgggctgt gcaggtggcc
 901 cggggcatga actacctaca caatgatgcc cctgtgccca tcatccaccg ggacctcaag
 961 tccatcaaca tcctgatcct ggaggccatc gagaaccaca acctcgcaga cacggtgctc
1021 aagatcacgg acttcggcct cgcccgcgag tggcacaaga ccaccaagat gagcgctgcg
1081 gggacctacg cctggatggc gccggaggtt atccgtctct ccctcttctc caaaagcagt
1141 gatgtctgga gcttcggggt gctgctgtgg gagctgctga cgggggaggt cccctaccgt
1201 gagatcgacg ccttggccgt ggcgtatggc gtggctatga ataagctgac gctgcccatt
1261 ccctccacgt gccccgagcc ctttgcccgc ctcctggagg aatgctggga cccagacccc
1321 cacgggcggc cagatttcgg tagcatcttg aagcggcttg aagtcatcga acagtcagcc
1381 ctgttccaga tgccactgga gtccttccac tcgctgcagg aagactggaa gctggagatt
1441 cagcacatgt ttgatgacct tcggaccaag gagaaggagc ttcggagccg tgaggaggag
1501 ctgctgcggg cggcacagga gcagcgcttc caggaggagc agctgcggcg gcgggagcag
1561 gagctggcag aacgtgagat ggacatcgtg gaacgggagc tgcacctgct catgtgccag
1621 ctgagccagg agaagccccg ggtccgcaag cgcaagggca acttcaagcg cagccgcctg
1681 ctcaagctgc gggaaggcgg cagccacatc agcctgccct ctggctttga gcataagatc
1741 acagtccagg cctctccaac tctggataag cggaaaggat ccgatggggc cagccccccct
1801 gcaagcccca gcatcatccc ccggctgagg gccattcgcc tgactcccgt ggactgtggt
1861 ggcagcagca gtggcagcag cagtggagga agtgggacat ggagccgcgg tgggcccccca
1921 aagaaggaag aactggtcgg gggcaagaag aagggacgaa cgtgggggcc cagctccacc
1981 ctgcagaagg agcgggtggg aggagaggag aggctgaagg ggctggggga aggaagcaaa
```

Figure 10 (cont.)

```
2041 cagtggtcat caagtgcccc caacctgggc aagtccccca aacacacacc cagtcgccgc
2101 tggcttcgcc agcctcaatg agatggagga gttcgcggag gcagaggatg gaggcagcag
2161 cgtgcccccct tccccctact cgaccccgtc ctacctctca gtgccactgc ctgccgagcc
2221 ctccccgggg gcgcgggcgc cgtgggagcc gacgccgtcc gcgccccccg ctcggtgggg
2281 acacggcgcc cggcggcgct gcgacctggc gctgctaggc tgcgccacgc tgctggggggc
2341 tgtgggcctg ggcgccgacg tggccgaggc gcgcgcggcc gacggtgagg agcagcggcg
2401 ctggctcgac ggcctcttct ttccccgcgc cggccgcttc ccgcggggcc tcagcccacc
2461 cgcgcgtccc cacggccgcc gcgaagacgt gggccccggc ctgggcctgg cgccctcggc
2521 caccctcgtg tcgctgtcgt ccgtgtccga ctgcaactcc acgcgttcac tgctgcgctc
2581 tgacagtgac gaggccgcac cggccgcgcc ctccccacca ccctccccgc ccgcgcccac
2641 acccacgccc tcgcccagca ccaacccccct ggtggacctg gagctggaga gcttcaagaa
2701 ggacccccgc cagtcgctca cgcccaccca cgtcacggct gcatgcgctg tgagccgcgg
2761 gcaccggcgg acgccatcgg atggggcgct ggggcagcgg gggccgcccg agcccgcggg
2821 ccatggccct ggccctcgtg accttctgga cttcccccgc ctgcccgacc cccaggccct
2881 gttcccagcc cgccgccggc cccctgagtt cccaggccgc cccaccaccc tgacctttgc
2941 cccgagacct cggccggctg ccagtcgccc ccgcttggac ccctggaaac tggtctcctt
3001 cggccggaca ctcaccatct cgcctcccag caggccagac actccggaga gccctgggcc
3061 ccccagcgtg cagcccacac tgctggacat ggacatggag gggcagaacc aagacagcac
3121 agtgcccctg tgcggggccc acggctccca ctaaggcctg cccaccaccg cccgcctggg
3181 cagccatgaa tgtagcgccc caggccctgc cccagcccgc catgccacaa ggtgggggag
3241 gccctgggca ggatgttcac tctatttatt ggggaaggag ggaggggggg gacacttaac
3301 ttattccttt gtaccccagg gggtggagcc ctgtgcccac cctgcactgg ggggagggtg
3361 ggcagggata ctcagggaca gggcatcatg ggggatttgg cacaaaatgg agcattaaag
3421 gtaacccctg ccccc
```

SEQ ID NO:87

```
   1 gggcccgccc ctggtcacag ccagactgac tcagtttccc tgggaggtcc cgctcgagcc
  61 cgtccttccc ctccctctgc ccgcccccag ccctcgcccc accctcggcg cccgcacatc
 121 tgcctgctca gctccagacg gcgcccggac ccccgggcgc gggatccagc caggtgggag
 181 ccccgcagat gaggtctctg aaggtgtgcc tgaaccagtg ccagcctgcc ctgtctgcag
 241 catcggcctg atggggtggt gactgatccc tcagggctcc ggagccatgt ggcccaacgg
 301 cagttccctg gggccctgtt tccggcccac aaacattacc ctggaggaga gacggctgat
 361 cgcctcgccc tggttcgccg cctccttctg cgtggtgggc ctggcctcca acctgctggc
 421 cctgagcgtg ctggcgggcg cgcggcaggg gggttcgcac acgcgctcct ccttcctcac
 481 cttcctctgc ggcctcgtcc tcaccgactt cctggggctg ctggtgaccg gtaccatcgt
 541 ggtgtcccag cacgccgcgc tcttcgagtg gcacgccgtg gaccctggct gccgtctctg
 601 tcgcttcatg ggcgtcgtca tgatcttctt cggcctgtcc ccgctgctgc tgggggccgc
 661 catggcctca gagcgctacc tgggtatcac ccggcccttc tcgcgcccgg cggtcgcctc
 721 gcagcgccgc gcctgggcca ccgtggggct ggtgtgggcg gccgcgctgg cgctgggcct
 781 gctgcccctg ctgggcgtgg gtcgctacac cgtgcaatac ccggggtcct ggtgcttcct
 841 gacgctgggc gccgagtccg gggacgtggc cttcgggctg ctcttctcca tgctgggcgg
 901 cctctcggtc gggctgtcct tcctgctgaa cacggtcagc gtggccaccc tgtgccacgt
 961 ctaccacggg caggaggcgg cccagcagcg tccccgggac tccgaggtgg agatgatggc
1021 tcagctcctg gggatcatgg tggtggccag cgtgtgttgg ctgccccttc tggtcttcat
1081 cgcccagaca gtgctgcgaa acccgcctgc catgagcccc gccgggcagc tgtcccgcac
1141 cacggagaag gagctgctca tctacttgcg cgtggccacc tggaaccaga tcctggaccc
1201 ctgggtgtat atcctgttcc gccgcgccgt gctccggcgt ctccagcctc gcctcagcac
1261 ccggcccagg tcgctgtccc tccagcccca gctcacgcag cgctccgggc tgcagtagga
1321 agtggacaga gcgcccctcc cgcgcctttc cgcggagccc ttggcccctc ggacagccca
1381 tctgcctgtt ctgaggattc aggggctggg ggtgctggat ggacagtggg catcagcagc
1441 agggtttggg gttgacccca atccaacccg gggaccccca actcctccct gatcctttta
1501 ccaagcactc tcccttcctc ggccccttttt tcccatccag agctcccacc ccttctctgc
1561 gtccctccca accccaggaa gggcatgcag acattggaag agggtcttgc attgctattt
1621 ttttttttag acggagtctt gctctgtccc ccaggctgga gtgcagtggc gcaatctcag
```

Figure 10 (cont.)

```
1681 ctcactgcaa cctccacctc ccgggttcaa gcgattctcc tgcctcagcc tcctgagtag
1741 ctgggactat aggcgcgcgc caccacgccc ggctaatttt tgtattttta gtagagacgg
1801 ggtttcaccg tgttggccag gctggtcttg aactcctgac ctcaggtgat tcaccagcct
1861 cagcctccca aagtgctggg atcacaggca tgaaccacca cacctggcca tttttttttt
1921 ttttttaga cggagtctca ctctgtggcc cagcctggag tacagtggca cgatctcggc
1981 tcactgcaac ctccgcctcc cgggttcaag cgattctcgt gcctcagcct cccgagcagc
2041 tgggattaca ggcgtaagcc actgcgcccg gccttgcatg ctctttgacc ctgaatttga
2101 cctacttgct ggggtacagt tgcttccttt tgaacctcca acagggaagg ctctgtccag
2161 aaaggattga atgtgaacgg gggcaccccc ttttcttgcc aaaatatatc tctgcctttg
2221 gttttat
```

SEQ ID NO:88

```
   1 cccggacatg gccgccaaca tgtacagggt cggagactac gtctactttg agaactcctc
  61 cagcaaccca tacctgatcc ggagaatcga ggagctcaac aagacggcca atgggaacgt
 121 ggaggccaaa gtggtgtgct tctaccggag gcgggacatc tccagcaccc tcatcgccct
 181 ggccgacaag cacgcaaccc tgtcagtctg ctataaggcc ggaccggggg cggacaacgg
 241 cgaggaaggg gaaatagaag aggaaatgga gaatccggaa atggtggacc tgcccgagaa
 301 actaaagcac cagctgcggc atcgggagct gttcctctcc cggcagctgg agtctctgcc
 361 cgccacgcac atcaggggca agtgcagcgt caccctgctc aacgagaccg agtcgctcaa
 421 gtcctacctg gagcgggagg atttcttctt ctattctcta gtctacgacc cacagcagaa
 481 gaccctgctg gcagataaag gagagattcg agtaggaaac cggtaccagg cagacatcac
 541 cgacttgtta aaagaaggcg aggaggatgg ccgagaccag tccaggttgg agacccaggt
 601 gtgggaggcg cacaacccac tcacagacaa gcagatcgac cagttcctgg tggtggcccg
 661 ctctgtgggc accttcgcac gggccctgga ctgcagcagc tccgtccgac agcccagcct
 721 gcacatgagc gccgcagctg cctcccgaga catcaccctg ttccacgcca tggatactct
 781 ccacaagaac atctacgaca tctccaaggc catctcggcg ctggtgccgc agggcgggcc
 841 cgtgctctgc agggacgaga tggaggagtg gtctgcatca gaggccaacc ttttcgagga
 901 agccctggaa aaatatggga aggatttcac ggacattcag caagatttc tcccgtggaa
 961 gtcgctgacc agcatcattg agtactacta catgtggaag accaccgaca gatacgtgca
1021 gcagaaacgc ttgaaagcag ctgaagctga gagcaagtta aagcaagttt atattcccaa
1081 ctataacaag ccaaatccga accaaatcag cgtcaacaac gtcaaggccg gtgtggtgaa
1141 cggcacgggg gcgccgggcc agagccctgg ggctggccgg gcctgcgaga gctgttacac
1201 cacacagtct taccagtggt attcttgggg tccccctaac atgcagtgtc gtctctgcgc
1261 atcttgttgg acatattgga agaaatatgg tggcttgaaa atgccaaccc ggttagatgg
1321 agagaggcca ggaccaaacc gcagtaacat gagtccccac ggcctcccag cccggagcag
1381 cgggagcccc aagtttgcca tgaagaccag gcaggctttc tatctgcaca cgacgaagct
1441 gacgcggatc gcccggcgcc tgtgccgtga gatcctgcgc ccgtggcacg ctgcgcggaa
1501 cccctacctg cccatcaaca gcgcggccat caaggccgag tgcacggcgc ggctgcccga
1561 agcctcccag agcccgctgg tgctgaagca ggcggtacgc aagccgctgg aagccgtgct
1621 tcggtatctt gagacccacc cccgcccccc caagcctgac cccgtgaaaa gcgtgtccag
1681 cgtgctcagc agcctgacgc ccgccaaggt ggcccccgtc atcaacaacg gctcccccac
1741 catcctgggc aagcgcagct acgagcagca caacggggtg gacggcaaca tgaagaagcg
1801 cctcttgatg cccagtaggg gtctggcaaa ccacggacag accaggcaca tgggaccaag
1861 ccggaacctc ctgctcaacg ggaagtccta ccccaccaaa gtgcgcctga tccggggggg
1921 ctccctgccc ccagtcaagc ggcggcggat gaactggatc gacgccccgg gtgacgtgtt
1981 ctacatgccc aaagaggaga ccaggaagat ccgcaagctg ctctcatcct cggaaaccaa
2041 gcgtgctgcc cgccggccct acaagcccat cgccctgcgc cagagccagg ccctgccgcc
2101 gcggccaccg ccacctgcgc ccgtcaacga cgagcccatc gtcatcgagg actaggggcc
2161 gcccccacct gcggccgccc cccgcccctc gcccgcccac acggcccctt cccagccagc
2221 ccgccgcccg cccctcagtt tggtagtgcc ccacctcccg ccctcacctg aagagaaacg
2281 cgctccttgg cggacactgg gggaggagag gaagaagcgc ggctaactta ttccgagaat
2341 gccgaggagt tgtcgttttt agctttgtgt ttactttttg gctggagcgg agatgagggg
2401 ccaccccgtg cccctgtgct gcggggcctt ttgcccggag gccgggccct aaggttttgt
2461 tgtgttctgt tgaaggtgcc attttaaatt ttatttttat tacttttttt gtagatgaac
```

Figure 10 (cont.)

```
2521 ttgagctctg taacttacac ctggaatgtt aggatcgtgc ggccgcggcc ggccgagctg
2581 cctggcgggg ttggcccttg tcttttcaag taattttcat attaaacaaa aacaaagaaa
2641 aaaaatctta taaaaaggaa aa
```

SEQ ID NO:89

```
  1 atgagagagt acaaagtggt ggtgctgggc tcgggcggcg tgggcaagtc cgcgctcacc
 61 gtgcagttcg tgacgggctc cttcatcgag aagtacgacc cgaccatcga agacttttac
121 cgcaaggaga ttgaggtgga ctcgtcgccg tcggtgctgg agatcctgga tacggcgggc
181 accgagcagt tcgcgtccat gcgggacctg tacatcaaga acggccaggg cttcatcctg
241 gtctacagcc tcgtcaacca gcagagcttc caggacatca agcccatgcg ggaccagatc
301 atccgcgtga agcggtacga gcgcgtgccc atgatcctgg tgggcaacaa ggtggacctg
361 gagggtgagc gcgaggtctc gtacggggag ggcaaggccc tggctgagga gtggagctgc
421 cccttcatgg agacgtcggc caaaaacaaa gcctcggtag acgagctatt tgccgagatc
481 gtgcggcaga tgaactacgc ggcgcagtcc aacggcgatg agggctgctg ctcggcctgc
541 gtgatcctct ga
```

SEQ ID NO:90

```
   1 gagctgcggg cgctgctgct gtggggccgc cgcctgcggc ctttgctgcg ggcgccggcg
  61 ctggcggccg tgccgggagg aaaaccaatt ctgtgtcctc ggaggaccac agcccagttg
 121 ggccccaggc gaaacccagc ctggagcttg caggcaggac gactgttcag cacgcagacc
 181 gccgaggaca aggaggaacc cctgcactcg attatcagca gcacagagag cgtgcagggt
 241 tccacttcca aacatgagtt ccaggccgag acaaagaagc ttttggacat tgttgcccgg
 301 tccctgtact cagaaaaaga ggtgtttata cgggagctga tctccaatgc cagcgatgcc
 361 ttggaaaaac tgcgtcacaa actggtgtct gacggccaag cactgccaga aatggagatt
 421 cacttgcaga ccaatgccga gaaaggcacc atcaccatcc aggatactgg tatcgggatg
 481 acacaggaag agctggtgtc caacctgggg acgattgcca gatcggggtc aaaggccttc
 541 ctggatgctc tgcagaacca ggctgaggcc agcagcaaga tcatcggcca gtttggagtg
 601 ggtttctact cagctttcat ggtggctgac agagtggagg tctattcccg ctcggcagcc
 661 ccggggagcc tgggttacca gtggctttca gatggttctg gagtgtttga aatcgccgaa
 721 gcttcgggag ttagaaccgg gacaaaaatc atcatccacc tgaaatccga ctgcaaggag
 781 ttttccagcg aggcccgggt gcgagatgtg gtaacgaagt acagcaactt cgtcagcttc
 841 cccttgtact tgaatggaag gcggatgaac accttgcagg ccatctggat gatggacccc
 901 aaggatgtcc gtgagtggca acatgaggag ttctaccgct acgtcgcgca ggctcacgac
 961 aagccccgct acaccctgca ctataagacg gacgcaccgc tcaacatccg cagcatcttc
1021 tacgtgcccg acatgaaacc gtccatgttt gatgtgagcc gggagctggg ctccagcgtt
1081 gcactgtaca gccgcaaagt cctcatccag accaaggcca cggacatcct gcccaagtgg
1141 ctgcgcttca tccgaggtgt ggtggacagt gaggacattc ccctgaacct cagccgggag
1201 ctgctgcagg agagcgcact catcaggaaa ctccgggacg ttttacagca gaggctgatc
1261 aaattcttca ttgaccagag taaaaaagat gctgagaagt atgcaaagtt ttttgaagat
1321 tacggcctgt tcatgcggga gggcattgtg accgccaccg agcaggaggt caaggaggac
1381 atagcaaagc tgctgcgcta cgagtcctcg gcgctgccct ccgggcagct aaccagcctc
1441 tcagaatacg ccagccgcat gcgggccggc acccgcaaca tctactacct gtgcgccccc
1501 aaccgtcacc tggcagagca ctcaccctac tatgaggcca tgaagaagaa agacacagag
1561 gttctcttct gctttgagca gtttgatgag ctcaccctgc tgcaccttcg tgagtttgac
1621 aagaagaagc tgatctctgt ggagacggac atagtcgtgg atcactacaa ggaggagaag
1681 tttgaggaca ggtccccagc cgccgagtgc ctatcagaga aggagacgga ggagctcatg
1741 gcctggatga gaaatgtgct ggggtcgcgt gtcaccaacg tgaaggtgac cctccgactg
1801 gacacccacc ctgccatggt caccgtgctg gagatggggg ctgcccgcca cttcctgcgc
1861 atgcagcagc tggccaagac ccaggaggag cgcgcacagc tcctgcagcc cacgctggag
1921 atcaacccca ggcacgcgct catcaagaag ctgaatcagc tgcgcgcaag cgagcctggc
1981 ctggctcagc tgctggtgga tcagatatac gagaacgcca tgattgctgc tggacttgtt
2041 gacgacccta gggccatggt gggccgcttg aatgagctgc ttgtcaaggc cctggagcga
2101 cactgacagc caggggccca gaaggactga caccacagat gacagcccca cctccttgag
```

Figure 10 (cont.)

```
2161 ctttatttac ctaaatttaa aggtatttct taacccga

SEQ ID NO:91
   1 agtgatgtcc ttgcattgcc catttttaag caagaagagt cgagtttgcc tcctgataat
  61 gagaataaaa tcctgccttt tcaatatgtg ctttgtgctg ctacctctcc agcagtgaaa
 121 ctccatgatg aaaccctaac gtatctcaat caaggacagt cttatgaaat tcgaatgcta
 181 gacaatagga aacttggaga acttccagaa attaatggca aattggtgaa gagtatattc
 241 cgtgtggtgt tccatgacag aaggcttcag tacactgagc atcagcagct agagggctgg
 301 aggtggaacc gacctggaga cagaattctt gacatagata tcccgatgtc tgtgggtata
 361 atcgatccta gggctaatcc aactcaacta aatacagtgg agttcctgtg ggaccctgca
 421 aagaggacat ctgtgtttat tcaggtgcac tgtattagca cagagttcac tatgaggaaa
 481 catggtggag aaaagggggt gccattccga gtacaaatag ataccttcaa ggagaatgaa
 541 aacggggaat atactgagca cttacactcg gccagctgcc agatcaaagt tttcaagcca
 601 aaggtgcaga cagaaagcaa aaaacggata gggaaaaaat ggagaaacga acacctcatg
 661 aaaaggagaa atatcagcct tcctatgaga caaccatact cacagagtgt tctccatggc
 721 ccgagatcac gtatgtcaat aactccccat cacctggctt caacagttcc catagcagtt
 781 tttctcttgg ggaaggaaat ggttcaccaa accaccagcc agagccaccc cctccagtca
 841 cagataacct cttaccaaca accacacctc aggaagctca gcagtggttg catcgaaatc
 901 gtttttctac attcacaagg cttttcacaa acttctcagg ggcagattta ttgaaattaa
 961 ctagagatga tgtgatccaa atctgtggcc ctgcagatgg aatcagactt tttaatgcat
1021 taaaaggccg gatggtgcgt ccaaggttaa ccatttatgt ttgtcaggaa tcactgcagt
1081 tgagggagca gcaacaacag cagcagcaac agcagcagaa gcatgaggat ggagactcaa
1141 atggtacttt cttcgtttac catgctatct atctagaaga actaacagct gttgaattga
1201 cagaaaaaat tgctcagctt ttcagcattt ccccttgcca gatcagccag atttacaagc
1261 aggggccaac aggaattcat gtgctcatca gtgatgagat gatacagaac tttcaggaag
1321 aagcatgttt tattctggac acaatgaaag cagaaaccaa tgatagctat catatcatac
1381 tgaagtagga gtgcggcgtt tcgtgcccag tggctgctcc ttccttcacc tctgaaaacg
1441 gccctcttga aggggatat gaatggagat ttgaaggtct gcaagaacct gactcgtctg
1501 actgtgtgtg gaggagtcca ggccatggag gcagaatcct ggccctctgt gttggcccaa
1561 gctcttgtgg tacacacaga ttactgccca atatgcagtt ctgcagctgt tttagttaaa
1621 tttctggacc ttgttgttgt taaatatcag tagaaactct acataattta gagtgtatgt
1681 agggcataat gatgatggga attgtgtgat gtttaacagg aagatcttaa attttgtgat
1741 atggagccct gtaatttttt tcttatataa aaatgggtat ctatattcat

SEQ ID NO:92
   1 aggtctgttc cgcatgaaac tcctgctggg gaaggacttc cctgcctccc cacccaaggg
  61 ctacttcctg accaagatct tccacccgaa cttgggcgcc aatggcgaga tgtgcgtcaa
 121 cgtgctcaag agggactgga cggctgagct gggcatccga cacgtactgc tgaccatcaa
 181 gtgcctgctg atccacccta accccgagtc tgcactcaac gaggaggcgg gccgcctgct
 241 cttggagaac tacgaggagt atgcggctcg ggcccgtctg ctcacagaga tccacggggg
 301 cgccggcggg cccagcggca gggccaaagc cgggcgggcc ctggccagtg gcactgcagc
 361 ttcctccacc gactctgggg ccccaggggg cttgggaggg gctgagggtc ccatggccaa
 421 gaagcatgct ggcgagcgcg ataagaagct ggcggccaag aaaaagacgg acaagaagcg
 481 ggcgctacgg cggctgtagt gggctctctt cctccttcca ccgtgacccc aacctctcct
 541 gtcccctccc tccaactctg tctctaagtt atttaaatta tggctggggt cggggagggt
 601 acagggggca ctgagacctg gatttgtttt tttaaataaa gttggaaaag ca

SEQ ID NO:93
   1 gtcgtgttct ccgagttcct gtctctctgc caacgccgcc cggatggctt cccaaaaccg
  61 cgacccagcc gccactagcg tcgccgccgc ccgtaaagga gctgagccga gcgggggcgc
 121 cgcccggggt ccggtgggca aaaggctaca gcaggagctg atgaccctca tgatgtctgg
 181 cgataaaggg atttctgcct tccctgaatc agacaacctt ttcaaatggg tagggaccat
 241 ccatggagca gctggaacag tatatgaaga cctgaggtat aagctctcgc tagagttccc
```

Figure 10 (cont.)

```
 301 cagtggctac ccttacaatg cgcccacagt gaagttcctc acgccctgct atcaccccaa
 361 cgtggacacc cagggtaaca tatgcctgga catcctgaag gaaaagtggt ctgccctgta
 421 tgatgtcagg accattctgc tctccatcca gagccttcta ggagaaccca acattgatag
 481 tcccttgaac acacatgctg ccgagctctg gaaaaacccc acagctttta agaagtacct
 541 gcaagaaacc tactcaaagc aggtcaccag ccaggagccc tgacccaggc tgcccagcct
 601 gtccttgtgt cgtcttttta atttttcctt agatggtctg tcctttttgt gatttctgta
 661 taggactctt tatcttgagc tgtggtattt ttgttttgtt tttgtctttt aaattaagcc
 721 tcggttgagc ccttgtatat taaataaatg catttttgtc ctttttaga c

SEQ ID NO:94
   1 ctccagcagc acccgagagg gtcaggagaa aagcggagga agctgggtag gccctgaggg
  61 gcctcggtaa gccatcatga ccaccccggca agccacgaag gatcccctcc tccggggtgt
 121 atctcctacc cctagcaaga ttccggtacg ctctcagaaa cgcacgcctt tccccactgt
 181 tacatcgtgc gccgtggacc aggagaacca agatccaagg agatgggtgc agaaaccacc
 241 gctcaatatt caacgccccc tcgttgattc agcaggcccc aggccgaaag ccaggcacca
 301 ggcagagaca tcacaaagat tggtggggat cagtcagcct cggaacccct tggaagagct
 361 caggcctagc cctaggggtc aaaatgtggg gcctgggccc cctgcccaga cagaggctcc
 421 agggaccata gagtttgtgg ctgaccctgc agccctggcc accatcctgt caggtgaggg
 481 tgtgaagagc tgtcacctgg ggcgccagcc tagtctggct aaaagagtac tggttcgagg
 541 aagtcaggga ggcaccaccc agagggtcca gggtgttcgg gcctctgcat atttggcccc
 601 cagaaccccc acccaccgac tggaccctgc cagggcttcc tgcttctcta ggctggaggg
 661 accaggacct cgaggccgga cattgtgtcc ccagaggcta caggctctga tttcaccttc
 721 aggaccttcc tttcaccctt ccactcgccc cagtttccag gagctaagaa gggagacagc
 781 tggcagcagc cggacttcag tgagccaggc ctcaggattg ctcctggaga ccccagtcca
 841 gcctgctttc tctcttccta aaggagaacg cgaggttgtc actcactcag atgaaggagg
 901 tgtggcctct cttggtctgg cccagcgagt accattaaga gaaaaccgag aaatgtcaca
 961 taccagggac agccatgact cccacctgat gccctcccct gcccctgtgg cccagccctt
1021 gcctggccat gtggtgccat gtccatcacc ctttggacgg gctcagcgtg taccctcccc
1081 aggccctcca actctgacct catattcagt gttgcggcgt ctcaccgttc aacctaaaac
1141 ccggttcaca cccatgccat caaccccccag agttcagcag gcccagtggc tgcgtggtgt
1201 ctcccctcag tcctgctctg aagatcctgc cctgccctgg gagcaggttg ccgtccggtt
1261 gtttgaccag gagagttgta taaggtcact ggagggttct gggaaaccac cggtggccac
1321 tccttctgga ccccactcta acagaacccc cagcctccag gaggtgaaga ttcaacgcat
1381 cggtatcctg caacagctgt tgagacagga agtagagggg ctggtagggg gccagtgtgt
1441 ccctcttaat ggaggctctt ctctggatat ggttgaactt cagcccctgc tgactgagat
1501 ttctagaact ctgaatgcca cagagcataa ctctgggact tcccaccttc ctggactgtt
1561 aaaacactca gggctgccaa agccctgtct tccagaggag tgcggggaac cacagccctg
1621 ccctccggca gagcctgggc ccccagaggc cttctgtagg agtgagcctg agataccaga
1681 gccctccctc caggaacagc ttgaagtacc agagccctac cctccagcag aacccaggcc
1741 cctagagtcc tgctgtagga gtgagcctga gataccggag tcctctcgcc aggaacagct
1801 tgaggtacct gagccctgcc ctccagcaga acccaggccc ctagagtcct actgtaggat
1861 tgagcctgag ataccggagt cctctcgcca ggaacagctt gaggtacctg agccctgccc
1921 tccagcagaa cccgggcccc ttcagcccag cacccagggg cagtctggac ccccagggcc
1981 ctgccctagg gtagagctgg gggcatcaga gccctgcacc ctggaacata gaagtctaga
2041 gtccagtcta ccaccctgct gcagtcagtg ggctccagca accaccagcc tgatcttctc
2101 ttcccaacac ccgctttgtg ccagcccccc tatctgctca ctccagtctt tgagaccccc
2161 agcaggccag gcaggcctca gcaatctggc ccctcgaacc ctagccctga gggagcgcct
2221 caaatcgtgt ttaaccgcca tccactgctt ccacgaggct cgtctggacg atgagtgtgc
2281 cttttacacc agccgagccc ctccctcagg ccccacccgg gtctgcacca accctgtggc
2341 tacattactc gaatggcagg atgccctgtg tttcattcca gttggttctg ctgcccccca
2401 gggctctcca tgatgagaca accactcctg ccctgccgta cttcttcctt ttagccctta
2461 tttattgtcg gtctgcccat gggactggga gccgcccact tttgtcctca ataaagtttc
2521 taaagta
```

Figure 10 (cont.)

SEQ ID NO:95

```
   1 agaataatca tgggccagac tgggaagaaa tctgagaagg gaccagtttg ttggcggaag
  61 cgtgtaaaat cagagtacat gcgactgaga cagctcaaga ggttcagacg agctgatgaa
 121 gtaaaggtat gtttagttcc aatcgtcaga aaattttgga aagaacggaa atcttaaacc
 181 aagaatggaa acagcgaagg atacagcctg tgcacatcct gacttctgtg agctcattgc
 241 gcgggactag ggagtgttcg gtgaccagtg acttggattt tccaacacaa gtcatcccat
 301 taaagactct gaatgcagtt gcttcagtac ccataatgta ttcttggtct cccctacagc
 361 agaattttat ggtggaagat gaaactgttt tacataacat tccttatatg ggagatgaag
 421 ttttagatca ggatggtact ttcattgaag aactaataaa aaattatgat gggaaagtac
 481 acggggatag agaatgtggg tttataaatg atgaaatttt tgtggagttg gtgaatgccc
 541 ttggtcaata taatgatgat gacgatgatg atgatggaga cgatcctgaa gaaagagaag
 601 aaaagcagaa agatctggag gatcaccgag atgataaaga aagccgccca cctcggaaat
 661 ttccttctga taaaattttt gaagccattt cctcaatgtt tccagataag ggcacagcag
 721 aagaactaaa ggaaaaatat aaagaactca ccgaacagca gctcccaggc gcacttcctc
 781 ctgaatgtac ccccaacata gatggaccaa atgctaaatc tgttcagaga gagcaaagct
 841 tacactcctt tcatacgctt ttctgtaggc gatgttttaa atatgactgc ttcctacatc
 901 cttttcatgc aacacccaac acttataagc ggaagaacac agaaacagct ctagacaaca
 961 aaccttgtgg accacagtgt taccagcatt tggagggagc aaaggagttt gctgctgctc
1021 tcaccgctga gcggataaag accccaccaa aacgtccagg aggccgcaga agaggacggc
1081 ttcccaataa cagtagcagg cccagcaccc ccaccattaa tgtgctggaa tcaaaggata
1141 cagacagtga tagggaagca gggactgaaa cgggggggaga gaacaatgat aaagaagaag
1201 aagagaagaa agatgaaact tcgagctcct ctgaagcaaa ttctcggtgt caaacaccaa
1261 taaagatgaa gccaaatatt gaacctcctg agaatgtgga gtggagtggt gctgaagcct
1321 caatgtttag agtcctcatt ggcacttact atgacaattt ctgtgccatt gctaggttaa
1381 ttgggaccaa aacatgtaga caggtgtatg agtttagagt caaagaatct agcatcatag
1441 ctccagctcc cgctgaggat gtggatactc ctccaaggaa aaagaagagg aaacaccggt
1501 tgtgggctgc acactgcaga aagatacagc tgaaaaagga cggctcctct aaccatgttt
1561 acaactatca accctgtgat catccacggc agccttgtga cagttcgtgc ccttgtgtga
1621 tagcacaaaa tttttgtgaa aagttttgtc aatgtagttc agagtgtcaa aaccgctttc
1681 cgggatgccg ctgcaaagca cagtgcaaca ccaagcagtg cccgtgctac ctggctgtcc
1741 gagagtgtga ccctgacctc tgtcttactt gtggagccgc tgaccattgg gacagtaaaa
1801 atgtgtcctg caagaactgc agtattcagc ggggctccaa aaagcatcta ttgctggcac
1861 catctgacgt ggcaggctgg gggattttta tcaaagatcc tgtgcagaaa aatgaattca
1921 tctcagaata ctgtggagag attatttctc aagatgaagc tgacagaaga gggaaagtgt
1981 atgataaata catgtgcagc tttctgttca acttgaacaa tgattttgtg gtggatgcaa
2041 cccgcaaggg taacaaaatt cgttttgcaa atcattcggt aaatccaaac tgctatgcaa
2101 aagttatgat ggttaacggt gatcacagga taggtatttt tgccaagaga gccatccaga
2161 ctggcgaaga gctgtttttt gattacagat acagccaggc tgatgccctg aagtatgtcg
2221 gcatcgaaag agaaatggaa atcccttgac atctgctacc tcctcccccc tcctctgaaa
2281 cagctgcctt agcttcagga acctcgagta ctgtgggcaa tttagaaaaa gaacatgcag
2341 tttgaaattc tgaatttgca aagtactgta agaataattt atagtaatga gtttaaaaat
2401 caacttttta ttgccttctc accagctgca aagtgttttg taccagtgaa tttttgcaat
2461 aatgcagtat ggtacatttt tcaactttga ataaagaata cttgaacttg tc
```

SEQ ID NO: 96

```
   1 caggtctgag gcgaagctag gtgagccgtg ggaagaaaag agggagcagc tagggcgcgg
  61 gtctccctcc tcccggagtt tggaacggct gaagttcacc ttccagcccc tagcgccgtt
 121 cgcgccgcta ggcctggctt ctgaggcggt tgcggtgctc ggtcgccgcc taagcggggc
 181 agggtgcgaa caggggcttc gggccacgct tctcttggcg acaggatttt gctgtgaagt
 241 ccgtccggga aacggaggaa aaaaagagtt gcgggaggct gtctgctaat aacggttctt
 301 gatacatatt tgccagactt caagatttca gaaaaggggt gaaagagaag attgcaactt
 361 tgagtcagac ctgtaggcct gatagactga ttaaaccaca gaaggtgacc tgctgagaaa
 421 agtggtacaa atactgggaa aaacctgctc ttctgcgtta agtgggagac aatgtcacaa
 481 gttaaaagct cttattccta tgatgccccc tcggatttca tcaatttttc atccttggat
```

Figure 10 (cont.)

```
 541 gatgaaggag atactcaaaa catagattca tggtttgagg agaaggccaa tttggagaat
 601 aagttactgg ggaagaatgg aactggaggg ctttttcagg gcaaaactcc tttgagaaag
 661 gctaatcttc agcaagctat tgtcacacct ttgaaaccag ttgacaacac ttactacaaa
 721 gaggcagaaa aagaaaatct tgtggaacaa tccattccgt caaatgcttg ttcttccctg
 781 gaagttgagg cagccatatc aagaaaaact ccagcccagc ctcagagaag atctcttagg
 841 ctttctgctc agaaggattt ggaacagaaa gaaaagcatc atgtaaaaat gaaagccaag
 901 agatgtgcca ctcctgtaat catcgatgaa attctaccct ctaagaaaat gaaagtttct
 961 aacaacaaaa agaagccaga ggaagaaggc agtgctcatc aagatactgc tgaaaacaat
1021 gcatcttccc cagagaaagc caagggtaga catactgtgc cttgtatgcc acctgcaaag
1081 cagaagtttc taaaaagtac tgaggagcaa gagctggaga agagtatgaa aatgcagcaa
1141 gaggtggtgg agatgcggaa aaagaatgaa gaattcaaga aacttgctct ggctggaata
1201 gggcaacctg tgaagaaatc agtgagccag gtcaccaaat cagttgactt ccacttccgc
1261 acagatgagc gaatcaaaca acatcctaag aaccaggagg aatataagga agtgaacttt
1321 acatctgaac tacgaaagca tccttcatct cctgcccgag tgactaaggg atgtaccatt
1381 gttaagcctt tcaacctgtc ccaaggaaag aaaagaacat ttgatgaaac agtttctaca
1441 tatgtgcccc ttgcacagca agttgaagac ttccataaac gaacccctaa cagatatcat
1501 ttgaggagca agaaggatga tattaacctg ttaccctcca aatcttctgt gaccaagatt
1561 tgcagagacc cacagactcc tgtactgcaa accaaacacc gtgcacgggc tgtgacctgc
1621 aaaagtacag cagagctgga ggctgaggag ctcgagaaat tgcaacaata caaattcaaa
1681 gcacgtgaac ttgatcccag aatacttgaa ggtgggccca tcttgcccaa gaaaccacct
1741 gtgaaaccac ccaccgagcc tattggcttt gatttggaaa ttgagaaaag aatccaggag
1801 cgagaatcaa agaagaaaac agaggatgaa cactttgaat ttcattccag accttgccct
1861 actaagattt tggaagatgt tgtgggtgtt cctgaaaaga aggtacttcc aatcaccgtc
1921 cccaagtcac cagcctttgc attgaagaac agaattcgaa tgcccaccaa agaagatgag
1981 gaagaggacg aaccggtagt gataaaagct caacctgtgc cacattatgg ggtgcctttt
2041 aagccccaaa tcccagaggc aagaactgtg gaaatatgcc ctttctcgtt tgattctcga
2101 gacaaagaac gtcagttaca gaaggagaag aaaataaaag aactgcagaa aggggaggtg
2161 cccaagttca aggcacttcc cttgcctcat tttgacacca ttaacctgcc agagaagaag
2221 gtaaagaatg tgacccagat tgaacctttc tgcttggaga ctgacagaag aggtgctctg
2281 aaggcacaga cttggaagca ccagctggaa gaagaactga gacagcagaa agaagcagct
2341 tgtttcaagg ctcgtccaaa caccgtcatc tctcaggagc cctttgttcc caagaaagag
2401 aagaaatcag ttgctgaggg cctttctggt tctctagttc aggaaccttt tcagctggct
2461 actgagaaga gagccaaaga gcggcaggag ctggagaaga gaatggctga ggtagaagcc
2521 cagaaagccc agcagttgga ggaggccaga ctacaggagg aagagcagaa aaaagaggag
2581 ctggccaggc tacggagaga actggtgcat aaggcaaatc caatacgcaa gtaccagggt
2641 ctggagataa agtcaagtga ccagcctctg actgtgcctg tatctcccaa attctccact
2701 cgattccact gctaaactca gctgtgagct gcggataccg cccggcaatg ggacctgctc
2761 ttaacctcaa acctaggacc gtcttgcttt gtcattgggc atggagagaa cccatttctc
2821 cagactttta cctacccgtg cctgagaaag catacttgac aactgtggac tccagttttg
2881 ttgagaattg ttttcttaca ttactaaggc taataatgag atgtaactca tgaatgtctc
2941 gattagactc catgtagtta cttcctttaa accatcagcc ggccttttat atgggtcttc
3001 actctgacta gaatttagtc tctgtgtcag cacagtgtaa tctctattgc tattgcccct
3061 tacgactctc accctctccc cacttttttt aaaaatttta accagaaaat aaagatagtt
3121 aaatcctaag atagagatta agtcatggtt taaatgagga acaatcagta aatcagattc
3181 tgtcctcttc tctgcatacc gtgaatttat agttaaggat ccctttgctg tgagggtaga
3241 aaacctcacc aactgcacca gtgaggaaga agactgcgtg gattcatggg gagcctcaca
3301 gcagccacgc agcaggctct gggtggggct gccgttaagg cacagttctt tccttactgg
3361 tgctgataac aacagggaac cgtgcagtgt gcattttaag acc
```

SEQ ID NO:97

```
   1 cttcaacccg cgccggcggc gactgcagtt cctgcgagcg aggagcgcgg gacctgctga
  61 cacgctgacg ccttcgagcg cggcccgggg cccggagcgg ccggagcagc ccgggtcctg
 121 accccggccc ggctcccgct ccgggctctg ccggcgggcg ggcgagcgcg gcgcggtccg
 181 ggccgggggg atgtctcggc ggacgcgctg cgaggatctg gatgagctgc actaccagga
```

Figure 10 (cont.)

```
 241 cacagattca gatgtgccgg agcagaggga tagcaagtgc aaggtcaaat ggacccatga
 301 ggaggacgag cagctgaggg ccctggtgag gcagtttgga cagcaggact ggaagttcct
 361 ggccagccac ttccctaacc gcactgacca gcaatgccag tacaggtggc tgagagtttt
 421 gaatccagac cttgtcaagg ggccatggac caaagaggaa gaccaaaaag tcatcgagct
 481 ggttaagaag tatggcacaa agcagtggac actgattgcc aagcacctga agggccggct
 541 ggggaagcag tgccgtgaac gctggcacaa ccacctcaac cctgaggtga agaagtcttg
 601 ctggaccgag gaggaggacc gcatcatctg cgaggcccac aaggtgctgg gcaaccgctg
 661 ggccgagatc gccaagatgt tgccagggag gacagacaat gctgtgaaga atcactggaa
 721 ctctaccatc aaaaggaagg tggacacagg aggcttcttg agcgagtcca aagactgcaa
 781 gcccccagtg tacttgctgc tggagctcga ggacaaggac ggcctccaga gtgcccagcc
 841 cacggaaggc cagggaagtc ttctgaccaa ctggccctcc gtccctccta ccataaagga
 901 ggaggaaaac agtgaggagg aacttgcagc agccaccaca tcgaaggaac aggagcccat
 961 cggtacagat ctggacgcag tgcgaacacc agagcccttg gaggaattcc cgaagcgtga
1021 ggaccaggaa ggctccccac cagaaacgag cctgccttac aagtgggtgg tggaggcagc
1081 taacctcctc atccctgctg tgggttctag cctctctgaa gccctggact tgatcgagtc
1141 ggaccctgat gcttggtgtg acctgagtaa atttgacctc cctgaggaac catctgcaga
1201 ggacagtatc aacaacagcc tagtgcagct gcaagcgtca catcagcagc aagtcctgcc
1261 accccgccag ccttccgccc tggtgcccag tgtgaccgag taccgcctgg atggccacac
1321 catctcagac ctgagccgga gcagccgggg cgagctgatc cccatctccc ccagcactga
1381 agtcgggggc tctggcattg gcacaccgcc ctctgtgctc aagcggcaga ggaagaggcg
1441 tgtggctctg tcccctgtca ctgagaatag caccagtctg tccttcctgg attcctgtaa
1501 cagcctcacg cccaagagca cacctgttaa gaccctgccc ttctcgccct cccagtttct
1561 gaacttctgg aacaaacagg acacattgga gctggagagc cctcgctga catccacccc
1621 agtgtgcagc cagaaggtgg tggtcaccac accactgcac cgggacaaga cacccctgca
1681 ccagaaacat gctgcgtttg taaccccaga tcagaagtac tccatggaca acactcccca
1741 cacgccaacc ccgttcaaga acgccctgga gaagtacgga cccctgaagc ccctgccaca
1801 gaccccgcac ctggaggagg acttgaagga ggtgctgcgt tctgaggctg gcatcgaact
1861 catcatcgag gacgacatca ggcccgagaa gcagaagagg aagcctgggc tgcggcggag
1921 ccccatcaag aaagtccgga agtctctggc tcttgacatt gtggatgagg atgtgaagct
1981 gatgatgtcc acactgccca agtctctatc cttgccgaca actgcccctt caaactcttc
2041 cagcctcacc ctgtcaggta tcaaagaaga caacagcttg ctcaaccagg gcttcttgca
2101 ggccaagccc gagaaggcag cagtggccca gaagccccga agccacttca cgacacctgc
2161 ccctatgtcc agtgcctgga agacggtggc ctgcgggggg accagggacc agcttttcat
2221 gcaggagaaa gcccggcagc tcctgggccg cctgaagccc agccacacat ctcggaccct
2281 catcttgtcc tgaggtgttg agggtgtcac gagcccattc tcatgtttac aggggttgtg
2341 ggggcagagg gggtctgtga atctgagagt cattcaggtg acctcctgca gggagccttc
2401 tgccaccagc ccctccccag actctcaggt ggaggcaaca gggccatgtg ctgccctgtt
2461 gccgagccca gctgtgggcg gctcctggtg ctaacaacaa agttccactt ccaggtctgc
2521 ctggttccct ccccaaggcc acagggagct ccgtcagctt ctcccaagcc cacgtcaggc
2581 ctggcctcat ctcagaccct gcttaggatg ggggatgtgg ccaggggtgc tcctgtgctc
2641 accctctctt ggtgcatttt tttggaagaa taaaattgcc tctctctt
```

SEQ ID NO:98

```
   1 atgaggttga cgctactttg ttgcacctgg agggaagaac gtatgggaga ggaaggaagc
  61 gagttgcccg tgtgtgcaag ctgcggccag aggatctatg atggccagta cctccaggcc
 121 ctgaacgcgg actggcacgc agactgcttc aggtgttgtg actgcagtgc ctccctgtcg
 181 caccagtact atgagaagga tgggcagctc ttctgcaaga aggactactg ggcccgctat
 241 ggcgagtcct gccatgggtg ctctgagcaa atcaccaagg gactggttat ggtggctggg
 301 gagctgaagt accacccga gtgtttcatc tgcctcacgt gtgggacctt tatcggtgac
 361 ggggacacct acacgctggt ggagcactcc aagctgtact gcgggcactg ctactaccag
 421 actgtggtga cccccgtcat cgagcagatc ctgcctgact cccctggctc ccacctgccc
 481 cacaccgtca ccctggtgtc catcccagcc tcatctcatg gcaagcgtgg actttcagtc
 541 tccattgacc ccccgcacgg cccaccgggc tgtggcaccg agcactcaca caccgtccgc
 601 gtccagggag tggatccggg ctgcatgagc ccagatgtga agaattccat ccacgtcgga
```

Figure 10 (cont.)

```
 661 gaccggatct tggaaatcaa tggcacgccc atccgaaatg tgcccctgga cgagattgac
 721 ctgctgattc aggaaaccag ccgcctgctc cagctgaccc tcgagcatga ccctcacgat
 781 acactgggcc acgggctggg gcctgagacc agccccctga gctctccggc ttatactccc
 841 agcggggagg cgggcagctc tgcccggcag aaacctgtct tcgcaaggac ctgggtcgct
 901 ctgagtccct ccgcgtagtc tgccggccac accgcatctt ccggccgtcg gacctcatcc
 961 acggggaggt gctgggcaag ggctgcttcg gccaggctat caaggtgaca caccgtgaga
1021 caggtgaggt gatggtgatg aaggagctga tccggttcga cgaggagacc cagaggacgt
1081 tcctcaagga ggtgaaggtc atgcgatgcc tggaacaccc caacgtgctc aagttcatcg
1141 gggtgctcta caaggacaag aggctcaact tcatcactga gtacatcaag ggcggcacgc
1201 tccggggcat catcaagagc atggacagcc agtacccatg gagccagaga gtgagctttg
1261 ccaaggacat cgcatcaggg atggcctacc tccactccat gaacatcatc caccgagacc
1321 tcaactccca caactgcctg gtccgcgaga acaagaatgt ggtggtggct gacttcgggc
1381 tggcgcgtct catggtggac gagaagactc agcctgaggg cctgcggagc ctcaagaagc
1441 cagaccgcaa gaagcgctac accgtggtgg gcaaccccta ctggatggca cctgagatga
1501 tcaacggccg cagctatgat gagaaggtgg atgtgttctc ctttgggatc gtcctgtgcg
1561 agatcatcgg gcgggtgaac gcagaccctg actacctgcc ccgcaccatg gactttggcc
1621 tcaacgtgcg aggattcctg gaccgctact gccccccaaa ctgcccccccg agcttcttcc
1681 ccatcaccgt gcgctgttgc gatctggacc ccgagaagag gccatccttt gtgaagctgg
1741 aacactggct ggagaccctc cgcatgcacc tggccggcca cctgccactg ggcccacagc
1801 tggagcagct ggacagaggt ttctgggaga cctaccggcg cggcgagagc ggactgcctg
1861 cccaccctga ggtccccgac tga
```

SEQ ID NO:99

```
   1 atgcctggct tcgactacaa gttcctggag aagcccaagc gacggctgct gtgcccactg
  61 tgcgggaagc ccatgcgcga gcctgtgcag gtttccacct gcggccaccg tttctgcgat
 121 acctgcctgc aggagttcct cagtgaagga gtcttcaagt gccctgagga ccagcttcct
 181 ctggactatg ccaagatcta cccagacccg gagctggaag tacaagtatt gggcctgcct
 241 atccgctgca tccacagtga ggagggctgc cgctggagtg ggccactacg tcatctacag
 301 ggccacctga atacctgcag cttcaatgtc attccctgcc ctaatcgctg ccccatgaag
 361 ctgagccgcc gtgatctacc tgcacacttg cagcatgact gccccaagcg gcgcctcaag
 421 tgcgagtttt gtggctgtga cttcagtggg gaggcctatg aggtggatga gagttctctg
 481 ggctttggtt atcccaagtt catctcccac caggacattc gaaagcgaaa ctatgtgcgg
 541 gatgatgcag tcttcatccg tgctgctgtt gaactgcccc ggaagatcct cagctga
```

SEQ ID NO:104

```
   1 ttgcaggctg ctgggctggg gctaagggct gctcagtttc cttcagcggg gcactgggaa
  61 gcgccatggc actgcagggc atctcggtcg tggagctgtc cggcctggcc ccgggcccgt
 121 tctgtgctat ggtcctggct gacttcgggg cgcgtgtggt acgcgtggac cggcccggct
 181 cccgctacga cgtgagccgc ttgggccggg gcaagcgctc gctagtgctg gacctgaagc
 241 agccgcgggg agccgccgtg ctgcggcgtc tgtgcaagcg gtcggatgtg ctgctggagc
 301 ccttccgccg cggtgtcatg gagaaactcc agctgggccc agagattctg cagcgggaaa
 361 atccaaggct tatttatgcc aggctgagtg gatttggcca gtcaggaagc ttctgccggt
 421 tagctggcca cgatatcaac tatttggctt tgtcaggtgt tctctcaaaa attggcagaa
 481 gtggtgagaa tccgtatgcc ccgctgaatc tcctggctga ctttgctggt ggtggcctta
 541 tgtgtgcact gggcattata atggctcttt ttgaccgcac acgcactggc aagggtcagg
 601 tcattgatgc aaatatggtg gaaggaacag catatttaag ttcttttctg tggaaaactc
 661 agaaatcgag tctgtgggaa gcacctcgag gacagaacat gttggatggt ggagcacctt
 721 tctatacgac ttacaggaca gcagatgggg aattcatggc tgttggagca atagaacccc
 781 agttctacga gctgctgatc aaaggacttg gactaaagtc tgatgaactt cccaatcaga
 841 tgagcatgga tgattggcca gaaatgaaga agaagtttgc agatgtattt gcaaagaaga
 901 cgaaggcaga gtggtgtcaa atctttgacg gcacagatgc ctgtgtgact ccggttctga
 961 cttttgagga ggttgttcat catgatcaca acaaggaacg ggctcgtttt atcaccagtg
1021 aggagcagga cgtgagcccc cgccctgcac ctctgctgtt aaacacccca gccatccctt
1081 ctttcaaaag ggatcctttc ataggagaac acactgagga gatacttgaa gaatttggat
```

Figure 10 (cont.)

```
1141 tcagccgcga agagatttat cagcttaact cagataaaat cattgaaagt aataaggtaa
1201 aagctagtct ctaacttcca ggcccacggc tcaagtgaat ttgaatactg catttacagt
1261 gtagagtaac acataacatt gtatgcatgg aaacatggag gaacagtatt acagtgtcct
1321 accactctaa tcaagaaaag aattacagac tctgattcta cagtgatgat tgaattctaa
1381 aaatggttat cattagggct tttgatttat aaaactttgg gtacttatac taaattatgg
1441 tagttattct gccttccagt ttgcttgata tatttgttga tattaagatt cttgacttat
1501 attttgaatg ggttctagtg aaaaaggaat gatatattct tgaagacatc gatatacatt
1561 tatttacact cttgattcta caatgtagaa aatgaggaaa tgccacaaat tgtatggtga
1621 taaaagtcac gtgaaacaga gtgattggtt gcatccaggc cttttgtctt ggtgttcatg
1681 atctccctct aagcacattc caaactttag caacagttat cacactttgt aatttgcaaa
1741 gaaaagtttc acctgtattg aatcagaatg ccttcaactg aaaaaaacat atccaaaata
1801 atgaggaaat gtgttggctc actacgtaga gtccagaggg acagtcagtt ttagggttgc
1861 ctgtatccag taactcgggg cctgtttccc cgtgggtctc tgggctgtca gctttccttt
1921 ctccatgtgt ttgatttctc ctcaggctgg tagcaagttc tggatcttat acccaacaca
1981 cagcaacatc cagaaataaa gatct
```

SEQ ID NO:114

```
   1 cggaggcgct gggcgcacgg cgcggagccg gccggagctc gaggccggcg gcggcgggag
  61 agcgacccgg gcggcctcgt agcggggccc cggatccccg agtggcggcc ggagcctcga
 121 aaagagattc tcagcgctga ttttgagatg atgggcttgg gaaacgggcg tcgcagcatg
 181 aagtcgccgc ccctcgtgct ggccgccctg gtggcctgca tcatcgtctt gggcttcaac
 241 tactggattg cgagctcccg gagcgtggac ctccagacac ggatcatgga gctggaaggc
 301 agggtccgca gggcggctgc agagagaggc gccgtggagc tgaagaagaa cgagttccag
 361 ggagagctgg agaagcagcg ggagcagctt gacaaaatcc agtccagcca caacttccag
 421 ctggagagcg tcaacaagct gtaccaggac gaaaaggcgg ttttggtgaa taacatcacc
 481 acaggtgaga ggctcatccg agtgctgcaa gaccagttaa agaccctgca gaggaattac
 541 ggcaggctgc agcaggatgt cctccagttt cagaagaacc agaccaacct ggagaggaag
 601 ttctcctacg acctgagcca gtgcatcaat cagatgaagg aggtgaagga acagtgtgag
 661 gagcgaatag aagaggtcac caaaaagggg aatgaagctg tagcttccag agacctgagt
 721 gaaaacaacg accagagaca gcagctccaa gccctcagtg agcctcagcc caggctgcag
 781 gcagcaggcc tgccacacac agaggtgcca caagggaagg gaaacgtgct tggtaacagc
 841 aagtcccaga caccagcccc cagttccgaa gtggttttgg attcaaagag acaagttgag
 901 aaagaggaaa ccaatgagat ccaggtggtg aatgaggagc ctcagaggga caggctgccg
 961 caggagccag gccgggagca ggtggtggaa gacagacctg taggtggaag aggcttcggg
1021 ggagccggag aactgggcca gaccccacag gtgcaggctg ccctgtcagt gagccaggaa
1081 aatccagaga tggagggccc tgagcgagac cagcttgtca tccccgacgg acaggaggag
1141 gagcaggaag ctgccgggga agggagaaac cagcagaaac tgagaggaga agatgactac
1201 aacatggatg aaaatgaagc agaatctgag acagacaagc aagcagccct ggcagggaat
1261 gacagaaaca tagatgtttt taatgttgaa gatcagaaaa gagacaccat aaatttactt
1321 gatcagcgtg aaaagcggaa tcatacactc tgaattgaac tggaatcaca tatttcacaa
1381 cagggccgaa gagatgacta taaaatgttc atgagggact gaatactgaa aactgtgaaa
1441 tgtactaaat aaaatgtaca tctgaagatg attattgtga aattttagta tgcactttgt
1501 gtaggaaaaa atggaatggt cttttaaaca gcttttgggg gggtactttg gaagtgtcta
1561 ataaggtgtc acaatttttg gtagtaggta tttcgtgaga agttcaacac caaaactgga
1621 acatagttct ccttcaagtg ttggcgacag cggggcttcc tgattctgga atataacttt
1681 gtgtaaatta acagccacct atagaagagt ccatctgctg tgaaggagag acagagaact
1741 ctgggttccg tcgtcctgtc cacgtgctgt accaagtgct ggtgccagcc tgttacctgt
1801 tctcactgaa aagtctggct aatgctcttg tgtagtcact tctgattctg acaatcaatc
1861 aatcaatggc ctagagcact gactgttaac acaaacgtca ctagcaaagt agcaacagct
1921 ttaagtctaa atacaaagct gttctgtgtg agaatttttt aaaaggctac ttgtataata
1981 acccttgtca tttttaatgt acaaaacgct attaagtggc ttagaatttg aacatttgtg
2041 gtctttattt actttgcttc gtgtgtgggc aaagcaacat cttccctaaa tatatattac
2101 caagaaaagc aagaagcaga ttaggttttt gacaaaacaa acaggccaaa agggggctga
2161 cctggagcag agcatggtga gaggcaaggc atgagagggc aagtttgttg tggacagatc
```

Figure 10 (cont.)

2221 tgtgcctact ttattactgg agtaaaagaa aacaaagttc attgatgtcg aaggatatat
2281 acagtgttag aaattaggac tgtttagaaa aacaggaata caatggttgt ttttatcata
2341 gtgtacacat ttagcttgtg gtaaatgact cacaaaactg attttaaaat caagttaatg
2401 tgaattttga aaattactac ttaatcctaa ttcacaataa caatggcatt aaggtttgac
2461 ttgagttggt tcttagtatt atttatggta aataggctct taccacttgc aaataactgg
2521 ccacatcatt aatgactgac ttcccagtaa ggctctctaa ggggtaagta ggaggatcca
2581 caggatttga gatgctaagg ccccagagat cgtttgatcc aaccctctta ttttcagagg
2641 ggaaaatggg gcctagaagt tacagagcat ctagctggtg cgctggcacc cctggcctca
2701 cacagactcc cgagtagctg ggactacagg cacacagtca ctgaagcagg ccctgtttgc
2761 aattcacgtt gccacctcca acttaaacat tcttcatatg tgatgtcctt agtcactaag
2821 gttaaacttt cccacccaga aaaggcaact tagataaaat cttagagtac tttcatactc
2881 ttctaagtcc tcttccagcc tcactttgag tcctccttgg ggttgatagg aattttctct
2941 tgctttctca ataaagtctc tattcatctc atgtttaatt tgtacgcata gaattgctga
3001 gaaataaaat gttctgttca acttaaaaaa aaaaaaaaaa aa

SEQ ID NO:115

1 cgggcgatgc cgcgctgcgg gggggccgca cagccgccgc caccgccacc gccgccgggt
61 ggggtgggag gggcgggaac gcgcgccgcc gcctccaggg tgggcgcctt tcgccgtgga
121 cgccgaccgt ccgggacgag ggtttcatca ccttaaatgg ttttgaacca atgaaggtgt
181 attcccttaa aaagacggac agcccatcgt gtgaactata gagtttgtgg acagatttat
241 attgggttca tagtggcgtc atgcacgcag actcctgcaa gttcccctaa gttcttagag
301 gactgctttg ccttttgatc tgagagttgc aaagttccat aaagaatggc ccttgtggat
361 aagcacaaag tcaagagaca gcgattggac agaatttgtg aaggtatccg cccccagatc
421 atgaacggcc ccctgcaccc ccgcccccctg gtggcgctgc tggacggccg cgactgcact
481 gtggagatgc ccatcctgaa ggacctggcc actgtggcct tctgtgacgc gcagtcgacg
541 caggaaatcc acgagaaggt tctaaacgaa gccgtgggcg ccatgatgta ccacaccatc
601 accctcacca gggaggacct ggagaagttc aaggccctga gagtgatcgt gcggataggc
661 agtggctatg acaacgtgga catcaaggct gccggcgagc tcggaattgc cgtgtgcaac
721 atcccgtctg cagccgtgga agagacagcg gactctacca tctgccacat cctcaacctg
781 taccggagga acacgtggct gtaccaggca ctgcgggaag gcacgcgggt tcagagcgtg
841 gagcagatcc gcgaggtggc ctcgggagcg gcccgcatcc gtggggagac gctgggcctc
901 attggctttg gtcgcacggg gcaggcggtt gcagttcgag ccaaggcctt tggattcagc
961 gtcatatttt atgaccccta cttgcaggat gggatcgagc ggtccctggg cgtgcagagg
1021 gtctacaccc tgcaggattt gctgtatcag agcgactgcg tctccttgca ctgcaatctc
1081 aacgaacata accaccacct catcaatgac tttaccataa agcagatgag gcagggagca
1141 ttccttgtga acgcagcccg tggcggcctg gtggacgaga aagccttagc acaagccctc
1201 aaggagggca ggatacgagg ggcagccctc gacgtgcatg agtcagagcc cttcagcttt
1261 gctcagggtc cgttgaaaga tgccccgaat ctcatctgca ctcctcacac tgcctggtac
1321 agtgagcagg cgtcactgga gatgagggag gcagctgcca ccgagatccg ccgagccatc
1381 acaggtcgca tcccagaaag cttaagaaat tgtgtgaaca aggaattctt tgtcacatca
1441 gcgccttggt cagtaataga ccagcaagca attcatcctg agctcaatgg tgccacatac
1501 agatatccgc caggcatcgt gggtgtggct ccaggaggac ttcctgcagc catggaaggg
1561 atcatccctg gaggcatccc agtgactcac aacctcccga cagtggcaca tccttcccaa
1621 gcgccctctc ccaaccagcc cacaaaacac ggggacaatc gagagcaccc caacgagcaa
1681 tagcagagaa tgccagaagg taatcactca gatacacttg ggaccaagag acagtgaaaa
1741 atagatgaac taagagaaaa agaatcggat ggtctttgta actgattctg gacatatgca
1801 tcattgatgt tgcagtgttg aaactacaag agctagaaaa ctgaagatgt cgtctgctta
1861 cggaagcgct gaaagactag gatgtgattt attaacgacc aacttctgtt attgtgtgtt
1921 aagtttttca tctgtgcatc aaatcacaaa aagaataaat agagcttttt cctttatcag
1981 tcccttgggc acagcaggtc ctgaacaccc tgctctacaa tgttgcatca agagttcaaa
2041 caacaaaata aaaaatatta agaggaaatc cccatcctgt gacttgagtc ccttaagtct
2101 acaggggctg gtgacctctt tttgctaata ggaaaatcac attactacaa aatggggaga

Figure 10 (cont.)

```
2161 aaactgtttg cctgtggtag acacctgcac gcataggatt gaagacagta caggctgctg
2221 tacagagaag cgcctctcac atctgaactg catactgagc gggcaagtcg gttgtaagtt
2281 cagtaaaacc ctctgatgat gcaaaaaaaa aaaaaaagta ttaagtttca caagctgttt
2341 gtactcaaat atattttctc agtttcag
```

SEQ ID NO:116

```
   1 catttgggga cgctctcagc tctcggcgca cggcccagct tccttcaaaa tgtctactgt
  61 tcacgaaatc ctgtgcaagc tcagcttgga gggtgatcac tctacacccc caagtgcata
 121 tgggtctgtc aaagcctata ctaactttga tgctgagcgg gatgctttga acattgaaac
 181 agccatcaag accaaaggtg tggatgaggt caccattgtc aacattttga ccaaccgcag
 241 caatgcacag agacaggata ttgccttcgc ctaccagaga aggaccaaaa aggaacttgc
 301 atcagcactg aagtcagcct tatctggcca cctggagacg gtgattttgg gcctattgaa
 361 gacacctgct cagtatgacg cttctgagct aaaagcttcc atgaaggggc tgggaaccga
 421 cgaggactct ctcattgaga tcatctgctc cagaaccaac caggagctgc aggaaattaa
 481 cagagtctac aaggaaatgt acaagactga tctggagaag gacattattt cggacacatc
 541 tggtgacttc cgcaagctga tggttgccct ggcaaagggt agaagagcag aggatggctc
 601 tgtcattgat tatgaactga ttgaccaaga tgctcgggat ctctatgacg ctggagtgaa
 661 gaggaaagga actgatgttc ccaagtggat cagcatcatg accgagcgga gcgtgcccca
 721 cctccagaaa gtatttgata ggtacaagag ttacagccct tatgacatgt tggaaagcat
 781 caggaaagag gttaaaggag acctggaaaa tgctttcctg aacctggttc agtgcattca
 841 gaacaagccc ctgtattttg ctgatcggct gtatgactcc atgaagggca aggggacgcg
 901 agataaggtc ctgatcagaa tcatggtctc ccgcagtgaa gtggacatgt tgaaaattag
 961 gtctgaattc aagagaaagt acggcaagtc cctgtactat tatatccagc aagacactaa
1021 gggcgactac cagaaagcgc tgctgtacct gtgtggtgga gatgactgaa gcccgacacg
1081 gcctgagcgt ccagaaatgg tgctcaccat gcttccagct aacaggtcta gaaaaccagc
1141 ttgcgaataa cagtccccgt ggccatccct gtgagggtga cgttagcatt acccccaacc
1201 tcattttagt tgcctaagca ttgcctggcc ttcctgtcta gtctctcctg taagccaaag
1261 aaatgaacat tccaaggagt tggaagtgaa gtctatgatg tgaaacactt tgcctcctgt
1321 gtactgtgtc ataaacagat gaataaactg aatttgtact tt
```

SEQ ID NO:117

```
   1 gccccaggtg cgcttcccct agagagggat tttccggtct cgtgggcaga ggaacaacca
  61 ggaacttggg ctcagtctcc accccacagt ggggcggatc cgtcccggat aagacccgct
 121 gtctggccct gagtagggtg tgacctccgc agccgcagag gaggagcgca gcccggcctc
 181 gaagaacttc tgcttgggtg gctgaactct gatcttgacc tagagtcatg gccatggcaa
 241 ccaaaggagg tactgtcaaa gctgcttcag gattcaatgc catggaagat gcccagaccc
 301 tgaggaaggc catgaaaggg ctcggcaccg atgaagacgc cattattagc gtccttgcct
 361 accgcaacac cgcccagcgc caggagatca ggacagccta caagagcacc atcggcaggg
 421 acttgataga cgacctgaag tcagaactga gtggcaactt cgagcaggtg attgtgggga
 481 tgatgacgcc cacggtgctg tatgacgtgc aagagctgcg aagggccatg aagggagccg
 541 gcactgatga gggctgccta attgagatcc tggcctcccg gacccctgag gagatccggc
 601 gcataagcca aacctaccag cagcaatatg gacggagcct tgaagatgac attcgctctg
 661 acacatcgtt catgttccag cgagtgctgg tgtctctgtc agctggtggg agggatgaag
 721 gaaattatct ggacgatgct ctcgtgagac aggatgccca ggacctgtat gaggctggag
 781 agaagaaatg gggacagat gaggtgaaat ttctaactgt tctctgttcc cggaaccgaa
 841 atcacctgtt gcatgtgttt gatgaataca aaaggatatc acagaaggat attgaacaga
 901 gtattaaatc tgaaacatct ggtagctttg aagatgctct gctggctata gtaaagtgca
 961 tgaggaacaa atctgcatat tttgctgaaa agctctataa atcgatgaag ggcttgggca
1021 ccgatgataa caccctcatc agagtgatgg tttctcgagc agaaattgac atgttggata
1081 tccgggcaca cttcaagaga ctctatggaa agtctctgta ctcgttcatc aagggtgaca
1141 catctggaga ctacaggaaa gtactgcttg ttctctgtgg aggagatgat taaaataaaa
```

Figure 10 (cont.)

```
1201 atcccagaag gacaggagga ttctcaacac tttgaatttt tttaacttca tttttctaca
1261 ctgctattat cattatctca gaatgcttat ttccaattaa aacgcctaca gctgcctcct
1321 agaatataga ctgtctgtat tattattcac ctataattag tcattatgat gctttaaagc
1381 tgtacttgca tttcaaagct tataagatat aaatggagat tttaaagtag aaataaatat
1441 gtattccatg tttttaaaag attactttct actttgtgtt tcacagacat tgaatatatt
1501 aaattattcc atattttctt ttcagtgaaa aattttttaa atggaagact gttctaaaat
1561 cacttttttc cctaatccaa tttttagagt ggctagtagt ttcttcattt gaaattgtaa
1621 gcatccggtc agtaagaatg cccatccagt tttctatatt tcatagtcaa agccttgaaa
1681 gcatctacaa atctcttttt ttaggttttg tccatagcat cagttgatcc ttactaagtt
1741 tttcatggga gacttccttc atcacatctt atgttgaaat cactttctgt agtcaaagta
1801 taccaaaacc aatttatctg aactaaattc taaagtatgg ttatacaaac catatacatc
1861 tggttaccaa acataaatgc tgaacattcc atattattat agttaatgtc ttaatccagc
1921 ttgcaagtga atggaaaaaa aaataagctt caaactaggt attctgggaa tgatgtaatg
1981 ctctgaattt agtatgatat aaagaaaact tttttgtgct aaaaatactt tttaaaatca
2041 atttgttgta ttgtagtaat ttctatttgc actgtgcctt tcaactccag aaacattctg
2101 aagatgtact tggatttaat taaaaagttc actttgt
```

SEQ ID NO:118

```
   1 gctgctgcgc ccgcggctcc ccagtgcccc gagtgccccg cgggccccgc gagcgggagt
  61 gggacccagc cctaggcaga acccaggcgc cgcgcccggg acgcccgcgg agagagccac
 121 tcccgcccac gtcccatttc gcccctcgcg tccggagtcc ccgtggccag atctaaccat
 181 gagctaccct ggctatcccc cgcccccagg tggctaccca ccagctgcac caggtggtgg
 241 tccctgggga ggtgctgcct accctcctcc gcccagcatg ccccccatcg ggctggataa
 301 cgtggccacc tatgcggggc agttcaacca ggactatctc tcgggaatgg cggccaacat
 361 gtctgggaca tttggaggag ccaacatgcc caacctgtac cctggggccc ctggggctgg
 421 ctacccacca gtgccccctg gcggctttgg gcagcccccc tctgcccagc agcctgttcc
 481 tccctatggg atgtatccac ccccaggagg aaacccaccc tccaggatgc cctcatatcc
 541 gccataccca ggggcccctg tgccgggcca gcccatgcca ccccccggac agcagccccc
 601 aggggcctac cctgggcagc caccagtgac ctaccctggt cagcctccag tgccactccc
 661 tgggcagcag cagccagtgc cgagctaccc aggatacccg gggtctggga ctgtcacccc
 721 cgctgtgccc ccaacccagt ttggaagccg aggcaccatc actgatgctc ccggctttga
 781 ccccctgcga gatgccgagg tcctgcggaa ggccatgaaa ggcttcggga cggatgagca
 841 ggccatcatt gactgcctgg ggagtcgctc caacaagcag cggcagcaga tcctactttc
 901 cttcaagacg gcttacggca aggatttgat caaagatctg aaatctgaac tgtcaggaaa
 961 ctttgagaag acaatcttgg ctctgatgaa gaccccagtc ctctttgaca tttatgagat
1021 aaaggaagcc atcaaggggg ttggcactga tgaagcctgc ctgattgaga tcctcgcttc
1081 ccgcagcaat gagcacatcc gagaattaaa cagagcctac aaagcagaat tcaaaaagac
1141 cctggaagag gccattcgaa gcgacacatc agggcacttc cagcggctcc tcatctctct
1201 ctctcaggga aaccgtgatg aaagcacaaa cgtggacatg tcactcgccc agagagatgc
1261 ccaggagctg tatgcggccg gggagaaccg cctgggaaca gacgagtcca agttcaatgc
1321 ggttctgtgc tcccggagcc gggcccacct ggtagcagtt ttcaatgagt accagagaat
1381 gacaggccgg gacattgaga agagcatctg ccgggagatg tccggggacc tggaggaggg
1441 catgctggcc gtggtgaaat gtctcaagaa taccccagcc ttctttgcgg agaggctcaa
1501 caaggccatg aggggggcag gaacaaagga ccggaccctg attcgcatca tggtgtctcg
1561 cagcgagacc gacctcctgg acatcagatc agagtataag cggatgtacg gcaagtcgct
1621 gtaccacgac atctcgggag atacttcagg ggattaccgg aagattctgc tgaagatctg
1681 tggtggcaat gactgaacag tgactggtgg ctcacttctg cccacctgcc ggcaacacca
1741 gtgccaggaa aaggccaaaa gaatgtctgt ttctaacaaa tccacaaata gccccgagat
1801 tcaccgtcct agagcttagg cctgtcttcc accccctcctg acccgtatag tgtgccacag
1861 gacctgggtc ggtctagaac tctctcagga tgccttttct accccatccc tcacagcctc
1921 ttgctgctaa aatagatgtt tcatttttct gaaaaaa
```

SEQ ID NO:119

Figure 10 (cont.)

1 ggctcatgct cgggagcgtg gttgagcggc tggcgcggtt gtcctggagc aggggcgcag
61 gaattctgat gtgaaactaa cagtctgtga gccctggaac ctccactcag agaagatgaa
121 ggatatcgac ataggaaaag agtatatcat ccccagtcct gggtatagaa gtgtgaggga
181 gagaaccagc acttctggga cgcacagaga ccgtgaagat tccaagttca ggagaactcg
241 accgttggaa tgccaagatg ccttggaaac agcagcccga gccgagggcc tctctcttga
301 tgcctccatg cattctcagc tcagaatcct ggatgaggag catcccaagg gaaagtacca
361 tcatggcttg agtgctctga agcccatccg gactacttcc aaacaccagc acccagtgga
421 caatgctggg ctttttcct gtatgacttt ttcgtggctt tcttctctgg cccgtgtggc
481 ccacaagaag gggagctct caatggaaga cgtgtggtct ctgtccaagc acgagtcttc
541 tgacgtgaac tgcagaagac tagagagact gtggcaagaa gagctgaatg aagttgggcc
601 agacgctgct tccctgcgaa gggttgtgtg gatcttctgc cgcaccaggc tcatcctgtc
661 catcgtgtgc ctgatgatca cgcagctggc tggcttcagt ggaccagcct tcatggtgaa
721 acacctcttg gagtataccc aggcaacaga gtctaacctg cagtacagct tgttgttagt
781 gctgggcctc ctcctgacgg aaatcgtgcg gtcttggtcg cttgcactga cttgggcatt
841 gaattaccga accggtgtcc gcttgcgggg ggccatccta accatggcat ttaagaagat
901 ccttaagtta aagaacatta aagagaaatc cctgggtgag ctcatcaaca tttgctccaa
961 cgatgggcag agaatgtttg aggcagcagc cgttggcagc ctgctggctg gaggacccgt
1021 tgttgccatc ttaggcatga tttataatgt aattattctg ggaccaacag gcttcctggg
1081 atcagctgtt tttatcctct tttacccagc aatgatgttt gcatcacggc tcacagcata
1141 tttcaggaga aaatgcgtgg ccgccacgga tgaacgtgtc cagaagatga atgaagttct
1201 tacttacatt aaatttatca aaatgtatgc ctgggtcaaa gcattttctc agagtgttca
1261 aaaaatccgc gaggaggagc gtcggatatt ggaaaaagct gggtacttcc agagcatcac
1321 tgtgggtgtg gctcccattg tggtggtgat tgccagcgtg gtgaccttct ctgttcatat
1381 gaccctgggc ttcgatctga cagcagcaca ggctttcaca gtggtgacag tcttcaattc
1441 catgactttt gctttgaaag taacaccgtt ttcagtaaag tccctctcag aagcctcagt
1501 ggctgttgac agatttaaga gtttgtttct aatggaagag gttcacatga taaagaacaa
1561 accagccagt cctcacatca agatagagat gaaaaatgcc accttggcat gggactcctc
1621 ccactccagt atccagaact cgcccaagct gacccccaaa atgaaaaaag acaagagggc
1681 ttccaggggc aagaaagaga aggtgaggca gctgcagcgc actgagcatc aggcggtgct
1741 ggcagagcag aaaggccacc tcctcctgga cagtgacgag cggcccagtc ccgaagagga
1801 agaaggcaag cacatccacc tgggccacct gcgcttacag aggacactgc acagcatcga
1861 tctggagatc caagagggta aactggttgg aatctgtggc agtgtgggaa gtggaaaaac
1921 ctctctcatt tcagccattt taggccagat gacgcttcta gagggcagca ttgcaatcag
1981 tggaaccttc gcttatgtgg cccagcaggc ctggatcctc aatgctactc tgagagacaa
2041 catcctgttt gggaaggaat atgatgaaga aagatacaac tctgtgctga acagctgctg
2101 cctgaggcct gacctggcca ttcttcccag cagcgacctg acggagattg gagagcgagg
2161 agccaacctg agcggtgggc agcgccagag gatcagcctt gcccgggcct tgtatagtga
2221 caggagcatc tacatcctgg acgacccct cagtgcctta gatgcccatg tgggcaacca
2281 catcttcaat agtgctatcc ggaaacatct caagtccaag acagttctgt ttgttaccca
2341 ccagttacag tacctggttg actgtgatga agtgatcttc atgaaagagg gctgtattac
2401 ggaaagaggc acccatgagg aactgatgaa tttaaatggt gactatgcta ccatttttaa
2461 taacctgttg ctgggagaga caccgccagt tgagatcaat tcaaaaaagg aaaccagtgg
2521 ttcacagaag aagtcacaag acaagggtcc taaaacagga tcagtaaaga aggaaaaagc
2581 agtaaagcca gaggaagggc agcttgtgca gctggaagag aaagggcagg gttcagtgcc
2641 ctggtcagta tatggtgtct acatccaggc tgctgggggc cccttggcat tcctggttat
2701 tatggccctt ttcatgctga atgtaggcag caccgccttc agcacctggt ggttgagtta
2761 ctggatcaag caaggaagcg ggaacaccac tgtgactcga gggaacgaga cctcggtgag
2821 tgacagcatg aaggacaatc ctcatatgca gtactatgcc agcatctacg ccctctccat
2881 ggcagtcatg ctgatcctga aagccattcg aggagttgtc tttgtcaagg gcacgctgcg
2941 agcttcctcc cggctgcatg acgagctttt ccgaaggatc cttcgaagcc ctatgaagtt
3001 ttttgacacg acccccacag ggaggattct caacaggttt tccaaagaca tggatgaagt
3061 tgacgtgcgg ctgccgttcc aggccgagat gttcatccag aacgttatcc tggtgttctt
3121 ctgtgtggga atgatcgcag gagtcttccc gtggttcctt gtggcagtgg ggccccttgt

Figure 10 (cont.)

```
3181 catcctcttt tcagtcctgc acattgtctc cagggtcctg attcgggagc tgaagcgtct
3241 ggacaatatc acgcagtcac ctttcctctc ccacatcacg tccagcatac agggccttgc
3301 caccatccac gcctacaata aagggcagga gtttctgcac agataccagg agctgctgga
3361 tgacaaccaa gctccttttt ttttgtttac gtgtgcgatg cggtggctgg ctgtgcggct
3421 ggacctcatc agcatcgccc tcatcaccac cacggggctg atgatcgttc ttatgcacgg
3481 gcagattccc ccagcctatg cgggtctcgc catctcttat gctgtccagt taacggggct
3541 gttccagttt acggtcagac tggcatctga gacagaagct cgattcacct cggtggagag
3601 gatcaatcac tacattaaga ctctgtcctt ggaagcacct gccagaatta agaacaaggc
3661 tccctcccct gactggcccc aggagggaga ggtgaccttt gagaacgcag agatgaggta
3721 ccgagaaaac ctccctctcg tcctaaagaa agtatccttc acgatcaaac ctaaagagaa
3781 gattggcatt gtggggcgga caggatcagg gaagtcctcg ctggggatgg ccctcttccg
3841 tctggtggag ttatctggag gctgcatcaa gattgatgga gtgagaatca gtgatattgg
3901 ccttgccgac ctccgaagca aactctctat cattcctcaa gagccggtgc tgttcagtgg
3961 cactgtcaga tcaaatttgg accccttcaa ccagtacact gaagaccaga tttgggatgc
4021 cctggagagg acacacatga aagaatgtat tgctcagcta cctctgaaac ttgaatctga
4081 agtgatggag aatgggggata acttctcagt gggggaacgg cagctcttgt gcatagctag
4141 agccctgctc cgccactgta agattctgat tttagatgaa gccacagctg ccatggacac
4201 agagacagac ttattgattc aagagaccat ccgagaagca tttgcagact gtaccatgct
4261 gaccattgcc catcgcctgc acacggttct aggctccgat aggattatgg tgctggccca
4321 gggacaggtg gtggagtttg acaccccatc ggtccttctg tccaacgaca gttcccgatt
4381 ctatgccatg tttgctgctg cagagaacaa ggtcgctgtc aagggctgac tcctccctgt
4441 tgacgaagtc tcttttcttt agagcattgc cattccctgc ctggggcggg cccctcatcg
4501 cgtcctccta ccgaaacctt gcctttctcg attttatctt tcgcacagca gttccggatt
4561 ggcttgtgtg tttcactttt agggagagtc atattttgat tattgtattt attccatatt
4621 catgtaaaca aaatttagtt tttgttctta attgcactct aaaaggttca gggaaccgtt
4681 attataattg tatcagaggc ctataatgaa gctttatacg tgtagctata tctatatata
4741 attctgtaca tagcctatat ttacagtgaa aatgtaagct gtttatttta tattaaaata
4801 agcactgtgc taataacagt gcatattcct ttctatcatt tttgtacagt ttgctgtact
4861 agagatctgg ttttgctatt agactgtagg aagagtagca tttcattctt ctctagctgg
4921 tggtttcacg gtgccaggtt ttctgggtgt ccaaaggaag acgtgtggca atagtgggcc
4981 ctccgacagc cccctctgcc gcctccccac ggccgctcca ggggtggctg gagacgggtg
5041 ggcggctgga gaccatgcag agcgccgtga gttctcaggg ctcctgcctt ctgtcctggt
5101 gtcacttact gtttctgtca ggagagcagc ggggcgaagc ccaggcccct tttcactccc
5161 tccatcaaga atggggatca cagagacatt cctccgagcc ggggagtttc tttcctgcct
5221 tcttcttttt gctgttgttt ctaaacaaga atcagtctat ccacagagag tcccactgcc
5281 tcaggttcct atggctggcc actgcacaga gctctccagc tccaagacct gttggttcca
5341 agccctggag ccaactgctg ctttttgagg tggcactttt tcatttgcct attcccacac
5401 ctccacagtt cagtggcagg gctcaggatt tcgtgggtct gttttccttt ctcaccgcag
5461 tcgtcgcaca gtctctctct ctctctcccc tcaaagtctg caactttaag cagctcttgc
5521 taatcagtgt ctcacactgg cgtagaagtt tttgtactgt aaagagacct acctcaggtt
5581 gctggttgct gtgtggtttg gtgtgttccc gcaaaccccc tttgtgctgt ggggctggta
5641 gctcaggtgg gcgtggtcac tgctgtcatc aattgaatgg tcagcgttgc atgtcgtgac
5701 caactagaca ttctgtcgcc ttagcatgtt tgctgaacac cttgtggaag caaaaatctg
5761 aaaatgtgaa taaaattatt ttggattttg t
```

SEQ ID NO:120

```
  1 aaacttcccg cacgcgttac aggagccagg tcggtataag cgccacgcct cgccgcccgt
 61 caagctgtcc acatccctgg cctcagcccg ccacatcacc ctgacctgct tacgcccaga
121 ttttcttcaa tcacatctga ataaatcact tgaagaaagc ttatagcttc attgcaccat
181 gtgtggcatt tgggcgctgt ttggcagtga tgattgcctt tctgttcagt gtctgagtgc
241 tatgaagatt gcacacagag gtccagatgc attccgtttt gagaatgtca atggatacac
301 caactgctgc tttggatttc accggttggc ggtagttgac ccgctgtttg gaatgcagcc
361 aattcgagtg aagaaatatc cgtatttgtg gctctgttac aatggtgaaa tctacaacca
421 taagaagatg caacagcatt ttgaatttga ataccagacc aaagtggatg gtgagataat
```

Figure 10 (cont.)

```
 481 ccttcatctt tatgacaaag gaggaattga gcaaacaatt tgtatgttgg atggtgtgtt
 541 tgcatttgtt ttactggata ctgccaataa gaaagtgttc ctgggtagag atacatatgg
 601 agtcagacct ttgtttaaag caatgacaga agatggattt ttggctgtat gttcagaagc
 661 taaaggtctt gttacattga agcactccgc gactcccttt ttaaaagtgg agccttttct
 721 tcctggacac tatgaagttt tggatttaaa gccaaatggc aaagttgcat ccgtggaaat
 781 ggttaaatat catcactgtc gggatgtacc cctgcacgcc ctctatgaca atgtggagaa
 841 actctttcca ggttttgaga tagaaactgt gaagaacaac ctcaggatcc tttttaataa
 901 tgctgtaaag aaacgtttga tgacagacag aaggattggc tgccttttat caggggggctt
 961 ggactccagc ttggttgctg ccactctgtt gaagcagctg aaagaagccc aagtacagta
1021 tcctctccag acatttgcaa ttggcatgga agacagcccc gatttactgg ctgctagaaa
1081 ggtggcagat catattggaa gtgaacatta tgaagtcctt tttaactctg aggaaggcat
1141 tcaggctctg gatgaagtca tattttcctt ggaaacttat gacattacaa cagttcgtgc
1201 ttcagtaggt atgtatttaa tttccaagta tattcggaag aacacagata gcgtggtgat
1261 cttctctgga gaaggatcag atgaacttac gcagggttac atatatttttc acaaggctcc
1321 ttctcctgaa aaagccgagg aggagagtga gaggcttctg agggaactct atttgtttga
1381 tgttctccgc gcagatcgaa ctactgctgc ccatggtctt gaactgagag tcccatttct
1441 agatcatcga ttttttttcct attacttgtc tctgccacca gaaatgagaa ttccaaagaa
1501 tgggatagaa aaacatctcc tgagagagac gtttgaggat tccaatctga tacccaaaga
1561 gattctctgg cgaccaaaag aagccttcag tgatggaata acttcagtta agaattcctg
1621 gtttaagatt ttacaggaat acgttgaaca tcaggttgat gatgcaatga tggcaaatgc
1681 agcccagaaa tttcccttca atactcctaa aaccaaagaa ggatattact accgtcaagt
1741 ctttgaacgc cattacccag gccgggctga ctggctgagc cattactgga tgcccaagtg
1801 gatcaatgcc actgaccctt ctgcccgcac gctgacccac tacaagtcag ctgtcaaagc
1861 ttaggtggtc tttatgctgt aatgtgaaag caaatatttc ttcgtgttgg atggggactg
1921 tgggtagata ggggaacaat gagagtcaac tcaggctaac ttgggtttga aaaaaataaa
1981 attcctaaat tt
```

SEQ ID NO:121

```
   1 aggttcaagt ggagctctcc taaccgacgc gcgtctgtgg agaagcggct tggtcggggg
  61 tggtctcgtg gggtcctgcc tgtttagtcg ctttcagggt tcttgagccc cttcacgacc
 121 gtcaccatgg aagtgtcacc attgcagcct gtaaatgaaa atatgcaagt caacaaaata
 181 aagaaaaatg aagatgctaa gaaaagactg tctgttgaaa gaatctatca aaagaaaaca
 241 caattggaac atattttgct ccgcccagac acctacattg gttctgtgga attagtgacc
 301 cagcaaatgt gggtttacga tgaagatgtt ggcattaact atagggaagt cacttttgtt
 361 cctggtttgt acaaaatctt tgatgagatt ctagttaatg ctgcggacaa caaacaaagg
 421 gacccaaaaa tgtcttgtat tagagtcaca attgatccgg aaaacaattt aattagtata
 481 tggaataatg gaaaaggtat tcctgttgtt gaacacaaag ttgaaaagat gtatgtccca
 541 gctctcatat ttggacagct cctaacttct agtaactatg atgatgatga aaagaaagtg
 601 acaggtggtc gaaatggcta tggagccaaa ttgtgtaaca tattcagtac caaatttact
 661 gtggaaacag ccagtagaga atacaagaaa atgttcaaac agacatggat ggataatatg
 721 ggaagagctg gtgagatgga actcaagccc ttcaatggag aagattatac atgtatcacc
 781 tttcagcctg atttgtctaa gtttaaaatg caaagcctgg acaaagatat tgttgcacta
 841 atggtcagaa gagcatatga tattgctgga tccaccaaag atgtcaaagt ctttcttaat
 901 ggaaataaac tgccagtaaa aggatttcgt agttatgtgg acatgtattt gaaggacaag
 961 ttggatgaaa ctggtaactc cttgaaagta atacatgaac aagtaaacca caggtgggaa
1021 gtgtgtttaa ctatgagtga aaaaggcttt cagcaaatta gctttgtcaa cagcattgct
1081 acatccaagg gtggcagaca tgttgattat gtagctgatc agattgtgac taaacttgtt
1141 gatgttgtga agaagaagaa caagggtggt gttgcagtaa aagcacatca ggtgaaaaat
1201 cacatgtgga tttttgtaaa tgccttaatt gaaaacccaa cctttgactc tcagacaaaa
1261 gaaaacatga ctttacaacc caagagcttt ggatcaacat gccaattgag tgaaaaattt
1321 atcaaagctg ccattggctg tggtattgta gaaagcatac taaactgggt gaagtttaag
1381 gcccaagtcc agttaaacaa gaagtgttca gctgtaaaac ataatagaat caagggaatt
```

Figure 10 (cont.)

```
1441 cccaaactcg atgatgccaa tgatgcaggg ggccgaaact ccactgagtg tacgcttatc
1501 ctgactgagg gagattcagc caaaactttg gctgtttcag gccttggtgt ggttgggaga
1561 gacaaatatg gggttttccc tcttagagga aaaatactca atgttcgaga agcttctcat
1621 aagcagatca tggaaaatgc tgagattaac aatatcatca agattgtggg tcttcagtac
1681 aagaaaaact atgaagatga agattcattg aagacgcttc gttatgggaa gataatgatt
1741 atgacagatc aggaccaaga tggttcccac atcaaaggct tgctgattaa ttttatccat
1801 cacaactggc cctctcttct gcgacatcgt tttctggagg aatttatcac tcccattgta
1861 aaggtatcta aaaacaagca agaaatggca ttttacagcc ttcctgaatt tgaagagtgg
1921 aagagttcta ctccaaatca taaaaaatgg aaagtcaaat attacaaagg tttgggcacc
1981 agcacatcaa aggaagctaa agaatacttt gcagatatga aaagacatcg tatccagttc
2041 aaatattctg gtcctgaaga tgatgctgct atcagcctgg cctttagcaa aaaacagata
2101 gatgatcgaa aggaatggtt aactaatttc atggaggata gaagacaacg aaagttactt
2161 gggcttcctg aggattactt gtatggacaa actaccacat atctgacata taatgacttc
2221 atcaacaagg aacttatctt gttctcaaat tctgataacg agagatctat cccttctatg
2281 gtggatggtt tgaaaccagg tcagagaaag gttttgttta cttgcttcaa acggaatgac
2341 aagcgagaag taaaggttgc ccaattagct ggatcagtgg ctgaaatgtc ttcttatcat
2401 catggtgaga tgtcactaat gatgaccatt atcaatttgg ctcagaattt tgtgggtagc
2461 aataatctaa acctcttgca gcccattggt cagtttggta ccaggctaca tggtggcaag
2521 gattctgcta gtccacgata catctttaca atgctcagct ctttggctcg attgttattt
2581 ccaccaaaag atgatcacac gttgaagttt ttatatgatg acaaccagcg tgttgagcct
2641 gaatggtaca ttcctattat tcccatggtg ctgataaatg gtgctgaagg aatcggtact
2701 gggtggtcct gcaaaatccc caactttgat gtgcgtgaaa ttgtaaataa catcaggcgt
2761 ttgatggatg gagaagaacc tttgccaatg cttccaagtt acaagaactt caagggtact
2821 attgaagaac tggctccaaa tcaatatgtg attagtggtg aagtagctat tcttaattct
2881 acaaccattg aaatctcaga gcttcccgtc agaacatgga cccagacata caaagaacaa
2941 gttctagaac ccatgttgaa tggcaccgag aagacacctc ctctcataac agactatagg
3001 gaataccata cagataccac tgtgaaattt gttgtgaaga tgactgaaga aaaactggca
3061 gaggcagaga gagttggact acacaaagtc ttcaaactcc aaactagtct cacatgcaac
3121 tctatggtgc tttttgacca cgtaggctgt ttaaagaaat atgacacggt gttggatatt
3181 ctaagagact tttttgaact cagacttaaa tattatggat taagaaaaga atggctccta
3241 ggaatgcttg gtgctgaatc tgctaaactg aataatcagg ctcgctttat cttagagaaa
3301 atagatggca aaataatcat tgaaaataag cctaagaaag aattaattaa agttctgatt
3361 cagaggggat atgattcgga tcctgtgaag gcctggaaag aagcccagca aaaggttcca
3421 gatgaagaag aaaatgaaga gagtgacaac gaaaaggaaa ctgaaaagag tgactccgta
3481 acagattctg gaccaacctt caactatctt cttgatatgc ccctttggta tttaaccaag
3541 gaaaagaaag atgaactctg caggctaaga aatgaaaaag aacaagagct ggacacatta
3601 aaaagaaaga gtccatcaga tttgtggaaa gaagacttgg ctacatttat tgaagaattg
3661 gaggctgttg aagccaagga aaaacaagat gaacaagtcg gacttcctgg gaaagggggg
3721 aaggccaagg ggaaaaaaac acaaatggct gaagttttgc cttctccgcg tggtcaaaga
3781 gtcattccac gaataaccat agaaatgaaa gcagaggcag aaaagaaaaa taaaaagaaa
3841 attaagaatg aaaatactga aggaagccct caagaagatg gtgtggaact agaaggccta
3901 aaacaaagat tagaaaagaa acagaaaaga gaaccaggta caaagacaaa gaaacaaact
3961 acattggcat ttaagccaat caaaaaagga aagaagagaa atccctggtc tgattcagaa
4021 tcagatagga gcagtgacga aagtaatttt gatgtccctc cacgagaaac agagccacgg
4081 agagcagcaa caaaaacaaa attcacaatg gatttggatt cagatgaaga tttctcagat
4141 tttgatgaaa aaactgatga tgaagatttt gtcccatcag atgctagtcc acctaagacc
4201 aaaacttccc caaaacttag taacaaagaa ctgaaaccac agaaaagtgt cgtgtcagac
4261 cttgaagctg atgatgttaa gggcagtgta ccactgtctt caagccctcc tgctacacat
4321 ttcccagatg aaactgaaat tacaaaccca gttcctaaaa agaatgtgac agtgaagaag
4381 acagcagcaa aaagtcagtc ttccacctcc actaccggtg ccaaaaaaag ggctgcccca
4441 aaaggaacta aaagggatcc agctttgaat tctggtgtct ctcaaaagcc tgatcctgcc
4501 aaaaccaaga atcgccgcaa aaggaagcca tccacttctg atgattctga ctctaatttt
4561 gagaaaattg tttcgaaagc agtcacaagc aagaaatcca agggggagag tgatgacttc
4621 catatggact ttgactcagc tgtggctcct cgggcaaaat ctgtacgggc aaagaaacct
```

Figure 10 (cont.)

```
4681 ataaagtacc tggaagagtc agatgaagat gatctgtttt aaaatgtgag gcgattattt
4741 taagtaatta tcttaccaag cccaagactg gttttaaagt tacctgaagc tcttaacttc
4801 ctcccctctg aatttagttt ggggaaggtg tttttagtac aagacatcaa agtgaagtaa
4861 agcccaagtg ttctttagct ttttataata ctgtctaaat agtgaccatc tcatgggcat
4921 tgttttcttc tctgctttgt ctgtgttttg agtctgcttt cttttgtctt taaaacctga
4981 tttttaagtt cttctgaact gtagaaatag ctatctgatc acttcagcgt aaagcagtgt
5041 gtttattaac catccactaa gctaaaacta gagcagtttg atttaaaagt gtcactcttc
5101 ctccttttct actttcagta gatatgagat agagcataat tatctgtttt atcttagttt
5161 tatacataat ttaccatcag atagaacttt atggttctag tacagatact ctactacact
5221 cagcctctta tgtgccaagt ttttctttaa gcaatgagaa attgctcatg ttcttcatct
5281 tctcaaatca tcagaggcca aagaaaaaca ctttggctgt gtctataact tgacacagtc
5341 aatagaatga agaaaattag agtagttatg tgattatttc agctcttgac ctgtcccctc
5401 tggctgcctc tgagtctgaa tctcccaaag agagaaacca atttctaaga ggactggatt
5461 gcagaagact cggggacaac atttgatcca agatcttaaa tgttatattg ataaccatgc
5521 tcagcaatga gctattagat tcattttggg aaatctccat aatttcaatt tgtaaacttt
5581 gttaagacct gtctacattg ttatatgtgt gtgacttgag taatgttatc aacgtttttg
5641 taaatattta ctatgttttt ctattagcta aattccaaca attttgtact ttaataaa
```

SEQ ID NO:122

```
   1 gcgccatgga gcagtggcgg cagtgcggcc gctggctcat cgattgcaag gtcctgccgc
  61 ccaaccaccg ggtggtgtgg ccctcggccg tggtcttcga cctggcgcag gcgctgcgcg
 121 acggggtcct tctgtgccag ctgctgcaca acctctcccc cggctccatc gacctcaagg
 181 acatcaactt ccggccgcag atgtcccagt ttctgtgttt gaagaacata cgcaccttcc
 241 tgaaagtctg ccacgataaa tttggattaa ggaacagcga gctgtttgac ccctttgacc
 301 tcttcgatgt gcgagacttt ggaaaggtca tctccgcggt gtcgaggctc tccctgcaca
 361 gcatcgcgca gaacaaaggg atcaggcctt ttccctcaga ggagaccaca gagaatgacg
 421 atgacgtcta ccgcagcctg gaggagctgg ccgacgagca tgacctgggg gaggacatct
 481 acgactgcgt cccgtgtgag gatggagggg acgacatcta cgaggacatc atcaaggtgg
 541 aggtgcagca gcccatgatt agatacatgc agaaaatggg catgactgaa gatgacaaga
 601 ggaactgctg cctgctggag atccaggaga ccgaggccaa gtactaccgc accctggagg
 661 acattgagaa gaactacatg agccccctgc ggctggtgct gagcccggcg gacatggcag
 721 ctgtcttcat taacctggag gacctgatca aggtgcatca cagcttcctg agggccatcg
 781 acgtgtccgt gatggtgggg ggcagcacgc tggccaaggt cttcctcgat ttcaaggaaa
 841 ggcttctgat ctacggggag tactgcagcc acatggagca cgcccagaac acactgaacc
 901 agctcctggc cagccgggag gacttcaggc agaaagtcga ggagtgcaca ctgaaggtcc
 961 aggatggaaa atttaagctg caagacctgc tggtggtccc catgcagagg gtgctcaaat
1021 accacctgct cttgaaggag cttctgagcc attctgcgga acggcctgag aggcagcagc
1081 tcaaagaagc actggaagcc atgcaggact tggcgatgta catcaatgaa gttaaacggg
1141 acaaggagac cttgaggaaa atcagcgaat ttcagagttc tatagaaaat ttgcaagtga
1201 aactggagga atttggaaga ccaaagattg acggggaact gaaagtccgg tccatagtca
1261 accacaccaa gcaggacagg tacttgttcc tgtttgacaa ggtggtcatc gtctgcaagc
1321 ggaagggcta cagctacgag ctcaaggaga tcatcgagct gctgttccac aagatgaccg
1381 acgaccccat gaacaacaag gacgtcaaga agtctcacgg gaaaatgtgg tcctacggct
1441 tctacctaat tcaccttcaa ggaaagcagg gcttccagtt tttctgcaaa acagaagata
1501 tgaagaggaa gtggatggag cagtttgaga tggccatgtc aaacatcaag ccagacaaag
1561 ccaatgccaa ccaccacagt ttccagatgt acacgtttga caagaccacc aactgcaaag
1621 cctgcaaaat gttcctcagg ggcaccttct accagggata catgtgtacc aagtgtggcg
1681 tcggggcaca caaggagtgc ctggaagtga tacctccctg caagttcact tctcctgcag
1741 atctggacgc ctccggagcg ggaccaggtc ccaagatggt ggccatgcag aattaccatg
1801 gcaacccagc ccctcccggg aagcctgtgc tgaccttcca gacgggcgac gtgcttgagc
1861 tgctgagggg cgaccctgag tctccgtggt gggagggtcg tctggtacaa accaggaagt
1921 cagggtattt ccccagctca tctgtgaagc cctgccctgt ggatggaagg ccgcccatca
1981 gccggccgcc atcccgggag atcgactaca ctgcataccc ctggtttgca ggtaacatgg
2041 agaggcagca gacggacaac ctgctcaagt cccacgccag cgggacctac ctgatcaggg
```

Figure 10 (cont.)

```
2101 agcggcctgc cgaggctgag cgctttgcaa taagcatcaa gttcaatgat gaggtgaagc
2161 acatcaaggt ggtggagaag gacaactgga tccacatcac agaggccaag aaattcgaca
2221 gcctcctgga gttggtggag tactaccagt gccactcact gaaggagagc ttcaagcagc
2281 tggacaccac actcaagtac ccctacaagt cccgggaacg ttcggcctcc agggcctcca
2341 gccggtcccc agcttcctgt gcttcctaca acttttcttt tctcagtcct cagggcctca
2401 gctttgcttc tcagggcccc tccgctccct tctggtcagt gttcacgccc cgcgtcatcg
2461 gcacagctgt ggccaggtat aactttgccg cccgagatat gagggagctt tcgctgcggg
2521 agggtgacgt ggtgaggatc tacagccgca tcggcggaga ccagggctgg tggaagggcg
2581 agaccaacgg acggattggc tggtttcctt caacgtacgt agaagaggag ggcatccagt
2641 gacggcagga acgtggacaa gactcgcaga ttttcttggg agagtcactc cagccctgaa
2701 gtctgtctct agctcctctg tgactcagag gggaaatacc aacctcccag tct
```

FIGURE 13
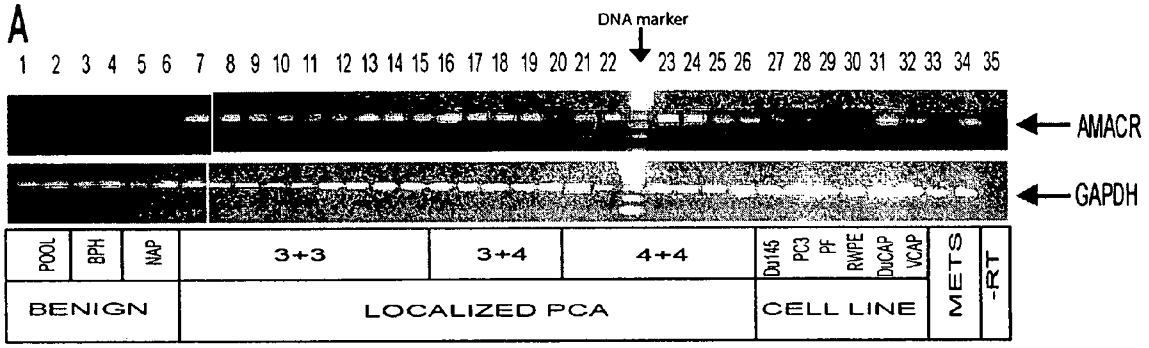
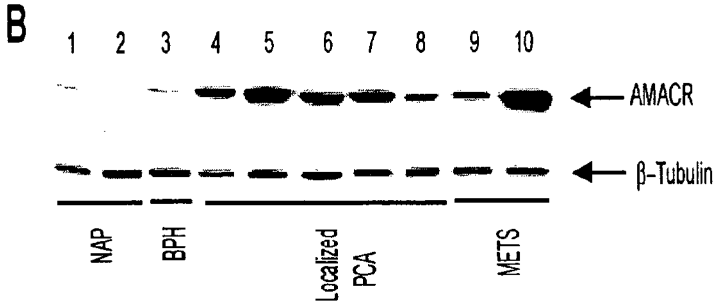

AMACR IN PCA CELL LINES

AMACR IN PCA SERA

Immunoblot Analysis for AMACR in Prostate Cancer and Normal Sera

| Sample | PSA |
|---|---|
| 2-10 | Positive |
| 61-65 | Negative |

IMMUNOBLOT ANALYSIS OF URINE SAMPLES FOR AMACR

U1-U10 : FEMALES WITH BLADDER CANCER
U11-U20 : MALES WITH BLADDER CANCER AND INC PROSTATE

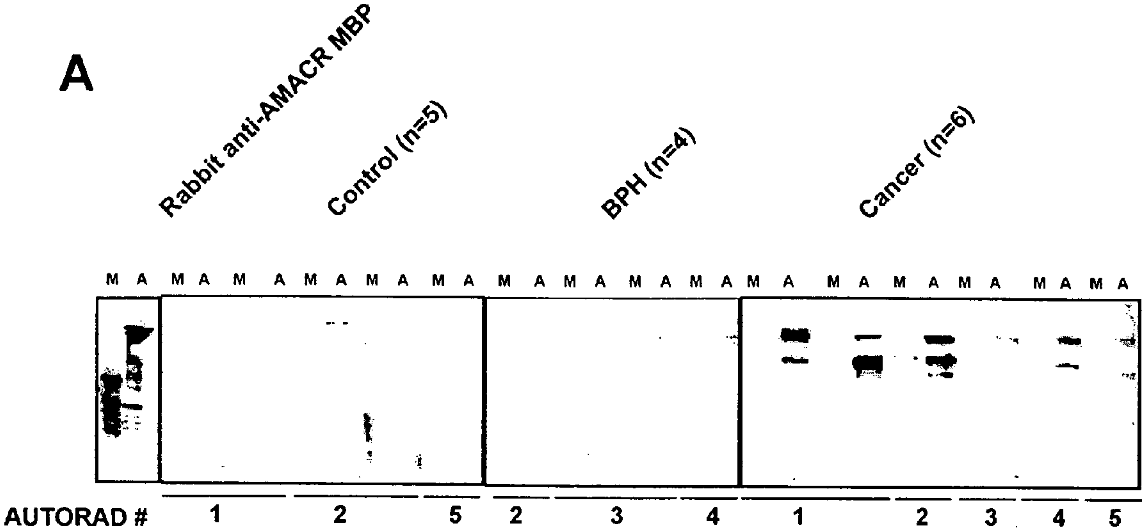
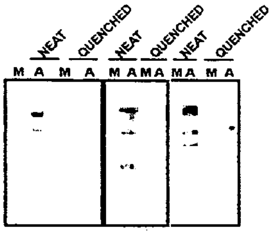
Figure 29

Figure 31
a
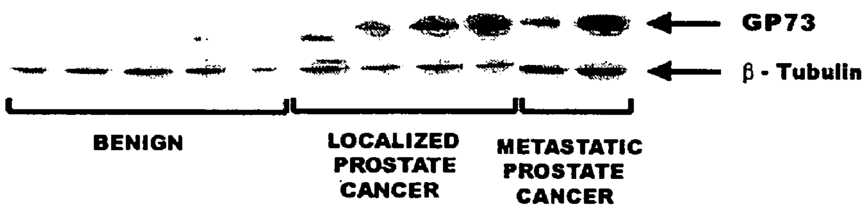
b
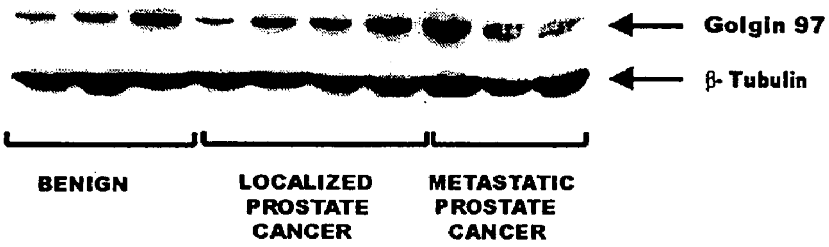

SEQUENCE LISTING

```
<160> NUMBER OF SEQ ID NOS: 123

<210> SEQ ID NO 1
<211> LENGTH: 1783
```

-continued

<212> TYPE: DNA
<213> ORGANISM: Homo sapiens

<400> SEQUENCE: 1

```
tcgagcccgc tttccaggga ccctacctga gggcccacag gtgaggcagc ctggcctagc     60

aggccccacg ccaccgcctc tgcctccagg ccgcccgctg ctgcggggcc accatgctcc    120

tgcccaggcc tggagactga cccgaccccg gcactacctc gaggctccgc ccccacctgc    180

tggaccccag ggtcccaccc tggcccagga ggtcagccag ggaatcatta acaagaggca    240

gtgacatggc gcagaaggag ggtggccgga ctgtgccatg ctgctccaga cccaaggtgg    300

cagctctcac tgcggggacc ctgctacttc tgacagccat cggggcggca tcctgggcca    360

ttgtggctgt tctcctcagg agtgaccagg agccgctgta cccagtgcag gtcagctctg    420

cggacgctcg gctcatggtc tttgacaaga cggaagggac gtggcggctg ctgtgctcct    480

cgcgctccaa cgccagggta gccggactca gctgcgagga gatgggcttc ctcagggcac    540

tgacccactc cgagctggac gtgcgaacgg cgggcgccaa tggcacgtcg ggcttcttct    600

gtgtggacga ggggaggctg ccccacaccc agaggctgct ggaggtcatc tccgtgtgtg    660

attgccccag aggccgtttc ttggccgcca tctgccaaga ctgtggccgc aggaagctgc    720

ccgtggaccg catcgtggga ggccgggaca ccagcttggg ccggtggccg tggcaagtca    780

gccttcgcta tgatggagca cacctctgtg gggatccct gctctccggg gactgggtgc     840

tgacagccgc ccactgcttc ccggagcgga accgggtcct gtcccgatgg cgagtgtttg    900

ccggtgccgt ggcccaggcc tctccccacg gtctgcagct gggggtgcag gctgtggtct    960

accacggggg ctatcttccc tttcgggacc ccaacagcga ggagaacagc aacgatattg   1020

ccctggtcca cctctccagt cccctgcccc tcacagaata catccagcct gtgtgcctcc   1080

cagctgccgg ccaggccctg gtggatggca agatctgtac cgtgacgggc tggggcaaca   1140

cgcagtacta tggccaacag gccggggtac tccaggaggc tcgagtcccc ataatcagca   1200

atgatgtctg caatggcgct gacttctatg gaaaccagat caagcccaag atgttctgtg   1260

ctggctaccc cgagggtggc attgatgcct gccagggcga cagcggtggt ccctttgtgt   1320

gtgaggacag catctctcgg acgccacgtt ggcggctgtg tggcattgtg agttggggca   1380

ctggctgtgc cctggcccag aagccaggcg tctacaccaa agtcagtgac ttccgggagt   1440

ggatcttcca ggccataaag actcactccg aagccagcgg catggtgacc cagctctgac   1500

cggtggcttc tcgctgcgca gcctccaggg cccgaggtga tcccggtggt gggatccacg   1560

ctgggccgag gatgggacgt tttcttcttt gggcccggtc cacaggtcca aggacaccct   1620

ccctccaggg tcctctcttc cacagtggcg ggcccactca gccccgagac cacccaacct   1680

caccctcctg acccccatgt aaatattgtt ctgctgtctg ggactcctgt ctaggtgccc   1740

ctgatgatgg gatgctcttt aaataataaa gatggttttg att                     1783
```

<210> SEQ ID NO 2
<211> LENGTH: 2623
<212> TYPE: DNA
<213> ORGANISM: Homo sapiens

<400> SEQUENCE: 2

```
gaggaggccc gagaggagtc ggtggcagcg gcggcggcgg gaccggcagc agcagcagca     60

gcagcagcag caaccactag cctcctgccc cgcggcgttg cgacgagccc cacgagccgc    120

tcaccccgcc gttctcagcg ctgcccgacc ccgctggcgc gcctcccgcc gcagtcccgg    180
```

-continued

```
cagcgcctca gttgtcctcc gactcgccct cggccttcgc gcagcgcagc acagccgcac    240
gcaccgcagc acagcacagc acagcccagg catagcttcg gcacagcccc ggctccggct    300
cctgcggcag ctcctctggc acgtccctgc gccgacattc tggaggttgg atgctcttgt    360
ccaaaatcaa ctcgcttgcc cacctgcgcg ccgcgccctg caacgacctg cacgccacca    420
agctggcgcc cggcaaggag aaggagcccc tggagtcgca gtaccaggtg ggcccgctac    480
tgggcagcgg cggcttcggc tcggtctact caggcatccg cgtctccgac aacttgccgg    540
tggccatcaa acacgtggag aaggaccgga tttccgactg ggagagagctg cctaatggca    600
ctcgagtgcc catggaagtg gtcctgctga agaaggtgag ctcgggtttc tccggcgtca    660
ttaggctcct ggactggttc gagaggcccg acagtttcgt cctgatcctg gagaggcccg    720
agccggtgca agatctcttc gacttcatca cggaaagggg agccctgcaa gaggagctgg    780
cccgcagctt cttctggcag gtgctggagg ccgtgcggca ctgccacaac tgcggggtgc    840
tacaccgcga catcaaggac gaaaacatcc ttatcgacct caatcgcggc gagctcaagc    900
tcatcgactt cgggtcgggg gcgctgctca aggacaccgt ctacacggac ttcgatggga    960
cccgagtgta tagccctcca gagtggatcc gctaccatcg ctaccatggc aggtcggcgg   1020
cagtctggtc cctggggatc ctgctgtatg atatggtgtg tggagatatt cctttcgagc   1080
atgacgaaga gatcatcagg ggccaggttt tcttcaggca gagggtctct tcagaatgtc   1140
agcatctcat tagatggtgc ttggccctga gaccatcaga taggccaacc ttcgaagaaa   1200
tccagaacca tccatggatg caagatgttc tcctgcccca ggaaactgct gagatccacc   1260
tccacagcct gtcgccgggg cccagcaaat agcagccttt ctggcaggtc ctcccctctc   1320
ttgtcagatg cccgagggag gggaagcttc tgtctccagc ttcccgagta ccagtgacac   1380
gtctcgccaa gcaggacagt gcttgataca ggaacaacat ttacaactca ttccagatcc   1440
caggcccctg gaggctgcct cccaacagtg gggaagagtg actctccagg ggtcctaggc   1500
ctcaactcct cccatagata ctctcttctt ctcataggtg tccagcattg ctggactctg   1560
aaatatcccg gggggtgggg gtgggggtgg gcagaaccct gccaatggaa ctctttcttc   1620
atcatgagtt ctgctgaatg ccgcgatggg tcaggtaggg gggaaacagg ttgggatggg   1680
ataggactag cacattttaa gtccctgtca cctcttccga ctctttctga gtgccttctg   1740
tggggactcc ggctgtgctg ggagaaatac ttgaacttgc ctcttttacc tgctgcttct   1800
ccaaaaatct gcctgggttt tgttccctat ttttctctcc tgtcctccct caccccctcc   1860
ttcatatgaa aggtgccatg gaagaggcta cagggccaaa cgctgagcca cctgcccttt   1920
tttctgcctc ctttagtaaa actccgagtg aactggtctt ccttttttggt ttttacttaa   1980
ctgtttcaaa gccaagacct cacacacaca aaaaaatgca caaaccaagc aatcaacaga   2040
aaagctgtaa atgtgtgtac agttggcatg gtagtataca aaaagattgt agtggatcta   2100
atttttaaga aattttgcct ttaagttatt ttacctgttt ttgtttcttg ttttgaaaga   2160
tgcgcattct aacctggagg tcaatgttat gtatttattt atttatttat ttggttccct   2220
tcctattcca agcttccata gctgctgccc tagttttctt tcctcctttc ctcctctgac   2280
ttggggacct tttgggggag ggctgcgacg cttgctctgt ttgtggggtg acgggactca   2340
ggcgggacag tgctgcagct ccctggcttc tgtggggccc ctcacctact tacccaggtg   2400
ggtcccggct ctgtgggtga tgggaggggc cattgctgac tgtgtatata ggataattat   2460
gaaacacagt tctggatggt gtgccttcca gatcctctct ggggctgtgt tttgagcagc   2520
aggtagcctg ctggttttat ctgagtgaaa tactgtacag ggaataaaa gagatcttat   2580
```

-continued tttttttta tacttgcgtt tggaataaaa accctttggc ttt 2623

<210> SEQ ID NO 3
<211> LENGTH: 2226
<212> TYPE: DNA
<213> ORGANISM: Homo sapiens

<400> SEQUENCE: 3
gaacaatgaa gaaagcccca cagccactgt tgctgagcag ggagaggata ttacctccaa 60
aaaagacagg ggagtattaa agattgtcaa aagagtgggg aatggtgagg aaacgccgat 120
gattggagac aaagtttatg tccattacaa aggaaaattg tcaaatggaa agaagtttga 180
ttccagtcat gatagaaatg aaccatttgt ctttagtctt ggcaaaggcc aagtcatcaa 240
ggcatgggac attggggtgg ctaccatgaa gaaaggagag atatgccatt tactgtgcaa 300
accagaatat gcatatggct cggctggcag tctccctaaa attccctcga atgcaactct 360 ctttttgag attgagctcc ttgatttcaa aggagaggat ttatttgaag atggaggcat 420
tatccggaga accaaacgga aaggagaggg atattcaaat ccaaacgaag gagcaacagt 480
agaaatccac ctggaaggcc gctgtggtgg aaggatgttt gactgcagag atgtggcatt 540
cactgtgggc gaaggagaag accacgacat tccaattgga attgacaaag ctctggagaa 600
aatgcagcgg gaagaacaat gtattttata tcttggacca agatatggtt ttggagaggc 660
agggaagcct aaatttggca ttgaacctaa tgctgagctt atatatgaag ttacacttaa 720
gagcttcgaa aaggccaaag aatcctggga gatggatacc aaagaaaaat tggagcaggc 780
tgccattgtc aaagagaagg gaaccgtata cttcaaggga ggcaaataca tgcaggcggt 840
gattcagtat gggaagatag tgtcctggtt agagatggaa tatggtttat cagaaaagga 900
atcgaaagct tctgaatcat ttctccttgc tgcctttctg aacctggcca tgtgctacct 960
gaagcttaga gaatacacca aagctgttga atgctgtgac aaggcccttg gactggacag 1020
tgccaatgag aaaggcttgt ataggagggg tgaagcccag ctgctcatga acgagtttga 1080
gtcagccaag ggtgactttg agaaagtgct ggaagtaaac ccccagaata aggctgcaag 1140
actgcagatc tccatgtgcc agaaaaaggc caaggagcac aacgagcggg accgcaggat 1200
atacgccaac atgttcaaga agtttgcaga gcaggatgcc aaggaagagg ccaataaagc 1260
aatgggcaag aagacttcag aaggggtcac taatgaaaaa ggaacagaca gtcaagcaat 1320
ggaagaagag aaacctgagg gccacgtatg acgccacgcc aaggagggaa gagtcccagt 1380
gaactcggcc cctcctcaat gggctttccc ccaactcagg acagaacagt gtttaatgta 1440
aagtttgtta tagtctatgt gattctggaa gcaaatggca aaaccagtag cttcccaaaa 1500
acagcccccc tgctgctgcc cggagggttc actgaggggt ggcacgggac cactccaggt 1560
ggaacaaaca gaaatgactg tggtgtggag ggagtgagcc agcagcttaa gtccagctca 1620
tttcagtttc tatcaacctt caagtatcca attcagggtc cctggagatc atcctaacaa 1680
tgtggggctg ttaggtttta cctttgaact ttcatagcac tgcagaaacc tttaaaaaaa 1740
aaatgcttca tgaatttctc ctttcctaca gttgggtagg gtaggggaag gaggataagc 1800
ttttgttttt taaatgactg aagtgctata aatgtagtct gttgcatttt taaccaacag 1860
aacccacagt agaggggtct catgtctccc cagttccaca gcagtgtcac agacgtgaaa 1920
gccagaacct cagaggccac ttgcttgctg acttagcctc ctcccaaagt ccccctcctc 1980
agccagcctc cttgtgagag tggctttcta ccacacacag cctgtccctg ggggagtaat 2040

-continued

```
tctgtcattc ctaaaacacc cttcagcaat gataatgagc agatgagagt ttctggatta   2100

gcttttccta ttttcgatga agttctgaga tactgaaatg tgaaaagagc aatcagaatt   2160

gtgctttttc tcccctcctc tattcctttt agggaataat attcaataca cagtacttcc   2220

tcccag                                                              2226
```

<210> SEQ ID NO 4
<211> LENGTH: 7515
<212> TYPE: DNA
<213> ORGANISM: Homo sapiens

<400> SEQUENCE: 4

```
atggaggagg tggtgattgc cggcatgttc gggaagctgc cagagtcgga gaacttgcag     60

gagttctggg acaacctcat cggcggtgtg gacatggtca cggacgatga ccgtcgctgg    120

aaggctgggc tctacggcct gccccggcgg tccggcaagc tgaaggacct gtctaggttt    180

gatgcctcct tcttcggagt ccaccccaag caggcacaca cgatggaccc tcagctgcgg    240

ctgctgctgg aagctaccta tgaagccatc gtggacggag gcatcaaccc agattcactc    300

cgaggaacac acactggcgt ctgggtgggc gtgagcggct ctgagacctc ggaggccctg    360

agccgagacc ccgagacact cgtgggctac agcatggtgg gctgccagcg agcgatgatg    420

gccaaccggc tctccttctt cttcgacttc agagggccca gcatcgcact ggacacagcc    480

tgctcctcca gcctgatggc cctgcagaac gcctaccagg ccatccacag cgggcagtgc    540

cctgccgcca tcgtgggggg catcaacgtc ctgctgaagc ccaacacctc cgtgcagttc    600

ttgaggctgg ggatgctcag ccccgagggc acctgcaagg ccttcgacac agcggggaat    660

gggtactgcc gctcggaggg tgtggtggct gtcctgctga ccaagaagtc cctggcccgg    720

aaggtctaca ccaccatcct gaacaaaggc accaatacag atggcttcaa ggagcaaggc    780

gtgaccttcc ctcaggatat ccaggagcag cctatccgct cgttgtacca gtcggccgga    840

gtggcccctg agtcatttga atacatcgaa gcccacggac caggcaccaa ggtgggcgac    900

cccaggagc gtaatggcat cacccgagcc ctgtgcgcca cccgccagga gccgctgctc    960

atcggctcca ccaagtccaa catggggcac ccggagccag cctcggggct cgacgccctg   1020

gccaaggtgc tgctgtccct ggagcacggg ctctgggccc ccaacctgca cttccatagc   1080

cccaaccctg agatcccagc gctgttggat gggcggctgc aggtggtgga ccagcccctg   1140

cccgtccgtg gcggcaacgt gggcatcaac tcctttggct tcgggggctc caacatgcac   1200

atcatcctga ggcccaacac gcagtccgcc cccgcacccg ccccacatgc caccctgccc   1260

cgtctgctgc gggccagcgg acgcacccct gaggccgtgc agaagctgct ggagcagggc   1320

ctccggcaca gccagggcct ggctttcctg agcatgctga acgacatcgc ggctgtcccc   1380

gccaccgcca tgcccttccg tggctacgct gtgctgggtg gtgagacgcg gtggcccaga   1440

gtgcagcagg tgcccgctgg cgagcgcccg ctctggttca tctgctctgg gatgggcaca   1500

cagtggcgtg gaatggggct gagccttatg cgcctggacc gcttccgaga ttccatccta   1560

cgctccgatg aggctgtgaa ccgattcggc ctgaaggtgt cacagctgct gctgagcaca   1620

gacgagagca cctttgatga catcgtccat tcgtttgtga gcctgactgc catccagata   1680

ggcctcatag acctgctgag ctgcatggga cctgaggcag atggcatcgt cggccactcc   1740

ctgggggagt ggctgtcggt acgcgacggc tgcctgtccc aggaggaggc cgtcctcgct   1800

gcctactgga ggggacagtg catcaaagaa gccccacttc ccgccggcgc catggcagcc   1860

gtgggcttgt cctgggagga gtgtaaacag cgctgccccc ctgcggtggt gcccgcctgc   1920
```

-continued

```
cacaactcca aggacacagt caccatctcg ggacctcagg ccccggtgtt tgagttcgtg   1980
gagcagctga ggaaggaggg tgtgtttgcc aaggaggtgc ggaccggcgg tatggccttc   2040
cactcctact tcatggaggc catcgcaccc ccactgctgc aggagctcaa gaaggtgatc   2100
cgggagccga agccacgttc agcccgctgg ctcagcacct ctatccccga ggcccagtgg   2160
cacagcagcc tggcacgcac gtcttccgcc gagtacaatg tcaacaacct ggtgagccct   2220
gtgctgttcc aggaggccct gtggcacgtg cctgagcacg cggtggtgct ggagatcgcc   2280
ccgaccccgt gccctcaggc tgtcctgaag cgggtccgta agccgagctg caccatcatc   2340
ccccgtatga agaaggatca cagggacaac ctggagttct tcctggccgg catcggcagg   2400
ctgcacctct caggcatcga cgccaacccc aatgccttgt tcccacctgt ggagtcccca   2460
gctccccgag gaactcccct catctcccca ctcatcaagt gggaccacag cctggcctgg   2520
gacgcgccgg ccgccgagga cttccccaac ggttcaggtt ccccctcagc caccatctac   2580
acatgcacac caagctccga gtctcctgac cgctacctgg tggaccacac catcgacggt   2640
cgcgtcctct tccccgccac tggctacctg agcatagtgt ggaagacgct ggcccgcgcc   2700
tgggctgggc tcgagcagct gcctgtggtg tttgaggatg tggtgcagca ccaggccacc   2760
atcctgccca agactgggac agtgtccttg gaggtacggc tcctggaggc caccggtgcc   2820
ttcgaggtgt cagagaacgg caacctggta gtgagtggga aggtgtacca gtgggatgac   2880
cctgacccca ggctcttcga ccacccggaa agtccccacc ccaattcccc acggagtccc   2940
ctcttcctgg cccaggcaga agtttacaag gagctgcgtc tgcgtggcta cgactacggc   3000
cctcatttcc agggcatcct ggaggccagc ctggaaggtg actcggggag gctgctgtgg   3060
aaggataact gggtgagctt catggacacc atgctgcaga tgtccatcct gggctcggcc   3120
aagcacggcc tgtacctacc cacccgtgtc accgccatcc acatcgaccc tgccacccac   3180
aggcagaagc tgtacacact gcaggacaag gcccaagtgg ctgacgtggt ggtgagcagg   3240
tggccgaggg tcacagtggc gggaggcgtc cacatctccg ggctccacac tgagtcggcc   3300
ccgcggcggc acgaggagca gcaggtgccc atcctggaga agttttgctt cactccccac   3360
acggaggagg ggtgcctgtc tgagcacgct gccctcgagg aggagctgca actgtgcaag   3420
gggctggtcg aggcactcga gaccaaggtg acccagcagg ggctgaagat ggtggtgccg   3480
gactggacgg ggcccagatc cccccgggac ccctcacagc aggaactgcc ccggctgttg   3540
tcggctgcct gcaggcttca gctcaacggg aacctgcagc tggagctggc gcaggtgctg   3600
gcccaggaga ggcccaagct gccagaggac cctctgctca gcggcctcct ggactccccg   3660
gcactcaagg cctgcctgga cactgccgtg gagaacatgc ccagcctgaa gatgaaggtg   3720
gtggaggtgc tggccggcca cggtcacctg tattcccgca tcccaggcct gctcagcccc   3780
catcccctgc tgcagctgag ctacacggcc accgaccgcc acccccaggc cctggaggct   3840
gcccaggccg agctgcagca gcacgacgtt gcccagggcc agtgggatcc cgcagaccct   3900
gcccccagcg ccctgggcag cgcggacctc ctggtgtgca actgtgctgt ggctgccctc   3960
ggggacccgg cctcagctct cagcaacatg gtggctgccc tgagagaagg gggctttctg   4020
ctcctgcaca cactgctccg gggggcaccct cgggacatcg tggccttcct cacctccact   4080
gagccgcagt atggccaggg catcctgagc caggacgcgt gggagagcct cttctccagg   4140
gtgtcgctgc gcctggtggg cctgaagaag tccttctacg gcgccacgct cttcctgtgc   4200
cgccggccca ccccgcagga cagccccatc ttcctgccgg tggacgatac cagcttccgc   4260
```

-continued

```
tgggtggagt ctctgaaggg catcctggct gacgaagact cttcccggcc tgtgtggctg   4320
aaggccatca actgtgccac ctcgggcgtg gtgggcttgg tgaactgtct ccgccgagag   4380
cccggcggaa ccgtccggtg tgtgctgctc tccaacctca gcagcacctc ccacgtcccg   4440
gaggtggacc cgggctccgc agaactgcag aaggtgttgc agggagacct ggtgatgaac   4500
gtctaccgcg acggggcctg gggggttttc cgccacttcc tgctggagga caagcctgag   4560
gagccgacgg cacatgcctt tgtgagcacc ctcacccggg gggacctgtc ctccatccgc   4620
tgggtctgct cctcgctgcg ccatgcccag cccacctgcc ctggcgccca gctctgcacg   4680
gtctactacg cctccctcaa cttccgcgac atcatgctgg ccactggcaa gctgtcccct   4740
gatgccatcc cagggaagtg gacctcccag gacagcctgc taggtatgga gttctcgggc   4800
cgagacgcca gcggcaagcg tgtgatggga ctggtgcctg ccaagggcct ggccacctct   4860
gtcctgctgt caccggactt cctctgggat gtgccttcca actggacgct ggaggaggcg   4920
gcctcggtgc ctgtcgtcta cagcacggcc tactacgcgc tggtggtgcg tgggcgggtg   4980
cgccccgggg agacgctgct catccactcg ggctcgggcg gcgtgggcca ggccgccatc   5040
gccatcgccc tcagtctggg ctgccgcgtc ttcaccaccg tggggtcggc tgagaagcgg   5100
gcgtacctcc aggccaggtt cccccagctc gacagcacca gcttcgccaa ctcccgggac   5160
acatccttcg agcagcatgt gctgtggcac acgggcggga agggcgttga cctggtcttg   5220
aactccttgg cggaagagaa gctgcaggcc agcgtgaggt gcttcggtac gcacggtcgc   5280
ttcctggaaa ttggcaaatt cgacctttct cagaaccacc cgctcggcat ggctatcttc   5340
ctgaagaacg tgacattcca cggggtccta ctggatgcgt tcttcaacga gagcagtgct   5400
gactggcggg aggtgtgggc gcttgtcgag gccgccatcc gggatggggt ggtacggccc   5460
ctcaagtgca cggtgttcca tggggcccag gtggaggacg ccttccgcta catggcccaa   5520
gggaagcaca ttggcaaagt cgtcgtgcag gtgcttgcgg aggagccggc agtgctgaag   5580
ggggccaaac ccaagctgat gtcggccatc tccaagacct tctgcccggc ccacaagagc   5640
tacatcatcg ctggtggtct gggtggcttc ggcctggagt tggcgcagtg gctgatacag   5700
cgtggggtgc agaagctcgt gttgacttct cgctccggga tccggacagg ctaccaggcc   5760
aagcaggtcc gccggtggag gcgccagggg ctacaggtgc aggtgtccac cagcaacatc   5820
agctcactgg agggggcccg gggcctcatt gccgaggcgg cgcagcttgg gcccgtgggg   5880
ggcgtcttca acctggccgt ggtcttgaga gatggcttgc tggagaacca gaccccagag   5940
ttcttccagg acgtctgcaa gcccaagtac agcggcaccc tgaacctgga cagggtgacc   6000
cgagaggcgt gccctgagct ggactacttt gtggtcttct cctctgtgag ctgcgggcgt   6060
ggcaatgcgg gacagagcaa ctacggcttt gccaattccg ccatggagcg tatctgtgag   6120
aaacgccggc acgaaggcct cccaggcctg gccgtgcagt ggggcgccat cggcaccgtg   6180
ggcattttgg tggagacgat gagcaccaac gacacgatcg tcagtggcac gctgcccacg   6240
cgcattggcg tccttggcct ggaggtgctg gacctcttcc tgaaccagcc ccacatggtc   6300
ctgagcagct ttgtgctggc tgagaaggct gcggcctata gggacaggga cagccagcgg   6360
gacctggtgg aggccgtggc acacatcctg ggcatccgcg acttggctgc tgtcaacctg   6420
ggcggctcac tggcggacct gggcctggac tcgctcatga gcgcgccggt gcgccagacg   6480
ctggagcgtg agctcaacct ggtgctgtcc gtgcgcgagg tgcggcaact cacgctccgg   6540
aaactgcagg agctgtcctc aaaggcggat gaagccagcg agctggcatg ccccacgccc   6600
aaggaggatg gtctggccca gcagcagact cagctgaacc tgcgctccct gctggtgaaa   6660
```

-continued

```
ccggagggcc ccaccctgat gcggctcaac tccgtgcaga gctcggagcg gcccctgttc   6720
ctggtgcacc caatcgaggc taccaccgtg ttccacagcc tcggtcccgg tctcagcatc   6780
cccacctatg gcctgcagtg caccccggct gcgccccttg acagcatcca cagcctggct   6840
gcctactaca tcgactgcat caggcaggtg cagcccgagg gcccctaccg cgtggccggc   6900
tactcctacg gggcctgcgt ggcctttgaa atgtgctccc agctgcaggc ccagcagagc   6960
ccagcccccca cccacaacag cctcttcctg ttcgacggct cgcccaccta cgtactggcc   7020
tacacccaga gctaccgggc aaagctgacc ccaggctgta aggctgaggc tgagacggag   7080
gccatatgct tcttcgtgca gcagttcacg gacatggagc acaacagggt gctggaggcg   7140
ctgctgccgc tgaagggcct agaggagcgt gtggcagccg ccgtggacct gatcatcaag   7200
agccaccagg gcctggaccg ccaggagctg agctttgcgg cccggtcctt ctactacagg   7260
ctgcgtgccg ctgaccagta tacacccaag gccaagtaca gtggcaacgt gatgctactg   7320
cgggccaaga cgggtggccg ctacggcgag gacctgggcg cggactacaa cctctcccag   7380
gtatgcgacg ggaaagtatc cgtccatatc atcgagggtg accaccgcac gctgctggag   7440
ggcagcggcc tggagtccat catcagcatc atccacagct ccctggctga gccacgtgtg   7500
agtcgggagg gctag                                                     7515
```

<210> SEQ ID NO 5
<211> LENGTH: 2653
<212> TYPE: DNA
<213> ORGANISM: Homo sapiens

<400> SEQUENCE: 5

```
ctcaaaaggg gccggatttc cttctcctgg aggcagatgt tgcctctctc tctcgctcgg     60
attggttcag tgcactctag aaacactgct gtggtggaga aactggaccc caggtctgga    120
gcgaattcca gcctgcaggg ctgataagcg aggcattagt gagattgaga gagactttac    180
cccgccgtgg tggttggagg gcgcgcagta gagcagcagc acaggcgcgg gtcccgggag    240
gccggctctg ctcgcgccga gatgtggaat ctccttcacg aaaccgactc ggctgtggcc    300
accgcgcgcc gcccgcgctg gctgtgcgct ggggcgctgg tgctggcggg tggcttcttt    360
ctcctcggct tcctcttcgg gtggtttata aaatcctcca atgaagctac taacattact    420
ccaaagcata atatgaaagc atttttggat gaattgaaag ctgagaacat caagaagttc    480
ttatataatt ttacacagat accacattta gcaggaacag aacaaaactt tcagcttgca    540
aagcaaattc aatcccagtg gaaagaattt ggcctggatt ctgttgagct agcacattat    600
gatgtcctgt tgtcctaccc aaataagact catcccaact acatctcaat aattaatgaa    660
gatggaaatg agattttcaa cacatcatta tttgaaccac ctcctccagg atatgaaaat    720
gtttcggata ttgtaccacc tttcagtgct ttctctcctc aaggaatgcc agagggcgat    780
ctagtgtatg ttaactatgc acgaactgaa gacttcttta aattggaacg ggacatgaaa    840
atcaattgct ctgggaaaat tgtaattgcc agatatggga aagttttcag aggaaataag    900
gttaaaaatg cccagctggc aggggccaaa ggagtcattc tctactccga ccctgctgac    960
tactttgctc ctggggtgaa gtcctatcca gatggttgga atcttcctgg aggtggtgtc   1020
cagcgtggaa atatcctaaa tctgaatggt gcaggagacc ctctcacacc aggttaccca   1080
gcaaatgaat atgcttatag gcgtggaatt gcagaggctg ttggtcttcc aagtattcct   1140
gttcatccaa ttggatacta tgatgcacag aagctcctag aaaaaatggg tggctcagca   1200
```

-continued

```
ccaccagata gcagctggag aggaagtctc aaagtgccct acaatgttgg acctggcttt   1260

actggaaact tttctacaca aaaagtcaag atgcacatcc actctaccaa tgaagtgaca   1320

agaatttaca atgtgatagg tactctcaga ggagcagtgg aaccagacag atatgtcatt   1380

ctgggaggtc accgggactc atgggtgttt ggtggtattg accctcagag tggagcagct   1440

gttgttcatg aaattgtgag gagctttgga acactgaaaa aggaagggtg gagacctaga   1500

agaacaattt tgtttgcaag ctgggatgca gaagaatttg gtcttcttgg ttctactgag   1560

tgggcagagg agaattcaag actccttcaa gagcgtggcg tggcttatat taatgctgac   1620

tcatctatag aaggaaacta cactctgaga gttgattgta caccgctgat gtacagcttg   1680

gtacacaacc taacaaaaga gctgaaaagc cctgatgaag gctttgaagg caaatctctt   1740

tatgaaagtt ggactaaaaa aagtccttcc ccagagttca gtggcatgcc caggataagc   1800

aaattgggat ctggaaatga ttttgaggtg ttcttccaac gacttggaat tgcttcaggc   1860

agagcacggt atactaaaaa ttgggaaaca aacaaattca gcggctatcc actgtatcac   1920

agtgtctatg aaacatatga gttggtggaa aagttttatg atccaatgtt taaatatcac   1980

ctcactgtgg cccaggttcg aggagggatg gtgtttgagc tagccaattc catagtgctc   2040

ccttttgatt gtcgagatta tgctgtagtt ttaagaaagt atgctgacaa aatctacagt   2100

atttctatga aacatccaca ggaaatgaag acatacagtg tatcatttga ttcacttttt   2160

tctgcagtaa agaattttac agaaattgct tccaagttca gtgagagact ccaggacttt   2220

gacaaaagca acccaatagt attaagaatg atgaatgatc aactcatgtt tctggaaaga   2280

gcatttattg atccattagg gttaccagac aggccttttt ataggcatgt catctatgct   2340

ccaagcagcc acaacaagta tgcaggggag tcattcccag gaatttatga tgctctgttt   2400

gatattgaaa gcaaagtgga cccttccaag gcctggggag aagtgaagag acagatttat   2460

gttgcagcct tcacagtgca ggcagctgca gagactttga gtgaagtagc ctaagaggat   2520

tctttagaga atccgtattg aatttgtgtg gtatgtcact cagaaagaat cgtaatgggt   2580

atattgataa attttaaaat tggtatattt gaaataaagt tgaatattat atataaaaaa   2640

aaaaaaaaaa aaa                                                      2653
```

<210> SEQ ID NO 6
<211> LENGTH: 1750
<212> TYPE: DNA
<213> ORGANISM: Homo sapiens

<400> SEQUENCE: 6

```
cctcactgac tataaaagaa tagagaagga agggcttcag tgaccggctg cctggctgac     60

ttacagcagt cagactctga caggatcatg gctatgatgg aggtccaggg gggacccagc    120

ctgggacaga cctgcgtgct gatcgtgatc ttcacagtgc tcctgcagtc tctctgtgtg    180

gctgtaactt acgtgtactt taccaacgag ctgaagcaga tgcaggacaa gtactccaaa    240

agtggcattg cttgtttctt aaaagaagat gacagttatt gggaccccaa tgacgaagag    300

agtatgaaca gcccctgctg gcaagtcaag tggcaactcc gtcagctcgt tagaaagatg    360

attttgagaa cctctgagga aaccatttct acagttcaag aaaagcaaca aaatatttct    420

cccctagtga gagaaagagg tcctcagaga gtagcagctc acataactgg gaccagagga    480

agaagcaaca cattgtcttc tccaaactcc aagaatgaaa aggctctggg ccgcaaaata    540

aactcctggg aatcatcaag gagtgggcat tcattcctga gcaacttgca cttgaggaat    600

ggtgaactgg tcatccatga aaaagggttt tactacatct attcccaaac atactttcga    660
```

-continued

```
tttcaggagg aaataaaaga aaacacaaag aacgacaaac aaatggtcca atatatttac    720

aaatacacaa gttatcctga ccctatattg ttgatgaaaa gtgctagaaa tagttgttgg    780

tctaaagatg cagaatatgg actctattcc atctatcaag gggaatatt tgagcttaag    840

gaaaatgaca gaatttttgt ttctgtaaca aatgagcact tgatagacat ggaccatgaa    900

gccagttttt ttggggcctt tttagttggc taactgacct ggaaagaaaa agcaataacc    960

tcaaagtgac tattcagttt tcaggatgat acactatgaa gatgtttcaa aaaatctgac   1020

caaaacaaac aaacagaaaa cagaaaacaa aaaaacctct atgcaatctg agtagagcag   1080

ccacaaccaa aaaattctac aacacacact gttctgaaag tgactcactt atcccaagag   1140

aatgaaattg ctgaaagatc tttcaggact ctacctcata tcagtttgct agcagaaatc   1200

tagaagactg tcagcttcca aacattaatg caatggttaa catcttctgt ctttataatc   1260

tactccttgt aaagactgta gaagaaagag caacaatcca tctctcaagt agtgtatcac   1320

agtagtagcc tccaggtttc cttaagggac aacatcctta agtcaaaaga gagaagaggc   1380

accactaaaa gatcgcagtt tgcctggtgc agtggctcac acctgtaatc ccaacatttt   1440

gggaacccaa ggtgggtaga tcacgagatc aagagatcaa gaccatagtg accaacatag   1500

tgaaacccca tctctactga aagtacaaaa attagctggg tgtgttggca catgcctgta   1560

gtcccagcta cttgagaggc tgaggcaaga gaattgtttg aacccgggag gcagaggttg   1620

cagtgtggtg agatcatgcc actacactcc agcctggcga cagagcgaga cttggtttca   1680

aaaaaaaaaa aaaaaaaaac ttcagtaagt acgtgttatt tttttcaata aaattctatt   1740

acagtatgtc                                                          1750
```

<210> SEQ ID NO 7
<211> LENGTH: 6597
<212> TYPE: DNA
<213> ORGANISM: Homo sapiens

<400> SEQUENCE: 7

```
ggtcacatga ctccagtcta gctcgcattg cggctcccgc ccgggcgagt tctcgccccc     60

gcgcggccgt tgccgaggag acggcgcatg tcccgccgcg cgttgccccc tctgcagtac    120

ccccgcccct cttctcccac cacaatgaga tcctaagatg gcggtggctg cggcggttgg    180

cgctgcgtag ctgaggtcga aaaggcggcc actggggccg aggcagccag gaaacgtgtg    240

ggcctctctg ctgcggtctc cgagggccga ccgctgccgg cggcgggtcg tgggggctga    300

ctgtcgctct gcctttgaca ggagaggctg cttcttgtag aggaaacagc tttgaagtgt    360

ggagcgggaa aggagcagtt tctgagctgc aaaaactagt ttctaaacag agagttaatt    420

gttaaatcca gtatggccac aggaggaggt ccctttgaag atggcatgaa tgatcaggat    480

ttaccaaact ggagtaatga gaatgttgat gacaggctca acaatatgga ttggggtgcc    540

caacagaaga aagcaaatag atcatcagaa aagaataaga aaaagtttgg tgtagaaagt    600

gataaaagag taaccaatga tatttctccg gagtcgtcac caggagttgg aaggcgaaga    660

acaaagactc cacatacgtt ccccacacagt agatacatga gtcagatgtc tgtcccagag    720

caggcagaat tagagaaact gaaacagcgg ataaacttca gtgatttaga tcagagaagc    780

attggaagtg attcccaagg tagagcaaca gctgctaaca acaaacgtca gcttagtgaa    840

aaccgaaagc ccttcaactt tttgcctatg cagattaata ctaacaagag caaagatgca    900

tctacaagtc cccaaacag agaaacgatt ggatcagcac agtgtaaaga gttgtttgct    960
```

-continued

```
tctgctttaa gtaatgacct cttgcaaaac tgtcaggtgt ctgaagaaga tgggagggga   1020
gaacctgcaa tggagagcag ccagattgta agcaggcttg ttcaaattcg cgattatatt   1080
actaaagcta gttccatgcg ggaagatctt gtagagaaaa atgagagatc tgctaatgtt   1140
gagcgcctta ctcatctaat agatcacctt aaagaacaag agaagtcata tatgaaattt   1200
cttaaaaaaa tccttgccag agatcctcag caggagccta tggaagagat agaaaatttg   1260
aagaaacaac atgatttatt aaaaagaatg ttacaacagc aggagcaact aagagctcta   1320
cagggacggc aggctgcact tctagctctg caacataaag cagagcaagc tattgcagtg   1380
atggatgatt ctgttgttgc agaaactgca ggtagcttat ctggcgtcag tatcacatct   1440
gaactaaatg aagaattgaa tgacttaatt cagcgttttc ataatcagct tcgtgattct   1500
cagcctccag ctgttccaga caatagaaga caggcagaaa gtctttcatt aactagggag   1560
gtttcccaga gcaggaaacc atcagcttca gaacgtttac ctgatgagaa agtcgaactt   1620
tttagcaaaa tgagagtgct acaggaaaag aaacaaaaaa tggacaaatt gcttggagaa   1680
cttcatacac ttcgagatca gcatcttaac aattcatcat cctctccaca aaggagtgtc   1740
gatcagagaa gtacttcagc tccctctgct tctgtaggct tggcaccggt tgtcaatgga   1800
gaatccaata gcctcacatc atctgttcct tatcctactg cttctctagt atctcagaat   1860
gagagtgaaa acgaaggcca cctcaatcca tctgaaaaac tccagaagtt aaatgaagtt   1920
cgaaagagat tgaatgagct aagagaatta gttcattatt atgaacaaac gtcagacatg   1980
atgacagatg ctgtgaatga aaacaggaaa gatgaagaaa ctgaagagtc agaatatgat   2040
tctgagcatg aaaattccga gcctgttact aacattcgaa atccacaagt agcttccact   2100
tggaatgaag taaatagtca tagtaatgca cagtgtgttt ctaataatag agatgggcga   2160
acagttaatt ctaattgtga aattaacaac agatctgctg ccaacataag ggctctaaac   2220
gtgcctcctt ctttagattg tcgatataat agagaagggg aacaggagat tcatgttgca   2280
caaggtgaag atgatgagga ggaggaggaa gaagcagaag aggagggagt cagtggagct   2340
tcattatcta gtcacaggag cagtctggtt gatgagcatc cagaagatgc tgaatttgaa   2400
cagaagatca accgacttat ggctgcaaaa cagaaactta gacagttaca agatcttgtt   2460
gctatggtac aggatgatga tgcagctcaa ggagttatct ctgccagtgc atcaaatttg   2520
gatgatttct acccagcaga agaagacacc aagcaaaatt caaataacac tagaggaaat   2580
gccaataaaa cacagaaaga tactggagta aatgaaaagg caagagagaa attttatgag   2640
gctaaactac agcagcaaca gagagagcta aaacaattgc aggaagaaag aaagaaactg   2700
attgacattc aggagaaaat tcaagcattg caaacggcat gccctgactt acagctgtca   2760
gctgctagtg tgggtaactg tcccaccaaa aaatatatgc cagctgttac ttcaacccca   2820
actgttaatc aacacgagac cagtacaagc aaatctgttt ttgagcctga agattcttca   2880
atagtagata atgagttgtg gtcagaaatg agaagacatg aaatgttgag ggaggagctg   2940
cgacagagaa gaaagcagct tgaagctctg atggctgaac atcagaggag gcaaggtcta   3000
gctgaaactg catctccagt ggctgtgtca ttgagaagtg atggatctga gaacctatgt   3060
actcctcagc aaagtagaac agaaaaaacg atggcaactt ggggagggtc tacccagtgt   3120
gcactagatg aagaaggaga tgaagacggt tacctttctg aaggaattgt tcggacagat   3180
gaagaggagg aagaagagca agatgccagt tccaatgata acttttctgt gtgtccttct   3240
racagtgtga atcataactc ctacaatgga aaggaaacta aaaataggtg gaagaacaat   3300
tgccctttttt cggcagatga aaattatcgt cctttagcca agacaaggca acagaatatc   3360
```

-continued

```
agcatgcaac ggcaagaaaa ccttcgttgg gtgtcagagc tctcttacgt agaagagaaa   3420
gaacaatggc aagaacaaat caatcagcta aagaaacagc ttgattttag tgtcagtatt   3480
tgtcagactt tgatgcaaga ccagcagact ctatcttgtc tgctacaaac tcttctcacg   3540
ggtccttaca gtgttatgcc cagcaatgtt gcatctcctc aagtacactt cataatgcac   3600
cagttgaacc agtgctatac tcagctaaca tggcaacaga ataatgttca gaggttgaaa   3660
caaatgctaa atgaacttat gcgccagcaa aatcagcatc cagaaaaacc tggaggcaag   3720
gaaagaggca gtagtgcatc gcaccctcct tctcccagtt tattttgtcc tttcagcttt   3780
ccaacacagc ctgtaaatct cttcaatata cctggattta ctaacttttc atcatttgca   3840
ccaggtatga atttcagccc tttatttcct tctaattttg gagatttttc tcagaatatc   3900
tctacaccca gtgaacagca gcaaccctta gcccagaatt cttcaggaaa aacagaatat   3960
atggcttttc caaaaccttt tgaaagcagt tcctctattg gagcagagaa accaaggaat   4020
aaaaaactgc ctgaagagga ggtggaaagc agtaggacac catggttata tgaacaagaa   4080
ggtgaagtag agaaaccatt tatcaagact ggattttcag tgtctgtaga aaaatctaca   4140
agtagtaacc gcaaaaatca attagataca aacggaagaa gacgccagtt tgatgaagaa   4200
tcactggaaa gctttagcag tatgcctgat ccagtagatc caacaacagt gactaaaaca   4260
ttcaagacaa gaaaagcgtc tgcacaggcc agcctggcat ctaaagataa aactcccaag   4320
tcaaaaagta agaagaggaa ttctactcag ctgaaaagca gagttaaaaa catcaggtat   4380
gaaagtgcca gtatgtctag cacatgtgaa ccttgcaaaa gtaggaacag acattcagcc   4440
cagactgaag agcctgttca agcaaaagta ttcagcagaa agaatcatga gcaactggaa   4500
aaaataataa aatgtaatag gtctacagaa atatcttcag aaactgggag tgatttttcc   4560
atgtttgaag ctttgcgaga tactatttat tctgaagtag ctacattaat ttctcaaaat   4620
gaatctcgtc cacattttct tattgaactc ttccatgagc tgcagctact aaacacagac   4680
tacttgagac agagggcttt atatgcattg caggacatag tatccagaca tatttctgag   4740
agccatgaaa aaggagaaaa tgtaaagtca gtaaactctg gtacttggat agcatcaaac   4800
tcagaactta ctcctagtga gagccttgct actactgatg atgaaacttt tgagaagaac   4860
tttgaaagag aaacccataa aataagtgag caaaatgatg ctgataatgc tagtgtcctg   4920
tctgtatcat caaattttga gccttttgca acagatgatc taggtaacac cgtgattcac   4980
ttagatcaag cattagccag aatgagagaa tatgagcgta tgaagactga ggctgaaagt   5040
aactcaaata tgagatgcat ctgcaggatt attgaggatg gagatggtgc tggtgcaggt   5100
actacagtta ataatttaga agaaactccc gttattgaaa atcgtagttc acaacaacct   5160
gtaagtgaag tttctaccat cccatgtcct agaattgata ctcagcagct ggaccggcaa   5220
attaaagcaa ttatgaaaga agtcattcct tttttgaagg agcacatgga tgaagtatgc   5280
tcctcgcagc ttctaacttc agtaaggcgc atggttttga cccttaccca gcaaaatgat   5340
gagagcaaag agtttgtaaa gttctttcat aaacaacttg gaagtatatt acaggattca   5400
ctggcaaaat ttgctggcag aaaactgaaa gactgtggag aagatcttct tgtagagata   5460
tctgaagtgt tgttcaatga attggctttc tttaagctta tgcaagattt ggataataat   5520
agtataactg ttaaacagag atgcaaaagg aaaatagaag caactggagt gatacaatct   5580
tgtgccaaag agctaaaagg attcttgaag atcatggctc acctgctgga gagattgatg   5640
atgaagacaa agacaaggat gaaactgaaa cagttaagca gactcaaaca tctgaggtgt   5700
```

-continued

```
atgatggtcc caaaaatgta agatctgata tttctgatca agaggaagat gaagaaagtg   5760

aaggatgtcc agtgtctatt aatttgtcta aagctgaaac tcaggcttta actaattatg   5820

gaagtggaga agatgaaaat gaggatgaag aaatggaaga atttgaagaa ggccctgtgg   5880

atgtccagac ttccctccag gctaacactg aagctactga agaaaatgaa catgatgaac   5940

aggtcctaca acgtgacttt aaaaagacag cagaaagcaa aaatgtccca ttggaacgag   6000

aagccactag taaaaatgac caaaataact gtcctgtgaa accctgttac ctcaatatct   6060

tggaagatga gcaaccttta aatagtgctg cccataagga gtcacctcct actgttgatt   6120

caactcaaca gcctaaccct ttgccgttac gtttacctga aatggaaccc ttagtgccta   6180

gagtcaaaga agttaaatct gctcaggaaa ctcctgaaag ctctctggct ggaagtcctg   6240

atactgaatc tccagtgtta gtgaatgact atgaagcaga atctggtaat ataagtcaaa   6300

agtctgatga agaagatttt gtaaaagttg aagatttacc actgaaactg acaatatatt   6360

cagaggcaga tctaagaaag aaaatggtag aagaagaaca gaaaaaccat ttatctggtg   6420

aaatatgtga aatgcagacc gaagaattag ctggaaattc tgagacacta aaagaacctg   6480

aaacggtggg agcccagagt atatgagatg tcttcagagg ctcatctaac tctgtcctta   6540

catactcaat gcatatatga aaacaatact aaataaacat ctgatctgta taaaaat      6597
```

<210> SEQ ID NO 8
<211> LENGTH: 479
<212> TYPE: DNA
<213> ORGANISM: Homo sapiens

<400> SEQUENCE: 8

```
ctccaaaggc aaaaatctcc agccctacag agactgagcg gtgcatcgag tccctgattg     60

ctgtcttcca gaagtatgct ggaaaggatg gttataacta cactctctcc aagacagagt    120

tcgtaagctt catgaataca gaactagctg ccttcacaaa gaaccagaag gaccctggtg    180

tccttgaccg catgatgaag aaactggaca ccaacagtga tggtcagcta gatttctcag    240

aatttcttaa tctgattggt ggcctagcta tggcttgcca tgactccttc ctcaaggctg    300

tcccttccca gaagcggacc tgaggacccc ttggccctgg ccttcaaacc cacccccttt    360

ccttccagcc tttctgtcat catctccaca gcccacccat cccctgagca cactaaccac    420

ctcatgcagg ccccacctgc caatagtaat aaagcaatgt cactttttta aaacatgaa     479
```

<210> SEQ ID NO 9
<211> LENGTH: 2465
<212> TYPE: DNA
<213> ORGANISM: Homo sapiens

<400> SEQUENCE: 9

```
gccgcttcct gcctggattc cacagcttcg cgccgtgtac tgtcgcccca tccctgcgcg     60

cccagcctgc caagcagcgt gccccggttg caggcgtcat gcagcgggcg cgacccacgc    120

tctgggccgc tgcgctgact ctgctggtgc tgctccgcgg gccgccggtg gcgcgggctg    180

gcgcgagctc ggcgggcttg ggtcccgtgg tgcgctgcga gccgtgcgac gcgcgtgcac    240

tggcccagtg cgcgcctccg cccgccgtgt gcgcggagct ggtgcgcgag ccgggctgcg    300

gctgctgcct gacgtgcgca ctgagcgagg gccagccgtg cggcatctac accgagcgct    360

gtggctccgg ccttcgctgc cagccgtcgc ccgacgaggc gcgaccgctg caggcgctgc    420

tggacggccg cgggctctgc gtcaacgcta gtgccgtcag ccgcctgcgc gcctacctgc    480

tgccagcgcc gccagctcca ggaaatgcta gtgagtcgga ggaagaccgc agcgccggca    540
```

-continued

```
gtgtggagag cccgtccgtc tccagcacgc accgggtgtc tgatcccaag ttccaccccc    600
tccattcaaa gataatcatc atcaagaaag ggcatgctaa agacagccag cgctacaaag    660
ttgactacga gtctcagagc acagataccc agaacttctc ctccgagtcc aagcgggaga    720
cagaatatgg tccctgccgt agagaaatgg aagacacact gaatcacctg aagttcctca    780
atgtgctgag tcccaggggt gtacacattc ccaactgtga caagaaggga ttttataaga    840
aaaagcagtg tcgcccttcc aaaggcagga agcggggctt ctgctggtgt gtggataagt    900
atgggcagcc tctcccaggc tacaccacca aggggaagga ggacgtgcac tgctacagca    960
tgcagagcaa gtagacgcct gccgcaaggt taatgtggag ctcaaatatg ccttattttg   1020
cacaaaagac tgccaaggac atgaccagca gctggctaca gcctcgattt atatttctgt   1080
ttgtggtgaa ctgatttttt ttaaaccaaa gtttagaaag aggtttttga aatgcctatg   1140
gtttctttga atggtaaact tgagcatctt ttcactttcc agtagtcagc aaagagcagt   1200
ttgaattttc ttgtcgcttc ctatcaaaat attcagagac tcgagcacag cacccagact   1260
tcatgcgccc gtggaatgct caccacatgt tggtcgaagc ggccgaccac tgactttgtg   1320
acttaggcgg ctgtgttgcc tatgtagaga acacgcttca cccccactcc ccgtacagtg   1380
cgcacaggct ttatcgagaa taggaaaacc tttaaacccc ggtcatccgg acatcccaac   1440
gcatgctcct ggagctcaca gccttctgtg gtgtcatttc tgaaacaagg gcgtggatcc   1500
ctcaaccaag aagaatgttt atgtcttcaa gtgacctgta ctgcttgggg actattggag   1560
aaaataaggt ggagtcctac ttgtttaaaa aatatgtatc taagaatgtt ctagggcact   1620
ctgggaacct ataaaggcag gtatttcggg ccctcctctt caggaatctt cctgaagaca   1680
tggcccagtc gaaggcccag gatggctttt gctgcggccc cgtggggtag gagggacaga   1740
gagacaggga gagtcagcct ccacattcag aggcatcaca agtaatggca caattcttcg   1800
gatgactgca gaaaatagtg ttttgtagtt caacaactca agacgaagct tatttctgag   1860
gataagctct ttaaaggcaa agctttattt tcatctctca tcttttgtcc tccttagcac   1920
aatgtaaaaa agaatagtaa tatcagaaca ggaaggagga atggcttgct ggggagccca   1980
tccaggacac tgggagcaca tagagattca cccatgtttg ttgaacttag agtcattctc   2040
atgcttttct ttataattca cacatatatg cagagaagat atgttcttgt taacattgta   2100
tacaacatag ccccaaatat agtaagatct atactagata atcctagatg aaatgttaga   2160
gatgctattt gatacaactg tggccatgac tgaggaaagg agctcacgcc cagagactgg   2220
gctgctctcc cggaggccaa acccaagaag gtctggcaaa gtcaggctca gggagactct   2280
gccctgctgc agacctcggt gtggacacac gctgcataga gctctccttg aaaacagagg   2340
ggtctcaaga cattctgcct acctattagc ttttctttat ttttttaact ttttgggggg   2400
aaaagtattt ttgagaagtt tgtcttgcaa tgtatttata aatagtaaat aaagttttta   2460
ccatt                                                               2465
```

<210> SEQ ID NO 10
<211> LENGTH: 807
<212> TYPE: DNA
<213> ORGANISM: Homo sapiens

<400> SEQUENCE: 10

```
atgccgcgct ccttcctggt caagaagcat ttcaacgcct ccaaaaagcc aaactacagc     60
gaactggaca cacatacagt gattatttcc ccgtatctct atgagagtta ctccatgcct    120
```

-continued

```
gtcataccac aaccagagat cctcagctca ggagcataca gccccatcac tgtgtggact    180

accgctgctc cattccacgc ccagctaccc aatggcctct ctcctctttc cggatactcc    240

tcatctttgg ggcgagtgag tccccctcct ccatctgaca cctcctccaa ggaccacagt    300

ggctcagaaa gccccattag tgatgaagag gaaagactac agtccaagct ttcagacccc    360

catgccattg aagctgaaaa gtttcagtgc aatttatgca ataagaccta ttcaactttt    420

tctgggctgg ccaaacataa gcagctgcac tgcgatgccc agtctagaaa atctttcagc    480

tgtaaatact gtgacaagga atatgtgagc ctgggcgccc tgaagatgca tattcggacc    540

cacacattac cttgtgtttg caagatctgc ggcaaggcgt tttccagacc ctggttgctt    600

caaggacaca ttagaactca cacgggggag aagccttttt cttgccctca ctgcaacaga    660

gcatttgcag acaggtcaaa tctgagggct catctgcaga cccattctga tgtaaagaaa    720

taccagtgca aaaactgctc caaaaccttc tccagaatgt ctctcctgca caaacatgag    780

gaatctggct gctgtgtagc acactga                                        807
```

<210> SEQ ID NO 11
<211> LENGTH: 1266
<212> TYPE: DNA
<213> ORGANISM: Homo sapiens

<400> SEQUENCE: 11

```
ctcggaagcc cgtcaccatg tcgtgcgagt cgtctatggt tctcgggtac tgggatattc     60

gtgggctggc gcacgccatc cgcctgctcc tggagttcac ggatacctct tatgaggaga    120

aacggtacac gtgcggggaa gctcctgact atgatcgaag ccaatggctg gatgtgaaat    180

tcaagctaga cctggacttt cctaatctgc cctacctcct ggatgggaag aacaagatca    240

cccagagcaa tgccatcttg cgctacatcg ctcgcaagca caacatgtgt ggtgagactg    300

aagaagaaaa gattcgagtg gacatcatag agaaccaagt aatggatttc cgcacacaac    360

tgataaggct ctgttacagc tctgaccacg aaaaactgaa gcctcagtac ttggaagagc    420

tacctggaca actgaaacaa ttctccatgt ttctgtggaa attctcatgg tttgccgggg    480

aaaagctcac ctttgtggat ttctcacct atgatatctt ggatcagaac cgtatatttg    540

accccaagtg cctggatgag ttcccaaacc tgaaggcttt catgtgccgt tttgaggctt    600

tggagaaaat cgctgcctac ttacagtctg atcagttctg caagatgccc atcaacaaca    660

agatggccca gtggggcaac aagcctgtat gctgagcagg aggcagactt gcagagcttg    720

ttttgtttca tcctgtccgt aaggggtcag cgctcttgct ttgctctttt caatgaatag    780

cacttatgtt actggtgtcc agctgagttt ctcttgggta taaaggctaa aagggaaaaa    840

ggatatgtgg agaatcatca agatatgaat tgaatcgctg cgatactgtg gcatttccct    900

actccccaac tgagttcaag ggctgtaggt tcatgcccaa gccctgagag tgggtactag    960

aaaaaacgag attgcacagt tggagagagc aggtgtgtta aatggactgg agtccctgtg   1020

aagactgggt gaggataaca caagtaaaac tgtggtactg atggacttaa ccggagttcg   1080

gaaaccgtcc tgtgtacaca tgggagttta gtgtgataaa ggcagtattt cagactggtg   1140

ggctagccaa tagagttggc aattgcttat tgaaactcat taaaaataat agagccccac   1200

ttgacactat tcactaaaat taatctggaa tttaaggccc aacattaaac acaaagctgt   1260

attgat                                                              1266
```

<210> SEQ ID NO 12
<211> LENGTH: 1308

-continued

<212> TYPE: DNA
<213> ORGANISM: Homo sapiens

<400> SEQUENCE: 12
gccacgtgct gctgggtctc agtcctccac ttcccgtgtc ctctggaagt tgtcaggagc 60
aatgttgcgc ttgtacgtgt tggtaatggg agtttctgcc ttcacccttc agcctgcggc 120
acacacaggg gctgccagaa gctgccggtt tcgtgggagg cattacaagc gggagttcag 180
gctggaaggg gagcctgtag ccctgaggtg cccccaggtg ccctactggt tgtgggcctc 240
tgtcagcccc cgcatcaacc tgacatggca taaaaatgac tctgctagga cggtcccagg 300
agaagaagag acacggatgt gggcccagga cggtgctctg tggcttctgc cagccttgca 360
ggaggactct ggcacctacg tctgcactac tagaaatgct tcttactgtg acaaaatgtc 420
cattgagctc agagtttttg agaatacaga tgctttcctg ccgttcatct catacccgca 480
aattttaacc ttgtcaacct ctggggtatt agtatgccct gacctgagtg aattcacccg 540
tgacaaaact gacgtgaaga ttcaatggta caaggattct cttcttttgg ataaagacaa 600
tgagaaattt ctaagtgtga gggggaccac tcacttactc gtacacgatg tggccctgga 660
agatgctggc tattaccgct gtgtcctgac atttgcccat gaaggccagc aatacaacat 720
cactaggagt attgagctac gcatcaagaa aaaaaaagaa gagaccattc ctgtgatcat 780 ttccccctc aagaccatat cagcttctct ggggtcaaga ctgacaatcc cgtgtaaggt 840
gtttctggga accggcacac ccttaaccac catgctgtgg tggacggcca atgacaccca 900
catagagagc gcctacccgg gaggccgcgt gaccgagggg ccacgccagg aatattcaga 960
aaataatgag aactacattg aagtgccatt gatttttgat cctgtcacaa gagaggattt 1020
gcacatggat tttaaatgtg ttgtccataa taccctgagt tttcagacac tacgcaccac 1080
agtcaaggaa gcctcctcca cgttctcctg ggcattgtg ctggccccac tttcactggc 1140
cttcttggtt ttggggggaa tatggatgca cagacggtgc aaacacagaa ctggaaaagc 1200
agatggtctg actgtgctat ggcctcatca tcaagacttt caatcctatc ccaagtgaaa 1260
taaatggaat gaaataattc aaacacaaaa aaaaaaaaaa aaaaaaaa 1308

<210> SEQ ID NO 13
<211> LENGTH: 5994
<212> TYPE: DNA
<213> ORGANISM: Homo sapiens

<400> SEQUENCE: 13
gcgctgcccg cctcgtcccc accccccaac cccccgcgcc cgccctcgga cagtccctgc 60
tcgcccgcgc gctgcagccc catctcctag cggcagccca ggcgcggagg gagcgagtcc 120
gccccgaggt aggtccagga cgggcgcaca gcagcagccg aggctggccg ggagagggag 180
gaagaggatg gcagggccac gccccagccc atgggccagg ctgctcctgg cagccttgat 240
cagcgtcagc ctctctggga ccttggcaaa ccgctgcaag aaggccccag tgaagagctg 300
cacggagtgt gtccgtgtgg ataaggactg cgcctactgc acagacgaga tgttcaggga 360
ccggcgctgc aacacccagg cggagctgct ggccgcgggc tgccagcggg agagcatcgt 420
ggtcatggag agcagcttcc aaatcacaga ggagacccag attgacacca ccctgcggcg 480
cagccagatg tccccccaag gcctgcgggt ccgtctgcgg cccggtgagg agcggcattt 540
tgagctggag gtgtttgagc cactggagag ccccgtggac ctgtacatcc tcatggactt 600
ctccaactcc atgtccgatg atctggacaa cctcaagaag atggggcaga acctggctcg 660

-continued

```
ggtcctgagc cagctcacca gcgactacac tattggattt ggcaagtttg tggacaaagt    720
cagcgtcccg cagacggaca tgaggcctga gaagctgaag gagccctggc ccaacagtga    780
cccccccttc tccttcaaga acgtcatcag cctgacagaa gatgtggatg agttccggaa    840
taaactgcag ggagagcgga tctcaggcaa cctggatgct cctgagggcg gcttcgatgc    900
catcctgcag acagctgtgt gcacgaggga cattggctgg cgcccggaca gcacccacct    960
gctggtcttc tccaccgagt cagccttcca ctatgaggct gatggcgcca acgtgctggc   1020
tggcatcatg agccgcaacg atgaacggtg ccacctggac accacgggca cctacaccca   1080
gtacaggaca caggactacc cgtcggtgcc caccctggtg cgcctgctcg ccaagcacaa   1140
catcatcccc atctttgctg tcaccaacta ctcctatagc tactacgaga agcttcacac   1200
ctatttccct gtctcctcac tgggggtgct gcaggaggac tcgtccaaca tcgtggagct   1260
gctggaggag gccttcaatc ggatccgctc caacctggac atccgggccc tagacagccc   1320
ccgaggcctt cggacagagg tcacctccaa gatgttccag aagacgagga ctgggtcctt   1380
tcacatccgg cggggggaag tgggtatata ccaggtgcag ctgcgggccc ttgagcacgt   1440
ggatgggacg cacgtgtgcc agctgccgga ggaccagaag ggcaacatcc atctgaaacc   1500
ttccttctcc gacggcctca agatggacgc gggcatcatc tgtgatgtgt gcacctgcga   1560
gctgcaaaaa gaggtgcggt cagctcgctg cagcttcaac ggagacttcg tgtgcggaca   1620
gtgtgtgtgc agcgagggct ggagtggcca gacctgcaac tgctccaccg gctctctgag   1680
tgacattcag ccctgcctgc gggagggcga ggacaagccg tgctccggcc gtggggagtg   1740
ccagtgcggg cactgtgtgt gctacggcga aggccgctac gagggtcagt tctgcgagta   1800
tgacaacttc cagtgtcccc gcacttccgg gttcctgtgc aatgaccgag gacgctgctc   1860
catgggccag tgtgtgtgtg agcctggttg gacaggccca agctgtgact gtcccctcag   1920
caatgccacc tgcatcgaca gcaatggggg catctgtaat ggacgtggcc actgtgagtg   1980
tggccgctgc cactgccacc agcagtcgct ctacacggac accatctgcg agatcaacta   2040
ctcggcgatc cacccgggcc tctgcgagga cctacgctcc tgcgtgcagt gccaggcgtg   2100
gggcaccggc gagaagaagg ggcgcacgtg tgaggaatgc aacttcaagg tcaagatggt   2160
ggacgagctt aagagagccg aggaggtggt ggtgcgctgc tccttccggg acgaggatga   2220
cgactgcacc tacagctaca ccatggaagg tgacggcgcc cctgggccca acagcactgt   2280
cctggtgcac aagaagaagg actgccctcc gggctccttc tggtggctca tcccccctgct   2340
cctcctcctc ctgccgctcc tggccctgct actgctgcta tgctggaagt actgtgcctg   2400
ctgcaaggcc tgcctggcac ttctcccgtg ctgcaaccga ggtcacatgg tgggctttaa   2460
ggaagaccac tacatgctgc gggagaacct gatggcctct gaccacttgg acacgcccat   2520
gctgcgcagc gggaacctca agggccgtga cgtggtccgc tggaaggtca ccaacaacat   2580
gcagcggcct ggctttgcca ctcatgccgc cagcatcaac ccccacagagc tggtgcccta   2640
cgggctgtcc ttgcgcctgg cccgcctttg caccgagaac ctgctgaagc ctgacactcg   2700
ggagtgcgcc cagctgcgcc aggaggtgga ggagaacctg aacgaggtct acaggcagat   2760
ctccggtgta cacaagctcc agcagaccaa gttccggcag cagcccaatg ccgggaaaaa   2820
gcaagaccac accattgtgg acacagtgct gatggcgccc cgctcggcca agccggccct   2880
gctgaagctt acagagaagc aggtggaaca gagggccttc cacgacctca aggtggcccc   2940
cggctactac accctcactg cagaccagga cgcccggggc atggtggagt tccaggaggg   3000
cgtggagctg gtggacgtac gggtgcccct ctttatccgg cctgaggatg acgacgagaa   3060
```

-continued

```
gcagctgctg gtggaggcca tcgacgtgcc cgcaggcact gccaccctcg gccgccgcct   3120
ggtaaacatc accatcatca aggagcaagc cagagacgtg gtgtcctttg agcagcctga   3180
gttctcggtc agccgcgggg accaggtggc ccgcatccct gtcatccggc gtgtcctgga   3240
cggcgggaag tcccaggtct cctaccgcac acaggatggc accgcgcagg gcaaccggga   3300
ctacatcccc gtggagggtg agctgctgtt ccagcctggg gaggcctgga aagagctgca   3360
ggtgaagctc ctggagctgc aagaagttga ctccctcctg cggggccgcc aggtccgccg   3420
tttccacgtc cagctcagca accctaagtt tggggcccac ctgggccagc cccactccac   3480
caccatcatc atcagggacc cagatgaact ggaccggagc ttcacgagtc agatgttgtc   3540
atcacagcca ccccctcacg gcgacctggg cgccccgcag aaccccaatg ctaaggccgc   3600
tgggtccagg aagatccatt tcaactggct gccccccttct ggcaagccaa tggggtacag   3660
ggtaaagtac tggattcagg gcgactccga atccgaagcc cacctgctcg acagcaaggt   3720
gccctcagtg gagctcacca acctgtaccc gtattgcgac tatgagatga aggtgtgcgc   3780
ctacggggct cagggcgagg gaccctacag ctccctggtg tcctgccgca cccaccagga   3840
agtgcccagc gagccagggc gtctggcctt caatgtcgtc tcctccacgg tgacccagct   3900
gagctgggct gagccggctg agaccaacgg tgagatcaca gcctacgagg tctgctatgg   3960
cctggtcaac gatgacaacc gacctattgg gcccatgaag aaagtgctgg ttgacaaccc   4020
taagaaccgg atgctgctta ttgagaacct tcgggagtcc cagccctacc gctacacggt   4080
gaaggcgcgc aacggggccg gctgggggcc tgagcgggag gccatcatca acctggccac   4140
ccagcccaag aggcccatgt ccatccccat catccctgac atccctatcg tggacgccca   4200
gagcggggag gactacgaca gcttccttat gtacagcgat gacgttctac gctctccatc   4260
gggcagccag aggcccagcg tctccgatga cactggctgc ggctggaagt tcgagcccct   4320
gctgggggag gagctggacc tgcggcgcgt cacgtggcgg ctgcccccgg agctcatccc   4380
gcgcctgtcg gccagcagcg ggcgctcctc cgacgccgag gcccccacgg ccccccggac   4440
gacggcggcg cgggcgggaa gggcggcagc cgtgccccgc agtgcgacac ccgggccccc   4500
cggagagcac ctggtgaatg gccggatgga ctttgccttc ccgggcagca ccaactccct   4560
gcacaggatg accacgacca gtgctgctgc ctatggcacc cacctgagcc cacacgtgcc   4620
ccaccgcgtg ctaagcacat cctccaccct cacacgggac tacaactcac tgacccgctc   4680
agaacactca cactcgacca cactgcccag ggactactcc accctcacct ccgtctcctc   4740
ccacgactct cgcctgactg ctggtgtgcc cgacacgccc acccgcctgg tgttctctgc   4800
cctggggccc acatctctca gagtgagctg gcaggagccg cggtgcgagc ggccgctgca   4860
gggctacagt gtggagtacc agctgctgaa cggcggtgag ctgcatcggc tcaacatccc   4920
caaccctgcc cagacctcgg tggtggtgga agacctcctg cccaaccact cctacgtgtt   4980
ccgcgtgcgg gcccagagcc aggaaggctg gggccgagag cgtgagggtg tcatcaccat   5040
tgaatcccag gtgcacccgc agagcccact gtgtcccctg ccaggctccg ccttcacttt   5100
gagcactccc agtgccccag gcccgctggt gttcactgcc ctgagcccag actcgctgca   5160
gctgagctgg gagcggccac ggaggcccaa tggggatatc gtcggctacc tggtgacctg   5220
tgagatggcc caaggaggag ggccagccac cgcattccgg gtggatggag acagccccga   5280
gagccggctg accgtgccgg gcctcagcga gaacgtgccc tacaagttca aggtgcaggc   5340
caggaccact gagggcttcg ggccagagcg cgagggcatc atcaccatag agtcccagga   5400
```

-continued

```
tggaggaccc ttcccgcagc tgggcagccg tgccgggctc ttccagcacc cgctgcaaag   5460

cgagtacagc agcatcacca ccacccacac cagcgccacc gagcccttcc tagtggatgg   5520

gctgaccctg gggggcccagc acctggaggc aggcggctcc ctcacccggc atgtgaccca  5580

ggagtttgtg agccggacac tgaccaccag cggaaccctt agcacccaca tggaccaaca   5640

gttcttccaa acttgaccgc accctgcccc acccccgcca tgtcccacta ggcgtcctcc   5700

cgactcctct cccggagcct cctcagctac tccatccttg cacccctggg ggcccagccc   5760

acccgcatgc acagagcagg ggctaggtgt ctcctgggag gcatgaaggg ggcaaggtcc   5820

gtcctctgtg ggcccaaacc tatttgtaac caaagagctg ggagcagcac aaggacccag   5880

cctttgttct gcacttaata aatggttttg ctactgctaa aaaaaaaaaa aaaaaaaaaa   5940

aaaaaaaaaa aaaaaaaaaa aaaaaaaaaa aaaaaaaaaa aaaaaaaaaa aaaa         5994
```

<210> SEQ ID NO 14
<211> LENGTH: 1898
<212> TYPE: DNA
<213> ORGANISM: Homo sapiens

<400> SEQUENCE: 14

```
ccgccgggct ggccatggag ctgctgtgcc acgaggtgga cccggtccgc agggccgtgc     60

gggaccgcaa cctgctccga gacgaccgcg tcctgcagaa cctgctcacc atcgaggagc    120

gctaccttcc gcagtgctcc tacttcaagt gcgtgcagaa ggacatccaa ccctacatgc    180

gcagaatggt ggccacctgg atgctggagg tctgtgagga acagaagtgc gaagaagagg    240

tcttccctct ggccatgaat tacctggacc gtttcttggc tggggtcccg actccgaagt    300

cccatctgca actcctgggt gctgtctgca tgttcctggc ctccaaactc aaagagacca    360

gcccgctgac cgcggagaag ctgtgcattt acaccgacaa ctccatcaag cctcaggagc    420

tgctggagtg ggaactggtg gtgctgggga agttgaagtg gaacctggca gctgtcactc    480

ctcatgactt cattgagcac atcttgcgca agctgcccca gcagcgggag aagctgtctc    540

tgatccgcaa gcatgctcag accttcattg ctctgtgtgc caccgacttt aagtttgcca    600

tgtacccacc gtcgatgatc gcaactggaa gtgtgggagc agccatctgt gggctccagc    660

aggatgagga agtgagctcg ctcacttgtg atgccctgac tgagctgctg gctaagatca    720

ccaacacaga cgtggattgt ctcaaagctt gccaggagca gattgaggcg gtgctcctca    780

atagcctgca gcagtaccgt caggaccaac gtgacggatc caagtcggag gatgaactgg    840

accaagccag cacccctaca gacgtgcggg atatcgacct gtgaggatgc cagttgggcc    900

gaaagagaga gacgcgtcca taatctggtc tcttcttctt tctggttgtt tttgttcttt    960

gtgttttagg gtgaaactta aaaaaaaaat tctgccccca cctagatcat atttaaagat   1020

cttttagaag tgagagaaaa aggtcctacg aaaacggaat aataaaaagc atttggtgcc   1080

tatttgaagt acagcataag ggaatccctt gtatatgcga acagttattg tttgattatg   1140

taaaagtaat agtaaaatgc ttacaggaaa acctgcagag tagttagaga atatgtatgc   1200

ctgcaatatg ggaacaaatt agaggagact tttttttttc atgttatgag ctagcacata   1260

cacccccttg tagtataatt tcaaggaact gtgtacgcca tttatggcat gattagattg   1320

caaagcaatg aactcaagaa ggaattgaaa taaggaggga catgatgggg aaggagtaca   1380

aaacaatctc tcaacatgat tgaaccattt gggatggaga agcacctttg ctctcagcca   1440

cctgttacta agtcaggagt gtagttggat ctctacatta atgtcctctt gctgtctaca   1500

gtagctgcta cctaaaaaaa gatgttttat tttgccagtt ggacacaggt gattggctcc   1560
```

-continued

```
tgggtttcat gttctgtgac atcctgcttc ttcttccaaa tgcagttcat tgcagacacc   1620

accatattgc tatctaatgg ggaaatgtag ctatgggcca taaccaaaac tcacatgaaa   1680

cggaggcaga tggagaccaa gggtgggatc cagaatggag tcttttctgt tattgtattt   1740

aaaagggtaa tgtggccttg gcatttcttc ttagaaaaaa actaattttt ggtgctgatt   1800

ggcatgtctg gttcacagtt tagcattgtt ataaaccatt ccattcgaaa agcactttga   1860

aaaattgttc ccgagcgata gatgggatgg tttatgca                            1898
```

<210> SEQ ID NO 15
<211> LENGTH: 4286
<212> TYPE: DNA
<213> ORGANISM: Homo sapiens

<400> SEQUENCE: 15

```
gagacattcc ggtgggggac tctggccagc ccgagcaacg tggatcctga gagcactccc     60

aggtaggcat ttgccccggt gggacgcctt gccagagcag tgtgtggcag gcccccgtgg    120

aggatcaaca cagtggctga acactgggaa ggaactggta cttggagtct ggacatctga    180

aacttggctc tgaaactgcg cagcggccac cggacgcctt ctggagcagg tagcagcatg    240

cagccgcctc caagtctgtg cggacgcgcc ctggttgcgc tggttcttgc ctgcggcctg    300

tcgcggatct ggggagagga gagaggcttc ccgcctgaca gggccactcc gcttttgcaa    360

accgcagaga taatgacgcc acccactaag accttatggc ccaagggttc caacgccagt    420

ctggcgcggt cgttggcacc tgcggaggtg cctaaaggag acaggacggc aggatctccg    480

ccacgcacca tctcccctcc cccgtgccaa ggacccatcg agatcaagga gactttcaaa    540

tacatcaaca cggttgtgtc ctgccttgtg ttcgtgctgg ggatcatcgg gaactccaca    600

cttctgagaa ttatctacaa gaacaagtgc atgcgaaacg gtcccaatat cttgatcgcc    660

agcttggctc tgggagacct gctgcacatc gtcattgaca tccctatcaa tgtctacaag    720

ctgctggcag aggactggcc atttggagct gagatgtgta agctggtgcc tttcatacag    780

aaagcctccg tgggaatcac tgtgctgagt ctatgtgctc tgagtattga cagatatcga    840

gctgttgctt cttggagtag aattaaagga attggggttc caaaatggac agcagtagaa    900

attgttttga tttgggtggt ctctgtggtt ctggctgtcc ctgaagccat aggttttgat    960

ataattacga tggactacaa aggaagttat ctgcgaatct gcttgcttca tcccgttcag   1020

aagacagctt tcatgcagtt ttacaagaca gcaaaagatt ggtggctgtt cagtttctat   1080

ttctgcttgc cattggccat cactgcattt ttttatacac taatgacctg tgaaatgttg   1140

agaaagaaaa gtggcatgca gattgcttta aatgatcacc taaagcagag acgggaagtg   1200

gccaaaaccg tcttttgcct ggtccttgtc tttgccctct gctggcttcc ccttcacctc   1260

agcaggattc tgaagctcac tctttataat cagaatgatc ccaatagatg tgaacttttg   1320

agctttctgt tggtattgga ctatattggt atcaacatgg cttcactgaa ttcctgcatt   1380

aacccaattg ctctgtattt ggtgagcaaa agattcaaaa actgctttaa gtcatgctta   1440

tgctgctggt gccagtcatt tgaagaaaaa cagtccttgg aggaaaagca gtcgtgctta   1500

aagttcaaag ctaatgatca cggatatgac aacttccgtt ccagtaataa atacagctca   1560

tcttgaaaga agaactattc actgtatttc attttcttta tattggaccg aagtcattaa   1620

aacaaaatga aacatttgcc aaaacaaaac aaaaaactat gtatttgcac agcacactat   1680

taaaatatta agtgtaatta ttttaacact cacagctaca tatgacattt tatgagctgt   1740
```

-continued ttacggcatg gaaagaaaat cagtgggaat taagaaagcc tcgtcgtgaa agcacttaat 1800
tttttacagt tagcacttca acatagctct taacaacttc caggatattc acacaacact 1860
taggcttaaa aatgagctca ctcagaattt ctattctttc taaaaagaga tttattttta 1920
aatcaatggg actctgatat aaaggaagaa taagtcactg taaaacagaa cttttaaatg 1980
aagcttaaat tactcaattt aaaattttaa aatcctttaa aacaactttt caattaatat 2040
tatcacacta ttatcagatt gtaattagat gcaaatgaga gagcagttta gttgttgcat 2100
ttttcggaca ctggaaacat ttaaatgatc aggagggagt aacagaaaga gcaaggctgt 2160
ttttgaaaat cattacactt tcactagaag cccaaacctc agcattctgc aatatgtaac 2220
caacatgtca caaacaagca gcatgtaaca gactggcaca tgtgccagct gaatttaaaa 2280
tataatactt ttaaaaagaa aattattaca tcctttacat tcagttaaga tcaaacctca 2340
caaagagaaa tagaatgttt gaaaggctat cccaaaagac ttttttgaat ctgtcattca 2400 catacccctgt gaagacaata ctatctacaa ttttttcagg attattaaaa tcttcttttt 2460
tcactatcgt agcttaaact ctgtttggtt ttgtcatctg taaatactta cctacataca 2520
ctgcatgtag atgattaaat gagggcaggc cctgtgctca tagctttacg atggagagat 2580
gccagtgacc tcataataaa gactgtgaac tgcctggtgc agtgtccaca tgacaaaggg 2640
gcaggtagca ccctctctca cccatgctgt ggttaaaatg gtttctagca tatgtataat 2700
gctatagtta aaatactatt tttcaaaatc atacagatta gtacatttaa cagctacctg 2760
taaagcttat tactaatttt tgtattattt ttgtaaatag ccaatagaaa agtttgcttg 2820
acatggtgct tttctttcat ctagaggcaa aactgctttt tgagaccgta agaacctctt 2880
agctttgtgc gttcctgcct aatttttata tcttctaagc aaagtgcctt aggatagctt 2940
gggatgagat gtgtgtgaaa gtatgtacaa gagaaaacgg aagagagagg aaatgaggtg 3000
gggttggagg aaacccatgg ggacagattc ccattcttag cctaacgttc gtcattgcct 3060
cgtcacatca atgcaaaagg tcctgatttt gttccagcaa aacacagtgc aatgttctca 3120
gagtgacttt cgaaataaat tgggcccaag agctttaact cggtcttaaa atatgcccaa 3180
atttttactt tgtttttctt ttaataggct gggccacatg ttggaaataa gctagtaatg 3240
ttgttttctg tcaatattga atgtgatggt acagtaaacc aaaacccaac aatgtggcca 3300
gaaagaaaga gcaataataa ttaattcaca caccatatgg attctattta taaatcaccc 3360
acaaacttgt tctttaattt catcccaatc actttttcag aggcctgtta tcatagaagt 3420
cattttagac tctcaatttt aaattaattt tgaatcacta atattttcac agtttattaa 3480
tatatttaat ttctatttaa atttagatt attttttatta ccatgtactg aatttttaca 3540
tcctgatacc ctttccttct ccatgtcagt atcatgttct ctaattatct tgccaaattt 3600
tgaaactaca cacaaaaagc atacttgcat tatttataat aaaattgcat tcagtggctt 3660
tttaaaaaaa atgtttgatt caaaacttta acatactgat aagtaagaaa caattataat 3720
ttctttacat actcaaaacc aagatagaaa aaggtgctat cgttcaactt caaaacatgt 3780
ttcctagtat taaggacttt aatatagcaa cagacaaaat tattgttaac atggatgtta 3840
cagctcaaaa gatttataaa agattttaac ctattttctc ccttattatc cactgctaat 3900
gtggatgtat gttcaaacac cttttagtat tgatagctta catatggcca aaggaataca 3960
gtttatagca aaacatgggt atgctgtagc taactttata aaagtgtaat ataacaatgt 4020
aaaaaattat atatctggga ggattttttg gttgcctaaa gtggctatag ttactgattt 4080
tttattatgt aagcaaaacc aataaaaatt taagtttttt taacaactac cttatttttc 4140

-continued

```
actgtacaga cactaattca ttaaatacta attgattgtt taaaagaaat ataaatgtga   4200

caagtggaca ttatttatgt taaatataca attatcaagc aagtatgaag ttattcaatt   4260

aaaatgccac atttctggtc tctggg                                         4286


<210> SEQ ID NO 16
<211> LENGTH: 3148
<212> TYPE: DNA
<213> ORGANISM: Homo sapiens

<400> SEQUENCE: 16

gaattcccgc ggagcagcgt gcgcggggcc ccgggagacg gcggcggtag cggcgcgggc     60

agagcaagga cgcggcggat cccactcgca cagcagcgca ctcggtgccc cgcgcagggt    120

cgcgatgctg cccggtttgg cactgctcct gctggccgcc tggacggctc gggcgctgga    180

ggtacccact gatggtaatg ctggcctgct ggctgaaccc cagattgcca tgttctgtgg    240

cagactgaac atgcacatga atgtccagaa tgggaagtgg gattcagatc catcagggac    300

caaaacctgc attgatacca aggaaggcat cctgcagtat tgccaagaag tctaccctga    360

actgcagatc accaatgtgg tagaagccaa ccaaccagtg accatccaga actggtgcaa    420

gcggggccgc aagcagtgca agacccatcc ccactttgtg attccctacc gctgcttagt    480

tggtgagttt gtaagtgatg cccttctcgt tcctgacaag tgcaaattct tacaccagga    540

gaggatggat gtttgcgaaa ctcatcttca ctggcacacc gtcgccaaag agacatgcag    600

tgagaagagt accaacttgc atgactacgg catgttgctg ccctgcggaa ttgacaagtt    660

ccgaggggta gagtttgtgt gttgcccact ggctgaagaa agtgacaatg tggattctgc    720

tgatgcggag gaggatgact cggatgtctg gtggggcgga gcagacacag actatgcaga    780

tgggagtgaa gacaaagtag tagaagtagc agaggaggaa gaagtggctg aggtggaaga    840

agaagaagcc gatgatgacg aggacgatga ggatggtgat gaggtagagg aagaggctga    900

ggaaccctac gaagaagcca cagagagaac caccagcatt gccaccacca ccaccaccac    960

cacagagtct gtggaagagg tggttcgaga ggtgtgctct gaacaagccg agacggggcc   1020

gtgccgagca atgatctccc gctggtactt tgatgtgact gaagggaagt gtgccccatt   1080

cttttacggc ggatgtggcg gcaaccggaa caactttgac acagaagagt actgcatggc   1140

cgtgtgtggc agcgccattc ctacaacagc agccagtacc cctgatgccg ttgacaagta   1200

tctcgagaca cctggggatg agaatgaaca tgcccatttc cagaaagcca aagagaggct   1260

tgaggccaag caccgagaga gaatgtccca ggtcatgaga gaatgggaag aggcagaacg   1320

tcaagcaaag aacttgccta aagctgataa gaaggcagtt atccagcatt tccaggagaa   1380

agtggaatct ttggaacagg aagcagccaa cgagagacag cagctggtgg agacacacat   1440

ggccagagtg gaagccatgc tcaatgaccg ccgccgcctg gccctggaga actacatcac   1500

cgctctgcag gctgttcctc ctcggcctcg tcacgtgttc aatatgctaa agaagtatgt   1560

ccgcgcagaa cagaaggaca gacagcacac cctaaagcat ttcgagcatg tgcgcatggt   1620

ggatcccaag aaagccgctc agatccggtc ccaggttatg acacacctcc gtgtgattta   1680

tgagcgcatg aatcagtctc tctccctgct ctacaacgtg cctgcagtgg ccgaggagat   1740

tcaggatgaa gttgatgagc tgcttcagaa agagcaaaac tattcagatg acgtcttggc   1800

caacatgatt agtgaaccaa ggatcagtta cggaaacgat gctctcatgc catctttgac   1860

cgaaacgaaa accaccgtgg agctccttcc cgtgaatgga gagttcagcc tggacgatct   1920
```

-continued

```
ccagccgtgg cattcttttg gggctgactc tgtgccagcc aacacagaaa acgaagttga   1980

gcctgttgat gcccgccctg ctgccgaccg aggactgacc actcgaccag gttctgggtt   2040

gacaaatatc aagacggagg agatctctga agtgaagatg gatgcagaat tccgacatga   2100

ctcaggatat gaagttcatc atcaaaaatt ggtgttcttt gcagaagatg tgggttcaaa   2160

caaaggtgca atcattggac tcatggtggg cggtgttgtc atagcgacag tgatcgtcat   2220

caccttggtg atgctgaaga agaaacagta cacatccatt catcatggtg tggtggaggt   2280

tgacgccgct gtcaccccag aggagcgcca cctgtccaag atgcagcaga acggctacga   2340

aaatccaacc tacaagttct ttgagcagat gcagaactag acccccgcca cagcagcctc   2400

tgaagttgga cagcaaaacc attgcttcac tacccatcgg tgtccattta tagaataatg   2460

tgggaagaaa caaacccgtt ttatgattta ctcattatcg ccttttgaca gctgtgctgt   2520

aacacaagta gatgcctgaa cttgaattaa tccacacatc agtaatgtat tctatctctc   2580

tttacatttt ggtctctata ctacattatt aatgggtttt gtgtactgta aagaatttag   2640

ctgtatcaaa ctagtgcatg aatagattct ctcctgatta tttatcacat agccccttag   2700

ccagttgtat attattcttg tggtttgtga cccaattaag tcctacttta catatgcttt   2760

aagaatcgat gggggatgct tcatgtgaac gtgggagttc agctgcttct cttgcctaag   2820

tattcctttc ctgatcacta tgcattttaa agttaaacat ttttaagtat ttcagatgct   2880

ttagagagat tttttttcca tgactgcatt ttactgtaca gattgctgct tctgctatat   2940

ttgtgatata ggaattaaga ggatacacac gtttgtttct tcgtgcctgt tttatgtgca   3000

cacattaggc attgagactt caagcttttc tttttttgtc cacgtatctt tgggtctttg   3060

ataaagaaaa gaatccctgt tcattgtaag cacttttacg gggcgggtgg ggaggggtgc   3120

tctgctggtc ttcaattacc aagaattc                                       3148
```

<210> SEQ ID NO 17
<211> LENGTH: 4434
<212> TYPE: DNA
<213> ORGANISM: Homo sapiens

<400> SEQUENCE: 17

```
gccgccctcg ccaccgctcc cggccgccgc gctccggtac acacaggatc cctgctgggc     60

accaacagct ccaccatggg gctggcctgg ggactaggcg tcctgttcct gatgcatgtg    120

tgtggcacca accgcattcc agagtctggc ggagacaaca gcgtgtttga catctttgaa    180

ctcaccgggg ccgcccgcaa ggggtctggg cgccgactgg tgaagggccc cgacccttcc    240

agcccagctt tccgcatcga ggatgccaac ctgatccccc ctgtgcctga tgacaagttc    300

caagacctgg tggatgctgt gcggacagaa aagggtttcc tccttctggc atccctgagg    360

cagatgaaga agacccgggg cacgctgctg gccctggagc ggaaagacca ctctggccag    420

gtcttcagcg tggtgtccaa tggcaaggcg ggcaccctgg acctcagcct gaccgtccaa    480

ggaaagcagc acgtggtgtc tgtggaagaa gctctcctgg caaccggcca gtggaagagc    540

atcaccctgt ttgtgcagga agacagggcc cagctgtaca tcgactgtga aaagatggag    600

aatgctgagt tggacgtccc catccaaagc gtcttcacca gagacctggc cagcatcgcc    660

agactccgca tcgcaaaggg gggcgtcaat gacaatttcc agggggtgct gcagaatgtg    720

aggtttgtct ttggaaccac accagaagac atcctcagga acaaaggctg ctccagctct    780

accagtgtcc tcctcaccct tgacaacaac gtggtgaatg gttccagccc tgccatccgc    840

actaactaca ttggccacaa gacaaaggac ttgcaagcca tctgcggcat ctcctgtgat    900
```

-continued

```
gagctgtcca gcatggtcct ggaactcagg ggcctgcgca ccattgtgac cacgctgcag     960
gacagcatcc gcaaagtgac tgaagagaac aaagagttgg ccaatgagct gaggcggcct    1020
cccctatgct atcacaacgg agttcagtac agaaataacg aggaatggac tgttgatagc    1080
tgcactgagt gtcactgtca gaactcagtt accatctgca aaaaggtgtc ctgccccatc    1140
atgccctgct ccaatgccac agttcctgat ggagaatgct gtcctcgctg ttggcccagc    1200
gactctgcgg acgatggctg gtctccatgg tccgagtgga cctcctgttc tacgagctgt    1260
ggcaatggaa ttcagcagcg cggccgctcc tgcgatagcc tcaacaaccg atgtgagggc    1320
tcctcggtcc agacacggac ctgccacatt caggagtgtg acaagagatt taaacaggat    1380
ggtggctgga gccactggtc cccgtggtca tcttgttctg tgacatgtgg tgatggtgtg    1440
atcacaagga tccggctctg caactctccc agcccccaga tgaacgggaa accctgtgaa    1500
ggcgaagcgc gggagaccaa agcctgcaag aaagacgcct gccccatcaa tggaggctgg    1560
ggtccttggt caccatggga catctgttct gtcacctgtg gaggaggggt acagaaacgt    1620
agtcgtctct gcaacaaccc cacaccccag tttggaggca aggactgcgt tggtgatgta    1680
acagaaaacc agatctgcaa caagcaggac tgtccaattg atggatgcct gtccaatccc    1740
tgctttgccg gcgtgaagtg tactagctac cctgatggca gctggaaatg tggtgcttgt    1800
ccccctggtt acagtggaaa tggcatccag tgcacagatg ttgatgagtg caaagaagtg    1860
cctgatgcct gcttcaacca caatggagag caccggtgtg agaacacgga ccccggctac    1920
aactgcctgc cctgcccccc acgcttcacc ggctcacagc ccttcggcca gggtgtcgaa    1980
catgccacgg ccaacaaaca ggtgtgcaag ccccgtaacc cctgcacgga tgggacccac    2040
gactgcaaca agaacgccaa gtgcaactac ctgggccact atagcgaccc catgtaccgc    2100
tgcgagtgca agcctggcta cgctggcaat ggcatcatct gcggggagga cacagacctg    2160
gatggctggc ccaatgagaa cctggtgtgc gtggccaatg cgacttacca ctgcaaaaag    2220
gataattgcc ccaaccttcc caactcaggg caggaagact atgacaagga tggaattggt    2280
gatgcctgtg atgatgacga tgacaatgat aaaattccag atgacaggga caactgtcca    2340
ttccattaca acccagctca gtatgactat gacagagatg atgtgggaga ccgctgtgac    2400
aactgtccct acaaccacaa cccagatcag gcagacacag acaacaatgg ggaaggagac    2460
gcctgtgctg cagacattga tggagacggt atcctcaatg aacgggacaa ctgccagtac    2520
gtctacaatg tggaccagag agacactgat atggatgggg ttggagatca gtgtgacaat    2580
tgccccttgg aacacaatcc ggatcagctg gactctgact cagaccgcat tggagatacc    2640
tgtgacaaca atcaggatat tgatgaagat ggccaccaga acaatctgga caactgtccc    2700
tatgtgccca atgccaacca ggctgaccat gacaaagatg gcaagggaga tgcctgtgac    2760
cacgatgatg acaacgatgg cattcctgat gacaaggaca actgcagact cgtgcccaat    2820
cccgaccaga aggactctga cggcgatggt cgaggtgatg cctgcaaaga tgattttgac    2880
catgacagtg tgccagacat cgatgacatc tgtcctgaga atgttgacat cagtgagacc    2940
gatttccgcc gattccagat gattcctctg gaccccaaag ggacatccca aaatgaccct    3000
aactgggttg tacgccatca gggtaaagaa ctcgtccaga ctgtcaactg tgatcctgga    3060
ctcgctgtag gttatgatga gtttaatgct gtggacttca gtggcacctt cttcatcaac    3120
accgaaaggg acgatgacta tgctggattt gtctttggct accagtccag cagccgcttt    3180
tatgttgtga tgtggaagca agtcacccag tcctactggg acaccaaccc cacgagggct    3240
```

-continued

```
cagggatact cgggcctttc tgtgaaagtt gtaaactcca ccacagggcc tggcgagcac   3300

ctgcggaacg ccctgtggca cacaggaaac acccctggcc aggtgcgcac cctgtggcat   3360

gaccctcgtc acataggctg gaaagatttc accgcctaca gatggcgtct cagccacagg   3420

ccaaagacgg gtttcattag agtggtgatg tatgaaggga agaaaatcat ggctgactca   3480

ggacccatct atgataaaac ctatgctggt ggtagactag ggttgtttgt cttctctcaa   3540

gaaatggtgt tcttctctga cctgaaatac gaatgtagag atccctaatc atcaaattgt   3600

tgattgaaag actgatcata aaccaatgct ggtattgcac cttctggaac tatgggcttg   3660

agaaaacccc caggatcact tctccttggc ttccttcttt tctgtgcttg catcagtgtg   3720

gactcctaga acgtgcgacc tgcctcaaga aaatgcagtt ttcaaaaaca gactcagcat   3780

tcagcctcca atgaataaga catcttccaa gcatataaac aattgctttg gtttcctttt   3840

gaaaaagcat ctacttgctt cagttgggaa ggtgcccatt ccactctgcc tttgtcacag   3900

agcagggtgc tattgtgagg ccatctctga gcagtggact caaaagcatt ttcaggcatg   3960

tcagagaagg gaggactcac tagaattagc aaacaaaacc accctgacat cctccttcag   4020

gaacacgggg agcagaggcc aaagcactaa ggggagggcg catacccgag acgattgtat   4080

gaagaaaata tggaggaact gttacatgtt cggtactaag tcattttcag ggattgaaa    4140

gactattgct ggatttcatg atgctgactg gcgttagctg attaacccat gtaaataggc   4200

acttaaatag aagcaggaaa gggagacaaa gactggcttc tggacttcct ccctgatccc   4260

cacccttact catcacctgc agtggccaga attagggaat cagaatcgaa accagtgtaa   4320

ggcagtgctg gctgccattg cctggtcaca ttgaaattgg tggcttcatt ctagatgtag   4380

cttgtgcaga tgtagcagga aaataggaaa acctaccatc tcagtgagca ccag         4434
```

<210> SEQ ID NO 18
<211> LENGTH: 1377
<212> TYPE: DNA
<213> ORGANISM: Homo sapiens

<400> SEQUENCE: 18

```
atttctcttt agttctttgc aagaaggtag agataaagac actttttcaa aaatggcaat     60

ggtatcagaa ttcctcaagc aggcctggtt tattgaaaat gaagagcagg aatatgttca    120

aactgtgaag tcatccaaag gtggtcccgg atcagcggtg agcccctatc ctaccttcaa    180

tccatcctcg gatgtcgctg ccttgcataa ggccataatg gttaaaggtg tggatgaagc    240

aaccatcatt gacattctaa ctaagcgaaa caatgcacag cgtcaacaga tcaaagcagc    300

atatctccag gaaacaggaa agcccctgga tgaaacactg aagaaagccc ttacaggtca    360

ccttgaggag gttgttttag ctctgctaaa aactccagcg caatttgatg ctgatgaact    420

tcgtgctgcc atgaagggcc ttggaactga tgaagatact ctaattgaga ttttggcatc    480

aagaactaac aaagaaatca gagacattaa cagggtctac agagaggaac tgaagagaga    540

tctggccaaa gacataacct cagacacatc tggagatttt cggaacgctt tgctttctct    600

tgctaagggt gaccgatctg aggactttgg tgtgaatgaa gacttggctg attcagatgc    660

cagggccttg tatgaagcag gagaaaggag aaaggggaca gacgtaaacg tgttcaatac    720

catccttacc accagaagct atccacaact tcgcagagtg tttcagaaat acaccaagta    780

cagtaagcat gacatgaaca aagttctgga cctggagttg aaaggtgaca ttgagaaatg    840

cctcacagct atcgtgaagt gcgccacaag caaaccagct ttctttgcag agaagcttca    900

tcaagccatg aaaggtgttg gaactcgcca taaggcattg atcaggatta tggtttcccg    960
```

-continued ttctgaaatt gacatgaatg atatcaaagc attctatcag aagatgtatg gtatctccct 1020
ttgccaagcc atcctggatg aaaccaaagg agattatgag aaaatcctgg tggctctttg 1080
tggaggaaac taaacattcc cttgatggtc tcaagctatg atcagaagac tttaattata 1140
tattttcatc ctataagctt aaataggaaa gtttcttcaa caggattaca gtgtagctac 1200
ctacatgctg aaaaatatag cctttaaatc atttttatat tataactctg tataatagag 1260
ataagtccat tttttaaaaa tgttttcccc aaaccataaa accctataca agttgttcta 1320
gtaacaatac atgagaaaga tgtctatgta gctgaaaata aaatgacgtc acaagac 1377

<210> SEQ ID NO 19
<211> LENGTH: 3370
<212> TYPE: DNA
<213> ORGANISM: Homo sapiens

<400> SEQUENCE: 19
gcccccgccc ggcccgcccc gctctcctag tcccttgcaa cctggcgctg catccgggcc 60
actgtcccag gtcccaggtc ccggcccgga gctatggagc ggcgctggcc cctggggcta 120
gggctggtgc tgctgctctg cgccccgctg cccccggggg cgcgcgccaa ggaagttact 180
ctgatggaca caagcaaggc acagggagag ctgggctggc tgctggatcc cccaaaagat 240
gggtggagtg aacagcaaca gatactgaat gggacacccc tctacatgta ccaggactgc 300
ccaatgcaag gacgcagaga cactgaccac tggcttcgct ccaattggat ctaccgcggg 360
gaggaggctt cccgcgtcca cgtggagctg cagttcaccg tgcgggactg caagagtttc 420
cctgggggag ccgggcctct gggctgcaag gagaccttca accttctgta catggagagt 480
gaccaggatg tgggcattca gctccgacgg cccttgttcc agaaggtaac cacggtggct 540
gcagaccaga gcttcaccat tcgagacctt gcgtctggct ccgtgaagct gaatgtggag 600
cgctgctctc tgggccgcct gacccgccgt ggcctctacc tcgctttcca caacccgggt 660
gcctgtgtgg ccctggtgtc tgtccgggtc ttctaccagc gctgtcctga gaccctgaat 720
ggcttggccc aattcccaga cactctgcct ggccccgctg ggttggtgga agtggcgggc 780
acctgcttgc cccacgcgcg ggccagcccc aggccctcag gtgcaccccg catgcactgc 840
agccctgatg gcgagtggct ggtgcctgta ggacggtgcc actgtgagcc tggctatgag 900
gaaggtggca gtggcgaagc atgtgttgcc tgccctagcg gctcctaccg gatggacatg 960
gacacacccc attgtctcac gtgcccccag cagagcactg ctgagtctga gggggccacc 1020
atctgtacct gtgagagcgg ccattacaga gctcccgggg agggccccca ggtggcatgc 1080
acaggtcccc cctcggcccc ccgaaacctg agcttctctg cctcagggac tcagctctcc 1140
ctgcgttggg aacccccagc agatacgggg ggacgccagg atgtcagata cagtgtgagg 1200
tgttcccagt gtcagggcac agcacaggac gggggggccct gccagccctg tggggtgggc 1260
gtgcacttct cgccgggggc ccgggcgctc accacacctg cagtgcatgt caatggcctt 1320
gaaccttatg ccaactacac ctttaatgtg gaagcccaaa atggagtgtc agggctgggc 1380
agctctggcc atgccagcac ctcagtcagc atcagcatgg ggcatgcaga gtcactgtca 1440
ggcctgtctc tgagactggt gaagaaagaa ccgaggcaac tagagctgac ctgggcgggg 1500
tcccggcccc gaagccctgg ggcgaacctg acctatgagc tgcacgtgct gaaccaggat 1560
gaagaacggt accagatggt tctagaaccc agggtcttgc tgacagagct gcagcctgac 1620
accacataca tcgtcagagt ccgaatgctg accccactgg gtcctggccc tttctcccct 1680

-continued

```
gatcatgagt ttcggaccag cccaccagtg tccaggggcc tgactggagg agagattgta   1740

gccgtcatct ttgggctgct gcttggtgca gccttgctgc ttgggattct cgttttccgg   1800

tccaggagag cccagcggca gaggcagcag aggcacgtga ccgcgccacc gatgtggatc   1860

gagaggacaa gctgtgctga agccttatgt ggtacctcca ggcatacgag gaccctgcac   1920

agggagcctt ggactttacc cggaggctgg tctaattttc cttcccggga gcttgatcca   1980

gcgtggctga tggtggacac tgtcatagga gaaggagagt ttggggaagt gtatcgaggg   2040

accctcaggc tccccagcca ggactgcaag actgtggcca ttaagacctt aaaagacaca   2100

tccccaggtg gccagtggtg gaacttcctt cgagaggcaa ctatcatggg ccagtttagc   2160

cacccgcata ttctgcatct ggaaggcgtc gtcacaaagc gaaagccgat catgatcatc   2220

acagaattta tggagaatgc agccctggat gccttcctga gggagcggga ggaccagctg   2280

gtccctgggc agctagtggc catgctgcag ggcatagcat ctggcatgaa ctacctcagt   2340

aatcacaatt atgtccaccg ggacctggct gccagaaaca tcttggtgaa tcaaaacctg   2400

tgctgcaagg tgtctgactt tggcctgact cgcctcctgg atgactttga tggcacatac   2460

gaaacccagg gaggaaagat ccctatccgt tggacagccc ctgaagccat tgcccatcgg   2520

atcttcacca cagccagcga tgtgtggagc tttgggattg tgatgtggga ggtgctgagc   2580

tttggggaca agccttatgg ggagatgagc aatcaggagg ttatgaagag cattgaggat   2640

gggtaccggt tgccccctcc tgtggactgc cctgcccctc tgtatgagct catgaagaac   2700

tgctgggcat atgaccgtgc ccgccggcca cacttccaga agcttcaggc acatctggag   2760

caactgcttg ccaaccccca ctccctgcgg accattgcca actttgaccc caggtgact   2820

cttcgcctgc ccagcctgag tggctcagat gggatcccgt atcgaaccgt ctctgagtgg   2880

ctcgagtcca tacgcatgaa acgctacatc ctgcacttcc actcggctgg gctggacacc   2940

atggagtgtg tgctggagct gaccgctgag gacctgacgc agatgggaat cacactgccc   3000

gggcaccaga agcgcattct ttgcagtatt cagggattca aggactgatc cctcctctca   3060

ccccatgccc aatcagggtg caaggagcaa ggacggggcc aaggtcgctc atggtcactc   3120

cctgcgcccc ttcccacaac ctgccagact aggctatcgg tgctgcttct gcccgcttta   3180

aggagaaccc tgctctgcac cccagaaaac ctctttgttt taaaagggag gtgggggtag   3240

aagtaaaagg atgatcatgg gagggagctc aggggttaat atatatacat acatacacat   3300

atatatattg ttgtaaataa acaggaaatg attttctgcc tccatcccac ccatcagggc   3360

tgcaggcact                                                          3370
```

<210> SEQ ID NO 20
<211> LENGTH: 1913
<212> TYPE: DNA
<213> ORGANISM: Homo sapiens

<400> SEQUENCE: 20

```
ccaagagcta cgcggcggcg gcggagcgca ggcctcgtgc cgttacggcc atcacggcgg     60

ccgcagtggc gtcctggagc cctcctcagt gctgaagctg ctgaaagatg gcagaagaag    120

tggtggtagt agccaaattt gattatgtgg cccaacaaga acaagagttg gacatcaaga    180

agaatgagag attatggctt ctggatgatt ctaagtcctg gtggcgagtt cgaaattcca    240

tgaataaaac aggttttgtg ccttctaact atgtggaaag gaaaaacagt gctcggaaag    300

catctattgt gaaaaaccta aaggatacct taggcattgg aaaagtgaaa agaaaaccta    360

gtgtgccaga ttctgcatct cctgctgatg atagttttgt tgacccaggg gaacgtctct    420
```

-continued

```
atgacctcaa catgcccgct tatgtgaaat ttaactacat ggctgagaga gaggatgaat    480

tatcattgat aaaggggaca aaggtgatcg tcatggagaa atgcagtgat gggtggtggc    540

gtggtagcta caatggacaa gttggatggt tcccttcaaa ctatgtaact gaagaaggtg    600

acagtccttt gggtgaccat gtgggttctc tgtcagagaa attagcagca gtcgtcaata    660

acctaaatac tgggcaagtg ttgcatgtgg tacaggctct ttacccattc agctcatcta    720

atgatgaaga acttaatttc gagaaaggag atgtaatgga tgttattgaa aaacctgaaa    780

atgacccaga gtggtggaaa tgcaggaaga tcaatggtat ggttggtcta gtaccaaaaa    840

actatgttac cgttatgcag aataatccat taacttcagg tttggaacca tcacctccac    900

agtgtgatta cattaggcct tcactcactg gaaagtttgc tggcaatcct tggtattatg    960

gcaaagtcac caggcatcaa gcagaaatgg cattaaatga aagaggacat gaaggggatt   1020

tcctcattcg tgatagtgaa tcttcgccaa atgatttctc agtatcacta aaagcacaag   1080

ggaaaaacaa gcattttaaa gtccaactaa aagagactgt ctactgcatt gggcagcgta   1140

aattcagcac catggaagaa cttgtagaac attacaaaaa ggcaccaatt tttacaagtg   1200

aacaaggaga aaaattatat cttgtcaagc atttatcatg atactgctga ccagaagtga   1260

ctgctgtgta gctgtaattt gtcatgtaat tgaagactga gaaaatgttg ggtccagtcg   1320

tgcttgattg gaaattgttg tttctaaatc tatatgagaa ttgacaataa gtatttttat   1380

tataactcag cccatacata tatactatgt atgcagtgca tctgcataga acagttcctt   1440

atccttggcc ttctgtttta ttgttttttt ctttgctgtt ttccctttgc ttctaatatt   1500

acagttttgt attttgtaaa caaaaatcaa ataatgcata tcagaatctt tatatggaag   1560

aaatccttta ttgcctttcc tttgtttcct tgtaaaggca ccctgttctg ttatggtttt   1620

tcattatata aaattattat atctatatat gacatatgct aaaatttctt ggagagtgtt   1680

aatcttttct gtgactaaat agcaataata agtggaaaat tagaaattat ttccaggtat   1740

tatatttgtc acaggccatt gtaaatacca agtatattgt gtctgccata atttttaaaa   1800

atacattcat tgtcttcagt catacagcaa gacacatgag acatagatta gaaaacatgt   1860

tgtacaattt taatttacaa ctgttggaaa taaaaatcac ttaatttttt tcc          1913
```

<210> SEQ ID NO 21
<211> LENGTH: 3257
<212> TYPE: DNA
<213> ORGANISM: Homo sapiens

<400> SEQUENCE: 21

```
catggcggcg actgcggcaa agcgagagcc tcggagacgc cgctgccgcc agcacagccg     60

gagacctgag ccgacactgg gggcagtccg cgagccccgc actctctcga tgagtcggag    120

aagtcccgtt gtatcagagt aagatggacg gtagctttga ttgtgattgt ggtgagctgg    180

agccacctga tcactaacaa aagacatctt ctgttaacca acagccgcca gggcttcctg    240

ttgaaataaa tatatagcaa caaaggaaaa aaagaagcaa aacggaaata gtgcttacca    300

gcaccttaga atgatgctgc tcaggaccag tccaacactg aatgtatctg cactgtgagg    360

agaatgttca tagaagcctg ttgtgtgcat atttattcac atttttgtta aatgttaaat    420

cgtttagcac ggtaatctga gtgcacagta tgtcatttca ttccgtttga gtttcttgtt    480

ttcgttaaat gtctgcagag ttgctgcccc tttcttgaac tatgagtact gcaatctttt    540

taattctcaa tatgaataga gctttttgag ctttaaatct aaggggaact cgacaggcct    600
```

-continued

```
gtttggcata tgcaatgaac atcaagaaac catcttgctg tggaagcata attatttttc    660
ttctcccttt ttgaaagatc tttccttttg atgccagttt tcttccttgt ttacacaagt    720
tcaatttgaa aggaaaaggc aatagtaagg gtttcaaaat ggcagagaaa tttgaaagtc    780
tcatgaacat tcatggtttt gatctgggtt ctaggtatat ggacttaaaa ccattgggtt    840
gtggaggcaa tggcttggtt ttttctgctg tagacaatga ctgtgacaaa agagtagcca    900
tcaagaaaat tgtccttact gatccccaga gtgtcaaaca tgctctacgt gaaatcaaaa    960
ttattagaag acttgaccat gataacattg tgaaagtgtt tgagattctt ggtcccagtg   1020
gaagccaatt aacagacgat gtgggctctc ttacggaact gaacagtgtt tacattgttc   1080
aggagtacat ggagacagac ttggctaatg tgctggagca gggcccttta ctggaagagc   1140
atgccaggct tttcatgtat cagctgctac gggggctcaa gtatattcac tctgcaaatg   1200
tactgcacag agatctcaaa ccagctaatc ttttcattaa tacggaagac ttggtgctga   1260
agataggtga ctttggtctt gcacggatca tggatcctca ttattcccat aagggtcatc   1320
tttctgaagg attggttact aaatggtaca gatctccacg tcttttactt tctcctaata   1380
attatactaa agccattgac atgtgggctg caggctgcat ctttgctgaa atgctgactg   1440
gtaaaaccct ttttgcaggt gcacatgaac ttgaacagat gcagctgatt ttagaatcta   1500
ttcctgttgt acatgaggaa gatcgtcagg agcttctcag cgtaattcca gtttacatta   1560
gaaatgacat gactgagcca cacaaacctt taactcagct gcttccagga attagtcgag   1620
aagcactgga tttcctggaa caaattttga catttagccc catggatcgg ttaacagcag   1680
aagaagcact ctcccatcct tacatgagca tatattcttt tccaatggat gagccaattt   1740
caagccatcc ttttcatatt gaagatgaag ttgatgatat tttgcttatg gatgaaactc   1800
acagtcacat ttataactgg gaaaggtatc atgattgtca gttttcagag catgattggc   1860
ctgtacataa caactttgat attgatgaag ttcagcttga tccaagagct ctgtccgatg   1920
tcactgatga agaagaagta caagttgatc cccgaaaata tttggatgga gatcgggaaa   1980
agtatctgga ggatcctgct tttgatacca attactctac tgagccttgt tggcaatact   2040
cagatcatca tgaaaacaaa tattgtgatc tggagtgtag ccatacttgt aactacaaaa   2100
cgaggtcatc atcatattta gataacttag tttggagaga gagtgaagtt aaccattact   2160
atgaacccaa gcttattata gatctttcca attggaaaga acaaagcaaa gaaaaatctg   2220
ataagaaagg caaatcaaaa tgtgaaagga atggattggt taaagcccag atagcgctag   2280
aggaagcatc acagcaactg gctggaaaag aaagggaaaa gaatcaggga tttgattttg   2340
attcctttat tgcaggaact attcagctta gttcccagca tgagcctact gatgttgttg   2400
ataaattaaa tgacttgaat agctcagtgt cccaactaga attgaaaagt ttgatatcaa   2460
agtcagtaag ccaagaaaaa caggaaaaag gaatggcaaa tctggctcaa ttagaagcct   2520
tgtaccagtc ttcttgggac agccagtttg tgagtggtgg ggaggactgt tttttcataa   2580
atcagttttg tgaggtaagg aaggatgaac aagttgagaa ggaaaacact tacactagtt   2640
acttggacaa gttctttagc aggaaagaag atactgaaat gctagaaact gagccagtag   2700
aggatgggaa gcttggggag agaggacatg aggaaggatt tctgaacaac agtggggagt   2760
tcctctttaa caagcagctc gagtccatag gcatcccaca gtttcacagt ccagttgggt   2820
caccacttaa gtcaatacag gccacattaa caccttctgc tatgaaatct tcccctcaaa   2880
ttcctcatca aacatacagc agcattctga aacatctgaa ctaaaacact cagcagacat   2940
ttatctttgt attcttcatg aaatgtgttt tgtctttttt tattactagt gtttaagtca   3000
```

-continued

```
tttttactt gaatcagatg gtgtcattta gtaaggattt tatgagttct tgttttttaa   3060
aatccagact ttctttttct acatgtgaga tagttttcat tttaactggc atgtcatttg   3120
cacacaaaaa taaagactag agcaaaataa tgcaacgcag gaggagaaaa gaaatgcact   3180
aagacaagaa cattctctca tagaacattg atctgtttta caggaaacaa accttgcctt   3240
gaaatttaca cagtgag                                                  3257
```

<210> SEQ ID NO 22
<211> LENGTH: 2354
<212> TYPE: DNA
<213> ORGANISM: Homo sapiens

<400> SEQUENCE: 22

```
ggtctttgag cgctaacgtc tttctgtctc cccgcggtgg tgatgacggt gaaaactgag     60
gctgctaagg gcaccctcac ttactccagg atgaggggca tggtggcaat tctcatcgct    120
ttcatgaagc agaggaggat gggtctgaac gactttattc agaagattgc caataactcc    180
tatgcatgca aacaccctga agttcagtcc atcttgaaga tctcccaacc tcaggagcct    240
gagcttatga atgccaaccc ttctcctcca ccaagtcctt ctcagcaaat caaccttggc    300
ccgtcgtcca atcctcatgc taaaccatct gactttcact tcttgaaagt gatcggaaag    360
ggcagttttg gaaaggttct tctagcaaga cacaaggcag aagaagtgtt ctatgcagtc    420
aaagttttac agaagaaagc aatcctgaaa aagaaagagg agaagcatat tatgtcggag    480
cggaatgttc tgttgaagaa tgtgaagcac cctttcctgg tgggccttca cttctctttc    540
cagactgctg acaaattgta ctttgtccta gactacatta atggtggaga gttgttctac    600
catctccaga gggaacgctg cttcctggaa ccacgggctc gtttctatgc tgctgaaata    660
gccagtgcct tgggctacct gcattcactg aacatcgttt atagagactt aaaaccagag    720
aatattttgc tagattcaca gggacacatt gtccttactg acttcggact ctgcaaggag    780
aacattgaac acaacagcac aacatccacc ttctgtggca cgccggagta tctcgcacct    840
gaggtgcttc ataagcagcc ttatgacagg actgtggact ggtggtgcct gggagctgtc    900
ttgtatgaga tgctgtatgg cctgccgcct ttttatagcc gaaacacagc tgaaatgtac    960
gacaacattc tgaacaagcc tctccagctg aaaccaaata ttacaaattc cgcaagacac   1020
ctcctggagg gcctcctgca gaaggacagg acaaagcggc tcggggccaa ggatgacttc   1080
atggagatta agagtcatgt cttcttctcc ttaattaact gggatgatct cattaataag   1140
aagattactc cccctttttaa cccaaatgtg agtgggccca acgacctacg gcactttgac   1200
cccgagttta ccgaagagcc tgtccccaac tccattggca agtcccctga cagcgtcctc   1260
gtcacagcca gcgtcaagga agctgccgag gctttcctag gcttttccta tgcgcctccc   1320
acggactctt tcctctgaac cctgttaggg cttggtttta aaggatttta tgtgtgtttc   1380
cgaatgtttt agttagcctt ttggtggagc cgccagctga caggacatct tacaagagaa   1440
tttgcacatc tctggaagct tagcaatctt attgcacact gttcgctgga agctttttga   1500
agagcacatt ctcctcagtg agctcatgag gttttcattt ttattcttcc ttccaacgtg   1560
gtgctatctc tgaaacgagc gttagagtgc cgccttagac ggaggcagga gtttcgttag   1620
aaagcggacg ctgttctaaa aaaggtctcc tgcagatctg tctgggctgt gatgacgaat   1680
attatgaaat gtgccttttc tgaagagatt gtgttagctc caaagctttt cctatcgcag   1740
tgtttcagtt ctttattttc ccttgtggat atgctgtgtg aaccgtcgtg tgagtgtggt   1800
```

-continued

```
atgcctgatc acagatggat tttgttataa gcatcaatgt gacacttgca ggacactaca   1860

acgtgggaca ttgtttgttt cttccatatt tggaagataa atttatgtgt agactttttt   1920

gtaagatacg gttaataact aaaatttatt gaaatggtct tgcaatgact cgtattcaga   1980

tgcttaaaga aagcattgct gctacaaata tttctatttt tagaaagggt ttttatggac   2040

caatgcccca gttgtcagtc agagccgttg gtgtttttca ttgtttaaaa tgtcacctgt   2100

aaaatgggca ttatttatgt tttttttttt gcattcctga taattgtatg tattgtataa   2160

agaacgtctg tacattgggt tataacacta gtatatttaa acttacaggc ttatttgtaa   2220

tgtaaaccac cattttaatg tactgtaatt aacatggtta taatacgtac aatccttccc   2280

tcatcccatc acacaacttt ttttgtgtgt gataaactga ttttggtttg caataaaacc   2340

ttgaaaaata ttta                                                     2354
```

<210> SEQ ID NO 23
<211> LENGTH: 1728
<212> TYPE: DNA
<213> ORGANISM: Homo sapiens

<400> SEQUENCE: 23

```
gagcagcaga atttcaactc cagtagactt gaatatgcct ctgggcaaag aagcagagct     60

aacgaggaaa gggatttaaa gagtttttct tgggtgtttg tcaaactttt attccctgtc    120

tgtgtgcaga ggggattcaa cttcaatttt tctgcagtgg ctctgggtcc agccccttac    180

ttaaagatct ggaaagcatg aagactgggc tttttttcct atgtctcttg ggaactgcag    240

ctgcaatccc gacaaatgca agattattat ctgatcattc caaaccaact gctgaaacgg    300

tagcacctga caacactgca atccccagtt taagggctga agctgaagaa aatgaaaaag    360

aaacagcagt atccacagaa gacgattccc accataaggc tgaaaaatca tcagtactaa    420

agtcaaaaga ggaaagccat gaacagtcag cagaacaggg caagagttct agccaagagc    480

tgggattgaa ggatcaagag gacagtgatg gtcacttaag tgtgaatttg gagtatgcac    540

caactgaagg tacattggac ataaaagaag atatgagtga gcctcaggag aaaaaactct    600

cagagaacac tgatttttttg gctcctggtg ttagttcctt cacagattct aaccaacaag    660

aaagtatcac aaagagagag gaaaaccaag aacaacctag aaattattca catcatcagt    720

tgaacaggag cagtaaacat agccaaggcc taagggatca aggaaaccaa gagcaggatc    780

caaatatttc caatggagaa gaggaagaag aaaaagagcc aggtgaagtt ggtacccaca    840

atgataacca agaaagaaag acagaattgc ccagggagca tgctaacagc aagcaggagg    900

aagacaatac ccaatctgat gatattttgg aagagtctga tcaaccaact caagtaagca    960

agatgcagga ggatgaattt gatcagggta accaagaaca agaagataac tccaatgcag   1020

aaatggaaga ggaaaatgca tcgaacgtca ataagcacat tcaagaaact gaatggcaga   1080

gtcaagaggg taaaactggc ctagaagcta tcagcaacca caaagagaca gaagaaaaga   1140

ctgtttctga ggctctgctc atggaaccta ctgatgatgg taataccacg cccagaaatc   1200

atggagttga tgatgatggc gatgatgatg gcgatgatgg cggcactgat ggccccaggc   1260

acagtgcaag tgatgactac ttcatcccaa gccaggcctt tctggaggcc gagagagctc   1320

aatccattgc ctatcacctc aaaattgagg agcaaagaga aaaagtacat gaaaatgaaa   1380

atataggtac cactgagcct ggagagcacc aagaggccaa gaaagcagag aactcatcaa   1440

atgaggagga aacgtcaagt gaaggcaaca tgagggtgca tgctgtggat tcttgcatga   1500

gcttccagtg taaaagaggc cacatctgta aggcagacca acagggaaaa cctcactgtg   1560
```

-continued

```
tctgccagga tccagtgact tgtcctccaa caaaacccct tgatcaagtt tgtggcactg   1620

acaatcagac ctatgctagt tcctgtcatc tattcgctac taaatgcaga ctggagggga   1680

ccaaaaaggg gcatcaactc cagctggatt attttggagc ctgcaaat                1728
```

<210> SEQ ID NO 24
<211> LENGTH: 1848
<212> TYPE: DNA
<213> ORGANISM: Homo sapiens

<400> SEQUENCE: 24

```
cggataagga caaaaaacgc cagaagaaaa gaggcatttt ccccaaagta gcaacaaata     60

tcatgagagc atggctcttc cagcatctca cacatccgta cccttccgaa gagcagaaga    120

aacagttagc gcaagacaca ggacttacaa ttctccaagt aaacaactgg tttattaatg    180

ccagaagaag aatagtacag cccatgattg accagtcaaa tcgagcagtg agccaaggag    240

cagcatatag tccagagggt cagcccatgg ggagctttgt gttggatggt cagcaacaca    300

tggggatccg gcctgcagga cctatgagtg gaatgggcat gaatatgggc atggatgggc    360

aatggcacta catgtaacct tcatcatgta aagcaatcgc aaagcaaggg ggaagtttgc    420

agagcatgcc aggggactac gtttctcagg gtggtcctat gggaatgagt atggcacagc    480

caagttacac tcctccccag atgaccccac accctactca attaagacat ggacccccaa    540

tgcattcata tttgccaagc catccccacc acccagccat gatgatgcac ggaggacccc    600

ctacccaccc tggaatgact atgtcagcac agagccccac aatgttaaat tctgtagatc    660

ccaatgttgg cggacaggtt atggacattc atgcccaata gtataaggga actcaaggga    720

aaaggaaaca cacgcaaaaa ctattttaag actttctgaa ctttgaccag atgttgacac    780

ttaatatgaa attccagaca gctgtgatta tttttttactt ttgtcatttt tcatcaagca    840

acagaggacc aatgcaacaa gaacacaaat gtgaaatcat gggctgactg agacaattct    900

gtccatgtaa agatcctctg gaaaaagact ccgagagtta taactactgt agtataaata    960

taggaactaa gttaaacttg tacatttctg ttgatcacgc cgttatgttg cctcaaatag   1020

ttttagaaga gaaaaaaaaa tatatccttg ttttccacac tatgtgtgtt gttcccaaaa   1080

gaatgactgt tttggttcat cagtgaattc accatccagg agagactgtg gtatatattt   1140

taaacctgtt gggccaatga gaaaagaacc acactggaga tcatgatgaa cttttggctg   1200

aacctcatca ctcgaactcc agcttcaaga atgtgttttc atgcccggcc tttgttcctc   1260

cataaatgtg tcctttagtt tcaaacagat ctttatagtt cgtgcttcat aagccaattc   1320

ttattattat ttttggggga ctcttcttca aagagcttgc caatgaagat ttaaagacag   1380

agcaggagct tcttccagga gttctgagcc ttggttgtgg acaaaacaat cttaagttgg   1440

gcagctttcc tcaacacaaa aaaaagttat taatggtcat tgaaccataa ctaggacttt   1500

atcagaaact caaagcttgg gggataaaaa ggagcaagag aatactgtaa caaacttcgt   1560

acagagttcg gtctattaat tgtttcatgt tagatattct atgtgtttac ctcaattgaa   1620

aaaaaaaaga atgtttttgc tagtatcaga tctgctgtgg aattggtatt gtatgtccat   1680

gaattcttct tttctcagca cgtgttcctc actagaagaa aatgctgtta cctttaagct   1740

ttgtcaaatt tacattaaaa tacttgtatg aggactgtga cgttatgtta aaaaaaaaaa   1800

ggtgttaagt cacaaaaagc ggtaataaat atttcatttt tgattttt                1848
```

<210> SEQ ID NO 25

-continued

<211> LENGTH: 3164
<212> TYPE: DNA
<213> ORGANISM: Homo sapiens

<400> SEQUENCE: 25
agcacactga ggaggcgatc cgccagcagg aggtggagca gctggacttc cgagacctcc 60
tggggaagaa ggtgagtaca aagaccctat cggaagacga cctgaaggag atcccagccg 120
agcagatgga tttccgtgcc aacctgcagc ggcaagtgaa gccaaagact gtgtctgagg 180
aagagaggaa ggtgcacagc cccagcagg tcgattttcg ctctgtcctg gccaagaagg 240
ggacttccaa gaccccgtg cctgagaagg tgccaccgcc aaaacctgcc accccggatt 300
ttcgctcagt gctgggtggc aagaagaaat taccagcaga gaatggcagc agcagtgccg 360
agaccctgaa tgccaaggca gtggagagtt ccaagcccct gagcaatgca cagccttcag 420
ggcccttgaa acccgtgggc aacgccaagc ctgctgagac cctgaagcca atgggcaacg 480
ccaagcctgc cgagaccctg aagcccatgg gcaatgccaa gcctgatgag aacctgaaat 540
ccgctagcaa agaagaactc aagaaagacg ttaagaatga tgtgaactgc aagagaggcc 600
atgcagggac cacagataat gaaaagagat cagagagcca ggggacagcc ccagccttca 660
agcagaagct gcaagatgtt catgtggcag agggcaagaa gctgctgctc cagtgccagg 720
tgtcttctga ccccccagcc accatcatct ggacgctgaa cggaaagacc atcaagacca 780
ccaagttcat catcctctcc caggaaggct cactctgctc cgtctccatc gagaaggcac 840
tgcctgagga cagaggctta tacaagtgtg tagccaagaa tgacgctggc caggcggagt 900
gctcctgcca agtcaccgtg gatgatgctc cagccagtga gaacaccaag gccccagaga 960
tgaaatcccg gaggcccaag agctctcttc ctcccgtgct aggaactgag agtgatgcga 1020
ctgtgaaaaa gaaacctgcc cccaagacac ctccgaaggc agcaatgccc cctcagatca 1080
tccagttccc tgaggaccag aaggtacgcg caggagagtc agtggagctg tttggcaaag 1140
tgacaggcac tcagcccatc acctgtacct ggatgaagtt ccgaaagcag atccaggaaa 1200
gcgagcacat gaaggtggag aacagcgaga atggcagcaa gctcaccatc ctggccgcgc 1260
gccaggagca ctgcggctgc tacacactgc tggtggagaa caagctgggc agcaggcagg 1320
cccaggtcaa cctcactgtc gtggataagc cagacccccc agctggcaca ccttgtgcct 1380
ctgacattcg gagctcctca ctgaccctgt cctggtatgg ctcctcatat gatgggggca 1440
gtgctgtaca gtcctacagc atcgagatct gggactcagc caacaagacg tggaaggaac 1500
tagccacatg ccgcagcacc tctttcaacg tccaggacct gctgcctgac cacgaatata 1560
agttccgtgt acgtgcaatc aacgtgtatg gaaccagtga gccaagccag gagtctgaac 1620
tcacaacggt aggagagaaa cctgaagagc cgaaggatga agtggaggtg tcagacgatg 1680
atgagaagga gcccgaggtt gattaccgga cagtgacaat caatactgaa caaaaagtat 1740
ctgacttcta cgacattgag gagagattag gatctgggaa atttggacag gtctttcgac 1800
ttgtagaaaa gaaaactcga aaagtctggg cagggaagtt cttcaaggca tattcagcaa 1860
aagagaaaga gaatatccgg caggagatta gcatcatgaa ctgcctccac caccctaagc 1920
tggtccagtg tgtggatgcc tttgaagaaa aggccaacat cgtcatggtc ctggagatcg 1980
tgtcaggagg ggagctgttt gagcgcatca ttgacgagga ctttgagctg acggagcgtg 2040
agtgcatcaa gtacatgcgg cagatctcgg agggagtgga gtacatccac aagcagggca 2100
tcgtgcacct ggacctcaag ccggagaaca tcatgtgtgt caacaagacg ggcaccagga 2160
tcaagctcat cgactttggt ctggccagga ggctggagaa cgcggggtct ctgaaggtcc 2220

-continued

```
tctttggcac cccagaattt gtggctcctg aagtgatcaa ctatgagccc atcggctacg   2280
ccacagacat gtggagcatc ggggtcatct gctacatcct agtcagtggc ctttccccct   2340
tcatgggaga caacgataac gaaaccttgg ccaacgttac ctcagccacc tgggacttcg   2400
acgacgaggc attcgatgag atctccgacg atgccaagga tttcatcagc aatctgctga   2460
agaaagatat gaaaaaccgc ctggactgca cgcagtgcct tcagcatcca tggctaatga   2520
aagataccaa gaacatggag gccaagaaac tctccaagga ccggatgaag aagtacatgg   2580
caagaaggaa atggcagaaa acgggcaatg ctgtgagagc cattggaaga ctgtcctcta   2640
tggcaatgat ctcagggctc agtggcagga aatcctcaac agggtcacca accagcccgc   2700
tcaatgcaga aaaactagaa tctgaagaag atgtgtccca agctttcctt gaggctgttg   2760
ctgaggaaaa gcctcatgta aaaccctatt tctctaagac cattcgcgat ttagaagttg   2820
tggagggaag tgctgctaga tttgactgca agattgaagg atacccagac cccgaggttg   2880
tctggttcaa agatgaccag tcaatcaggg agtcccgcca cttccagata gactacgatg   2940
aggacgggaa ctgctcttta attattagtg atgtttgcgg ggatgacgat gccaagtaca   3000
cctgcaaggc tgtcaacagt cttggagaag ccacctgcac agcagagctc attgtggaaa   3060
cgatggagga aggtgaaggg gaaggggaag aggaagaaga gtgaaacaaa gccagagaaa   3120
agcagtttct aagtcatatt aaaaggacta tttctctaaa actc                    3164
```

```
<210> SEQ ID NO 26
<211> LENGTH: 3851
<212> TYPE: DNA
<213> ORGANISM: Homo sapiens

<400> SEQUENCE: 26

ctctcccaac cgcctcgtcg cactcctcag gctgagagca ccgctgcact cgcggccggc     60
gatgcgggac cccggcgcgg ccgctccgct ttcgtccctg ggcctctgtg ccctggtgct    120
ggcgctgctg ggcgcactgt ccgcgggcgc cggggcgcag ccgtaccacg gagagaaggg    180
catctccgtg ccggaccacg gcttctgcca gcccatctcc atcccgctgt gcacggacat    240
cgcctacaac cagaccatcc tgcccaacct gctgggccac acgaaccaag aggacgcggg    300
cctcgaggtg caccagttct acccgctggt gaaggtgcag tgttctcccg aactccgctt    360
tttcttatgc tccatgtatg cgcccgtgtg caccgtgctc gatcaggcca tcccgccgtg    420
tcgttctctg tgcgagcgcg cccgccaggg ctgcgaggcg ctcatgaaca agttcggctt    480
ccagtggccc gagcggctgc gctgcgagaa cttcccggtg cacggtgcgg gcgagatctg    540
cgtgggccag aacacgtcgg acggctccgg gggcccaggc ggcggcccca ctgcctaccc    600
taccgcgccc tacctgccgg acctgccctt caccgcgctg cccccggggg cctcagatgg    660
cagggggcgt cccgccttcc ccttctcatg cccccgtcag ctcaaggtgc ccccgtacct    720
gggctaccgc ttcctgggtg agcgcgattg tggcgccccg tgcgaaccgg gccgtgccaa    780
cggcctgatg tactttaagg aggaggagag gcgcttcgcc cgcctctggg tgggcgtgtg    840
gtccgtgctg tgctgcgcct cgacgctctt taccgttctc acctacctgg tggacatgcg    900
gcgcttcagc tacccagagc ggcccatcat cttcctgtcg ggctgctact tcatggtggc    960
cgtggcgcac gtggccggct tccttctaga ggaccgcgcc gtgtgcgtgg agcgcttctc   1020
ggacgatggc taccgcacgg tggcgcaggg caccaagaag gagggctgca ccatcctctt   1080
catggtgctc tacttcttcg gcatggccag ctccatctgg tgggtcattc tgtctctcac   1140
```

-continued

```
ttggttcctg gcggccggca tgaagtgggg ccacgaggcc atcgaggcca actcgcagta   1200
cttccacctg gccgcgtggg ccgtgcccgc cgtcaagacc atcactatcc tggccatggg   1260
ccaggtagac ggggacctgc tgagcggggt gtgctacgtt ggcctctcca gtgtggacgc   1320
gctgcggggc ttcgtgctgg cgcctctgtt cgtctacctc ttcataggca cgtccttctt   1380
gctggccggc ttcgtgtccc tcttccgtat ccgcaccatc atgaaacacg acggcaccaa   1440
gaccgagaag ctggagaagc tcatggtgcg catcggcgtc ttcagcgtgc tctacacagt   1500
gcccgccacc atcgtcctgg cctgctactt ctacgagcag gccttccgcg agcactggga   1560
gcgcacctgg ctcctgcaga cgtgcaagag ctatgccgtg ccctgcccgc ccggccactt   1620
cccgcccatg agccccgact tcaccgtctt catgatcaag tacctgatga ccatgatcgt   1680
cggcatcacc actggcttct ggatctggtc gggcaagacc ctgcagtcgt ggcgccgctt   1740
ctaccacaga cttagccaca gcagcaaggg ggagactgcg gtatgagccc cggcccctcc   1800
ccacctttcc caccccagcc ctcttgcaag aggagaggca cggtagggaa aagaactgct   1860
gggtgggggc ctgtttctgt aactttctcc ccctctactg agaagtgacc tggaagtgag   1920
aagttctttg cagatttggg gcgaggggtg atttggaaaa gaagacctgg gtggaaagcg   1980
gtttggatga aaagatttca ggcaaagact tgcaggaaga tgatgataac ggcgatgtga   2040
atcgtcaaag gtacgggcca gcttgtgcct aatagaaggt tgagaccagc agagactgct   2100
gtgagtttct cccggctccg aggctgaacg gggactgtga gcgatccccc tgctgcaggg   2160
cgagtggcct gtccagaccc ctgtgaggcc ccgggaaagg tacagccctg tctgcggtgg   2220
ctgctttgtt ggaaagaggg agggcctcct gcggtgtgct tgtcaagcag tggtcaaacc   2280
ataatctctt ttcactgggg ccaaactgga gcccagatgg gttaatttcc agggtcagac   2340
attacggtct ctcctcccct gccccctccc gcctgttttt cctcccgtac tgctttcagg   2400
tcttgtaaaa taagcatttg gaagtcttgg gaggcctgcc tgctagaatc ctaatgtgag   2460
gatgcaaaag aaatgatgat aacattttga gataaggcca aggagacgtg gagtaggtat   2520
ttttgctact ttttcatttt ctggggaagg caggaggcag aaagacgggt gttttatttg   2580
gtctaatacc ctgaaaagaa gtgatgactt gttgcttttc aaaacaggaa tgcatttttc   2640
cccttgtctt tgttgtaaga gacaaaagag gaaacaaaag tgtctccctg tggaaaggca   2700
taactgtgac gaaagcaact tttataggca aagcagcgca aatctgaggt ttcccgttgg   2760
ttgttaattt ggttgagata aacattcctt tttaaggaaa agtgaagagc agtgtgctgt   2820
cacacaccgt taagccagag gttctgactt cgctaaagga aatgtaagag gttttgttgt   2880
ctgttttaaa taaatttaat tcggaacaca tgatccaaca gactatgtta aaatattcag   2940
ggaaatctct cccttcattt actttttctt gctataagcc tatatttagg tttcttttct   3000
atttttttct cccatttgga tcctttgagg taaaaaaaca taatgtcttc agcctcataa   3060
taaaggaaag ttaattaaaa aaaaaaagca aagagccatt ttgtcctgtt ttcttggttc   3120
catcaatctg tttattaaac atcatccata tgctgaccct gtctctgtgt ggttgggttg   3180
ggaggcgatc agcagatacc atagtgaacg aagaggaagg tttgaaccat gggccccatc   3240
tttaaagaaa gtcattaaaa gaaggtaaac ttcaaagtga ttctggagtt ctttgaaatg   3300
tgctggaaga cttaaattta ttaatcttaa atcatgtact ttttttctgt aatagaactc   3360
ggattctttt gcatgatggg gtaaagctta gcagagaatc atgggagcta acctttatcc   3420
cacctttgac actaccctcc aatcttgcaa cactatcctg tttctcagaa cagtttttaa   3480
atgccaatca tagagggtac tgtaaagtgt acaagttact ttatatatgt aatgttcact   3540
```

-continued

```
tgagtggaac tgctttttac attaaagtta aaatcgatct tgtgtttctt caaccttcaa   3600

aactatctca tctgtcagat ttttaaaact ccaacacagg ttttggcatc ttttgtgctg   3660

tatcttttaa gtgcatgtga aatttgtaaa atagagataa gtacagtatg tatattttgt   3720

aaatctccca tttttgtaag aaaatatata ttgtatttat acatttttac tttggatttt   3780

tgttttgttg gctttaaagg tctaccccac tttatcacat gtacagatca caaataaatt   3840

tttttaaata c                                                        3851
```

<210> SEQ ID NO 27
<211> LENGTH: 1476
<212> TYPE: DNA
<213> ORGANISM: Homo sapiens

<400> SEQUENCE: 27

```
ggggctcggg acggccgggc tgggagctgg agcccacagc gggaagcggc cgccgcccgg     60

gcctcgcagg gctaggcgag gcgagggggg gcggggccgg gcgctacggg aaggggaggc    120

cgcgcggacc gggagccgca ccgcgccagc cgggctgcag cggccgcgca ccaaggctgc    180

gatggggctg gagacggaga aggcggacgt acagctcttc atggacgacg actcctacag    240

ccaccacagc ggcctcgagt acgccgaccc cgagaagttc gcggactcgg accaggaccg    300

ggatccccac cggctcaact cgcatctcaa gctgggcttc gaggatgtga tcgcagagcc    360

ggtgactacg cactcctttg acaaagtgtg gatctgcagc catgccctct ttgaaatcag    420

caaatacgta atgtacaagt tcctgacggt gttcctggcc attcccctgg ccttcattgc    480

gggaattctc tttgccaccc tcagctgtct gcacatctgg attttaatgc cttttgtaaa    540

gacctgccta atggttctgc cttcagtgca gacaatatgg aagagtgtga cagatgttat    600

cattgctcca ttgtgtacga gcgtaggacg atgcttctct tctgtcagcc tgcaactgag    660

ccaggattga atacttggac cccaggtctg gagattggga tactgtaata cttctttgtt    720

attataacat aaaagcacca ctgttctgtt catttcctag ctgttctaat taagaaaact    780

attaagatga gcaaccacat ttagaaatgt ttattgacag gtcttttcaa ataatgcttt    840

tctaattaat agccaaagat ttcatatcta actttgtaac cagaattata cagtaagttg    900

acaccactta gatttaaagg cagacagttt tgctttagta caatagtata cattttataa    960

tgatgaactt ataatgatta agggacattt ctataaaaat actacaatag ttttatgcac   1020

aacttcccat taaaaatgag atttcttatt tgtttgtctg tttttactct gggagtaata   1080

ctttttaaat tacctttaca tatatagtca ctggcatact gagaatatac aatgatcctg   1140

gaaattgcag taacaaaagc acacaacgat tatagtaact ataagataca ataaaacaaa   1200

taaatatgaa agtagattca tgaaaatgta ttcctttaaa atattgtttt cctacaggcc   1260

tatttaacaa gatgtttcat tttactgtat attttgtagt taatataaat gttgctctaa   1320

tcagattgct taaaagcatt tttattatat ttatgttgtt gaactaatat atgaaataag   1380

taaatgtagc tcccacaagg taaacttcat tggtaagatt gcactgttct gattatgtaa   1440

gcatttgtac atcttctttg gaaataaaag ataaaa                             1476
```

<210> SEQ ID NO 28
<211> LENGTH: 4116
<212> TYPE: DNA
<213> ORGANISM: Homo sapiens

<400> SEQUENCE: 28

-continued

```
gtttagaaca gcctacagac ccagtggcac gagacgggcc tctctcccaa acatcttcca     60
agccagatcc tagtcagtgg gaaagcccca gcttcaaccc ctttgggagc cactctgttc    120
tgcagaactc cccacccctc tcttctgagg gctcctacca ctttgaccca gataactttg    180
acgaatccat ggatcccttt aaaccaacta cgaccttaac aagcagtgac ttttgttctc    240
ccactggtaa tcacgttaat gaaatcttag aatcacccaa gaaggcaaag tcgcgtttaa    300
taacgactac tgaacaagtg aaatttctct gttttctgtt gagtggctgt aaggtgaaga    360
agcatgaaac tcagtctctc gccctggatg catgttctcg ggatgaaggg gcagtgatct    420
cccagatttc agacatttct aatagggatg gccatgctac tgatgaggag aaactggcat    480
ccacgtcatg tggtcagaaa tcagctggtg ccgaggtgaa aggtgagcca gaggaagacc    540
tggagtactt tgaatgttcc aatgttcctg tgtctaccat aaatcatgcg ttttcatcct    600
cagaagcagg catagagaag gagacgtgcc agaagatgga agaagacggg tccactgtgc    660
ttgggctgct ggagtcctct gcagagaagg cccctgtgtc ggtgtcctgt ggaggtgaga    720
gccccctgga tgggatctgc ctcagcgaat cagacaagac agccgtgctc accttaataa    780
gagaagagat aattactaaa gagattgaag caaatgaatg gaagaagaaa tacgaagaga    840
cccggcaaga agttttggag atgaggaaaa ttgtagctga atatgaaaag actattgctc    900
aaatgattga tgaacaaagg acaagtatga cctctcagaa gagcttccag caactgacca    960
tggagaagga acaggccctg gctgacctta actctgtgga aaggtccctt tctgatctct   1020
tcaggagata tgagaacctg aaaggtgttc tggaagggtt caagaagaat gaagaagcct   1080
tgaagaaatg tgctcaggat tacttagcca gagttaaaca agaggagcag cgataccagg   1140
ccctgaaaat ccacgcagaa gagaaactgg acaaagccaa tgaagagatt gctcaggttc   1200
gaacaaaagc aaaggctgag agtgcagctc tccatgctgg actccgcaaa gagcagatga   1260
aggtggagtc cctggaaagg gccctgcagc agaagaacca agaaattgaa gaactgacaa   1320
aaatctgtga tgagctgatt gcaaagctgg gaaagactga ctgagacact ccccctgtta   1380
gctcaacaga tctgcatttg gctgcttctc ttgtgaccac aattatcttg ccttatccag   1440
gaataattgc ccctttgcag agaaaaaaaa aaacttaaaa aaagcacatg cctactgctg   1500
cctgtcccgc tttgctgcca atgcaacagc cctggaagaa accctagagg gttgcatagt   1560
ctagaaagga gtgtgacctg acagtgctgg agcctcctag tttcccccta tgaaggttcc   1620
cttaggctgc tgagtttggg tttgtgattt atctttagtt tgttttaaag tcatctttac   1680
tttcccaaat gtgttaaatt tgtaactcct ctttggggtc ttctccacca cctgtctgat   1740
ttttttgtga tctgtttaat cttttaattt tttagtatca gtggttttat ttaaggagac   1800
agtttggcct attgttactt ccaatttata atcaagaagg ggctctggat cccctttttaa   1860
attacacaca ctctcacaca catacatgta tgtttataga tgctgctgct cttttccctg   1920
aagcatagtc aagtaagaac tgctctacag aaggacatat ttccttggat gtgagaccct   1980
attttgaaat agagtcctga ctcagaacac caacttaaga atttgggga ttaaagatgt    2040
gaagaccaca gtcttgggtt ttcatatctg gagaagacta tttgccatga cgttttgttg   2100
ccctggtatt tggacactcc tcagctttaa tgggtgtggc ccctttaggg ttagtcctca   2160
gactaatgat agtgtctgct ttctgcatga acggcaatat gggactccct ccaagctagg   2220
gtttggcaag tctgccctag agtcatttac tctcctctgc ctccatttgt taatacagaa   2280
tcaacattta gtcttcatta tcttttttttt ttttttgag acagagtttc gatctatttt   2340
aagtatgtga agaaaatcta cttgtaaaag gctcagatct taattaaaag gtaattgtag   2400
```

-continued

```
cacattacca attataaggt gaagaaatgt tttttcccca agtgtgatgc attgttcttc   2460
agatgttgaa aagaaagcaa aaaatacctt ctaacttaag acagaatttt taacaaaatg   2520
agcagtaaaa gtcacatgaa ccactccaaa aatcagtgca ttttgcatat ttttaaacaa   2580
agacagcttg ttgaatactg agaagaggag tgcaaggaga aggtctgtac taacaaagcc   2640
aaattcctca agctcttact ggactcagtt cagagtggtg ggccattaac cccaacatgg   2700
aatttttcca tataaatctc aatgaattcc ctttcatttg aataggcaaa cccaaatcca   2760
tgcaagtgtt ttaaagcact gtcctgtctt aatcttacat gctgaaagtc ttcatggtga   2820
tatgcactat attcagtata cgtatgtttt cctacttctc ttgtaaaact gttgcatgat   2880
ccaacttcag caatgaattg tgcctagtgg agaacctcta tagatcttaa aaaatgaatt   2940
attctttagc agtgtattac tcacatgggt gcaatcttta gccccaggga ggtcaataat   3000
gtcttttaaa gccagaagtc acattttacc aatatgcatt tatcataatt ggtgcttagg   3060
ctgtatattc aagcctgttg tcttaacatt ttgtataaaa aagaacaaca gaaattatct   3120
gtcatttgag aagtggcttg acaatcattt gagctttgaa agcagtcact gtggtgtaat   3180
atgaatgctg tcctagtggt catagtacca agggcacgtg tctccccttg gtataactga   3240
tttccttttt agtcctctac tgctaaataa gttaatttttg cattttgcag aaagaaacat   3300
tgattgctaa atctttttgc tgctgtgttt tggtgttttc atgtttactt gttttatatt   3360
gatctgtttt aagtatgaga ggcttatagt gccctccatt gtaaatccat agtcatcttt   3420
ttaagcttat tgtgtttaag aaagtagcta tgtgttaaac agaggtgatg gcagcccttc   3480
cctagcacac tggtggaaga gaccccttaa gaacctgacc ccagtgaatg aagctgatgc   3540
acagggagca ccaaaggacc ttcgttaagt gataattgtc ctggcctctc agccatgacc   3600
gttatgagga aatatccccc attcgaactt aacagatgcc tcctctccaa agagaattaa   3660
aatcgtagct tgtacagatc aagagaatat actgggcaga atgaagtatg tttgtttatt   3720
tttctttaaa aataaaggat tttggaactc tggagagtaa gaatatagta tagagtttgc   3780
ctcaacacat gtgagggcca aataacctgc tagctaggca gtaataaact ctgttacaga   3840
agagaaaaag ggccgggcac agtggcttat tcctgtaatc ccaacactgt ggaaggccga   3900
ggcaggagga tcacttgagt ccaggagttt gaaacctacc taggcaacat ggtgaaacct   3960
tgtctctacc aaaataaaaa ttagctgggc atggtggcac gtgcctgtgg tcccagctac   4020
ttgggaggct gaggtgggag cctgggaggt caaggctgca gtgagccatg atcatgccac   4080
tgcactccat cctgggtgac agcaagatct tgtctc                             4116
```

<210> SEQ ID NO 29
<211> LENGTH: 540
<212> TYPE: DNA
<213> ORGANISM: Homo sapiens

<400> SEQUENCE: 29

```
cgagttcccc gaggtgtacg tgcccaccgt cttcgagaac tatgtggccg acattgaggt     60
ggacggcaag caggtggagc tggcgctgtg ggacacggcg ggccaggagg actacgaccg    120
cctgcggccg ctctcctacc cggacaccga cgtcattctc atgtgcttct cggtggacag    180
cccggactcg ctggagaaca tccccgagaa gtgggtcccc gaggtgaagc acttctgtcc    240
caatgtgccc atcatcctgg tggccaacaa aaaagacctg cgcagcgacg agcatgtccg    300
cacagagctg gcccgcatga agcaggaacc cgtgcgcacg gatgacggcc gcgccatggc    360
```

-continued cgtgcgcatc caagcctacg actacctcga gtgctctgcc aagaccaagg aaggcgtgcg 420
cgaggtcttc gagacggcca cgcgcgccgc gctgcagaag cgctacggct cccagaacgg 480
ctgcatcaac tgctgcaagg tgctatgagg gccgcgcccg tcgcgcctgc ccctgccggc 540

<210> SEQ ID NO 30
<211> LENGTH: 1063
<212> TYPE: DNA
<213> ORGANISM: Homo sapiens

<400> SEQUENCE: 30
cggggagacc atggggcccc tctcagcccc ttcctgcaca cacctcatca cttggaaggg 60
ggtcctgctc acagcatcac ttttaaactt ctggaatccg cccaccactg ccgaagtcac 120
gattgaagcc cagccaccca aagtttctga ggggaaggat gttcttctac ttgttcacaa 180
tttgccccag aatcttcctg gctacttctg gtacaaaggg gaaatgacgg acctctacca 240
ttacattata tcgtatatag ttgatggtaa aataattata tatgggcctg catacagtgg 300
aagagaaaca gtatattcca acgcatccct gctgatccag aatgtcaccc ggaaggatgc 360
aggaacctac accttacaca tcataaagcg aggtgatgag actagagaag aaattcgaca 420
tttcaccttc accttatact atggtccaga cctccccaga atttaccctt cattcaccta 480
ttacggttca ggagaaaacc tcgacttgtc ctgcttcacg gaatctaacc caccggcaga 540
gtatttttgg acaattaatg ggaagtttca gcaatcagga caaaagctct ttatccccca 600
aattactaga aatcatagcg ggctctatgt ttgctctgtt cataactcag ccactggcaa 660
ggaaatctcc aaatccatga cagtcaaagt ctctggtccc tgccatggag acctgacaga 720
gtttcagtca tgactgcaac aactgagaca ctgagaaaaa gaacaggctg ataccttcat 780
gaaattcaag acaaagaaga aaaaaactca atgttattgg actaaataat caaaaggata 840
atgttttcat aattttttat tggaaaatgt gctgattctt tgaatgtttt attctccaga 900
tttatgaact ttttttcttc agcaattggt aaagtatact tttgtaaaca aaaattgaaa 960
tatttgcttt tgctgtctat ctgaatgccc cagaattgtg aaactactca tgagtactca 1020
taggtttatg gtaataaagt tatttgcaca tgttccgtag ttt 1063

<210> SEQ ID NO 31
<211> LENGTH: 1117
<212> TYPE: DNA
<213> ORGANISM: Homo sapiens

<400> SEQUENCE: 31
gcaccaacca gcaccatgcc catgatactg gggtactggg acatccgcgg gctggcccac 60
gccatccgcc tgctcctgga atacacagac tcaagctatg aggaaaagaa gtacacgatg 120
ggggacgctc ctgattatga cagaagccag tggctgaatg aaaaattcaa gctgggcctg 180
gactttccca atctgcccta cttgattgat ggggctcaca agatcaccca gagcaacgcc 240
atcttgtgct acattgcccg caagcacaac ctgtgtgggg agacagaaga ggagaagatt 300
cgtgtggaca ttttggagaa ccagaccatg gacaaccata tgcagctggg catgatctgc 360
tacaatccag aatttgagaa actgaagcca aagtacttgg aggaactccc tgaaaagcta 420
aagctctact cagagtttct ggggaagcgg ccatggtttg caggaaacaa gatcactttt 480
gtagattttc tcgtctatga tgtccttgac ctccaccgta tatttgagcc caactgcttg 540
gacgccttcc caaatctgaa ggacttcatc tcccgctttg agggcttgga gaagatctct 600
gcctacatga agtccagccg cttcctccca agacctgtgt tctcaaagat ggctgtctgg 660

-continued

```
ggcaacaagt agggccttga aggcaggagg tgggagtgag gagcccatac tcagcctgct    720

gcccaggctg tgcagcgcag ctggactctg catcccagca cctgcctcct cgttcctttc    780

tcctgtttat tcccatcttt actcccaaga cttcattgtc cctcttcact cccccctaaac    840

ccctgtccca tgcaggccct ttgaagcctc agctacccac tatccttcgt gaacatcccc    900

tcccatcatt acccttccct gcactaaagc cagcctgacc ttccttcctg ttagtggttg    960

tgtctgcttt aaagcctgcc tggcccctcg cctgtggagc tcagccccga gctgtccccg   1020

tgttgcatga aggagcagca ttgactggtt tacaggccct gctcctgcag catggtccct   1080

gcctaggcct acctgatgga agtaaagcct caaccac                            1117
```

<210> SEQ ID NO 32
<211> LENGTH: 1869
<212> TYPE: DNA
<213> ORGANISM: Homo sapiens

<400> SEQUENCE: 32

```
ttcaggaacc ggtttggtgc tggtgctgga ggcggctatg gctttggagg tggtgccggt     60

agtggatttg gtttcggcgg tggagctggt ggtggctttg ggctcggtgg cggagctggc    120

tttggaggtg gcttcggtgg ccctggcttt cctgtctgcc ctcctggagg tatccaagag    180

gtcactgtca accagagtct cctgactccc ctcaacctgc aaatcgaccc cagcatccag    240

agggtgagga ccgaggagcg cgagcagatc aagaccctca acaataagtt tgcctccttc    300

atcgacaagg tgcggttcct ggagcagcag aacaaggttc tggacaccaa gtggaccctg    360

ctgcaggagc agggcaccaa gactgtgagg cagaacctgg agccgttgtt cgagcagtac    420

atcaacaacc tcaggaggca gctggacagc atcgtggggg aacggggccg cctggactca    480

gagctgagaa acatgcagga cctggtggaa gacttcaaga acaagtatga ggatgaaatc    540

aacaagcgta ccactgctga gaatgagttt gtgatgctga agaaggatgt agatgctgcc    600

tacatgaaca aggtggagct ggaggccaag gttgatgcac tgatggatga gattaacttc    660

atgaagatgt tctttgatgc ggagctgtcc cagatgcaga cgcatgtctc tgacacctca    720

gtggtcctct ccatggacaa caaccgcaac ctggacctgg atagcatcat cgctgaggtc    780

aaggcccagt atgaggagat tgccaaccgc agccggacag aagccgagtc ctggtatcag    840

accaagtatg aggagctgca gcagacagct ggccggcatg gcgatgacct ccgcaacacc    900

aagcatgaga tctctgagat gaaccggatg atccagaggc tgagagccga gattgacaat    960

gtcaagaaac agtgcgccaa tctgcagaac gccattgcgg atgccgagca gcgtggggag   1020

ctggccctca aggatgccag gaacaagctg gccgagctgg aggaggccct gcagaaggcc   1080

aagcaggaca tggcccggct gctgcgtgag taccaggagc tcatgaacac caagctggcc   1140

ctggacgtgg agatcgccac ttaccgcaag ctgctggagg gcgaggaatg cagactcagt   1200

ggagaaggag ttggaccagt caacatctct gttgtcacaa gcagtgtttc ctctggatat   1260

ggcagtggca gtggctatgg cggtggcctc ggtggaggtc ttggcggcgg cctcggtgga   1320

ggtcttgccg gaggtagcag tggaagctac tactccagca gcagtggggg tgtcggccta   1380

ggtggtgggc tcagtgtggg gggctctggc ttcagtgcaa gcagtggccg agggctgggg   1440

gtgggctttg gcagtggcgg gggtagcagc tccagcgtca aatttgtctc caccacctcc   1500

tcctcccgga agagcttcaa gagctaagaa cctgctgcaa gtcactgcct tccaagtgca   1560

gcaacccagc ccatggagat tgcctcttct aggcagttgc tcaagccatg ttttatcctt   1620
```

-continued

```
ttctggagag tagtctagac caagccaatt gcagaaccac attctttggt tcccaggaga   1680

gccccattcc cagcccctgg tctcccgtgc cgcagttcta tattctgctt caaatcagcc   1740

ttcaggtttc ccacagcatg gcccctgctg acacgagaac ccaaagtttt cccaaatcta   1800

aatcatcaaa acagaatccc caccccaatc ccaaattttg ttttggttct aactacctcc   1860

agaatgtgt                                                           1869
```

<210> SEQ ID NO 33
<211> LENGTH: 664
<212> TYPE: DNA
<213> ORGANISM: Homo sapiens

<400> SEQUENCE: 33

```
agtgatcagg gccaaagcgg tcagtgagaa ggaagtggac tctggaaacg acatttatgg     60

caaccctatc aagaggatcc agtatgagat caagcagata aagatgttca aagggcctga    120

gaaggatata gagtttatct acacggcccc ctcctcggca gtgtgtgggg tctcgctgga    180

cgttggagga aagaaggaat atctcattgc aggaaaggcc gagggggacg gcaagatgca    240

catcaccctc tgtgacttca tcgtgccctg ggacaccctg agcaccaccc agaagaagag    300

cctgaaccac aggtaccaga tgggctgcga gtgcaagatc acgcgctgcc ccatgatccc    360

gtgctacatc tcctccccgg acgagtgcct ctggatggac tgggtcacag agaagaacat    420

caacgggcac caggccaagt tcttcgcctg catcaagaga agtgacggct cctgtgcgtg    480

gtaccgcggc gcggcgcccc ccaagcagga gtttctcgac atcgaggacc cataagcagg    540

cctccaacgc ccctgtggcc aactgcaaaa aaagcctcca agggtttcga ctggtccagc    600

tctgacatcc cttcctggaa acagcatgaa taaaacactc atcccatggg tccaaattaa    660

tatg                                                                 664
```

<210> SEQ ID NO 34
<211> LENGTH: 2598
<212> TYPE: DNA
<213> ORGANISM: Homo sapiens

<400> SEQUENCE: 34

```
tgtcgccacc atggctccgc accgccccgc gcccgcgctg ctttgcgcgc tgtccctggc     60

gctgtgcgcg ctgtcgctgc ccgtccgcgc ggccactgcg tcgcgggggg cgtcccaggc    120

gggggcgccc caggggcggg tgcccgaggc gcggcccaac agcatggtgg tggaacaccc    180

cgagttcctc aaggcaggga aggagcctgg cctgcagatc tggcgtgtgg agaagttcga    240

tctggtgccc gtgcccacca acctttatgg agacttcttc acgggcgacg cctacgtcat    300

cctgaagaca gtgcagctga ggaacggaaa tctgcagtat gacctccact actggctggg    360

caatgagtgc agccaggatg agagcggggc ggccgccatc tttaccgtgc agctggatga    420

ctacctgaac ggccgggccg tgcagcaccg tgaggtccag ggcttcgagt cggccacctt    480

cctaggctac ttcaagtctg gcctgaagta caagaaagga ggtgtggcat caggattcaa    540

gcacgtggta cccaacgagg tggtggtgca gagactcttc caggtcaaag ggcggcgtgt    600

ggtccgtgcc accgaggtac ctgtgtcctg ggagagcttc aacaatggcg actgcttcat    660

cctggacctg ggcaacaaca tccaccagtg gtgtggttcc aacagcaatc ggtatgaaag    720

actgaaggcc acacaggtgt ccaagggcat ccgggacaac gagcggagtg gccgggcccg    780

agtgcacgtg tctgaggagg gcactgagcc cgaggcgatg ctccaggtgc tgggccccaa    840

gccggctctg cctgcaggta ccgaggacac cgccaaggag gatgcggcca accgcaagct    900
```

-continued

```
ggccaagctc tacaaggtct ccaatggtgc agggaccatg tccgtctccc tcgtggctga    960

tgagaacccc ttcgcccagg gggccctgaa gtcagaggac tgcttcatcc tggaccacgg   1020

caaagatggg aaaatctttg tctggaaagg caagcaggca aacacggagg agaggaaggc   1080

tgccctcaaa acagcctctg acttcatcac caagatggac taccccaagc agactcaggt   1140

ctcggtcctt cctgagggcg gtgagacccc actgttcaag cagttcttca agaactggcg   1200

ggacccagac cagacagatg gcctgggctt gtcctacctt tccagccata tcgccaacgt   1260

ggagcgggtg cccttcgacg ccgccaccct gcacacctcc actgccatgg ccgcccagca   1320

cggcatggat gacgatggca caggccagaa acagatctgg agaatcgaag gttccaacaa   1380

ggtgcccgtg gaccctgcca catatggaca gttctatgga ggcgacagct acatcattct   1440

gtacaactac cgccatggtg gccgccaggg gcagataatc tataactggc agggtgccca   1500

gtctacccag gatgaggtcg ctgcatctgc catcctgact gctcagctgg atgaggagct   1560

gggaggtacc cctgtccaga gccgtgtggt ccaaggcaag gagcccgccc acctcatgag   1620

cctgtttggt gggaagccca tgatcatcta caagggcggc acctcccgcg agggcgggca   1680

gacagcccct gccagcaccc gcctcttcca ggtccgcgcc aacagcgctg gagccacccg   1740

ggctgttgag gtattgccta aggctggtgc actgaactcc aacgatgcct ttgttctgaa   1800

aacccctca gccgcctacc tgtgggtggg tacaggagcc agcgaggcag agaagacggg    1860

ggcccaggag ctgctcaggg tgctgcgggc ccaacctgtg caggtggcag aaggcagcga   1920

gccagatggc ttctgggagg ccctgggcgg gaaggctgcc taccgcacat ccccacggct   1980

gaaggacaag aagatggatg cccatcctcc tcgcctcttt gcctgctcca acaagattgg   2040

acgttttgtg atcgaagagg ttcctggtga gctcatgcag gaagacctgg caacggatga   2100

cgtcatgctt ctggacacct gggaccaggt ctttgtctgg gttggaaagg attctcaaga   2160

agaagaaaag acagaagcct tgacttctgc taagcggtac atcgagacgg acccagccaa   2220

tcgggatcgg cggacgccca tcaccgtggt gaagcaaggc tttgagcctc cctcctttgt   2280

gggctggttc cttggctggg atgatgatta ctggtctgtg gaccccttgg acagggccat   2340

ggctgagctg gctgcctgag gaggggcagg gcccacccat gtcaccggtc agtgcctttt   2400

ggaactgtcc ttccctcaaa gaggccttag agcgagcaga gcagctctgc tatgagtgtg   2460

tgtgtgtgtg tgtgttgttt cttttttttt tttttacagt atccaaaaat agccctgcaa   2520

aaattcagag tccttgcaaa attgtctaaa atgtcagtgt ttgggaaatt aaatccaata   2580

aaaacatttt gaagtgtg                                                 2598
```

<210> SEQ ID NO 35
<211> LENGTH: 329
<212> TYPE: DNA
<213> ORGANISM: Homo sapiens
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (292)..(292)
<223> OTHER INFORMATION: n is a, c, g, or t
<220> FEATURE:
<221> NAME/KEY: misc_feature
<222> LOCATION: (307)..(307)
<223> OTHER INFORMATION: n is a, c, g, or t
<220> FEATURE:
<221> NAME/KEY: misc_feature
<222> LOCATION: (316)..(316)

-continued

<223> OTHER INFORMATION: n is a, c, g, or t
<220> FEATURE:
<221> NAME/KEY: misc_feature
<222> LOCATION: (322)..(322)
<223> OTHER INFORMATION: n is a, c, g, or t

<400> SEQUENCE: 35

```
gaagtaaaag atttttattg ttctatagac acttctgaaa agagatctaa ttgagaaaat     60

atacaaagca tttaagagtt tcatccccag agactgactg aaggcgttac agccctcctc    120

tccaaggctc agggctgaga acggttagca tatcgaatga tcagtaaaaa catgcaaaag    180

tgagaaggaa agggaaaaag gtgcattccc ctaagctgag gggatggaa tttcagaaca     240

gaggangcag ggtggacaag taccaaggtg gctctccctt tccctctgtg tnatctttca    300

aaaccanttc caagcntgga tnaaagcaa                                      329
```

<210> SEQ ID NO 36
<211> LENGTH: 1555
<212> TYPE: DNA
<213> ORGANISM: Homo sapiens

<400> SEQUENCE: 36

```
caaagtctga gccccgctcc gctgatgcct gtctgcagaa tccgcaccaa ccagcaccat     60

gcccatgact ctggggtact gggacatccg tgggctggcc cacgccatcc gcttgctcct    120

ggaatacaca gactcaagct atgtggaaaa gaagtacacg ctgggggacg ctcctgacta    180

tgacagaagc cagtggctga atgaaaaatt caagctgggc ctggactttc ccaatctgcc    240

ctacttgatt gatggggctc acaagatcac ccagagcaat gccatcctgc gctacattgc    300

ccgcaagcac aacctgtgtg gggagacaga agaggagaag attcgtgtgg acattttgga    360

gaaccaggtt atggataacc acatggagct ggtcagactg tgctatgacc cagattttga    420

gaaactgaag ccaaaatact tggaggaact ccctgaaaag ctaaagctct actcagagtt    480

tctggggaag cggccatggt ttgcaggaga caagatcacc tttgtggatt tccttgccta    540

tgatgtcctt gacatgaagc gtatatttga gcccaagtgc ttggacgcct tcctaaactt    600

gaaggacttc atctcccgct ttgagggttt gaagaagatc tctgcctaca tgaagtccag    660

ccaattcctc cgaggtcttt tgtttggaaa gtcagctaca tggaacagca aatagggccc    720

agtgatgcca gaagatggga gggaggagcc aaccttgctg cctgcgaccc tggaggacag    780

cctgactccc tggacctgcc ttcttccttt ttccttcttt ctactctctt ctcttcccca    840

aggcctcatt ggcttccttt cttctaacat catccctccc cgcatcgagg ctctttaaag    900

cttcagctcc ccactgtcct ccatcaaagt ccccctccta acgtcttcct ttccctgcac    960

taacgccaac ctgactgctt ttcctgtcag tgcttttctc ttctttgaga agccagactg   1020

atctctgagc tccctagcac tgtcctcaaa gaccatctgt atgccctgct ccctttgctg   1080

ggtccctacc ccagctccgt gtgatgccca gtaaagcctg aaccatgcct gccatgtctt   1140

gtcttattcc ctgaggctcc cttgactcag gactgtgctc gaattgtggg tggtttttg    1200

tcttctgttg tccacagcca gagcttagtg gatgggtgtg tgtgtgtgtg tgttgggggt   1260

ggtgatcagg caggttcata aatttccttg gtcatttctg ccctctagcc acatccctct   1320

gttcctcact gtggggatta ctacagaaag gtgctctgtg ccaagttcct cactcattcg   1380

cgctcctgta ggccgtctag aactggcatg gttcaaagag gggctaggct gatggggaag   1440

ggggctgagc agctcccagg cagactgcct tctttcaccc tgtcctgata gacttccctg   1500

atctagatat ccttcgtcat gacacttctc aataaaacgt atcccaccgt attgt        1555
```

-continued

<210> SEQ ID NO 37
<211> LENGTH: 4812
<212> TYPE: DNA
<213> ORGANISM: Homo sapiens
<220> FEATURE:
<221> NAME/KEY: misc_feature
<222> LOCATION: (784)..(1133)
<223> OTHER INFORMATION: n is a, c, g, or t

<400> SEQUENCE: 37
ggttgagaat gcttgcacca agcttgtcca ggcagctcag atgcttcagt cagaccctta 60
ctcagtgcct gctcgagatt atctaattga tgggtcaagg ggcatcctct ctggaacatc 120
agacctgctc cttaccttcg atgaggctga ggtccgtaaa attattagag tttgcaaagg 180
aattttggaa tatcttacag tggcagaggt ggtggagact atggaagatt tggtcactta 240
cacaaagaat cttgggccag gaatgactaa gatggccaag atgattgacg agagacagca 300
ggagctcact caccaggagc accgagtgat gttggtgaac tcgatgaaca ccgtgaaaga 360
gttgctgcca gttctcattt cagctatgaa gatttttgta acaactaaaa actcaaaaaa 420
ccaaggcata gaggaagctt taaaaaatcg caattttact gtagaaaaaa tgagtgctga 480
aattaatgag ataattcgtg tgttacaact cacctcttgg gatgaagatg cctgggccag 540
caaggacact gaagccatga agagagcatt ggcctccata gactccaaac tgaaccaggc 600
caaaggttgg ctccgtgacc ctagtgcctc cccaggggat gctggtgagc aggccatcag 660
acagatctta gatgaagctg gaaaagttgg tgaactctgt gcaggcaaag aacgcaggga 720
gattctggga acttgcaaaa tgctagggca gatgactgat caagtggctg acctccgtgc 780
cagnnnnnnn nnnnnnnnnn nnnnnnnnnn nnnnnnnnnn nnnnnnnnnn nnnnnnnnnn 840
nnnnnnnnnn nnnnnnnnnn nnnnnnnnnn nnnnnnnnnn nnnnnnnnnn nnnnnnnnnn 900
nnnnnnnnnn nnnnnnnnnn nnnnnnnnnn nnnnnnnnnn nnnnnnnnnn nnnnnnnnnn 960
nnnnnnnnnn nnnnnnnnnn nnnnnnnnnn nnnnnnnnnn nnnnnnnnnn nnnnnnnnnn 1020
nnnnnnnnnn nnnnnnnnnn nnnnnnnnnn nnnnnnnnnn nnnnnnnnnn nnnnnnnnnn 1080
nnnnnnnnnn nnnnnnnnnn nnnnnnnnnn nnnnnnnnnn nnnnnnnnnn nnnaggctcg 1140
agccttggcc aaacaggtgg ccacggccct gcagaacctg cagaccaaaa ccaaccgggc 1200
tgtggccaac agcagaccgg ccaaagcagc tgtacacctt gagggcaaga ttgagcaagc 1260
acagcggtgg attgataatc ccacagtgga tgaccgtgga gtcggtcagg ctgccatccg 1320
ggggcttgtg gccgaagggc atcgtctggc taatgttatg atggggcctt atcggcaaga 1380
tcttctcgcc aagtgtgacc gagtggacca gctgacagcc cagctggctg acctggctgc 1440
cagaggggaa ggggagagtc ctcaggcacg agcacttgca tctcagctcc aagactcctt 1500
aaaggatcta aaagctcgga tgcaggaggc catgactcag gaagtgtcag atgttttcag 1560
cgataccaca actcccatca agctgttggc agtggcagcc acggcgcctc ctgatgcgcc 1620
taacagggaa gaggtatttg atgagagggc agctaacttt gaaaaccatt caggaaagct 1680
tggtgctacg gccgagaagg cggctgcggt tggtactgct aataaatcaa cagtggaagg 1740
cattcaggcc tcagtgaaga cggcccgaga actcacaccc caggtggtct cggctgctcg 1800
tatcttactt aggaaccctg gaaatcaagc tgcttatgaa cattttgaga ccatgaagaa 1860
ccagtggatc gataatgttg aaaaaatgac agggctggtg gacgaagcca ttgataccaa 1920
atctctgttg gatgcttcag aagaagcaat taaaaaagac ctggacaagt gcaaggtagc 1980

-continued

```
tatggccaac attcagcctc agatgctggt tgctggggca accagtattg ctcgtcgggc   2040
caaccggatc ctgctggtgg ctaagaggga ggtggagaat tccgaggatc ccaagttccg   2100
tgaggctgtg aaagctgcct ctgatgaatt gagcaaaacc atctccccga tggtgatgga   2160
tgcaaaagct gtggctggaa acatttccga ccctggactg caaaagagct tcctggactc   2220
aggatatcgg atcctgggag ctgtggccaa ggtcagagaa gccttccaac ctcaggagcc   2280
tgacttcccg ccgcctccac cagaccttga acaactccga ctaacagatg agcttgctcc   2340
tcccaaacca cctctgcctg aaggtgaggt ccctccacct aggcctccac caccagagga   2400
aaaggatgaa gagttccctg agcagaaggc cggggaggtg attaaccagc caatgatgat   2460
ggctgccaga cagctccatg atgaagctcg caaatggtcc agcaagggca atgacatcat   2520
tgcagcagcc aagcgcatgg ctctgctgat ggctgagatg tctcggctgg taagaggggg   2580
cagtggtacc aagcgggcac tcattcagtg tgccaaggac atcgccaagg cctcagatga   2640
ggtgactcgg ttggccaagg aggttgccaa gcagtgcaca gataaacgga ttagaaccaa   2700
cctcttacag gtatgtgagc gaatcccaac cataagcacc cagctcaaaa tcctgtccac   2760
agtgaaggcc accatgctgg gccggaccaa catcagtgat gaggagtctg agcaggccac   2820
agagatgctg gttcacaatg cccagaacct catgcagtct gtgaaggaga ctgtgcggga   2880
agctgaagct gcttcaatca aaattcgaac agatgctgga tttacactgc gctgggttag   2940
aaagactccc tggtaccagt aggcacctgg ctgagcctgg ctggcacaga aacctctact   3000
aaaaagaagg aaaatgatct gagtcccagg agctgcccag agttgctggg agctgaaaaa   3060
tcacatcctg gcctggcaca tcagaaagga atgggggcct cttcaaatta gaagacattt   3120
atactctttt ttcatggaca ctttgaaatg tgtttctgta taaagcctgt attctcaaac   3180
acagttacac ttgtgcaccc tctatcccaa taggcagact gggtttctag cccatggact   3240
tcacataagc tcagaatcca agtgaacact agccagacac tctgctctgc ccttgttccc   3300
taggggacac ttccctctgt ttctctttcc ttggctccca ttcactcttc cagaatccca   3360
agacccaggg cccaggcaaa tcagttacta agaagaaaat tgctgtgcct cccaaaattg   3420
ttttgagctt tccatgttgc tgccaaccat accttccttc cctgggctgt gctacctggg   3480
tccttttcag aagtgagctt tgctgctaca ggggaaggtg gcctctgtgg agccccagca   3540
tatgggggcc tggattcatt tcctgccctt cctcagttta atccttctag tttcccacaa   3600
tataaaactg tacttcactg tcaggaagaa atcacagaat catatgattc tgcttttacc   3660
atgcccctga gcaatgtctg tgctagggaa acttcccgtc ccatatcctg cctcagcccg   3720
ccaaggtagc catcccatga acacactgtg tcctggtgct ctctgccact ggaagggcag   3780
agtagccagg gtgtggccct gccatcttcc cagcagggcc actcccggca ctccatgctt   3840
agtcactgcc tgcagaggtc tgtgctgagg ccttatcatt cattcttagc tcttaattgt   3900
tcattttgag ctgaaatgct gcattttaat tttaaccaaa acatgtctcc tatcctggtt   3960
tttgtagcct tcctccacat cctttctaaa caagatttta aagacatgta ggtgtttgtt   4020
catctgtaac tctaaaagat ccttttttaaa ttcagtccta agaaagagga gtgcttgtcc   4080
cctaagagtg tttaatggca aggcagccct gtctgaagga cacttcctgc ctaagggaga   4140
gtggtatttg cagactagaa ttctagtgct gctgaagatg aatcaatggg aaatactact   4200
cctgtaattc ctacctccct gcaaccaact acaaccaagc tctctgcatc tactcccaag   4260
tatggggttc aagagagtaa tgggtttcat atttcttatc accacagtaa gttcctacta   4320
ggcaaaatga gagggcagtg tttccttttt ggtacttatt actgctaagt atttcccagc   4380
```

-continued

```
acatgaaacc ttattttttc ccaaagccag aaccagatga gtaaaggagt aagaaccttg   4440

cctgaacatc cttccttccc acccatcgct gtgtgttagt tcccaacatc gaatgtgtac   4500

aacttaagtt ggtcctttac actcaggctt tcactatttc ctttataatg aggatgatta   4560

ttttcaaggc cctcagcata tttgtatagt tgcttgcctg atataaatgc aatattaatg   4620

cctttaaagt atgaatctat gccaaagatc acttgttgtt ttactaaaga aagattactt   4680

agaggaaata agaaaaatca tgtttgctct cccggttctt ccagtggttt gagacactgg   4740

tttacacttt atgccggatg tgcttttctc caatatcagt gctcgagaca cagtgaagca   4800

aattaaaaaa aa                                                        4812
```

<210> SEQ ID NO 38
<211> LENGTH: 2038
<212> TYPE: DNA
<213> ORGANISM: Homo sapiens

<400> SEQUENCE: 38

```
atatccagcc tttgccgaat acatcctatc tgccacacat ccagcgtgag gtccctccag     60

ctacaaggtg ggcaccatgg cggagaagtt tgactgccac tactgcaggg atcccttgca    120

ggggaagaag tatgtgcaaa aggatggcca ccactgctgc ctgaaatgct ttgacaagtt    180

ctgtgccaac acctgtgtgg aatgccgcaa gcccatcggt gcggactcca aggaggtgca    240

ctataagaac cgcttctggc atgacacctg cttccgctgt gccaagtgcc ttcacccctt    300

ggccaatgag acctttgtgg ccaaggacaa caagatcctg tgcaacaagt gcaccactcg    360

ggaggactcc cccaagtgca aggggtgctt caaggccatt gtggcaggag atcaaaacgt    420

ggagtacaag gggaccgtct ggcacaaaga ctgcttcacc tgtagtaact gcaagcaagt    480

catcgggact ggaagcttct tccctaaagg ggaggacttc tactgcgtga cttgccatga    540

gaccaagttt gccaagcatt gcgtgaagtg caacaaggcc atcacatctg gaggaatcac    600

ttaccaggat cagccctggc atgccgattg ctttgtgtgt gttacctgct ctaagaagct    660

ggctgggcag cgtttcaccg ctgtggagga ccagtattac tgcgtggatt gctacaagaa    720

ctttgtggcc aagaagtgtg ctggatgcaa gaaccccatc actgggaaaa ggactgtgtc    780

aagagtgagc cacccagtct ctaaagctag gaagcccccca gtgtgccacg ggaaacgctt    840

gcctctcacc ctgtttccca gcgccaacct ccggggcagg catccgggtg gagagaggac    900

ttgtccctcg tgggtggtgg ttctttatag aaaaaatcga agcttagcag ctcctcgagg    960

cccgggtttg gtaaaggctc cagtgtggtg gcctatgaag gacaatcctg gcacgactac   1020

tgcttccact gcaaaaaatg ctccgtgaat ctggccaaca agcgctttgt tttccaccag   1080

gagcaagtgt attgtcccga ctgtgccaaa aagctgtaaa ctgacagggg ctcctgtcct   1140

gtaaaatggc atttgaatct cgttctttgt gtccttactt tctgccctat accatcaata   1200

ggggaagagt ggtccttccc ttctttaaag ttctccttcc gtcttttctc ccattttaca   1260

gtattactca aataagggca cacagtgatc atattagcat ttagcaaaaa gcaaccctgc   1320

agcaaagtga atttctgtcc ggctgcaatt taaaaatgaa aacttaggta gattgactct   1380

tctgcatgtt tctcatagag cagaaaagtg ctaatcattt agccacttag tgatgtaagc   1440

aagaagcata ggagataaaa cccccactga gatgcctctc atgcctcagc tgggacccac   1500

cgtgtagaca cacgacatgc aagagttgca gcggctgctc caactcactg ctcaccctct   1560

tctgtgagca ggaaaagaac cctactgaca tgcatggttt aacttcctca tcagaactct   1620
```

-continued

```
gcccttcctt ctgttctttt gtgctttcaa ataactaaca cgaacttcca gaaaattaac   1680

atttgaactt agctgtaatt ctaaactgac ctttccccgt actaacgttt ggtttccccg   1740

tgtggcatgt tttctgagcg ttcctacttt aaagcatgga acatgcaggt gatttgggaa   1800

gtgtagaaag acctgagaaa acgagcctgt ttcagaggaa catcgtcaca acgaatactt   1860

ctggaagctt aacaaaacta accctgctgt cctttttatt gtttttaatt aatatttttg   1920

ttttaattga tagcaaaata gtttatgggt ttggaaactt gcatgaaaat attttagccc   1980

cctcagatgt tcctgcagtg ctgaaattca tcctacggaa gtaaccgcaa aactctag     2038
```

<210> SEQ ID NO 39
<211> LENGTH: 691
<212> TYPE: DNA
<213> ORGANISM: Homo sapiens
<220> FEATURE:
<221> NAME/KEY: misc_feature
<222> LOCATION: (37)..(238)
<223> OTHER INFORMATION: The n at this position can be a, c, t, or g.
<220> FEATURE:
<221> NAME/KEY: misc_feature
<222> LOCATION: (240)..(268)
<223> OTHER INFORMATION: The n at this position can be a, c, t, or g.

<400> SEQUENCE: 39

```
tgccgcccta caccgtggtc tatttcccag ttcgagnnnn nnnnnnnnnn nnnnnnnnnn     60

nnnnnnnnnn nnnnnnnngc tgctggcaga tcagggccag agctggaagg aggaggtggt    120

gaccgtggag acgtggcagg agggctcact caaagcctcc tgcctatacg ggcagctccc    180

caagttccag gacggagacc tcaccctgta ccagtccaat accatcctgc gtcacctggn    240

nnnnnnnnnn nnnnnnnnnn nnnnnnnngg ctctatggga aggaccagca ggaggcagcc    300

ctggtggaca tggtgaatga cggcgtggag gacctccgct gcaaatacat ctccctcatc    360

tacaccaact atgaggcggg caaggatgac tatgtgaagg cactgcccgg gcaactgaag    420

ccttttgaga ccctgctgtc ccagaaccag ggaggcaaga ccttcattgt gggagaccag    480

atctccttcg ctgactacaa cctgctggac ttgctgctga tccatgaggt cctagcccct    540

ggctgcctgg atgcgttccc cctgctctca gcatatgtgg ggcgcctcag tgcccggccc    600

aagctcaagg ccttcctggc ctcccctgag tacgtgaacc tccccatcaa tggcaacggg    660

aaacagtgag ggttgggggg actctgagcg g                                   691
```

<210> SEQ ID NO 40
<211> LENGTH: 2511
<212> TYPE: DNA
<213> ORGANISM: Homo sapiens
<220> FEATURE:
<221> NAME/KEY: misc_feature
<222> LOCATION: (799)..(953)
<223> OTHER INFORMATION: The n at this position can be a, c, t, or g.

<400> SEQUENCE: 40

```
cttttcacac tggccttaaa gaggatatat tagaagttga agtaggaagg gagccagaga     60

ggccgatggc gcaaaggtac gacgatctac cccattacgg gggcatggat ggagtaggca    120

tcccctccac gatgtatggg gacccgcatg cagccaggtc catgcagccg gtccaccacc    180

tgaaccacgg gcctcctctg cactcgcatc agtacccgca cacagctcat accaacgcca    240

tggcccccag catgggctcc tctgtcaatg acgctttaaa gagagataaa gatgccattt    300

atggacaccc cctcttccct ctcttagcac tgatttttga gaaatgtgaa ttagctactt    360

gtaccccccg cgagccgggg gtggcgggcg gggacgtctg ctcgtcagag tcattcaatg    420
```

-continued

```
aagatatagc cgtgttcgcc aaacagattc gcgcagaaaa acctctattt tcttctaatc    480
cagaactgga taacttgatg attcaagcca tacaagtatt aaggtttcat ctattggaat    540
tagagaaggt acacgaatta tgtgacaatt tctgccaccg gtatattagc tgtttgaaag    600
ggaaaatgcc tatcgatttg gtgatagacg atagagaagg aggatcaaaa tcagacagtg    660
aagatataac aagatcagca aatctaactg accagccctc ttggaacaga gatcatgatg    720
acacggcatc tactcgttca ggaggaaccc caggcccttc cagcggtggc cacacgtcac    780
acagtgggga caacagcann nnnnnnnnnn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnncaccctt    960
acccttctga agaacagaaa aagcagttgg cacaagacac gggactcacc atccttcaag   1020
tgaacaattg gtttattaat gcccggagaa gaatagtgca gcccatgata gaccagtcca   1080
accgagcagt aagtcaagga acaccttata atcctgatgg acagcccatg ggaggtttcg   1140
taatggacgg tcagcaacat atgggaatta gagcaccagg acctatgagt ggaatgggca   1200
tgaatatggg catggagggg cagtggcact acatgtaacc ttcatctagt taaccaatcg   1260
caaagcaagg gggaaggctg caaagtatgc caggggagta tgtagcccgg ggtggtccaa   1320
tgggtgtgag tatgggacag ccaagttata cccaacccca gatgcccccc catcctgctc   1380
agctgcgtca tgggcccccc atgcatacgt acattcctgg acaccctcac cacccaacag   1440
tgatgatgca tggaggaccg ccccaccctg gaatgccaat gtcagcatca agccccacag   1500
ttcttaatac aggagaccca acaatgagtg gacaagtcat ggacattcat gctcagtagc   1560
ttaagggaat atgcattgtc tgcaatggtg actgatttca aatcatgttt tttctgcaat   1620
gactgtggag ttccattctt ggcatctact ctggaccaag gagcatccct aattcttcat   1680
agggaccttt aaaaagcagg aaataccaac tgaagtcaat ttgggggaca tgctaaataa   1740
ctatataaga cattaagaga acaaagagtg aaatattgta aatgctatta tactgttatc   1800
catattacgt tgtttcttat agattttta aaaaaaatgt gaaattttc cacactatgt   1860
gtgttgtttc catagctctt cacttcctcc agaagcctcc ttacattaaa aagccttaca   1920
gttatcctgc aagggacagg aaggtctgat ttgcaggatt tttagagcat taaaataact   1980
atcaggcaga agaatctttc ttctcgccta ggatttcagc catgcgcgcg ctctctctct   2040
ttctctctct tttcctctct ctccctcttt ctagcctggg gcttgaattt gcatgtctaa   2100
ttcatttact caccatattt gaattggcct gaacagatgt aaatcgggaa ggatgggaaa   2160
aactgcagtc atcaacaatg attaatcagc tgttgcaggc agtgtcttaa ggagactggt   2220
aggaggaggc atggaaacca aaaggccgtg tgtttagaag cctaattgtc acatcaagca   2280
tcattgtccc catgcaacaa ccaccacctt atacatcact tcctgtttta agcagctcta   2340
aaacatagac tgaagattta tttttaatat gttgacttta tttctgagca aagcatcggt   2400
catgtgtgta ttttttcata gtcccacctt ggagcattta tgtagacatt gtaaataaat   2460
tttgtgcaaa aaggactgga aaaatgaact gtattattgc aattttttt t             2511
```

<210> SEQ ID NO 41
<211> LENGTH: 441
<212> TYPE: DNA
<213> ORGANISM: Homo sapiens

<400> SEQUENCE: 41

-continued

```
ctcaataagc caaccatgtc tttcaaggat tacatccaag agaggagtga cccagtggag      60

caaggcaaac cagttatacc tgcagctgtg ctggccggct tcacaggaag tggacctatt     120

cagctgtggc agtttctcct ggagctgcta tcagacaaat cctgccagtc attcatcagc     180

tggactggag acggatggga gtttaagctc gccgaccccg atgaggtggc ccgccggtgg     240

ggaaagagga aaaataagcc caagatgaac tacgagaagc tgagccgggg cttacgctac     300

tattacgaca agaacatcat ccacaagacg tcggggaagc gctacgtgta ccgcttcgtg     360

tgcgacctcc agaacttgct ggggttcacg cccgaggaac tgcacgccat cctgggcgtc     420

cagcccgaca cggaggactg a                                               441
```

<210> SEQ ID NO 42
<211> LENGTH: 1531
<212> TYPE: DNA
<213> ORGANISM: Homo sapiens

<400> SEQUENCE: 42

```
ggacgacaag gcgttcacca aggagctgga ccagtgggtc gagcagctga acgagtgtaa      60

gcagctgaac gagaaccaag tgcggacgct gtgcgagaag gcaaaggaaa ttttaacaaa     120

agaatcaaat gtgcaagagg ttcgttgccc tgttactgtc tgtggagatg tgcatggtca     180

atttcatgat cttatggaac tctttagaat tggtggaaaa tcaccggata caaactactt     240

attcatgggt gactatgtag acagaggata ttattcagtg gagactgtga ctcttcttgt     300

agcattaaag gtgcgttatc cagaacgcat tacaatattg agaggaaatc acgaaagccg     360

acaaattacc caagtatatg gcttttatga tgaatgtctg cgaaagtatg ggaatgccaa     420

cgtttggaaa tattttacag atctctttga ttatcttcca cttacagctt tagtagatgg     480

acagatattc tgcctccatg gtggcctctc tccatccata gacacactgg atcatataag     540

agccctggat cgtttacagg aagttccaca tgagggccca atgtgtgatc tgttatggtc     600

agatccagat gatcgtggtg gatggggtat ttcaccacgt ggtgctggct acacatttgg     660

acaagacatt tctgaaacct ttaaccatgc caatggtctc acactggttt ctcgtgccca     720

ccagcttgta atggagggat acaattggtg tcatgatcgg aatgtggtta ccattttcag     780

tgcacccaat tactgttatc gttgtgggaa ccaggctgct atcatggaat tagatgacac     840

tttaaaatat tccttccttc aatttgaccc agcgcctcgt cgtggtgagc ctcatgttac     900

acggcgcacc ccagactact tcctataaat ttctcctggg aaacctgcct ttgtatgtgg     960

aagtatacct ggctttttaa aatatatgta tttaaaaaca aaaagcaaca gtaatctatg    1020

tgtttctgta acaaattggg atctgtcttg gcattaaacc acatcatgga ccaaatgtgc    1080

catactaatg atgagcattt agcacaattt gagactgaaa tttagtacac tatgttctag    1140

gtcagtctaa cagtttgcct gctgtattta tagtaaccat tttcctttgg actgttcaag    1200

caaaaaaggt aactaactgc ttcatctcct tttgcgctta tttggaaatt ttagttatag    1260

tgtttaactg gcatggatta atagagttgg agttttattt ttaagaaaaa ttcacaagct    1320

aacttccact aatccattat cctttatttt attgaaatgt ataattaact taactgaaga    1380

aaaggttctt cttgggagta tgttgtcata acatttaaag agatttccct tcatttaaac    1440

taaattactg ttttatgttg atctgcatat ttctgtatat ttgtcatgac agtgcttgca    1500

tcctatttgg tgtactcagc aaataaactt t                                   1531
```

<210> SEQ ID NO 43
<211> LENGTH: 1260

-continued

<212> TYPE: DNA
<213> ORGANISM: Homo sapiens

<400> SEQUENCE: 43
cctgtgagca ccacgtcaac ggctcccggc ccccatgcac gggggaggga gataccccca 60
agtgtagcaa gatctgtgag cctggctaca gcccgaccta caaacaggac aagcactacg 120
gatacaattc ctacagcgtc tccaatagcg agaaggacat catggccgag atctacaaaa 180
acggccccgt ggagggagct ttctctgtgt attcggactt cctgctctac aagtcaggag 240
tgtaccaaca cgtcaccgga gagatgatgg gtggccatgc catccgcatc ctgggctggg 300
gagtggagaa tggcacaccc tactggctgg ttgccaactc ctggaacact gactggggtg 360
acaatggctt ctttaaaata ctcagaggac aggatcactg tggaatcgaa tcagaagtgg 420
tggctggaat tccacgcacc gatcagtact gggaaaagat ctaatctgcc gtgggcctgt 480
cgtgccagtc ctgggggcga gatgggggta gaaatgcatt ttattcttta agttcacgta 540
agatacaagt ttcagacagg gtctgaagga ctggattggc caaacatcag acctgtcttc 600
caaggagacc aagtcctggc tacatcccag cctgtggtta cagtgcagac aggccatgtg 660
agccaccgct gccagcacag agcgtccttc cccctgtaga ctagtgccgt agggagtacc 720
tgttgcccca gctgactgtg gccccctccg tgatccatcc atctccaggg agcaagacag 780
agacccagga atggaaagcg gagttcctaa caggatgaaa gttcccccat cagttccccc 840
agtacctcca agcaagtagc tttccacatt tgtcacagaa atcagaggag agatggtgtt 900
gggagccctt tggagaacgc cagtctccca ggccccctgc atctatcgag tttgcaatgt 960
cacaacctct ctgatcttgt gctcagcatg attctttaat agaagtttta ttttttcgtg 1020
cactctgcta atcatgtggg tgagccagtg gaacagcggg agacctgtgc tagttttaca 1080
gattgcctcc ttatgacgcg gctcaaaagg aaaccaagtg gtcaggagtt gtttctgacc 1140
cactgatctc tactaccaca aggagaatag tttaggagaa accagctttt actgtttttg 1200
aaaaattaca gcttcaccct gtcaagttaa caaggaatgc ctgtgccaat aaaaggtttc 1260

<210> SEQ ID NO 44
<211> LENGTH: 5418
<212> TYPE: DNA
<213> ORGANISM: Homo sapiens
<220> FEATURE:
<221> NAME/KEY: misc_feature
<222> LOCATION: (1210)..(1219)
<223> OTHER INFORMATION: The “n” at this position can be either “a”, “t”, “g”, or “c”.

<400> SEQUENCE: 44
gtgtcccata gtgtttccaa acttggaaag ggcgggggag ggcgggagga tgcggagggc 60
ggaggtatgc agacaacgag tcagagtttc cccttgaaag cctcaaaagt gtccacgtcc 120
tcaaaaagaa tggaaccaat ttaagaagcc agccccgtgg ccacgtccct tcccccattc 180
gctccctcct ctgcgccccc gcaggctcct cccagctgtg gctgcccggg cccccagccc 240
cagccctccc attggtggag gcccttttgg aggcacccta gggccaggga aacttttgcc 300
gtataaatag ggcagatccg ggctttatta ttttagcacc acggcagcag gaggtttcgg 360
ctaagttgga ggtactggcc acgactgcat gcccgcgccc gccaggtgat acctccgccg 420
gtgacccagg ggctctgcga cacaaggagt ctgcatgtct aagtgctaga catgctcagc 480
tttgtggata cgcggacttt gttgctgctt gcagtaacct tatgcctagc aacatgccaa 540
tctttacaag aggaaactgt aagaaagggc ccagccggag atagaggacc acgtggagaa 600

-continued

```
aggggtccac caggcccccc aggcagagat ggtgaagatg gtcccacagg ccctcctggt    660
ccacctggtc ctcctggccc ccctggtctc ggtgggaact ttgctgctca gtatgatgga    720
aaaggagttg gacttggccc tggaccaatg ggcttaatgg gacctagagg cccacctggt    780
gcagctggag ccccaggccc tcaaggtttc caaggacctg ctggtgagcc tggtgaacct    840
ggtcaaactg gtcctgcagg tgctcgtggt ccagctggcc ctcctggcaa ggctggtgaa    900
gatggtcacc ctggaaaacc cggacgacct ggtgagagag gagttgttgg accacagggt    960
gctcgtggtt tccctggaac tcctggactt cctggcttca aaggcattag ggacacaat    1020
ggtctggatg gattgaaggg acagcccggt gctcctggtg tgaagggtga acctggtgcc   1080
cctggtgaaa atggaactcc aggtcaaaca ggagcccgtg ggcttcctgg tgagagagga   1140
cgtgttggtg cccctggccc agctggtgcc cgtggcagtg atggaagtgt gggtcccgtg   1200
ggtcctgctn nnnnnnnnng gtctgctggc cctccaggct tcccaggtgc ccctggcccc   1260
aagggtgaaa ttggagctat tggtaacgct ggtcctgctg gtcccgccgg tccccgtggt   1320
gaagtgggtc ttccaggcct ctccggcccc gttggacctc ctggtaatcc tggagcaaac   1380
ggccttactg gtgccaaggg tgctgctggc cttcccggcg ttgctggggc tcccggcctc   1440
cctggacccc gcggtattcc tggccctgtt ggtgctgccg gtgctactgg tgccagagga   1500
cttgttggtg agcctggtcc agctggctcc aaaggagaga gcggtaacaa gggtgagccc   1560
ggctctgctg ggccccaagg tcctcctggt cccagtggtg aagaaggaaa gagaggccct   1620
aatggggaag ctggatctgc cggccctcca ggacctcctg ggctgagagg tagtcctggt   1680
tctcgtggtc ttcctggagc tgatggcaga gctggcgtca tgggccctcc tggtagtcgt   1740
ggtgcaagtg gccctgctgg agtccgagga cctaatggag atgctggtcg ccctggggag   1800
cctggtctca tgggacccag aggtcttcct ggttcccctg gaaatatcgg ccccgctgga   1860
aaagaaggtc ctgtcggcct ccctggcatc gacggcaggc ctggcccaat tggccccgtt   1920
ggagcaagag gagagcctgg caacattgga ttccctggac ccaaaggccc cactggtgac   1980
cctggcaaaa acggtgataa aggtcatgct ggtcttgctg gtgctcgggg tgctccaggt   2040
cctgatggaa acaatggtgc tcagggacct cctggaccac agggtgttca aggtggaaaa   2100
ggtgaacagg gtcccgctgg tcctccaggc ttccagggtc tgcctggccc ctcaggtccc   2160
gctggtgaag ttggcaaacc aggagaaagg ggtctccatg gtgagtttgg tctccctggt   2220
cctgctggtc caagagggga acgcggtccc ccaggtgaga gtggtgctgc cggtcctact   2280
ggtcctattg gaagccgagg tccttctgga cccccagggc ctgatggaaa caagggtgaa   2340
cctggtgtgg ttggtgctgt gggcactgct ggtccatctg gtcctagtgg actcccagga   2400
gagaggggtg ctgctggcat acctggaggc aagggagaaa agggtgaacc tggtctcaga   2460
ggtgaaattg gtaaccctgg cagagatggt gctcgtggtg ctcatggtgc tgtaggtgcc   2520
cctggtcctg ctggagccac aggtgaccgg ggcgaagctg gggctgctgg tcctgctggt   2580
cctgctggtc ctcggggaag ccctggtgaa cgtggcgagg tcggtcctgc tggccccaac   2640
ggatttgctg gtccggctgg tgctgctggt caaccgggtg ctaaaggaga aagaggaggc   2700
aaagggccta agggtgaaaa cggtgttgtt ggtcccacag gccccgttgg agctgctggc   2760
ccagctggtc caaatggtcc ccccggtcct gctggaagtc gtggtgatgg aggccccccct  2820
ggtatgactg gtttccctgg tgctgctgga cggactggtc ccccaggacc ctctggtatt   2880
tctggccctc ctggtccccc tggtcctgct gggaaagaag ggcttcgtgg tcctcgtggt   2940
```

-continued

```
gaccaaggtc cagttggccg aactggagaa gtaggtgcag ttggtccccc tggcttcgct   3000
ggtgagaagg gtccctctgg agaggctggt actgctggac ctcctggcac tccaggtcct   3060
cagggtcttc ttggtgctcc tggtattctg ggtctccctg gctcgagagg tgaacgtggt   3120
ctacctggtg ttgctggtgc tgtgggtgaa cctggtcctc ttggcattgc cggccctcct   3180
ggggcccgtg gtcctcctgg tgctgtgggt agtcctggag tcaacggtgc tcctggtgaa   3240
gctggtcgtg atggcaaccc tgggaacgat ggtcccccag gtcgcgatgg tcaacccgga   3300
cacaagggag agcgcggtta ccctggcaat attggtcccg ttggtgctgc aggtgcacct   3360
ggtcctcatg gccccgtggg tcctgctggc aaacatggaa accgtggtga aactggtcct   3420
tctggtcctg ttggtcctgc tggtgctgtt ggcccaagag gtcctagtgg cccacaaggc   3480
attcgtggcg ataagggaga gcccggtgaa aaggggccca gaggtcttcc tggcttcaag   3540
ggacacaatg gattgcaagg tctgcctggt atcgctggtc accatggtga tcaaggtgct   3600
cctggctccg tgggtcctgc tggtcctagg ggccctgctg gtccttctgg ccctgctgga   3660
aaagatggtc gcactggaca tcctggtacg gttggacctg ctggcattcg aggccctcag   3720
ggtcaccaag gccctgctgg ccccccctggt cccccctggcc ctcctggacc tccaggtgta   3780
agcggtggtg gttatgactt tggttacgat ggagacttct acagggctga ccagcctcgc   3840
tcagcacctt ctctcagacc caaggactat gaagttgatg ctactctgaa gtctctcaac   3900
aaccagattg agacccttct tactcctgaa ggctctagaa agaacccagc tcgcacatgc   3960
cgtgacttga gactcagcca cccagagtgg agcagtggtt actactggat tgaccccaac   4020
caaggatgca ctatggaagc catcaaagta tactgtgatt tccctaccgg cgaaacctgt   4080
atccgggccc aacctgaaaa catcccagcc aagaactggt ataggagctc caaggacaag   4140
aaacacgtct ggctaggaga aactatcaat gctggcagcc agtttgaata taatgttgaa   4200
ggagtgactt ccaaggaaat ggctacccaa cttgccttca tgcgcctgct ggccaactat   4260
gcctctcaga acatcaccta ccactgcaag aacagcattg catacatgga tgaggagact   4320
ggcaacctga aaaaggctgt cattctacag ggctctaatg atgttgaact tgttgctgag   4380
ggcaacagca ggttcactta cactgttctt gtagatggct gctctaaaaa gacaaatgaa   4440
tggggaaaga caatcattga atacaaaaca aataagccat cacgcctgcc cttccttgat   4500
attgcacctt tggacatcgg tggtgctgac catgaattct ttgtggacat tggcccagtc   4560
tgtttcaaat aaatgaactc aatctaaatt aaaaaagaaa gaaatttgaa aaaactttct   4620
ctttgccatt tcttcttctt cttttttaac tgaaagctga atccttccat ttcttctgca   4680
catctacttg cttaaattgt gggcaaaaga gaaaaagaag gattgatcag agcattgtgc   4740
aatacagttt cattaactcc ttccccgct cccccaaaaa tttgaatttt tttttcaaca   4800
ctcttacacc tgttatggaa aatgtcaacc tttgtaagaa aaccaaaata aaaattgaaa   4860
aataaaaacc ataaacattt gcaccacttg tggcttttga atatcttcca cagagggaag   4920
tttaaaaccc aaacttccaa aggtttaaac tacctcaaaa cactttccca tgagtgtgat   4980
ccacattgtt aggtgctgac ctagacagag atgaactgag gtccttgttt tgttttgttc   5040
ataatacaaa ggtgctaatt aatagtattt cagatacttg aagaatgttg atggtgctag   5100
aagaatttga gaagaaatac tcctgtattg agttgtatcg tgtggtgtat tttttaaaaa   5160
atttgattta gcattcatat tttccatctt attcccaatt aaaagtatgc agattatttg   5220
cccaaagttg tcctcttctt cagattcagc atttgttctt tgccagtctc attttcatct   5280
tcttccatgg ttccacagaa gctttgtttc ttgggcaagc agaaaaatta aattgtacct   5340
```

-continued

```
attttgtata tgtgagatgt ttaaataaat tgtgaaaaaa atgaaataaa gcatgtttgg   5400

ttttccaaaa gaacatat                                                  5418
```

<210> SEQ ID NO 45
<211> LENGTH: 2566
<212> TYPE: DNA
<213> ORGANISM: Homo sapiens

<400> SEQUENCE: 45

```
cagaccacag gaatacctaa tgcctttttt ctcttcctgt ctttgtccct cacactacag     60

caggcccctc ccttccctct tcaacctcat cctccctccc cacaggccca gagaaccagt    120

tgggctttgt tctcctgcag gctatggttc atcatgcaaa tagctcctgt gtcagaaatg    180

ctttttggct tcaaataaca gaaaagctaa caccagcttt atcaataata atatcggtgg    240

tttacttaag gtgtccagag atggtggaga acaggattgg tttcctcctc aatgtcaagg    300

actcaaagac tctttctgtg gtagggccac atcctaaacc ctgtatcctg tgattattta    360

cctgacaggg caaaagagat tttgcagatg caattaaggt taaggacctt gacgtgggaa    420

gattgtgatt atttacctga cagggcaaaa gagattttgc agatgcaatt aaggttaagg    480

accttgacgt gggaagatta ttctggatta tctaggtggg cgcaatttga tcacatgggt    540

ccccagaagt ggagaacctt tcccacctgt agaaagccag agagctggca cctgagaagg    600

acagaactgt cactgcagga tttgaagatg aaggggccca tgagccaagg aatgccagtg    660

acctatagag gctaaaaaac agcaaggaaa tggactctcc ccagagcctc cagaggaatg    720

cagccctgtt gatcacatga tcaccagatg gctgccccag agccaaatgt cgcttcctga    780

gcaccatact caaaggcagg ggaagtggat ggagggcagg agctccattc ttgtttgcca    840

ctctcctttt gtcaattggg aaaaaattcc agaaactctg ggagccctcc ccttacattt    900

cctgggtcat ggggccagcc ctagctgctg gagggactga gaactgctgt tgagcagttt    960

acctgacggc atctgccatg gcttggcagg aactctggct ttgggagaga gcagcagcaa   1020

ggtattcaag caccacctcc acccagcccc tcccacattt cactcaggac tgagtaaagg   1080

agacactcag atgctactca gatgctggct tcagctaagt attttgcaaa gcctctcgtg   1140

ttcttacaag tttgtggcta tcatgacaaa atggagcagc ctactatatc tacatataca   1200

actatggggg acctagtttt atctcattta ccacaatgtt ttcaatcatt ttttggatga   1260

cataattttt agcctcttct ctaaatgctt cctcaagctt tccttgcctt ccagccactg   1320

caaatgactt gcagtttccc ctacatggca cctgaccctt gtgcctccct ccctctgccc   1380

atggcccaga aagccctttc ctgtgccctc tggcttcctg ataaactcct atcatcttca   1440

agagccagtt cccatgccag ctctccccaa gtgctccact gaggcttccg taacacctct   1500

gttcccacat cgggttgact gtctttgttt tgtcattgct tgctctggct gtgtctccct   1560

cattagactg ggatgccttc aaggtaggga ccctatctgg gtcagcttgg caccccaaag   1620

cgtaccacag cacctgattc tgaggaggct ctcagtagat atctgttgag taaccagaat   1680

gtagggtggt cctgatggtt tctgacattg aatagaaaac agctccctat ttgatcttaa   1740

aataatcact ataacctgga catactgtac tagatgctgt ttttgtctga cttctactct   1800

gtcaatctct ttgcacctcc atttgttcat ctgtgaaatg aagaaaatgc tcatggagtt   1860

cagtgaagat taaatgaatg aatataggta gactgcctaa tctggcactt gccacgcagc   1920

tgacttcaat atagtagctc taatattatg gtccttgagg atcttactgt cttatggccc   1980
```

-continued

```
agaactgcat ttgattaaag aaggctcccc taaaaaaaga gtcatacata ttccatttgt   2040

cctttcagaa ggccgtgaag catttacact ctttaagaca aattcccatc caaaaatagt   2100

taagatttct aaaatatttt gatgctgaaa gaggtgtgct tcagttgggt ggcaaatttg   2160

cttctatgga agatttttaa tacaggttgt ttctatttta ctttttctgg ctgaaaggat   2220

tttacattta ttcaaagtca aaagggaaaa gaaatccaag aactacagaa gagcagttga   2280

agtgatttat gcttgatttc taaatgcaac ttatgtttat acataattta aaactcaaag   2340

aaagcatgct tatacaatca tgtgcaactt taaactttaa gaactctgga tgaatacatg   2400

gtggcaacag tccatgacac ctgaaaacat catttgtgga gtggcgtaga gttcagtgtt   2460

cgcagtcgca tattacaacc atgtttcaca cagccctgct cggtttgatt ttctccacgt   2520

ggttgataat tgtcttcagt tgctgctaag tgattttgca aatttc                 2566


<210> SEQ ID NO 46
<211> LENGTH: 1847
<212> TYPE: DNA
<213> ORGANISM: Homo sapiens

<400> SEQUENCE: 46

gtccccgcgc cagagacgca gccgcgctcc caccacccac acccaccgcg ccctcgttcg     60

cctcttctcc gggagccagt ccgcgccacc gccgccgccc aggccatcgc caccctccgc    120

agccatgtcc accaggtccg tgtcctcgtc ctcctaccgc aggatgttcg gcggcccggg    180

caccgcgagc cggccgagct ccagccggag ctacgtgact acgtccaccc gcacctacag    240

cctgggcagc gcgctgcgcc ccagcaccag ccgcagcctc tacgcctcgt ccccgggcgg    300

cgtgtatgcc acgcgctcct ctgccgtgcg cctgcggagc agcgtgcccg gggtgcggct    360

cctgcaggac tcggtggact tctcgctggc cgacgccatc aacaccgagt tcaagaacac    420

ccgcaccaac gagaaggtgg agctgcagga gctgaatgac cgcttcgcca actacatcga    480

caaggtgcgc ttcctggagc agcagaataa gatcctgctg gccgagctcg agcagctcaa    540

gggccaaggc aagtcgcgcc tgggggacct ctacgaggag gagatgcggg agctgcgccg    600

gcaggtggac cagctaacca acgacaaagc ccgcgtcgag gtggagcgcg acaacctggc    660

cgaggacatc atgcgcctcc gggagaaatt gcaggaggag atgcttcaga gagaggaagc    720

cgaaaacacc ctgcaatctt tcagacagga tgttgacaat gcgtctctgg cacgtcttga    780

ccttgaacgc aaagtggaat ctttgcaaga agagattgcc tttttgaaga aactccacga    840

agaggaaatc caggagctgc aggctcagat tcaggaacag catgtccaaa tcgatgtgga    900

tgtttccaag cctgacctca cggctgccct gcgtgacgta cgtcagcaat atgaaagtgt    960

ggctgccaag aacctgcagg aggcagaaga atggtacaaa tccaagtttg ctgacctctc   1020

tgaggctgcc aaccggaaca atgacgccct gcgccaggca aagcaggagt ccactgagta   1080

ccggagacag gtgcagtccc tcacctgtga agtggatgcc cttaaaggaa ccaatgagtc   1140

cctggaacgc cagatgcgtg aaatggaaga gaactttgcc gttgaagctg ctaactacca   1200

agacactatt ggccgcctgc aggatgagat tcagaatatg aaggaggaaa tggctcgtca   1260

ccttcgtgaa taccaagacc tgctcaatgt taagatggcc cttgacattg agattgccac   1320

ctacaggaag ctgctggaag gcgaggagag caggatttct ctgcctcttc caaacttttc   1380

ctccctgaac ctgagggaaa ctaatctgga ttcactccct ctggttgata cccactcaaa   1440

aaggacactt ctgattaaga cggttgaaac tagagatgga caggttatca acgaaacttc   1500

tcagcatcac gatgaccttg aataaaaatt gcacacactc agtgcagcaa tatattacca   1560
```

-continued gcaagaataa aaaagaaatc catatcttaa agaaacagct ttcaagtgcc tttctgcagt 1620
ttttcaggag cgcaagatag atttggaata ggaataagct ctagttctta acaaccgaca 1680
ctcctacaag atttagaaaa aagtttacaa cataatctag tttacagaaa aatcttgtgc 1740
tagaatactt tttaaaaggt attttgaata ccattaaaac tgcttttttt tttccagcaa 1800
gtatccaacc aacttggttc tgcttcaata aatctttgga aaaactc 1847

<210> SEQ ID NO 47
<211> LENGTH: 3864
<212> TYPE: DNA
<213> ORGANISM: Homo sapiens

<400> SEQUENCE: 47
ggccagccga atccaagccg tgtgtactgc gtgctcagca ctgcccgaca gtcctagcta 60
aacttcgcca actccgctgc ctttgccgcc accatgccca aaacgatcag tgtgcgtgtg 120
accaccatgg atgcagagct ggagtttgcc atccagccca acaccaccgg gaagcagcta 180
tttgaccagg tggtgaaaac tattggcttg agggaagttt ggttctttgg tctgcagtac 240
caggacacta aaggtttctc cacctggctg aaactcaata agaaggtgac tgcccaggat 300
gtgcggaagg aaagcccccct gctctttaag ttccgtgcca agttctaccc tgaggatgtg 360
tccgaggaat tgattcagga catcactcag cgcctgttct ttctgcaagt gaaagagggc 420
attctcaatg atgatattta ctgcccgcct gagaccgctg tgctgctggc ctcgtatgct 480
gtccagtcta agtatggcga cttcaataag gaagtgcata agtctggcta cctggccgga 540
gacaagttgc tcccgcagag agtcctggaa cagcacaaac tcaacaagga ccagtgggag 600
gagcggatcc aggtgtggca tgaggaacac cgtggcatgc tcagggagga tgctgtcctg 660
gaatatctga agattgctca agatctggag atgtatggtg tgaactactt cagcatcaag 720
aacaagaaag gctcagagct gtggctgggg gtggatgccc tgggtctcaa catctatgag 780
cagaatgaca gactaactcc caagataggc ttcccctgga gtgaaatcag gaacatctct 840
ttcaatgata agaaatttgt catcaagccc attgacaaaa aagccccgga cttcgtcttc 900
tatgctcccc ggctgcggat taacaagcgg atcttggcct tgtgcatggg gaaccatgaa 960
ctatacatgc gccgtcgcaa gcctgatacc attgaggtgc agcagatgaa ggcacaggcc 1020
cgggaggaga agcaccagaa gcagatggag cgtgctatgc tggaaaatga gaagaagaag 1080
cgtgaaatgg cagagaagga gaaagagaag attgaacggg agaaggagga gctgatggag 1140
aggctgaagc agatcgagga acagactaag aaggctcagc aagaactgga agaacagacc 1200
cgtagggctc tggaacttga gcaggaacgg aagcgtgccc agagcgaggc tgaaaagctg 1260
gccaaggagc gtcaagaagc tgaagaggcc aaggaggcct tgctgcaggc ctcccgggac 1320
cagaaaaaga ctcaggaaca gctggccttg gaaatggcag agctgacagc tcgaatctcc 1380
cagctggaga tggcccgaca gaagaaggag agtgaggctg tggagtggca gcagaaggcc 1440
cagatggtac aggaagactt ggagaagacc cgtgctgagc tgaagactgc catgagtaca 1500
cctcatgtgg cagagcctgc tgagaatgag caggatgagc aggatgagaa tggggcagag 1560
gctagtgctg acctacgggc tgatgctatg gccaaggacc gcagtgagga ggaacgtacc 1620
actgaggcag agaagaatga gcgtgtgcag aagcacctga aggccctcac ttcggagctg 1680
gccaatgcca gagatgagtc caagaagact gccaatgaca tgatccatgc tgagaacatg 1740
cgactgggcc gagacaaata caagaccctg cgccagatcc ggcagggcaa caccaagcag 1800

-continued

```
cgcattgacg aatttgagtc tatgtaatgg gcacccagcc tctagggacc cctcctccct   1860
ttttccttgt ccccacactc ctacacctaa ctcacctaac tcatactgtg ctggagccac   1920
taactagagc agccctggag tcatgccaag catttaatgt agccatggga ccaaacctag   1980
ccccttagcc cccacccact tccctgggca aatgaatggc tcactatggt gccaatggaa   2040
cctcctttct cttctctgtt ccattgaatc tgtatggcta gaatatccta cttctccagc   2100
ctagaggtac tttccacttg attttgcaaa tgcccttaca cttactgttg tcctatggga   2160
gtcaagtgtg gagtaggttg gaagctagct cccctcctct ccccctaccac tgtcttcttc   2220
agggtcctga gatttacacg gttggagtgt tatgcggtct agggaatgag acaggaccta   2280
ggatatcttc tccaggatgt caactgacct aaaatttgcc ctcccatccc gtttagagtt   2340
atttaggctt tgtaacgatt gggggataaa aagatgttca gtcatttttg tttctacctc   2400
ccagatcgga tctgttgcaa actcagcctc aataagcctt gtcgttgact ttagggactc   2460
aatttctccc cagggtggat gggggaaatg gtgccttcaa gaccttcacc aaacatacta   2520
gaagggcatt ggccattcta ttgtggcaag gctgagtaga agatcctacc ccaattcctt   2580
gtaggagtat aggccggtct aaagtgagct ctatgggcag atctacccct tacttattat   2640
tccagatctg cagtcacttc gtgggatctg cccctccctg cttcaatacc caaatcctct   2700
ccagctataa cagtagggat gagtacccaa aagctcagcc agccccatca ggactcttgt   2760
gaaaagagag gatatgttca cacctagcgt cagtattttc cctgctaggg gttttaggtc   2820
tcttcccctc tcagagctac ttgggccata gctcctgctc cacagccatc ccagccttgg   2880
catctagagc ttgatgccag taggctcaac tagggagtga gtgcaaaaag ctgagtatgg   2940
tgagagaagc ctgtgccctg atccaagttt actcaaccct ctcaggtgac caaaatcccc   3000
ttctcatcac tcccctccaa agaggtgact gggccctgcc tctgtttgac aaacctctaa   3060
cccaggtctt gacaccagct gttctgtccc ttggagctgt aaaccagaga gctgctgggg   3120
attctggcct agtcccttcc acacccccac cccttgctct caacccagga gcatccacct   3180
ccttctctgt ctcatgtgtg ctcttcttct ttctacagta ttatgtactc tactgatatc   3240
taaatattga tttctgcctt ccttgctaat gcaccattag aagatattag tcttggggca   3300
ggatgatttt ggcctcatta ctttaccacc cccacacctg gaaagcatat actatattac   3360
aaaatgacat tttgccaaaa ttattaatat aagaagcttt cagtattagt gatgtcatct   3420
gtcactatag gtcatacaat ccattcttaa agtacttgtt atttgttttt attattactg   3480
tttgtcttct ccccagggtt cagtcctcaa ggggccatcc tgtcccacca tgcagtgccc   3540
ctagcttaga gcctccctca attccccctg gccaccaccc cccactctgt gcctgacctt   3600
gaggagtctt gtgtgcattg ctgtgaatta gctcacttgg tgatatgtcc tatattggct   3660
aaattgaaac ctggaattgt ggggcaatct attaatagct gccttaaagt cagtaactta   3720
cccttaggga ggctgggggga aaaggttaga ttttgtattc aggggttttt tgtgtacttt   3780
ttgggttttt taaaaattgt ttttggaggg gtttatgctc aatccatgtt ctatttcagt   3840
gccaataaaa tttaggaaga cttc                                          3864
```

<210> SEQ ID NO 48
<211> LENGTH: 2270
<212> TYPE: DNA
<213> ORGANISM: Homo sapiens

<400> SEQUENCE: 48

```
ggtgtgcccg gagaggctga gcagcctgcg cctgagctgg tggaggtgga agtgggcagc     60
```

-continued

```
acagcccttc tgaagtgcgg cctctcccag tcccaaggca acctcagcca tgtcgactgg    120
ttttctgtcc acaaggagaa gcggacgctc atcttccgtg tgcgccaggg ccagggccag    180
agcgaacctg gggagtacga gcagcggctc agcctccagg acagaggggc tactctggcc    240
ctgactcaag tcacccccca agacgagcgc atcttcttgt gccagggcaa gcgccctcgg    300
tcccaggagt accgcatcca gctccgcgtc tacaaagctc cggaggagcc aaacatccag    360
gtcaaccccc tgggcatccc tgtgaacagt aaggagcctg aggaggtcgc tacctgtgta    420
gggaggaacg ggtaccccat tcctcaagtc atctggtaca agaatggccg gcctctgaag    480
gaggagaaga accgggtcca cattcagtcg tcccagactg tggagtcgag tggtttgtac    540
accttgcaga gtattctgaa ggcacagctg gttaaagaag acaaagatgc ccagttttac    600
tgtgagctca actaccggct gcccagtggg aaccacatga aggagtccag ggaagtcacc    660
gtccctgttt tctacccgac agaaaaagtg tggctggaag tggagcccgt gggaatgctg    720
aaggaagggg accgcgtgga aatcaggtgt ttggctgatg gcaaccctcc accacacttc    780
agcatcagca agcagaaccc cagcaccagg gaggcagagg aagagacaac caacgacaac    840
ggggtcctgg tgctggagcc tgcccggaag gaacacagtg ggcgctatga atgtcagggc    900
ctggacttgg acaccatgat atcgctgctg agtgaaccac aggaactact ggtgaactat    960
gtgtctgacg tccgagtgag tcccgcagca cactgagaga caggaaggca gcagcctcac   1020
cctgacctgt gaggcagaga gtagccagga cctcgagttc cagtggctga gagaagagac   1080
aggccaggtg ctggaaaggg ggcctgtgct tcagttgcat gacctgaaac gggaggcagg   1140
aggcggctat cgctgcgtgg cgtctgtgcc cagcataccc ggcctgaacc gcacacagct   1200
ggtcaacgtg gccatttttg gcccccccttg gatggcattc aaggagagga aggtgtgggt   1260
gaaagagaat atggtgttga atctgtcttg tgaagcgtca gggcaccccc ggcccaccat   1320
ctcctggaac gtcaacggca cggcaagtga acaagaccaa gatccacagc gagtcctgag   1380
caccctgaat gtcctcgtga ccccggagct gttggagaca ggtgttgaat gcacggcctc   1440
caacgacctg ggcaaaaaca ccagcatcct cttcctggag ctggtcaatt taaccaccct   1500
cacaccagac tccaacacaa ccactggcct cagcacttcc actgccagtc ctcataccag   1560
agccaacagc acctccacag agagaaagct gccggagccg gagagccggg gcgtggtcat   1620
cgtggctgtg attgtgtgca tcctggtcct ggcggtgctg ggcgctgtcc tctatttcct   1680
ctataagaag ggcaagctgc cgtgcaggcg ctcagggaag caggagatca cgctgccccc   1740
gtctcgtaag agcgaacttg tagttgaagt taagtcagat aagctcccag aagagatggg   1800
cctcctgcag ggcagcagcg gtgacaagag ggctccggga gaccagggag agaaatacat   1860
cgatctgagg cattagcccc gaatcacttc agctcccttc cctgcctgga ccattcccag   1920
ctccctgctc actcttctct cagccaaagc ctccaaaggg actagagaga agcctcctgc   1980
tcccctcgcc tgcacacccc ctttcagagg gccactgggt taggacctga ggacctcact   2040
tggccctgca aggcccgctt ttcagggacc agtccaccac catctccacg ttgagtgaag   2100
ctcatcccaa gcaaggagcc ccagtctccc gagcgggtag gagagtttct tgtagaacgt   2160
gttttttctt tacacacatt atggctgtaa atacctggct cctgccagca gctgagctgg   2220
gtagcctctc tgagctggga ttacaggtgt gagccactgc gcccagccaa              2270
```

<210> SEQ ID NO 49
<211> LENGTH: 2127
<212> TYPE: DNA

-continued

<213> ORGANISM: Homo sapiens

<400> SEQUENCE: 49

```
caaacttggt ggcaacttgc ctcccggtgc gggcgtctct cccccaccgt ctcaacatgc     60
ttaggggtcc ggggcccggg ctgctgctgc tggccgtcct gtgcctgggg acagcggtgc    120
cctccacggg agcctcgaag agcaagaggc aggctcagca aatggttcag ccccagtccc    180
cggtggctgt cagtcaaagc aagcccggtt gttatgacaa tggaaaacac tatcagataa    240
atcaacagtg ggagcggacc tacctaggca atgcgttggt ttgtacttgt tatggaggaa    300
gccgaggttt taactgcgag agtaaacctg aagctgaaga gacttgcttt gacaagtaca    360
ctgggaacac ttaccgagtg ggtgacactt atgagcgtcc taaagactcc atgatctggg    420
actgtacctg catcggggct gggcgaggga gaataagctg taccatcgca aaccgctgcc    480
atgaaggggg tcagtcctac aagattggtg acacctggag gagaccacat gagactggtg    540
gttacatgtt agagtgtgtg tgtcttggta atggaaaagg agaatggacc tgcaagccca    600
tagctgagaa gtgttttgat catgctgctg ggacttccta tgtggtcgga gaaacgtggg    660
agaagcccta ccaaggctgg atgatggtag attgtacttg cctgggagaa ggcagcggac    720
gcatcacttg cacttctaga aatagatgca acgatcagga cacaaggaca tcctatagaa    780
ttggagacac ctggagcaag aaggataatc gaggaaacct gctccagtgc atctgcacag    840
gcaacggccg aggagagtgg aagtgtgaga ggcacacctc tgtgcagacc acatcgagcg    900
gatctggccc cttcaccgat gttcgtgcag ctgtttacca accgcagcct cacccccagc    960
ctcctcccta tggccactgt gtcacagaca gtggtgtggt ctactctgtg gggatgcagt   1020
ggctgaagac acaaggaaat aagcaaatgc tttgcacgtg cctgggcaac ggagtcagct   1080
gccaagagac agctgtaacc cagacttacg gtggcaactc aaatggagag ccatgtgtct   1140
taccattcac ctacaatggc aggacgtgca gcacaacttc gaattatgag caggaccaga   1200
aatactcttt ctgcacagac cacactgttt tggttcagac tcgaggagga aattccaatg   1260
gtgccttgtg ccacttcccc ttcctataca acaaccacaa ttacactgat tgcacttctg   1320
agggcagaag agacaacatg aagtggtgtg ggaccacaca gaactatgat gccgaccaga   1380
agtttgggtt ctgccccatg gctgcccacg aggaaatctg cacaaccaat gaaggggtca   1440
tgtaccgcat tggagatcag tgggataagc agcatgacat gggtcacatg atgaggtgca   1500
cgtgtgttgg gaatggtcgt ggggaatgga catgcattgc ctactcgcag cttcgagatc   1560
agtgcattgt tgatgacatc acttacaatg tgaacgacac attccacaag cgtcatgaag   1620
aggggcacat gctgaactgt acatgcttcg gtcagggtcg ggcaggtgg aagtgtgatc   1680
ccgtcgacca atgccaggat tcagagactg ggacgtttta tcaaattgga gattcatggg   1740
agaagtatgt gcatggtgtc agataccagt gctactgcta tggccgtggc attggggagt   1800
ggcattgcca acctttacag acctatccaa gctcaagtgg tcctgtcgaa gtatttatca   1860
ctgagactcc gagtcagccc aactcccacc ccatccagtg gaatgcacca cagccatctc   1920
acatttccaa gtacattctc aggtggagac ctgtgagtat cccacccaga aaccttggat   1980
actgagtctc ctaatcttat caattctgat ggtttctttt tttcccagct tttgagccaa   2040
caactctgat taactattcc tatagcattt actatatttg tttagtgaac aaacaatatg   2100
tggtcaatta aattgacttg tagactg                                       2127
```

<210> SEQ ID NO 50
<211> LENGTH: 1918

-continued

<212> TYPE: DNA
<213> ORGANISM: Homo sapiens

<400> SEQUENCE: 50
acccccgcac ccagctccgc aggaccggcg ggcgcgcgcg ggctctggag gccacgggca 60
tgatgcttcg ggtcctggtg ggggctgtcc tccctgccat gctactggct gccccaccac 120
ccatcaacaa gctggcactg ttcccagata agagtgcctg gtgcgaagcc aagaacatca 180
cccagatcgt gggccacagc ggctgtgagg ccaagtccat ccagaacagg gcgtgcctag 240
gacagtgctt cagctacagc gtccccaaca ccttcccaca gtccacagag tccctggttc 300
actgtgactc ctgcatgcca gcccagtcca tgtgggagat tgtgacgctg gagtgcccgg 360
gccacgagga ggtgcccagg gtggacaagc tggtggagaa gatcctgcac tgtagctgcc 420
aggcctgcgg caaggagcct agtcacgagg ggctgagcgt ctatgtgcag ggcgaggacg 480
ggccgggatc ccagcccggc acccaccctc acccccatcc ccaccccat cctggcgggc 540 agacccctga gcccgaggac ccccctgggg ccccccacac agaggaagag gggggctgagg 600 actgaggccc ccccaactct tcctcccctc tcatccccct gtggaatgtt gggtctcact 660
ctctggggaa gtcaggggag aagctgaagc ccccctttgg cactggatgg acttggcttc 720
agactcggac ttgaatgctg cccggttgcc atggagatct gaaggggcgg ggttagagcc 780
aagctgcaca atttaatata ttcaagagtg gggggaggaa gcagaggtct tcagggctct 840
ttttttgggg ggggtggtct cttcctgtct ggcttctaga gatgtgcctg tgggaggggg 900
aggaagttgg ctgagccatt gagtgctggg ggaggccatc caagatggca tgaatcgggc 960
taaggtccct gggggtgcag atggtactgc tgaggtcccg ggcttagtgt gagcatcttg 1020
ccagcctcag gcttgaggga gggctgggct agaaagacca ctggcagaaa caggaggctc 1080
cggcccacag gtttccccaa ggcctctcac cccacttccc atctccaggg aagcgtcgcc 1140
ccagtggcac tgaagtggcc ctccctcagc ggaggggttt gggagtcagg cctgggcagg 1200
accctgctga ctcgtggcgc gggagctggg agccaggctc tccgggcctt tctctggctt 1260
ccttggcttg cctggtgggg gaaggggagg aggggaagaa ggaaagggaa gagtcttcca 1320
aggccagaag gagggggaca accccccaag accatccctg aagacgagca tccccctcct 1380
ctccctgtta gaaatgttag tgccccgcac tgtgccccaa gttctaggcc ccccagaaag 1440
ctgccagagc cggccgcctt ctcccctctc ccagggatgc tctttgtaaa tatcggatgg 1500
gtgtgggagt gaggggttac ctccctcgcc ccaaggttcc agaggcccta ggcgggatgg 1560
gctcgctgaa cctcgaggaa ctccaggacg aggaggacat gggacttgcg tggacagtca 1620
gggttcactt gggctctctc tagctcccca attctgcctg cctcctccct cccagctgca 1680
ctttaaccct agaaggtggg gacctggggg gagggacagg gcaggcgggc ccatgaagaa 1740
agcccctcgt tgcccagcac tgtctgcgtc tgctcttctg tgcccagggt ggctgccagc 1800
ccactgcctc ctgcctgggg tggcctggcc ctcctggctg ttgcgacgcg ggcttctgga 1860
gcttgtcacc attggacagt ctccctgatg gaccctcagt cttctcatga ataaattc 1918

<210> SEQ ID NO 51
<211> LENGTH: 1222
<212> TYPE: DNA
<213> ORGANISM: Homo sapiens

<400> SEQUENCE: 51
atccgtcccg gataagaccc gctgtctggc cctgagtagg gtgtgacctc cgcagccgca 60

-continued gaggaggagc gcagcccggc ctcgaagaac ttctgcttgg gtggctgaac tctgatcttg 120
acctagagtc atggccatgg caaccaaagg aggtactgtc aaagctgctt caggattcaa 180
tgccatggaa gatgcccaga ccctgaggaa ggccatgaaa gggctcggca ccgatgaaga 240
cgccattatt agcgtccttg cctaccgcaa caccgcccag cgccaggaga tcaggacagc 300
ctacaagagc accatcggca gggacttgat agacgacctg aagtcagaac tgagtggcaa 360
cttcgagcag gtgattgtgg ggatgatgac gcccacggtg ctgtatgacg tgcaagagct 420
gcgaagggcc atgaagggag ccggcactga tgagggctgc ctaattgaga tcctggcctc 480
ccggacccct gaggagatcc ggcgcataag ccaaacctac cagcagcaat atggacggag 540
ccttgaagat gacattcgct ctgacacatc gttcatgttc cagcgagtgc tggtgtctct 600
gtcagctggt gggagggatg aaggaaatta tctggacgat gctctcgtga gacaggatgc 660
ccaggacctg tatgaggctg gagagaagaa atgggggaca gatgaggtga aatttctaac 720
tgttctctgt tcccggaacc gaaatcacct gttgcatggt ttgatgaata caaaaggata 780
tcacagaagg atattgaaca gagtattaaa tctgaaacat ctggtagctt tgaagatgct 840
ctgctggcta tagtaaagtg catgaggaac aaatctgcat attttgctga aaagctctat 900
aaatcgatga agggcttggg caccgatgat aacaccctca tcagagtgat ggtttctcga 960
gcagaaattg acatgttgga tatccgggca cacttcaaga gactctatgg aaagtctctg 1020
tactcgttca tcaagggtga cacatctgga gactacagga aagtactgct tgttctctgt 1080
ggaggagatg attaaaataa aaatcccaga aggacaggag gattctcaac actttgaatt 1140
tttttaactt catttttcta cactgctatt atcattatct cagaatgctt atttccaatt 1200
aaaacgccta cagctgcctc ct 1222

<210> SEQ ID NO 52
<211> LENGTH: 2468
<212> TYPE: DNA
<213> ORGANISM: Homo sapiens

<400> SEQUENCE: 52
tggggcagcc gcgcccgcgg tgttttccgc ccggcgctgg cggctgctgc gcccgcggct 60
ccccagtgcc ccgagtgccc cgcgggcccc gcgagcggga gtgggaccca gcccctaggc 120
agaacccagg cgccgcgccc gggacgcccg cggagagagc cactcccgcc cacgtcccat 180
ttcgcccctc gcgtccggag tcctcgtggc cagatctaac catgagctac cctggctatc 240
ccccgccccc aggtggctac ccaccagctg caccaggtgg tggtccctgg ggaggtgctg 300
cctaccctcc tccgcccagc atgcccccca tcgggctgga taacgtggcc acctatgcgg 360
ggcagttcaa ccaggactat ctctcgggaa tggcggccaa catgtctggg acatttggag 420
gagccaacat gcccaacctg taccctgggg cccctggggc tggctaccca ccagtgcccc 480
ctggcggctt tgggcagccc ccctctgccc agcagcctgt tcctccctat gggatgtatc 540
cacccccagg aggaaaccca ccctccagga tgccctcata tccgccatac ccaggggccc 600
ctgtgccggg ccagcccatg ccaccccccg gacagcagcc cccaggggcc taccctgggc 660
agccaccagt gacctaccct ggtcagcctc cagtgccact ccctgggcag cagcagccag 720
tgccgagcta cccaggatac ccggggtctg ggactgtcac ccccgctgtg cccccaaccc 780
agtttggaag ccgaggcacc atcactgatg ctcccggctt tgaccccctg cgagatgccg 840
aggtcctgcg gaaggccatg aaaggcttcg ggacggatga gcaggccatc attgactgcc 900
tggggagtcg ctccaacaag cagcggcagc agatcctact ttccttcaag acggcttacg 960

-continued

```
gcaaggattt gatcaaagat ctgaaatctg aactgtcagg aaactttgag aagacaatct   1020
tggctctgat gaagacccca gtcctctttg acatttatga gataaaggaa gccatcaagg   1080
gggttggcac tgatgaagcc tgcctgattg agatcctcgc ttcccgcagc aatgagcaca   1140
tccgagaatt aaacagagcc tacaaagcag aattcaaaaa gaccctggaa gaggccattc   1200
gaagcgacac atcagggcac ttccagcggc tcctcatctc tctctctcag ggaaaccgtg   1260
atgaaagcac aaacgtggac atgtcactcg cccagagaga tgcccaggag ctgtatgcgg   1320
ccggggagaa ccgcctggga acagacgagt ccaagttcaa tgcggttctg tgctcccgga   1380
gccgggccca cctggtagca gttttcaatg agtaccagag aatgacaggc cgggacattg   1440
agaagagcat ctgccgggag atgtccgggg acctggagga gggcatgctg gccgtggtga   1500
aatgtctcaa gaatacccca gccttctttg cggagaggct caacaaggcc atgagggggg   1560
caggaacaaa ggaccggacc ctgattcgca tcatggtgtc tcgcagcgag accgacctcc   1620
tggacatcag atcagagtat aagcggatgt acggcaagtc gctgtaccac gacatctcgg   1680
gagatacttc aggggattac cggaagattc tgctgaagat ctgtggtggc aatgactgaa   1740
cagtgactgg tggctcactt ctgcccacct gccggcaaca ccagtgccag gaaaaggcca   1800
aaagaatgtc tgtttctaac aaatccacaa atagccccga gattcaccgt cctagagctt   1860
aggcctgtct tccacccctc ctgacccgta tagtgtgcca caggacctgg gtcggtctag   1920
aactctctca ggatgccttt tctaccccat ccctcacagc ctcttgctgc taaaatagat   1980
gtttcatttt tctgactcat gcaatcattc ccctttgcct gtggctaaga cttggcttca   2040
tttcgtcatg taattgtata tttttatttg gaggcatatt ttcttttctt acagtcattg   2100
ccagacagag gcatacaagt ctgtttgctg catacacatt tctggtgagg gcgactgggt   2160
gggtgaagca ccgtgtcctc gctgaggaga gaaagggagg cgtgcctgag aaggtagcct   2220
gtgcatctgg tgagtgtgtc acgagctttg ttactgccaa actcactcct ttttagaaaa   2280
aacaaaaaaa aagggccaga aagtcattcc ttccatcttc cttgcagaaa ccacgagaac   2340
aaagccagtt ccctgtcagt gacagggctt cttgtaattt gtggtatgtg ccttaaacct   2400
gaatgtctgt agccaaaact tgtttccaca ttaagagtca gccagctctg gaatggtctg   2460
gaaatgtc                                                            2468
```

<210> SEQ ID NO 53
<211> LENGTH: 4907
<212> TYPE: DNA
<213> ORGANISM: Homo sapiens

<400> SEQUENCE: 53

```
tagacgcacc ctctgaagat ggtgactccc tcctgagaag ctggacccct tggtaaaaga     60
caaggccttc tccaagaaga atatgaaagt gttactcaga cttatttgtt tcatagctct    120
actgatttct tctctggagg ctgataaatg caaggaacgt gaagaaaaaa taattttagt    180
gtcatctgca aatgaaattg atgttcgtcc ctgtcctctt aacccaaatg aacacaaagg    240
cactataact tggtataaag atgacagcaa gacacctgta tctacagaac aagcctccag    300
gattcatcaa cacaaagaga aactttggtt tgttcctgct aaggtggagg attcaggaca    360
ttactattgc gtggtaagaa attcatctta ctgcctcaga attaaaataa gtgcaaaatt    420
tgtggagaat gagcctaact tatgttataa tgcacaagcc atatttaagc agaaactacc    480
cgttgcagga gacggaggac ttgtgtgccc ttatatggag ttttttaaaa atgaaaataa    540
```

-continued

```
tgagttacct aaattacagt ggtataagga ttgcaaacct ctacttcttg acaatataca    600
ctttagtgga gtcaaagata ggctcatcgt gatgaatgtg gctgaaaagc atagagggaa    660
ctatacttgt catgcatcct acacatactt gggcaagcaa tatcctatta cccgggtaat    720
agaatttatt actctagagg aaaacaaacc cacaaggcct gtgattgtga gcccagctaa    780
tgagacaatg gaagtagact tgggatccca gatacaattg atctgtaatg tcaccggcca    840
gttgagtgac attgcttact ggaagtggaa tgggtcagta attgatgaag atgacccagt    900
gctaggggaa gactattaca gtgtggaaaa tcctgcaaac aaaagaagga gtaccctcat    960
cacagtgctt aatatatcgg aaattgaaag tagattttat aaacatccat ttacctgttt   1020
tgccaagaat acacatggta tagatgcagc atatatccag ttaatatatc cagtcactaa   1080
tttccagaag cacatgattg gtatatgtgt cacgttgaca gtcataattg tgtgttctgt   1140
tttcatctat aaaatcttca agattgacat tgtgctttgg tacagggatt cctgctatga   1200
ttttctccca ataaaagctt cagatggaaa gacctatgac gcatatatac tgtatccaaa   1260
gactgttggg gaagggtcta cctctgactg tgatattttt gtgtttaaag tcttgcctga   1320
ggtcttggaa aaacagtgtg gatataagct gttcatttat ggaagggatg actacgttgg   1380
ggaagacatt gttgaggtca ttaatgaaaa cgtaaagaaa agcagaagac tgattatcat   1440
tttagtcaga gaaacatcag gcttcagctg gctgggtggt tcatctgaag agcaaatagc   1500
catgtataat gctcttgttc aggatggaat taaagttgtc ctgcttgagc tggagaaaat   1560
ccaagactat gagaaaatgc cagaatcgat taaattcatt aagcagaaac atggggctat   1620
ccgctggtca ggggacttta cacagggacc acagtctgca aagacaaggt tctggaagaa   1680
tgtcaggtac cacatgccag tccagcgacg gtcaccttca tctaaacacc agttactgtc   1740
accagccact aaggagaaac tgcaaagaga ggctcacgtg cctctcgggt agcatggaga   1800
agttgccaag agttctttag gtgcctcctg tcttatggcg ttgcaggcca ggttatgcct   1860
catgctgact tgcagagttc atggaatgta actatatcat cctttatccc tgaggtcacc   1920
tggaatcaga ttattaaggg aataagccat gacgtcaata gcagcccagg gcacttcaga   1980
gtagagggct tgggaagatc ttttaaaaag gcagtaggcc cggtgtggtg gctcacgcct   2040
ataatcccag cactttggga ggctgaagtg ggtggatcac cagaggtcag gagttcgaga   2100
ccagcccagc caacatggca aaaccccatc tctactaaaa atacaaaaat gagctaggca   2160
tggtggcaca cgcctgtaat cccagctaca cctgaggctg aggcaggaga attgcttgaa   2220
ccggggagac ggaggttgca gtgagccgag tttgggccac tgcactctag cctggcaaca   2280
gagcaagact ccgtctcaaa aaaagggcaa taaatgccct ctctgaatgt ttgaactgcc   2340
aagaaaaggc atggagacag cgaactagaa gaaagggcaa gaaggaaata gccaccgtct   2400
acagatggct tagttaagtc atccacagcc caagggcggg gctatgcctt gtctggggac   2460
cctgtagagt cactgaccct ggagcggctc tcctgagagg tgctgcaggc aaagtgagac   2520
tgacacctca ctgaggaagg gagacatatt cttggagaac tttccatctg cttgtatttt   2580
ccatacacat ccccagccag aagttagtgt ccgaagaccg aattttattt tacagagctt   2640
gaaaactcac ttcaatgaac aaagggattc tccaggattc caaagttttg aagtcatctt   2700
agctttccac aggagggaga gaacttaaaa aagcaacagt agcagggaat tgatccactt   2760
cttaatgctt tcctccctgg catgaccatc ctgtcctttg ttattatcct gcattttacg   2820
tctttggagg aacagctccc tagtggcttc ctccgtctgc aatgtccctt gcacagccca   2880
cacatgaacc atccttccca tgatgccgct cttctgtcat cccgctcctg ctgaaacacc   2940
```

-continued

```
tcccaggggc tccacctgtt caggagctga agcccatgct ttcccaccag catgtcactc   3000

ccagaccacc tccctgccct gtcctccagc ttcccctcgc tgtcctgctg tgtgaattcc   3060

caggttggcc tggtggccat gtcgcctgcc cccagcactc ctctgtctct gctcttgcct   3120

gcacccttcc tcctcctttg cctaggaggc cttctcgcat tttctctagc tgatcagaat   3180

tttaccaaaa ttcagaacat cctccaattc cacagtctct gggagacttt ccctaagagg   3240

cgacttcctc tccagccttc tctctctggt caggcccact gcagagatgg tggtgagcac   3300

atctgggagg ctggtctccc tccagctgga attgctgctc tctgagggag aggctgtggt   3360

ggctgtctct gtccctcact gccttccagg agcaatttgc acatgtaaca tagatttatg   3420

taatgcttta tgtttaaaaa cattccccaa ttatcttatt taatttttgc aattattcta   3480

attttatata tagagaaagt gacctatttt ttaaaaaaat cacactctaa gttctattga   3540

acctaggact tgagcctcca tttctggctt ctagtctggt gttctgagta cttgatttca   3600

ggtcaataac ggtcccccct cactccacac tggcacgttt gtgagaagaa atgacatttt   3660

gctaggaagt gaccgagtct aggaatgctt ttattcaaga caccaaattc caaacttcta   3720

aatgttggaa ttttcaaaaa ttgtgtttag attttatgaa aaactcttct actttcatct   3780

attctttccc tagaggcaaa catttcttaa aatgtttcat tttcattaaa aatgaaagcc   3840

aaatttatat gccaccgatt gcaggacaca agcacagttt taagagttgt atgaacatgg   3900

agaggacttt tggtttttat atttctcgta tttaatatgg gtgaacacca acttttattt   3960

ggaataataa ttttcctcct aaacaaaaac acattgagtt taagtctctg actcttgcct   4020

ttccacctgc tttctcctgg gcccgctttg cctgcttgaa ggaacagtgc tgttctggag   4080

ctgctgttcc aacagacagg gcctagcttt catttgacac acagactaca gccagaagcc   4140

catggagcag ggatgtcacg tcttgaaaag cctattagat gttttacaaa tttaattttg   4200

cagattattt tagtctgtca tccagaaaat gtgtcagcat gcatagtgct aagaaagcaa   4260

gccaatttgg aaacttaggt tagtgacaaa attggccaga gagtgggggt gatgatgacc   4320

aagaattaca agtagaatgg cagctggaat ttaaggaggg acaagaatca atggataagc   4380

gtgggtggag gaagatccaa acagaaaagt gcaaagttat tccccatctt ccaagggttg   4440

aattctggag gaagaagaca cattcctagt tccccgtgaa cttcctttga cttattgtcc   4500

ccactaaaac aaaacaaaaa acttttaatg ccttccacat taattagatt ttcttgcagt   4560

ttttttatgg catttttta aagatgccct aagtgttgaa gaagagtttg caaatgcaac   4620

aaaatattta attaccggtt gttaaaactg gtttagcaca atttatattt tccctctctt   4680

gcctttctta tttgcaataa aaggtattga gccatttttt aaatgacatt tttgataaat   4740

tatgtttgta ctagttgatg aaggagtttt ttttaacctg tttatataat tttgcagcag   4800

aagccaaatt ttttgtatat taaagcacca aattcatgta cagcatgcat cacggatcaa   4860

tagactgtac ttattttcca ataaaatttt caaactttgt actgtta                 4907
```

<210> SEQ ID NO 54
<211> LENGTH: 1004
<212> TYPE: DNA
<213> ORGANISM: Homo sapiens

<400> SEQUENCE: 54

```
ccctgcactc tcgctctcct gccccacccc gaggtaaagg gggcgactaa gagaagatgg     60

tgttgctcac cgcggtcctc ctgctgctgg ccgcctatgc ggggccggcc cagagcctgg    120
```

-continued

```
gctccttcgt gcactgcgag ccctgcgacg agaaagccct ctccatgtgc ccccccagcc    180

ccctgggctg cgagctggtc aaggagccgg gctgcggctg ctgcatgacc tgcgccctgg    240

ccgaggggca gtcgtgcggc gtctacaccg agcgctgcgc ccaggggctg cgctgcctcc    300

cccggcagga cgaggagaag ccgctgcacg ccctgctgca cggccgcggg gtttgcctca    360

acgaaaagag ctaccgcgag caagtcaaga tcgagagaga ctcccgtgag cacgaggagc    420

ccaccacctc tgagatggcc gaggagacct actcccccaa gatcttccgg cccaaacaca    480

cccgcatctc cgagctgaag gctgaagcag tgaagaagga ccgcagaaag aagctgaccc    540

agtccaagtt tgtcggggga gccgagaaca ctgcccaccc ccggatcatc tctgcacctg    600

agatgagaca ggagtctgag cagggcccct gccgcagaca catggaggct tccctgcagg    660

agctcaaagc cagcccacgc atggtgcccc gtgctgtgta cctgcccaat tgtgaccgca    720

aaggattcta caagagaaag cagtgcaaac cttcccgtgg ccgcaaacgt ggcatctgct    780

ggtgcgtgga caagtacggg atgaagctgc caggcatgga gtacgttgac ggggactttc    840

agtgccacac cttcgacagc agcaacgttg agtgatgcgt ccccccccaa cctttccctc    900

acccccctcc acccccagcc ccgactccag ccagcgcctc cctccacccc aggacgccac    960

tcatttcatc tcatttaagg gaaaaatata tatctatcta tttg                    1004
```

<210> SEQ ID NO 55
<211> LENGTH: 772
<212> TYPE: DNA
<213> ORGANISM: Homo sapiens

<400> SEQUENCE: 55

```
cgcagcgggt cctctctatc tagctccagc ctctcgcctg cgccccactc cccgcgtccc     60

gcgtcctagc cgaccatggc cgggccccctg cgcgccccgc tgctcctgct ggccatcctg    120

gccgtggccc tggccgtgag ccccgcggcc ggctccagtc ccggcaagcc gccgcgccta    180

gtgggaggcc ccatggacgc cagcgtggag gaggagggtg tgcggcgtgc actggacttt    240

gccgtcggcg agtacaacaa agccagcaac gacatgtacc acagccgcgc gctgcaggtg    300

gtgcgcgccc gcaagcagat cgtagctggg gtgaactact tcttggacgt ggagctgggc    360

cgaaccacgt gtaccaagac ccagcccaac ttggacaact gccccttcca tgaccagcca    420

catctgaaaa ggaaagcatt ctgctctttc cagatctacg ctgtgccttg gcagggcaca    480

atgaccttgt cgaaatccac ctgtcaggac gcctaggggt ctgtaccggg ctggcctgtg    540

cctatcacct cttatgcaca cctcccaccc cctgtattcc cacccctgga ctggtggccc    600

ctgccttggg gaaggtctcc ccatgtgcct gcaccaggag acagacagag aaggcagcag    660

gcggcctttg ttgctcagca aggggctctg ccctccctcc ttccttcttg cttctcatag    720

ccccggtgtg cggtgcatac acccccacct cctgcaataa aatagtagca tc            772
```

<210> SEQ ID NO 56
<211> LENGTH: 2128
<212> TYPE: DNA
<213> ORGANISM: Homo sapiens

<400> SEQUENCE: 56

```
gaaagatgga tcactccagc tcaaagagaa catgtgggaa tgaaaggaca ggctgggccc     60

aaaggagaaa agggtgatgc tggggaggag cttcctggcc ctcctgaacc ttctgggcct    120

gttggaccca cggcaggagc agaagcagag ggctctggcc taggctgggg ctcggacgtc    180

ggctctggct ctggtgacct ggtgggcagt gagcagctgc tgagaggtcc tccaggaccc    240
```

-continued

```
ccagggccac ctggcttacc tgggattcca ggaaaaccag gaactgatgt tttcatggga    300

ccccctggat ctcctggaga ggatggacct gctggtgaac ctgggccccc gggccctgag    360

ggacagcctg gagttgatgg agccaccggc cttcccggga tgaaagggga gaagggagca    420

agagggccta atggctcagt tggtgaaaag ggtgaccctg gcaacagagg cttacctgga    480

cccccgggga aaaagggaca agctggccct cctggggtca tgggaccccc agggcctcct    540

ggaccccctg ggcccccagg ccctggatgc acaatgggac ttggattcga ggataccgaa    600

ggctctggaa gcacccagct attgaatgaa cccaaactct ccagaccaac ggctgcaatt    660

ggtctcaaag gagagaaagg agaccgggga cccaagggag aaagggggat ggatggagcc    720

agtattgtgg gacccccctgg gccgagaggg ccacctgggc acatcaaggt cttgtctaat    780

tccttgatca atatcaccca tggattcatg aatttctcgg acattcctga gctggtgggg    840

cctccggggc cggacgggtt gcctgggctg ccaggatttc cagggtccta gaggaccaaa    900

aggtgacact ggtttacctg gctttccagg actaaaagga gaacagggcg agaagggaga    960

gccgggtgcc atcctgacag aggacattcc tctggaaagg ctgatgggga aaaagggtga   1020

acctggaatg catggagccc caggaccaat ggggcccaaa ggaccaccag gacataaagg   1080

agaatttggc cttcccgggc gacctggtcg cccaggactg aatggcctca agggtaccaa   1140

aggagatcca ggggtcatta tgcagggccc acctggctta cctggccctc caggcccccc   1200

tgggccacct ggagctgtga ttaacatcaa aggagccatt ttcccaatac ccgtccgacc   1260

acactgcaaa atgccagttg atactgctca tcctgggagt ccagagctca tcacttttca   1320

cggtgttaaa ggagagaaag gatcctgggg tcttcctggc tcaaagggag aaaaaggcga   1380

ccagggagcc cagggaccac caggtcctcc acttgatcta gcttacctga gacactttct   1440

gaacaacttg aagggggaga atggagacaa ggggttcaaa ggtgaaaaag gagaaaaagg   1500

agacattaat ggcagcttcc ttatgtctgg gcctccaggc ctgcccggaa atccaggccc   1560

ggctggccaa aaaggggaga cagtcgttgg gccccaagga cccccaggtg ctcctggtct   1620

gcctgggcca cctggctttg gaagacctgg tgatcctggg ccaccggggc ccccggggcc   1680

accaggacct ccagctatcc tgggagcagc tgtggccctt ccaggtcccc ctggccctcc   1740

aggacagcca gggcttcccg gatccagaaa cctggtcaca gcattcagca acatggatga   1800

catgctgcag aaagcgcatt tggttataga aggaacattc atctacctga gggacagcac   1860

tgagtttttc attcgtgtta gagatggctg gaaaaaatta cagctgggag aactgatccc   1920

cattcctgcc gacagccctc caccccctgc gctttccagc aacccacatc agcttctgcc   1980

tccaccaaac cctatttcaa gtgccaatta tgagaagcct gctctgcatt tggctgctct   2040

gaacatgcca ttttctgggg acattcgagc tgattttcag tgcttcaagc aggccagagc   2100

tgcaggactg ttgtccacct accgagca                                      2128
```

<210> SEQ ID NO 57
<211> LENGTH: 4309
<212> TYPE: DNA
<213> ORGANISM: Homo sapiens

<400> SEQUENCE: 57

```
tagaaattgt taattttaac aatccagagc aggccaacga ggctttgctc tcccgacccg     60

aactaaaggt ccctcgctcc gtgcgctgct acgagcggtg tctcctgggg ctccaatgca    120

gcgagctgtg cccgaggggt tcggaaggcg caagctgggc agcgacatgg ggaacgcgga    180
```

-continued gcgggctccg gggtctcgga gctttgggcc agtacccacg ctgctgctgc tcgccgcggc 240
gctactggcc gtgtcggacg cactcgggcg cccctccgag gaggacgagg agctagtggt 300
gccggagctg gagcgcgccc cgggacacgg gaccacgcgc ctccgcctgc acgcctttga 360
ccagcagctg gatctggagc tgcggcccga cagcagcttt ttggcgcccg gcttcacgct 420
ccagaacgtg gggcgcaaat ccgggtccga gacgccgctt ccggaaaccg acctggcgca 480
ctgcttctac tccggcaccg tgaatggcga tcccagctcg gctgccgccc tcagcctctg 540
cgagggcgtg cgcggcgcct tctacctgct gggggaggcg tatttcatcc agccgctgcc 600
cgccgccagc gagcgcctcg ccaccgccgc cccaggggag aagccgccgg caccactaca 660
gttccacctc ctgcggcgga atcggcaggg cgacgtcggc ggcacgtgcg gggtcgtgga 720
cgacgagccc cggccgactg ggaaagcgga gaccgaagac gaggacgaag ggactgaggg 780
cgaggacgaa ggggctcagt ggtcgccgca ggacccggca ctgcaaggcg taggacagcc 840
cacaggaact ggaagcataa gaaagaagcg atttgtgtcc agtcaccgct atgtggaaac 900
catgcttgtg gcagaccagt cgatggcaga attccacggc agtggtctaa agcattacct 960
tctcacgttg ttttcggtgg cagccagatt gtacaaacac cccagcattc gtaattcagt 1020
tagcctggtg gtggtgaaga tcttggtcat ccacgatgaa cagaaggggc cggaagtgac 1080
ctccaatgct gccctcactc tgcggaactt ttgcaactgg cagaagcagc acaacccacc 1140
cagtgaccgg gatgcagagc actatgacac agcaattctt ttcaccagac aggacttgtg 1200
tgggtcccag acatgtgata ctcttgggat ggctgatgtt ggaactgtgt gtgatccgag 1260
cagaagctgc tccgtcatag aagatgatgg tttacaagct gccttcacca cagcccatga 1320
attaggccac gtgtttaaca tgccacatga tgatgcaaag cagtgtgcca gccttaatgg 1380
tgtgaaccag gattcccaca tgatggcgtc aatgctttcc aacctggacc acagccagcc 1440
ttggtctcct tgcagtgcct acatgattac atcatttctg gataatggtc atggggaatg 1500
tttgatggac aagcctcaga atcccataca gctcccaggc gatctccctg gcacctcgta 1560
cgatgccaac cggcagtgcc agtttacatt tggggaggac tccaaacact gccccgatgc 1620
agccagcaca tgtagcacct tgtggtgtac cggcacctct ggtggggtgc tggtgtgtca 1680
aaccaaacac ttcccgtggg cggatggcac cagctgtgga gaagggaaat ggtgtatcaa 1740
cggcaagtgt gtgaacaaaa ccgacagaaa gcattttgat acgccttttc atggaagctg 1800
gggaatgtgg gggccttggg gagactgttc gagaacgtgc ggtggaggag tccagtacac 1860
gatgagggaa tgtgacaacc cagtcccaaa gaatggaggg aagtactgtg aaggcaaacg 1920
agtgcgctac agatcctgta accttgagga ctgtccagac aataatggaa aaacctttag 1980
agaggaacaa tgtgaagcac acaacgagtt ttcaaaagct tcctttggga gtgggcctgc 2040
ggtggaatgg attcccaagt acgctggcgt ctcaccaaag gacaggtgca agctcatctg 2100
ccaagccaaa ggcattggct acttcttcgt tttgcagccc aaggttgtag atggtactcc 2160
atgtagccca gattccacct ctgtctgtgt gcaaggacag tgtgtaaaag ctggttgtga 2220
tcgcatcata gactccaaaa agaagtttga taaatgtggt gtttgcgggg gaaatggatc 2280
tacttgtaaa aaaatatcag gatcagttac tagtgcaaaa cctggatatc atgatatcat 2340
cacaattcca actggagcca ccaacatcga agtgaaacag cggaaccaga ggggatccag 2400
gaacaatggc agctttcttg ccatcaaagc tgctgatggc acatatattc ttaatggtga 2460
ctacactttg tccaccttag agcaagacat tatgtacaaa ggtgttgtct tgaggtacag 2520
cggctcctct gcggcattgg aaagaattcg cagctttagc cctctcaaag agcccttgac 2580

-continued catccaggtt cttactgtgg gcaatgccct tcgacctaaa attaaataca cctacttcgt 2640
aaagaagaag aaggaatctt tcaatgctat ccccactttt tcagcatggg tcattgaaga 2700
gtggggcgaa tgttctaagt catgtgaatt gggttggcag agaagactgg tagaatgccg 2760
agacattaat ggacagcctg cttccgagtg tgcaaaggaa gtgaagccag ccagcaccag 2820
accttgtgca gaccatccct gcccccagtg gcagctgggg gagtggtcat catgttctaa 2880
gacctgtggg aagggttaca aaaaaagaag cttgaagtgt ctgtcccatg atggaggggt 2940
gttatctcat gagagctgtg atcctttaaa gaaacctaaa catttcatag acttttgcac 3000
aatggcagaa tgcagttaag tggtttaagt ggtgttagct ttgagggcaa ggcaaagtga 3060
ggaagggctg gtgcagggaa agcaagaagg ctggagggat ccagcgtatc ttgccagtaa 3120
ccagtgaggt gtatcagtaa ggtgggatta tgggggtaga tagaaaagga gttgaatcat 3180
cagagtaaac tgccagttgc aaatttgata ggatagttag tgaggattat taacctctga 3240
gcagtgatat agcataataa agccccgggc attattatta ttatttcttt tgttacatct 3300
attacaagtt tagaaaaaac aaagcaattg tcaaaaaaag ttagaactat tacaacccct 3360
gtttcctggt acttatcaaa tacttagtat catgggggtt gggaaatgaa aagtaggaga 3420
aaagtgagat tttactaaga cctgttttac tttacctcac taacaatggg gggagaaagg 3480
agtacaaata ggatctttga ccagcactgt ttatggctgc tatggtttca gagaatgttt 3540
atacattatt tctaccgaga attaaaactt cagattgttc aacatgagag aaaggctcag 3600
caacgtgaaa taacgcaaat ggcttcctct ttcctttttt ggaccatctc agtctttatt 3660
tgtgtaattc attttgagga aaaaacaact ccatgtattt attcaagtgc attaaagtct 3720
acaatggaaa aaaagcagtg aagcattaga tgctggtaaa agctagagga gacacaatga 3780
gcttagtacc tccaacttcc tttctttcct accatgtaac cctgctttgg gaatatggat 3840
gtaaagaagt aacttgtgtc tcatgaaaat cagtacaatc acacaaggag gatgaaacgc 3900
cggaacaaaa atgaggtgtg tagaacaggg tcccacaggt ttggggacat tgagatcact 3960
tgtcttgtgg tggggaggct gctgaggggt agcaggtcca tctccagcag ctggtccaac 4020
agtcgtatcc tggtgaatgt ctgttcagct cttctgtgag aatatgattt tttccatatg 4080
tatatagtaa aatatgttac tataaattac atgtacttta taagtattgg tttgggtgtt 4140
ccttccaaga aggactatag ttagtaataa atgcctataa taacatattt atttttatac 4200
atttatttct aatgaaaaaa acttttaaat tatatcgctt ttgtggaagt gcatataaaa 4260
tagagtattt atacaatata tgttactaga aataaaagaa cacttttgg 4309

<210> SEQ ID NO 58
<211> LENGTH: 3488
<212> TYPE: DNA
<213> ORGANISM: Homo sapiens

<400> SEQUENCE: 58
gggcccgggc gcgcgggagc gggagcggcc gggggagccg gagcgcacca tggaggcggc 60
ggcaggcggc cgcggctgtt tccagccgca cccggggctg cagaagacgc tggagcagtt 120
ccacctgagc tccatgagct cgctgggcgg cccggccgct ttctcggcgc gctgggcgca 180
ggaggcctac aagaaggaga gcgccaagga ggcgggcgcg gccgcggtgc cggcgccggt 240
gcccgcagcc accgagccgc cgcccgtgct gcacctgccc gccatccagc cgccgccgcc 300
cgtgctgccc gggcccttct tcatgccgtc cgaccgctcc accgagcgct gcgagaccgt 360

-continued

```
actggaaggc gagaccatct cgtgcttcgt ggtgggaggc gagaagcgcc tgtgtctgcc    420
gcagattctc aactcggtgc tgcgcgactt ctcgctgcag cagatcaacg cggtgtgcga    480
cgagctccac atctactgct cgcgctgcac ggccgaccag ctggagatcc tcaaagtcat    540
gggcatcctg cccttctcgg cgccctcgtg cgggctcatc accaagacgg acgccgagcg    600
cctgtgcaac gcgctgctct acggcggcgc ctacccgccg ccctgcaaga aggagctggc    660
cgccagcctg gcgctgggcc tggagctcag cgagcgcagc gtccgcgtgt accacgagtg    720
cttcggcaag tgtaaggggc tgctggtgcc cgagctctac agcagcccga gcgccgcctg    780
catccagtgc ctggactgcc gcctcatgta cccgccgcac aagttcgtgg tgcactcgca    840
caaggccctg gagaaccgga cctgccactg ggcttcgac tcggccaact ggcgggccta    900
catcctgctg agccaggatt acacgggcaa ggaggagcag gcgcgcctcg gccgctgcct    960
ggacgacgtg aaggagaaat tcgactatgg caacaagtac aagcggcggg tgccccgggt   1020
ctcctctgag cctccggcct ccataagacc caaaacagat gacacctctt cccagtcccc   1080
cgcgccttcc gaaaaggaca agccgtccag ctggctgcgg accttggccg gctcttccaa   1140
taagagcctg ggctgtgttc accctcgcca gcgcctctct gctttccgac cctggtcccc   1200
cgcagtgtca gcgagtgaga aagagctctc cccacacctc ccggccctca tccgagacag   1260
cttctactcc tacaagagct ttgagacagc cgtggcgccc aacgtggccc tcgcaccgcc   1320
ggcccagcag aaggttgtga gcagccctcc gtgtgccgcc gccgtctccc gggcccccga   1380
gcctctcgcc acttgcaccc agcctcggaa gcggaagctg actgtggaca ccccaggagc   1440
cccagagacg ctggcgcccg tggctgcccc agaggaggac aaggactcgg aggcggaggt   1500
ggaagttgaa agcagggagg aattcacctc ctccttgtcc tcgctctctt ccccgtcctt   1560
tacctcatcc agctccgcca aggacctggg ctccccgggt gcgcgtgccc tgccctcggc   1620
cgtccctgat gctgcggccc ctgccgacgc cccccagtggg ctggaggcgg agctggagca   1680
cctgcggcag gcactggagg gcggcctgga caccaaggaa gccaaagaga agttcctgca   1740
tgaggtggtc aagatgcgcg tgaagcagga ggagaagctc agcgcagccc tgcaggccaa   1800
gcgcagcctc caccaggagc tggagttcct acgcgtggcc aagaaggaga agctgcggga   1860
ggccacggag gccaagcgta acctgcggaa ggagatcgag cgtctccgcg ccgagaacga   1920
gaagaagatg aaagaggcca acgagtcacg gctgcgcctg aagcgggagc tggagcaggc   1980
gcggcaggcc cgggtgtgcg acaagggctg cgaggcgggc cgcctgcgcg ccaagtactc   2040
ggcccagatc gaagacctgc aggtgaagct gcagcacgcg gaggcggacc gggagcagct   2100
gcgggccgac ctgctgcggg agcgcgaggc ccgggagcac ctggagaagg tggtgaagga   2160
gctgcaggaa cagctgtggc cgcgggcccg ccccgaggct gcgggcagcg agggcgctgc   2220
ggagctggag ccgtagattc cgtgcctgcc gccgcagcgc cgccgacaac gcgggtgcag   2280
gggggcgcgg ctgggcggtg cagctccgcc cggctccgcc cctgcagccc acacagcaca   2340
acgtcttacc gtgcctatta ccaagcgagt gtttgtaacc atgtagtttt ggaacccact   2400
gcaaaatttt ctactggcca agttcaagtg agtaagccgc gtcccccaac tacagctgga   2460
gacggggcca gctcggcggc ctgctggtcc tctgcttgct ggaacattct aacatttaca   2520
cttttgttat aagctattta aaaccagtaa ggagacttga aattcagaaa atcaacacat   2580
ttttaaatga ctaacttcta aaagccccaa cacatgacgc catctgaaga cccgcaacgg   2640
agtgggggtg gcggccgccc caccctcccc acccggggaa gccatcacag ctcatctgcc   2700
cgcggctgcg tgaggacagc aggggttttt cttcagagtc tattttttca gcgacaagga   2760
```

-continued

```
cccaggtctt cctgctgctg ccagggagag cagggacagt gccgcgtgcg agatgagctc   2820

gaacactgcc cgccttactg ccgcctaccc cgcccgccac gccgccgtcg atgccagcgc   2880

tgtccccacg ggtaccagga agtgcagagc cgcacaggag ctgccccgga gctgagggga   2940

cggtcttcgg ctcctctgca ccccgtgatt ctgcccacgc tcctccacca cgaggcactg   3000

acctgcgtcg ggtggtgacc gtggctggcg gtcacgccct cagcccctcc gggcacacgt   3060

gccgcctgac cgggcgaccc ttttcagttc ggcaaacgtc gctcccttca ttttgggact   3120

gaggctgcag cattggaaca aaagagcatt atttcaattt ttctttcttt ttttttgttc   3180

gttcatttaa acgtatattt agaactgcac tttgtccaca accttccctt ctctttctat   3240

tccccagtga actgaggttt ttaccgattt atagagcagt caaatccgaa gtgctcgagt   3300

gcttagaaac cccctctggt gcttggttga acaagggaat cacaagaaaa cgaaaatgca   3360

aaaactgaac ttcgggggtc gttctgtgcc ttccagcatc ttgtacagca aatcctgact   3420

cgtgtctttt tacccccaag atatctgtct tcagtagcga ctgaatctgc cactctcaga   3480

ataagttc                                                            3488
```

<210> SEQ ID NO 59
<211> LENGTH: 3108
<212> TYPE: DNA
<213> ORGANISM: Homo sapiens

<400> SEQUENCE: 59

```
gccgccgccg ccatccgccg ccgcagccag cttccgccgc cgcaggaccg gcccctgccc     60

cagcctccgc agccgcggcg cgtccacgcc cgcccgcgcc cagggcgagt cggggtcgcc    120

gcctgcacgc ttctcagtgt tccccgcgcc ccgcatgtaa cccggccagg cccccgcaac    180

tgtgtcccct gcagctccag ccccgggctg catccccccg ccccgacacc agctctccag    240

cctgctcgtc caggatggcc gcggccaagg ccgagatgca gctgatgtcc ccgctgcaga    300

tctctgaccc gttcggatcc tttcctcact cgcccaccat ggacaactac cctaagctgg    360

aggagatgat gctgctgagc aacggggctc cccagttcct cggcgccgcc ggggccccag    420

agggcagcgg cagcaacagc agcagcagca gcagcggggg cggtggaggc ggcgggggcg    480

gcagcaacag cagcagcagc agcagcacct tcaaccctca ggcggacacg ggcgagcagc    540

cctacgagca cctgaccgca gagtcttttc ctgacatctc tctgaacaac gagaaggtgc    600

tggtggagac cagttacccc agccaaacca ctcgactgcc ccccatcacc tatactggcc    660

gcttttccct ggagcctgca cccaacagtg gcaacacctt gtggcccgag cccctcttca    720

gcttggtcag tggcctagtg agcatgacca acccaccggc ctcctcgtcc tcagcaccat    780

ctccagcggc ctcctccgcc tccgcctccc agagcccacc cctgagctgc gcagtgccat    840

ccaacgacag cagtcccatt tactcagcgg cacccacctt ccccacgccg aacactgaca    900

ttttccctga gccacaaagc caggccttcc cgggctcggc agggacagcg ctccagtacc    960

cgcctcctgc ctaccctgcc gccaagggtg gcttccaggt tcccatgatc cccgactacc   1020

tgtttccaca gcagcagggg gatctgggcc tgggcacccc agaccagaag cccttccagg   1080

gcctggagag ccgcacccag cagccttcgc taacccctct gtctactatt aaggcctttg   1140

ccactcagtc gggctcccag gacctgaagg ccctcaatac cagctaccag tcccagctca   1200

tcaaacccag ccgcatgcgc aagtacccca accggcccag caagacgccc ccccacgaac   1260

gcccttacgc ttgcccagtg gagtcctgtg atcgccgctt ctcccgctcc gacgagctca   1320
```

-continued

```
cccgccacat ccgcatccac acaggccaga agcccttcca gtgccgcatc tgcatgcgca   1380

acttcagccg cagcgaccac ctcaccaccc acatccgcac ccacacaggc gaaaagccct   1440

tcgcctgcga catctgtgga agaaagtttg ccaggagcga tgaacgcaag aggcatacca   1500

agatccactt gcggcagaag gacaagaaag cagacaaaag tgttgtggcc tcttcggcca   1560

cctcctctct ctcttcctac ccgtccccgg ttgctacctc ttacccgtcc ccggttacta   1620

cctcttatcc atccccggcc accacctcat acccatcccc tgtgcccacc tccttctcct   1680

ctcccggctc ctcgacctac ccatcccctg tgcacagtgg cttcccctcc ccgtcggtgg   1740

ccaccacgta ctcctctgtt ccccctgctt tcccggccca ggtcagcagc ttcccttcct   1800

cagctgtcac caactccttc agcgcctcca cagggctttc ggacatgaca gcaacctttt   1860

ctcccaggac aattgaaatt tgctaaaggg aaaggggaaa gaaagggaaa agggagaaaa   1920

agaaacacaa gagacttaaa ggacaggagg aggagatggc cataggagag gagggttcct   1980

cttaggtcag atggaggttc tcagagccaa gtcctccctc tctactggag tggaaggtct   2040

attggccaac aatcctttct gcccacttcc ccttccccaa ttactattcc ctttgacttc   2100

agctgcctga aacagccatg tccaagttct tcacctctat ccaaagaact tgatttgcat   2160

ggattttgga taaatcattt cagtatcatc tccatcatat gcctgacccc ttgctccctt   2220

caatgctaga aaatcgagtt ggcaaaatgg ggtttgggcc cctcagagcc ctgccctgca   2280

cccttgtaca gtgtctgtgc catggatttc gtttttcttg ggtactcttt gatgtgaaga   2340

taatttgcat attctattgt attatttgga gttaggtcct cacttggggg aaaaaaaaaa   2400

aagaaaagcc aagcaaacca atggtgatcc tctattttgt gatgatgctg tgacaataag   2460

tttgaacctt ttttttgaa acagcagtcc cagtattctc agagcatgtg tcagagtgtt   2520

gttccgttaa cctttttgta aatactgctt gaccgtactc tcacatgtgg caaaatatgg   2580

tttggttttt cttttttttt ttttttgaaa gtgtttttc ttcgtccttt tggtttaaaa   2640

agtttcacgt cttggtgcct tttgtgtgat gcgccttgct gatggcttga catgtgcaat   2700

tgtgagggac atgctcacct ctagccttaa ggggggcagg gagtgatgat ttgggggagg   2760

ctttgggagc aaaataagga agagggctga gctgagcttc ggttctccag aatgtaagaa   2820

aacaaaatct aaaacaaaat ctgaactctc aaaagtctat ttttttaact gaaaatgtaa   2880

atttataaat atattcagga gttggaatgt tgtagttacc tactgagtag gcggcgattt   2940

ttgtatgtta tgaacatgca gttcattatt ttgtggttct attttacttt gtacttgtgt   3000

ttgcttaaac aaagtgactg tttggcttat aaacacattg aatgcgcttt attgcccatg   3060

ggatatgtgg tgtatatcct tccaaaaaat taaaacgaaa ataaagta                3108
```

<210> SEQ ID NO 60
<211> LENGTH: 3775
<212> TYPE: DNA
<213> ORGANISM: Homo sapiens

<400> SEQUENCE: 60

```
cattcataag actcagagct acggccacgg cagggacacg cggaaccaag acttggaaac     60

ttgattgttg tggttcttct tgggggttat gaaatttcat taatcttttt tttttccggg    120

gagaaagttt ttggaaagat tcttccagat atttcttcat tttcttttgg aggaccgact    180

tacttttttt ggtcttcttt attactcccc tccccccgtg ggacccgccg gacgcgtgga    240

ggagaccgta gctgaagctg attctgtaca gcgggacagc gctttctgcc cctgggggag    300

caacccctcc ctcgcccctg ggtcctacgg agcctgcact ttcaagaggt acagcggcat    360
```

-continued

```
cctgtggggg cctgggcacc gcaggaagac tgcacagaaa ctttgccatt gttggaacgg    420
gacgttgctc cttccccgag cttccccgga cagcgtactt tgaggactcg ctcagctcac    480
cggggactcc cacggctcac cccggacttg caccttactt ccccaacccg gccatagcct    540
tggcttcccg gcgacctcag cgtggtcaca ggggcccccc tgtgcccagg gaaatgtttc    600
aggctttccc cggagactac gactccggct cccggtgcag ctcctcaccc tctgccgagt    660
ctcaatatct gtcttcggtg gactccttcg gcagtccacc caccgccgcg gcctcccagg    720
agtgcgccgg tctcggggaa atgcccggtt ccttcgtgcc cacggtcacc gcgatcacaa    780
ccagccagga cctccagtgg cttgtgcaac ccaccctcat ctcttccatg gcccagtccc    840
aggggcagcc actggcctcc cagcccccgg tcgtcgaccc ctacgacatg ccgggaacca    900
gctactccac accaggcatg agtggctaca gcagtggcgg agcgagtggc agtggtgggc    960
cttccaccag cggaactacc agtgggcctg ggcctgcccg cccagcccga gcccggccta   1020
ggagaccccg agaggagacg ctcaccccag aggaagagga gaagcgaagg gtgcgccggg   1080
aacgaaataa actagcagca gctaaatgca ggaaccggcg gagggagctg accgaccgac   1140
tccaggcgga gacagatcag ttggaggaag aaaaagcaga gctggagtcg gagatcgccg   1200
agctccaaaa ggagaaggaa cgtctggagt ttgtgctggt ggcccacaaa ccgggctgca   1260
agatccccta cgaagagggg cccgggccgg gcccgctggc ggaggtgaga gatttgccgg   1320
gctcagcacc ggctaaggaa gatggcttca gctggctgct gccgcccccg ccaccaccgc   1380
ccctgccctt ccagaccagc caagacgcac cccccaacct gacggcttct ctctttacac   1440
acagtgaagt tcaagtcctc ggcgacccct tccccgttgt taacccttcg tacacttctt   1500
cgtttgtcct cacctgcccg gaggtctccg cgttcgccgg cgcccaacgc accagcggca   1560
gtgaccagcc ttccgatccc ctgaactcgc cctccctcct cgctcggtga actctttaga   1620
cacacaaaac aaacaaacac atgggggaga gagacttgga agaggaggag gaggaggaga   1680
aggaggagag agaggggaag agacaaagtg ggtgtgtggc ctccctggct cctccgtctg   1740
accctctgcg gccactgcgc cactgccatc ggacaggagg attccttgtg ttttgtcctg   1800
cctcttgttt ctgtgccccg gcgaggccgg agagctggtg actttgggga caggggggtgg  1860
gaaggggatg gacaccccca gctgactgtt ggctctctga cgtcaaccca agctctgggg   1920
atgggtgggg agggggcgg gtgacgccca ccttcgggca gtcctgtgtg aggatgaagg   1980
gacgggggtg ggaggtaggc tgtggggtgg gctggagtcc tctccagaga ggctcaacaa   2040
ggaaaaatgc cactccctac ccaatgtctc ccacacccac cctttttttg gggtgcccag   2100
gttggtttcc cctgcactcc cgaccttagc ttattgatcc cacatttcca tggtgtgaga   2160
tcctctttac tctgggcaga agtgagcccc cccttaaagg gaattcgatg ccccccctaga  2220
ataatctcat ccccccaccc gacttctttt gaaatgtgaa cgtccttcct tgactgtcta   2280
gccactccct cccagaaaaa ctggctctga ttggaatttc tggcctccta aggctcccca   2340
ccccgaaatc agcccccagc cttgtttctg atgacagtgt tatcccaaga ccctgccccc   2400
tgccagccga ccctcctggc cttcctcgtt gggccgctct gatttcaggc agcaggggct   2460
gctgtgatgc cgtcctgctg gagtgattta tactgtgaaa tgagttggcc agattgtggg   2520
gtgcagctgg gtggggcagc acacctctgg ggggataatg tccccactcc cgaaagcctt   2580
tcctcggtct cccttccgtc catccccctt cttcctcccc tcaacagtga gttagactca   2640
agggggtgac agaaccgaga agggggtgac agtcctccat ccacgtggcc tctctctctc   2700
```

-continued

```
tcctcaggac cctcagccct ggccttttttc tttaaggtcc cccgaccaat ccccagccta   2760

ggacgccaac ttctcccacc ccttggcccc tcacatcctc tccaggaagg cagtgagggg   2820

ctgtgacatt tttccggaga agatttcaga gctgaggctt tggtaccccc aaaccccccaa   2880

tatttttgga ctggcagact caaggggctg gaatctcatg attccatgcc cgagtccgcc   2940

catccctgac catggttttg gctctcccac cccgccgttc cctgcgcttc atctcatgag   3000

gatttcttta tgaggcaaat ttatattttt taatatcggg gggtggacca cgccgccctc   3060

catccgtgct gcatgaaaaa cattccacgt gccccttgtc gcgcgtctcc catcctgatc   3120

ccagacccat tccttagcta tttatccctt tcctggtttc cgaaaggcaa ttatatctat   3180

tatgtataag taaatatatt atatatggat gtgtgtgtgt gcgtgcgcgt gagtgtgtga   3240

gcgcttctgc agcctcggcc taggtcacgt tggccctcaa agcgagccgt tgaattggaa   3300

actgcttcta gaaactctgg ctcagcctgt ctcgggctga cccttttctg atcgtctcgg   3360

cccctctgat tgttcccgat ggtctctctc cctctgtctt ttctcctccg cctgtgtcca   3420

tctgaccgtt ttcacttgtc tcctttctga ctgtccctgc caatgctcca gctgtcgtct   3480

gactctgggt tcgttgggga catgagattt tatttttttgt gagtgagact gagggatcgt   3540

agatttttac aatctgtatc tttgacaatt ctgggtgcga gtgtgagagt gtgagcaggg   3600

cttgctcctg ccaaccacaa ttcaatgaat ccccgacccc cctaccccat gctgtacttg   3660

tggttctctt tttgtatttt gcatctgacc ccggggggct gggacagatt ggcaatgggc   3720

cgtcccctct ccccttggtt ctgcactgtt gccaataaaa agctcttaaa aacgc         3775
```

<210> SEQ ID NO 61
<211> LENGTH: 2021
<212> TYPE: DNA
<213> ORGANISM: Homo sapiens

<400> SEQUENCE: 61

```
agcgagcttg cagcctcacc gacgagtctc aactaaaagg gactcccgga gctaggggtg     60

gggactcggc ctcacacagt gagtgccggc tattggactt ttgtccagtg acagctgaga    120

caacaaggac cacgggagga ggtgtaggag agaagcgccg cgaacagcga tcgcccagca    180

ccaagtccgc ttccaggctt tcggtttctt tgcctccatc ttgggtgcgc cttcccggcg    240

tctaggggag cgaaggctga ggtggcagcg gcaggagagt ccggccgcga caggacgaac    300

tcccccactg gaaaggattc tgaaagaaat gaagtcagcc ctcagaaatg aagttgactg    360

cctgctggct ttctgttgac tggcccggag ctgtactgca agacccttgt gagcttccct    420

agtctaagag taggatgtct gctgaagtca tccatcaggt tgaagaagca cttgatacag    480

atgagaagga gatgctgctc tttttgtgcc gggatgttgc tatagatgtg gttccaccta    540

atgtcaggga ccttctggat attttacggg aaagaggtaa gctgtctgtc ggggacttgg    600

ctgaactgct ctacagagtg aggcgatttg acctgctcaa acgtatcttg aagatggaca    660

gaaaagctgt ggagacccac ctgctcagga accctcacct tgtttcggac tatagagtgc    720

tgatggcaga gattggtgag gatttggata aatctgatgt gtcctcatta attttcctca    780

tgaaggatta catgggccga ggcaagataa gcaaggagaa ggtttcttgg accttgtggt    840

tgagttggag aaactaaatc tggttgcccc agatcaactg gatttattag aaaaatgcct    900

aaagaacatc cacagaatag acctgaagac aaaaatccag aagtacaagc agtctgttca    960

aggagcaggg acaagttaca ggaatgttct ccaagcagca atccaaaaga gtctcaagga   1020

tccttcaaat aacttcaggc tccataatgg gagaagtaaa gaacaaagac ttaaggaaca   1080
```

-continued gcttggcgct caacaagaac cagtgaagaa atccattcag gaatcagaag ctttttttgcc 1140 tcagagcata cctgaagaga gatacaagat gaagagcaag cccctaggaa tctgcctgat 1200
aatcgattgc attggcaatg agacagagct tcttcgagac accttcactt ccctgggcta 1260
tgaagtccag aaattcttgc atctcagtat gcatggtata tcccagattc ttggccaatt 1320
tgcctgtatg cccgagcacc gagactacga cagctttgtg tgtgtcctgg tgagccgagg 1380
aggctcccag agtgtgtatg gtgtggatca gactcactca gggctccccc tgcatcacat 1440
caggaggatg ttcatgggag attcatgccc ttatctagca gggaagccaa agatgttttt 1500
tattcagaac tatgtggtgt cagagggcca gctggaggac agcagcctct tggaggtgga 1560
tgggccagcg atgaagaatg tggaattcaa ggctcagaag cgagggctgt gcacagttca 1620
ccgagaagct gacttcttct ggagcctgtg tactgcggac atgtccctgc tggagcagtc 1680
tcacagctca ccatccctgt acctgcagtg cctctcccag aaactgagac aagaaagaaa 1740
acgcccactc ctggatcttc acattgaact caatggctac atgtatgatt ggaacagcag 1800
agtttctgcc aaggagaaat attatgtctg gctgcagcac actctgagaa agaaacttat 1860
cctctcctac acataagaaa ccaaaaggct gggcgtagtg gctcacacct gtaatcccag 1920
cactttggga ggccaaggag ggcagatcac ttcaggtcag gagttcgaga ccagcctggc 1980
caacatggta aacgctgtcc ctagtaaaaa tacaaaaatt a 2021

<210> SEQ ID NO 62
<211> LENGTH: 3254
<212> TYPE: DNA
<213> ORGANISM: Homo sapiens

<400> SEQUENCE: 62
agagttgcac tgagtgtggc tgaagcagcg aggcgggagt ggaggtgcgc ggagtcaggc 60
agacagacag acacagccag ccagccaggt cggcagtata gtccgaactg caaatcttat 120
tttcttttca ccttctctct aactgcccag agctagcgcc tgtggctccc gggctggtgt 180
ttcgggagtg tccagagagc ctggtctcca gccgcccccg ggaggagagc cctgctgccc 240
aggcgctgtt gacagcggcg gaaagcagcg gtacccacgc gcccgccggg ggaagtcggc 300
gagcggctgc agcagcaaag aactttcccg gctgggagga ccggagacaa gtggcagagt 360
cccggagcca acttttgcaa gcctttcctg cgtcttaggc ttctccacgg cggtaaagac 420
cagaaggcgg cggagagcca cgcaagagaa gaaggacgtg cgctcagctt cgctcgcacc 480
ggttgttgaa cttgggcgag cgcgagccgc ggctgccggg cgccccctcc ccctagcagc 540
ggaggagggg acaagtcgtc ggagtccggg cggccaagac ccgccgccgg ccggccactg 600
cagggtccgc actgatccgc tccgcgggga gagccgctgc tctgggaagt gagttcgcct 660
gcggactccg aggaaccgct gcgcacgaag agcgctcagt gagtgaccgc gacttttcaa 720
agccgggtag cgcgcgcgag tcgacaagta agagtgcggg aggcatctta attaaccctg 780
cgctccctgg agcgagctgg tgaggagggc gcagcgggga cgacagccag cgggtgcgtg 840
cgctcttaga gaaactttcc ctgtcaaagg ctccgggggg cgcgggtgtc ccccgcttgc 900
cacagccctg ttgcggcccc gaaacttgtg cgcgcagccc aaactaacct cacgtgaagt 960
gacggactgt tctatgactg caaagatgga aacgaccttc tatgacgatg ccctcaacgc 1020
ctcgttcctc ccgtccgaga gcggacctta tggctacagt aaccccaaga tcctgaaaca 1080
gagcatgacc ctgaacctgg ccgacccagt ggggagcctg aagccgcacc tccgcgccaa 1140

-continued gaactcggac ctcctcacct cgcccgacgt ggggctgctc aagctggcgt cgcccgagct 1200
ggagcgcctg ataatccagt ccagcaacgg gcacatcacc accacgccga cccccaccca 1260
gttcctgtgc cccaagaacg tgacagatga gcaggagggc ttcgccgagg gcttcgtgcg 1320
cgccctggcc gaactgcaca gccagaacac gctgcccagc gtcacgtcgg cggcgcagcc 1380
ggtcaacggg gcaggcatgg tggctcccgc ggtagcctcg gtggcagggg gcagcggcag 1440
cggcggcttc agcgccagcc tgcacagcga gccgccggtc tacgcaaacc tcagcaactt 1500
caacccaggc gcgctgagca gcggcggcgg ggcgccctcc tacggcgcgg ccggcctggc 1560
ctttcccgcg caaccccagc agcagcagca gccgccgcac cacctgcccc agcagatgcc 1620
cgtgcagcac ccgcggctgc aggccctgaa ggaggagcct cagacagtgc ccgagatgcc 1680
cggcgagaca ccgcccctgt cccccatcga catggagtcc caggagcgga tcaaggcgga 1740
gaggaagcgc atgaggaacc gcatcgctgc ctccaagtgc cgaaaaagga agctggagag 1800
aatcgcccgg ctggaggaaa aagtgaaaac cttgaaagct cagaactcgg agctggcgtc 1860
cacggccaac atgctcaggg aacaggtggc acagcttaaa cagaaagtca tgaaccacgt 1920
taacagtggg tgccaactca tgctaacgca gcagttgcaa acattttgaa gagagaccgt 1980
cgggggctga ggggcaacga agaaaaaaaa taacacagag agacagactt gagaacttga 2040
caagttgcga cggagagaaa aaagaagtgt ccgagaacta aagccaaggg tatccaagtt 2100
ggactgggtt gcgtcctgac ggcgccccca gtgtgcacga gtgggaagga cttggcgcgc 2160
cctcccttgg cgtggagcca gggagcggcc gcctgcgggc tgccccgctt tgcggacggg 2220
ctgtccccgc gcgaacggaa cgttggactt ttcgttaaca ttgaccaaga actgcatgga 2280
cctaacattc gatctcattc agtattaaag gggggagggg gagggggtta caaactgcaa 2340
tagagactgt agattgcttc tgtagtactc cttaagaaca caaagcgggg ggagggttgg 2400
ggaggggcgg caggagggag gtttgtgaga gcgaggctga gcctacagat gaactctttc 2460
tggcctgcct tcgttaactg tgtatgtaca tatatatatt ttttaatttg atgaaagctg 2520
attactgtca ataaacagct tcatgccttt gtaagttatt tcttgtttgt ttgtttgggt 2580
atcctgccca gtgttgtttg taaataagag atttggagca ctctgagttt accatttgta 2640
ataaagtata taattttttt atgttttgtt tctgaaaatt ccagaaagga tatttaagaa 2700
aatacaataa actattggaa agtactcccc taacctcttt tctgcatcat ctgtagatac 2760
tagctatcta ggtggagttg aaagagttaa gaatgtcgat taaaatcact ctcagtgctt 2820
cttactatta agcagtaaaa actgttctct attagacttt agaaataaat gtacctgatg 2880
tacctgatgc tatggtcagg ttatactcct cctcccccag ctatctatat ggaattgctt 2940
accaaaggat agtgcgatgt ttcaggaggc tggaggaagg ggggttgcag tggagaggga 3000
cagcccactg agaagtcaaa catttcaaag tttggattgt atcaagtggc atgtgctgtg 3060
accatttata atgttagtag aaattttaca ataggtgctt attctcaaag caggaattgg 3120
tggcagattt tacaaaagat gtatccttcc aatttggaat cttctctttg acaattccta 3180
gataaaaaga tggcctttgc ttatgaatat ttataacagc attcttgtca caataaatgt 3240
attcaaatac caat 3254

<210> SEQ ID NO 63
<211> LENGTH: 3254
<212> TYPE: DNA
<213> ORGANISM: Homo sapiens

<400> SEQUENCE: 63

-continued

```
agagttgcac tgagtgtggc tgaagcagcg aggcgggagt ggaggtgcgc ggagtcaggc      60
agacagacag acacagccag ccagccaggt cggcagtata gtccgaactg caaatcttat     120
tttcttttca ccttctctct aactgcccag agctagcgcc tgtggctccc gggctggtgt     180
ttcgggagtg tccagagagc ctggtctcca gccgcccccg ggaggagagc cctgctgccc     240
aggcgctgtt gacagcggcg gaaagcagcg gtacccacgc gcccgccggg ggaagtcggc     300
gagcggctgc agcagcaaag aactttcccg gctgggagga ccggagacaa gtggcagagt     360
cccggagcca acttttgcaa gcctttcctg cgtcttaggc ttctccacgg cggtaaagac     420
cagaaggcgg cggagagcca cgcaagagaa gaaggacgtg cgctcagctt cgctcgcacc     480
ggttgttgaa cttgggcgag cgcgagccgc ggctgccggg cgccccctcc ccctagcagc     540
ggaggagggg acaagtcgtc ggagtccggg cggccaagac ccgccgccgg ccggccactg     600
cagggtccgc actgatccgc tccgcgggga gagccgctgc tctgggaagt gagttcgcct     660
gcggactccg aggaaccgct gcgcacgaag agcgctcagt gagtgaccgc gacttttcaa     720
agccgggtag cgcgcgcgag tcgacaagta agagtgcggg aggcatctta attaaccctg     780
cgctccctgg agcgagctgg tgaggagggc gcagcgggga cgacagccag cgggtgcgtg     840
cgctcttaga gaaactttcc ctgtcaaagg ctccgggggg cgcgggtgtc cccccgcttgc    900
cacagccctg ttgcggcccc gaaacttgtg cgcgcagccc aaactaacct cacgtgaagt     960
gacggactgt tctatgactg caaagatgga aacgaccttc tatgacgatg ccctcaacgc    1020
ctcgttcctc ccgtccgaga gcggacctta tggctacagt aaccccaaga tcctgaaaca    1080
gagcatgacc ctgaacctgg ccgacccagt ggggagcctg aagccgcacc tccgcgccaa    1140
gaactcggac ctcctcacct cgcccgacgt ggggctgctc aagctggcgt cgcccgagct    1200
ggagcgcctg ataatccagt ccagcaacgg gcacatcacc accacgccga cccccaccca    1260
gttcctgtgc cccaagaacg tgacagatga gcaggagggc ttcgccgagg gcttcgtgcg    1320
cgccctggcc gaactgcaca gccagaacac gctgcccagc gtcacgtcgg cggcgcagcc    1380
ggtcaacggg gcaggcatgg tggctcccgc ggtagcctcg gtggcagggg gcagcggcag    1440
cggcggcttc agcgccagcc tgcacagcga gccgccggtc tacgcaaacc tcagcaactt    1500
caacccaggc gcgctgagca gcggcggcgg ggcgccctcc tacggcgcgg ccggcctggc    1560
ctttcccgcg caaccccagc agcagcagca gccgccgcac cacctgcccc agcagatgcc    1620
cgtgcagcac ccgcggctgc aggccctgaa ggaggagcct cagacagtgc ccgagatgcc    1680
cggcgagaca ccgcccctgt cccccatcga catggagtcc caggagcgga tcaaggcgga    1740
gaggaagcgc atgaggaacc gcatcgctgc ctccaagtgc cgaaaaaagga agctggagag   1800
aatcgcccgg ctggaggaaa aagtgaaaac cttgaaagct cagaactcgg agctggcgtc    1860
cacggccaac atgctcaggg aacaggtggc acagcttaaa cagaaagtca tgaaccacgt    1920
taacagtggg tgccaactca tgctaacgca gcagttgcaa acattttgaa gagagaccgt    1980
cgggggctga ggggcaacga agaaaaaaaa taacacagag agacagactt gagaacttga    2040
caagttgcga cggagagaaa aaagaagtgt ccgagaacta aagccaaggg tatccaagtt    2100
ggactgggtt gcgtcctgac ggcgccccca gtgtgcacga gtgggaagga cttggcgcgc    2160
cctcccttgg cgtggagcca gggagcggcc gcctgcgggc tgccccgctt tgcggacggg    2220
ctgtccccgc gcgaacggaa cgttggactt ttcgttaaca ttgaccaaga actgcatgga    2280
cctaacattc gatctcattc agtattaaag gggggagggg gagggggtta caaactgcaa    2340
```

-continued

```
tagagactgt agattgcttc tgtagtactc cttaagaaca caaagcgggg ggagggttgg   2400

ggaggggcgg caggagggag gtttgtgaga gcgaggctga gcctacagat gaactctttc   2460

tggcctgcct tcgttaactg tgtatgtaca tatatatatt ttttaatttg atgaaagctg   2520

attactgtca ataaacagct tcatgccttt gtaagttatt tcttgtttgt ttgtttgggt   2580

atcctgccca gtgttgtttg taaataagag atttggagca ctctgagttt accatttgta   2640

ataaagtata taattttttt atgttttgtt tctgaaaatt ccagaaagga tatttaagaa   2700

aatacaataa actattggaa agtactcccc taacctcttt tctgcatcat ctgtagatac   2760

tagctatcta ggtggagttg aaagagttaa gaatgtcgat taaaatcact ctcagtgctt   2820

cttactatta agcagtaaaa actgttctct attagacttt agaaataaat gtacctgatg   2880

tacctgatgc tatggtcagg ttatactcct cctcccccag ctatctatat ggaattgctt   2940

accaaaggat agtgcgatgt ttcaggaggc tggaggaagg ggggttgcag tggagaggga   3000

cagcccactg agaagtcaaa catttcaaag tttggattgt atcaagtggc atgtgctgtg   3060

accatttata atgttagtag aaattttaca ataggtgctt attctcaaag caggaattgg   3120

tggcagattt tacaaaagat gtatccttcc aatttggaat cttctctttg acaattccta   3180

gataaaaaga tggcctttgc ttatgaatat ttataacagc attcttgtca caataaatgt   3240

attcaaatac caat                                                      3254
```

<210> SEQ ID NO 64
<211> LENGTH: 1832
<212> TYPE: DNA
<213> ORGANISM: Homo sapiens

<400> SEQUENCE: 64

```
gtgccgctcc ttggtggggg ctgttcatgg cggttccggg gtctccaaca tttttcccgg     60

ctgtggtcct aaatctgtcc aaagcagagg cagtggagct tgaggttctt gctggtgtga    120

aatgactgag tacaaactgg tggtggttgg agcaggtggt gttgggaaaa gcgcactgac    180

aatccagcta atccagaacc actttgtaga tgaatatgat cccaccatag aggattctta    240

cagaaaacaa gtggttatag atggtgaaac ctgtttgttg gacatactgg atacagctgg    300

acaagaagag tacagtgcca tgagagacca atacatgagg acaggcgaag gcttcctctg    360

tgtatttgcc atcaataata gcaagtcatt tgcggatatt aacctctaca gggagcagat    420

taagcgagta aaagactcgg atgatgtacc tatggtgcta gtgggaaaca agtgtgattt    480

gccaacaagg acagttgata caaaacaagc ccacgaactg gccaagagtt acgggattcc    540

attcattgaa acctcagcca agaccagaca gggtgttgaa gatgcttttt acacactggt    600

aagagaaata cgccagtacc gaatgaaaaa actcaacagc agtgatgatg ggactcaggg    660

ttgtatggga ttgccatgtg tggtgatgta acaagatact tttaaagttt tgtcagaaaa    720

gagccacttt caagctgcac tgacaccctg gtcctgactt ccctggagga gaagtattcc    780

tgttgctgtc ttcagtctca cagagaagct cctgctactt ccccagctct cagtagttta    840

gtacaataat ctctatttga gaagttctca gaataactac ctcctcactt ggctgtctga    900

ccagagaatg cacctcttgt tactccctgt tatttttctg ccctgggttc ttccacagca    960

caaacacacc tctgccaccc caggtttttc atctgaaaag cagttcatgt ctgaaacaga   1020

gaaccaaacc gcaaacgtga aattctattg aaaacagtgt cttgagctct aaagtagcaa   1080

ctgctggtga ttttttttt ctttttactg ttgaacttag aactatgcta atttttggag   1140

aaatgtcata aattactgtt ttgccaagaa tatagttatt attgctgttt ggtttgttta   1200
```

-continued

```
taatgttatc ggctctattc tctaaactgg catctgctct agattcataa atacaaaaat   1260

gaatactgaa ttttgagtct atcctagtct tcacaacttt gacgtaatta aatccaactt   1320

tcacagtgaa gtgccttttt cctagaagtg gtttgtagac ttcctttata atatttcagt   1380

ggaatagatg tctcaaaaat ccttatgcat gaaatgaatg tctgagatac gtctgtgact   1440

tatctaccat tgaaggaaag ctatatctat ttgagagcag atgccatttt gtacatgtat   1500

gaaattggtt ttccagaggc ctgttttggg gctttcccag gagaaagatg aaactgaaag   1560

cacatgaata atttcactta ataattttta cctaatctcc actttttttca taggttacta   1620

cctatacaat gtatgtaatt tgtttcccct agcttactga taaacctaat attcaatgaa   1680

cttccatttg tattcaaatt tgtgtcatac cagaaagctc tacatttgca gatgttcaaa   1740

tattgtaaaa ctttggtgca ttgttattta atagctgtga tcagtgattt tcaaacctca   1800

aatatagtat attaacaaat tacattttca ct                                 1832
```

<210> SEQ ID NO 65
<211> LENGTH: 3890
<212> TYPE: DNA
<213> ORGANISM: Homo sapiens

<400> SEQUENCE: 65

```
atgaaggtga taagcttatt cattttggtg ggatttatag gagagttcca aagtttttca     60

agtgcctcct ctccagtcaa ctgccagtgg gacttctatg ccccttggtc agaatgcaat    120

ggctgtacca agactcagac tcgcaggcgg tcagttgctg tgtatgggca gtatggaggc    180

cagccttgtg ttggaaatgc ttttgaaaca cagtcctgtg aacctacaag aggatgtcca    240

acagaggagg gatgtggaga gcgtttcagg tgcttttcag gtcagtgcat cagcaaatca    300

ttggtttgca atggggattc tgactgtgat gaagacagtg ctgatgaaga cagatgtgag    360

gactcagaaa ggagaccttc ctgtgatatc gataaacctc ctcctaacat agaacttact    420

ggaaatggtt acaatgaact cactggccag tttaggaaca gagtcatcaa taccaaaagt    480

tttggtggtc aatgtagaaa ggtgtttagt ggggatggaa aagatttcta caggctgagt    540

ggaaatgtcc tgtcctatac attccaggtg aaaataaata atgattttaa ttatgaattt    600

tacaatagta cttggtctta tgtaaaacat acgtcgacag aacacacatc atctagtcgg    660

aagcgctcct tttttagatc ttcatcatct tcttcacgca gttatacttc acataccaat    720

gaaatccata aaggaaagag ttaccaactg ctggttgttg agaacactgt tgaagtggct    780

cagttcatta ataacaatcc agaattttta caacttgctg agccattctg gaaggagctt    840

tcccacctcc cctctctgta tgactacagt gcctaccgaa gattaatcga ccagtacggg    900

acacattatc tgcaatctgg gtcgttagga ggagaataca gagttctatt ttatgtggac    960

tcagaaaaat taaaacaaaa tgattttaat tcagtcgaag aaaagaaatg taaatcctca   1020

ggttggcatt ttgtcgttaa attttcaagt catggatgca aggaactgga aaacgcttta   1080

aaagctgctt caggaaccca gaacaatgta ttgcgaggag aaccgttcat cagaggggga   1140

ggtgcaggct tcatatctgg ccttagttac ctagagctgg acaatcctgc tggaaacaaa   1200

aggcgatatt ctgcctgggc agaatctgtg actaatcttc ctcaagtcat aaaacaaaag   1260

ctgacacctt tatatgagct ggtaaaggaa gtaccttgtg cctctgtgaa aaaactatac   1320

ctgaaatggg ctcttgaaga gtatctggat gaatttgacc cctgtcattg ccggccttgt   1380

caaaatggtg gtttggctac tgttgagggg acccattgtc tgtgccattg caaaccgtac   1440
```

-continued

```
acatttggtg cggcgtgtga gcaaggagtc ctcgtaggga atcaagcagg aggggttgat   1500
ggaggttgga gttgctggtc ctcttggagc ccctgtgtcc aagggaagaa aacaagaagc   1560
cgtgaatgca ataacccacc tcccagtggg ggtgggagat cctgcgttgg agaaacgaca   1620
gaaagcacac aatgcgaaga tgaggagctg gagcacttga ggttgcttga accacattgc   1680
tttcctttgt ctttggttcc aacagaattc tgtccatcac ctcctgcctt gaaagatgga   1740
tttgttcaag atgaaggtcc aatgtttcct gtggggaaaa atgtagtgta cacttgcaat   1800
gaaggatact ctcttattgg aaacccagtg gccagatgtg gagaagattt acggtggctt   1860
gttggggaaa tgcattgtca gaaaattgcc tgtgttctac ctgtactgat ggatggcata   1920
cagagtcacc cccaaaaacc tttctacaca gttggtgaga aggtgactgt ttcctgttca   1980
ggtggcatgt ccttagaagg tccttcagca tttctctgtg gctccagcct taagtggagt   2040
cctgagatga agaatgcccg ctgtgtacaa aaagaaaatc cgttaacaca ggcagtgcct   2100
aaatgtcagc gctgggagaa actgcagaat tcaagatgtg tttgtaaaat gccctacgaa   2160
tgtggacctt ccttggatgt atgtgctcaa gatgagagaa gcaaaaggat actgcctctg   2220
acagtttgca agatgcatgt tctccactgt cagggtagaa attacaccct tactggtagg   2280
gacagctgta ctctgcctgc ctcagctgag aaagcttgtg gtgcctgccc actgtgggga   2340
aaatgtgatg ctgagagcag caaatgtgtc tgccgagaag catcggagtg cgaggaagaa   2400
gggtttagca tttgtgtgga agtgaacggc aaggagcaga cgatgtctga gtgtgaggcg   2460
ggcgctctga gatgcagagg gcagagcatc tctgtcacca gcataaggcc ttgtgctgcg   2520
gaaacccagt aggctcctgg aggccatggt cagcttgctt ggaatccagc aggcagctgg   2580
ggctgagtga aaacatctgc acaactgggc actggacagc ttttccttct tctccagtgt   2640
ctaccttcct cctcaactcc cagccatctg tataaacaca atcctttgtt ctcccaaatc   2700
tgaatcgaat tactcttttg cctccttttt aatgtcagta aggatatgag cctttgcaca   2760
ggctggctgc gtgttcttga aataggtgtt accttctctg ggccttggtt ttttaaaatc   2820
tgtaaaatta gaggattgca ctagagaaac ttgaatgctc cattcaggcc tatcatttta   2880
ttaagtatga ttgacacagc ccatgggcca gaacacactc tacaaaatga ctaggataac   2940
agaaagaacg tgatctcctg attagagagg gtggttttcc tcaatggaac caaatataaa   3000
gaggacttga acaaaaatga cagatacaaa ctatttctat cctgagtagt aatctcacac   3060
ttcatcctat agagtcaacc accacagata ggaattcctt attctttttt taattttttt   3120
aagacagagt ctcactttgt tgcccaggct ggagcgcagt ggggtgatct catctccctg   3180
caacctccgc ctcctgggtt gaagcgattc ttgtgcctca gcttcccaag cagctgggat   3240
tacaggtgcc cgccaccacg cccagctaat ttttgcattt ttagtagaga tgggtttcac   3300
catgttggcc atgctcgtct ccaactcctg acctcaggta atccgtctgc cttggcctcc   3360
caaatgctgg gattacagac atgaaccacc acgcctggct ggaatactta ctcttgtcgg   3420
gagattgaac cactaaaatg ttagagcaga attcattatg ctgtggtcac aggggtgtct   3480
tgtctgagaa caaatacaat tcagtcttct ctttggggtt ttagtatgtg tcaaacatag   3540
gactggaagt ttgcccctgt tctttttttct tttgaaagaa catcagttca tgcctgaggc   3600
atgagtgact gtgcatttga gatagttttc cctattctgt ggatacagtc ccagagtttt   3660
cagggagtac acaggtagat tagtttgaag cattgacctt ttatttattc cttatttctc   3720
tttcatcaaa acaaaacagc agctgtggga ggagaaatga gagggcttaa atgaaattta   3780
aaataagcta tattatacaa atactatctc tgtattgttc tgaccctggt aaatatattt   3840
```

-continued caaaacttca gatgacaagg attagaacac tcattaagat gctattcttc 3890

<210> SEQ ID NO 66
<211> LENGTH: 725
<212> TYPE: DNA
<213> ORGANISM: Homo sapiens

<400> SEQUENCE: 66
ctaacccaga aacatccaat tctcaaactg aagctcgcac tctcgcctcc agcatgaaag 60
tctctgccgc ccttctgtgc ctgctgctca tagcagccac cttcattccc caagggctcg 120
ctcagccaga tgcaatcaat gccccagtca cctgctgtta taacttcacc aataggaaga 180
tctcagtgca gaggctcgcg agctatagaa gaatcaccag cagcaagtgt cccaaagaag 240
ctgtgatctt caagaccatt gtggccaagg agatctgtgc tgaccccaag cagaagtggg 300
ttcaggattc catggaccac ctggacaagc aaacccaaac tccgaagact tgaacactca 360
ctccacaacc caagaatctg cagctaactt attttcccct agctttcccc agacaccctg 420
ttttatttta ttataatgaa ttttgtttgt tgatgtgaaa cattatgcct taagtaatgt 480
taattcttat ttaagttatt gatgttttaa gtttatcttt catggtacta gtgtttttta 540
gatacagaga cttggggaaa ttgcttttcc tcttgaacca cagttctacc cctgggatgt 600
tttgagggtc tttgcaagaa tcattaatac aaagaatttt ttttaacatt ccaatgcatt 660
gctaaaatat tattgtggaa atgaatattt tgtaactatt acaccaaata aatatatttt 720
tgtac 725

<210> SEQ ID NO 67
<211> LENGTH: 3451
<212> TYPE: DNA
<213> ORGANISM: Homo sapiens
<220> FEATURE:
<221> NAME/KEY: misc_feature
<222> LOCATION: (841)..(1225)
<223> OTHER INFORMATION: The "n" at this position can be either "a",
"t", "g", or "c".

<400> SEQUENCE: 67
ttcaatgttg atgtgaaaaa ttcaatgact ttcagcggcc cggtggaaga catgtttgga 60
tatactgttc aacaatatga aaatgaagaa ggaaaaatggg tgcttattgg ttctccgtta 120
gttggccaac ccaaaaacag aactggagat gtctataagt gtccagttgg gagaggtgaa 180
tcattacctt gcgtaaagtt ggatctacca gttaatacat caattcccaa tgtcacagaa 240
gtaaaggaga acatgacatt tggatcaact ttagtcacca acccaaatgg aggatttctg 300
gcttgtgggc ccttatatgc ctatagatgt ggacatttgc attacacaac tggaatctgt 360
tctgacgtca gccccacatt tcaagtcgtg aattccattg cccctgtaca agaatgcagc 420
actcaactgg acatagtcat agtgctggat ggttccaaca gtatttaccc atgggacagt 480
gttacagctt ttttaaatga ccttcttgaa agaatggata ttggtcctaa acagacacag 540
gttggaattg tacagtatgg agaaaacgtg acccatgagt tcaacctcaa taagtattct 600
tccaccgaag aggtacttgt tgcagcaaag aaaatagtcc agagaggtgg ccgccagact 660
atgacagctc ttggaataga cacagcaaga aaggaggcat tcacggaagc ccggggtgcc 720
cgaagaggag ttaaaaaagt catggttatt gtgacagatg gagagtctca tgacaatcat 780
cgactgaaga aggtcatcca agactgtgaa gatgaaaaca ttcaacggtt ttccatagct 840
nnnnnnnnnn nnnnnnnnnn nnnnnnnnnn nnnnnnnnnn nnnnnnnnnn nnnnnnnnnn 900

-continued

```
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn nnnnnnnnnn nnnnnnnnnn   1020
nnnnnnnctt catatgaaat ggaaatgtct cagactggct tcagtgctca ttattcacag   1080
nnnnnnnnnn nnnnnnnnnn nnnnnnnnnn nnnnnnnnnn nnnnnnnnnn nnnnnnnnnn   1140
nnnnnnnnnn nnnnnnnnnn nnnnnnnnnn nnnnnnnnnn nnnnnnnnnn nnnnnnnnnn   1200
nnnnnnnnnn nnnnnnnnnn nnnnngttac actgtaaact ctgctactgc ttcttctgga   1260
gatgtgctct atattgctgg acagcctcgg tacaatcata caggccaggt cattatctac   1320
aggatggaag atggaaacat caaaattctc cagacgctca gtggagaaca gattggttcc   1380
tactttggca gtattttaac aacaactgac attgacaagg attctaatac tgacattctt   1440
ctagtcggag cccctatgta catgggaaca gagaaggagg agcaaggaaa agtgtatgtg   1500
tatgctctca atcagacaag gtttgaatat caaatgagcc tggaacctat taagcagacg   1560
tgctgttcat ctcggcagca caattcatgc acaacagaaa acaaaaatga gccatgcggg   1620
gctcgttttg gaactgcaat tgctgctgta aaagacctca atcttgatgg atttaatgac   1680
atcgtgatag gagctccgct ggagatgatc acgggggagc tgtgtacatt tatcatggaa   1740
gtggcaagac tataaggaaa gagtatgcac aacgtattcc atcaggtggg gatggtaaga   1800
cactgaaatt ttttggccag tctatccacg gagaaatgga tttaaatggt gacggtctga   1860
cagatgtgac tattgggggc cttggtggtg ctgccctctt ctggtcccga gatgtggccg   1920
tagttaaagt gaccatgaat tttgagccaa ataaagtgaa tattcaaaag aaaaactgcc   1980
atatggaggg aaaggaaaca gtatgcataa atgctacagt gtgttttgat gtgaaattaa   2040
agtctaaaga agacacgatt tatgaagctg atttgcagta ccgtgtcacc ctagattcac   2100
taagacaaat atcacgaagt tttttctctg gaactcaaga gagaaaggtt caaaggaaca   2160
tcacagttcg aaaatcagaa tgcactaagc actccttcta catgttgaca agcatgactt   2220
tcaggactct gtgagaataa cgttggactt taatcttacc gatccagaaa atgggcctgt   2280
tcttgatgat tctctaccaa actcagtaca tgaatatatt ccctttgcca aagattgtgg   2340
aaataaggaa aaatgtatct cagacctcag cctgcatgtc gccaccactg aaaaggacct   2400
gctgattgtc cgatcccaga atgataagtt caacgttagc ctcacagtca aaaatacaaa   2460
ggacagtgcc tataacacca ggacaatagt gcattattct ccaaatctag tttttttcagg   2520
aattgaggct atccaaaaag acagttgtga atctaatcat aatatcacat gtaaagttgg   2580
atatcccttc ctgagaagag gagagatggt aactttcaaa atattgtttc agtttaacac   2640
atcctatctc atggaaaatg tgaccattta tttaagtgca acaagtgaca gcgaagaacc   2700
tcctgaaacc ctttctgata atgtagtaaa catttctatc ccggtaaaat atgaagttgg   2760
actacagttt tacagctctg caagtgaata ccacatttca attgctgcca atgagacagt   2820
ccctgaagtt attaattcta ctgaggacat tggaaatgaa attaatatct tctacttgat   2880
tagaaaaagt ggatcttttc caatgccaga gcttaagctg tcaatttcat tccccaatat   2940
gacatcaaat ggttaccctg tgctgtaccc aactggattg tcatcttctg agaatgcaaa   3000
ctgcagaccc catatctttg aggatccttt cagtatcaac tctggaaaga aaatgactac   3060
atcaactgac catctcaaac gaggcacaat tctggactgc aatacatgta aatttgctac   3120
catcacatgt aatctcactt cttctgacat cagccaagtc aatgtttcgc ttatcttgtg   3180
gaaaccaact tttataaaat catatttttc cagcttaaat cttactataa ggggagaact   3240
```

-continued

```
tcggagtgaa aatgcatctc tggttttaag tagcagcaat caaaaaagag agcttgctat   3300

tcaaatatcc aaagatgggc taccgggcag agtgccatta tgggtcatcc tgctgagtgc   3360

ttttgccgga ttgttgctgt taatgctgct cattttagca ctgtggaaga ttggattctt   3420

caaaagacca ctgaaaaaga aaatggagaa a                                  3451
```

<210> SEQ ID NO 68
<211> LENGTH: 1772
<212> TYPE: DNA
<213> ORGANISM: Homo sapiens

<400> SEQUENCE: 68

```
gtatcactca gaatctggca gccagttccg tcctgacaga gttcacagca tatattggtg     60

gattcttgtc catagtgcat ctgctttaag aattaacgaa agcagtgtca agacagtaag    120

gattcaaacc atttgccaaa aatgagtcta agtgcattta ctctcttcct ggcattgatt    180

ggtggtacca gtggccagta ctatgattat gattttcccc tatcaattta tgggcaatca    240

tcaccaaact gtgcaccaga atgtaactgc cctgaaagct acccaagtgc catgtactgt    300

gatgagctga aattgaaaag tgtaccaatg gtgcctcctg gaatcaagta tctttacctt    360

aggaataacc agattgacca tattgatgaa aaggcctttg agaatgtaac tgatctgcag    420

tggctcattc tagatcacaa ccttctagaa aactccaaga taaaagggag agttttctct    480

aaattgaaac aactgaagaa gctgcatata aaccacaaca acctgacaga gtctgtgggc    540

ccacttccca aatctctgga ggatctgcag cttactcata acaagatcac aaagctgggc    600

tcttttgaag gattggtaaa cctgaccttc atccatctcc agcacaatcg gctgaaagag    660

gatgctgttt cagctgcttt taaaggtctt aaatcactcg aataccttga cttgagcttc    720

aatcagatag ccagactgcc ttctggtctc cctgtctctc ttctaactct ctacttagac    780

aacaataaga tcagcaacat ccctgatgag tatttcaagc gttttaatgc attgcagtat    840

ctgcgtttat ctcacaacga actggctgat agtggaatac ctggaaattc tttcaatgtg    900

tcatccctgg ttgagctgga tctgtcctat aacaagctta aaaacatacc aactgtcaat    960

gaaaaccttg aaaactatta cctggaggtc aatcaacttg agaagtttga cataaagagc   1020

ttctgcaaga tcctggggcc attatcctac tccaagatca agcatttgcg tttggatggc   1080

aatcgcatct cagaaaccag tcttccaccg gatatgtatg aatgtctacg tgttgctaac   1140

gaagtcactc ttaattaata tctgtatcct ggaacaatat tttatggtta tgtttttctg   1200

tgtgtcagtt ttcatagtat ccatatttta ttactgttta ttacttccat gaattttaaa   1260

atctgaggga aatgttttgt aaacatttat ttttttttaaa gaaaagatga aaggcaggcc   1320

tatttcatca caagaacaca cacatataca cgaatagaca tcaaactcaa tgctttattt   1380

gtaaatttag tgttttttta tttctactgt caaatgatgt gcaaaacctt ttactggttg   1440

catggaaatc agccaagttt tataatcctt aaatcttaat gttcctcaaa gcttggatta   1500

aatacatatg gatgttactc tcttgcacca aattatcttg atacattcaa atttgtctgg   1560

ttaaaaaata ggtggtagat attgaggcca agaatattgc aaaatacatg aagcttcatg   1620

cacttaaaga agtattttta gaataagaat ttgcatactt acctagtgaa acttttctag   1680

aattattttt cactctaagt catgtatgtt tctctttgat tatttgcatg ttatgtttaa   1740

taagctacta gcaaaataaa acatagcaaa tg                                 1772
```

<210> SEQ ID NO 69
<211> LENGTH: 2198

-continued

<212> TYPE: DNA
<213> ORGANISM: Homo sapiens

<400> SEQUENCE: 69

```
tggacagagg agcagtaaca atccccactc tccaattgtg gaagagttcc aagtcccata     60
caacaaactc caggtgatct ttaagtcaga cttttccaat gaagagcgtt ttacggggtt    120
tgctgcatac tatgttgcca cagacataaa tgaatgcaca gattttgtag atgtcccttg    180
tagccacttc tgcaacaatt tcattggtgg ttacttctgc tcctgccccc cggaatattt    240
cctccatgat gacatgaaga attgcggagt taattgcagt ggggatgtat tcactgcact    300
gattggggag attgcaagtc ccaattatcc caaaccatat ccagagaact caaggtgtga    360
ataccagatc cggttggaga aagggttcca agtggtggtg accttgcgga gagaagattt    420
tgatgtggaa gcagctgact cagcgggaaa ctgccttgac agtttagttt ttgttgcagg    480
agatcggcaa tttggtcctt actgtggtca tggattccct gggcctctaa atattgaaac    540
caagagtaat gctcttgata tcatcttcca aactgatcta acagggcaaa aaaagggctg    600
gaaacttcgc tatcatggag atccaatgcc ctgccctaag gaagacactc ccaattctgt    660
ttgggagcct gcgaaggcaa aatatgtctt tagagatgtg gtgcagataa cctgtctgga    720
tgggtttgaa gttgtggagg gacgtgttgg tgcaacatct ttctattcga cttgtcaaag    780
caatggaaag tggagtaatt ccaaactgaa atgtcaacct gtggactgtg gcattcctga    840
atccattgag aatggtaaag ttgaagaccc agagagcact ttgtttggtt ctgtcatccg    900
ctacacttgt gaggagccat attactacat ggaaaatgga ggaggtgggg agtatcactg    960
tgctggtaac gggagctggg tgaatgaggt gctgggcccg gagctgccga aatgtgttcc   1020
aggtctgtgg agtccccaga gaaccctttg aagaaaaaca gaggataatt ggaggatccg   1080
atgcagatat taaaaacttc ccctggcaag tcttctttga caacccatgg gctggtggag   1140
cgctcattaa tgagtactgg gtgctgacgg ctgctcatgt tgtggaggga aacagggagc   1200
caacaatgta tgttgggtcc acctcagtgc agacctcacg gctggcaaaa tccaagatgc   1260
tcactcctga gcatgtgttt attcatccgg gatggaagct gctggaagtc ccagaaggac   1320
gaaccaattt tgataatgac attgcactgg tgcggctgaa agacccagtg aaaatgggac   1380
ccaccgtctc tcccatctgc ctaccaggca cctcttccga ctacaacctc atggatgggg   1440
acctgggact gatctcaggc tggggccgaa cagagaagag agatcgtgct gttcgcctca   1500
aggcggcaag gttacctgta gctcctttaa gaaaatgcaa agaagtgaaa gtggagaaac   1560
ccacagcaga tgcagaggcc tatgttttca ctcctaacat gatctgtgct ggaggagaga   1620
agggcatgga tagctgtaaa ggggacagtg gtggggcctt tgctgtacag gatcccaatg   1680
acaagaccaa attctacgca gctggcctgg tgtcctgggg gccccagtgt gggacctatg   1740
ggctctacac acgggtaaag aactatgttg actggataat gaagactatg caggaaaata   1800
gcaccccccg tgaggactaa tccagataca tcccaccagc ctctccaagg gtggtgacca   1860
atgcattacc ttctgttcct tatgatattc tcattatttc atcatgactg aaagaagaca   1920
cgagcgaatg atttaaatag aacttgattg ttgagacgcc ttgctagagg tagagtttga   1980
tcatagaatt gtgctggtca tacatttgtg gtctgactcc ttggggtcct ttccccggag   2040
tacctattgt agataacact atgggtgggg cactcctttc ttgcactatt ccacagggat   2100
accttaattc tttgtttcct ctttacctgt tcaaaattcc atttacttga tcattctcag   2160
tatccactgt ctatgtacaa taaaggatgt ttataagc                           2198
```

-continued

<210> SEQ ID NO 70
<211> LENGTH: 2177
<212> TYPE: DNA
<213> ORGANISM: Homo sapiens

<400> SEQUENCE: 70
aaactctgat ctggggagga accaggacta catagatcaa ggcagttttc ttctttgaga 60
aactatccca gatatcatca tagagtcttc tgctcttcct caactaccaa agaaaaacat 120
cagcgaagca gcaggccatg caccccccaa aaactccatc tggggctctt catagaaaaa 180
ggaaaatggc agcctggccc ttctccaggc tgtggaaagt ctctgatcca attctcttcc 240
aaatgacctt gatcgctgct ctgttgcctg ctgttcttgg caattgtggt cctccaccca 300
ctttatcatt tgctgccccg atggatatta cgttgactga gacacgcttc aaaactggaa 360
ctactctgaa atacacctgc ctccctggct acgtcagatc ccattcaact cagacgctta 420
cctgtaattc tgatggcgaa tgggtgtata acaccttctg tatctacaaa cgatgcagac 480
acccaggaga gttacgtaat gggcaagtag agattaagac agatttatct tttggatcac 540
aaatagaatt cagctgttca gaaggatttt tcttaattgg ctcaaccact agtcgttgtg 600
aagtccaaga tagaggagtt ggctggagtc atcctctccc acaatgtgaa attgtcaagt 660
gtaagcctcc tccagacatc aggaatggaa ggcacagcgg tgaagaaaat ttctacgcat 720
acggcttttc tgtcacctac agctgtgacc cccgcttctc actcttgggc catgcctcca 780
tttcttgcac tgtggagaat gaaacaatag gtgtttggag accaagccct cctacctgtg 840
aaaaaatcac ctgtcgcaag ccagatgttt cacatgggga aatggtctct ggatttggac 900
ccatctataa ttacaaagac actattgtgt ttaagtgcca aaaaggtttt gttctcagag 960
gcagcagtgt aattcattgt gatgctgata gcaaatggaa tccttctcct cctgcttgtg 1020
agcccaatag ttgtattaat ttaccagaca ttccacatgc ttcctgggaa acatatccta 1080
ggccgacaaa agaggatgtg tatgttgttg ggactgtgtt aaggtaccgc tgtcatcctg 1140
gctacaaacc cactacagat gagcctacga ctgtgatttg tcagaaaaat ttgagatgga 1200
ccccatacca aggatgtgag gcgttatgtt gccctgaacc aaagctaaat aatggtgaaa 1260
tcactcaaca caggaaaagt cgtcctgcca atcactgtgt ttatttctat ggagatgaga 1320
tttcattttc atgtcatgag accagtaggt tttcagctat atgccaagga gatggcacgt 1380
ggagtccccg aacaccatca tgtggagaca tttgcaattt tcctcctaaa attgcccatg 1440
ggcattataa acaatctagt tcatacagct tttcaaaga agagattata tatgaatgtg 1500
ataaaggcta cattctggtc ggacaggcga aactctcctg cagttattca cactggtcag 1560
ctccagcccc tcaatgtaaa gctctgtgtc ggaaaccaga attagtgaat ggaaggttgt 1620
ctgtggataa ggatcagtat gttgagcctg aaaatgtcac catccaatgt gattctggct 1680
atggtgtggt tggtccccaa agtatcactt gctctgggaa cagaacctgg tacccagagg 1740
tgcccaagtg tgagtgggag acccccgaag gctgtgaaca agtgctcaca ggcaaaagac 1800
tcatgcagtg tctcccaaac ccagaggatg tgaaaatggc cctggaggta tataagctgt 1860
ctctggaaat tgaacaactg gaactacaga gagacagcgc aagacaatcc actttggata 1920
aagaactata atttttctca aaagaaggag gaaaaggtgt cttgctggct tgcctcttgc 1980
aattcaatac agatcagttt agcaaatcta ctgtcaattt ggcagtgata ttcatcataa 2040
taaatatcta gaaatgataa tttgctaaag tttagtgctt tgagattgtg aaattattaa 2100
tcatcctctg tgtggctcat gtttttgctt ttcaacacac aaagcacaaa ttttttttcg 2160

-continued

```
attaaaaatg tatgtat                                                2177


<210> SEQ ID NO 71
<211> LENGTH: 387
<212> TYPE: DNA
<213> ORGANISM: Homo sapiens
<220> FEATURE:
<221> NAME/KEY: misc_feature
<222> LOCATION: (27)..(53)
<223> OTHER INFORMATION: The "n" at this position can be either "a",
      "t", "g", or "c".

<400> SEQUENCE: 71

gccctgctgg ccctgctggt gctcccnnnn nnnnnnnnnn nnnnnnnnnn nnnggtcctc     60

aaggcccacg tggtgacaaa ggtgaaacag gtgaacgtgg agctgctggc atcaaaggac    120

atcgaggatt ccctggtaat ccaggtgccc caggttctcc agggccctgc tggtcagcag    180

ggtgcaatcg gcagtccagg acctgcaggc cccagaggac ctgttggacc cagtggacct    240

cctggcaaag atggaaccag tggacatcca ggtcccattg gaccaccagg gcctcgaggt    300

aacagaggtg aaagaggatc tgagggctcc ccaggccacc cagggcaacc aggccctcct    360

ggacctcctg gtgcccctgg tccttgc                                         387


<210> SEQ ID NO 72
<211> LENGTH: 14749
<212> TYPE: DNA
<213> ORGANISM: Homo sapiens
<220> FEATURE:
<221> NAME/KEY: misc_feature
<222> LOCATION: (4989)..(4997)
<223> OTHER INFORMATION: n is a, c, g, or t
<220> FEATURE:
<221> NAME/KEY: misc_feature
<222> LOCATION: (10041)..(10537)
<223> OTHER INFORMATION: n is a, c, g, or t
<220> FEATURE:
<221> NAME/KEY: misc_feature
<222> LOCATION: (11852)..(11893)
<223> OTHER INFORMATION: n is a, c, g, or t

<400> SEQUENCE: 72

gggcgcgggg agagggcgcg ggagcggctc gcgcggcagg taccatgcgg acgcgcgagc     60

ccggcgaggg ccccggcagg cccggtccct gctcgggggc gcgctgagac ggcgggtgag    120

ctccacgaga gcgccgtcgc cacttcgggc caactttgcg attcccgaca gttaagcaat    180

ggggagacat ttggctttgc tcctgcttct gctccttctc ttccaacatt ttggagacag    240

tgatggcagc caacgacttg aacagactcc tctgcagttt acacacctcg agtacaacgt    300

caccgtgcag gagaactctg cagctaagac ttatgtgggg catcctgtca agatgggtgt    360

ttacattaca catccagcgt gggaagtaag gtacaaaatt gtttccggag acagtgaaaa    420

cctgttcaaa gctgaagagt acattctcgg agacttttgc tttctaagaa taaggaccaa    480

aggaggaaat acagctattc ttaatagaga agtgaaggat cactacacat tgatagtgaa    540

agcacttgaa aaaaatacta atgtggaggc gcgaacaaag gtcagggtgc aggtgctgga    600

tacaaatgac ttgagaccgt tattctcacc cacctcatac agcgtttctt tacctgaaaa    660

cacagctata aggaccagta tcgcaagagt cagcgccacg gatgcagaca taggaaccaa    720

cggggaattt tactacagtt ttaaagatcg aacagatatg tttgctattc acccaaccag    780

tggtgtgata gtgttaactg gtagacttga ttacctagag accaagctct atgagatgga    840

aatcctcgct gcggaccgtg gcatgaagtt gtatgggagc agtggcatca gcagcatggc    900
```

-continued

```
caagctaacg gtgcacatcg aacaggccaa tgaatgtgct ccggtgataa cagcagtgac    960
attgtcacca tcagaactgg acagggaccc agcatatgca attgtgacag tggatgactg   1020
cgatcagggt gccaatggtg acatagcatc tttaagcatc gtggcaggtg accttctcca   1080
gcagtttaga acagtgaggt cctttccagg gagtaaggag tataaagtca aagccatcgg   1140
tggcattgat tgggacagtc atcctttcgg ctacaatctc acactacagg ctaaagataa   1200
aggaactccg ccccagttct cttctgttaa agtcattcac gtgacttctc cacagttcaa   1260
agccgggcca gtcaagtttg aaaaggatgt ttacagagca gaaataagtg aatttgctcc   1320
tcccaacaca cctgtggtca tggtaaaggc cattcctgct tattcccatt tgaggtatgt   1380
ttttaaaagt acacctggaa aagctaaatt cagtttaaat tacaacactg gtctcatttc   1440
tattttagaa ccagttaaaa gacagcaggc agcccatttt gaacttgaag taacaacaag   1500
tgacagaaaa gcgtccacca aggtcttggt gaaagtctta ggtgcaaata gcaatccccc   1560
tgaatttacc cagacagcgt acaaagctgc ttttgatgag aacgtgccca ttggtactac   1620
tgtcatgagc ctgagtgccg tagaccctga tgagggtgag aacgggtacg tgacatacag   1680
tatcgcaaat ttaaatcatg tgccgtttgc gattgaccat ttcactggtg ccgtgagtac   1740
gtcagaaaac ctggactacg aactgatgcc tcgggtttat actctgagga ttcgtgcatc   1800
agactggggc ttgccgtacc gccgggaagt cgaagtcctt gctacaatta ctctcaataa   1860
cttgaatgac aacacacctt tgtttgagaa aataaattgt gaagggacaa ttcccagaga   1920
tctaggcgtg ggagagcaaa taaccactgt ttctgctatt gatgcagatg aacttcagtt   1980
ggtacagtat cagattgaag ctggaaatga actggatttc tttagtttaa accccaactc   2040
gggggtattg tcattaaagc gatcgctaat ggatggctta ggtgcaaagg tgtctttcac   2100
agtctgagaa tcacagctac agatggagaa aattttgcca caccattata tatcaacata   2160
acagtggctg ccagtcacaa gctggtaaac ttgcagtgtg aagagactgg tgttgccaaa   2220
atgctggcag agaagctcct gcaggcaaat aaattacaca accagggaga ggtggaggat   2280
attttcttcg attctcactc tgtcaatgct cacataccgc agtttagaag cactcttccg   2340
actggtattc aggtaaagga aaaccagcct gtgggttcca gtgtaatttt catgaactcc   2400
actgaccttg acactggctt caatggaaaa ctggtctatg ctgtttctgg aggaaatgag   2460
gatagttgct tcatgattga tatggaaaca ggaatgctga aaattttatc tcctcttgac   2520
cgtgaaacaa cagacaaata caccctgaat attaccgtct atgaccttgg gataccccag   2580
aaggctgcgt ggcgtcttct acatgtcgtg gttgtcgatg ccaatgataa tccacccgag   2640
tttttacagg agagctattt tgtggaagtg agtgaagaca aggaggtaca tagtgaaatc   2700
atccaggttg aagccacaga taaagacctg gggcccaacg gacacgtgac gtactcaatt   2760
gttacagaca cagacacatt ttcaattgac agcgtgacgg gtgttgttaa catcgcacgc   2820
cctctggatc gagagctgca gcatgagcac tccttaaaga ttgaggccag ggaccaagcc   2880
agagaagagc ctcagctgtt ctccactgtc gttgtgaaag tatcactaga agatgttaat   2940
gacaacccac ctacatttat tccacctaat tatcgtgtga aagtccgaga ggatcttcca   3000
gaaggaaccg tcatcatgtg gttagaagcc cacgatcctg atttaggtca gtctggtcag   3060
gtcagcacac agccttctgg accacggaga aggaaacttc gatgtggata aactcagtgg   3120
agcagttagg atcgtccagc agttggactt tgagaagaag caagtgtata atctcactgt   3180
gagggccaaa gacaagggaa agccagtttc tctgtcttct acttgctatg ttgaagttga   3240
```

-continued

```
ggtggttgat gtgaatgaga acctgcaccc acccgtgttt tccagctttg tggaaaaggg   3300
gacagtgaaa gaagatgcac ctgttggttc attggtaatg acggtgtcgg ctcatgatga   3360
ggacgccaga agagatgggg agatccgata ctccattaga gatggctctg gcgttggtgt   3420
tttcaaaata ggtgaagaga caggtgtcat agagacgtca gatcgactgg accgtgaatc   3480
gacctcccat tattggctaa cagtctttgc aaccgatcag ggtgtcgtgc ctctttcatc   3540
gttcatagag atctacatag aggttgagga tgtcaatgac aatgcaccac agacatcaga   3600
gcctgtttat tacccagaaa tcatggaaaa ttctcctaaa gatgtatctg tggtccagat   3660
cgaggcattt gatccagatt cgagctctaa tgacaagctc atgtacaaaa ttacaagtgg   3720
aaatccacaa ggattctttt caatacatcc taaaacaggt ctcatcacaa ctacgtcaag   3780
gaagctagac cgagaacagc aagatgaaca catattagag gttactgtga cagacaatgg   3840
tagtcccccc aaatcaacca ttgcaagagt cattgtgaaa atccttgatg aaaatgacaa   3900
caaacctcag tttctgcaaa agttctacaa aatcagactc cctgagcggg aaaagccaga   3960
ccgagaaaga aatgccagac gggagccgct ctatcgcgtc atagccaccg acaaggatga   4020
gggccccaat gcagaaatct cctacagcat cgaagacggg aatgagcatg gcaaattttt   4080
catcgaaccg aaaactggag tggtttcgtc caagaggttt tcagcagctg gagaatatga   4140
tattctttca attaaggcag ttgacaatgg tcgccctcaa aagtcatcaa ccaccagact   4200
ccatattgaa tggatctcca agcccaaacc gtccctggag cccatttcat ttgaagaatc   4260
attttttacc tttactgtga tggaaagtga ccccgttgct cacatgattg gagtaatatc   4320
tgtggagcct cctggcatac ccctttggtt tgacatcact ggtggcaact acgacagtca   4380
cttcgatgtg gacaagggaa ctggaaccat cattgttgcc aaacctcttg atgcagaaca   4440
gaagtcaaac tacaacctca cagtcgaggc tacagatgga accaccacta tcctcactca   4500
ggtattcatc aaagtaatag acacaaatga ccatcgtcct cagttttcta catcaaagta   4560
tgaagttgtt attcctgaag atacagcgcc agaaacagaa attttgcaaa tcagtgctgt   4620
ggatcaggat gagaaaaaca aactaatcta cactctgcag agcagtagag atccactgag   4680
tctcaagaaa tttcgtcttg atcctgcaac cggctctctc tatacttctg agaaactgga   4740
tcatgaagct gttcaccagc acaccctcac ggtcatggta cgagatcaag atgtgcctgt   4800
aaaacgcaac tttgcaagga ttgtggtcaa tgtcagcgac acgaatgacc acgccccgtg   4860
gttcaccgct tcctcctaca aagggcgggt ttatgaatcg gcagccgttg gctcagttgt   4920
gttgcaggtg acggctctgg acaaggacaa agggaaaaat gctgaagtgc tgtactcgat   4980
cgagtcagnn nnnnnnngaa atattggaaa ttcttttatg attgatcctg tcttgggctc   5040
tattaaaact gccaaagaat tagatcgaag taaccaagcg gagtatgatt taatggtaaa   5100
agctacagat aagggcagtc caccaatgag tgaaataact tctgtgcgta tctttgtcac   5160
aattgctgac aacgcctctc cgaagtttac atcaaaagaa tattctgttg aacttagtga   5220
aactgtcagc attgggagtt tcgttgggat ggttacagcc catagtcaat catcagtggt   5280
gtatgaaata aaagatggaa atacaggtga tgcttttgat attaatccac attctggaac   5340
tatcatcact cagaaagccc tggactttga aactttgccc atttacacat tgataataca   5400
aggaactaac atggctggtt tgtccactaa tacaacggtt ctagttcact tgcaggatga   5460
gaatgacaac gcgccagttt ttatgcaggc agaatataca ggactcatta gtgaatcagc   5520
ctcaattaac agcgtggtcc taacagacag gaatgtccca ctggtgattc gagcagctga   5580
tgctgataaa gactcaaatg ctttgcttgt atatcacatt gttgaaccat ctgtacacac   5640
```

-continued

```
atattttgct attgattcta gcactggtgc tattcataca gtactaagtc tggactatga   5700
agaaacaagt atttttcact ttaccgtcca agtgcatgac atgggaaccc cacgtttatt   5760
tgctgagtat gcagcgaatg taacagtaca tgtaattgac attaatgact gcccccctgt   5820
gtttgccaag ccattatatg aagcatctct tttgttacca acatacaaag gagtaaaagt   5880
catcacagta aatgctacag atgctgattc aagtgcattc tcacagttga tttactccat   5940
caccgaaggc aacatcgggg agaagttttc tatggactac aagactggtg ctctcactgt   6000
ccaaaacaca actcagttaa gaagccgcta cgagctaacc gttagagctt ccgatggcag   6060
atttgccggc cttacctctg tcaaaattaa tgtgaaagaa agcaaagaaa gtcacctaaa   6120
gtttacccag gatgtctact ctgcggtagt gaaagagaat tccaccgagg ccgaaacatt   6180
agctgtcatt actgctattg ggaatccaat caatgagcct ttgttttatc acatcctcaa   6240
cccagatcgc agatttaaaa taagccgcac ttcaggagtt ctgtcaacca ctggcacgcc   6300
cttcgatcgt gagcagcagg aggcgtttga tgtggttgta gaagtgacag aggaacataa   6360
gccttctgca gtggcccacg ttgtcgtgaa ggtcattgta gaagaccaaa atgataatgc   6420
gccggtgttt gtcaaccttc cctactacgc cgttgttaaa gtggacactg aggtgggcca   6480
tgtcattcgc tatgtcactg ctgtagacag agacagtggc agaaacgggg aagtgcatta   6540
ctacctcaag gaacatcatg aacactttca aattggaccc ttgggtgaaa tttcactgaa   6600
aaagcaattt gagcttgaca ccttaaataa agaatatctt gttacagtgg ttgcaaaaga   6660
tggagggaac ccggcctttt cagcggaagt tatcgttccg atcactgtca tgaataaagc   6720
catgcctgtg tttgaaaaac ctttctacag tgcagagatt gcagagagca tccaggtgca   6780
cagccctgtg gtccacgtgc aggctaacag cccggaaggc ctgaaagtgt tctacagcat   6840
cacagacgga gaccctttca gccagttcac tattaacttc aatactggag ttatcaatgt   6900
catagctcct ctggactttg aggcccaccc ggcatataag ctgagcatac gcgcaactga   6960
ctccttgacg ggcgctcatg ctgaagtatt tgtggacatc atagtagacg acatcaatga   7020
taaccctcct gtgtttgctc agcagtctta tgcggtgacc ctgtctgagg catctgtaat   7080
tggaacgtct gttgttcaag ttagagccac cgattctgat tcagaaccaa atagaggaat   7140
ctcataccag atgtttggga atcacagcaa gagtcatgat cattttcatg tagacagcag   7200
cactggcctc atctcactac tcagaaccct ggattacgag cagtcccggc agcacacgat   7260
ttttgtgagg gcagttgatg gtggtatgcc cacgctgagc agtgatgtga ttgtcacggt   7320
ggacgttacc gacctcaatg ataatccacc actctttgaa caacagattt atgaagccag   7380
aattagcgag cacgcccctc atgggcattt cgtgacctgt gtaaaagcct atgatgcaga   7440
cagttcagac atagacaagt tgcagtattc cattctgtct ggcaatgatc ataaacattt   7500
tgtcattgac agtgcaacag ggattatcac cctctcaaac ctgcaccggc acgccctgaa   7560
gccattttac agtcttaacc tgtcagtgtc tgatggagtt tttagaagtt ccacccaggt   7620
tcatgtaact gtaattggag gcaatttgca cagtcctgct ttccttcaga acgaatatga   7680
agtggaacta gctgaaaacg ctcccctaca taccctggtg atggaggtga aaactacgga   7740
tggggattct ggtatttatg gtcacgttac ttaccatatt gtaaatgact ttgccaaaga   7800
cagattttac ataaatgaga gaggacagat atttactttg gaaaaacttg atcgagaaac   7860
cccggcggag aaagtgatct cagtccgttt aatggctaag gatgctggag gaaaagttgc   7920
tttctgcacc gtgaatgtca tccttacaga tgacaatgac aatgcaccac aatttcgagc   7980
```

-continued

```
aaccaaatac gaagtgaata tcgggtccag tgctgctaaa gggacttcag tcgttaaagt   8040
tcttgcaagt gatgccgatg agggctccaa tgccgacatc acctatgcca ttgaagcaga   8100
ctctgaaagt gtaaaagaga atttggaaat taacaaactg tccggcgtaa tcactacaaa   8160
ggagagcctc attggcttgg aaaatgaatt cttcactttc tttgttagag ctgtggataa   8220
tgggtctcca tcaaaagaat ctgttgttct tgtctatgtt aaaatccttc caccggaaat   8280
gcagcttcca aaattttcag aacctttcta tacctttaca gtgtcagagg acgtgcctat   8340
tggaacagag atagatctca tccgagcaga acatagtggg actgttcttt acagcctggt   8400
caaagggaat actccagaaa gcaataggga tgagtccttt gtgattgaca gacagagcgg   8460
gagactgaag ttggagaaga gtcttgatca tgagacaact aagtggtatc agttttccat   8520
actggccagg tgcactcaag atgaccatga gatggtggct tctgtagatg ttagtatcca   8580
agtgaaagat gcaaatgaca acagcccggt ctttgaatct agtccatatg aggcattcat   8640
tgttgaaaac ctgccagggg gaagtagagt aattcagatc agggcatctg atgctgactc   8700
aggaaccaac ggccaagtta tgtatagcct ggatcagtca caaagtgtgg aagtcattga   8760
atcctttgcc attaacatgg aaacaggctg gattacaact ttaaaggaac ttgaccatga   8820
aaagagagac aattaccaga ttaaagtggt tgcatcagat catggtgaaa agatccagct   8880
atcctccaca gccattgtgg atgttaccgt caccgatgtc aacgatagtc caccacgatt   8940
cacggccgag atctataaag ggactgtgag tgaggatgac ccccaaggtg ggggtgattgc  9000
catcttaagt accacggatg ctgattctga agagatcaac agacaagtta catatttcat   9060
aacaggaggg gatcctttag gacagtttgc cgttgaaact atacagaatg aatggaaggt   9120
atatgtgaag aaacctctag acagggaaaa aagggacaat taccttctta ctatcacggc   9180
aactgatggc accttctcat caaaagcgat agttgaagtg aaagttctgg atgcaaatga   9240
caacagtcca gtttgtgaaa agactttata ttcagacact attcctgaag acgtccttcc   9300
tggaaaattg atcatgcaga tctctgctac agacgcagac atccgctcta acgctgaaat   9360
tacttacacg ttattgggtt caggtgcaga aaaattcaaa ctaaatccag acacaggtga   9420
actgaaaacg tcaacccccc ttgatcgtga ggagcaagct gtttatcatc ttctcgtcag   9480
ggccacagat ggaggaggaa gattctgcca agccagtatt gtgctcacgc tagaagatgt   9540
gaacgataac gcccccgaat tctctgccga tccttatgcc atcaccgtgt ttgaaaacac   9600
agagccggga acgctgctga caagagtgca ggccacagat gccgacgcag gattaaatcg   9660
gaagatttta tactcactga ttgactctgc tgatgggcag ttctccatta acgaattatc   9720
tggaattatt cagttagaaa aacctttgga cagagaactc caggcagtat acaccctctc   9780
tttgaaagct gtggatcaag gcttgccaag gaggctgact gccactggca ctgtgattgt   9840
atcagttctt gacataaatg acaacccccc tgtgtttgag taccgtgaat atggtgccac   9900
cgtgtctgag gacattcttg ttggaactga agttcttcaa gtgtatgcag caagtcggga   9960
tattgaagca aatgcagaaa tcacctactc aataataagt ggaaatgaac atgggaaatt  10020
cagcatagat tctaaaacag nnnnnnnnnn nnnnnnnnnn nnnnnnnnnn nnnnnnnnnn  10080
nnnnnnnnnn nnnnnnnnnn nnnnnnnnnn nnnnnnnnnn nnnnnnnnnn nnnnnnnnnn  10140
nnnnnnnnnn nnnnnnnnnn nnnnnnnnnn nnnnnnnnnn nnnnnnnnnn nnnnnnnnnn  10200
nnnnnnnnnn nnnnnnnnnn nnnnnnnnnn nnnnnnnnnn nnnnnnnnnn nnnnnnnnnn  10260
nnnnnnnnnn nnnnnnnnnn nnnnnnnnnn nnnnnnnnnn nnnnnnnnnn nnnnnnnnnn  10320
nnnnnnnnnn nnnnnnnnnn nnnnnnnnnn nnnnnnnnnn nnnnnnnnnn nnnnnnnnnn  10380
```

-continued

```
nnnnnnnnnn nnnnnnnnnn nnnnnnnnnn nnnnnnnnnn nnnnnnnnnn nnnnnnnnnn  10440
nnnnnnnnnn nnnnnnnnnn nnnnnnnnnn nnnnnnnnnn nnnnnnnnnn nnnnnnnnnn  10500
nnnnnnnnnn nnnnnnnnnn nnnnnnnnnn nnnnnnngaa aataagccag tgggcttcag  10560
cgtgctgcag ctggtagtaa cagatgagga ttcttcccat aacggtccac ccttcttctt  10620
tactattgta actggaaatg atgagaaggc ttttgaagtt aacccgcaag gagtcctcct  10680
gacatcatct gccatcaaga ggaaggagaa agatcattac ttactgcagg tgaaggtggc  10740
agataatgga aagcctcagt tgtcatcttt gacatacatt gacattaggg taattgagga  10800
gagcatctat ccgcctgcga ttttgcccct ggagattttc atcacctctt ctggagaaga  10860
atactcaggt ggcgtcattg ggaagatcca tgccacagac caggacgtgt atgatactct  10920
aacctacagt ctcgaccctc agatggacaa cctgttctct gtttccagca caggggggcaa  10980
gctgatagca cacaaaaagc tagacatagg gcaatacctt ctcaatgtca gcgtaacaga  11040
tgggaagttc acgacggtgg ccgacatcac agtgcatatc agacaagtca cacaggagat  11100
gttgaaccac accatcgcga tccgctttgc caacctcact ccggaagaat tcgttggtga  11160
ctactggcgc aacttccagc gagctttacg gaacatcctg ggtgtgagga ggaacgacat  11220
acagattgtt agtttgcagt cctctgaacc tcacccacat ctggacgtct tactttttgt  11280
agagaaacca ggtagtgctc agatctcaac aaaacaactt ctgcacaaga ttaactcttc  11340
cgtgactgac attgaggaaa tcattggagt taggatactg aatgtattcc agaaactctg  11400
cgcgggactg gactgcccct ggaagttctg cgatgaaaag gtgtctgtgg atgaaagtgt  11460
gatgtcaaca cacagcacag ccagactgag ttttgtgact ccccgccacc acagggcagc  11520
ggtgtgtctc tgcaaagagg gaaggtgccc acctgtccac catggctgtg aagatgatcc  11580
gtgccctgag ggatccgaat gtgtgtctga tccctgggag gagaaacaca cctgtgtctg  11640
tcccagcggc aggtttggtc agtgcccagg gagttcatct atgacactga ctggaaacag  11700
ctacgtgaaa taccgtctga cggaaaatga aaacaaatta gagatgaaac tgaccatgag  11760
gctcagaaca tattccacgc atgcggttgt catgtatgct cgaggaactg actatagcat  11820
cttggagatt catcatggaa ggtgcagtca annnnnnnnn nnnnnnnnnn nnnnnnnnnn  11880
nnnnnnnnnn nnncattcag gtcaatgatg ggcagtggca cgcagtggcc ctggaagtga  11940
atggaaacta tgctcgcttg gttctagacc aagttcatac tgcatcgggc acagccccag  12000
ggactctgaa aaccctgaac ctggataact atgtgttttt tggtggccac atccgtcagc  12060
agggaacaag gcatggaaga agtcctcaag ttggtaatgg tttcaggggt tgtatggact  12120
ccatttattt gaatgggcag gagctccctt taaacagcaa acccagaagc tatgcacaca  12180
tcgaagagtc ggtggatgta tctccaggct gcttcctgac ggccacggaa gactgcgcca  12240
gcaacccttg ccagaatgga ggcgtttgca atccgtcacc tgctggaggt tattactgca  12300
aatgcagtgc cttgtacata gggacccact gtgagataag cgtcaatccg tgttcctcca  12360
agccatgcct ctatgggggc acgtgtgttg tcgacaacgg aggctttgtt tgccagtgta  12420
gaggattata tactggtcag aggtgtcagc ttagtccata ctgcaaagat gaaccctgta  12480
agaatggcgg aacatgcttt gacagtttgg atggcgccgt ttgtcagtgt gattcgggtt  12540
ttaggggaga aaggtgtcag agtgatatcg acgagtgctc tggaaaccct tgcctgcacg  12600
gggccctctg tgagaacacg cacggctcct atcactgcaa ctgcagccac gagtacaggg  12660
gacgtcactg cgaggatgct gcgcccaacc agtatgtgtc cacgccgtgg aacattgggt  12720
```

-continued

```
tggcggaagg aattggaatc gttgtgtttg ttgcagggat atttttactg gtggtggtgt  12780
ttgttctctg ccgtaagatg attagtcgga aaaagaagca tcaggctgaa cctaaagaca  12840
agcacctggg acccgctacg gctttcttgc aaagaccgta ttttgattcc aagctaaata  12900
agaacattta ctcagacata ccaccccagg tgcctgtccg gcctatttcc tacaccccga  12960
gtattccaag tgactcaaga aacaatctgg accgaaattc cttcgaagga tctgctatcc  13020
cagagcatcc cgaattcagc acttttaacc ccgagtctgt gcacgggcac cgaaaagcag  13080
tggcggtctg cagcgtggcg ccaaacctgc ctcccccacc ccctcaaac tccccttctg  13140
acagcgactc catccagaag cctagctggg actttgacta tgacacaaaa gtggtggatc  13200
ttgatccctg tctttccaag aagcctctag aggaaaagcc ttcccagcca tacagtgccc  13260
gggaaagcct gtctgaagtg cagtctctga gctccttcca gtccgaatcg tgcgatgaca  13320
atgggtatca ctgggataca tcagattgga tgccaagcgt tcctctgccg gacatacaag  13380
agttccccaa ctatgaggtg attgatgagc agacacccct gtactcagca gatccaaacg  13440
ccatcgatac ggactattac cctggaggct acgacatcga aagtgatttt cctccacccc  13500
cagaagactt ccccgcagct gatgagctac caccgttacc gcccgaattc agcaatcagt  13560
ttgaatccat ccaccctcct agagacatgc ctgccgcggg tagcttgggt tcttcatcaa  13620
gaaaccggca gaggttcaac ttgaatcagt atttgcccaa tttttatccc ctcgatatgt  13680
ctgaacctca aacaaaaggc actggtgaga atagtacttg tagagaaccc catgcccctt  13740
acccgccagg gtatcaaaga cacttcgagg cgcccgctgt cgagagcatg cccatgtctg  13800
tgtacgcctc caccgcctcc tgctctgacg tgtcagcctg ctgcgaagtg gagtccgagg  13860
tcatgatgag tgactatgag agcggggacg acggccactt cgaagaggtg acgatcccgc  13920
ccctggattc ccagcagcac acggaagtct gactctcaac tccccccaaa gtgcctgact  13980
ttagtgaacc tagaggtgat gtgagtaatc cgcgctgttc tttgcagcag tgcttccaag  14040
ctttttttgg tgagccgaat gggcatggct gcgctggatc ctgcgcctct ggacgtgcta  14100
gccatttcca gtgtcccaac tactgtcatc gtgaggtttt catcggctgt gccatttccc  14160
aacgtctttt gggatttaca tctgtctgtg ttaaaataat caaacgaaaa atcagtcctg  14220
tgttgtcagc atgattcatg tatttatata gatttgatta ttttaatttt cctgtctctt  14280
tttttgtaa attttatgta cagatttgat ttttcatagt tttaactaga tttccaagat  14340
attttgtgca tttgtttcaa ctgaattttg gtggtgtcag tgccattatc tagcaccctg  14400
attttttttt ttttactata accagggttt cattctgtct ttttccactg aagtgtgaca  14460
ttttgttagt acatttcagt gtagtcattc atttctagct gtacatagga tgaaggagag  14520
atcagataca tgaacatgtc ttacatgggt tgctgtattt agaattataa acatttttca  14580
ttattggaaa gtgtaacggg gaccttctgc atacctgttt agaaccaaaa ccaccatgac  14640
acagttttta tagtgtctgt atatttgtga tgcaatggtc ttgtaaaggt ttttaatgaa  14700
aactaccatt agccagtctt tcttactgac aataaattat taataaaat             14749
```

<210> SEQ ID NO 73
<211> LENGTH: 5508
<212> TYPE: DNA
<213> ORGANISM: Homo sapiens

<400> SEQUENCE: 73

```
gattttaggt gatgggcaag tcagaaagtc agatggatat aactgatatc aacactccaa     60
agccaaagaa gaaacagcga tggactccac tggagatcag cctctcggtc cttgtcctgc    120
```

-continued

```
tcctcaccat catagctgtg acaatgatcg cactctatgc aacctacgat gatggtattt    180
gcaagtcatc agactgcata aaatcagctg ctcgactgat ccaaaacatg gatgccacca    240
ctgagccttg tacagacttt ttcaaatatg cttgcggagg ctggttgaaa cgtaatgtca    300
ttcccgagac cagctcccgt tacggcaact ttgacatttt aagagatgaa ctagaagtcg    360
ttttgaaaga tgtccttcaa gaacccaaaa ctgaagatat agtagcagtg cagaaagcaa    420
aagcattgta caggtcttgt ataaatgaat ctgctattga tagcagaggt ggagaacctc    480
tactcaaact gttaccagac atatatgggt ggccagtagc aacagaaaac tgggagcaaa    540
aatatggtgc ttcttggaca gctgaaaaag ctattgcaca actgaattct aaatatggga    600
aaaaagtcct tattaatttg tttgttggca ctgatgataa gaattctgtg aatcatgtaa    660
ttcatattga ccaacctcga cttggcctcc cttctagaga ttactatgaa tgcactggaa    720
tctataaaga ggcttgtaca gcatatgtgg attttatgat ttctgtggcc agattgattc    780
gtcaggaaga aagattgccc atcgatgaaa accagcttgc tttggaaatg aataaagtta    840
tggaattgga aaaagaaatt gccaatgcta cggctaaacc tgaagatcga aatgatccaa    900
tgcttctgta taacaagatg acattggccc agatccaaaa taacttttca ctagagatca    960
atgggaagcc attcagctgg ttgaatttca caaatgaaat catgtcaact gtgaatatta   1020
gtattacaaa tgaggaagat gtggttgttt atgctccaga atatttaacc aaacttaagc   1080
ccattcttac caaatattct gccagagatc ttcaaaattt aatgtcctgg agattcataa   1140
tggatcttgt aagcagcctc agccgaacct acaaggagtc cagaaatgct ttccgcaagg   1200
ccctttatgg tacaacctca gaaacagcaa cttggagacg ttgtgcaaac tatgtcaatg   1260
ggaatatgga aaatgctgtg gggaggcttt atgtggaagc agcatttgct ggagagagta   1320
aacatgtggt cgaggatttg attgcacaga tccgagaagt ttttattcag actttagatg   1380
acctcacttg gatggatgcc gagacaaaaa agagagctga agaaaaggcc ttagcaatta   1440
aagaaaggat cggctatcct gatgacattg tttcaaatga taacaaactg aataatgagt   1500
acctcgagtt gaactacaaa gaagatgaat acttcgagaa cataattcaa aatttgaaat   1560
tcagccaaag taaacaactg aagaagctcc gagaaaaggt ggacaaagat gagtggataa   1620
gtggagcagc tgtagtcaat gcattttact cttcaggaag aaatcagata gtcttcccag   1680
ccggcattct gcagcccccc ttctttagtg cccagcagtc caactcattg aactatgggg   1740
gcatcggcat ggtcatagga cacgaaatca cccatggctt cgatgacaat ggcagaaact   1800
ttaacaaaga tggagacctc gttgactggt ggactcaaca gtctgcaagt aactttaagg   1860
agcaatccca gtgcatggtg tatcagtatg gaaacttttc ctgggacctg gcaggtggac   1920
agcaccttaa tggaattaat acactgggag aaaacattgc tgataatgga ggtcttggtc   1980
aagcatacag agcctatcag aattatatta aaaagaatgg cgaagaaaaa ttacttcctg   2040
gacttgacct aaatcacaaa caactatttt tcttgaactt tgcacaggtg tggtgtggaa   2100
cctataggcc agagtatgcg gttaactcca ttaaaacaga tgtgcacagt ccaggcaatt   2160
tcaggattat tgggactttg cagaactctg cagagttttc agaagccttt cactgccgca   2220
agaattcata catgaatcca gaaaagaagt gccgggtttg gtgatcttca aaagaagcat   2280
tgcagccctt ggctagactt gccaacacca cagaaatggg gaattctcta atcgaaagaa   2340
aatgggccct aggggtcact gtactgactt gagggtgatt aacagagagg gcaccatcac   2400
aatacagata acattaggtt gtcctagaaa gggtgtggag ggaggaaggg ggtctaaggt   2460
```

-continued

```
ctatcaagtc aatcatttct cactgtgtac ataatgctta atttctaaag ataatattac   2520
tgtttatttc tgtttctcat atggtctacc agtttgctga tgtccctaga aaacaatgca   2580
aaacctttga ggtagaccag gatttctaat caaaagggaa aagaagatgt tgaagaatac   2640
agttaggcac cagaagaaca gtaggtgaca ctatagttta aaacacattg cctaactact   2700
agtttttact tttatttgca acatttacag tccttcaaaa tccttccaaa gaattcttat   2760
acacattggg gccttggagc ttacatagtt ttaaactcat ttttgccata catcagttat   2820
tcattctgtg atcatttatt ttaagcactc ttaaagcaaa aaatgaatgt ctaaaattgt   2880
tttttgttgt acctgctttg actgatgctg agattcttca ggcttcctgc aatttctaa    2940
gcaatttctt gctctatctc tcaaaacttg gtatttttca gagatttata taaatgtaaa   3000
aataataatt tttatattta attattaact acatttatga gtaactatta ttataggtaa   3060
tcaatgaata ttgaagtttc agcttaaaat aaacagttgt gaaccaagat ctataaagcg   3120
atatacagat gaaaatttga gactatttaa acttataaat catattgatg aaaagattta   3180
agcacaaact ttagggtaaa aattgccatt ggacagttgt ctagagatat atatacttgt   3240
ggttttcaaa ttggactttc aaaattaaat ctgtccctga gagtgtctct gataaaaggg   3300
caaatctgca cctatgtagc tctgcatctc ctgtcttttc aggtttgtca tcagatggaa   3360
atattttgat aataaattga aattgtgaac tcattgctcc ctaagactgt gacaactgtc   3420
taactttaga agtgcatttc tgaatagaaa tgggaggcct ctgatggacc ttctagaatt   3480
ataagtcaca aagagttctg gaaaagaact gtttactgct tgataggaat tcatcttttg   3540
aggcttctgt tcctctcttt tcctgttgta ttgactattt tcgttcatta cttgattaag   3600
attttacaaa agaggagcac ttccaaaatt cttatttttc ctaacaaaag atgaaagcag   3660
ggaatttcta tctaaatgat gagtattagt tccctgtctc ttgaaaaatg cccatttgcc   3720
tttaaaaaaa aaagttacag aaatactata acatatgtac ataaattgca taaagcataa   3780
gtatacagtt caataaactt aactttaact gaacaatggc cctgtagcca gcacctgtaa   3840
gaaacagagc agtaccagcg ctctaaaagc acctccttgt cactttatta ctcccagaac   3900
aacaactatc ctgacttcta atatcattca ctagctttgc ctggttttgt cttttatgca   3960
gatagaatca atcagtatgt attcttttgt gcctggcttc tttctctcag ccttacattt   4020
gtgagattcc tctgtattgt gctgattgtg gatcttttca ttctcattgc agaataatgt   4080
tctattgtgg gacttattac aatttgttca tcctattgtt gatgggcact tgagaacttt   4140
ccattttggc gctattacaa atagtgcaac tatgaatgta ctgcatgtta ccatcttact   4200
tgagccttta atggacttat ttcttcaaat ccttccaaaa attattataa gcattgaaat   4260
tatagtttca agccaactgt ggataccctt accctttcct cctttatcac aaccaccgtt   4320
acaagtatac ttatatttcc ctaaaataca tttaaaactt acctaagtga catttgtagt   4380
tggagtaata ggagcttcca gctctaataa aacagctgtc tctaacttat tttatttcca   4440
tcatgtcaga gcaggtgaag agccagaagt gaagagtgac tagtacaaat tataaaaagc   4500
cactagactc ttcactgtta gctttttaaa acattaggct cccatcccta tggaggaaca   4560
actctccagt gcctggatcc cctctgtcta caaatataag attttctggg cctaaaggat   4620
agatcaaagt caaaaatagc aatgcctccc tatccctcac acatccagac atcatgaatt   4680
ttacatggta ctcttgttga gttctgtaga gccttctgat gtctctaaag cactaccgat   4740
tctttggagt tgtcacatca gataagacat atctctaatt ccatccataa atccagttct   4800
actatggctg agttctggtc aaagaaagaa agtttagaag ctgagacaca aagggttggg   4860
```

-continued agctgatgaa actcacaaat gatggtagga agaagctctc gacaataccc gttggcaagg 4920
agtctgcctc catgctgcag tgttcgagtg gattgtaggt gcaagatgga aaggattgta 4980
ggtgcaagct gtccagagaa aagagtcctt gttccagccc tattctgcca ctcctgacag 5040
ggtgaccttg ggtatttgca atattccttt gggcctctgc ttctctcacc taaaaaaaga 5100
gaattagatt atattggtgg ttctcagcaa gagaaggagt atgtgtccaa tgctgccttc 5160
ccatgaatct gtctcccagt tatgaatcag tgggcaggat aaactgaaaa ctcccattta 5220
cgtgtctgaa tcgagtgaga caaaatttta gtccaaataa caagtaccaa agttttatca 5280
agtttgggtc tgtgctgctg ttactgttaa ccatttaagt ggggcaaaac cttgctaatt 5340
ttctcaaaag catttatcat tcttgttgcc acagctggag ctctcaaact aaaagacatt 5400
tgttattttg gaaagaagaa agactctatt ctcaaagttt cctaatcaga aatttttatc 5460
agtttccagt ctcaaaaata caaaataaaa acaaacgttt ttaatact 5508

<210> SEQ ID NO 74
<211> LENGTH: 1495
<212> TYPE: DNA
<213> ORGANISM: Homo sapiens

<400> SEQUENCE: 74
atgtccaatc agggaagtaa gtacgtcaat aaggaaattc aaaatgctgt caacggggtg 60
aaacagataa agactctcat agaaaaaaca aacgaagagc gcaagacact gctcagcaac 120
ctagaagaag ccaagaagaa gaaagaggat gccctaaatg agaccaggga atcagagaca 180
aagctgaagg agctcccagg agtgtgcaat gagaccatga tggccctctg ggaagagtgt 240
aagccctgcc tgaaacagac ctgcatgaag ttctacgcac gcgtctgcag aagtggctca 300
ggcctggttg gccgccagct tgaggagttc ctgaaccaga gctcgccctt ctacttctgg 360
atgaatggtg accgcatcga ctccctgctg gagaacgacc ggcagcagac gcacatgctg 420
gatgtcatgc aggaccactt cagccgcgcg tccagcatca tagacgagct cttccaggac 480
aggttcttca cccgggagcc ccaggatacc taccactacc tgcccttcag cctgccccac 540
cggaggcctc acttcttctt tcccaagtcc cgcatcgtcc gcagcttgat gcccttctct 600
ccgtacgagc ccctgaactt ccacgccatg ttccagccct tccttgagat gatacacgag 660
gctcagcagg ccatggacat ccacttccat agcccggcct tccagcaccc gccaacagaa 720
ttcatacgag aaggcgacga tgaccggact gtgtgccggg agatccgcca caactccacg 780
ggctgcctgc ggatgaagga ccagtgtgac aagtgccggg agatcttgtc tgtggactgt 840
tccaccaaca acccctccca ggctaagctg cggcgggagc tcgacgaatc cctccaggtc 900
gctgagaggt tgaccaggaa atacaacgag ctgctaaagt cctaccagtg gaagatgctc 960
aacacctcct ccttgctgga gcagctgaac gagcagttta actgggtgtc ccggctggca 1020
aacctcacgc aaggcgaaga ccagtactat ctgcgggtca ccacggtggc ttcccacact 1080
tctgactcgg acgttccttc cggtgtcact gaggtggtcg tgaagctctt tgactctgat 1140
cccatcactg tgacggtccc tgtagaagtc tccaggaaga accctaaatt tatggagacc 1200
gtggcggaga aagcgctgca ggaataccgc aaaaagcacc gggaggagtg agatgtggat 1260
gttgcttttg cacctacggg ggcatctgag tccagctccc cccaagatga gctgcagccc 1320
cccagagaga gctctgcacg tcaccaagta accaggcccc agcctccagg cccccaactc 1380
cgcccagcct ctccccgctc tggatcctgc actctaacac tcgactctgc tgctcatggg 1440

-continued

```
aagaacagaa ttgctcctgc atgcaactaa ttcaataaaa ctgtcttgtg agctg        1495
```

<210> SEQ ID NO 75
<211> LENGTH: 967
<212> TYPE: DNA
<213> ORGANISM: Homo sapiens

<400> SEQUENCE: 75

```
gaaggaaaaa gagcaacaga tccagggagc attcacctgc cctgtctcca aacagccttg     60

tgcctcacct acccccaacc tcccagaggg agcagctatt taaggggagc aggagtgcag    120

aacaaacaag acggcctggg gatacaactc tggagtcctc tgagagagcc accaaggagg    180

agcaggggag cgacggccgg ggcagaagtt gagaccaccc agcagaggag ctaggccagt    240

ccatctgcat ttgtcaccca agaactctta ccatgaagac cctcctactg ttggcagtga    300

tcatgatctt tggcctactg caggcccatg ggaatttggt gaatttccac agaatgatca    360

agttgacgac aggaaaggaa gccgcactca gttatggctt ctacggctgc cactgtggcg    420

tgggtggcag aggatccccc aaggatgcaa cggatcgctg ctgtgtcact catgactgtt    480

gctacaaacg tctggagaaa cgtggatgtg gcaccaaatt tctgagctac aagtttagca    540

actcggggag cagaatcacc tgtgcaaaac aggactcctg cagaagtcaa ctgtgtgagt    600

gtgataaggc tgctgccacc tgttttgcta gaaacaagac gacctacaat aaaaagtacc    660

agtactattc caataaacac tgcagaggga gcacccctcg ttgctgagtc ccctcttccc    720

tggaaacctt ccacccagtg ctgaatttcc ctctctcata ccctccctcc ctaccctaac    780

caagttcctt ggccatgcag aaagcatccc tcacccatcc tagaggccag gcaggagccc    840

ttctataccc acccagaatg agacatccag cagatttcca gccttctact gctctcctcc    900

acctcaactc cgtgcttaac caaagaagct gtactccggg gggtctcttc tgaataaagc    960

aattagc                                                              967
```

<210> SEQ ID NO 76
<211> LENGTH: 2515
<212> TYPE: DNA
<213> ORGANISM: Homo sapiens

<400> SEQUENCE: 76

```
gctccatcaa gtatgatggt gaaggatgaa tatgtgcatg actttgaggg acagccatcg     60

ttgtccactg aaggacattc aattcaaacc atccagcatc caccaagtaa tcgtgcatcg    120

acagagacat acagcacccc agctctgtta gccccatctg agtctaatgc taccagcact    180

gccaactttc ccaacattcc tgtggcttcc acaagtcagc ctgccagtat actggggggc    240

agccatagtg aaggactgtt gcagatagca tcagggcctc agccaggaca gcagcagaat    300

ggatttactg gtcagccagc tacttaccat cataacagca ctaccacctg gactggaagt    360

aggactgcac catacacacc taatttgcct caccaccaaa acggccatct tcagcaccac    420

ccgcctatgc cgccccatcc cggacattac tggcctgttc acaatgagct tgcattccag    480

cctcccattt ccaatcatcc tgctcctgag tattggtgtt ccattgctta ctttgaaatg    540

gatgttcagg taggagagac atttaaggtt ccttcaagct gccctattgt tactgttgat    600

ggatacgtgg acccttctgg aggagatcgc ttttgtttgg gtcaactctc caatgtccac    660

aggacagaag ccattgagag agcaaggttg cacataggca aaggtgtgca gttggaatgt    720

aaaggtgaag gtgatgtttg ggtcaggtgc cttagtgacc acgcggtctt tgtacagagt    780

tactacttag acagagaagc tgggcgtgca cctggagatg ctgttcataa gatctaccca    840
```

-continued

```
agtgcatata taaaggtctt tgatttgcgt cagtgtcatc gacagatgca gcagcaggcg    900
gctactgcac aagctgcagc agctgcccag gcagcagccg tggcaggaaa catccctggc    960
ccaggatcag taggtggaat agctccagct atcagtctgt cagctgctgc tggaattggt   1020
gttgatgacc ttcgtcgctt atgcatactc aggatgagtt ttgtgaaagg ctggggaccg   1080
gattacccaa gacagagcat caaagaaaca ccttgctgga ttgaaattca cttacaccgg   1140
gccctccagc tcctagacga agtacttcat accatgccga ttgcagaccc acaaccttta   1200
gactgaggtc ttttaccgtt ggggccctta accttatcag gatggtggac tacaaaatac   1260
aatcctgttt ataatctgaa gatatatttc acttttgttc tgctttatct tttcataaag   1320
ggttgaaaat gtgtttgctg ccttgctcct agcagacaga aactggatta aaacaatttt   1380
tttttcctc ttcagaactt gtcaggcatg gctcagagct tgaagattag gagaaacaca    1440
ttcttattaa ttcttcacct gttatgtatg aaggaatcat tccagtgcta gaaaatttag   1500
ccctttaaaa cgtcttagag ccttttatct gcagaacatc gatatgtata tcattctaca   1560
gaataatcca gtattgctga ttttaaaggc agagaagttc tcaaagttaa ttcacctatg   1620
ttattttgtg tacaagttgt tattgttgaa catacttcaa aaataatgtg ccatgtgggt   1680
gagttaattt taccaagagt aactttactc tgtgtttaaa aagtaagtta ataatgtatt   1740
gtaatctttc atccaaaata ttttttgcaa gttatattag tgaagatggt ttcaattcag   1800
attgtcttgc aacttcagtt ttatttttgc caaggcaaaa aactcttaat ctgtgtgtat   1860
attgagaatc ccttaaaatt accagacaaa aaaatttaaa attacgtttg ttattcctag   1920
tggatgactg ttgatgaagt atacttttcc cctgttaaac agtagttgta ttcttctgta   1980
tttctaggca caaggttggt tgctaagaag cctataagag gaatttcttt tccttcattc   2040
atagggaaag gttttgtatt ttttaaaaca ctaaaagcag cgtcactcta cctaatgtct   2100
cactgttctg caaaggtggc aatgcttaaa ctaaataatg aataaactga atattttgga   2160
aactgctaaa ttctatgtta aatactgtgc agaataatgg aaacattaca gttcataata   2220
ggtagtttgg atatttttgt acttgatttg atgtgacttt ttttggtata atgtttaaat   2280
catgtatgtt atgatattgt ttaaaattca gtttttgtat cttggggcaa gactgcaaac   2340
ttttttatat cttttggtta ttctaagccc tttgccatca atgatcatat caattggcag   2400
tgactttgta tagagaattt aagtagaaaa gttgcagatg tattgactgt accacagaca   2460
caatatgtat gctttttacc tagctggtag cataaataaa actgaatctc aacat        2515
```

<210> SEQ ID NO 77
<211> LENGTH: 2017
<212> TYPE: DNA
<213> ORGANISM: Homo sapiens

<400> SEQUENCE: 77

```
gcaggcccgt tggaagtggt tgtgacaacc ccagcaatgt ggagaagcct ggggcttgcc     60
ctggctctct gtctcctccc atcgggagga acagagagcc aggaccaaag ctccttatgt    120
aagcaacccc cagcctggag cataagagat caagatccaa tgctaaactc caatggttca    180
gtgactgtgg ttgctcttct tcaagccagc tgatacctgt gcatactgca ggcatctaaa    240
ttagaagacc tgcgagtaaa actgaagaaa gaaggatatt ctaatatttc ttatattgtt    300
gttaatcatc aaggaatctc ttctcgatta aaatacacac atcttaagaa taaggtttca    360
gagcatattc ctgtttatca acaagaagaa aaccaaacag atgtctggac tcttttaaat    420
```

-continued

```
ggaagcaaag atgacttcct catatatgat agatgtggcc gtcttgtata tcatcttggt    480
ttgccttttt ccttcctaac tttcccatat gtagaagaag ccattaagat tgcttactgt    540
gaaaagaaat gtggaaactg ctctctcacg actctcaaag atgaagactt ttgtaaacgt    600
gtatctttgg ctactgtgga taaaacagtt gaaactccat cgcctcatta ccatcatgag    660
catcatcaca atcatggaca tcagcacctt ggcagcagtg agctttcaga gaatcagcaa    720
ccaggagcac caaatgctcc tactcatcct gctcctccag gccttcatca ccaccataag    780
cacaagggtc agcataggca gggtcaccca gagaaccgag atatgccagc aagtgaagat    840
ttacaagatt tacaaaagaa gctctgtcga aagagatgta taaatcaatt actctgtaaa    900
ttgcccacag attcagagtt ggctcctagg agctgatgct gccattgtcg acatctgata    960
tttgaaaaaa cagggtctgc aatcacctga cagtgtaaag aaaacctccc atctttatgt   1020
agctgacagg gacttcgggc agaggagaac ataactgaat cttgtcagtg acgtttgcct   1080
ccagctgcct gacaaataag tcagcagctt atacccacag aagccagtgc cagttgacgc   1140
tgaaagaatc aggcaaaaaa gtgagaatga ccttcaaact aaatatttaa aataggacat   1200
actccccaat ttagtctaga cacaatttca tttccagcat ttttataaac taccaaatta   1260
gtgaaccaaa aatagaaatt agatttgtgc aaacatggag aaatctactg aattggcttc   1320
cagattttaa attttatgtc atagaaatat tgactcaaac catatttttt atgatggagc   1380
aactgaaagg tgattgcagc ttttggttaa tatgtctttt tttttctttt tccagtgttc   1440
tatttgcttt aatgagaata gaaacgtaaa ctatgaccta ggggtttctg ttggataatt   1500
agcagtttag aatggaggaa gaacaacaaa gacatgcttt ccattttttt ctttacttat   1560
ctctcaaaac aatattactt tgtcttttca atcttctact tttaactaat aaaataagtg   1620
gattttgtat tttaagatcc agaaatactt aacacgtgaa tattttgcta aaaaagcata   1680
tataactatt ttaaatatcc atttatcttt tgtatatcta agactcatcc tgatttttac   1740
tatcacacat gaataaagcc tttgtatctt tctttctcta atgttgtatc atactcttct   1800
aaaacttgag tggctgtctt aaaagatata aggggaaaga taatattgtc tgtctctata   1860
ttgcttagta agtatttcca tagtcaatga tggtttaata ggtaaaccaa accctataaa   1920
cctgacctcc tttatggtta atactattaa gcaagaatgc agtacagaat tggatacagt   1980
acggatttgt ccaaataaat tcaataaaaa ccttaaa                            2017
```

<210> SEQ ID NO 78
<211> LENGTH: 1468
<212> TYPE: DNA
<213> ORGANISM: Homo sapiens

<400> SEQUENCE: 78

```
caaccacttg acaacctggt tagaagatgc ccgccagcat tccaattcca acatggtcat     60
tatgcttatt ggaaataaaa gtgatttaga atctagaaga gaagtaaaaa aagaagaagg    120
tgaagctttt gcacgagaac atggactcat cttcatggaa acgtctgcta agactgcttc    180
caatgtagaa gaggcattta ttaatacagc aaaagaaatt tatgaaaaaa ttcaagaagg    240
agtctttgac attaataatg aggcaaatgg cattaaaatt ggccctcagc atgctgctac    300
caatgcaaca catgcaggca atcagggagg acagcaggct gggggcggct gctgttgagt    360
ctgtttttac tgtctagctg cccaacgggg cctactcact tattctttca ccccctctcc    420
tcctgctcag ctgagacatg aaactatttg aaatggcttt atgtcacaga agactttaat    480
ccgtcaaatt cttgtataac tttgaataaa tggttaatgt tcacttaaaa gacagatttt    540
```

-continued

```
ggagattgta ttcatatcta tttgcatttg atttctaggt caattgatgt gattattttt    600

gttaaatgtt gtcttgtgcc cttaactacg aactgaattg tattaaacac tacaaagtca    660

tcttgagtat tttaaatcgg tttgtgtagt taggtttccc aacatctgtg gttacctaat    720

gtttaatatt atagaactgt cctcagaaac tttgtcaatt ttcacggcta taaggaaaca    780

gaaggactct tttaattctg tatttatcat ttactttctg tatatatagt ttaataacct    840

gcttgggtgt aatttgccaa gcttgaattc tttaatgcat ttgcataaat tctatactgt    900

ttagagctta aagctacaga agcattgtta ggaattgctt ggacactgaa ttttaaactt    960

tttgacattg ttaacaagca tgttcatctt ttcttgtcac tagtccaaga aaaatatgct   1020

taatgtatat tacaaaggct ttgtatatgt taacctgttt taatgccaaa agtttgcttt   1080

gtccacaatt tccttaagac ctcttcagaa agggatttgt ttgccttaat gaatactgtt   1140

gggaaaaaac acagtataat gagtgaaaag ggcagaagca agaaatttct acatcttagc   1200

gactccaaga agaatgagta tccacattta gatggcacat tatgaggact ttaatctttc   1260

cttaaacaca ataatgtttt ctttttctt ttattcacat gatttctaag tatatttttc   1320

atgcaggaca gtttttcaac cttgatgtac agtgactgtg taaaattttt ctttcagtgg   1380

caacctctat aatctttaaa atatggtgag catcttgtct gttttgaagg ggatatgaca   1440

ataaatctat cagatggaaa atcctgtt                                      1468
```

<210> SEQ ID NO 79
<211> LENGTH: 3590
<212> TYPE: DNA
<213> ORGANISM: Homo sapiens

<400> SEQUENCE: 79

```
cctgggtctg acgcggccct gttcgagggg gcctctcttg tttatttatt tattttccgt     60

gggtgcctcc gagtgtgcgc gcgctctcgc tacccggcgg ggagggggtg gggggagggc    120

ccgggaaaag ggggagttgg agccggggtc gaaacgccgc gtgacttgta ggtgagagaa    180

cgccgagccg tcgccgcagc ctccgccgcc gagaagccct tgttcccgct gctgggaagg    240

agagtctgtg ccgacaagat ggcggacggg gagctgaacg tggacagcct catcacccgg    300

ctgctggagg tacgaggatg tcgtccagga aagattgtgc agatgactga agcagaagtt    360

cgaggcttat gtatcaagtc tcgggagatc tttctcagcc agcctattct tttggaattg    420

gaagcaccgc tgaaaatttg tggagatatt catggacaat atacagattt actgagatta    480

tttgaatatg gaggtttccc accagaagcc aactatcttt tcttaggaga ttatgtggac    540

agaggaaagc agtctttgga aaccatttgt ttgctattgg cttataaaat caaatatcca    600

gagaacttct ttctcttaag aggaaaccat gagtgtgcta gcatcaatcg catttatgga    660

ttctatgatg aatgcaaacg aagatttaat attaaattgt ggaagacctt cactgattgt    720

tttaactgtc tgcctatagc agccattgtg gatgagaaga tcttctgttg tcatggagga    780

ttgtcaccag acctgcaatc tatggagcag attcggagaa ttatgagacc tactgatgtc    840

cctgatacag gtttgctctg tgatttgcta tggtctgatc cagataagga tgtgcaaggc    900

tggggagaaa atgatcgtgg tgtttccttt acttttggag ctgatgtagt cagtaaattt    960

ctgaatcgtc atgatttaga tttgatttgt cgagctcatc aggtggtgga agatggatat   1020

gaatttttg ctaaacgaca gttggtaacc ttattttcag ccccaaatta ctgtggcgag   1080

tttgataatg ctggtggaat gatgagtgtg gatgaaactt tgatgtgttc atttcagata   1140
```

-continued

```
ttgaaaccat ctgaaaagaa agctaaatac cagtatggtg gactgaattc tggacgtcct   1200
gtcactccac ctcgaacagc taatccgccg aagaaaaggt gaagaaagga attctgtaaa   1260
gaaaccatca gatttgttaa ggacatactt cataatatat aagtgtgcac tgtaaaacca   1320
tccagccatt tgacaccctt tatgatgtca cacctttaac ttaaggagac gggtaaagga   1380
tcttaaattt ttttctaata gaaagatgtg ctacactgta ttgtaataag tatactctgt   1440
tatagtcaac aaagttaaat ccaaattcaa aattatccat taaagttaca tcttcatgta   1500
tcacaatttt taaagttgaa aagcatccca gttaaactag atgtgatagt taaaccagat   1560
gaaagcatga tgatccatct gtgtaatgtg gttttagtgt tgcttggttg tttaattatt   1620
ttgagcttgt tttgttttttg tttgttttca ctagaataat ggcaaatact tctaattttt   1680
ttccctaaac atttttaaaa gtgaaatatg ggaagagctt tacagacatt caccaactat   1740
tattttccct tgtttatcta cttagatatc tgtttaatct tactaagaaa actttcgcct   1800
cattacatta aaaaggaatt ttagagattg attgttttaa aaaaaaatac gcacattgtc   1860
caatccagtg attttaatca tacagtttga ctgggcaaac tttacagctg atagtgaata   1920
ttttgcttta tacaggaatt gacactgatt tggatttgtg cactctaatt tttaacttat   1980
tgatgctcta ttgtgcagta gcatttcatt taagataagg ctcatatagt attacccaac   2040
tagttggtaa tgtgattatg tggtaccttg gctttaggtt ttcattcgca cggaacacct   2100
tttggcatgc ttaacttcct ggtaacacct tcacctgcat tggttttctt tttcttttt   2160
ctttcttttt ttttttttt tttttttga gttgttgttt gtttttagat ccacagtaca   2220
tgagaatcct tttttgacaa gccttggaaa gctgacactg tctctttttc ctccctctat   2280
acgaaggatg tatttaaatg aatgctggtc agtgggacat tttgtcaact atgggtattg   2340
ggtgcttaac tgtctaatat tgccatgtga atgttgtata cgattgtaag gcttatgtca   2400
ctaaagattt ttattctgat tttttcataa tcaaaggtca tatgatactg tatagacaag   2460
ctttgtagtg aagtatagta gcaataattt ctgtacctga tcaagtttat tgcagccttt   2520
cttttcctat ttctttttt taagggttag tattaacaaa tggcaatgag tagaaaagtt   2580
aacatgaaga ttttagaagg agagaactta caggacacag atttgtgatt ctttgactgt   2640
gacactattg gatgtgattc taaaagcttt tattgagcat tgtcaaattt gtaagcttca   2700
tagggatgga catcatatct ataatgccct tctatatgtg ctaccataga tgtgacattt   2760
ttgaccttaa tatcgtcttt gaaaatgtta aattgagaaa cctgttaact tacattttat   2820
gaattggcac attgtattac ttactgcaag agatatttca ttttcagcac agtgcaaaag   2880
ttctttaaaa tgcatatgtc tttttttcta attccgtttt gttttaaagc acattttaaa   2940
tgtagttttc tcatttagta aaagttgtct aattgatatg aagcctgact gattttttttt   3000
ttccttacag tgagacattt aagcacacat tttattcaca tagatactat gtccttgaca   3060
tattgaaatg attcttttct gaaagtattc atgatctgca tatgatgtat taggttaggt   3120
cacaaaggtt ttatctgagg tgatttaaat aacttcctga ttggagtgtg taagctgagc   3180
gatttctaat aaaattttag ttgtacactt ttagtagtca tagtgaagca ggtctagaaa   3240
ataagccttt ggcagggaaa aagggcaatg ttgattaatc tcagtattaa accacattaa   3300
tctgtatccc attgtctggc ttttgtaaat tcatccaggt caagactaag tatgttggtt   3360
aataggaatc cttttttttt tttaaagact aaatgtgaaa aaataatcac tacttaagct   3420
aattaatatt ggtcattaaa tttaaaggat ggaaatttat catgtttaaa aattattcaa   3480
gcactcttaa aaccacttaa acagcctcca gtcataaaaa tgtgttcttt acaaatattt   3540
```

-continued gcttggcaac acgacttgaa ataaataaaa ctttgtttct taggagaaaa 3590

<210> SEQ ID NO 80
<211> LENGTH: 1750
<212> TYPE: DNA
<213> ORGANISM: Homo sapiens

<400> SEQUENCE: 80
gcaacctgcc ccattatccc tggctgcgaa acaaccatcg agatttccaa agggcgaaca 60
gggctgggcc tgagcatcgt tgggggttca gacacgctgc tgggtgccat tattatccat 120
gaagtttatg aagaaggagc agcatgtaaa gatggaagac tctgggctgg agatcagatc 180
ttagaggtga atggaattga cttgagaaag gccacacatg atgaagcaat caatgtcctg 240
agacagacgc cacagagagt gcgcctgaca ctctacagag atgaggcccc atacaaagag 300
gaggaagtgt gtgacaccct cactattgag ctgcagaaga agccgggaaa aggcctagga 360
ttaagtattg ttggtaaaag aaacgatact ggagtatttg tgtcagacat tgtcaaagga 420
ggaattgcag atgccgatgg aagactgatg cagggagacc agatattaat ggtgaatggg 480
gaagacgttc gtaatgccac ccaagaagcg gttgccgctt tgctaaagtg ttccctaggc 540
acagtaacct tggaagttgg aagaatcaaa gctggtccat tccattcaga gaggaggcca 600
tctcaaagca gccaggtgag tgaaggcagc ctgtcatctt tcacttttcc actctctgga 660
tccagtacat ctgagtcact ggaaagtagc tcaaagaaga atgcattggc atctgaaata 720
cagggattaa gaacagtcga aatgaaaaag ggccctactg actcactggg aatcagcatt 780
gctggaggag taggcagccc acttggtgat gtgcctatat ttattgcaat gatgcaccca 840
actggagttg cagcacagac ccaaaaactc agagttgggg ataggattgt caccatctgt 900
ggcacatcca ctgagggcat gactcacacc caagcagtta acctactgaa aaatgcatct 960
ggctccattg aaatgcaggt ggttgctgga ggagacgtga gtgtggtcac aggtcatcag 1020
caggagcctg caagttccag tctttctttc actgggctga cgtcaagcag tatatttcag 1080
gatgatttag gacctcctca atgtaagtct attacactag agcgaggacc agatggctta 1140
ggcttcagta tagttggagg atatggcagc cctcatggag acttacccat ttatgttaaa 1200
acagtgtttg caaagggagc agcctctgaa gacggacgtc tgaaaagggg cgatcagatc 1260
attgctgtca atgggcagag tctagaagga gtcacccatg aagaagctgt tgccatcctt 1320
aaacggacaa aaggcactgt cactttgatg gttctctctt gaattggctg ccagaattga 1380
accaacccaa cccctagctc acctcctact gtaaagagaa tgcactggtc ctgacaattt 1440
ttatgctgtg ttcagccggg tcttcaaaac tgtagggggg aaataacact taagtttctt 1500
tttctcatct agaaatgctt tccttactga caacctaaca tcatttttct tttcttcttg 1560
cattttgtga acttaaagag aaggaatatt tgtgtaggtg aatctcgttt ttatttgtgg 1620
agatatctaa tgttttgtag tcacatgggc aagaattatt acatgctaag ctggttagta 1680
taaagaaaga taattctaaa gctaaccaaa gaaaatggct tcagtaaatt aggatgaaaa 1740
atgaaaatat 1750

<210> SEQ ID NO 81
<211> LENGTH: 3254
<212> TYPE: DNA
<213> ORGANISM: Homo sapiens

<400> SEQUENCE: 81

-continued

```
ggagcgcaat ggcgtccaac cccgaacggg gggagattct gctcacggaa ctgcaggggg     60
attcccgaag tcttccgttt tctgagaatg tgagtgctgt tcaaaaatta gacttttcag    120
atacaatggt gcagcagaaa ttggatgata tcaaggatcg aattaagaga gaaataagga    180
aagaactgaa aatcaaagaa ggagctgaaa atctgaggaa agtcacaaca gataaaaaaa    240
gtttggctta tgtagacaac attttgaaaa aatcaaataa aaaattagaa gaactacatc    300
acaagctgca ggaattaaat gcacatattg ttgtatcaga tccagaagat attacagatt    360
gcccaaggac tccagatact ccaaataatg accctcgttg ttctactagc aacaatagat    420
tgaaggcctt acaaaaacaa ttggatatag aacttaaagt aaaacaaggt gcagagaata    480
tgatacagat gtattcaaat ggatcttcaa aggatcggaa actccatggt acagctcagc    540
aactgctcca ggacagcaag acaaaaatag aagtcatacg aatgcagatt cttcaggcag    600
tccagactaa tgaattggct tttgataatg caaaacctgt gataagtcct cttgaacttc    660
ggatggaaga attaaggcat cattttagga tagagtttgc agtagcagaa ggtgcaaaga    720
atgtaatgaa attacttggc tcaggaaaag taacagacag aaaagcactt tcagaagctc    780
aagcaagatt taatgaatca agtcagaagt tggacctttt aaagtattca ttagagcaaa    840
gattaaacga agtccccaag aatcatccca aaagcaggat tattattgaa gaactttcac    900
ttgttgctgc atcaccaaca ctaagtccac gtcaaagtat gatatctacg caaaatcaat    960
atagtacact atccaaacca gcagcactaa caggtacttt ggaagttcgt cttatgggct   1020
gccaagatat cctagagaat gtccctggac ggtcaaaagc aacatcagtt gcactgcctg   1080
gttggagtcc aagtgaaacc agatcatctt tcatgagcag aacgagtaaa agtaaaagcg   1140
gaagtagtcg aaatcttcta aaaaccgatg acttgtccaa tgatgtctgt gctgttttga   1200
agctcgataa tactgtggtt ggccaaacta gctggaaacc catttccaat cagtcatggg   1260
accagaagtt tacactggaa ctggacaggt cacgtgaact ggaaatttca gtttattggc   1320
gtgattggcg gtctctgtgt gctgtaaaat ttctgaggtt agaagatttt ttagacaacc   1380
aacggcatgg catgtgtctc tatttggaac cacagggtac tttatttgca gaggttacct   1440
tttttaatcc agttattgaa agaagaccaa aacttcaaag acaaaagaaa atttttcaa    1500
agcaacaagg caaaacattt ctcagagctc ctcaaatgaa tattaatatt gccacttggg   1560
gaaggctagt aagaagagct attcctacag taaatcattc tggcaccttc agccctcaag   1620
ctcctgtgcc tactacagtg ccagtggttg atgtacgcat ccctcaacta gcacctccag   1680
ctagtgattc tacagtaacc aaattggact ttgatcttga gcctgaacct cctccagccc   1740
caccacgagc ttcttctctt ggagaaatag atgaatcttc tgaattaaga gttttggata   1800
taccaggaca ggattcagag actgtttttg atattcagaa tgacagaaat agtatacttc   1860
caaaatctca atctgaatac aagcctgata ctcctcagtc aggcctagaa tatagtggta   1920
ttcaagaact tgaggacaga agatctcagc aaaggtttca gtttaatcta caagatttca   1980
ggtgttgtgc tgtcttggga agaggacatt ttggaaaggt gcttttagct gaatataaaa   2040
acacaaatga gatgtttgct ataaaagcct taaagaaagg agatattgtg gctcgagatg   2100
aagtagacag cctgatgtgt gaaaaaagaa tttttgaaac tgtgaatagt gtaaggcatc   2160
cctttttggt gaaccttttt gcatgtttcc aaaccaaaga gcatgtttgc tttgtaatgg   2220
aatatgctgc cggtggggac ctaatgatgc acattcatac tgatgtcttt tctgaaccaa   2280
gagctgtatt ttatgctgct tgtgtagttc ttgggttgca gtatttacat gaacacaaaa   2340
ttgtttatag agatttgaaa ttggataact tattgctaga tacagagggc tttgtgaaaa   2400
```

-continued

```
ttgctgattt tggtctttgc aaagaaggaa tgggatatgg agatagaaca agcacatttt   2460
gtggcactcc tgaatttctt gccccagaag tattaacaga aacttcttat acaagggctg   2520
tagattggtg gggccttggc gtgcttatat atgaaatgct tgttggtgag tctccctttc   2580
ctggtgatga tgaagaggaa gtttttgaca gtattgtaaa tgatgaagta aggtatccaa   2640
ggttcttatc tacagaagcc atttctataa tgagaaggct gttaagaaga aatcctgaac   2700
ggcgccttgg ggctagcgag aaagatgcag aggatgtaaa aaagcaccca tttttccggc   2760
taattgattg gagcgctctg atggacaaaa aagtaaagcc accatttata cctaccataa   2820
gaggacgaga agatgttagt aattttgatg atgaatttac ctcagaagca cctattctga   2880
ctccacctcg agaaccaagg atactttcgg aagaggagca ggaaatgttc agagattttg   2940
actacattgc tgattggtgt taagttgcta gacactgcga aaccaagctg actcacaaga   3000
agacctctta aaaatagcaa cccttcattt gctctctgtg ccaccaatag cttctgagtt   3060
ttttgttgtt gttgttttta ttgaaacacg tgaagatttg tttaaaagta ccattctaat   3120
acttcttcaa aagtggctcc tcattgtact tcagcgtaaa tatgagcact ggaaacagtt   3180
tcatggagtt taagttgagt gaacatcggc catgaaaatc catcacgaat acttttggat   3240
caatagtcta tttt                                                     3254
```

<210> SEQ ID NO 82
<211> LENGTH: 509
<212> TYPE: DNA
<213> ORGANISM: Homo sapiens

<400> SEQUENCE: 82

```
atgaaattca agttacatgt gaattctgcc aggcaataca aggacctgtg gaatatgagt     60
gatgacaaac cctttctatg tactgcgcct ggatgtggcc agagtgaagt caccctgctg    120
agaaatgaag tggcacagct gaaacagctt cttctggctc ataaagattg ccctgtaacc    180
gccatgcaga agaaatctgg ctatcatact gctgataaag atgatagttc agaagacatt    240
tcagtgccga gtagtccaca tacagaagct atacagcata gttcggtcag cacatccaat    300
ggagtcagtt caacctccaa ggcagaagct gtagccactt cagtcctcac ccagatggcg    360
gaccagagta cagagcctgc tctttcacag atcgttatgg ctccttcctc ccagtcacag    420
ccctcaggaa gttgattaaa aacctgcagt acaacagttt tagatactca ttagtgactt    480
caaagggaaa tcaaggaaag accagtttc                                      509
```

<210> SEQ ID NO 83
<211> LENGTH: 719
<212> TYPE: DNA
<213> ORGANISM: Homo sapiens

<400> SEQUENCE: 83

```
gaattctgga agttcattga agagtctgaa attagggact tatttcaaat ttggacatgg     60
ctagtcgagg cgcaacaaga cccaacggcc caaatactgg aaataaaata tgccagttca    120
aactagtact tctgggagag tccgctgttg gcaaatcaag cctagtgctt cgttttgtga    180
aaggccaatt tcatgaattt caagagagta ccattggggc tgcttttcta acccaaactg    240
tatgtcttga tgacactaca gtaaagtttg aaatctggga tacagctggt caagaaggat    300
accatagcct agcaccaatg tactacagag gagcacaagc agccatagtt gtatatgata    360
tcacaaatga ggagtccttt gcaagagcaa aaaattgggt taaagaactt cagaggcaag    420
```

-continued

```
caagtcctaa cattgtaata gctttatcgg gaaacaaggc cgacctagca aataaaagag    480

cagtagattt ccaggaagca cagtcctatg cagatgacaa tagtttatta ttcatggaga    540

catccgctaa aacatcaatg aatgtaaatg aaatattcat ggcaatagct aaaaaattgc    600

caaagaatga accacaaaat ccaggagcaa attctgccag aggaggagga gtagacctta    660

ccgaacccac acaaccaacc aggaatcagt gttgtagtaa ctaaacctct agtttgaac     719
```

<210> SEQ ID NO 84
<211> LENGTH: 1433
<212> TYPE: DNA
<213> ORGANISM: Homo sapiens

<400> SEQUENCE: 84

```
gacgctctgg gccgccacct ccgcggaccc tgagcgcaag agccaagccg ccagcgctgc     60

gatgtgggcc acgctgccgc tgctctgcgc cggggcctgg ctcctgggag tccccgtctg    120

cggtgccgcc gaactgtgcg tgaactcctt agagaagttt cacttcaagt catggatgtc    180

taagcaccgt aagacctaca gtacggagga gtaccaccac aggctgcaga cgtttgccag    240

caactggagg aagataaacg cccacaacaa tgggaaccac acatttaaaa tggcactgaa    300

ccaattttca gacatgagct ttgctgaaat aaaacacaag tatctctggt cagagcctca    360

gaattgctca gccaccaaaa gtaactacct tcgaggtact ggtccctacc caccttccgt    420

ggactggcgg aaaaaaggaa attttgtctc acctgtgaaa aatcagggtg cctgcggcag    480

ttgctggact ttctccacca ctggggccct ggagtctgcg atcgccatcg caaccggaaa    540

gatgctgtcc ttggcggaac agcagctggt ggactgcgcc caggacttca ataatcacgg    600

ctgccaaggg ggtctcccca gccaggcttt cgagtatatc ctgtacaaca aggggatcat    660

gggtgaagac acctacccct accagggcaa ggatggttat tgcaagttcc aacctggaaa    720

ggccatcggc tttgtcaagg atgtagccaa catcacaatc tatgacgagg aagcgatggt    780

ggaggctgtg gccctctaca accctgtgag ctttgccttt gaggtgactc aggacttcat    840

gatgtataga accggcatct actccagtac ttcctgccat aaaactccag ataaagtaaa    900

ccatgcagta ctggctgttg ggtatggaga aaaaaatggg atcccttact ggatcgtgaa    960

aaactcttgg ggtccccagt ggggaatgaa cgggtacttc ctcatcgagc gcggaaagaa   1020

catgtgtggc ctggctgcct gcgcctccta ccccatccct ctggtgtgag ccgtggcagc   1080

cgcagcgcag actggcggag aaggagagga acgggcagcc tgggcctggg tggaaatcct   1140

gccctggagg aagttgtggg gagatccact gggaccccca acattctgcc ctcacctctg   1200

tgcccagcct ggaaacctac agacaaggag gagttccacc atgagctcac ccgtgtctat   1260

gacgcaaaga tcaccagcca tgtgccttag tgtccttctt aacagactca aaccacatgg   1320

accacgaata ttctttctgt ccagaagggc tactttccac atatagagct ccagggactg   1380

tcttttctgt attcgctgtt caataaacat tgagtgagca cctccccaga tgg          1433
```

<210> SEQ ID NO 85
<211> LENGTH: 2093
<212> TYPE: DNA
<213> ORGANISM: Homo sapiens

<400> SEQUENCE: 85

```
ggtcggggcc cgcggccgct cgcgcctctc gatgggcagc tcgcacttgc tcaacaaggg     60

cctgccgctt ggcgtccgac ctccgatcat gaacgggccc ctgcacccgc ggcccctggt    120

ggcattgctg gatggccggg actgcacagt ggagatgccc atcctgaagg acgtggccac    180
```

-continued

```
tgtggccttc tgcgacgcgc agtccacgca ggagatccat gagaaggtcc tgaacgaggc    240
tgtgggggcc ctgatgtacc acaccatcac tctcaccagg gaggacctgg agaagttcaa    300
agccctccgc atcatcgtcc ggattggcag tggttttgac aacatcgaca tcaagtcggc    360
cggggattta ggcattgccg tctgcaacgt gcccgcggcg tctgtggagg agacggccga    420
ctcgacgctg tgccacatcc tgaacctgta ccggcgggcc acctggctgc accaggcgct    480
gcgggagggc acacgagtcc agagcgtcga gcagatccgc gaggtggcgt ccggcgctgc    540
caggatccgc ggggagacct tgggcatcat cggacttgtc gcgtggggca ggcagtggcg    600
ctgcgggcca aggccttcgg cttcaacgtg ctcttctacg acccttactt gtcggatggc    660
gtggagcggg cgctggggct gcagcgtgtc agcaccctgc aggacctgct cttccacagc    720
gactgcgtga ccctgcactg cggcctcaac gagcacaacc accacctcat caacgacttc    780
accgtcaagc agatgagaca aggggccttc ctggtgaaca cagcccgggg tggcctggtg    840
gatgagaagg cgctggccca ggccctgaag gagggccgga tccgcggcgc ggccctggat    900
gtgcacgagt cggaaccctt cagctttagc cagggccctc tgaaggatgc acccaacctc    960
atctgcaccc cccatgctgc atggtacagc gagcaggcat ccatcgagat gcgagaggag   1020
gcggcacggg agatccgcag agccatcaca ggccggatcc cagacagcct gaagaactgt   1080
gtcaacaagg accatctgac agccgccacc cactgggcca gcatggaccc cgccgtcgtg   1140
caccctgagc tcaatggggc tgcctatagg taccctccgg gcgtggtggg cgtggccccc   1200
actggcatcc cagctgctgt ggaaggtatc gtccccagcg ccatgtccct gtcccacggc   1260
ctgccccctg tggcccaccc gccccacgcc ccttctcctg gccaaaccgt caagcccgag   1320
gcggatagag accacgccag tgaccagttg tagcccggga ggagctctcc agcctcggcg   1380
cctgggcaga gggcccggaa accctcggac cagagtgtgt ggaggaggca tctgtgtggt   1440
ggccctggca ctgcagagac tggtccgggc tgtcaggagg cgggaggggg cagcgctggg   1500
cctcgtgtcg cttgtcgtcg tccgtcctgt gggcgctctg ccctgtgtcc ttcgcgttcc   1560
tcgttaagca gaagaagtca gtagttattc tcccatgaac gttcttgtct gtgtacagtt   1620
tttagaacat tacaaaggat ctgtttgctt agctgtcaac aaaaagaaaa cctgaaggag   1680
catttggaag tcaatttgag gttttttttt ttgttttttt tttttttgta tgttggaacg   1740
tgccccagaa tgaggcagtt ggcaaacttc tcaggacaat gaatccttcc cgtttttctt   1800
tttatgccac acagtgcatt gttttttcta cctgcttgtc ttatttttag aataatttag   1860
aaaaacaaaa caaaggctgt ttttcctaat tttggcatga acccccccctt gttccaaatg   1920
aagacggcat cacgaagcag ctccaaaagg aaaagcttgg gcggtgccca gcgtgcccgc   1980
tgcccatcga cgtctgtcct ggggacgtgg agggtggcag cgtccccgcc tgcaccagtg   2040
ccgtcctgct gatgtggtag gctagcaata ttttggttaa aatcatgttt gtg          2093
```

<210> SEQ ID NO 86
<211> LENGTH: 3435
<212> TYPE: DNA
<213> ORGANISM: Homo sapiens

<400> SEQUENCE: 86

```
cgcgcggcca ggccctctta gccctctgcc gtttgggggg cacgggtgaa cctgccgccc     60
cactcccacc ccgccccgcc ccgcccgtac agccaaatcg gaagggacga gcctgccctt    120
tgaaagggtt ttttttcttg ctcctgcgga gggcgcccca gccatggccc tcaggagctc    180
```

-continued

```
cctagacccc gcagggactg ccctccatcc cggccgccgg ggcccgccct ctgcatcccg    240
cgggcagcct gtgtgaagcg gcctcccgca gcccccggcc cctcccccat ggaggaggag    300
gagggggcgg tggccaagga gtggggcacg acccccgcgg ggcccgtctg gaccgcggtg    360
ttcgactacg aggcggcggg cgacgaggag ctgaccctgc ggaggggcga tcgcgtccag    420
gtgctttccc aagactgtgc ggtgtccggc gacgagggct ggtggaccgg gcagctcccc    480
agcggccgcg tgggcgtctt ccccagcaac tacgtggccc ccggcgcccc cgctgcaccc    540
gcgggcctcc agctgcccca ggagatcccc ttccacgagc tgcagctaga ggagatcatc    600
ggtgtggggg gctttggcaa ggtctatcgg gccctgtggc gtggcgagga ggtggcagtc    660
aaggccgccc ggctggaccc tgagaaggac ccggcagtga cagcggagca ggtgtgccag    720
gaagcccggc tctttggagc cctgcagcac cccaacataa ttgcccttag ggcgcctgc     780
ctcaaccccc cacacctctg cctagtgatg gagtatgccc ggggtggtgc actgagcagg    840
gtgctggcag gtcgccgggt gccacctcac gtgctggtca actgggctgt gcaggtggcc    900
cggggcatga actacctaca caatgatgcc cctgtgccca tcatccaccg ggacctcaag    960
tccatcaaca tcctgatcct ggaggccatc gagaaccaca acctcgcaga cacggtgctc   1020
aagatcacgg acttcggcct cgcccgcgag tggcacaaga ccaccaagat gagcgctgcg   1080
gggacctacg cctggatggc gccggaggtt atccgtctct ccctcttctc caaaagcagt   1140
gatgtctgga gcttcggggt gctgctgtgg gagctgctga cgggggaggt cccctaccgt   1200
gagatcgacg ccttggccgt ggcgtatggc gtggctatga ataagctgac gctgcccatt   1260
ccctccacgt gccccgagcc ctttgcccgc ctcctggagg aatgctggga cccagacccc   1320
cacgggcggc cagatttcgg tagcatcttg aagcggcttg aagtcatcga acagtcagcc   1380
ctgttccaga tgccactgga gtccttccac tcgctgcagg aagactggaa gctggagatt   1440
cagcacatgt ttgatgacct tcggaccaag gagaaggagc ttcggagccg tgaggaggag   1500
ctgctgcggg cggcacagga gcagcgcttc caggaggagc agctgcggcg gcgggagcag   1560
gagctggcag aacgtgagat ggacatcgtg gaacgggagc tgcacctgct catgtgccag   1620
ctgagccagg agaagccccg ggtccgcaag cgcaagggca acttcaagcg cagccgcctg   1680
ctcaagctgc gggaaggcgg cagccacatc agcctgccct ctggctttga gcataagatc   1740
acagtccagg cctctccaac tctggataag cggaaaggat ccgatggggc cagccccccct  1800
gcaagcccca gcatcatccc ccggctgagg gccattcgcc tgactcccgt ggactgtggt   1860
ggcagcagca gtggcagcag cagtggagga agtgggacat ggagccgcgg tgggcccccca  1920
aagaaggaag aactggtcgg gggcaagaag aagggacgaa cgtgggggcc cagctccacc   1980
ctgcagaagg agcgggtggg aggagaggag aggctgaagg ggctggggga aggaagcaaa   2040
cagtggtcat caagtgcccc caacctgggc aagtccccca aacacacacc cagtcgccgc   2100
tggcttcgcc agcctcaatg agatggagga gttcgcggag gcagaggatg gaggcagcag   2160
cgtgcccccct tccccctact cgaccccgtc ctacctctca gtgccactgc ctgccgagcc  2220
ctccccgggg gcgcgggcgc cgtgggagcc gacgccgtcc gcgcccccccg ctcggtgggg  2280
acacggcgcc cggcggcgct gcgacctggc gctgctaggc tgcgccacgc tgctgggggc   2340
tgtgggcctg ggcgccgacg tggccgaggc gcgcgcggcc gacggtgagg agcagcggcg   2400
ctggctcgac ggcctcttct ttccccgcgc cggccgcttc ccgcggggcc tcagcccacc   2460
cgcgcgtccc cacggccgcc gcgaagacgt gggccccggc ctgggcctgg cgccctcggc   2520
caccctcgtg tcgctgtcgt ccgtgtccga ctgcaactcc acgcgttcac tgctgcgctc   2580
```

-continued tgacagtgac gaggccgcac cggccgcgcc ctccccacca ccctccccgc ccgcgcccac 2640
acccacgccc tcgcccagca ccaaccccct ggtggacctg gagctggaga gcttcaagaa 2700
ggacccccgc cagtcgctca cgcccaccca cgtcacggct gcatgcgctg tgagccgcgg 2760
gcaccggcgg acgccatcgg atggggcgct ggggcagcgg gggccgcccg agcccgcggg 2820
ccatggccct ggccctcgtg accttctgga cttcccccgc ctgcccgacc cccaggccct 2880
gttcccagcc cgccgccggc cccctgagtt cccaggccgc cccaccaccc tgacctttgc 2940
cccgagacct cggccggctg ccagtcgccc ccgcttggac ccctggaaac tggtctcctt 3000
cggccggaca ctcaccatct cgcctcccag caggccagac actccggaga gccctgggcc 3060
ccccagcgtg cagcccacac tgctggacat ggacatggag gggcagaacc aagacagcac 3120
agtgcccctg tgcggggccc acggctccca ctaaggcctg cccaccaccg cccgcctggg 3180
cagccatgaa tgtagcgccc caggccctgc cccagcccgc catgccacaa ggtgggggag 3240
gccctgggca ggatgttcac tctatttatt ggggaaggag ggaggggggg gacacttaac 3300
ttattccttt gtaccccagg gggtggagcc ctgtgcccac cctgcactgg ggggagggtg 3360
ggcagggata ctcagggaca gggcatcatg ggggatttgg cacaaaatgg agcattaaag 3420
gtaacccctg ccccc 3435

<210> SEQ ID NO 87
<211> LENGTH: 2227
<212> TYPE: DNA
<213> ORGANISM: Homo sapiens

<400> SEQUENCE: 87
gggcccgccc ctggtcacag ccagactgac tcagtttccc tgggaggtcc cgctcgagcc 60
cgtccttccc ctccctctgc ccgcccccag ccctcgcccc accctcggcg cccgcacatc 120
tgcctgctca gctccagacg gcgcccggac ccccgggcgc gggatccagc caggtgggag 180
ccccgcagat gaggtctctg aaggtgtgcc tgaaccagtg ccagcctgcc ctgtctgcag 240
catcggcctg atggggtggt gactgatccc tcagggctcc ggagccatgt ggcccaacgg 300
cagttccctg ggccctgtt tccggcccac aaacattacc ctggaggaga gacggctgat 360
cgcctcgccc tggttcgccg cctccttctg cgtggtgggc ctggcctcca acctgctggc 420
cctgagcgtg ctggcgggcg cgcggcaggg gggttcgcac acgcgctcct ccttcctcac 480
cttcctctgc ggcctcgtcc tcaccgactt cctggggctg ctggtgaccg gtaccatcgt 540
ggtgtcccag cacgccgcgc tcttcgagtg gcacgccgtg gaccctggct gccgtctctg 600
tcgcttcatg ggcgtcgtca tgatcttctt cggcctgtcc ccgctgctgc tgggggccgc 660
catggcctca gagcgctacc tgggtatcac ccggcccttc tcgcgcccgg cggtcgcctc 720
gcagcgccgc gcctgggcca ccgtggggct ggtgtgggcg gccgcgctgg cgctgggcct 780
gctgcccctg ctgggcgtgg gtcgctacac cgtgcaatac ccggggtcct ggtgcttcct 840
gacgctgggc gccgagtccg ggacgtggc cttcgggctg ctcttctcca tgctgggcgg 900
cctctcggtc gggctgtcct tcctgctgaa cacggtcagc gtggccaccc tgtgccacgt 960
ctaccacggg caggaggcgg cccagcagcg tccccgggac tccgaggtgg agatgatggc 1020
tcagctcctg ggatcatgg tggtggccag cgtgtgttgg ctgcccttc tggtcttcat 1080 cgcccagaca gtgctgcgaa acccgcctgc catgagcccc gccgggcagc tgtcccgcac 1140
cacggagaag gagctgctca tctacttgcg cgtggccacc tggaaccaga tcctggaccc 1200

-continued

```
ctgggtgtat atcctgttcc gccgcgccgt gctccggcgt ctccagcctc gcctcagcac   1260

ccggcccagg tcgctgtccc tccagcccca gctcacgcag cgctccgggc tgcagtagga   1320

agtggacaga gcgcccctcc cgcgcctttc cgcggagccc ttggcccctc ggacagccca   1380

tctgcctgtt ctgaggattc aggggctggg ggtgctggat ggacagtggg catcagcagc   1440

agggttttgg gttgacccca atccaacccg gggaccccca actcctccct gatcctttta   1500

ccaagcactc tcccttcctc ggcccctttt tcccatccag agctcccacc ccttctctgc   1560

gtccctccca accccaggaa gggcatgcag acattggaag agggtcttgc attgctattt   1620

tttttttag acggagtctt gctctgtccc ccaggctgga gtgcagtggc gcaatctcag   1680

ctcactgcaa cctccacctc ccgggttcaa gcgattctcc tgcctcagcc tcctgagtag   1740

ctgggactat aggcgcgcgc caccacgccc ggctaatttt tgtattttta gtagagacgg   1800

ggtttcaccg tgttggccag gctggtcttg aactcctgac ctcaggtgat tcaccagcct   1860

cagcctccca aagtgctggg atcacaggca tgaaccacca cacctggcca tttttttttt   1920

ttttttaga cggagtctca ctctgtggcc cagcctggag tacagtggca cgatctcggc   1980

tcactgcaac ctccgcctcc cgggttcaag cgattctcgt gcctcagcct cccgagcagc   2040

tgggattaca ggcgtaagcc actgcgcccg gccttgcatg ctctttgacc ctgaatttga   2100

cctacttgct ggggtacagt tgcttccttt tgaacctcca acagggaagg ctctgtccag   2160

aaaggattga atgtgaacgg gggcaccccc ttttcttgcc aaaatatatc tctgcctttg   2220

gttttat                                                             2227
```

<210> SEQ ID NO 88
<211> LENGTH: 2662
<212> TYPE: DNA
<213> ORGANISM: Homo sapiens

<400> SEQUENCE: 88

```
cccggacatg gccgccaaca tgtacagggt cggagactac gtctactttg agaactcctc     60

cagcaaccca tacctgatcc ggagaatcga ggagctcaac aagacggcca atgggaacgt    120

ggaggccaaa gtggtgtgct tctaccggag gcgggacatc tccagcaccc tcatcgccct    180

ggccgacaag cacgcaaccc tgtcagtctg ctataaggcc ggaccggggg cggacaacgg    240

cgaggaaggg gaaatagaag aggaaatgga gaatccggaa atggtggacc tgcccgagaa    300

actaaagcac cagctgcggc atcgggagct gttcctctcc cggcagctgg agtctctgcc    360

cgccacgcac atcaggggca agtgcagcgt caccctgctc aacgagaccg agtcgctcaa    420

gtcctacctg gagcgggagg atttcttctt ctattctcta gtctacgacc cacagcagaa    480

gaccctgctg gcagataaag gagagattcg agtaggaaac cggtaccagg cagacatcac    540

cgacttgtta aaagaaggcg aggaggatgg ccgagaccag tccaggttgg agacccaggt    600

gtgggaggcg cacaacccac tcacagacaa gcagatcgac cagttcctgg tggtggcccg    660

ctctgtgggc accttcgcac gggccctgga ctgcagcagc tccgtccgac agcccagcct    720

gcacatgagc gccgcagctg cctcccgaga catcaccctg ttccacgcca tggatactct    780

ccacaagaac atctacgaca tctccaaggc catctcggcg ctggtgccgc agggcgggcc    840

cgtgctctgc agggacgaga tggaggagtg gtctgcatca gaggccaacc ttttcgagga    900

agccctggaa aaatatggga aggatttcac ggacattcag caagattttc tcccgtggaa    960

gtcgctgacc agcatcattg agtactacta catgtggaag accaccgaca gatacgtgca   1020

gcagaaacgc ttgaaagcag ctgaagctga gagcaagtta aagcaagttt atattcccaa   1080
```

-continued ctataacaag ccaaatccga accaaatcag cgtcaacaac gtcaaggccg gtgtggtgaa 1140
cggcacgggg gcgccgggcc agagccctgg ggctggccgg gcctgcgaga gctgttacac 1200
cacacagtct taccagtggt attcttgggg tccccctaac atgcagtgtc gtctctgcgc 1260
atcttgttgg acatattgga agaaatatgg tggcttgaaa atgccaaccc ggttagatgg 1320
agagaggcca ggaccaaacc gcagtaacat gagtccccac ggcctcccag cccggagcag 1380
cgggagcccc aagtttgcca tgaagaccag gcaggctttc tatctgcaca cgacgaagct 1440
gacgcggatc gcccggcgcc tgtgccgtga gatcctgcgc ccgtggcacg ctgcgcggaa 1500
cccctacctg cccatcaaca gcgcggccat caaggccgag tgcacggcgc ggctgcccga 1560
agcctcccag agcccgctgg tgctgaagca ggcggtacgc aagccgctgg aagccgtgct 1620
tcggtatctt gagacccacc cccgcccccc caagcctgac cccgtgaaaa gcgtgtccag 1680
cgtgctcagc agcctgacgc ccgccaaggt ggcccccgtc atcaacaacg gctcccccac 1740
catcctgggc aagcgcagct acgagcagca caacggggtg gacggcaaca tgaagaagcg 1800
cctcttgatg cccagtaggg gtctggcaaa ccacggacag accaggcaca tgggaccaag 1860
ccggaacctc ctgctcaacg ggaagtccta ccccaccaaa gtgcgcctga tccggggggg 1920
ctccctgccc ccagtcaagc ggcggcggat gaactggatc gacgccccgg gtgacgtgtt 1980
ctacatgccc aaagaggaga ccaggaagat ccgcaagctg ctctcatcct cggaaaccaa 2040
gcgtgctgcc cgccggccct acaagcccat cgccctgcgc cagagccagg ccctgccgcc 2100
gcggccaccg ccacctgcgc ccgtcaacga cgagcccatc gtcatcgagg actaggggcc 2160
gcccccacct gcggccgccc cccgcccctc gcccgcccac acggcccctt cccagccagc 2220
ccgccgcccg cccctcagtt tggtagtgcc ccacctcccg ccctcacctg aagagaaacg 2280
cgctccttgg cggacactgg gggaggagag gaagaagcgc ggctaactta ttccgagaat 2340
gccgaggagt tgtcgttttt agctttgtgt ttactttttg gctggagcgg agatgagggg 2400
ccaccccgtg cccctgtgct gcggggcctt ttgcccggag gccgggccct aaggttttgt 2460
tgtgttctgt tgaaggtgcc attttaaatt ttatttttat tacttttttt gtagatgaac 2520
ttgagctctg taacttacac ctggaatgtt aggatcgtgc ggccgcggcc ggccgagctg 2580
cctggcgggg ttggcccttg tcttttcaag taattttcat attaaacaaa aacaaagaaa 2640
aaaaatctta taaaaaggaa aa 2662

<210> SEQ ID NO 89
<211> LENGTH: 552
<212> TYPE: DNA
<213> ORGANISM: Homo sapiens

<400> SEQUENCE: 89
atgagagagt acaaagtggt ggtgctgggc tcgggcggcg tgggcaagtc cgcgctcacc 60
gtgcagttcg tgacgggctc cttcatcgag aagtacgacc cgaccatcga agacttttac 120
cgcaaggaga ttgaggtgga ctcgtcgccg tcggtgctgg agatcctgga tacggcgggc 180
accgagcagt tcgcgtccat gcgggacctg tacatcaaga acggccaggg cttcatcctg 240
gtctacagcc tcgtcaacca gcagagcttc caggacatca agcccatgcg ggaccagatc 300
atccgcgtga agcggtacga gcgcgtgccc atgatcctgg tgggcaacaa ggtggacctg 360
gagggtgagc gcgaggtctc gtacggggag ggcaaggccc tggctgagga gtggagctgc 420
cccttcatgg agacgtcggc caaaaacaaa gcctcggtag acgagctatt tgccgagatc 480

-continued

```
gtgcggcaga tgaactacgc ggcgcagtcc aacggcgatg agggctgctg ctcggcctgc    540

gtgatcctct ga                                                        552


<210> SEQ ID NO 90
<211> LENGTH: 2198
<212> TYPE: DNA
<213> ORGANISM: Homo sapiens

<400> SEQUENCE: 90

gagctgcggg cgctgctgct gtggggccgc cgcctgcggc ctttgctgcg ggcgccggcg     60

ctggcggccg tgccgggagg aaaaccaatt ctgtgtcctc ggaggaccac agcccagttg    120

ggccccaggc gaaacccagc ctggagcttg caggcaggac gactgttcag cacgcagacc    180

gccgaggaca aggaggaacc cctgcactcg attatcagca gcacagagag cgtgcagggt    240

tccacttcca aacatgagtt ccaggccgag acaaagaagc ttttggacat tgttgcccgg    300

tccctgtact cagaaaaaga ggtgtttata cgggagctga tctccaatgc cagcgatgcc    360

ttggaaaaac tgcgtcacaa actggtgtct gacggccaag cactgccaga aatggagatt    420

cacttgcaga ccaatgccga gaaaggcacc atcaccatcc aggatactgg tatcgggatg    480

acacaggaag agctggtgtc caacctgggg acgattgcca gatcggggtc aaaggccttc    540

ctggatgctc tgcagaacca ggctgaggcc agcagcaaga tcatcggcca gtttggagtg    600

ggtttctact cagctttcat ggtggctgac agagtggagg tctattcccg ctcggcagcc    660

ccggggagcc tgggttacca gtggctttca gatggttctg gagtgtttga aatcgccgaa    720

gcttcgggag ttagaaccgg gacaaaaatc atcatccacc tgaaatccga ctgcaaggag    780

ttttccagcg aggcccgggt gcgagatgtg gtaacgaagt acagcaactt cgtcagcttc    840

cccttgtact tgaatggaag gcggatgaac accttgcagg ccatctggat gatggacccc    900

aaggatgtcc gtgagtggca acatgaggag ttctaccgct acgtcgcgca ggctcacgac    960

aagccccgct acaccctgca ctataagacg gacgcaccgc tcaacatccg cagcatcttc   1020

tacgtgcccg acatgaaacc gtccatgttt gatgtgagcc gggagctggg ctccagcgtt   1080

gcactgtaca gccgcaaagt cctcatccag accaaggcca cggacatcct gcccaagtgg   1140

ctgcgcttca tccgaggtgt ggtggacagt gaggacattc ccctgaacct cagccgggag   1200

ctgctgcagg agagcgcact catcaggaaa ctccgggacg ttttacagca gaggctgatc   1260

aaattcttca ttgaccagag taaaaaagat gctgagaagt atgcaaagtt ttttgaagat   1320

tacggcctgt tcatgcggga gggcattgtg accgccaccg agcaggaggt caaggaggac   1380

atagcaaagc tgctgcgcta cgagtcctcg gcgctgccct ccgggcagct aaccagcctc   1440

tcagaatacg ccagccgcat gcgggccggc acccgcaaca tctactacct gtgcgccccc   1500

aaccgtcacc tggcagagca ctcaccctac tatgaggcca tgaagaagaa agacacagag   1560

gttctcttct gctttgagca gtttgatgag ctcaccctgc tgcaccttcg tgagtttgac   1620

aagaagaagc tgatctctgt ggagacggac atagtcgtgg atcactacaa ggaggagaag   1680

tttgaggaca ggtccccagc cgccgagtgc ctatcagaga aggagacgga ggagctcatg   1740

gcctggatga gaaatgtgct ggggtcgcgt gtcaccaacg tgaaggtgac cctccgactg   1800

gacacccacc ctgccatggt caccgtgctg gagatggggg ctgcccgcca cttcctgcgc   1860

atgcagcagc tggccaagac ccaggaggag cgcgcacagc tcctgcagcc cacgctggag   1920

atcaacccca ggcacgcgct catcaagaag ctgaatcagc tgcgcgcaag cgagcctggc   1980

ctggctcagc tgctggtgga tcagatatac gagaacgcca tgattgctgc tggacttgtt   2040
```

-continued gacgacccta gggccatggt gggccgcttg aatgagctgc ttgtcaaggc cctggagcga 2100
cactgacagc caggggggcca gaaggactga caccacagat gacagcccca cctccttgag 2160
ctttatttac ctaaatttaa aggtatttct taaccccga 2198

<210> SEQ ID NO 91
<211> LENGTH: 1790
<212> TYPE: DNA
<213> ORGANISM: Homo sapiens

<400> SEQUENCE: 91
agtgatgtcc ttgcattgcc catttttaag caagaagagt cgagtttgcc tcctgataat 60
gagaataaaa tcctgccttt tcaatatgtg ctttgtgctg ctacctctcc agcagtgaaa 120
ctccatgatg aaaccctaac gtatctcaat caaggacagt cttatgaaat tcgaatgcta 180
gacaatagga aacttggaga acttccagaa attaatggca aattggtgaa gagtatattc 240
cgtgtggtgt tccatgacag aaggcttcag tacactgagc atcagcagct agagggctgg 300
aggtggaacc gacctggaga cagaattctt gacatagata tcccgatgtc tgtgggtata 360
atcgatccta gggctaatcc aactcaacta aatacagtgg agttcctgtg ggaccctgca 420
aagaggacat ctgtgtttat tcaggtgcac tgtattagca cagagttcac tatgaggaaa 480
catggtggag aaaagggggt gccattccga gtacaaatag ataccttcaa ggagaatgaa 540
aacggggaat atactgagca cttacactcg gccagctgcc agatcaaagt tttcaagcca 600
aaggtgcaga cagaaagcaa aaaacggata gggaaaaaat ggagaaacga acacctcatg 660
aaaaggagaa atatcagcct tcctatgaga caaccatact cacagagtgt tctccatggc 720
ccgagatcac gtatgtcaat aactccccat cacctggctt caacagttcc catagcagtt 780
tttctcttgg ggaaggaaat ggttcaccaa accaccagcc agagccaccc cctccagtca 840
cagataacct cttaccaaca accacacctc aggaagctca gcagtggttg catcgaaatc 900
gtttttctac attcacaagg cttttcacaa acttctcagg ggcagattta ttgaaattaa 960
ctagagatga tgtgatccaa atctgtggcc ctgcagatgg aatcagactt tttaatgcat 1020
taaaaggccg gatggtgcgt ccaaggttaa ccatttatgt ttgtcaggaa tcactgcagt 1080
tgagggagca gcaacaacag cagcagcaac agcagcagaa gcatgaggat ggagactcaa 1140
atggtacttt cttcgtttac catgctatct atctagaaga actaacagct gttgaattga 1200
cagaaaaaat tgctcagctt ttcagcattt ccccttgcca gatcagccag atttacaagc 1260
aggggccaac aggaattcat gtgctcatca gtgatgagat gatacagaac tttcaggaag 1320
aagcatgttt tattctggac acaatgaaag cagaaaccaa tgatagctat catatcatac 1380
tgaagtagga gtgcggcgtt tcgtgcccag tggctgctcc ttccttcacc tctgaaaacg 1440
gccctcttga agggggatat gaatggagat ttgaaggtct gcaagaacct gactcgtctg 1500
actgtgtgtg gaggagtcca ggccatggag gcagaatcct ggccctctgt gttggcccaa 1560
gctcttgtgg tacacacaga ttactgccca atatgcagtt ctgcagctgt tttagttaaa 1620
tttctggacc ttgttgttgt taaatatcag tagaaactct acataattta gagtgtatgt 1680
agggcataat gatgatggga attgtgtgat gtttaacagg aagatcttaa attttgtgat 1740
atggagccct gtaatttttt tcttatataa aaatgggtat ctatattcat 1790

<210> SEQ ID NO 92
<211> LENGTH: 652
<212> TYPE: DNA

-continued

<213> ORGANISM: Homo sapiens

<400> SEQUENCE: 92
aggtctgttc cgcatgaaac tcctgctggg gaaggacttc cctgcctccc cacccaaggg 60
ctacttcctg accaagatct tccacccgaa cttgggcgcc aatggcgaga tgtgcgtcaa 120
cgtgctcaag agggactgga cggctgagct gggcatccga cacgtactgc tgaccatcaa 180
gtgcctgctg atccacccta accccgagtc tgcactcaac gaggaggcgg gccgcctgct 240
cttggagaac tacgaggagt atgcggctcg ggcccgtctg ctcacagaga tccacggggg 300
cgccggcggg cccagcggca gggccaaagc cgggcgggcc ctggccagtg gcactgcagc 360
ttcctccacc gactctgggg ccccaggggg cttgggaggg gctgagggtc ccatggccaa 420
gaagcatgct ggcgagcgcg ataagaagct ggcggccaag aaaaagacgg acaagaagcg 480
ggcgctacgg cggctgtagt gggctctctt cctccttcca ccgtgacccc aacctctcct 540
gtcccctccc tccaactctg tctctaagtt atttaaatta tggctggggt cggggagggt 600
acagggggca ctgagacctg gatttgtttt tttaaataaa gttggaaaag ca 652

<210> SEQ ID NO 93
<211> LENGTH: 771
<212> TYPE: DNA
<213> ORGANISM: Homo sapiens

<400> SEQUENCE: 93
gtcgtgttct ccgagttcct gtctctctgc caacgccgcc cggatggctt cccaaaaccg 60
cgacccagcc gccactagcg tcgccgccgc ccgtaaagga gctgagccga gcgggggcgc 120
cgcccggggt ccggtgggca aaaggctaca gcaggagctg atgaccctca tgatgtctgg 180
cgataaaggg atttctgcct tccctgaatc agacaacctt ttcaaatggg tagggaccat 240
ccatggagca gctggaacag tatatgaaga cctgaggtat aagctctcgc tagagttccc 300
cagtggctac ccttacaatg cgcccacagt gaagttcctc acgccctgct atcaccccaa 360
cgtggacacc cagggtaaca tatgcctgga catcctgaag gaaaagtggt ctgccctgta 420
tgatgtcagg accattctgc tctccatcca gagccttcta ggagaaccca acattgatag 480
tcccttgaac acacatgctg ccgagctctg gaaaaacccc acagctttta agaagtacct 540
gcaagaaacc tactcaaagc aggtcaccag ccaggagccc tgacccaggc tgcccagcct 600
gtccttgtgt cgtcttttta atttttcctt agatggtctg tcctttttgt gatttctgta 660
taggactctt tatcttgagc tgtggtattt ttgttttgtt tttgtctttt aaattaagcc 720
tcggttgagc ccttgtatat taaataaatg catttttgtc ctttttttaga c 771

<210> SEQ ID NO 94
<211> LENGTH: 2527
<212> TYPE: DNA
<213> ORGANISM: Homo sapiens

<400> SEQUENCE: 94
ctccagcagc acccgagagg gtcaggagaa aagcggagga agctgggtag gccctgaggg 60
gcctcggtaa gccatcatga ccacccggca agccacgaag gatcccctcc tccggggtgt 120
atctcctacc cctagcaaga ttccggtacg ctctcagaaa cgcacgcctt tccccactgt 180
tacatcgtgc gccgtggacc aggagaacca agatccaagg agatgggtgc agaaaccacc 240
gctcaatatt caacgccccc tcgttgattc agcaggcccc aggccgaaag ccaggcacca 300
ggcagagaca tcacaaagat tggtggggat cagtcagcct cggaacccct tggaagagct 360

-continued caggcctagc cctaggggtc aaaatgtggg gcctgggccc cctgcccaga cagaggctcc 420
agggaccata gagtttgtgg ctgaccctgc agccctggcc accatcctgt caggtgaggg 480
tgtgaagagc tgtcacctgg ggcgccagcc tagtctggct aaaagagtac tggttcgagg 540
aagtcaggga ggcaccaccc agagggtcca gggtgttcgg gcctctgcat atttggcccc 600
cagaaccccc acccaccgac tggaccctgc cagggcttcc tgcttctcta ggctggaggg 660
accaggacct cgaggccgga cattgtgtcc ccagaggcta caggctctga tttcaccttc 720
aggaccttcc tttcaccctt ccactcgccc cagtttccag gagctaagaa gggagacagc 780
tggcagcagc cggacttcag tgagccaggc ctcaggattg ctcctggaga ccccagtcca 840
gcctgctttc tctcttccta aaggagaacg cgaggttgtc actcactcag atgaaggagg 900
tgtggcctct cttggtctgg cccagcgagt accattaaga gaaaaccgag aaatgtcaca 960
taccagggac agccatgact cccacctgat gccctcccct gcccctgtgg cccagccctt 1020
gcctggccat gtggtgccat gtccatcacc ctttggacgg gctcagcgtg taccctcccc 1080
aggccctcca actctgacct catattcagt gttgcggcgt ctcaccgttc aacctaaaac 1140
ccggttcaca cccatgccat caacccccag agttcagcag gcccagtggc tgcgtggtgt 1200
ctcccctcag tcctgctctg aagatcctgc cctgccctgg gagcaggttg ccgtccggtt 1260
gtttgaccag gagagttgta taaggtcact ggagggttct gggaaaccac cggtggccac 1320
tccttctgga ccccactcta acagaacccc cagcctccag gaggtgaaga ttcaacgcat 1380
cggtatcctg caacagctgt tgagacagga agtagagggg ctggtagggg gccagtgtgt 1440
ccctcttaat ggaggctctt ctctggatat ggttgaactt cagcccctgc tgactgagat 1500
ttctagaact ctgaatgcca cagagcataa ctctgggact tcccaccttc ctggactgtt 1560
aaaacactca gggctgccaa agccctgtct tccagaggag tgcggggaac cacagccctg 1620
ccctccggca gagcctgggc ccccagaggc cttctgtagg agtgagcctg agataccaga 1680
gccctccctc caggaacagc ttgaagtacc agagccctac cctccagcag aacccaggcc 1740
cctagagtcc tgctgtagga gtgagcctga gataccggag tcctctcgcc aggaacagct 1800
tgaggtacct gagccctgcc ctccagcaga acccaggccc ctagagtcct actgtaggat 1860
tgagcctgag ataccggagt cctctcgcca ggaacagctt gaggtacctg agccctgccc 1920
tccagcagaa cccgggcccc ttcagcccag cacccagggg cagtctggac cccagggcc 1980 ctgccctagg gtagagctgg gggcatcaga gccctgcacc ctggaacata gaagtctaga 2040
gtccagtcta ccaccctgct gcagtcagtg ggctccagca accaccagcc tgatcttctc 2100
ttcccaacac ccgctttgtg ccagcccccc tatctgctca ctccagtctt tgagaccccc 2160
agcaggccag gcaggcctca gcaatctggc ccctcgaacc ctagccctga gggagcgcct 2220
caaatcgtgt ttaaccgcca tccactgctt ccacgaggct cgtctggacg atgagtgtgc 2280
cttttacacc agccgagccc ctccctcagg ccccacccgg gtctgcacca accctgtggc 2340
tacattactc gaatggcagg atgccctgtg tttcattcca gttggttctg ctgcccccca 2400
gggctctcca tgatgagaca accactcctg ccctgccgta cttcttcctt ttagccctta 2460
tttattgtcg gtctgcccat gggactggga gccgcccact tttgtcctca ataaagtttc 2520
taaagta 2527

<210> SEQ ID NO 95
<211> LENGTH: 2512
<212> TYPE: DNA

-continued

<213> ORGANISM: Homo sapiens

<400> SEQUENCE: 95

```
agaataatca tgggccagac tgggaagaaa tctgagaagg gaccagtttg ttggcggaag     60
cgtgtaaaat cagagtacat gcgactgaga cagctcaaga ggttcagacg agctgatgaa    120
gtaaaggtat gtttagttcc aatcgtcaga aaattttgga aagaacggaa atcttaaacc    180
aagaatggaa acagcgaagg atacagcctg tgcacatcct gacttctgtg agctcattgc    240
gcgggactag ggagtgttcg gtgaccagtg acttggattt tccaacacaa gtcatcccat    300
taaagactct gaatgcagtt gcttcagtac ccataatgta ttcttggtct cccctacagc    360
agaattttat ggtggaagat gaaactgttt tacataacat tccttatatg ggagatgaag    420
ttttagatca ggatggtact ttcattgaag aactaataaa aaattatgat gggaaagtac    480
acggggatag agaatgtggg tttataaatg atgaaatttt tgtggagttg gtgaatgccc    540
ttggtcaata taatgatgat gacgatgatg atgatggaga cgatcctgaa gaaagagaag    600
aaaagcagaa agatctggag gatcaccgag atgataaaga aagccgccca cctcggaaat    660
ttccttctga taaaattttt gaagccattt cctcaatgtt tccagataag ggcacagcag    720
aagaactaaa ggaaaaatat aaagaactca ccgaacagca gctcccaggc gcacttcctc    780
ctgaatgtac ccccaacata gatggaccaa atgctaaatc tgttcagaga gagcaaagct    840
tacactcctt tcatacgctt ttctgtaggc gatgttttaa atatgactgc ttcctacatc    900
cttttcatgc aacacccaac acttataagc ggaagaacac agaaacagct ctagacaaca    960
aaccttgtgg accacagtgt taccagcatt tggagggagc aaaggagttt gctgctgctc   1020
tcaccgctga gcggataaag accccaccaa aacgtccagg aggccgcaga agaggacggc   1080
ttcccaataa cagtagcagg cccagcaccc ccaccattaa tgtgctggaa tcaaaggata   1140
cagacagtga tagggaagca gggactgaaa cgggggggaga gaacaatgat aaagaagaag   1200
aagagaagaa agatgaaact tcgagctcct ctgaagcaaa ttctcggtgt caaacaccaa   1260
taaagatgaa gccaaatatt gaacctcctg agaatgtgga gtggagtggt gctgaagcct   1320
caatgtttag agtcctcatt ggcacttact atgacaattt ctgtgccatt gctaggttaa   1380
ttgggaccaa aacatgtaga caggtgtatg agtttagagt caaagaatct agcatcatag   1440
ctccagctcc cgctgaggat gtggatactc ctccaaggaa aaagaagagg aaacaccggt   1500
tgtgggctgc acactgcaga aagatacagc tgaaaaagga cggctcctct aaccatgttt   1560
acaactatca accctgtgat catccacggc agccttgtga cagttcgtgc ccttgtgtga   1620
tagcacaaaa tttttgtgaa aagttttgtc aatgtagttc agagtgtcaa aaccgctttc   1680
cgggatgccg ctgcaaagca cagtgcaaca ccaagcagtg cccgtgctac ctggctgtcc   1740
gagagtgtga ccctgacctc tgtcttactt gtggagccgc tgaccattgg gacagtaaaa   1800
atgtgtcctg caagaactgc agtattcagc ggggctccaa aaagcatcta ttgctggcac   1860
catctgacgt ggcaggctgg gggattttta tcaaagatcc tgtgcagaaa aatgaattca   1920
tctcagaata ctgtggagag attatttctc aagatgaagc tgacagaaga gggaaagtgt   1980
atgataaata catgtgcagc tttctgttca acttgaacaa tgattttgtg gtggatgcaa   2040
cccgcaaggg taacaaaatt cgttttgcaa atcattcggt aaatccaaac tgctatgcaa   2100
aagttatgat ggttaacggt gatcacagga taggtatttt tgccaagaga gccatccaga   2160
ctggcgaaga gctgtttttt gattacagat acagccaggc tgatgccctg aagtatgtcg   2220
gcatcgaaag agaaatggaa atcccttgac atctgctacc tcctcccccc tcctctgaaa   2280
```

-continued

```
cagctgcctt agcttcagga acctcgagta ctgtgggcaa tttagaaaaa gaacatgcag   2340

tttgaaattc tgaatttgca aagtactgta agaataattt atagtaatga gtttaaaaat   2400

caacttttta ttgccttctc accagctgca aagtgttttg taccagtgaa tttttgcaat   2460

aatgcagtat ggtacatttt tcaactttga ataaagaata cttgaacttg tc           2512


<210> SEQ ID NO 96
<211> LENGTH: 3403
<212> TYPE: DNA
<213> ORGANISM: Homo sapiens

<400> SEQUENCE: 96

caggtctgag gcgaagctag gtgagccgtg ggaagaaaag agggagcagc tagggcgcgg     60

gtctccctcc tcccggagtt tggaacggct gaagttcacc ttccagcccc tagcgccgtt    120

cgcgccgcta ggcctggctt ctgaggcggt tgcggtgctc ggtcgccgcc taagcggggc    180

agggtgcgaa caggggcttc gggccacgct tctcttggcg acaggatttt gctgtgaagt    240

ccgtccggga aacggaggaa aaaaagagtt gcgggaggct gtctgctaat aacggttctt    300

gatacatatt tgccagactt caagatttca gaaaaggggt gaaagagaag attgcaactt    360

tgagtcagac ctgtaggcct gatagactga ttaaaccaca gaaggtgacc tgctgagaaa    420

agtggtacaa atactgggaa aaacctgctc ttctgcgtta agtgggagac aatgtcacaa    480

gttaaaagct cttattccta tgatgccccc tcggatttca tcaatttttc atccttggat    540

gatgaaggag atactcaaaa catagattca tggtttgagg agaaggccaa tttggagaat    600

aagttactgg ggaagaatgg aactggaggg ctttttcagg gcaaaactcc tttgagaaag    660

gctaatcttc agcaagctat tgtcacacct ttgaaaccag ttgacaacac ttactacaaa    720

gaggcagaaa aagaaaatct tgtggaacaa tccattccgt caaatgcttg ttcttccctg    780

gaagttgagg cagccatatc aagaaaaact ccagcccagc ctcagagaag atctcttagg    840

ctttctgctc agaaggattt ggaacagaaa gaaaagcatc atgtaaaaat gaaagccaag    900

agatgtgcca ctcctgtaat catcgatgaa attctaccct ctaagaaaat gaaagtttct    960

aacaacaaaa agaagccaga ggaagaaggc agtgctcatc aagatactgc tgaaaacaat   1020

gcatcttccc cagagaaagc caagggtaga catactgtgc cttgtatgcc acctgcaaag   1080

cagaagtttc taaaaagtac tgaggagcaa gagctggaga agagtatgaa aatgcagcaa   1140

gaggtggtgg agatgcggaa aaagaatgaa gaattcaaga aacttgctct ggctggaata   1200

gggcaacctg tgaagaaatc agtgagccag gtcaccaaat cagttgactt ccacttccgc   1260

acagatgagc gaatcaaaca acatcctaag aaccaggagg aatataagga agtgaacttt   1320

acatctgaac tacgaaagca tccttcatct cctgcccgag tgactaaggg atgtaccatt   1380

gttaagcctt tcaacctgtc ccaaggaaag aaaagaacat ttgatgaaac agtttctaca   1440

tatgtgcccc ttgcacagca agttgaagac ttccataaac gaacccctaa cagatatcat   1500

ttgaggagca agaaggatga tattaacctg ttaccctcca aatcttctgt gaccaagatt   1560

tgcagagacc cacagactcc tgtactgcaa accaaacacc gtgcacgggc tgtgacctgc   1620

aaaagtacag cagagctgga ggctgaggag ctcgagaaat tgcaacaata caaattcaaa   1680

gcacgtgaac ttgatcccag aatacttgaa ggtgggccca tcttgcccaa gaaaccacct   1740

gtgaaaccac ccaccgagcc tattggcttt gatttggaaa ttgagaaaag aatccaggag   1800

cgagaatcaa agaagaaaac agaggatgaa cactttgaat ttcattccag accttgccct   1860
```

-continued

```
actaagattt tggaagatgt tgtgggtgtt cctgaaaaga aggtacttcc aatcaccgtc   1920
cccaagtcac cagcctttgc attgaagaac agaattcgaa tgcccaccaa agaagatgag   1980
gaagaggacg aaccggtagt gataaaagct caacctgtgc cacattatgg ggtgcctttt   2040
aagccccaaa tcccagaggc aagaactgtg gaaatatgcc ctttctcgtt tgattctcga   2100
gacaaagaac gtcagttaca gaaggagaag aaaataaaag aactgcagaa aggggaggtg   2160
cccaagttca aggcacttcc cttgcctcat tttgacacca ttaacctgcc agagaagaag   2220
gtaaagaatg tgacccagat tgaacctttc tgcttggaga ctgacagaag aggtgctctg   2280
aaggcacaga cttggaagca ccagctggaa gaagaactga gacagcagaa agaagcagct   2340
tgtttcaagg ctcgtccaaa caccgtcatc tctcaggagc cctttgttcc caagaaagag   2400
aagaaatcag ttgctgaggg cctttctggt tctctagttc aggaaccttt tcagctggct   2460
actgagaaga gagccaaaga gcggcaggag ctggagaaga gaatggctga ggtagaagcc   2520
cagaaagccc agcagttgga ggaggccaga ctacaggagg aagagcagaa aaaagaggag   2580
ctggccaggc tacggagaga actggtgcat aaggcaaatc caatacgcaa gtaccagggt   2640
ctggagataa agtcaagtga ccagcctctg actgtgcctg tatctcccaa attctccact   2700
cgattccact gctaaactca gctgtgagct gcggataccg cccggcaatg ggacctgctc   2760
ttaacctcaa acctaggacc gtcttgcttt gtcattgggc atggagagaa cccatttctc   2820
cagactttta cctacccgtg cctgagaaag catacttgac aactgtggac tccagttttg   2880
ttgagaattg ttttcttaca ttactaaggc taataatgag atgtaactca tgaatgtctc   2940
gattagactc catgtagtta cttcctttaa accatcagcc ggccttttat atgggtcttc   3000
actctgacta gaatttagtc tctgtgtcag cacagtgtaa tctctattgc tattgcccct   3060
tacgactctc accctctccc cacttttttt aaaaatttta accagaaaat aaagatagtt   3120
aaatcctaag atagagatta agtcatggtt taaatgagga acaatcagta aatcagattc   3180
tgtcctcttc tctgcatacc gtgaatttat agttaaggat ccctttgctg tgagggtaga   3240
aaacctcacc aactgcacca gtgaggaaga agactgcgtg gattcatggg gagcctcaca   3300
gcagccacgc agcaggctct gggtggggct gccgttaagg cacagttctt tccttactgg   3360
tgctgataac aacagggaac cgtgcagtgt gcattttaag acc                     3403
```

<210> SEQ ID NO 97
<211> LENGTH: 2688
<212> TYPE: DNA
<213> ORGANISM: Homo sapiens

<400> SEQUENCE: 97

```
cttcaacccg cgccggcggc gactgcagtt cctgcgagcg aggagcgcgg gacctgctga     60
cacgctgacg ccttcgagcg cggcccgggg cccggagcgg ccggagcagc ccgggtcctg    120
accccggccc ggctcccgct ccgggctctg ccggcgggcg ggcgagcgcg gcgcggtccg    180
ggccgggggg atgtctcggc ggacgcgctg cgaggatctg gatgagctgc actaccagga    240
cacagattca gatgtgccgg agcagaggga tagcaagtgc aaggtcaaat ggacccatga    300
ggaggacgag cagctgaggg ccctggtgag gcagtttgga cagcaggact ggaagttcct    360
ggccagccac ttccctaacc gcactgacca gcaatgccag tacaggtggc tgagagtttt    420
gaatccagac cttgtcaagg ggccatggac caaagaggaa gaccaaaaag tcatcgagct    480
ggttaagaag tatggcacaa agcagtggac actgattgcc aagcacctga agggccggct    540
ggggaagcag tgccgtgaac gctggcacaa ccacctcaac cctgaggtga agaagtcttg    600
```

-continued

```
ctggaccgag gaggaggacc gcatcatctg cgaggcccac aaggtgctgg gcaaccgctg    660
ggccgagatc gccaagatgt tgccagggag gacagacaat gctgtgaaga atcactggaa    720
ctctaccatc aaaaggaagg tggacacagg aggcttcttg agcgagtcca aagactgcaa    780
gcccccagtg tacttgctgc tggagctcga ggacaaggac ggcctccaga gtgcccagcc    840
cacggaaggc cagggaagtc ttctgaccaa ctggccctcc gtccctccta ccataaagga    900
ggaggaaaac agtgaggagg aacttgcagc agccaccaca tcgaaggaac aggagcccat    960
cggtacagat ctggacgcag tgcgaacacc agagcccttg gaggaattcc cgaagcgtga   1020
ggaccaggaa ggctccccac cagaaacgag cctgccttac aagtgggtgg tggaggcagc   1080
taacctcctc atccctgctg tgggttctag cctctctgaa gccctggact tgatcgagtc   1140
ggaccctgat gcttggtgtg acctgagtaa atttgacctc cctgaggaac catctgcaga   1200
ggacagtatc aacaacagcc tagtgcagct gcaagcgtca catcagcagc aagtcctgcc   1260
accccgccag ccttccgccc tggtgcccag tgtgaccgag taccgcctgg atggccacac   1320
catctcagac ctgagccgga gcagccgggg cgagctgatc cccatctccc ccagcactga   1380
agtcgggggc tctggcattg gcacaccgcc ctctgtgctc aagcggcaga ggaagaggcg   1440
tgtggctctg tcccctgtca ctgagaatag caccagtctg tccttcctgg attcctgtaa   1500
cagcctcacg cccaagagca cacctgttaa gaccctgccc ttctcgccct cccagtttct   1560
gaacttctgg aacaaacagg acacattgga gctggagagc cctcgctga catccacccc    1620
agtgtgcagc cagaaggtgg tggtcaccac accactgcac cgggacaaga caccccctgca   1680
ccagaaacat gctgcgtttg taaccccaga tcagaagtac tccatggaca acactcccca   1740
cacgccaacc ccgttcaaga acgccctgga gaagtacgga cccctgaagc ccctgccaca   1800
gaccccgcac ctggaggagg acttgaagga ggtgctgcgt tctgaggctg gcatcgaact   1860
catcatcgag gacgacatca ggcccgagaa gcagaagagg aagcctgggc tgcggcggag   1920
ccccatcaag aaagtccgga agtctctggc tcttgacatt gtggatgagg atgtgaagct   1980
gatgatgtcc acactgccca agtctctatc cttgccgaca actgcccctt caaactcttc   2040
cagcctcacc ctgtcaggta tcaaagaaga caacagcttg ctcaaccagg gcttcttgca   2100
ggccaagccc gagaaggcag cagtggccca gaagccccga agccacttca cgacacctgc   2160
ccctatgtcc agtgcctgga agacggtggc ctgcgggggg accagggacc agcttttcat   2220
gcaggagaaa gcccggcagc tcctgggccg cctgaagccc agccacacat ctcggaccct   2280
catcttgtcc tgaggtgttg agggtgtcac gagcccattc tcatgtttac aggggttgtg   2340
ggggcagagg gggtctgtga atctgagagt cattcaggtg acctcctgca gggagccttc   2400
tgccaccagc ccctccccag actctcaggt ggaggcaaca gggccatgtg ctgccctgtt   2460
gccgagccca gctgtgggcg gctcctggtg ctaacaacaa agttccactt ccaggtctgc   2520
ctggttccct ccccaaggcc acagggagct ccgtcagctt ctcccaagcc cacgtcaggc   2580
ctggcctcat ctcagaccct gcttaggatg gggatgtgg ccaggggtgc tcctgtgctc    2640
accctctctt ggtgcatttt tttggaagaa taaaattgcc tctctctt                2688
```

<210> SEQ ID NO 98
<211> LENGTH: 1883
<212> TYPE: DNA
<213> ORGANISM: Homo sapiens

<400> SEQUENCE: 98

-continued

```
atgaggttga cgctactttg ttgcacctgg agggaagaac gtatgggaga ggaaggaagc     60

gagttgcccg tgtgtgcaag ctgcggccag aggatctatg atggccagta cctccaggcc    120

ctgaacgcgg actggcacgc agactgcttc aggtgttgtg actgcagtgc ctccctgtcg    180

caccagtact atgagaagga tgggcagctc ttctgcaaga aggactactg ggcccgctat    240

ggcgagtcct gccatgggtg ctctgagcaa atcaccaagg gactggttat ggtggctggg    300

gagctgaagt accaccccga gtgtttcatc tgcctcacgt gtgggacctt tatcggtgac    360

ggggacacct acacgctggt ggagcactcc aagctgtact gcgggcactg ctactaccag    420

actgtggtga cccccgtcat cgagcagatc ctgcctgact cccctggctc ccacctgccc    480

cacaccgtca ccctggtgtc catcccagcc tcatctcatg gcaagcgtgg actttcagtc    540

tccattgacc ccccgcacgg cccaccgggc tgtggcaccg agcactcaca caccgtccgc    600

gtccagggag tggatccggg ctgcatgagc ccagatgtga agaattccat ccacgtcgga    660

gaccggatct tggaaatcaa tggcacgccc atccgaaatg tgcccctgga cgagattgac    720

ctgctgattc aggaaaccag ccgcctgctc cagctgaccc tcgagcatga ccctcacgat    780

acactgggcc acgggctggg gcctgagacc agccccctga gctctccggc ttatactccc    840

agcggggagg cgggcagctc tgcccggcag aaacctgtct tcgcaaggac ctgggtcgct    900

ctgagtccct ccgcgtagtc tgccggccac accgcatctt ccggccgtcg gacctcatcc    960

acggggaggt gctgggcaag ggctgcttcg gccaggctat caaggtgaca caccgtgaga   1020

caggtgaggt gatggtgatg aaggagctga tccggttcga cgaggagacc cagaggacgt   1080

tcctcaagga ggtgaaggtc atgcgatgcc tggaacaccc caacgtgctc aagttcatcg   1140

gggtgctcta caaggacaag aggctcaact tcatcactga gtacatcaag ggcggcacgc   1200

tccggggcat catcaagagc atggacagcc agtacccatg gagccagaga gtgagctttg   1260

ccaaggacat cgcatcaggg atggcctacc tccactccat gaacatcatc caccgagacc   1320

tcaactccca caactgcctg gtccgcgaga acaagaatgt ggtggtggct gacttcgggc   1380

tggcgcgtct catggtggac gagaagactc agcctgaggg cctgcggagc ctcaagaagc   1440

cagaccgcaa gaagcgctac accgtggtgg gcaaccccta ctggatggca cctgagatga   1500

tcaacggccg cagctatgat gagaaggtgg atgtgttctc ctttgggatc gtcctgtgcg   1560

agatcatcgg gcgggtgaac gcagaccctg actacctgcc ccgcaccatg gactttggcc   1620

tcaacgtgcg aggattcctg gaccgctact gccccccaaa ctgcccccccg agcttcttcc   1680

ccatcaccgt gcgctgttgc gatctggacc ccgagaagag gccatccttt gtgaagctgg   1740

aacactggct ggagaccctc cgcatgcacc tggccggcca cctgccactg ggcccacagc   1800

tggagcagct ggacagaggt ttctgggaga cctaccggcg cggcgagagc ggactgcctg   1860

cccaccctga ggtccccgac tga                                           1883
```

<210> SEQ ID NO 99
<211> LENGTH: 597
<212> TYPE: DNA
<213> ORGANISM: Homo sapiens

<400> SEQUENCE: 99

```
atgcctggct tcgactacaa gttcctggag aagcccaagc gacggctgct gtgcccactg     60

tgcgggaagc ccatgcgcga gcctgtgcag gtttccacct gcggccaccg tttctgcgat    120

acctgcctgc aggagttcct cagtgaagga gtcttcaagt gccctgagga ccagcttcct    180

ctggactatg ccaagatcta cccagacccg gagctggaag tacaagtatt gggcctgcct    240
```

-continued atccgctgca tccacagtga ggagggctgc cgctggagtg ggccactacg tcatctacag 300
ggccacctga atacctgcag cttcaatgtc attccctgcc ctaatcgctg ccccatgaag 360
ctgagccgcc gtgatctacc tgcacacttg cagcatgact gccccaagcg gcgcctcaag 420
tgcgagtttt gtggctgtga cttcagtggg gaggcctatg aggtggatga gagttctctg 480
ggctttggtt atcccaagtt catctcccac caggacattc gaaagcgaaa ctatgtgcgg 540
gatgatgcag tcttcatccg tgctgctgtt gaactgcccc ggaagatcct cagctga 597

<210> SEQ ID NO 100
<211> LENGTH: 23
<212> TYPE: DNA
<213> ORGANISM: Artificial
<220> FEATURE:
<223> OTHER INFORMATION: Synthetic

<400> SEQUENCE: 100
cgtatgcccc gctgaatctc gtg 23

<210> SEQ ID NO 101
<211> LENGTH: 24
<212> TYPE: DNA
<213> ORGANISM: Artificial
<220> FEATURE:
<223> OTHER INFORMATION: Synthetic

<400> SEQUENCE: 101
tggccaatca tccgtgctca tctg 24

<210> SEQ ID NO 102
<211> LENGTH: 24
<212> TYPE: DNA
<213> ORGANISM: Artificial
<220> FEATURE:
<223> OTHER INFORMATION: Synthetic

<400> SEQUENCE: 102
cggagtcaac ggatttggtc gtat 24

<210> SEQ ID NO 103
<211> LENGTH: 24
<212> TYPE: DNA
<213> ORGANISM: Artificial
<220> FEATURE:
<223> OTHER INFORMATION: Synthetic

<400> SEQUENCE: 103
agccttctcc atggtggtga agac 24

<210> SEQ ID NO 104
<211> LENGTH: 2005
<212> TYPE: DNA
<213> ORGANISM: Homo sapiens

<400> SEQUENCE: 104
ttgcaggctg ctgggctggg gctaagggct gctcagtttc cttcagcggg gcactgggaa 60
gcgccatggc actgcagggc atctcggtcg tggagctgtc cggcctggcc ccgggcccgt 120
tctgtgctat ggtcctggct gacttcgggg cgcgtgtggt acgcgtggac cggcccggct 180
cccgctacga cgtgagccgc ttgggccggg gcaagcgctc gctagtgctg gacctgaagc 240
agccgcgggg agccgccgtg ctgcggcgtc tgtgcaagcg gtcggatgtg ctgctggagc 300

-continued

```
ccttccgccg cggtgtcatg gagaaactcc agctgggccc agagattctg cagcgggaaa    360

atccaaggct tatttatgcc aggctgagtg gatttggcca gtcaggaagc ttctgccggt    420

tagctggcca cgatatcaac tatttggctt tgtcaggtgt tctctcaaaa attggcagaa    480

gtggtgagaa tccgtatgcc ccgctgaatc tcctggctga ctttgctggt ggtggcctta    540

tgtgtgcact gggcattata atggctcttt ttgaccgcac acgcactggc aagggtcagg    600

tcattgatgc aaatatggtg gaaggaacag catatttaag ttcttttctg tggaaaactc    660

agaaatcgag tctgtgggaa gcacctcgag gacagaacat gttggatggt ggagcacctt    720

tctatacgac ttacaggaca gcagatgggg aattcatggc tgttggagca atagaacccc    780

agttctacga gctgctgatc aaaggacttg gactaaagtc tgatgaactt cccaatcaga    840

tgagcatgga tgattggcca gaaatgaaga agaagtttgc agatgtattt gcaaagaaga    900

cgaaggcaga gtggtgtcaa atctttgacg gcacagatgc ctgtgtgact ccggttctga    960

cttttgagga ggttgttcat catgatcaca acaaggaacg gggctcgttt atcaccagtg   1020

aggagcagga cgtgagcccc cgccctgcac ctctgctgtt aaacacccca gccatccctt   1080

ctttcaaaag ggatcctttc ataggagaac acactgagga gatacttgaa gaatttggat   1140

tcagccgcga agagatttat cagcttaact cagataaaat cattgaaagt aataaggtaa   1200

aagctagtct ctaacttcca ggcccacggc tcaagtgaat ttgaatactg catttacagt   1260

gtagagtaac acataacatt gtatgcatgg aaacatggag gaacagtatt acagtgtcct   1320

accactctaa tcaagaaaag aattacagac tctgattcta cagtgatgat tgaattctaa   1380

aaatggttat cattagggct tttgatttat aaaactttgg gtacttatac taaattatgg   1440

tagttattct gccttccagt ttgcttgata tatttgttga tattaagatt cttgacttat   1500

attttgaatg ggttctagtg aaaaaggaat gatatattct tgaagacatc gatatacatt   1560

tatttacact cttgattcta caatgtagaa aatgaggaaa tgccacaaat tgtatggtga   1620

taaaagtcac gtgaaacaga gtgattggtt gcatccaggc cttttgtctt ggtgttcatg   1680

atctccctct aagcacattc caaactttag caacagttat cacactttgt aatttgcaaa   1740

gaaaagtttc acctgtattg aatcagaatg ccttcaactg aaaaaaacat atccaaaata   1800

atgaggaaat gtgttggctc actacgtaga gtccagaggg acagtcagtt ttagggttgc   1860

ctgtatccag taactcgggg cctgtttccc cgtgggtctc tgggctgtca gctttccttt   1920

ctccatgtgt ttgatttctc ctcaggctgg tagcaagttc tggatcttat acccaacaca   1980

cagcaacatc cagaaataaa gatct                                          2005
```

<210> SEQ ID NO 105
<211> LENGTH: 24
<212> TYPE: DNA
<213> ORGANISM: Artificial
<220> FEATURE:
<223> OTHER INFORMATION: Synthetic

<400> SEQUENCE: 105

```
tggccaatca tccgtgctca tctg                                             24
```

<210> SEQ ID NO 106
<211> LENGTH: 24
<212> TYPE: DNA
<213> ORGANISM: Artificial
<220> FEATURE:
<223> OTHER INFORMATION: Synthetic

<400> SEQUENCE: 106

-continued agccttctcc atggtggtga agac 24

<210> SEQ ID NO 107
<211> LENGTH: 24
<212> TYPE: DNA
<213> ORGANISM: Artificial
<220> FEATURE:
<223> OTHER INFORMATION: Synthetic

<400> SEQUENCE: 107
agccttctcc atggtggtga agac 24

<210> SEQ ID NO 108
<211> LENGTH: 21
<212> TYPE: DNA
<213> ORGANISM: Artificial
<220> FEATURE:
<223> OTHER INFORMATION: Synthetic

<400> SEQUENCE: 108
gccagactgg gaagaaatct g 21

<210> SEQ ID NO 109
<211> LENGTH: 21
<212> TYPE: DNA
<213> ORGANISM: Artificial
<220> FEATURE:
<223> OTHER INFORMATION: Synthetic

<400> SEQUENCE: 109
tgtgctggaa aatccaagtc a 21

<210> SEQ ID NO 110
<211> LENGTH: 24
<212> TYPE: DNA
<213> ORGANISM: Artificial
<220> FEATURE:
<223> OTHER INFORMATION: Synthetic

<400> SEQUENCE: 110
cggagtcaac ggatttggtc gtat 24

<210> SEQ ID NO 111
<211> LENGTH: 24
<212> TYPE: DNA
<213> ORGANISM: Artificial
<220> FEATURE:
<223> OTHER INFORMATION: Synthetic

<400> SEQUENCE: 111
agccttctcc atggtggtga agac 24

<210> SEQ ID NO 112
<211> LENGTH: 35
<212> TYPE: DNA
<213> ORGANISM: Artificial
<220> FEATURE:
<223> OTHER INFORMATION: Synthetic

<400> SEQUENCE: 112
ggggtaccat gggcggccgc gaacaaaagt tgatt 35

<210> SEQ ID NO 113
<211> LENGTH: 33
<212> TYPE: DNA

-continued

<213> ORGANISM: Artificial
<220> FEATURE:
<223> OTHER INFORMATION: Synthetic

<400> SEQUENCE: 113
ggggaattct catgccagca atagatgctt ttt 33

<210> SEQ ID NO 114
<211> LENGTH: 3042
<212> TYPE: DNA
<213> ORGANISM: Homo sapiens

<400> SEQUENCE: 114
cggaggcgct gggcgcacgg cgcggagccg gccggagctc gaggccggcg gcggcgggag 60
agcgacccgg gcggcctcgt agcggggccc cggatccccg agtggcggcc ggagcctcga 120
aaagagattc tcagcgctga ttttgagatg atgggcttgg gaaacgggcg tcgcagcatg 180
aagtcgccgc ccctcgtgct ggccgccctg gtggcctgca tcatcgtctt gggcttcaac 240
tactggattg cgagctcccg gagcgtggac ctccagacac ggatcatgga gctggaaggc 300
agggtccgca gggcggctgc agagagaggc gccgtggagc tgaagaagaa cgagttccag 360
ggagagctgg agaagcagcg ggagcagctt gacaaaatcc agtccagcca caacttccag 420
ctggagagcg tcaacaagct gtaccaggac gaaaaggcgg ttttggtgaa taacatcacc 480
acaggtgaga ggctcatccg agtgctgcaa gaccagttaa agaccctgca gaggaattac 540
ggcaggctgc agcaggatgt cctccagttt cagaagaacc agaccaacct ggagaggaag 600
ttctcctacg acctgagcca gtgcatcaat cagatgaagg aggtgaagga acagtgtgag 660
gagcgaatag aagaggtcac caaaaagggg aatgaagctg tagcttccag agacctgagt 720
gaaaacaacg accagagaca gcagctccaa gccctcagtg agcctcagcc caggctgcag 780
gcagcaggcc tgccacacac agaggtgcca caagggaagg gaaacgtgct tggtaacagc 840
aagtcccaga caccagcccc cagttccgaa gtggttttgg attcaaagag acaagttgag 900
aaagaggaaa ccaatgagat ccaggtggtg aatgaggagc ctcagaggga caggctgccg 960
caggagccag gccgggagca ggtggtggaa gacagacctg taggtggaag aggcttcggg 1020
ggagccggag aactgggcca gaccccacag gtgcaggctg ccctgtcagt gagccaggaa 1080
aatccagaga tggagggccc tgagcgagac cagcttgtca tccccgacgg acaggaggag 1140
gagcaggaag ctgccgggga agggagaaac cagcagaaac tgagaggaga agatgactac 1200
aacatggatg aaaatgaagc agaatctgag acagacaagc aagcagccct ggcagggaat 1260
gacagaaaca tagatgtttt taatgttgaa gatcagaaaa gagacaccat aaatttactt 1320
gatcagcgtg aaaagcggaa tcatacactc tgaattgaac tggaatcaca tatttcacaa 1380
cagggccgaa gagatgacta taaaatgttc atgagggact gaatactgaa aactgtgaaa 1440
tgtactaaat aaaatgtaca tctgaagatg attattgtga aattttagta tgcactttgt 1500
gtaggaaaaa atggaatggt cttttaaaca gcttttgggg gggtactttg gaagtgtcta 1560
ataaggtgtc acaatttttg gtagtaggta tttcgtgaga agttcaacac caaaactgga 1620
acatagttct ccttcaagtg ttggcgacag cggggcttcc tgattctgga atataacttt 1680
gtgtaaatta acagccacct atagaagagt ccatctgctg tgaaggagag acagagaact 1740
ctgggttccg tcgtcctgtc cacgtgctgt accaagtgct ggtgccagcc tgttacctgt 1800
tctcactgaa aagtctggct aatgctcttg tgtagtcact tctgattctg acaatcaatc 1860
aatcaatggc ctagagcact gactgttaac acaaacgtca ctagcaaagt agcaacagct 1920

-continued

```
ttaagtctaa atacaaagct gttctgtgtg agaatttttt aaaaggctac ttgtataata   1980
acccttgtca tttttaatgt acaaaacgct attaagtggc ttagaatttg aacatttgtg   2040
gtctttattt actttgcttc gtgtgtgggc aaagcaacat cttccctaaa tatatattac   2100
caagaaaagc aagaagcaga ttaggttttt gacaaaacaa acaggccaaa agggggctga   2160
cctggagcag agcatggtga gaggcaaggc atgagagggc aagtttgttg tggacagatc   2220
tgtgcctact ttattactgg agtaaaagaa aacaaagttc attgatgtcg aaggatatat   2280
acagtgttag aaattaggac tgtttagaaa aacaggaata caatggttgt ttttatcata   2340
gtgtacacat ttagcttgtg gtaaatgact cacaaaactg attttaaaat caagttaatg   2400
tgaattttga aaattactac ttaatcctaa ttcacaataa caatggcatt aaggtttgac   2460
ttgagttggt tcttagtatt atttatggta aataggctct taccacttgc aaataactgg   2520
ccacatcatt aatgactgac ttcccagtaa ggctctctaa ggggtaagta ggaggatcca   2580
caggatttga gatgctaagg ccccagagat cgtttgatcc aaccctctta ttttcagagg   2640
ggaaaatggg gcctagaagt tacagagcat ctagctggtg cgctggcacc cctggcctca   2700
cacagactcc cgagtagctg ggactacagg cacacagtca ctgaagcagg ccctgtttgc   2760
aattcacgtt gccacctcca acttaaacat tcttcatatg tgatgtcctt agtcactaag   2820
gttaaacttt cccacccaga aaaggcaact tagataaaat cttagagtac tttcatactc   2880
ttctaagtcc tcttccagcc tcactttgag tcctccttgg ggttgatagg aattttctct   2940
tgctttctca ataaagtctc tattcatctc atgtttaatt tgtacgcata gaattgctga   3000
gaaataaaat gttctgttca acttaaaaaa aaaaaaaaaa aa                      3042
```

<210> SEQ ID NO 115
<211> LENGTH: 2368
<212> TYPE: DNA
<213> ORGANISM: Homo sapiens

<400> SEQUENCE: 115

```
cgggcgatgc cgcgctgcgg gggggccgca cagccgccgc caccgccacc gccgccgggt     60
ggggtgggag gggcgggaac gcgcgccgcc gcctccaggg tgggcgcctt tcgccgtgga    120
cgccgaccgt ccgggacgag ggtttcatca ccttaaatgg ttttgaacca atgaaggtgt    180
attcccttaa aaagacggac agcccatcgt gtgaactata gagtttgtgg acagatttat    240
attgggttca tagtggcgtc atgcacgcag actcctgcaa gttcccctaa gttcttagag    300
gactgctttg ccttttgatc tgagagttgc aaagttccat aaagaatggc ccttgtggat    360
aagcacaaag tcaagagaca gcgattggac agaatttgtg aaggtatccg cccccagatc    420
atgaacggcc ccctgcaccc ccgcccccctg gtggcgctgc tggacggccg cgactgcact    480
gtggagatgc ccatcctgaa ggacctggcc actgtggcct tctgtgacgc gcagtcgacg    540
caggaaatcc acgagaaggt tctaaacgaa gccgtgggcg ccatgatgta ccacaccatc    600
accctcacca gggaggacct ggagaagttc aaggccctga gagtgatcgt gcggataggc    660
agtggctatg acaacgtgga catcaaggct gccggcgagc tcggaattgc cgtgtgcaac    720
atcccgtctg cagccgtgga agagacagcg gactctacca tctgccacat cctcaacctg    780
taccggagga acacgtggct gtaccaggca ctgcgggaag gcacgcgggt tcagagcgtg    840
gagcagatcc gcgaggtggc ctcgggagcg gcccgcatcc gtggggagac gctgggcctc    900
attggctttg gtcgcacggg gcaggcggtt gcagttcgag ccaaggcctt tggattcagc    960
```

-continued

```
gtcatatttt atgaccccta cttgcaggat gggatcgagc ggtccctggg cgtgcagagg   1020

gtctacaccc tgcaggattt gctgtatcag agcgactgcg tctccttgca ctgcaatctc   1080

aacgaacata accaccacct catcaatgac tttaccataa agcagatgag gcagggagca   1140

ttccttgtga acgcagcccg tggcggcctg gtggacgaga aagccttagc acaagccctc   1200

aaggagggca ggatacgagg ggcagccctc gacgtgcatg agtcagagcc cttcagcttt   1260

gctcagggtc cgttgaaaga tgccccgaat ctcatctgca ctcctcacac tgcctggtac   1320

agtgagcagg cgtcactgga gatgagggag gcagctgcca ccgagatccg ccgagccatc   1380

acaggtcgca tcccagaaag cttaagaaat tgtgtgaaca aggaattctt tgtcacatca   1440

gcgccttggt cagtaataga ccagcaagca attcatcctg agctcaatgg tgccacatac   1500

agatatccgc caggcatcgt gggtgtggct ccaggaggac ttcctgcagc catggaaggg   1560

atcatccctg gaggcatccc agtgactcac aacctcccga cagtggcaca tccttcccaa   1620

gcgccctctc ccaaccagcc cacaaaacac ggggacaatc gagagcaccc caacgagcaa   1680

tagcagagaa tgccagaagg taatcactca gatacacttg ggaccaagag acagtgaaaa   1740

atagatgaac taagagaaaa agaatcggat ggtctttgta actgattctg gacatatgca   1800

tcattgatgt tgcagtgttg aaactacaag agctagaaaa ctgaagatgt cgtctgctta   1860

cggaagcgct gaaagactag gatgtgattt attaacgacc aacttctgtt attgtgtgtt   1920

aagtttttca tctgtgcatc aaatcacaaa aagaataaat agagcttttt cctttatcag   1980

tcccttgggc acagcaggtc ctgaacaccc tgctctacaa tgttgcatca agagttcaaa   2040

caacaaaata aaaaatatta agaggaaatc cccatcctgt gacttgagtc ccttaagtct   2100

acaggggctg gtgacctctt tttgctaata ggaaaatcac attactacaa aatggggaga   2160

aaactgtttg cctgtggtag acacctgcac gcataggatt gaagacagta caggctgctg   2220

tacagagaag cgcctctcac atctgaactg catactgagc gggcaagtcg gttgtaagtt   2280

cagtaaaacc ctctgatgat gcaaaaaaaa aaaaaaagta ttaagtttca caagctgttt   2340

gtactcaaat atattttctc agtttcag                                      2368
```

<210> SEQ ID NO 116
<211> LENGTH: 1362
<212> TYPE: DNA
<213> ORGANISM: Homo sapiens

<400> SEQUENCE: 116

```
catttgggga cgctctcagc tctcggcgca cggcccagct tccttcaaaa tgtctactgt     60

tcacgaaatc ctgtgcaagc tcagcttgga gggtgatcac tctacacccc caagtgcata    120

tgggtctgtc aaagcctata ctaactttga tgctgagcgg gatgctttga acattgaaac    180

agccatcaag accaaaggtg tggatgaggt caccattgtc aacattttga ccaaccgcag    240

caatgcacag agacaggata ttgccttcgc ctaccagaga aggaccaaaa aggaacttgc    300

atcagcactg aagtcagcct tatctggcca cctggagacg gtgattttgg gcctattgaa    360

gacacctgct cagtatgacg cttctgagct aaaagcttcc atgaaggggc tgggaaccga    420

cgaggactct ctcattgaga tcatctgctc cagaaccaac caggagctgc aggaaattaa    480

cagagtctac aaggaaatgt acaagactga tctggagaag gacattattt cggacacatc    540

tggtgacttc cgcaagctga tggttgccct ggcaaagggt agaagagcag aggatggctc    600

tgtcattgat tatgaactga ttgaccaaga tgctcgggat ctctatgacg ctggagtgaa    660

gaggaaagga actgatgttc ccaagtggat cagcatcatg accgagcgga gcgtgcccca    720
```

-continued

```
cctccagaaa gtatttgata ggtacaagag ttacagccct tatgacatgt tggaaagcat    780

caggaaagag gttaaaggag acctggaaaa tgctttcctg aacctggttc agtgcattca    840

gaacaagccc ctgtattttg ctgatcggct gtatgactcc atgaagggca aggggacgcg    900

agataaggtc ctgatcagaa tcatggtctc ccgcagtgaa gtggacatgt tgaaaattag    960

gtctgaattc aagagaaagt acggcaagtc cctgtactat tatatccagc aagacactaa   1020

gggcgactac cagaaagcgc tgctgtacct gtgtggtgga gatgactgaa gcccgacacg   1080

gcctgagcgt ccagaaatgg tgctcaccat gcttccagct aacaggtcta gaaaaccagc   1140

ttgcgaataa cagtccccgt ggccatccct gtgagggtga cgttagcatt acccccaacc   1200

tcattttagt tgcctaagca ttgcctggcc ttcctgtcta gtctctcctg taagccaaag   1260

aaatgaacat tccaaggagt tggaagtgaa gtctatgatg tgaaacactt tgcctcctgt   1320

gtactgtgtc ataaacagat gaataaactg aatttgtact tt                      1362
```

<210> SEQ ID NO 117
<211> LENGTH: 2137
<212> TYPE: DNA
<213> ORGANISM: Homo sapiens

<400> SEQUENCE: 117

```
gccccaggtg cgcttcccct agagagggat tttccggtct cgtgggcaga ggaacaacca     60

ggaacttggg ctcagtctcc accccacagt ggggcggatc cgtcccggat aagacccgct    120

gtctggccct gagtagggtg tgacctccgc agccgcagag gaggagcgca gcccggcctc    180

gaagaacttc tgcttgggtg gctgaactct gatcttgacc tagagtcatg gccatggcaa    240

ccaaaggagg tactgtcaaa gctgcttcag gattcaatgc catggaagat gcccagaccc    300

tgaggaaggc catgaaaggg ctcggcaccg atgaagacgc cattattagc gtccttgcct    360

accgcaacac cgcccagcgc caggagatca ggacagccta caagagcacc atcggcaggg    420

acttgataga cgacctgaag tcagaactga gtggcaactt cgagcaggtg attgtgggga    480

tgatgacgcc cacggtgctg tatgacgtgc aagagctgcg aagggccatg aagggagccg    540

gcactgatga gggctgccta attgagatcc tggcctcccg gacccctgag gagatccggc    600

gcataagcca aacctaccag cagcaatatg gacggagcct tgaagatgac attcgctctg    660

acacatcgtt catgttccag cgagtgctgg tgtctctgtc agctggtggg agggatgaag    720

gaaattatct ggacgatgct ctcgtgagac aggatgccca ggacctgtat gaggctggag    780

agaagaaatg gggggacagat gaggtgaaat ttctaactgt tctctgttcc cggaaccgaa    840

atcacctgtt gcatgtgttt gatgaataca aaaggatatc acagaaggat attgaacaga    900

gtattaaatc tgaaacatct ggtagctttg aagatgctct gctggctata gtaaagtgca    960

tgaggaacaa atctgcatat tttgctgaaa agctctataa atcgatgaag ggcttgggca   1020

ccgatgataa caccctcatc agagtgatgg tttctcgagc agaaattgac atgttggata   1080

tccgggcaca cttcaagaga ctctatggaa agtctctgta ctcgttcatc aagggtgaca   1140

catctggaga ctacaggaaa gtactgcttg ttctctgtgg aggagatgat taaaataaaa   1200

atcccagaag gacaggagga ttctcaacac tttgaatttt tttaacttca tttttctaca   1260

ctgctattat cattatctca gaatgcttat ttccaattaa aacgcctaca gctgcctcct   1320

agaatataga ctgtctgtat tattattcac ctataattag tcattatgat gctttaaagc   1380

tgtacttgca tttcaaagct tataagatat aaatggagat tttaaagtag aaataaatat   1440
```

-continued

```
gtattccatg tttttaaaag attactttct actttgtgtt tcacagacat tgaatatatt   1500

aaattattcc atattttctt ttcagtgaaa aattttttaa atggaagact gttctaaaat   1560

cactttttc cctaatccaa tttttagagt ggctagtagt ttcttcattt gaaattgtaa    1620

gcatccggtc agtaagaatg cccatccagt tttctatatt tcatagtcaa agccttgaaa   1680

gcatctacaa atctcttttt ttaggttttg tccatagcat cagttgatcc ttactaagtt   1740

tttcatggga gacttccttc atcacatctt atgttgaaat cactttctgt agtcaaagta   1800

taccaaaacc aatttatctg aactaaattc taaagtatgg ttatacaaac catatacatc   1860

tggttaccaa acataaatgc tgaacattcc atattattat agttaatgtc ttaatccagc   1920

ttgcaagtga atggaaaaaa aaataagctt caaactaggt attctgggaa tgatgtaatg   1980

ctctgaattt agtatgatat aaagaaaact tttttgtgct aaaaatactt tttaaaatca   2040

attttgttga ttgtagtaat ttctatttgc actgtgcctt tcaactccag aaacattctg   2100

aagatgtact tggatttaat taaaaagttc actttgt                            2137
```

<210> SEQ ID NO 118
<211> LENGTH: 1958
<212> TYPE: DNA
<213> ORGANISM: Homo sapiens

<400> SEQUENCE: 118

```
gctgctgcgc ccgcggctcc ccagtgcccc gagtgccccg cgggccccgc gagcgggagt     60

gggacccagc cctaggcaga acccaggcgc cgcgcccggg acgcccgcgg agagagccac    120

tcccgcccac gtcccatttc gcccctcgcg tccggagtcc ccgtggccag atctaaccat    180

gagctaccct ggctatcccc cgcccccagg tggctaccca ccagctgcac caggtggtgg    240

tccctgggga ggtgctgcct accctcctcc gcccagcatg ccccccatcg ggctggataa    300

cgtggccacc tatgcggggc agttcaacca ggactatctc tcgggaatgg cggccaacat    360

gtctgggaca tttggaggag ccaacatgcc caacctgtac cctggggccc ctggggctgg    420

ctacccacca gtgccccctg gcggctttgg gcagcccccc tctgcccagc agcctgttcc    480

tccctatggg atgtatccac ccccaggagg aaacccaccc tccaggatgc cctcatatcc    540

gccataccca ggggcccctg tgccgggcca gcccatgcca ccccccggac agcagccccc    600

aggggcctac cctgggcagc caccagtgac ctaccctggt cagcctccag tgccactccc    660

tgggcagcag cagccagtgc cgagctaccc aggataccgg gggtctggga ctgtcacccc    720

cgctgtgccc ccaacccagt ttggaagccg aggcaccatc actgatgctc ccggctttga    780

ccccctgcga gatgccgagg tcctgcggaa ggccatgaaa ggcttcggga cggatgagca    840

ggccatcatt gactgcctgg ggagtcgctc caacaagcag cggcagcaga tcctactttc    900

cttcaagacg gcttacggca aggatttgat caaagatctg aaatctgaac tgtcaggaaa    960

ctttgagaag acaatcttgg ctctgatgaa gaccccagtc ctctttgaca tttatgagat   1020

aaaggaagcc atcaaggggg ttggcactga tgaagcctgc ctgattgaga tcctcgcttc   1080

ccgcagcaat gagcacatcc gagaattaaa cagagcctac aaagcagaat tcaaaaagac   1140

cctggaagag gccattcgaa gcgacacatc agggcacttc cagcggctcc tcatctctct   1200

ctctcaggga aaccgtgatg aaagcacaaa cgtggacatg tcactcgccc agagagatgc   1260

ccaggagctg tatgcggccg gggagaaccg cctgggaaca gacgagtcca agttcaatgc   1320

ggttctgtgc tcccggagcc gggcccacct ggtagcagtt ttcaatgagt accagagaat   1380

gacaggccgg gacattgaga agagcatctg ccgggagatg tccggggacc tggaggaggg   1440
```

-continued catgctggcc gtggtgaaat gtctcaagaa taccccagcc ttctttgcgg agaggctcaa 1500
caaggccatg aggggggcag gaacaaagga ccggaccctg attcgcatca tggtgtctcg 1560
cagcgagacc gacctcctgg acatcagatc agagtataag cggatgtacg gcaagtcgct 1620
gtaccacgac atctcgggag atacttcagg ggattaccgg aagattctgc tgaagatctg 1680
tggtggcaat gactgaacag tgactggtgg ctcacttctg cccacctgcc ggcaacacca 1740
gtgccaggaa aaggccaaaa gaatgtctgt ttctaacaaa tccacaaata gccccgagat 1800
tcaccgtcct agagcttagg cctgtcttcc acccctcctg acccgtatag tgtgccacag 1860
gacctgggtc ggtctagaac tctctcagga tgccttttct accccatccc tcacagcctc 1920
ttgctgctaa aatagatgtt tcatttttct gaaaaaaa 1958

<210> SEQ ID NO 119
<211> LENGTH: 5791
<212> TYPE: DNA
<213> ORGANISM: Homo sapiens

<400> SEQUENCE: 119
ggctcatgct cgggagcgtg gttgagcggc tggcgcggtt gtcctggagc aggggcgcag 60
gaattctgat gtgaaactaa cagtctgtga gccctggaac ctccactcag agaagatgaa 120
ggatatcgac ataggaaaag agtatatcat ccccagtcct gggtatagaa gtgtgaggga 180
gagaaccagc acttctggga cgcacagaga ccgtgaagat tccaagttca ggagaactcg 240
accgttggaa tgccaagatg ccttggaaac agcagcccga gccgagggcc tctctcttga 300
tgcctccatg cattctcagc tcagaatcct ggatgaggag catcccaagg gaaagtacca 360
tcatggcttg agtgctctga agcccatccg gactacttcc aaacaccagc acccagtgga 420
caatgctggg ctttttttcct gtatgacttt ttcgtggctt tcttctctgg cccgtgtggc 480
ccacaagaag ggggagctct caatggaaga cgtgtggtct ctgtccaagc acgagtcttc 540
tgacgtgaac tgcagaagac tagagagact gtggcaagaa gagctgaatg aagttgggcc 600
agacgctgct tccctgcgaa gggttgtgtg gatcttctgc cgcaccaggc tcatcctgtc 660
catcgtgtgc ctgatgatca cgcagctggc tggcttcagt ggaccagcct tcatggtgaa 720
acacctcttg gagtataccc aggcaacaga gtctaacctg cagtacagct tgttgttagt 780
gctgggcctc ctcctgacgg aaatcgtgcg gtcttggtcg cttgcactga cttgggcatt 840
gaattaccga accggtgtcc gcttgcgggg ggccatccta accatggcat ttaagaagat 900
ccttaagtta aagaacatta aagagaaatc cctgggtgag ctcatcaaca tttgctccaa 960
cgatgggcag agaatgtttg aggcagcagc cgttggcagc ctgctggctg gaggacccgt 1020
tgttgccatc ttaggcatga tttataatgt aattattctg ggaccaacag gcttcctggg 1080
atcagctgtt tttatcctct tttacccagc aatgatgttt gcatcacggc tcacagcata 1140
tttcaggaga aaatgcgtgg ccgccacgga tgaacgtgtc cagaagatga atgaagttct 1200
tacttacatt aaatttatca aaatgtatgc ctgggtcaaa gcattttctc agagtgttca 1260
aaaaatccgc gaggaggagc gtcggatatt ggaaaaagct gggtacttcc agagcatcac 1320
tgtgggtgtg gctcccattg tggtggtgat tgccagcgtg gtgaccttct ctgttcatat 1380
gaccctgggc ttcgatctga cagcagcaca ggctttcaca gtggtgacag tcttcaattc 1440
catgactttt gctttgaaag taacaccgtt ttcagtaaag tccctctcag aagcctcagt 1500
ggctgttgac agatttaaga gtttgtttct aatggaagag gttcacatga taaagaacaa 1560

-continued

```
accagccagt cctcacatca agatagagat gaaaaatgcc accttggcat gggactcctc   1620
ccactccagt atccagaact cgcccaagct gacccccaaa atgaaaaaag acaagagggc   1680
ttccaggggc aagaaagaga aggtgaggca gctgcagcgc actgagcatc aggcggtgct   1740
ggcagagcag aaaggccacc tcctcctgga cagtgacgag cggcccagtc ccgaagagga   1800
agaaggcaag cacatccacc tgggccacct gcgcttacag aggacactgc acagcatcga   1860
tctggagatc caagagggta aactggttgg aatctgtggc agtgtgggaa gtggaaaaac   1920
ctctctcatt tcagccattt taggccagat gacgcttcta gagggcagca ttgcaatcag   1980
tggaaccttc gcttatgtgg cccagcaggc ctggatcctc aatgctactc tgagagacaa   2040
catcctgttt gggaaggaat atgatgaaga aagatacaac tctgtgctga acagctgctg   2100
cctgaggcct gacctggcca ttcttcccag cagcgacctg acggagattg gagagcgagg   2160
agccaacctg agcggtgggc agcgccagag gatcagcctt gcccgggcct tgtatagtga   2220
caggagcatc tacatcctgg acgacccct cagtgcctta gatgcccatg tgggcaacca   2280
catcttcaat agtgctatcc ggaaacatct caagtccaag acagttctgt ttgttaccca   2340
ccagttacag tacctggttg actgtgatga agtgatcttc atgaaagagg gctgtattac   2400
ggaaagaggc acccatgagg aactgatgaa tttaaatggt gactatgcta ccatttttaa   2460
taacctgttg ctgggagaga caccgccagt tgagatcaat tcaaaaaagg aaaccagtgg   2520
ttcacagaag aagtcacaag acaagggtcc taaaacagga tcagtaaaga aggaaaaagc   2580
agtaaagcca gaggaagggc agcttgtgca gctggaagag aaagggcagg gttcagtgcc   2640
ctggtcagta tatggtgtct acatccaggc tgctgggggc cccttggcat tcctggttat   2700
tatggccctt ttcatgctga atgtaggcag caccgccttc agcacctggt ggttgagtta   2760
ctggatcaag caaggaagcg ggaacaccac tgtgactcga gggaacgaga cctcggtgag   2820
tgacagcatg aaggacaatc ctcatatgca gtactatgcc agcatctacg ccctctccat   2880
ggcagtcatg ctgatcctga aagccattcg aggagttgtc tttgtcaagg gcacgctgcg   2940
agcttcctcc cggctgcatg acgagctttt ccgaaggatc cttcgaagcc ctatgaagtt   3000
ttttgacacg acccccacag ggaggattct caacaggttt tccaaagaca tggatgaagt   3060
tgacgtgcgg ctgccgttcc aggccgagat gttcatccag aacgttatcc tggtgttctt   3120
ctgtgtggga atgatcgcag gagtcttccc gtggttcctt gtggcagtgg ggcccttgt   3180
catcctcttt tcagtcctgc acattgtctc cagggtcctg attcgggagc tgaagcgtct   3240
ggacaatatc acgcagtcac ctttcctctc ccacatcacg tccagcatac agggccttgc   3300
caccatccac gcctacaata aagggcagga gtttctgcac agataccagg agctgctgga   3360
tgacaaccaa gctccttttt ttttgtttac gtgtgcgatg cggtggctgg ctgtgcggct   3420
ggacctcatc agcatcgccc tcatcaccac cacggggctg atgatcgttc ttatgcacgg   3480
gcagattccc ccagcctatg cgggtctcgc catctcttat gctgtccagt taacggggct   3540
gttccagttt acggtcagac tggcatctga gacagaagct cgattcacct cggtggagag   3600
gatcaatcac tacattaaga ctctgtcctt ggaagcacct gccagaatta agaacaaggc   3660
tccctcccct gactggcccc aggagggaga ggtgaccttt gagaacgcag agatgaggta   3720
ccgagaaaac ctccctctcg tcctaaagaa agtatccttc acgatcaaac ctaaagagaa   3780
gattggcatt gtggggcgga caggatcagg gaagtcctcg ctggggatgg ccctcttccg   3840
tctggtggag ttatctggag gctgcatcaa gattgatgga gtgagaatca gtgatattgg   3900
ccttgccgac ctccgaagca aactctctat cattcctcaa gagccggtgc tgttcagtgg   3960
```

-continued

```
cactgtcaga tcaaatttgg accccttcaa ccagtacact gaagaccaga tttgggatgc   4020

cctggagagg acacacatga aagaatgtat tgctcagcta cctctgaaac ttgaatctga   4080

agtgatggag aatggggata acttctcagt gggggaacgg cagctcttgt gcatagctag   4140

agccctgctc cgccactgta agattctgat tttagatgaa gccacagctg ccatggacac   4200

agagacagac ttattgattc aagagaccat ccgagaagca tttgcagact gtaccatgct   4260

gaccattgcc catcgcctgc acacggttct aggctccgat aggattatgg tgctggccca   4320

gggacaggtg gtggagtttg acaccccatc ggtccttctg tccaacgaca gttcccgatt   4380

ctatgccatg tttgctgctg cagagaacaa ggtcgctgtc aagggctgac tcctccctgt   4440

tgacgaagtc tcttttcttt agagcattgc cattccctgc ctggggcggg cccctcatcg   4500

cgtcctccta ccgaaacctt gcctttctcg attttatctt tcgcacagca gttccggatt   4560

ggcttgtgtg tttcactttt agggagagtc atattttgat tattgtattt attccatatt   4620

catgtaaaca aaatttagtt tttgttctta attgcactct aaaaggttca gggaaccgtt   4680

attataattg tatcagaggc ctataatgaa gctttatacg tgtagctata tctatatata   4740

attctgtaca tagcctatat ttacagtgaa aatgtaagct gtttatttta tattaaaata   4800

agcactgtgc taataacagt gcatattcct ttctatcatt tttgtacagt ttgctgtact   4860

agagatctgg ttttgctatt agactgtagg aagagtagca tttcattctt ctctagctgg   4920

tggtttcacg gtgccaggtt ttctgggtgt ccaaaggaag acgtgtggca atagtgggcc   4980

ctccgacagc cccctctgcc gcctccccac ggccgctcca ggggtggctg gagacgggtg   5040

ggcggctgga gaccatgcag agcgccgtga gttctcaggg ctcctgcctt ctgtcctggt   5100

gtcacttact gtttctgtca ggagagcagc ggggcgaagc ccaggcccct tttcactccc   5160

tccatcaaga atggggatca cagagacatt cctccgagcc ggggagtttc tttcctgcct   5220

tcttcttttt gctgttgttt ctaaacaaga atcagtctat ccacagagag tcccactgcc   5280

tcaggttcct atggctggcc actgcacaga gctctccagc tccaagacct gttggttcca   5340

agccctggag ccaactgctg ctttttgagg tggcactttt tcatttgcct attcccacac   5400

ctccacagtt cagtggcagg gctcaggatt tcgtgggtct gttttccttt ctcaccgcag   5460

tcgtcgcaca gtctctctct ctctctcccc tcaaagtctg caactttaag cagctcttgc   5520

taatcagtgt ctcacactgg cgtagaagtt tttgtactgt aaagagacct acctcaggtt   5580

gctggttgct gtgtggtttg gtgtgttccc gcaaaccccc tttgtgctgt ggggctggta   5640

gctcaggtgg gcgtggtcac tgctgtcatc aattgaatgg tcagcgttgc atgtcgtgac   5700

caactagaca ttctgtcgcc ttagcatgtt tgctgaacac cttgtggaag caaaaatctg   5760

aaaatgtgaa taaaattatt ttggattttg t                                 5791
```

<210> SEQ ID NO 120
<211> LENGTH: 1992
<212> TYPE: DNA
<213> ORGANISM: Homo sapiens

<400> SEQUENCE: 120

```
aaacttcccg cacgcgttac aggagccagg tcggtataag cgccacgcct cgccgcccgt     60

caagctgtcc acatccctgg cctcagcccg ccacatcacc ctgacctgct tacgcccaga    120

ttttcttcaa tcacatctga ataaatcact tgaagaaagc ttatagcttc attgcaccat    180

gtgtggcatt tgggcgctgt ttggcagtga tgattgcctt tctgttcagt gtctgagtgc    240
```

-continued

```
tatgaagatt gcacacagag gtccagatgc attccgtttt gagaatgtca atggatacac    300
caactgctgc tttggatttc accggttggc ggtagttgac ccgctgtttg gaatgcagcc    360
aattcgagtg aagaaatatc cgtatttgtg gctctgttac aatggtgaaa tctacaacca    420
taagaagatg caacagcatt ttgaatttga ataccagacc aaagtggatg gtgagataat    480
ccttcatctt tatgacaaag gaggaattga gcaaacaatt tgtatgttgg atggtgtgtt    540
tgcatttgtt ttactggata ctgccaataa gaaagtgttc ctgggtagag atacatatgg    600
agtcagacct ttgtttaaag caatgacaga agatggattt ttggctgtat gttcagaagc    660
taaaggtctt gttacattga agcactccgc gactcccttt ttaaaagtgg agcctttttct    720
tcctggacac tatgaagttt tggatttaaa gccaaatggc aaagttgcat ccgtggaaat    780
ggttaaatat catcactgtc gggatgtacc cctgcacgcc ctctatgaca atgtggagaa    840
actctttcca ggttttgaga tagaaactgt gaagaacaac ctcaggatcc tttttaataa    900
tgctgtaaag aaacgtttga tgacagacag aaggattggc tgccttttat caggggggctt    960
ggactccagc ttggttgctg ccactctgtt gaagcagctg aaagaagccc aagtacagta   1020
tcctctccag acatttgcaa ttggcatgga agacagcccc gatttactgg ctgctagaaa   1080
ggtggcagat catattggaa gtgaacatta tgaagtcctt tttaactctg aggaaggcat   1140
tcaggctctg gatgaagtca tattttcctt ggaaacttat gacattacaa cagttcgtgc   1200
ttcagtaggt atgtatttaa tttccaagta tattcggaag aacacagata gcgtggtgat   1260
cttctctgga gaaggatcag atgaacttac gcagggttac atatattttc acaaggctcc   1320
ttctcctgaa aaagccgagg aggagagtga gaggcttctg agggaactct atttgtttga   1380
tgttctccgc gcagatcgaa ctactgctgc ccatggtctt gaactgagag tcccatttct   1440
agatcatcga tttttttcct attacttgtc tctgccacca gaaatgagaa ttccaaagaa   1500
tgggatagaa aaacatctcc tgagagagac gtttgaggat tccaatctga tacccaaaga   1560
gattctctgg cgaccaaaag aagccttcag tgatggaata acttcagtta agaattcctg   1620
gtttaagatt ttacaggaat acgttgaaca tcaggttgat gatgcaatga tggcaaatgc   1680
agcccagaaa tttcccttca atactcctaa aaccaaagaa ggatattact accgtcaagt   1740
ctttgaacgc cattacccag gccgggctga ctggctgagc cattactgga tgcccaagtg   1800
gatcaatgcc actgaccctt ctgcccgcac gctgacccac tacaagtcag ctgtcaaagc   1860
ttaggtggtc tttatgctgt aatgtgaaag caaatatttc ttcgtgttgg atggggactg   1920
tgggtagata ggggaacaat gagagtcaac tcaggctaac ttgggtttga aaaaaataaa   1980
attcctaaat tt                                                       1992
```

<210> SEQ ID NO 121
<211> LENGTH: 5698
<212> TYPE: DNA
<213> ORGANISM: Homo sapiens

<400> SEQUENCE: 121

```
aggttcaagt ggagctctcc taaccgacgc gcgtctgtgg agaagcggct tggtcggggg     60
tggtctcgtg gggtcctgcc tgtttagtcg ctttcagggt tcttgagccc cttcacgacc    120
gtcaccatgg aagtgtcacc attgcagcct gtaaatgaaa atatgcaagt caacaaaata    180
aagaaaaatg aagatgctaa gaaaagactg tctgttgaaa gaatctatca aaagaaaaca    240
caattggaac atattttgct ccgcccagac acctacattg gttctgtgga attagtgacc    300
cagcaaatgt gggtttacga tgaagatgtt ggcattaact atagggaagt cacttttgtt    360
```

-continued

```
cctggtttgt acaaaatctt tgatgagatt ctagttaatg ctgcggacaa caaacaaagg    420
gacccaaaaa tgtcttgtat tagagtcaca attgatccgg aaaacaattt aattagtata    480
tggaataatg gaaaaggtat tcctgttgtt gaacacaaag ttgaaaagat gtatgtccca    540
gctctcatat ttggacagct cctaacttct agtaactatg atgatgatga aaagaaagtg    600
acaggtggtc gaaatggcta tggagccaaa ttgtgtaaca tattcagtac caaatttact    660
gtggaaacag ccagtagaga atacaagaaa atgttcaaac agacatggat ggataatatg    720
ggaagagctg gtgagatgga actcaagccc ttcaatggag aagattatac atgtatcacc    780
tttcagcctg atttgtctaa gtttaaaatg caaagcctgg acaaagatat tgttgcacta    840
atggtcagaa gagcatatga tattgctgga tccaccaaag atgtcaaagt ctttcttaat    900
ggaaataaac tgccagtaaa aggatttcgt agttatgtgg acatgtattt gaaggacaag    960
ttggatgaaa ctggtaactc cttgaaagta atacatgaac aagtaaacca caggtgggaa   1020
gtgtgtttaa ctatgagtga aaaaggcttt cagcaaatta gctttgtcaa cagcattgct   1080
acatccaagg gtggcagaca tgttgattat gtagctgatc agattgtgac taaacttgtt   1140
gatgttgtga agaagaagaa caagggtggt gttgcagtaa aagcacatca ggtgaaaaat   1200
cacatgtgga tttttgtaaa tgccttaatt gaaaacccaa cctttgactc tcagacaaaa   1260
gaaaacatga ctttacaacc caagagcttt ggatcaacat gccaattgag tgaaaaattt   1320
atcaaagctg ccattggctg tggtattgta gaaagcatac taaactgggt gaagtttaag   1380
gcccaagtcc agttaaacaa gaagtgttca gctgtaaaac ataatagaat caagggaatt   1440
cccaaactcg atgatgccaa tgatgcaggg ggccgaaact ccactgagtg tacgcttatc   1500
ctgactgagg gagattcagc caaaactttg gctgtttcag gccttggtgt ggttgggaga   1560
gacaaatatg ggggttttcc tcttagagga aaaatactca atgttcgaga agcttctcat   1620
aagcagatca tggaaaatgc tgagattaac aatatcatca agattgtggg tcttcagtac   1680
aagaaaaact atgaagatga agattcattg aagacgcttc gttatgggaa gataatgatt   1740
atgacagatc aggaccaaga tggttcccac atcaaaggct tgctgattaa ttttatccat   1800
cacaactggc cctctcttct gcgacatcgt tttctggagg aatttatcac tcccattgta   1860
aaggtatcta aaaacaagca agaaatggca ttttacagcc ttcctgaatt tgaagagtgg   1920
aagagttcta ctccaaatca taaaaaatgg aaagtcaaat attacaaagg tttgggcacc   1980
agcacatcaa aggaagctaa agaatacttt gcagatatga aaagacatcg tatccagttc   2040
aaatattctg gtcctgaaga tgatgctgct atcagcctgg cctttagcaa aaaacagata   2100
gatgatcgaa aggaatggtt aactaatttc atggaggata gaagacaacg aaagttactt   2160
gggcttcctg aggattactt gtatggacaa actaccacat atctgacata taatgacttc   2220
atcaacaagg aacttatctt gttctcaaat tctgataacg agagatctat cccttctatg   2280
gtggatggtt tgaaaccagg tcagagaaag gttttgttta cttgcttcaa acggaatgac   2340
aagcgagaag taaaggttgc ccaattagct ggatcagtgg ctgaaatgtc ttcttatcat   2400
catggtgaga tgtcactaat gatgaccatt atcaatttgg ctcagaattt tgtgggtagc   2460
aataatctaa acctcttgca gcccattggt cagtttggta ccaggctaca tggtggcaag   2520
gattctgcta gtccacgata catctttaca atgctcagct ctttggctcg attgttattt   2580
ccaccaaaag atgatcacac gttgaagttt ttatatgatg acaaccagcg tgttgagcct   2640
gaatggtaca ttcctattat tcccatggtg ctgataaatg gtgctgaagg aatcggtact   2700
```

-continued

```
gggtggtcct gcaaaatccc caactttgat gtgcgtgaaa ttgtaaataa catcaggcgt   2760
ttgatggatg gagaagaacc tttgccaatg cttccaagtt acaagaactt caagggtact   2820
attgaagaac tggctccaaa tcaatatgtg attagtggtg aagtagctat tcttaattct   2880
acaaccattg aaatctcaga gcttcccgtc agaacatgga cccagacata caaagaacaa   2940
gttctagaac ccatgttgaa tggcaccgag aagacacctc ctctcataac agactatagg   3000
gaataccata cagataccac tgtgaaattt gttgtgaaga tgactgaaga aaaactggca   3060
gaggcagaga gagttggact acacaaagtc ttcaaactcc aaactagtct cacatgcaac   3120
tctatggtgc tttttgacca cgtaggctgt ttaaagaaat atgacacggt gttggatatt   3180
ctaagagact tttttgaact cagacttaaa tattatggat taagaaaaga atggctccta   3240
ggaatgcttg gtgctgaatc tgctaaactg aataatcagg ctcgctttat cttagagaaa   3300
atagatggca aaataatcat tgaaaataag cctaagaaag aattaattaa agttctgatt   3360
cagaggggat atgattcgga tcctgtgaag gcctggaaag aagcccagca aaaggttcca   3420
gatgaagaag aaaatgaaga gagtgacaac gaaaaggaaa ctgaaaagag tgactccgta   3480
acagattctg gaccaacctt caactatctt cttgatatgc ccctttggta tttaaccaag   3540
gaaaagaaag atgaactctg caggctaaga aatgaaaaag aacaagagct ggacacatta   3600
aaaagaaaga gtccatcaga tttgtggaaa gaagacttgg ctacatttat tgaagaattg   3660
gaggctgttg aagccaagga aaaacaagat gaacaagtcg gacttcctgg gaaagggggg   3720
aaggccaagg ggaaaaaaac acaaatggct gaagttttgc cttctccgcg tggtcaaaga   3780
gtcattccac gaataaccat agaaatgaaa gcagaggcag aaaagaaaaa taaaaagaaa   3840
attaagaatg aaaatactga aggaagccct caagaagatg gtgtggaact agaaggccta   3900
aaacaaagat tagaaaagaa acagaaaaga gaaccaggta caaagacaaa gaaacaaact   3960
acattggcat ttaagccaat caaaaaagga aagaagagaa atccctggtc tgattcagaa   4020
tcagatagga gcagtgacga aagtaatttt gatgtccctc cacgagaaac agagccacgg   4080
agagcagcaa caaaaacaaa attcacaatg gatttggatt cagatgaaga tttctcagat   4140
tttgatgaaa aaactgatga tgaagatttt gtcccatcag atgctagtcc acctaagacc   4200
aaaacttccc caaaacttag taacaaagaa ctgaaaccac agaaaagtgt cgtgtcagac   4260
cttgaagctg atgatgttaa gggcagtgta ccactgtctt caagccctcc tgctacacat   4320
ttcccagatg aaactgaaat tacaaaccca gttcctaaaa agaatgtgac agtgaagaag   4380
acagcagcaa aaagtcagtc ttccacctcc actaccggtg ccaaaaaaag ggctgcccca   4440
aaaggaacta aaagggatcc agctttgaat tctggtgtct ctcaaaagcc tgatcctgcc   4500
aaaaccaaga atcgccgcaa aaggaagcca tccacttctg atgattctga ctctaatttt   4560
gagaaaattg tttcgaaagc agtcacaagc aagaaatcca aggggagag tgatgacttc   4620
catatggact ttgactcagc tgtggctcct cgggcaaaat ctgtacgggc aaagaaacct   4680
ataaagtacc tggaagagtc agatgaagat gatctgtttt aaaatgtgag gcgattattt   4740
taagtaatta tcttaccaag cccaagactg gttttaaagt tacctgaagc tcttaacttc   4800
ctcccctctg aatttagttt ggggaaggtg tttttagtac aagacatcaa agtgaagtaa   4860
agcccaagtg ttctttagct ttttataata ctgtctaaat agtgaccatc tcatgggcat   4920
tgttttcttc tctgctttgt ctgtgttttg agtctgcttt cttttgtctt taaaacctga   4980
tttttaagtt cttctgaact gtagaaatag ctatctgatc acttcagcgt aaagcagtgt   5040
gtttattaac catccactaa gctaaaacta gagcagtttg atttaaaagt gtcactcttc   5100
```

-continued

```
ctccttttct actttcagta gatatgagat agagcataat tatctgtttt atcttagttt   5160

tatacataat ttaccatcag atagaacttt atggttctag tacagatact ctactacact   5220

cagcctctta tgtgccaagt ttttctttaa gcaatgagaa attgctcatg ttcttcatct   5280

tctcaaatca tcagaggcca aagaaaaaca ctttggctgt gtctataact tgacacagtc   5340

aatagaatga agaaaattag agtagttatg tgattatttc agctcttgac ctgtcccctc   5400

tggctgcctc tgagtctgaa tctcccaaag agagaaacca atttctaaga ggactggatt   5460

gcagaagact cggggacaac atttgatcca agatcttaaa tgttatattg ataaccatgc   5520

tcagcaatga gctattagat tcattttggg aaatctccat aatttcaatt tgtaaacttt   5580

gttaagacct gtctacattg ttatatgtgt gtgacttgag taatgttatc aacgtttttg   5640

taaatattta ctatgttttt ctattagcta aattccaaca attttgtact ttaataaa     5698
```

<210> SEQ ID NO 122
<211> LENGTH: 2753
<212> TYPE: DNA
<213> ORGANISM: Homo sapiens

<400> SEQUENCE: 122

```
gcgccatgga gcagtggcgg cagtgcggcc gctggctcat cgattgcaag gtcctgccgc     60

ccaaccaccg ggtggtgtgg ccctcggccg tggtcttcga cctggcgcag gcgctgcgcg    120

acggggtcct tctgtgccag ctgctgcaca acctctcccc cggctccatc gacctcaagg    180

acatcaactt ccggccgcag atgtcccagt ttctgtgttt gaagaacata cgcaccttcc    240

tgaaagtctg ccacgataaa tttggattaa ggaacagcga gctgtttgac ccctttgacc    300

tcttcgatgt gcgagacttt ggaaaggtca tctccgcggt gtcgaggctc tccctgcaca    360

gcatcgcgca gaacaaaggg atcaggcctt ttccctcaga ggagaccaca gagaatgacg    420

atgacgtcta ccgcagcctg gaggagctgg ccgacgagca tgacctgggg gaggacatct    480

acgactgcgt cccgtgtgag gatggagggg acgacatcta cgaggacatc atcaaggtgg    540

aggtgcagca gcccatgatt agatacatgc agaaaatggg catgactgaa gatgacaaga    600

ggaactgctg cctgctggag atccaggaga ccgaggccaa gtactaccgc accctggagg    660

acattgagaa gaactacatg agccccctgc ggctggtgct gagcccggcg gacatggcag    720

ctgtcttcat taacctggag gacctgatca aggtgcatca cagcttcctg agggccatcg    780

acgtgtccgt gatggtgggg ggcagcacgc tggccaaggt cttcctcgat ttcaaggaaa    840

ggcttctgat ctacggggag tactgcagcc acatggagca cgcccagaac acactgaacc    900

agctcctggc cagccgggag gacttcaggc agaaagtcga ggagtgcaca ctgaaggtcc    960

aggatggaaa atttaagctg caagacctgc tggtggtccc catgcagagg gtgctcaaat   1020

accacctgct cttgaaggag cttctgagcc attctgcgga acggcctgag aggcagcagc   1080

tcaaagaagc actggaagcc atgcaggact tggcgatgta catcaatgaa gttaaacggg   1140

acaaggagac cttgaggaaa atcagcgaat ttcagagttc tatagaaaat ttgcaagtga   1200

aactggagga atttggaaga ccaaagattg acggggaact gaaagtccgg tccatagtca   1260

accacaccaa gcaggacagg tacttgttcc tgtttgacaa ggtggtcatc gtctgcaagc   1320

ggaagggcta cagctacgag ctcaaggaga tcatcgagct gctgttccac aagatgaccg   1380

acgaccccat gaacaacaag gacgtcaaga agtctcacgg gaaaatgtgg tcctacggct   1440

tctacctaat tcaccttcaa ggaaagcagg gcttccagtt tttctgcaaa acagaagata   1500
```

-continued

```
tgaagaggaa gtggatggag cagtttgaga tggccatgtc aaacatcaag ccagacaaag   1560

ccaatgccaa ccaccacagt ttccagatgt acacgtttga caagaccacc aactgcaaag   1620

cctgcaaaat gttcctcagg ggcaccttct accagggata catgtgtacc aagtgtggcg   1680

tcggggcaca caaggagtgc ctggaagtga tacctccctg caagttcact tctcctgcag   1740

atctggacgc ctccggagcg ggaccaggtc ccaagatggt ggccatgcag aattaccatg   1800

gcaacccagc ccctcccggg aagcctgtgc tgaccttcca gacgggcgac gtgcttgagc   1860

tgctgagggg cgaccctgag tctccgtggt gggagggtcg tctggtacaa accaggaagt   1920

cagggtattt ccccagctca tctgtgaagc cctgccctgt ggatggaagg ccgcccatca   1980

gccggccgcc atcccgggag atcgactaca ctgcataccc ctggtttgca ggtaacatgg   2040

agaggcagca gacggacaac ctgctcaagt cccacgccag cgggacctac ctgatcaggg   2100

agcggcctgc cgaggctgag cgctttgcaa taagcatcaa gttcaatgat gaggtgaagc   2160

acatcaaggt ggtggagaag gacaactgga tccacatcac agaggccaag aaattcgaca   2220

gcctcctgga gttggtggag tactaccagt gccactcact gaaggagagc ttcaagcagc   2280

tggacaccac actcaagtac ccctacaagt cccgggaacg ttcggcctcc agggcctcca   2340

gccggtcccc agcttcctgt gcttcctaca acttttcttt tctcagtcct cagggcctca   2400

gctttgcttc tcagggcccc tccgctccct tctggtcagt gttcacgccc cgcgtcatcg   2460

gcacagctgt ggccaggtat aactttgccg cccgagatat gagggagctt tcgctgcggg   2520

agggtgacgt ggtgaggatc tacagccgca tcggcggaga ccagggctgg tggaagggcg   2580

agaccaacgg acggattggc tggtttcctt caacgtacgt agaagaggag ggcatccagt   2640

gacggcagga acgtggacaa gactcgcaga ttttcttggg agagtcactc cagccctgaa   2700

gtctgtctct agctcctctg tgactcagag gggaaatacc aacctcccag tct          2753


<210> SEQ ID NO 123
<211> LENGTH: 23
<212> TYPE: DNA
<213> ORGANISM: Artificial
<220> FEATURE:
<223> OTHER INFORMATION: Synthetic

<400> SEQUENCE: 123

cgtatgcccc gctgaatctc gtg                                             23
```

EXPRESSION PROFILE OF PROSTATE CANCER

This application is a divisional of application Ser. No. 10/210,120, filed Aug. 1, 2002, now U.S. Pat. No. 7,229,774 which claims priority to U.S. Provisional Application Ser. No. 60/309,581 filed Aug. 2, 2001 and U.S. Provisional Application Ser. No. 60/334,468 filed Nov. 15, 2001, each of which is herein incorporated by reference in its entirety.

This invention was made with government support under Grant No. 5 P50 CA69568 awarded by the National Institutes of Health. The Government has certain rights in the invention.

Filed herewith as Tables 3, 4, 5, 6, and 7, and expressly incorporated by reference is an appendix contained on one compact disc, submitted in two identical sets labeled "Copy 1" and "Copy 2," for a total of two compact discs. Each compact disc was prepared in IBM-PC machine format and is compatible with the MS-Windows operating system. The set of two compact discs contains the following 5 files, in ASCII format:

| Disc 1 | | |
|---|---|---|
| File Name | Creation Date | Size (bytes) |
| table3.txt | Aug. 01, 2002 | 1,964,212 |
| table4.txt | Aug. 01, 2002 | 1,498,092 |
| table5.txt | Aug. 01, 2002 | 3,374,515 |
| table6.txt | Aug. 01, 2002 | 82,030 |
| table7.txt | Aug. 01, 2002 | 18,882 |

FIELD OF THE INVENTION

The present invention relates to compositions and methods for cancer diagnostics, including but not limited to, cancer markers. In particular, the present invention provides gene expression profiles associated with prostate cancers. The present invention further provides novel markers useful for the diagnosis, characterization, and treatment of prostate cancers.

BACKGROUND OF THE INVENTION

Afflicting one out of nine men over age 65, prostate cancer (PCA) is a leading cause of male cancer-related death, second only to lung cancer (Abate-Shen and Shen, Genes Dev 14:2410 [2000]; Ruijter et al., Endocr Rev, 20:22 [1999]). The American Cancer Society estimates that about 184,500 American men will be diagnosed with prostate cancer and 39,200 will die in 2001.

Prostate cancer is typically diagnosed with a digital rectal exam and/or prostate specific antigen (PSA) screening. An elevated serum PSA level can indicate the presence of PCA. PSA is used as a marker for prostate cancer because it is secreted only by prostate cells. A healthy prostate will produce a stable amount—typically below 4 nanograms per milliliter, or a PSA reading of "4" or less—whereas cancer cells produce escalating amounts that correspond with the severity of the cancer. A level between 4 and 10 may raise a doctor's suspicion that a patient has prostate cancer, while amounts above 50 may show that the tumor has spread elsewhere in the body.

When PSA or digital tests indicate a strong likelihood that cancer is present, a transrectal ultrasound (TRUS) is used to map the prostate and show any suspicious areas. Biopsies of various sectors of the prostate are used to determine if prostate cancer is present. Treatment options depend on the stage of the cancer. Men with a 10-year life expectancy or less who have a low Gleason number and whose tumor has not spread beyond the prostate are often treated with watchful waiting (no treatment). Treatment options for more aggressive cancers include surgical treatments such as radical prostatectomy (RP), in which the prostate is completely removed (with or without nerve sparing techniques) and radiation, applied through an external beam that directs the dose to the prostate from outside the body or via low-dose radioactive seeds that are implanted within the prostate to kill cancer cells locally. Anti-androgen hormone therapy is also used, alone or in conjunction with surgery or radiation. Hormone therapy uses luteinizing hormone-releasing hormones (LH-RH) analogs, which block the pituitary from producing hormones that stimulate testosterone production. Patients must have injections of LH-RH analogs for the rest of their lives.

While surgical and hormonal treatments are often effective for localized PCA, advanced disease remains essentially incurable. Androgen ablation is the most common therapy for advanced PCA, leading to massive apoptosis of androgen-dependent malignant cells and temporary tumor regression. In most cases, however, the tumor reemerges with a vengeance and can proliferate independent of androgen signals.

The advent of prostate specific antigen (PSA) screening has led to earlier detection of PCA and significantly reduced PCA-associated fatalities. However, the impact of PSA screening on cancer-specific mortality is still unknown pending the results of prospective randomized screening studies (Etzioni et al., J. Natl. Cancer Inst., 91:1033 [1999]; Maattanen et al., Br. J. Cancer 79:1210 [1999]; Schroder et al., J. Natl. Cancer Inst., 90:1817 [1998]). A major limitation of the serum PSA test is a lack of prostate cancer sensitivity and specificity especially in the intermediate range of PSA detection (4-10 ng/ml). Elevated serum PSA levels are often detected in patients with non-malignant conditions such as benign prostatic hyperplasia (BPH) and prostatitis, and provide little information about the aggressiveness of the cancer detected. Coincident with increased serum PSA testing, there has been a dramatic increase in the number of prostate needle biopsies performed (Jacobsen et al., JAMA 274:1445 [1995]). This has resulted in a surge of equivocal prostate needle biopsies (Epstein and Potter J. Urol., 166:402 [2001]). Thus, development of additional serum and tissue biomarkers to supplement PSA screening is needed.

SUMMARY OF THE INVENTION

The present invention relates to compositions and methods for cancer diagnostics, including but not limited to, cancer markers. In particular, the present invention provides gene expression profiles associated with prostate cancers. The present invention further provides novel markers useful for the diagnosis, characterization, and treatment of prostate cancers.

In some embodiments, the present invention provides a method for characterizing prostate tissue in a subject, comprising: providing a prostate tissue sample from a subject; and detecting the presence or absence of expression of hepsin in the sample, thereby characterizing the prostate tissue sample. In some embodiments, detecting the presence of expression of hepsin comprises detecting the presence of hepsin mRNA. In other embodiments, detecting the presence of expression of hepsin mRNA comprises exposing the hepsin mRNA to a nucleic acid probe complementary to the hepsin mRNA. In yet other embodiments, detecting the presence of expression of hepsin comprises detecting the presence of a hepsin polypeptide. In some embodiments, detecting the presence of a hepsin polypeptide comprises exposing the hepsin polypeptide to an antibody specific to the hepsin polypeptide and detecting the binding of the antibody to the hepsin polypeptide. In some embodiments, the subject comprises a human subject. In some embodiments, the sample comprises tumor tissue. In some embodiments, the tumor tissue sample is a post-surgical tumor tissue sample and the method further comprises the step of c) identifying a risk of prostate specific antigen failure based on detecting the presence or absence of expression of hepsin. In some embodiments, characterizing prostate tissue comprises identifying a stage of prostate cancer in the tissue. In some embodiments, the stage includes but is not limited to, high-grade prostatic intraepithelial neoplasia, benign prostatic hyperplasia, prostate carcinoma, and metastatic prostate carcinoma. In some embodiments, the method further comprising the step of c) providing a prognosis to the subject. In some embodiments, the prognosis comprises a risk of developing prostate specific antigen failure. In other embodiments, the prognosis comprises a risk of developing prostate cancer.

The present invention also provides a method for characterizing prostate tissue in a subject, comprising: providing a prostate tissue sample from a subject; and detecting the presence or absence of expression of pim-1 in the sample, thereby characterizing the prostate tissue sample. In some embodiments, detecting the presence of expression of pim-1 comprises detecting the presence of pim-1 mRNA. In other embodiments, detecting the presence of expression of pim-1 mRNA comprises exposing the pim-1 mRNA to a nucleic acid probe complementary to the pim-1 mRNA. In yet other embodiments, detecting the presence of expression of pim-1 comprises detecting the presence of a pim-1 polypeptide. In some embodiments, detecting the presence of a pim-1 polypeptide comprises exposing the pim-1 polypeptide to an antibody specific to the pim-1 polypeptide and detecting the binding of the antibody to the pim-1 polypeptide. In some embodiments, the subject comprises a human subject. In some embodiments, the sample comprises tumor tissue. In some embodiments, the tumor tissue sample is a post-surgical tumor tissue sample and the method further comprises the step of c) identifying a risk of prostate specific antigen failure based on detecting the presence or absence of expression of pim-1. In some embodiments, characterizing prostate tissue comprises identifying a stage of prostate cancer in the tissue. In some embodiments, the stage includes but is not limited to, high-grade prostatic intraepithelial neoplasia, benign prostatic hyperplasia, prostate carcinoma, and metastatic prostate carcinoma. In some embodiments, the method further comprising the step of c) providing a prognosis to the subject. In some embodiments, the prognosis comprises a risk of developing prostate specific antigen failure. In other embodiments, the prognosis comprises a risk of developing prostate cancer.

The present invention further provides a method for characterizing prostate tissue in a subject, comprising: providing a prostate tissue sample; and detecting a decreased or increased expression relative to a non-cancerous prostate tissue control of two or more markers selected from the group consisting of HEPSIN, FKBP5, FASN, FOLH1, TNFSF10, PCM1, S100A11, IGFBP3, SLUG, GSTM3, IL1R2, ITGB4, CCND2, EDNRB, APP, THROMBOSPONDIN 1, ANNEXIN A1, EPHA1, NCK1, MAPK6, SGK, HEVIN, MEIS2, MYLK, FZD7, CAVEOLIN 2, TACC1, ARHB, PSG9, GSTM1, KERATIN 5, TIMP2, GELSOLIN, ITM2C, GSTM5, VINCULIN, FHL1, GSTP1, MEIS1, ETS2, PPP2CB, CATHEPSIN B, COL1A2, RIG, VIMENTIN, MOESIN, MCAM, FIBRONECTIN 1, NBL1, ANNEXIN A4, ANEXIN A11, IL1R1, IGFBP5, CYSTATIN C, COL15 A1, ADAMTS1, SKI, EGR1, FOSB, CFLAR, JUN, YWHAB, NRAS, C7, SCYA2, ITGA1, LUMICAN, C1S, C4BPA, COL3 A1, FAT, MMECD10, CLUSTERIN, PLA2G2A, thereby characterizing the prostate tissue sample. In some embodiments, the detecting comprises detecting three or more markers. In other embodiments, the detecting comprises detecting five or more markers. In still further embodiments, the detecting comprises detecting ten or more markers.

The present invention additionally provides a method for characterizing prostate cancer in a subject, comprising: providing a tumor sample from a subject diagnosed with prostate cancer; and detecting decreased expression relative to a non-cancerous prostate tissue control of two or more cancer markers selected from the group consisting of IGFBP5, MADH4, NBL1, SEPP1, RAB2, FAT, PP1CB, MPDZ, PRKCL2, ATF2, RAB5A, and Cathepsin H, wherein decreased expression is diagnostic of metastatic prostate cancer. In some embodiments, the detecting comprises detecting three or more markers. In other embodiments, the detecting comprises detecting five or more markers. In still further embodiments, the detecting comprises detecting ten or more markers.

The present invention further provides a method for characterizing prostate cancer in a subject, comprising providing a tumor sample from a subject diagnosed with prostate cancer; and detecting increased expression relative to a non-cancerous prostate tissue of two or more cancer markers selected from the group consisting of CTBP1, MAP3K10, TBXA2R, MTA1, RAP2, TRAP1, TFCP2, E2-EPF, UBCH10, TASTIN, EZH2, FLS353, MYBL2, LIMK1, TRAF4, wherein increased expression is diagnostic of metastatic prostate cancer. In some embodiments, the detecting comprises detecting three or more markers. In other embodiments, the detecting comprises detecting five or more markers. In still further embodiments, the detecting comprises detecting ten or more markers.

In some embodiments, the present invention provides a kit for characterizing prostate cancer in a subject, comprising: a reagent capable of specifically detecting the presence of absence of expression of hepsin; and instructions for using the kit for characterizing cancer in the subject. In some embodiments, the reagent comprises a nucleic acid probe complementary to a hepsin mRNA. In other embodiments, the reagent comprises an antibody that specifically binds to a hepsin polypeptide. In some embodiments, the instructions comprise instructions required by the United States Food and Drug Administration for use in in vitro diagnostic products.

In other embodiments, the present invention provides a kit for characterizing prostate cancer in a subject, comprising: a reagent capable of specifically detecting the presence of absence of expression of pim-1; and instructions for using the kit for characterizing cancer in the subject. In some embodiments, the reagent comprises a nucleic acid probe complementary to a pim-1 mRNA. In other embodiments, the reagent comprises an antibody that specifically binds to a pim-1 polypeptide. In some embodiments, the instructions comprise instructions required by the United States Food and Drug Administration for use in in vitro diagnostic products.

In still further embodiments, the present invention provides a kit for characterizing prostate cancer in a subject, comprising: two or more reagents capable of specifically detecting expression levels of two or more markers selected from the group consisting of FKBP5, FASN, FOLH1, TNFSF10, PCM1, S100A11, IGFBP3, SLUG, GSTM3, ATF2, RAB5A, IL1R2, ITGB4, CCND2, EDNRB, APP, THROMBOSPONDIN 1, ANNEXIN A1, EPHA1, NCK1, MAPK6, SGK, HEVIN, MEIS2, MYLK, FZD7, CAVEOLIN 2, TACC1, ARHB, PSG9, GSTM1, KERATIN 5, TIMP2, GELSOLIN, ITM2C, GSTM5, VINCULIN, FHL1, GSTP1, MEIS1, ETS2, PPP2CB, CATHEPSIN B. CATHEPSIN H, COL1A2, RIG, VIMENTIN, MOESIN, MCAM, FIBRONECTIN 1, NBL1, ANNEXIN A4, ANEXIN A11, IL1R1, IGFBP5, CYSTATIN C, COL15A1, ADAMTS1, SKI, EGR1, FOSB, CFLAR, JUN, YWHAB, NRAS, C7, SCYA2, ITGA1, LUMICAN, C1S, C4BPA, COL3A1, FAT, MMECD10, CLUSTERIN, PLA2G2A, MADh4, SEPP1, RAB2, PP1CB, MPDZ, PRKCL2, CTBP1, CTBP2, MAP3K10, TBXA2F, MTA1, RAP2, TRAP1, TFCP2, E2EPF, UBCH10, TASTIN, EZH2, FLS353, MYBL2, LIMK1, GP73, VAV2, TOP2A, ASNS, CTBP, AMACR, ABCC5 (MDR5), and TRAF4; and instructions for using the kit for characterizing cancer in the subject. In some embodiments, the kit comprises reagents capable of specifically detecting expression levels of three or more of the markers. In other embodiments, the kit comprises reagents capable of specifically detecting expression levels of five or more of the markers. In still further embodiments, the kit comprises reagents capable of specifically detecting expression levels of ten or more of the markers. In some embodiments, the instructions comprise instructions required by the United States Food and Drug Administration for use in in vitro diagnostic products.

In yet other embodiments, the present invention provides a kit for characterizing prostate cancer in a subject, comprising: two or more reagents capable of specifically detecting decreased expression levels of two or more markers selected from the group consisting of IGFBP5, MADH4, NBL1, SEPP1, RAB2, FAT, PP1CB, MPDZ, PRKCL2, ATF2, RAB5A, and Cathepsin H; and instructions for using the kit for characterizing cancer in the subject. In some embodiments, the kit comprises reagents capable of specifically detecting decreased expression levels of three or more of the markers. In other embodiments, the kit comprises reagents capable of specifically detecting decreased expression levels of five or more of the markers. In still further embodiments, the kit comprises reagents capable of specifically detecting decreased expression levels of ten or more of the markers. In some embodiments, the instructions comprise instructions required by the United States Food and Drug Administration for use in in vitro diagnostic products.

In an additional embodiment, the present invention provides a kit for characterizing prostate cancer in a subject, comprising: two or more reagents capable of specifically detecting increased expression levels of two or more markers selected from the group consisting of CTBP1, MAP3K10, TBXA2R, MTA1, RAP2, TRAP 1, TFCP2, E2-EPF, UBCH10, TASTIN, EZH2, FLS353, MYBL2, LIMK1, TRAF4; and instructions for using the kit for characterizing cancer in the subject. In some embodiments, the kit comprises reagents capable of specifically detecting decreased expression levels of three or more of the markers. In other embodiments, the kit comprises reagents capable of specifically detecting decreased expression levels of five or more of the markers. In still further embodiments, the kit comprises reagents capable of specifically detecting decreased expression levels of ten or more of the markers. In some embodiments, the instructions comprise instructions required by the United States Food and Drug Administration for use in in vitro diagnostic products.

The present invention also provides a method of screening compounds, comprising providing a prostate cell sample; and one or more test compounds; and contacting the prostate cell sample with the test compound; and detecting a change in hepsin expression in the prostate cell sample in the presence of the test compound relative to the absence of the test compound. In some embodiments, the detecting comprises detecting hepsin mRNA. In other embodiments, the detecting comprises detecting hepsin polypeptide. In some embodiments, the cell is in vitro. In other embodiments, the cell is in vivo. In some embodiments, the test compound comprises an antisense compound. In other embodiments, the test compound comprises a drug.

The present invention further provides a method of screening compounds, comprising providing a prostate cell sample; and one or more test compounds; and contacting the prostate cell sample with the test compound; and detecting a change in pim-1 expression in the prostate cell sample in the presence of the test compound relative to the absence of the test compound. In some embodiments, the detecting comprises detecting pim-1 mRNA. In other embodiments, the detecting comprises detecting pim-1 polypeptide. In some embodiments, the cell is in vitro. In other embodiments, the cell is in vivo. In some embodiments, the test compound comprises an antisense compound. In other embodiments, the test compound comprises a drug.

The present invention provides a prostate cancer expression profile map comprising gene expression level information for two or more markers selected from the group consisting of: FKBP5, FASN, FOLH1, TNFSF10, PCM1, S100A11, IGFBP3, SLUG, GSTM3, ATF2, RAB5A, IL1R2, ITGB4, CCND2, EDNRB, APP, THROMBOSPONDIN 1, ANNEXIN A1, EPHA1, NCK1, MAPK6, SGK, HEVIN, MEIS2, MYLK, FZD7, CAVEOLIN 2, TACC1, ARHB, PSG9, GSTM1, KERATIN 5, TIMP2, GELSOLIN, ITM2C, GSTM5, VINCULIN, FHL1, GSTP1, MEIS1, ETS2, PPP2CB, CATHEPSIN B, CATHEPSIN H, COL1A2, RIG, VIMENTIN, MOESIN, MCAM, FIBRONECTIN 1, NBL1, ANNEXIN A4, ANEXIN A11, IL1R1, IGFBP5, CYSTATIN C, COL15A1, ADAMTS1, SKI, EGR1, FOSB, CFLAR, JUN, YWHAB, NRAS, C7, SCYA2, ITGA1, LUMICAN, C1S, C4BPA, COL3A1, FAT, MMECD10, CLUSTERIN, PLA2G2A, MADh4, SEPP1, RAB2, PP1CB, MPDZ, PRKCL2, CTBP1, CTBP2, MAP3K10, TBXA2F, MTA1, RAP2, TRAP1, TFCP2, E2EPF, UBCH10, TASTIN, EZH2, FLS353, MYBL2, LIMK1, GP73, VAV2, TOP2A, ASNS, CTBP, AMACR, ABCC5 (MDR5), and TRAF4. In some embodiments, the map is digital information stored in computer memory. In some embodiments, the map comprises information for three or more markers. In other embodiments, the map comprises information for five or more markers. In still further embodiments, the map comprises information for ten or more markers.

The present invention also provides a prostate cancer expression profile map comprising gene expression level information for two or more markers selected from the group consisting of: IGFBP5, MADH4, NBL1, SEPP1, RAB2, FAT, PP1CB, MPDZ, PRKCL2, ATF2, RAB5A, and Cathepsin H. In some embodiments, the map is digital information stored in computer memory. In some embodiments, the map comprises information for three or more markers. In other embodiments, the map comprises information for five or more markers. In still further embodiments, the map comprises information for ten or more markers. In some embodiments, the prostate cancer is metastatic.

The present invention further provides a prostate cancer expression profile map comprising gene expression level information for two or more markers selected from the group consisting of: CTBP1, MAP3K10, TBXA2R, MTA1, RAP2, TRAP1, TFCP2, E2-EPF, UBCH10, TASTIN, EZH2, FLS353, MYBL2, LIMK1, TRAF4. In some embodiments, the map is digital information stored in computer memory. In some embodiments, the map comprises information for three or more markers. In other embodiments, the map comprises information for five or more markers. In still further embodiments, the map comprises information for ten or more markers. In some embodiments, the prostate cancer is metastatic.

In some embodiments, the present invention provides a method for characterizing prostate tissue in a subject, comprising providing a prostate tissue sample from a subject; and detecting the presence or absence of expression of EZH2 in the sample, thereby characterizing the prostate tissue sample. In some embodiments, detecting the presence of expression of EZH2 comprises detecting the presence of EZH2 mRNA (e.g., including, but not limited to, by exposing the hepsin mRNA to a nucleic acid probe complementary to the hepsin mRNA). In other embodiments, detecting the presence of expression of EZH2 comprises detecting the presence of a EZH2 polypeptide (e.g., including, but not limited to, by exposing the EZH2 polypeptide to an antibody specific to the EZH2 polypeptide and detecting the binding of the antibody to the EZH2 polypeptide). In some embodiments, the subject comprises a human subject. In some embodiments, the sample comprises tumor tissue. In some embodiments, characterizing the prostate tissue comprises identifying a stage of prostate cancer in the prostate tissue. In certain embodiments, the stage is selected from the group including, but not limited to, high-grade prostatic intraepithelial neoplasia, benign pro static hyperplasia, prostate carcinoma, and metastatic prostate carcinoma. In some embodiments, the method further comprises the step of providing a prognosis to the subject (e.g., a risk of developing metastatic prostate cancer).

In further embodiments, the present invention provides a kit for characterizing prostate cancer in a subject, comprising a reagent capable of specifically detecting the presence of absence of expression of EZH2; and instructions for using the kit for characterizing cancer in the subject. In some embodiments, the reagent comprises a nucleic acid probe complementary to a EZH2 mRNA. In other embodiments, the reagent comprises an antibody that specifically binds to a EZH2 polypeptide. In certain embodiments, the instructions comprise instructions required by the United States Food and Drug Administration for use in in vitro diagnostic products.

In still other embodiments, the present invention provides a method of screening compounds, comprising providing a prostate cell sample; and one or more test compounds; and contacting the prostate cell sample with the test compound; and detecting a change in EZH2 expression in the prostate cell sample in the presence of the test compound relative to the absence of the test compound. In some embodiments, wherein the detecting comprises detecting EZH2 mRNA. In other embodiments, the detecting comprises detecting EZH2 polypeptide. In some embodiments, the cell is in vitro; while in other embodiments, the cell is in vivo. In some embodiments, the test compound comprises an antisense compound. In certain embodiments, the test compound comprises a drug.

In yet other embodiments, the present invention provides a method for characterizing inconclusive prostate biopsy tissue in a subject, comprising providing an inconclusive prostate biopsy tissue sample from a subject; and detecting the presence of expression of AMACR in the sample, thereby characterizing the inconclusive prostate biopsy tissue sample. In some embodiments, detecting the presence of expression of AMACR comprises detecting the presence of AMACR mRNA (e.g., by exposing the AMACR mRNA to a nucleic acid probe complementary to at least a portion of the AMACR mRNA). In other embodiments, detecting the presence of expression of AMACR comprises detecting the presence of a AMACR polypeptide (e.g., by exposing the AMACR polypeptide to an antibody specific to the AMACR polypeptide and detecting the binding of the antibody to the AMACR polypeptide). In some embodiments, the subject comprises a human subject. In some embodiments, the presence of AMACR expression in the inconclusive biopsy tissue is indicative of prostate cancer in the subject. In certain embodiments, the method further comprises the step of detecting expression of a basal cell marker selected from the group consisting of 34βE12 and p63 and the absence of a basal cell marker expression and the presence of AMACR expression is indicative of prostate cancer in the subject.

The present invention further provides a method of detecting AMACR expression in a bodily fluid, comprising providing a bodily fluid from a subject; and a reagent for detecting AMACR expression in the biological fluid; and contacting the bodily fluid with the reagent under conditions such that the reagent detects AMACR expression in the bodily fluid. In some embodiments, the bodily fluid is selected from the group consisting of serum, urine, whole blood, lymph fluid, and mucus. In certain embodiments, the presence of AMACR in the bodily fluid is indicative of cancer (e.g., prostate cancer).

The present invention additionally provides a kit for characterizing inconclusive prostate biopsy tissue in a subject, comprising a reagent capable of specifically detecting the presence or absence of expression of AMACR; and instructions for using the kit for characterizing inconclusive biopsy tissue in the subject. In some embodiments, the reagent comprises a nucleic acid probe complementary to at least a portion of an AMACR mRNA. In other embodiments, the reagent comprises an antibody that specifically binds to a AMACR polypeptide. In still other embodiments, the kit further comprises a second reagent, the second reagent capable of specifically detecting the expression of a basal cell marker selected from the group consisting of 34βE12 and p63. In some embodiments, the instructions further comprise instructions for using the second reagent and the reagent for characterizing inconclusive biopsy tissue in the subject. In some embodiments, the instructions comprise instructions required by the United States Food and Drug Administration for use in in vitro diagnostic products.

The present invention further provides a method of characterizing tissue in a subject, comprising providing a tissue sample from a subject, the tissue sample selected from the group consisting of breast tissue, ovarian tissue, lymph tissue, and melanoma tissue; and detecting the presence or absence of expression of AMACR in the sample, thereby characterizing the breast tissue sample.

The present invention also provides a method of diagnosing cancer in a subject, comprising providing a tissue sample from a subject, the tissue sample selected from the group consisting of breast tissue, ovarian tissue, lymph tissue, and melanoma tissue; and wherein the subject is suspected of having cancer; and detecting the presence of expression of AMACR in the sample, thereby diagnosing cancer in the tissue sample of the subject.

The present invention provides a method of diagnosing cancer in a subject, comprising providing a blood sample from a subject suspected of having cancer; and detecting an immune response to AMACR in the blood sample, thereby diagnosing cancer in the subject. In some embodiments, the cancer is prostate cancer. In certain embodiments, detecting an immune response comprises detecting an antibody against the AMACR in the blood sample.

The present invention additionally provides a method of inhibiting the growth of cells, comprising providing a cell that expresses EZH2; and a reagent for inhibiting EZH2 expression in the cell; and contacting the cell with the reagent under conditions such that the expression of EZH2 in the cell is inhibited. In some embodiments, the reagent is an antisense oligonucleotide. In other embodiments, the reagent is a RNA duplex. In some embodiments, the reagent is a drug. In some embodiments, the cell is a prostate cancer cell. In some embodiments, the cell is in vitro; while in other embodiments, the cell is in vivo. In some embodiments, the contacting further results in a decrease in proliferation of the cell.

In certain embodiments, the present invention provides a method for characterizing prostate cancer in a subject, comprising providing a prostate tissue sample from a subject suspected of having prostate cancer; and detecting a decrease in expression of an annexin in the sample, thereby characterizing the prostate tissue sample. In some embodiments, the decrease in expression of an annexin is indicative of the presence of metastatic prostate cancer in the subject. In certain embodiments, the annexin is selected from the group including, but not limited to, Annexin 1, Annexin 2, Annexin 4, Annexin 6, Annexin 7, and Annexin 11.

In other embodiments, the present invention provides a method for characterizing prostate cancer in a subject, comprising providing a prostate tissue sample from a subject suspected of having prostate cancer; and detecting an increase in expression of a c-terminal binding protein in the sample, thereby characterizing the prostate tissue sample. In some embodiments, the c-terminal binding protein is selected from the group consisting of c-terminal binding protein 1 and c-terminal binding protein 2. In certain embodiments, the increase in expression of a c-terminal binding protein is indicative of the presence of metastatic prostate cancer in the subject. In some embodiments, the expression of a c-terminal binding protein is indicative of an increased risk of PSA failure.

In other embodiments, the present invention provides a method for characterizing prostate cancer in a subject, comprising providing a prostate tissue sample from a subject suspected of having prostate cancer; and detecting an increase or decrease in expression of GP73, thereby characterizing the prostate tissue sample. In some embodiments, an increase in expression of gp73 is indicative of localized prostate cancer. In other embodiments, the prostate tissue sample is prostate cancer and a decrease in the expression of gp73 is indicative of metastatic prostate cancer.

DESCRIPTION OF THE FIGURES

The patent file contains at least one drawing executed in color. Copies of this patent publication with color drawings will be provided by the U.S. Patent and Trademark Office upon request and payment of the necessary fee.

FIG. 1*a* shows a dendrogram describing the relatedness of the samples. FIG. 1*b* shows a cluster diagram of the samples groups compared against normal adjacent prostate pool as a reference. FIG. 1*c* shows a cluster diagram of the samples groups compared against commercial prostate pool reference.

FIG. 3*a* shows Northern blot analysis of human hepsin (top) and normalization with GAPDH (bottom). NAT indicates normal adjacent prostate tissue and PCA indicates prostate cancer. FIG. 3*b* shows tissue microarrays used for hepsin analysis. FIG. 3*c* shows a histogram of hepsin protein expression by tissue type. Benign prostate hyperplasia (BPH). High-grade intraepithelial neoplasia (HG-PIN). Localized prostate cancer (PCA). Hormone-refractory prostate cancer (MET). FIG. 3*d* shows Kaplan Meier Analysis.

FIG. 4 shows the expression of pim-1 in prostate cancer samples as determined by Northern blot analysis and immunohistochemistry. FIG. 4*a* shows a histogram of pim-1 protein expression by tissue type as assessed from 810 tissue microarray elements. High-grade intraepithelial neoplasia (HG-PIN). Localized prostate cancer (PCA). FIG. 4*b* shows a Kaplan-Meier analysis. The tope line represents patients with strong Pim-1 staining. The bottom line represents patients with absent/weak Pim-1 expression.

FIG. 7 shows data for gene selection based on computed t-statistics for the NAP and CP pools.

FIG. 9 describes exemplary accession numbers and sequence ID Numbers for exemplary genes of the present invention.

FIG. 10 provides exemplary sequences of some genes of the present invention.

FIG. 13 describes an analysis of AMACR transcript and protein levels in prostate cancer.

FIG. 16A shows AMACR protein expression in localized hormone naive PCA. FIG. 16B shows strong AMACR expression in a naive lymph node metastasis. Error bars represent the 95% CI of the mean expression of the primary naive prostate cancer and corresponding lymph node metastases.

FIG. 17A shows PCA demonstrating strong hormonal effect due to anti-androgen treatment. FIG. 17B shows Western Blot analysis representing the baseline AMACR expression in different prostate cell lines (Left) and Western Blot analysis of LNCaP cells for AMACR and PSA expression after treatment with an androgen or an anti-androgen for 24 h and 48 hours (right).

FIG. 20*a* shows a cluster diagram depicting genes that molecularly distinguish metastatic prostate cancer (MET) from clinically localized prostate cancer (PCA). FIG. 20*b* shows a DNA microarray analysis of prostate cancer that reveals upregulation of EZH2 in metastatic prostate cancer. FIG. 20*c* shows RT-PCR analysis of the EZH2 transcript in prostate tissue and cell lines. FIG. 20*d* shows increased expression of EZH2 protein in prostate cancer.

FIG. 21*a* shows tissue microarray analysis of EZH2 expression. The mean EZH2 protein expression for the indicated prostate tissues is summarized using error bars with 95% confidence intervals. FIG. 21*b* shows a Kaplan-Meier analysis demonstrating that patients with clinically localized prostate cancers that have high EZH2 expression (Moderate/Strong staining) have a greater risk for prostate cancer recurrence after prostatectomy (log rank test, p=0.03).

FIG. 22*a* shows an immunoblot analysis of RNA interference using siRNA duplexes targeting the EZH2 sequence in prostate cells. FIG. 22*b* shows that RNA interference of EZH2 decreases cell proliferation as assessed by cell counting assay. FIG. 22*c* shows that RNA interference of EZH2 inhibits cell proliferation as assessed by WST assay. FIG. 22*d* shows that RNA interference of EZH2 induces G2/M arrest of prostate cells.

FIG. 23*a* shows a schematic diagram of EZH2 constructs used in transfection/transcriptome analysis. ER, modified ligand binding domain of estrogen receptor. H-1 and H-2, homology domains 1 and 2 which share similarity between EZH2 and E(z). CYS, cysteine-rich domain. SET, SET domain. TAG, myc-epitope tag. NLS, nuclear localization signal. FIG. 23*b* shows confirmation of expression of EZH2 constructs used in a. An anti-myc antibody was used. FIG. 23*c* shows a cluster diagram of genes that are significantly repressed by EZH2 overexpression. FIG. 23*d* shows SAM analysis of gene expression profiles of EZH2 transfected cells compared against EZH2.5ET transfected cells. FIG. 23*e* shows a model for potential functional interactions of EZH2 as elucidated by transcriptome analysis and placed in the context of previously reported interactions. +, induction. −, repression.

FIG. 29 shows immunoblot analysis of the humoral response of AMACR.

FIG. 29*a* shows an immunoblot analysis of the humoral response to AMACR. FIG. 29*b* shows a control experiment where the humoral response was blocked.

FIG. 31 shows that GP73 protein is upregulated in prostate cancer. FIG. 31*a* shows Western blot analysis of GP73 protein in prostate cancer. FIG. 31*b* shows an immunoblot analysis of the Golgi resident protein Golgin 97.

GENERAL DESCRIPTION

Figure 1:
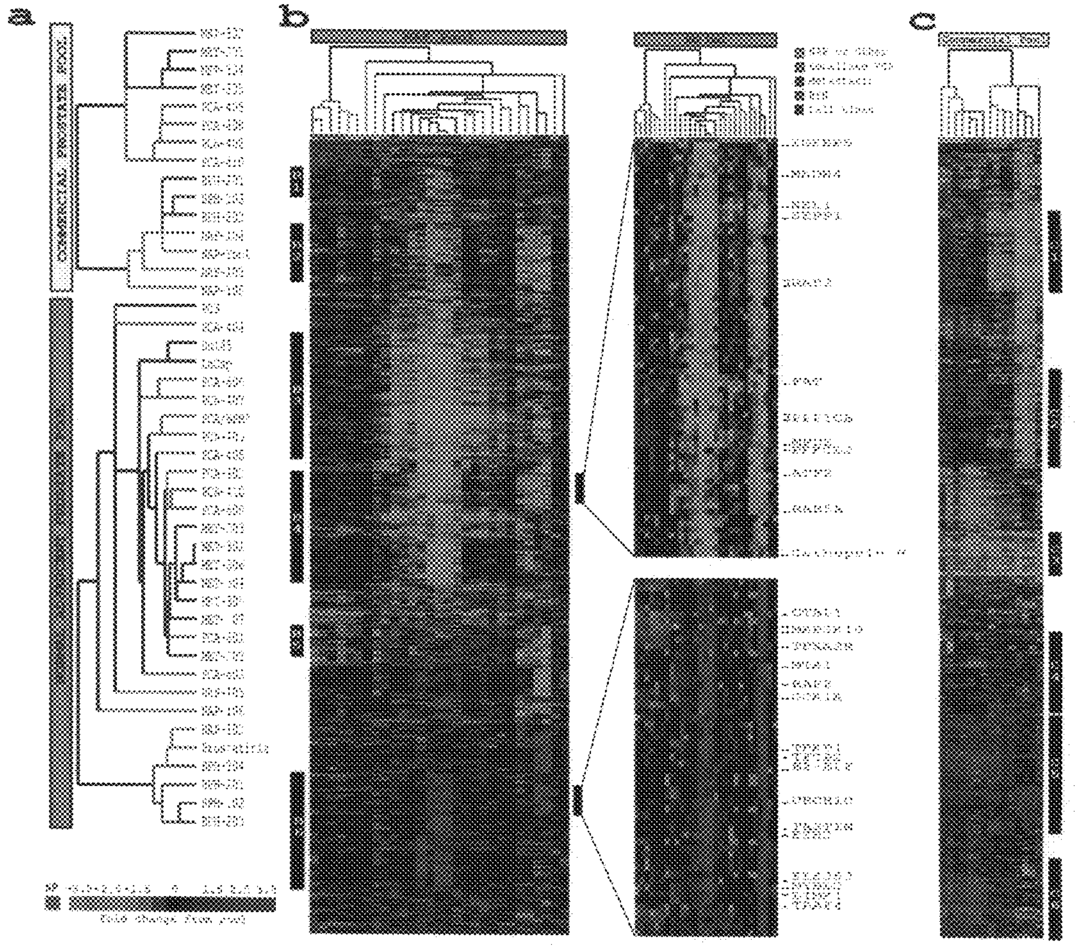
FIG. 1 shows a gene expression profile of prostate cancer samples.

Exploring the molecular circuitry that differentiates indolent PCA from aggressive PCA has the potential to lead to the discovery of prognostic markers and novel therapeutic targets. Insight into the mechanisms of prostate carcinogenesis is also gleaned by such a global molecular approach. Similar to breast cancer (Lopez-Otin and Diamandis, Endor. Rev., 19:365 [1998]), PCA develops in a complex milieu of genetic and environmental factors in which steroid hormone signaling plays a central role. The primary precursor lesion of PCA, high-grade prostatic intraepithelial neoplasia (HG-PIN), has several characteristics similar to other early invasive carcinomas (i.e., chromosomal abnormalities and cytologic features). Loss of specific chromosomal regions (e.g., 8p21, 10q, 13q, 17p) along with losses and mutations of tumor suppressor genes such as Nkx3.1, PTEN, Rb, and p53 have been implicated in the initiation and progression of prostate cancer (Abate-Shen and Shen, supra). With the emergence of global profiling strategies, a systematic analysis of genes involved in PCA is now possible. DNA microarray technology is revolutionizing the way fundamental biological questions are addressed in the post-genomic era. Rather than the traditional approach of focusing on one gene at a time, genomic-scale methodologies allow for a global perspective to be achieved. The power of this approach lies in its ability to comparatively analyze genome-wide patterns of mRNA expression (Brown and Botstein, Nat. Gent., 21:33 [1999]). Obtaining large-scale gene expression profiles of tumors allows for the identification of subsets of genes that function as prognostic disease markers or biologic predictors of therapeutic response (Emmert-Buck et al., Am. J. Pathol., 156:1109 [2000]). Golub et al. used DNA arrays in the molecular classification of acute leukemias (Golub et al., Science 286:531 [1999], demonstrating the feasibility of using microarrays for identifying new cancer classes (class discovery) and for assigning tumors to known classes (class prediction). Using a similar approach, Alizadeh et al. showed that diffuse large B-cell lymphoma could be dissected into two prognostic categories by gene expression profiling (Alizadeh et al., Nature 403:503

[2000]). They provided evidence that lymphomas possessing a gene expression signature characteristic of germinal center B cells had a more favorable prognosis than those expressing genes characteristic of activated peripheral B-cells. Similar large-scale classifications of breast cancer and melanoma have been undertaken, and as with the other studies, molecular classification was the primary focus (Alizadeh et al., supra).

Accordingly, the present invention provides an analysis of gene expression profiles in benign and malignant prostate tissue. Three candidate genes, AMACR, hepsin and pim-1, identified by DNA microarray analysis of PCA, were characterized at the protein level using PCA tissue microarrays. Analysis of the differential gene expression profiles of normal and neoplastic prostate has led to the identification of a select set of genes that define a molecular signature for PCA. The expression profiling experiments of the present invention demonstrate a role for multiple, collaborative gene expression alterations which ultimately manifest as the neoplastic phenotype. By making direct comparative hybridizations of normal and neoplastic tissues, genes that molecularly distinguish benign tissue from malignant are identified.

α-Methylacyl-CoA Racemase (AMACR) is an enzyme that plays an important role in bile acid biosynthesis and β-oxidation of branched-chain fatty acids (Ferdinandusse et al., J. Lipid Res., 41:1890 [2000]; Kotti et al., J. Biol. Chem., 275:20887 [2000]). Mutations of the AMACR gene have been shown to cause adult-onset sensory motor neuropathy (Ferdinandusse et al., Nat. Genet., 24:188 [2000]). In diagnostically challenging prostate biopsy cases, pathologists often employ the basal cell markers 34βE12 or p63, which stain the basal cell layer of benign glands that is not present in malignant glands. Thus, in many biopsy specimens, the pathologist must rely on absence of staining to make the final diagnosis of prostate cancer. Experiments conducted during the development of the present invention identified AMACR as a marker expressed in cancerous biopsy tissue. Thus, the clinical utility of AMACR in prostate needle biopsies is large. For example, at the University of Michigan Medical Center, approximately 400 prostate needle biopsies are performed per year and approximately 20% require the use of a basal-cell specific marker to evaluate difficult lesions, characterized by a small amount of atypical glands. Accordingly, it is contemplated that in combination with basal cell specific markers, such as 34βE12 or p63, screening for AMACR expression by the methods of the present invention results in fewer cases diagnosed as "atypical without a definitive diagnosis."

Identification of the over-expression of AMACR in prostate cancer has clinical utility beyond diagnostic uses. Experiments conducted during the development of the present invention revealed that the only non-cancerous tissue to expresses significant levels of AMACR protein is the human liver. The present invention is not limited to a particular mechanism. Indeed, an understanding of the mechanism in not necessary to practice the present invention. Nonetheless, it is contemplated that AMACR activity is required for prostate cancer growth and by virtue of its specificity serves as a therapeutic target.

Additional experiments conducted during the course of development of the present invention investigated AMACR expression in different groups of prostate cancer, including the aspect of neo-adjuvant hormonal withdrawal in localized disease. AMACR expression was found to be hormone independent in cell culture experiments. PSA, a gene known to be regulated by androgens, demonstrated hormone related alterations in expression under the same conditions. The present invention is not limited to a particular mechanism. Indeed, an understanding of the mechanism is not necessary to practice the present invention. Nonetheless, it is contemplated that these findings provide evidence that AMACR is not regulated by the androgen pathway. It is further contemplated that the decreased AMACR expression in hormone refractory tissue allows the use of AMACR as a biomarker for hormone resistance. It is also contemplated that, given the fact that hormone treatment in the mean of hormonal withdrawal did not affect AMACR expression in the cell culture, that some other mechanism than the androgen pathway is responsible for AMACR downregulation in the integrity of cancer tissue.

The present invention is not limited to a particular mechanism. Indeed, an understanding of the mechanism is not necessary to practice the present invention. Nonetheless, it is contemplated that, alternatively, AMACR is over expressed in the development of cancer, perhaps playing an important role in providing energy for the neoplastic cells. However, as the tumors become de-differentiated, they no longer require these sources of energy. It is contemplated that poorly differentiated tumors may take over other pathways to accomplish this same activity of branched fatty acid oxidation. There is no association with the proliferative rate of the tumor cells and AMACR expression.

AMACR expression was also examined in other cancers. Examination of other tumors demonstrated that colon cancer has the highest AMACR expression. As colorectal cancers are not known to be hormonally regulated, the fact that de-differentiation and decreased AMACR expression were correlated in PCA further supports the hypothesis that de-differentiation leads to decreased AMACR expression in the hormone refractory metastatic PCA. Hormone treatment is also a front line therapy in metastatic prostate cancer but is known to loose efficacy, selecting out hormone insensitive clones. The present invention is not limited to a particular mechanism. Indeed, an understanding of the mechanism is not necessary to practice the present invention. Nonetheless, it is contemplated that this phenomenon explains the observation that strong hormone treatment effect is consistent with decreased AMACR expression due to selection of potentially more de-differentiated cells.

The AMACR gene product is an enzyme, which plays an important role in bile acid biosynthesis and beta-oxidation of branched-chain fatty acids (Kotti et al., J. Biol. Chem. 275: 20887 [2000]; Ferdinandusse et al., J Lipid Res 42:137 [2001]). AMACR over expression occurs in tumors with a high percentage of lipids such as PCA and colorectal cancer. The relationship between fatty acid consumption and cancer is a controversial subject in the development of PCA and colorectal cancer (Moyad, Curr Opin Urol 11:457 [2001]; Willett, Oncologist 5:393 [2000]). An essential role for AMACR in the oxidation of bile acid intermediates has been demonstrated. AMACR encodes an enzyme which catalyzes the racemization of alpha-methyl branched carboxylic coenzyme A thioesters and is localized in peroxisomes and mitochondria (Schmitz et al., Eur J Biochem 231:815 [1995]). The present invention is not limited to a particular mechanism. Indeed, an understanding of the mechanism is not necessary to practice the present invention. Nonetheless, it is contemplated that, as AMACR is involved in the metabolism of lipids, that this leads to alterations in the oxidant balance of a cell. It is further contemplated that these changes are associated with DNA damage, malignant transformation, and other parameters of cell disturbance.

Additional experiments conducted during the course of development of the present invention demonstrated that AMACR mRNA and protein product are over expressed in a number of adenocarcinomas, including colorectal, prostate, breast, and ovarian and melanoma. Adenocarcinoma from the colorectum and prostate demonstrated consistent AMACR over expression (92% and 83% of tumor, respectively). Thus, AMACR is of use in the diagnosis of colonic neoplasia. For example, in some embodiments of the present invention, AMACR is used in the diagnosis of dysplasia. Specifically, in the setting of inflammatory bowel disease (IBD), where the identification of dysplasia may be diagnostically challenging, one evaluates putative lesions for their AMACR protein expression intensity. In some embodiments, this is performed in conjunction with the analysis of the adenomatous polyposis coli gene, since mutations in this gene are also believed to occur early in the development of colorectal neoplasia (Kinzler and Vogelstein, Cell 87:159 [1996]; Tsao and Shibata, Am J Pathol 145: 531 [1994]).

Colonic adenomas (Kinzler and Vogelstein, supra; Tsao and Shibata, supra) and high-grade PIN (McNeal and Bostwick, Hum Pathol 17:64 [1986]; McNeal et al., Lancet 1:60 [1986]) are well know precursors of invasive colonic and prostate cancer, respectively. Experiments conducted during the course of development of the present invention demonstrated that AMACR is over expressed in colorectal adenomas (75%) and high-grade PIN (64%). Further supporting AMACR expression in early neoplastic lesions was the presence of focal AMACR expression in some atrophic prostate lesions. Some atrophic lesions (i.e., proliferative inflammatory atrophy and postatrophic hyperplasia) have recently been recognized as proliferative in nature with molecular alterations suggestive of early neoplastic changes (De Marzo et al., Am J Pathol 155:1985 [1999]; Shah et al., Am J Pathol 158:1767 [2001]). Some morphologically benign prostate glands were also observed to have focal moderate AMACR staining. The present invention is not limited to a particular mechanism. Indeed, an understanding of the mechanism is not necessary to practice the present invention. Nonetheless, it is contemplated that AMACR may have a role in the early steps of cancer development.

Several cancers that are associated with AMACR over expression, including colorectal, prostate and breast cancer, have been linked to high-fat diet. The exact mechanism how high-fat diet contributes to tumorigenesis in these organ systems is unknown, but emerging evidence suggest that peroxisome proliferator activated receptor (PPAR) mediated pathway plays a critical role (Debril et al., J. Mol. Med. 79:30 [2001]). Diet fatty acids have been shown to function as peroxisome proliferators and bind to and activate PPARs (Zomer et al., J. Lipid Res. 41:1801 [2000]), a family of nuclear receptor transcriptional factors. Activation of PPAR mediated pathways in turn control cell proliferation and differentiation. In addition, it can also alter the cellular oxidant balance (Yeldandi et al., Mutat. Res. 448:159 [2000]). The present invention is not limited to a particular mechanism. Indeed, an understanding of the mechanism is not necessary to practice the present invention. Nonetheless, it is contemplated that these effects act in concert to contribute to the tumorigenesis of several cancers. This hypothesis is supported by the findings that peroxisome proliferators, when given to mice, enhance the development colon adenomatous polyps in mice (Saez et al., Nat. Med. 4:1058 [1998]). In addition, PPARs are expressed in several prostate cancer cell lines and their ligands, and peroxisome proliferators, when added to culture, affect the growth of these cell lines (Shappell et al., Cancer Res. 61:497 [2001]; Mueller et al., PNAS 97:10990 [2000]). A phase II clinical trial also showed that troglitazone, a PPARγ activator, could stabilize PSA level in patients with prostate cancer (Kubota et al., Cancer Res. 58:3344 [1998]; Hisatake et al., Cancer Res. 60:5494 [2000]).

AMACR is an involved in the β-oxidation of pristanic acid (Ferdinandusse et al., J. Lipid. Res. 41:1890 [2000]). Pristanic acid can function as a PPAR α activator and promote cell growth (Zomer et al., J. Lipid Res. 41:1801 [2000]). The present invention is not limited to a particular mechanism. Indeed, an understanding of the mechanism is not necessary to practice the present invention. Nonetheless, it is contemplated that hyperfunctioning of β-oxidation pathway leads to exhaustion of reducing molecules and alters the cellular oxidant status (Yeldandi et al., Mutat. Res. 448:159 [2000]).

The present invention further provides methods of targeting AMACR as a therapeutic target in cancer treatment. Over expressed in high percentage of colorectal, prostate, breast and melanoma, but not in adjacent normal tissues, AMACR is targeted using antibody or enzyme inhibitors. Toxicity is expected not to be a major concern because individuals with congenital absence of this enzyme have no or insignificant clinical manifestations (Clayton et al., Biochem. Soc. Trans. 29:298 [2001]).

Experiments conducted during the course of development of the present invention further demonstrated that AMACR is present in the serum of prostate cancer patients. In addition, a humoral response to AMACR was identified based on the presence of antibodies to AMACR in the serum of prostate cancer patients.

Annexins are a group of structurally related calcium-binding proteins, which have a domain that binds to phospholipids and an amino terminal domain that determines specificity (Smith et al., Trends. Genet. 10:241 [1994]; Mailliard et al., J. Biol. Chem. 271:719 [1996]). The annexins are involved in regulation of membrane trafficking, cellular adhesion and possible tumorigenesis. Experiments conducted during the course of development of the present invention used cDNA microarrays to study the expression patterns of multiple annexin family members in a wide range of prostate tissue samples in order to determine their role in PCA progression. Meta-analysis of gene expression data was employed to help further validate the cDNA expression array findings. Finally, high-density tissue microarrays were used to assess annexin protein expression levels by immunohistochemistry.

Eight annexins were evaluated for their mRNA expression levels in benign prostatic tissue, localized hormone naïve PCA and metastatic hormone refractory PCA samples. Five annexins (1, 2, 4, 7, and 11) demonstrated a progressive down regulation at the transcript level going from benign prostatic tissue to localized PCA to hormone refractory PCA. In order to validate the cDNA expression array finding of these 5 annexin family members, a meta-analysis was performed, which confirmed that when looking across 4 studies where at least two studies reported results, annexin 1, 2, 4, and 6 were significantly down regulated in localized PCA samples when compared to benign prostatic tissue. Therefore the meta-analysis confirmed results on annexin 1, 2, and 4. In these examples, summary statistics across all datasets found these annexins to be significantly down regulated at the cDNA level. However, not all of the 4 studies had significant down-regulation. Annexin 4, for example, was significantly down regulated in two of four studies but the resultant summary statistic, which also takes into account the number of samples evaluated, was statistically significant. Annexins 7, 8, and 13 were not found to be significantly under expressed. As demonstrated in FIG. 1, annexin 7 does decrease significantly when comparing localized PCA and metastatic PCA.

The protein expression levels of all above five annexins tested were statistically significantly decreased in hormone refractory PCA samples when compared to either localized PCA or benign prostate tissue. Four of 5 annexins also demonstrated a decrease in protein expression in clinically localized PCA as compared to benign prostate tissue. However, in none of these cases was the protein expression found to be significantly decreased. This second validation method at the protein level confirmed the cDNA expression array data for annexin 1, 2, 4, 7, and 11.

Based on gene expression array data described herein, localized PCA cells down regulate their mRNA levels of annexins but maintained the corresponding protein expression levels. The present invention is not limited to a particular mechanism. Indeed, an understanding of the mechanism is not necessary to practice the present invention. Nonetheless, it is contemplated that post-translational alteration may compensate for decrease mRNA, producing enough protein to maintain levels seen with benign samples. Since annexins play an important role in maintaining cellular adhesion, once the cells eventually lose this ability, tumor progression may occur. Therefore, as one might anticipate, annexin expression levels decreased significantly in the advanced hormone refractory PCA samples. This was confirmed at the protein level by significant decreases as demonstrated by immunohistochemistry.

A sequential down-regulation of annexins in both transcriptional and translational levels in metastatic PCA samples was observed. Annexin I, also called lipocortin, has been described as a phospholipase A2 inhibitor, and served as a substrate of epidermal growth factor receptor (Pepinsky et al., Nature 321:81 [1986]; Wallner et al., Nature 320:77 [1986]). The significant reduction of protein level has been shown in esophageal and prostate tumor cells (Paweletz et al., Cancer Res. 60:6293 [2000]). Annexin 2, also called p36, appears an efficient substrate of protein kinase C and Src pp60 (Hubaishy et al., Biochemistry 34:14527 [1995]). Annexin 4, called endonexin, regulates Cl-flux by mediating calmodulin kinase II (CaMKII) activity (Chan et al., J. Biol. Chem. 269:32464 [1994]). Annexin 7, synexin, is involved in Duchenne's muscular dystrophy (Selbert et al. Exp. Cell. Res. 222:199 [1996]). Its gene is located on human chromosome 10q21, and its protein expression was decreased in hormone refractory tumor cells. In conclusion, the results of experiments conducted during the course of development of the present invention suggest that down regulation of several annexin family members may play a role in the development of the lethal PCA phenotype.

Additional experiments conducted during the course of development of the present invention identified additional markers that exhibited altered (e.g., increased or decreased) expression in prostate cancer. Additional markers include, but are not limited to, EZH2, Annexins 1, 2, 4, 7, and 11, CTBP 1 and 2, GP73, ABCC5 (MDR5), ASNS, TOP2A, and Vav2. In particular, EZH2 was identified as a marker that was overexpressed in prostate cancer, and in particular, in metastatic prostate cancer. EZH2 was further identified as being correlated with clinical failure (e.g., increased PSA levels). In addition, siRNA inhibition of EZH2 resulted in a decrease in cell proliferation of a prostate cancer cell line.

The present invention thus identifies markers and targets for diagnostic and therapeutic agents in a variety of cancers.

DEFINITIONS

To facilitate an understanding of the present invention, a number of terms and phrases are defined below:

The term "epitope" as used herein refers to that portion of an antigen that makes contact with a particular antibody.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received an initial diagnosis (e.g., a CT scan showing a mass or increased PSA level) but for whom the stage of cancer is not known. The term further includes people who once had cancer (e.g., an individual in remission).

As used herein, the term "subject at risk for cancer" refers to a subject with one or more risk factors for developing a specific cancer. Risk factors include, but are not limited to, gender, age, genetic predisposition, environmental expose, previous incidents of cancer, preexisting non-cancer diseases, and lifestyle.

As used herein, the term "characterizing cancer in subject" refers to the identification of one or more properties of a cancer sample in a subject, including but not limited to, the presence of benign, pre-cancerous or cancerous tissue, the stage of the cancer, and the subject's prognosis. Cancers may be characterized by the identification of the expression of one or more cancer marker genes, including but not limited to, the cancer markers disclosed herein.

As used herein, the term "characterizing prostate tissue in a subject" refers to the identification of one or more properties of a prostate tissue sample (e.g., including but not limited to, the presence of cancerous tissue, the presence of pre-cancerous tissue that is likely to become cancerous, and the presence of cancerous tissue that is likely to metastasize). In some embodiments, tissues are characterized by the identification of the expression of one or more cancer marker genes, including but not limited to, the cancer markers disclosed herein.

As used herein, the term "cancer marker genes" refers to a gene whose expression level, alone or in combination with other genes, is correlated with cancer or prognosis of cancer.

The correlation may relate to either an increased or decreased expression of the gene. For example, the expression of the gene may be indicative of cancer, or lack of expression of the gene may be correlated with poor prognosis in a cancer patient. Cancer marker expression may be characterized using any suitable method, including but not limited to, those described in illustrative Examples 1-15 below.

As used herein, the term "a reagent that specifically detects expression levels" refers to reagents used to detect the expression of one or more genes (e.g., including but not limited to, the cancer markers of the present invention). Examples of suitable reagents include but are not limited to, nucleic acid probes capable of specifically hybridizing to the gene of interest, PCR primers capable of specifically amplifying the gene of interest, and antibodies capable of specifically binding to proteins expressed by the gene of interest. Other non-limiting examples can be found in the description and examples below.

As used herein, the term "detecting a decreased or increased expression relative to non-cancerous prostate control" refers to measuring the level of expression of a gene (e.g., the level of mRNA or protein) relative to the level in a non-cancerous prostate control sample. Gene expression can be measured using any suitable method, including but not limited to, those described herein.

As used herein, the term "detecting a change in gene expression (e.g., hepsin, pim-1, EZH2, or AMACR) in said prostate cell sample in the presence of said test compound relative to the absence of said test compound" refers to measuring an altered level of expression (e.g., increased or decreased) in the presence of a test compound relative to the absence of the test compound. Gene expression can be measured using any suitable method, including but not limited to, those described in Examples 1-15 below.

As used herein, the term "instructions for using said kit for detecting cancer in said subject" includes instructions for using the reagents contained in the kit for the detection and characterization of cancer in a sample from a subject. In some embodiments, the instructions further comprise the statement of intended use required by the U.S. Food and Drug Administration (FDA) in labeling in vitro diagnostic products. The FDA classifies in vitro diagnostics as medical devices and requires that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use. Where applicable, photographs or engineering drawings should be supplied; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; 8) Any additional information regarding the in vitro diagnostic product requested that is necessary for the FDA to make a substantial equivalency determination. Additional information is available at the Internet web page of the U.S. FDA.

As used herein, the term "prostate cancer expression profile map" refers to a presentation of expression levels of genes in a particular type of prostate tissue (e.g., primary, metastatic, and pre-cancerous prostate tissues). The map may be presented as a graphical representation (e.g., on paper or on a computer screen), a physical representation (e.g., a gel or array) or a digital representation stored in computer memory. Each map corresponds to a particular type of prostate tissue (e.g., primary, metastatic, and pre-cancerous) and thus provides a template for comparison to a patient sample. In preferred embodiments, maps are generated from pooled samples comprising tissue samples from a plurality of patients with the same type of tissue.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "stage of cancer" refers to a qualitative or quantitative assessment of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

As used herein, the term "providing a prognosis" refers to providing information regarding the impact of the presence of cancer (e.g., as determined by the diagnostic methods of the present invention) on a subject's future health (e.g., expected morbidity or mortality, the likelihood of getting cancer, and the risk of metastasis).

As used herein, the term "prostate specific antigen failure" refers to the development of high prostate specific antigen levels in a patient following prostate cancer therapy (e.g., surgery). See Examples 3 and 4 for examples of how prostate specific antigen failure is determined. As used herein, the term "risk of developing prostate specific antigen failure" refers to a subject's relative risk (e.g., the percent chance or a relative score) of developing prostate specific antigen failure following prostate cancer therapy.

As used herein, the term "post surgical tumor tissue" refers to cancerous tissue (e.g., prostate tissue) that has been removed from a subject (e.g., during surgery).

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention.

As used herein, the term "initial diagnosis" refers to results of initial cancer diagnosis (e.g. the presence or absence of cancerous cells). An initial diagnosis does not include information about the stage of the cancer of the risk of prostate specific antigen failure.

As used herein, the term "biopsy tissue" refers to a sample of tissue (e.g., prostate tissue) that is removed from a subject for the purpose of determining if the sample contains cancerous tissue. In some embodiment, biopsy tissue is obtained because a subject is suspected of having cancer. The biopsy tissue is then examined (e.g., by microscopy) for the presence or absence of cancer.

As used herein, the term "inconclusive biopsy tissue" refers to biopsy tissue for which histological examination has not determined the presence or absence of cancer.

As used herein, the term "basal cell marker" refers to a marker (e.g., an antibody) that binds to proteins present in the basal cell layer of benign prostate glands. Exemplary basal cell markers include, but are not limited to, 34βE12 and p63 (See e.g., O'Malley et al., Virchows Arch. Pathol. Anat. Histopathol., 417:191 [1990]; Wojno et al., Am. J. Surg. Pathol., 19:251 [1995]; Googe et al., Am. J. Clin. Pathol., 107:219 [1997]; Parsons et al., Urology 58:619; and Signoretti et al., Am. J. Pathol., 157:1769 [2000]).

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N-6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple. RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m$=81.5+0.41(% G+C), when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under "medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 μg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., Proc. Natl. Acad. Sci. USA 69:3038 [1972]). Other nucleic acids will not be replicated by this amplification enzyme. Similarly, in the case of T7 RNA polymerase, this amplification enzyme has a stringent specificity for its own promoters (Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target." In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to at least a portion of another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein, the term "target," refers to the region of nucleic acid bounded by the primers. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}P$-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., Molecular Cloning: A Laboratory Manual, Cold Spring Harbor Press, NY, pp 9.31-9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with $tk^-$ cell lines, the CAD gene that is used in conjunction with CAD-deficient cells and the mammalian hypoxanthine-guanine phosphoribosyl transferase (hprt) gene that is used in conjunction with $hprt^-$ cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention. In some embodiments of the present invention, test compounds include antisense compounds.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

DETAILED DESCRIPTION OF THE INVENTION

The present invention relates to compositions and methods for cancer diagnostics, including but not limited to, cancer markers. In particular, the present invention provides gene expression profiles associated with prostate cancers. Accordingly, the present invention provides method of characterizing prostate tissues, kits for the detection of markers, as well as drug screening and therapeutic applications.

I. Markers for Prostate Cancer

The present invention provides markers whose expression is specifically altered in cancerous prostate tissues. Such markers find use in the diagnosis and characterization of prostate cancer.

A. Identification of Markers

Experiments conducted during the development of the present invention resulted in the identification of genes whose expression level was altered (e.g., increased or decreased) in PCA. The methods utilized glass slide cDNA microarrays that included approximately 5000 known, named genes, 4400 ESTs, and 500 control elements, as well as normal and cancerous prostate tissue. Differentially expressed genes were divided into functional clusters. The expression of relevant genes was confirmed using Western blot analysis. Protein expression in prostate tissues was measured for several genes of interest.

The methods of the present invention (See e.g., Example 2) were used to identify clusters of genes that were up or down regulated in PCA, benign prostate tissue, pre-cancerous tissue, and normal prostate. From these clusters, two genes, hepsin and pim-1 were identified as genes that were of particular relevance. Immunohistochemistry (See e.g., Example 4) was used to characterize the presence of hepsin and pim-1 proteins in prostate tissue. Hepsin was found to stain strongly in pre-cancerous tissue (HG-PIN). In addition, hepsin was found to stain less strongly in PCA tissues of men found to have an increased risk of metastasis as measured by PSA failure (increased PSA following surgery), thus confirming the diagnostic utility of hepsin. In addition, deceased expression of pim-1 in PCA tissue was also found to be associated with increased risk of PSA failure. Accordingly, in some embodiments, the present invention provides methods of detecting and characterizing prostate tissues.

The methods of the present invention identified a further gene, alpha-methyl-CoA racemase (AMACR), that was found to be expressed in PCA, but not benign prostate tissue (See e.g., Example 5). AMACR was found to be present in the serum and urine of prostate or bladder cancer patients. In addition, a humoral response to AMACR was identified. In still further embodiments, the methods of the present invention were used to characterize the EZH2 gene. EZH2 was found to be up-regulated in metastatic prostate cancer. The inhibition of EZH2 expression in prostate cells inhibited cell proliferation in vitro, as well as inducing transcriptional repression of a variety of genes. The methods of the present invention further identified CtBP1 and CTBP2, as well as that GP73 as being over-expressed in metastatic prostate cancer relative to localized prostate cancer and benign tissue.

In still further embodiments, the methods of the present invention identified annexins 1, 2, 4, 7 and 11 as being significantly decreased in hormone refractory PCA when compared to localized hormone naïve Pca. Tissue microarray analysis revealed a significant decrease in protein expression for annexins 1, 2, 4, 7 and 11 in hormone refractory PCA as compared to localized Pca. No significant differences were detected between the clinically localized PCA and non-cancerous prostate tissues.

B. Detection of Markers

In some embodiments, the present invention provides methods for detection of expression of cancer markers (e.g., prostate cancer markers). In preferred embodiments, expression is measured directly (e.g., at the RNA or protein level). In some embodiments, expression is detected in tissue samples (e.g., biopsy tissue). In other embodiments, expression is detected in bodily fluids (e.g., including but not limited to, plasma, serum, whole blood, mucus, and urine). The present invention further provides panels and kits for the detection of markers. In preferred embodiments, the presence of a cancer marker is used to provide a prognosis to a subject. For example, the detection of hepsin or pim-1 in prostate tissues is indicative of a cancer that is likely to metastasize and the expression of hepsin is indicative of a pre-cancerous tissue that is likely to become cancerous. In addition, the expression of AMACR is indicative of cancerous tissue. The information provided is also used to direct the course of treatment. For example, if a subject is found to have a marker indicative of a highly metastasizing tumor, additional therapies (e.g., hormonal or radiation therapies) can be started at a earlier point when they are more likely to be effective (e.g., before metastasis). In addition, if a subject is found to have a tumor that is not responsive to hormonal therapy, the expense and inconvenience of such therapies can be avoided.

The present invention is not limited to the markers described above. Any suitable marker that correlates with cancer or the progression of cancer may be utilized, including but not limited to, those described in the illustrative examples below (e.g., FKBP5, FASN, FOLH1, TNFSF10, PCM1, S100A11, IGFBP3, SLUG, GSTM3, ATF2, RAB5A, IL1R2, ITGB4, CCND2, EDNRB, APP, THROMBOSPONDIN 1, ANNEXIN A1, EPHA1, NCK1, MAPK6, SGK, HEVIN, MEIS2, MYLK, FZD7, CAVEOLIN 2, TACC1, ARHB, PSG9, GSTM1, KERATIN 5, TIMP2, GELSOLIN, ITM2C, GSTM5, VINCULIN, FHL1, GSTP1, MEIS1, ETS2, PPP2CB, CATHEPSIN B, CATHEPSIN H, COL1A2, RIG, VIMENTIN, MOESIN, MCAM, FIBRONECTIN 1, NBL1, ANNEXIN A4, ANEXIN A11, IL1R1, IGFBP5, CYSTATIN C, COL15A1, ADAMTS1, SKI, EGR1, FOSB, CFLAR, JUN, YWHAB, NRAS, C7, SCYA2, ITGA1, LUMICAN, CIS, C4BPA, COL3A1, FAT, MMECD10, CLUSTERIN, PLA2G2A, MADh4, SEPP1, RAB2, PP1CB, MPDZ, PRKCL2, CTBP1, CTBP2, MAP3K10, TBXA2F, MTA1, RAP2, TRAP1, TFCP2, E2EPF, UBCH10, TASTIN, EZH2, FLS353, MYBL2, LIMK1, GP73, VAV2, TOP2A, ASNS, CTBP, AMACR, ABCC5 (MDR5), and TRAF4. Additional markers are also contemplated to be within the scope of the present invention. Any suitable method may be utilized to identify and characterize cancer markers suitable for use in the methods of the present invention, including but not limited to, those described in illustrative Examples 1-15 below. For example, in some embodiments, markers identified as being up or down-regulated in PCA using the gene expression microarray methods of the present invention are further characterized using tissue microarray, immunohistochemistry, Northern blot analysis, siRNA or antisense RNA inhibition, mutation analysis, investigation of expression with clinical outcome, as well as other methods disclosed herein.

In some embodiments, the present invention provides a panel for the analysis of a plurality of markers. The panel allows for the simultaneous analysis of multiple markers correlating with carcinogenesis and/or metastasis. For example, a panel may include markers identified as correlating with cancerous tissue, metastatic cancer, localized cancer that is likely to metastasize, pre-cancerous tissue that is likely to become cancerous, and pre-cancerous tissue that is not likely to become cancerous. Depending on the subject, panels may be analyzed alone or in combination in order to provide the best possible diagnosis and prognosis. Markers for inclusion on a panel are selected by screening for their predictive value using any suitable method, including but not limited to, those described in the illustrative examples below.

In other embodiments, the present invention provides an expression profile map comprising expression profiles of cancers of various stages or prognoses (e.g., likelihood of future metastasis). Such maps can be used for comparison with patient samples. In some embodiments comparisons are made using the method described in Example 2. However, the present invention is not limited to the method described in Example 2. Any suitable method may be utilized, including but not limited to, by computer comparison of digitized data. The comparison data is used to provide diagnoses and/or prognoses to patients.

1. Detection of RNA

In some preferred embodiments, detection of prostate cancer markers (e.g., including but not limited to, those disclosed herein) is detected by measuring the expression of corresponding mRNA in a tissue sample (e.g., prostate tissue). mRNA expression may be measured by any suitable method, including but not limited to, those disclosed below.

In some embodiments, RNA is detection by Northern blot analysis. Northern blot analysis involves the separation of RNA and hybridization of a complementary labeled probe. An exemplary method for Northern blot analysis is provided in Example 3.

In other embodiments, RNA expression is detected by enzymatic cleavage of specific structures (INVADER assay, Third Wave Technologies; See e.g., U.S. Pat. Nos. 5,846,717, 6,090,543; 6,001,567; 5,985,557; and 5,994,069; each of which is herein incorporated by reference). The INVADER assay detects specific nucleic acid (e.g., RNA) sequences by using structure-specific enzymes to cleave a complex formed by the hybridization of overlapping oligonucleotide probes.

In still further embodiments, RNA (or corresponding cDNA) is detected by hybridization to a oligonucleotide probe). A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

2. Detection of Protein

In other embodiments, gene expression of cancer markers is detected by measuring the expression of the corresponding protein or polypeptide. Protein expression may be detected by any suitable method. In some embodiments, proteins are detected by the immunohistochemistry method of Example 4.

In other embodiments, proteins are detected by their binding to an antibody raised against the protein. The generation of antibodies is described below.

Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to cancer markers is utilized.

In other embodiments, the immunoassay described in U.S. Pat. Nos. 5,599,677 and 5,672,480; each of which is herein incorporated by reference.

3. Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., likelihood of metastasis or PSA failure) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

4. Kits

In yet other embodiments, the present invention provides kits for the detection and characterization of prostate cancer. In some embodiments, the kits contain antibodies specific for a cancer marker, in addition to detection reagents and buffers. In other embodiments, the kits contain reagents specific for the detection of mRNA or cDNA (e.g., oligonucleotide probes or primers). In preferred embodiments, the kits contain all of the components necessary to perform a detection assay, including all controls, directions for performing assays, and any necessary software for analysis and presentation of results.

5. In Vivo Imaging

In some embodiments, in vivo imaging techniques are used to visualize the expression of cancer markers in an animal (e.g., a human or non-human mammal). For example, in some embodiments, cancer marker mRNA or protein is labeled using an labeled antibody specific for the cancer marker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the cancer markers of the present invention are described below.

The in vivo imaging methods of the present invention are useful in the diagnosis of cancers that express the cancer markers of the present invention (e.g., prostate cancer). In vivo imaging is used to visualize the presence of a marker indicative of the cancer. Such techniques allow for diagnosis without the use of an unpleasant biopsy. The in vivo imaging methods of the present invention are also useful for providing prognoses to cancer patients. For example, the presence of a marker indicative of cancers likely to metastasize can be detected. The in vivo imaging methods of the present invention can further be used to detect metastatic cancers in other parts of the body.

In some embodiments, reagents (e.g., antibodies) specific for the cancer markers of the present invention are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107, herein incorporated by reference).

In other embodiments, antibodies are radioactively labeled. The use of antibodies for in vivo diagnosis is well known in the art. Sumerdon et al., (Nucl. Med. Biol 17:247-254 [1990] have described an optimized antibody-chelator for the radioimmunoscintographic imaging of tumors using Indium-111 as the label. Griffin et al., (J Clin One 9:631-640 [1991]) have described the use of this agent in detecting tumors in patients suspected of having recurrent colorectal cancer. The use of similar agents with paramagnetic ions as labels for magnetic resonance imaging is known in the art (Lauffer, Magnetic Resonance in Medicine 22:339-342 [1991.]). The label used will depend on the imaging modality chosen. Radioactive labels such as Indium-11, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetium-99m (6 hours), and indium-111 (3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 [1980]) for In-11 and Tc-99m, and by Scheinberg et al. (Science 215:1511 [1982]). Other chelating agents may also be used, but the 1-(p-carboxymethoxybenzyl) EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 [1982]) for labeling of albumin with In-111, but which can be adapted for labeling of antibodies. A suitable method of labeling antibodies with Tc-99m which does not use chelation with DPTA is the pretinning method of Crockford et al., (U.S. Pat. No. 4,323,546, herein incorporated by reference).

A preferred method of labeling immunoglobulins with Tc-99m is that described by Wong et al. (Int. J. Appl. Radiat. Isot., 29:251 [1978]) for plasma protein, and recently applied successfully by Wong et al. (J. Nucl. Med., 23:229 [1981]) for labeling antibodies.

In the case of the radiometals conjugated to the specific antibody, it is likewise desirable to introduce as high a proportion of the radiolabel as possible into the antibody molecule without destroying its immunospecificity. A further improvement may be achieved by effecting radiolabeling in the presence of the specific cancer marker of the present invention, to insure that the antigen binding site on the antibody will be protected. The antigen is separated after labeling.

In still further embodiments, in vivo biophotonic imaging (Xenogen, Almeda, Calif.) is utilized for in vivo imaging. This real-time in vivo imaging utilizes luciferase. The luciferase gene is incorporated into cells, microorganisms, and animals (e.g., as a fusion protein with a cancer marker of the present invention). When active, it leads to a reaction that emits light. A CCD camera and software is used to capture the image and analyze it.

II. Antibodies

The present invention provides isolated antibodies. In preferred embodiments, the present invention provides monoclonal antibodies that specifically bind to an isolated polypeptide comprised of at least five amino acid residues of the cancer markers described herein (e.g., hepsin, pim-1, AMACR, EZH2, CTBP). These antibodies find use in the diagnostic methods described herein.

An antibody against a protein of the present invention may be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 [1975]). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30C to about 37° C. for about 1 minute to 10 minutes.

Various methods may be used for screening for a hybridoma producing the antibody (e.g., against a tumor antigen or autoantibody of the present invention). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody (e.g., against a cancer marker of the present invention) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, a cancer marker of the present invention (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

III. Drug Screening

In some embodiments, the present invention provides drug screening assays (e.g., to screen for anticancer drugs). The screening methods of the present invention utilize cancer markers identified using the methods of the present invention (e.g., including but not limited to, hepsin, pim-1, AMACR, EZH2, and CTBP). For example, in some embodiments, the present invention provides methods of screening for compound that alter (e.g., increase or decrease) the expression of cancer marker genes. In some embodiments, candidate compounds are antisense agents (e.g., oligonucleotides) directed against cancer markers. See Section IV below for a discussion of antisense therapy. In other embodiments, candidate compounds are antibodies that specifically bind to a cancer marker of the present invention.

In one screening method, candidate compounds are evaluated for their ability to alter cancer marker expression by contacting a compound with a cell expressing a cancer marker and then assaying for the effect of the candidate compounds on expression. In some embodiments, the effect of candidate compounds on expression of a cancer marker gene is assayed for by detecting the level of cancer marker mRNA expressed by the cell. mRNA expression can be detected by any suitable method. In other embodiments, the effect of candidate compounds on expression of cancer marker genes is assayed by measuring the level of polypeptide encoded by the cancer markers. The level of polypeptide expressed can be measured using any suitable method, including but not limited to, those disclosed herein.

Specifically, the present invention provides screening methods for identifying modulators, i.e., candidate or test compounds or agents (e.g., proteins, peptides, peptidomimetics, peptoids, small molecules or other drugs) which bind to cancer markers of the present invention, have an inhibitory (or stimulatory) effect on, for example, cancer marker expression or cancer markers activity, or have a stimulatory or inhibitory effect on, for example, the expression or activity of a cancer marker substrate. Compounds thus identified can be used to modulate the activity of target gene products (e.g., cancer marker genes) either directly or indirectly in a therapeutic protocol, to elaborate the biological function of the target gene product, or to identify compounds that disrupt normal target gene interactions. Compounds which inhibit the activity or expression of cancer markers are useful in the treatment of proliferative disorders, e.g., cancer, particularly metastatic (e.g., androgen independent) prostate cancer.

In one embodiment, the invention provides assays for screening candidate or test compounds that are substrates of a cancer markers protein or polypeptide or a biologically active portion thereof. In another embodiment, the invention provides assays for screening candidate or test compounds that bind to or modulate the activity of a cancer marker protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364: 555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249: 404-406 [1990]; Cwirla et al., Proc. Natl. Acad. Sci. 87:6378-6382 [1990]; Felici, J. Mol. Biol. 222:301 [1991]).

In one embodiment, an assay is a cell-based assay in which a cell that expresses a cancer marker protein or biologically active portion thereof is contacted with a test compound, and the ability of the test compound to the modulate cancer marker's activity is determined. Determining the ability of the test compound to modulate cancer marker activity can be accomplished by monitoring, for example, changes in enzymatic activity. The cell, for example, can be of mammalian origin.

The ability of the test compound to modulate cancer marker binding to a compound, e.g., a cancer marker substrate, can also be evaluated. This can be accomplished, for example, by coupling the compound, e.g., the substrate, with a radioisotope or enzymatic label such that binding of the compound, e.g., the substrate, to a cancer marker can be determined by detecting the labeled compound, e.g., substrate, in a complex.

Alternatively, the cancer marker is coupled with a radioisotope or enzymatic label to monitor the ability of a test compound to modulate cancer marker binding to a cancer markers substrate in a complex. For example, compounds (e.g., substrates) can be labeled with $^{125}I$, $^{35}S$ $^{14}C$ or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a cancer marker substrate) to interact with a cancer marker with or without the labeling of any of the interactants can be evaluated. For example, a microphysiorneter can be used to detect the interaction of a compound with a cancer marker without the labeling of either the compound or the cancer marker (McConnell et al. Science 257:1906-1912 [1992]). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and cancer markers.

In yet another embodiment, a cell-free assay is provided in which a cancer marker protein or biologically active portion thereof is contacted with a test compound and the ability of the test compound to bind to the cancer marker protein or biologically active portion thereof is evaluated. Preferred biologically active portions of the cancer markers proteins to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in 15 the assay should be maximal. An FRET binding event can be conveniently measured through standard fluorometric detection means well known in the art (e.g., using a fluorimeter).

In another embodiment, determining the ability of the cancer markers protein to bind to a target molecule can be accomplished using real-time Biomolecular Interaction Analysis (BIA) (see, e.g., Sjolander and Urbaniczky, Anal. Chem. 63:2338-2345 [1991] and Szabo et al. Curr. Opin. Struct. Biol. 5:699-705 [1995]). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize cancer markers, an anti-cancer marker antibody or its target molecule to facilitate separation of complexed from non-complexed forms of one or both of the proteins, as well as to accommodate automation of the assay. Binding of a test compound to a cancer marker protein, or interaction of a cancer marker protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase-cancer marker fusion proteins or glutathione-S-transferase/target fusion proteins can be adsorbed onto glutathione Sepharose beads (Sigma Chemical, St. Louis, Mo.) or glutathione-derivatized microtiter plates, which are then combined with the test compound or the test compound and either the non-adsorbed target protein or cancer marker protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Alternatively, the complexes can be dissociated from the matrix, and the level of cancer markers binding or activity determined using standard techniques. Other techniques for immobilizing either cancer markers protein or a target molecule on matrices include using conjugation of biotin and streptavidin. Biotinylated cancer marker protein or target molecules can be prepared from biotin-NHS(N-hydroxy-succinimide) using techniques known in the art (e.g., biotinylation kit, Pierce Chemicals, Rockford, EL), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with cancer marker protein or target molecules but which do not interfere with binding of the cancer markers protein to its target molecule. Such antibodies can be derivatized to the wells of the plate, and unbound target or cancer markers protein trapped in the wells by antibody conjugation. Methods for detecting such complexes, in addition to those described above for the GST-immobilized complexes, include immunodetection of complexes using antibodies reactive with the cancer marker protein or target molecule, as well as enzyme-linked assays which rely on detecting an enzymatic activity associated with the cancer marker protein or target molecule.

Alternatively, cell free assays can be conducted in a liquid phase. In such an assay, the reaction products are separated from unreacted components, by any of a number of standard techniques, including, but not limited to: differential centrifugation (see, for example, Rivas and Minton, Trends Biochem Sci 18:284-7 [1993]); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel et al., eds. Current Protocols in Molecular Biology 1999, J. Wiley: New York). Such resins and chromatographic techniques are known to one skilled in the art (See e.g., Heegaard J. Mol. Recognit 11:141-8 [1998]; Hageand Tweed J. Chromatogr. Biomed. Sci. Appl 699:499-525 [1997]). Further, fluorescence energy transfer may also be conveniently utilized, as described herein, to detect binding without further purification of the complex from solution.

The assay can include contacting the cancer markers protein or biologically active portion thereof with a known compound that binds the cancer marker to form an assay mixture, contacting the assay mixture with a test compound, and determining the ability of the test compound to interact with a cancer marker protein, wherein determining the ability of the test compound to interact with a cancer marker protein includes determining the ability of the test compound to preferentially bind to cancer markers or biologically active portion thereof, or to modulate the activity of a target molecule, as compared to the known compound.

To the extent that cancer markers can, in vivo, interact with one or more cellular or extracellular macromolecules, such as proteins, inhibitors of such an interaction are useful. A homogeneous assay can be used can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, cancer markers protein can be used as a "bait protein" in a two-hybrid assay or three-hybrid assay (see, e.g., U.S. Pat. No. 5,283,317; Zervos et al., Cell 72:223-232 [1993]; Madura et al., J. Biol. Chem. 268.12046-12054 [1993]; Bartel et al., Biotechniques 14:920-924 [1993]; Iwabuchi et al., Oncogene 8:1693-1696 [1993]; and Brent W0 94/10300; each of which is herein incorporated by reference), to identify other proteins, that bind to or interact with cancer markers ("cancer marker-binding proteins" or "cancer marker-bp") and are involved in cancer marker activity. Such cancer marker-bps can be activators or inhibitors of signals by the cancer marker proteins or targets as, for example, downstream elements of a cancer markers-mediated signaling pathway.

Modulators of cancer markers expression can also be identified. For example, a cell or cell free mixture is contacted with a candidate compound and the expression of cancer marker mRNA or protein evaluated relative to the level of expression of cancer marker mRNA or protein in the absence of the candidate compound. When expression of cancer marker mRNA or protein is greater in the presence of the candidate compound than in its absence, the candidate compound is identified as a stimulator of cancer marker mRNA or protein expression. Alternatively, when expression of cancer marker mRNA or protein is less (i.e., statistically significantly less) in the presence of the candidate compound than in its absence, the candidate compound is identified as an inhibitor of cancer marker mRNA or protein expression. The level of cancer markers mRNA or protein expression can be determined by methods described herein for detecting cancer markers mRNA or protein.

A modulating agent can be identified using a cell-based or a cell free assay, and the ability of the agent to modulate the activity of a cancer markers protein can be confirmed in vivo, e.g., in an animal such as an animal model for a disease (e.g., an animal with prostate cancer or metastatic prostate cancer; or an animal harboring a xenograft of a prostate cancer from an animal (e.g., human) or cells from a cancer resulting from metastasis of a prostate cancer (e.g., to a lymph node, bone, or liver), or cells from a prostate cancer cell line.

This invention further pertains to novel agents identified by the above-described screening assays (See e.g., below description of cancer therapies). Accordingly, it is within the scope of this invention to further use an agent identified as described herein (e.g., a cancer marker modulating agent, an antisense cancer marker nucleic acid molecule, a siRNA molecule, a cancer marker specific antibody, or a cancer marker-binding partner) in an appropriate animal model (such as those described herein) to determine the efficacy, toxicity, side effects, or mechanism of action, of treatment with such an agent. Furthermore, novel agents identified by the above-described screening assays can be, e.g., used for treatments as described herein.

IV. Cancer Therapies

In some embodiments, the present invention provides therapies for cancer (e.g., prostate cancer). In some embodiments, therapies target cancer markers (e.g., including but not limited to, hepsin, pim-1, AMACR, EZH2, and CTBP).

A. Antisense Therapies

In some embodiments, the present invention targets the expression of cancer markers. For example, in some embodiments, the present invention employs compositions comprising oligomeric antisense compounds, particularly oligonucleotides (e.g., those identified in the drug screening methods described above), for use in modulating the function of nucleic acid molecules encoding cancer markers of the present invention, ultimately modulating the amount of cancer marker expressed. This is accomplished by providing antisense compounds that specifically hybridize with one or more nucleic acids encoding cancer markers of the present invention. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of cancer markers of the present invention. In the context of the present invention, "modulation" means either an increase (stimulation) or a decrease (inhibition) in the expression of a gene. For example, expression may be inhibited to potentially prevent tumor proliferation.

It is preferred to target specific nucleic acids for antisense. "Targeting" an antisense compound to a particular nucleic acid, in the context of the present invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding a cancer marker of the present invention. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the present invention, "start codon" and "translation initiation codon" refer to the codon or codons that are used in vivo to initiate translation of an mRNA molecule transcribed from a gene encoding a tumor antigen of the present invention, regardless of the sequence(s) of such codons.

Translation termination codon (or "stop codon") of a gene may have one of three sequences (i.e., 5'-UAA, 5'-UAG and 5'-UGA; the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which refers to the region between the translation initiation codon and the translation termination codon, is also a region that may be targeted effectively. Other target regions include the 5' untranslated region (5' UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The cap region may also be a preferred target region.

Although some eukaryotic mRNA transcripts are directly translated, many contain one or more regions, known as "introns," that are excised from a transcript before it is translated. The remaining (and therefore translated) regions are known as "exons" and are spliced together to form a continuous mRNA sequence. mRNA splice sites (i.e., intron-exon junctions) may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

In some embodiments, target sites for antisense inhibition are identified using commercially available software programs (e.g., Biognostik, Gottingen, Germany; SysArris Software, Bangalore, India; Antisense Research Group, University of Liverpool, Liverpool, England; GeneTrove, Carlsbad, Calif.). In other embodiments, target sites for antisense inhibition are identified using the accessible site method described in U.S. Patent WO098537A2, herein incorporated by reference.

Once one or more target sites have been identified, oligonucleotides are chosen that are sufficiently complementary to the target (i.e., hybridize sufficiently well and with sufficient specificity) to give the desired effect. For example, in preferred embodiments of the present invention, antisense oligonucleotides are targeted to or near the start codon.

In the context of this invention, "hybridization," with respect to antisense compositions and methods, means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. It is understood that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired (i.e., under physiological conditions in the case of in vivo assays or therapeutic treatment, and in the case of in vitro assays, under conditions in which the assays are performed).

Antisense compounds are commonly used as research reagents and diagnostics. For example, antisense oligonucleotides, which are able to inhibit gene expression with specificity, can be used to elucidate the function of particular genes. Antisense compounds are also used, for example, to distinguish between functions of various members of a biological pathway.

The specificity and sensitivity of antisense is also applied for therapeutic uses. For example, antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides are useful therapeutic modalities that can be configured to be useful in treatment regimes for treatment of cells, tissues, and animals, especially humans.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases (i.e., from about 8 to about 30 linked bases), although both longer and shorter sequences may find use with the present invention. Particularly preferred antisense compounds are antisense oligonucleotides, even more preferably those comprising from about 12 to about 25 nucleobases.

Specific examples of preferred antisense compounds useful with the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other preferred oligonucleotide mimetics, both the sugar and the internucleoside linkage (i.e., the backbone) of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science 254:1497 (1991).

Most preferred embodiments of the invention are oligonucleotides with phosphorothioate backbones and oligonucleosides with heteroatom backbones, and in particular —$CH_2$, —NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$—, and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-; S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Helv. Chim. Acta 78:486 [1995]) i.e., an alkoxyalkoxy group. A further preferred modification includes 2'-dimethylaminooxyethoxy (i.e., a $O(CH_2)_2ON(CH_3)_2$ group), also known as 2'-DMAOE, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$.

Other preferred modifications include 2'-methoxy(2'-O—$CH_3$), 2'-aminopropoxy(2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2. degree ° C. and are presently preferred base substitutions, even more particularly when combined with 2'-O-methoxyethyl sugar modifications.

Another modification of the oligonucleotides of the present invention involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, (e.g., hexyl-S-tritylthiol), a thiocholesterol, an aliphatic chain, (e.g., dodecandiol or undecyl residues), a phospholipid, (e.g., di-hexadecyl-rac-glycerol or triethylammonium 1,2-di-O-hexadecyl-rac-glycero-3-H-phosphonate), a polyamine or a polyethylene glycol chain or adamantane acetic acid, a palmityl moiety, or an octadecylamine or hexylamino-carbonyl-oxycholesterol moiety.

One skilled in the relevant art knows well how to generate oligonucleotides containing the above-described modifications. The present invention is not limited to the antisensce oligonucleotides described above. Any suitable modification or substitution may be utilized.

It is not necessary for all positions in a given compound to be uniformly modified, and in fact more than one of the aforementioned modifications may be incorporated in a single compound or even at a single nucleoside within an oligonucleotide. The present invention also includes antisense compounds that are chimeric compounds. "Chimeric" antisense compounds or "chimeras," in the context of the present invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNaseH is a cellular endonuclease that cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the present invention may be formed as composite structures of two or more oligonucleotides, modified oligonucleotides, oligonucleosides and/or oligonucleotide mimetics as described above.

The present invention also includes pharmaceutical compositions and formulations that include the antisense compounds of the present invention as described below.

B. Genetic Therapies

The present invention contemplates the use of any genetic manipulation for use in modulating the expression of cancer markers of the present invention. Examples of genetic manipulation include, but are not limited to, gene knockout (e.g., removing the cancer marker gene from the chromosome using, for example, recombination), expression of antisense constructs with or without inducible promoters, and the like. Delivery of nucleic acid construct to cells in vitro or in vivo may be conducted using any suitable method. A suitable method is one that introduces the nucleic acid construct into the cell such that the desired event occurs (e.g., expression of an antisense construct).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to subject in a variety of ways. For example, in some embodiments of the present invention, vectors are administered into tumors or tissue associated with tumors using direct injection. In other embodiments, administration is via the blood or lymphatic circulation (See e.g., PCT publication 99/02685 herein incorporated by reference in its entirety). Exemplary dose levels of adenoviral vector are preferably $10^8$ to $10^{11}$ vector particles added to the perfusate.

C. Antibody Therapy

In some embodiments, the present invention provides antibodies that target prostate tumors that express a cancer marker of the present invention (e.g., hepsin, pim-1, EZH2, Annexin, CTBP, GP73, and AMACR). Any suitable antibody (e.g., monoclonal, polyclonal, or synthetic) may be utilized in the therapeutic methods disclosed herein. In preferred embodiments, the antibodies used for cancer therapy are humanized antibodies. Methods for humanizing antibodies are well known in the art (See e.g., U.S. Pat. Nos. 6,180,370, 5,585,089, 6,054,297, and 5,565,332; each of which is herein incorporated by reference).

In some embodiments, the therapeutic antibodies comprise an antibody generated against a cancer marker of the present invention (e.g., hepsin, pim-1, EZH2, Annexin, CTBP, GP73, and AMACR), wherein the antibody is conjugated to a cytotoxic agent. In such embodiments, a tumor specific therapeutic agent is generated that does not target normal cells, thus reducing many of the detrimental side effects of traditional chemotherapy. For certain applications, it is envisioned that the therapeutic agents will be pharmacologic agents that will serve as useful agents for attachment to antibodies, particularly cytotoxic or otherwise anticellular agents having the ability to kill or suppress the growth or cell division of endothelial cells. The present invention contemplates the use of any pharmacologic agent that can be conjugated to an antibody, and delivered in active form. Exemplary anticellular agents include chemotherapeutic agents, radioisotopes, and cytotoxins. The therapeutic antibodies of the present invention may include a variety of cytotoxic moieties, including but not limited to, radioactive isotopes (e.g., iodine-131, iodine-123, technicium-99m, indium-111, rhenium-188, rhenium-186, gallium-67, copper-67, yttrium-90, iodine-125 or astatine-211), hormones such as a steroid, antimetabolites such as cytosines (e.g., arabinoside, fluorouracil, methotrexate or aminopterin; an anthracycline; mitomycin C), vinca alkaloids (e.g., demecolcine; etoposide; mithramycin), and antitumor alkylating agent such as chlorambucil or melphalan. Other embodiments may include agents such as a coagulant, a cytokine, growth factor, bacterial endotoxin or the lipid A moiety of bacterial endotoxin. For example, in some embodiments, therapeutic agents will include plant-, fungus- or bacteria-derived toxin, such as an A chain toxins, a ribosome inactivating protein, α-sarcin, aspergillin, restrictocin, a ribonuclease, diphtheria toxin or pseudomonas exotoxin, to mention just a few examples. In some preferred embodiments, deglycosylated ricin A chain is utilized.

In any event, it is proposed that agents such as these may, if desired, be successfully conjugated to an antibody, in a manner that will allow their targeting, internalization, release or presentation to blood components at the site of the targeted tumor cells as required using known conjugation technology (See, e.g., Ghose et al., Methods Enzymol., 93:280 [1983]).

For example, in some embodiments the present invention provides immunotoxins targeted a cancer marker of the present invention (e.g., hepsin, pim-1, EZH2, Annexin, CTBP, GP73, and AMACR). Immunotoxins are conjugates of a specific targeting agent typically a tumor-directed antibody or fragment, with a cytotoxic agent, such as a toxin moiety. The targeting agent directs the toxin to, and thereby selectively kills, cells carrying the targeted antigen. In some embodiments, therapeutic antibodies employ crosslinkers that provide high in vivo stability (Thorpe et al., Cancer Res., 48:6396 [1988]).

In other embodiments, particularly those involving treatment of solid tumors, antibodies are designed to have a cytotoxic or otherwise anticellular effect against the tumor vasculature, by suppressing the growth or cell division of the vascular endothelial cells. This attack is intended to lead to a tumor-localized vascular collapse, depriving the tumor cells, particularly those tumor cells distal of the vasculature, of oxygen and nutrients, ultimately leading to cell death and tumor necrosis.

In preferred embodiments, antibody based therapeutics are formulated as pharmaceutical compositions as described below. In preferred embodiments, administration of an antibody composition of the present invention results in a measurable decrease in cancer (e.g., decrease or elimination of tumor).

D. Pharmaceutical Compositions

The present invention further provides pharmaceutical compositions (e.g., comprising the antisense or antibody compounds described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Certain embodiments of the invention provide pharmaceutical compositions containing (a) one or more antisense compounds and (b) one or more other chemotherapeutic agents that function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Other non-antisense chemotherapeutic agents are also within the scope of this invention. Two or more combined compounds may be used together or sequentially.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 μg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 μg to 100 g per kg of body weight, once or more daily, to once every 20 years.

V. Transgenic Animals Expressing Cancer Marker Genes

The present invention contemplates the generation of transgenic animals comprising an exogenous cancer marker gene of the present invention or mutants and variants thereof (e.g., truncations or single nucleotide polymorphisms). In preferred embodiments, the transgenic animal displays an altered phenotype (e.g., increased or decreased presence of markers) as compared to wild-type animals. Methods for analyzing the presence or absence of such phenotypes include but are not limited to, those disclosed herein. In some preferred embodiments, the transgenic animals further display an increased or decreased growth of tumors or evidence of cancer.

The transgenic animals of the present invention find use in drug (e.g., cancer therapy) screens. In some embodiments, test compounds (e.g., a drug that is suspected of being useful to treat cancer) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad. Sci. USA 82:6927 [1985]). Transfection is easily and efficiently obtained by culturing the blastomeres on a monolayer of virus-producing cells (Stewart, et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., truncation mutants). Methods for homologous recombination are described in U.S. Pat. No. 5,614,396, incorporated herein by reference.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); and ° C. (degrees Centigrade).

Example 1

Preparation of Total RNA and Reference Pools

The prostate surgical specimens were obtained from The University of Michigan Specialized Research Program in Prostate Cancer (S.P.O.R.E.) Tumor Bank with Institutional Review Board approval. Tumors samples were derived from patients with clinically localized and advanced hormone refractory prostate cancer. Table 1 shows the samples used in the present studies. All patients were operated on between 1993 and 1998 for clinically localized prostate cancer as determined by preoperative PSA, digital-rectal examination, and prostate needle biopsy. In addition, a subset of patients received bone and CAT scans to evaluate the possibility of metastatic spread. All patients received radical prostatectomy as a monotherapy (i.e., no hormonal or radiation therapy). The advanced prostate tumors were collected from a series of 12 rapid autopsies performed at the University of Michigan on men who died of hormone refractory prostate cancer. In brief, the majority of these patients had either widely metastatic prostate cancer which was treated with hormonal therapy followed by chemotherapy, or patients who presented with clinically localized disease which progressed and were then treated with both hormonal and chemotherapy. The majority of cases had multiple metastatic lesions to numerous sites. All autopsies were performed within 4-6 hours after death. The clinical and pathologic findings of these cases have recently been reported (Rubin et al., Clin. Cancer Res., 6:1038 [2000]). All samples used for the tissue microarray study were fixed in 10% formalin.

Tissues were homogenized using a polytron homogenizer (Brinkman Instruments) in Trizol (Gibco BRL) and the total RNA was isolated according to the standard Trizol protocol. The total RNA obtained was further subjected to an additional round of phenol chloroform extraction, precipitated and resuspended in RNAse free water. Total RNA was quantitated by spectrophotometric (260/280 nm) absorbance and integrity judged by denaturing-formaldehyde agarose gel electrophoresis. Total RNA from four normal tissues was combined in equal concentrations to obtain the reference pool. The human prostate total RNA used in the commercial reference pool was obtained from Clontech, Inc.

TABLE 1

Prostate Samples

| ID | PSA level | Tissue | Gleason Score |
|---|---|---|---|
| BPH-201 | 6.2 | Prostate | NA |
| BPH-202 | 3.9 | Prostate | NA |
| BPH-203 | 3.9 | Prostate | NA |
| BPH-204 | 4.6 | Prostate | NA |
| BPH-205 | 4.6 | Prostate | NA |
| BPH-206 | 4.6 | Prostate | NA |
| BPH-207 | 4.8 | Prostate | NA |
| BPH-208 | 13.6 | Prostate | NA |
| BPH-209 | 9.8 | Prostate | NA |
| BPH-210 | 4.6 | Prostate | NA |
| BPH-211 | 2.6 | Prostate | NA |
| BPH-212 | 7.1 | Prostate | NA |
| BPH-214 | | Prostate | NA |
| BPH-215 | 5.4 | Prostate | NA |
| Prostatitis | 9.8 | Prostate | NA |
| NAP-101 | 4.6 | Prostate | NA |
| NAP-102 | 9.8 | Prostate | NA |
| NAP-104 | 7 | Prostate | NA |
| NAP-105 | 0.09 | Prostate | NA |
| NAP-107 | 4.7 | Prostate | NA |
| PCA-401 | 5.2 | Prostate | 4 + 4 |
| PCA-402 | 22 | Prostate | 4 + 3 |
| PCA-403 | 4.7 | Prostate | 3 + 3 |
| PCA-404 | 8.5 | Prostate | 3 + 3 |
| PCA-405 | 4.6 | Prostate | 3 + 3 |
| PCA-406 | 7.8 | Prostate | 3 + 3 |
| PCA-407 | 7.8 | Prostate | 3 + 3 |
| PCA-408 | 5.4 | Prostate | 3 + 3 |
| PCA-409 | 7 | Prostate | 3 + 3 |
| PCA-410 | 44.6 | Prostate | 4 + 4 |
| PCA-414 | | Prostate | 3 + 4 |
| PCA-416 | 24.1 | Prostate | 4 + 4 |
| PCA-417 | 12.4 | Prostate | 4 + 4 |
| PCA-420 | | Prostate | 3 + 3 |
| PCA-421 | 13.6 | Prostate | 3 + 4 |
| MET-301 | | Lung | NA |
| MET-302 | | Liver | NA |
| MET-303 | | Liver | NA |
| MET-304 | | Stomach | NA |
| MET-305 | | Adrenal | NA |
| MET-306 | | Prostate | NA |
| MET-307 | | Lymph Node | NA |
| MET-308 | | Lymph Node | NA |
| MET-309 | | Lymph Node | NA |
| MET-310 | | Liver | NA |

TABLE 1-continued

Prostate Samples

| ID | PSA level | Tissue | Gleason Score |
|---|---|---|---|
| MET-311 | | Soft tissue | NA |
| MET-312 | | Liver | NA |
| MET-313 | | Soft tissue | NA |
| MET-314 | | Soft tissue | NA |
| MET-315 | | Soft tissue | NA |
| MET-316 | | Soft tissue | NA |
| MET-317 | | Liver | NA |
| MET-318 | | bone | NA |
| MET-319 | | bone | NA |
| MET-320 | | bone | NA |

Table 1. Samples employed in the study. Designating PSA level in ng/mL, Organ sources and Gleason scores. Normal adjacent prostate (NAP), Benign prostatic hyperplasia (BPH), Localized prostate cancer (PCA) and Hormone refractory metastatic prostate cancer (MET). NA refers to "not applicable".

Example 2

Microarray Analysis

This example describes the use of microarray analysis to identify genes that demonstrate an altered level of expression in cancerous or benign prostate tissues.

A. Experimental Methods

Microarray analysis of gene expression was conducted essentially as described by the Brown and Derisi Labs (available at the Internet site www.microarrays.org). The sequence-verified cDNA clones on the human cDNA microarray are available from the web site of Research Genetics. Based on the latest Unigene build, the 10 K human cDNA microarray used covers approximately 5520 known, named genes and 4464 ESTs. All chips have various control elements that include human, rat, and yeast genomic DNAs, SSC, yeast genes and "housekeeping genes," among others. In addition, 500 cancer- and apoptosis-related cDNAs from Research Genetics were used to serve as independent controls for clone tracking and function as duplicates for quality control. Three metastatic prostate cancer cell lines: DU-145, LnCAP, and PC3 were also profiled for gene expression.

Fluorescently labeled (Cy5) cDNA was prepared from total RNA from each experimental sample. The two reference samples used in this study were labeled using a second distinguishable fluorescent dye (Cy3) and included a pool of normal adjacent prostate tissue (NAP) from four patients (distinct from those used in the experimental samples) and a commercial pool of normal prostate tissues (CP). In addition to minimizing patient-to-patient variation, comparisons against pools of normal prostate tissue facilitate the discovery of genes that molecularly distinguish prostate neoplasms. The two reference pools are different in that one is comprised of normal adjacent prostate tissue, which may be influenced by paracrine effects mediated by PCA, and furthermore is exposed to the same environmental and genetic factors as the adjacent PCA. By contrast, the CP pool is derived from 19 individuals with no known prostate pathology and also represents a renewable commercially available reference resource.

Purified PCR products, generated using the clone inserts as template, were spotted onto poly-L-lysine coated microscope slides using an Omnigrid robotic arrayer (GeneMachines, CA) equipped with quill-type pins (Majer Scientific, AZ). One full print run generated approximately 100 DNA microarrays. Protocols for printing and post-processing of arrays are well known in the art.

B. Data Analysis

Primary analysis was done using the Genepix software package. Images of scanned microarrays were gridded and linked to a gene print list. Initially, data was viewed as a scatter plot of Cy3 versus Cy5 intensities. Cy3 to Cy5 ratios were determined for the individual genes along with various other quality control parameters (e.g., intensity over local background). The Genepix software analysis package flags spots as absent based on spot characteristics (refer to the web site of Axon Instruments, Inc.). Bad spots or areas of the array with obvious defects were manually flagged. Spots with small diameters (<50 microns) and spots with low signal strengths <350 fluorescence intensity units over local background in the more intense channel were discarded. Flagged spots were not included in subsequent analyses. Data were scaled such that the average median ratio value for all spots was normalized to 1.0 per array.

These files were then imported into a Microsoft Access database. The data for the required experiments were extracted from the database in a single table format with each row representing an array element, each column a hybridization and each cell the observed normalized median of ratios for the array element of the appropriate hybridization. Prior to clustering, the normalized median of ratio values of the genes were log base 2 transformed and filtered for presence across arrays and selected for expression levels and patterns depending on the experimental set as stated. Average linkage hierarchial clustering of an uncentered Pearson correlation similarity matrix was applied using the program Cluster (Eisen et al., PNAS 95:14863 [1998]), and the results were analyzed and figures generated with the program TreeView. TreeView and Cluster are available from Michael Eisen's lab at the Lawrence Berkeley National Lab.

C. Results

Over forty 10 K human cDNA microarrays were used to assess gene expression in four clinical states of prostate-derived tissues in relation to two distinct reference pools of normal specimens. FIG. 1 provides an overview of the variation in gene expression across the different tissue specimens analyzed. A hierarchical clustering algorithm was employed to group genes and experimental samples based on similarities of gene expression patterns over all the genes and samples tested, respectively.

1. Expression Dendrograms

Relationships between the experimental samples are summarized as dendrograms (FIG. 1*a*), in which the pattern and length of the branches reflect the relatedness of the samples. FIG. 1*a* shows dendrograms that reveal the variation in gene expression pattern between experimental samples with the two references employed. Individual samples in each group are indicated by the branches of the same color whereby METs are in dark blue, localized PCAs in orange, NAPs in light blue, BPHs in gray, and cell lines in pink. Asterisk (*) indicates a sample that was initially documented as BPH, but was later confirmed to have 5% cancer tissue. The details of metastatic samples used in this study are as follows: MET 301, from Lung; MET 302 and 303 from liver; MET 304, from stomach; MET 305 from adrenal gland; MET 306 from prostate; and MET 307 was from lymph node. Hierarchical clustering of the data identified distinct patterns of gene expression between the various groups analyzed. Each row represents a single gene with 1520 genes depicted in b, and 1006 genes depicted in c. The results represent the ratio of hybridization of fluorescent cDNA probes prepared from each experimental mRNA to the respective reference pools. These ratios are a measure of relative gene expression in each experimental sample and are depicted according to the color scale at the bottom left. Red and green colors in the matrix represent genes that are up- and down-regulated, respectively, relative to the reference pool employed. Black lines in the matrix represent transcript levels that are unchanged, while gray lines signify technically inadequate or missing data (NP, not present). Color saturation reflects the magnitude of the ratio relative to the median for each set of samples.

FIG. 1*b* shows a cluster diagram of the various sample groups compared against normal adjacent prostate pool as reference. Table 3 shows the associated data included in the normal adjacent prostate pool. Table 3 contains a CBCR-t Index number, Clone, ID, Unigene Cluster Ids, Accession ID, NID, gene symbol, and name fields for each gene used in the array. The name field contains genes having partial or complete homology based on homology searches. In addition, the table contains the numerical difference in expression levels compared to the reference pool for each gene. Prior to hierarchical average-linkage clustering, the data was filtered for at least a 2-fold change in expression ratio and ratio measurements present in 50% of the samples. By this method, 1520 genes were selected from the NAP reference data set. Indicated by vertical bars on the left (b 1 to b6) of FIG. 1*b* are regions identified with characteristic gene expression signatures. Clusters b1 and b5 show genes up-regulated in localized PCA but not in metastatic PCA. Clusters b2 and b4 highlight genes down-regulated in metastatic PCA and the cell lines DU145 and LnCAP. Cluster b3 identifies genes down-regulated in both localized PCA and metastatic PCA. Cluster b6 highlights genes that are primarily up-regulated in metastatic PCA alone. Portions of Clusters b4 and b6 are shown enlarged with selected genes shown using Human genome organization (HUGO) gene nomenclature.

FIG. 1*c* shows a cluster diagram of the various sample groups compared against the commercial prostate pool reference. Table 4 shows the associated data included in the commercial prostate pool (See description of Table 3). Prior to hierarchical average-linkage clustering, the data was filtered for at least a 3-fold change in expression ratio and ratio measurements present in 75% of the samples resulting in a total of 1006 genes. Regions with distinct patterns (c1-c6) are indicated by vertical bars to the right of FIG. 1*c*. Cluster c1 depicts genes down-regulated in both localized PCA and metastatic PCA. Cluster c2 represents genes down-regulated only in metastatic PCA. Cluster c3 shows genes that are highly represented in the commercial pool. Cluster c4 highlights genes that are up-regulated in localized PCA and in metastatic PCA. Cluster c5 represent genes with a low representation in the commercial pool. Cluster c6, represents genes that are down-regulated in metastatic PCA but are up-regulated in all other samples used.

Benign conditions of the prostate such as BPH and NAP cluster separately from malignant PCA cell lines or tissues, regardless of the reference pool used. Within the PCA cluster, it is also evident that metastatic PCA and clinically localized PCA formed distinct subgroups. Similarly, in the "benign" grouping, BPH tended to distinguish itself from NAP. Interestingly, one of the "BPH" samples initially clustered with the localized PCA group. Upon further histopathologic review, however, it was discovered that this sample contained a small focus of neoplastic tissue (~5%), thus accounting for its initial misclassification (now designated PCA+BPH in FIG. 1*a*).

Eisen matrix formats (Eisen et al., supra) of the variation in gene expression are also presented (FIG. 1 *b* and 1*c*). With a global perspective of the data, it is apparent that metastatic PCA dominates the analysis and has the greatest variation in gene expression of the samples tested. Bars on the left or right of each matrix represent clusters of coordinately expressed genes highlighting interrelationships between specimens. For example, Clusters b3 and c1 represent genes down-regulated in both localized and metastatic PCA (FIGS. 1*b* and 1*c*). By contrast, Clusters b6 and b4 highlight genes that are specifically up- and down-regulated in metastatic PCA, respectively (FIG. 1*b*). IGFBP-5, DAN1, FAT tumor suppressor and RAB5A are examples of genes that are down-regulated specifically in metastatic PCA and also have a proposed role in oncogenesis ("magnified" regions, FIG. 1*b*). Similarly, cancer-related genes that are up-regulated in metastatic PCA include MTA-1 (metastasis-associated 1), MYBL2, and FLS353 (preferentially expressed in colorectal cancer). Many genes in this "met-specific" cluster are shared by both the metastatic PCA tissue and the two PCA cell lines DU145 and LnCAP.

Table 5 shows data from the expression profiling of additional prostate tissue specimens profiled against a commercial prostate reference pool (CPP) (See description of Table 3). A total of 53 prostate specimens were profiled against the commercial pool. They include 4 normal adjacent prostate tissue (NAP), 14 benign prostatic hyperplasia (BPH), I prostatitis, 14 localized prostate cancer (PCA) and 20 hormone refractory metastatic PCA (MET). Prior to hierarchial average-linkage clustering, the data was filtered for at least 3-fold change in Cy5/Cy3 ratios and measurements present in 75% of the samples. By this method 1325 genes were selected. The data expands on FIG. 1*c* with an additional 40 samples, which include all from FIG. 1*b*, and also includes 28 additional prostate specimens.

2. Focused Clusters

Figure 6:
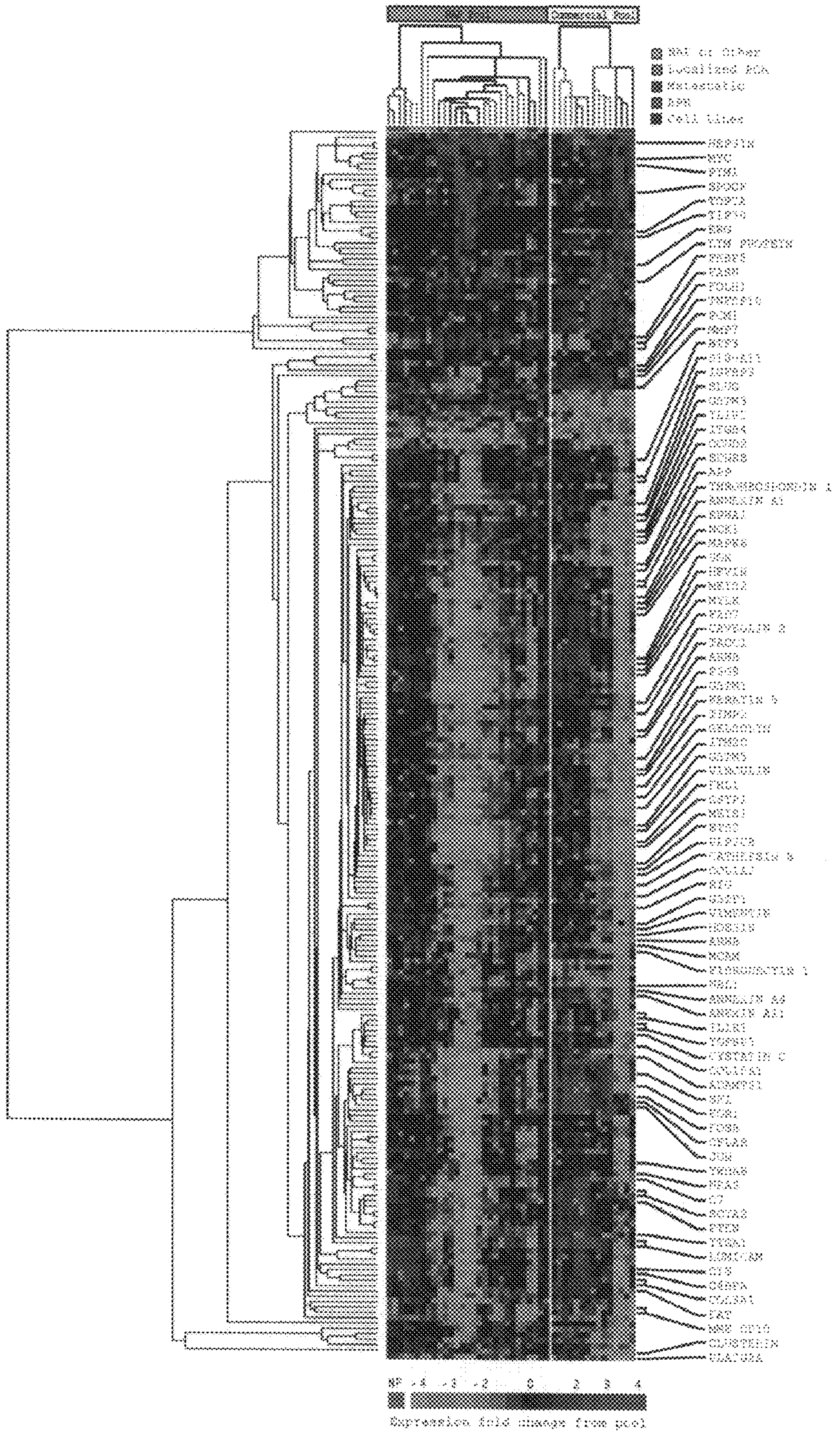
FIG. 6 shows a focused cluster of prostate cancer related genes.

Data was next assessed by examining functional groups of known, named genes. Cancer-related functional clusters were arbitrarily defined including cell growth/cell death, cell adhesion, anti-protease/protease, free radical scavengers, inflammation/immunity, phosphatase/kinase, transcription, and miscellaneous (FIGS. 2 and 6).

One of several available methods of gene selection was used to create a more limited set of genes for future exploration. In one method, t-statistics (based on MET/PCA vs. benign) were computed for each gene. The cell line samples were excluded from the analysis. Also, genes and ESTs that had data missing from 20% of samples were excluded from analysis. The t-statistics were ranked in two ways. First, they were ranked by absolute magnitude, which takes into account the inter-sample variability in expression ratios. Second, they were ranked by the magnitude of the numerator of the test statistic, which is based on the biological difference in expression ratios and designated as "effect size" (for MET/PCA vs. benign). A scatterplot of the genes with the 200 largest effect sizes and 200 largest t-statistics was then plotted (See FIG. 7). FIG. 7 shows gene selection based on computed t-statistics for each gene. Two groups were used in the analysis: PCA/MET and benign (NAP/BPH). FIG. 7*a* shows analysis of NAP pool data. FIG. 7*b* shows analysis of CP pool data. Selected genes are named and 200 genes for each data set are shown. Gene selection based on each method is shown. Selected gene names or symbols (as specified by Human genome organization (HUGO) gene nomenclature) are shown.

Genes that made both lists were also looked at separately in order to identify potential candidate genes. Implementing this methodology on both reference pool data sets (NAP and CP) yielded genes that included hepsin, pim-1, IM/ENIGMA, TIMP2, hevin, rig, and thrombospondin-1, among others. Several genes identified using gene selection methods are described in more detail in the context of "functional" clusters described in FIG. 2.

Figure 2:
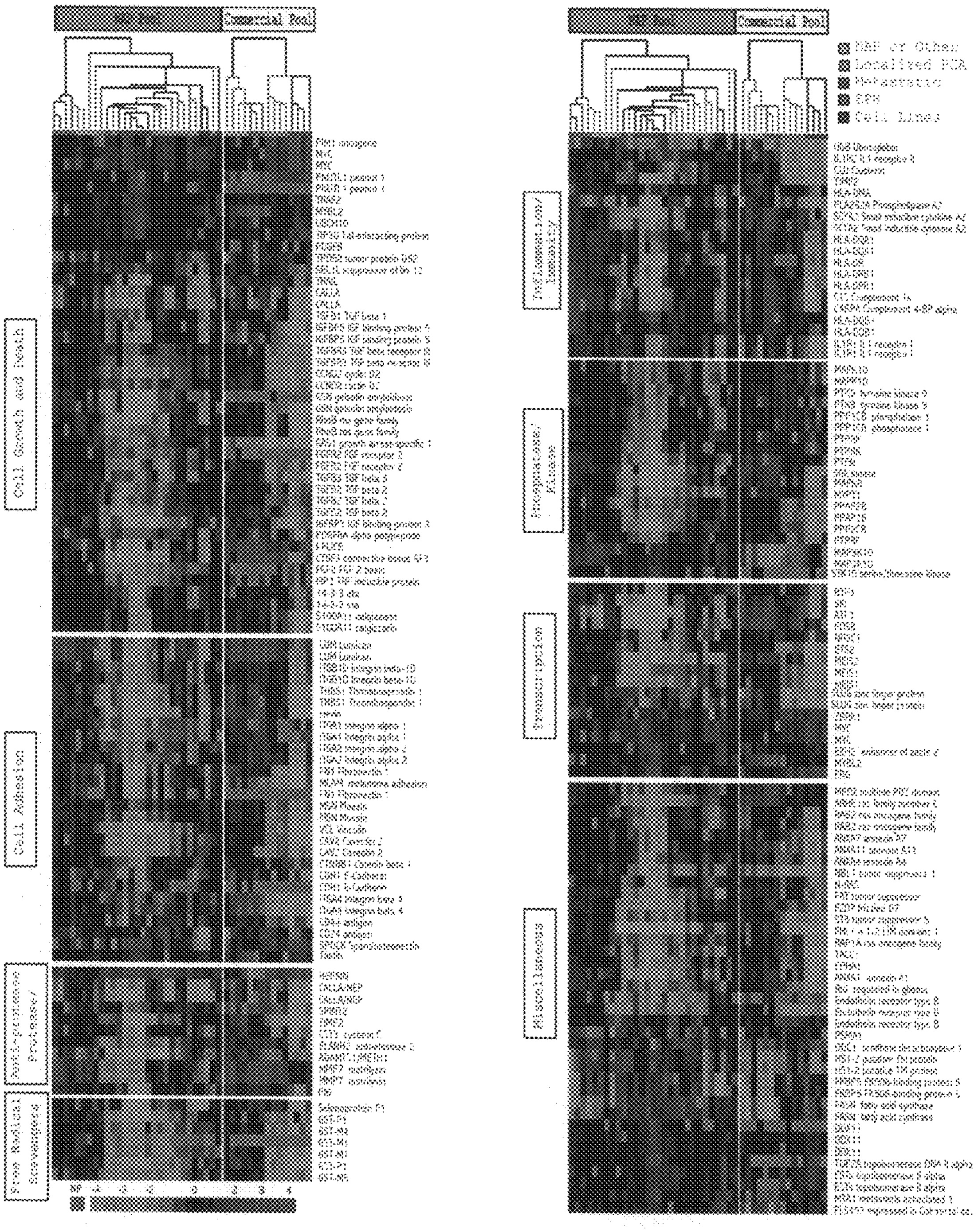
FIG. 2 shows functional clusters of genes differentially expressed in prostate cancer.

FIG. 2 shows the differential expression of functional clusters of select genes in prostate cancer. Gene names or symbols (as specified by Human genome organization (HUGO) gene nomenclature) are shown. The same convention for representing changes in transcript levels was used as in FIG. 1. The sample order from FIG. 1 was preserved for clarity.

Figure 8:
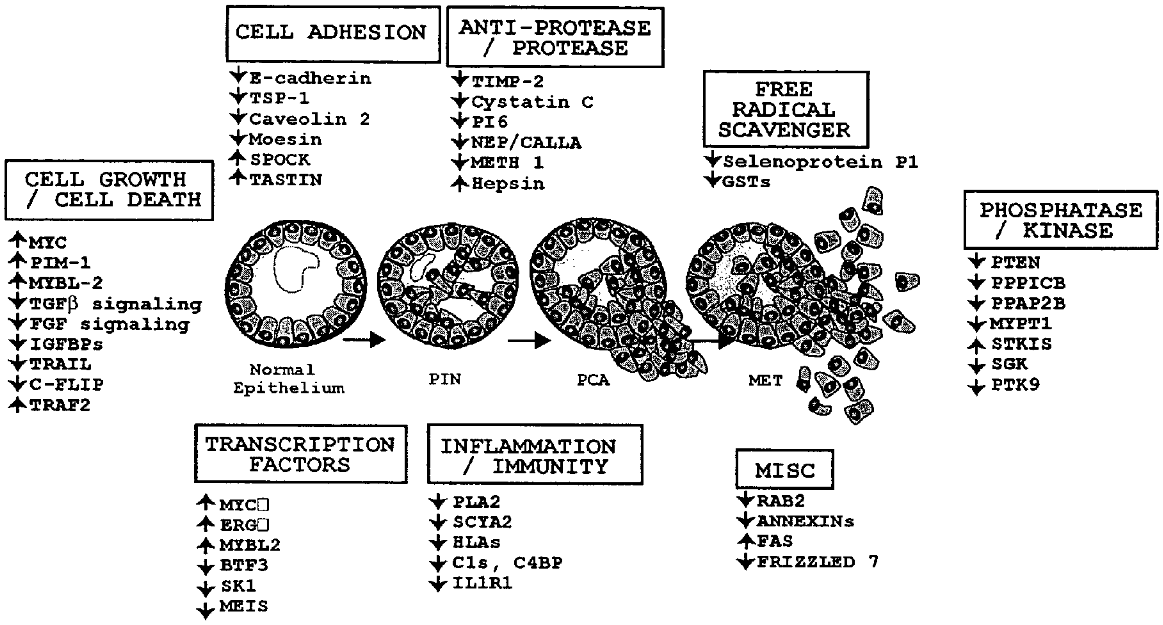
FIG. 8 shows an overview of genes differentially expressed in prostate cancer.

FIG. 8 shows a focused cluster of PCA-related genes. Table 6 shows the associated data (See description of Table 3). The same convention for representing changes in transcript levels was used as in FIG. 1. This cluster of 231 genes was generated by selecting for a 3.5-fold variation in at least 2 of any class, and ratio measurements present in 75% of the samples. Classes included: PCA vs. NAP, MET vs. NAP, PCA vs. CP and MET vs. CP.

The reliability of the hierarchical clustering results was assessed using three separate methods: that of Calinski and Harabasz (1974), Hartigan (1975) and Krzanowski and Lai (1985). The number of "stable" clusters estimated by all these methods is two. In the CP pool data set, that would elicit a valid benign cluster (NAP and BPH) and a malignant cluster (PCA and MET).

Many of the genes identified in these "focused" clusters have been implicated directly or indirectly as cancer biomarkers or mediators of carcinogenesis. Several have been shown to be dysregulated in PCA. For example, the tumor suppressor gene PTEN was down-regulated, while the proto-oncogene myc was up-regulated in the microarray analysis of PCA (FIG. 2) (Abate-Shen and Shen, supra). Likewise, decreased expression of E-cadherin and increased expression of fatty acid synthase, both of which have been shown to be dysregulated in PCA were observed (Tomita et al., Cancer Res., 60:3650 [2000] and Shurbaji et al., Hum. Pathol., 27:917 [1996]). In addition to uncharacterized expressed sequence tags (ESTs), there are numerous genes that were identified by the screen but not previously known to be associated with PCA. It is contemplated that they find use as cancer markers.

Exemplary nucleic acid sequences for some of the genes identified in focused clusters are shown in FIGS. 9 and 10. The present invention is not limited to the particular nucleic acid sequences described in FIGS. 9 and 10. One skilled in the art recognizes that additional variants, homologs, and mutants of the described sequences find use in the practice of the present invention.

3. Comparison Between NAP and CP Pools

Figure 5:
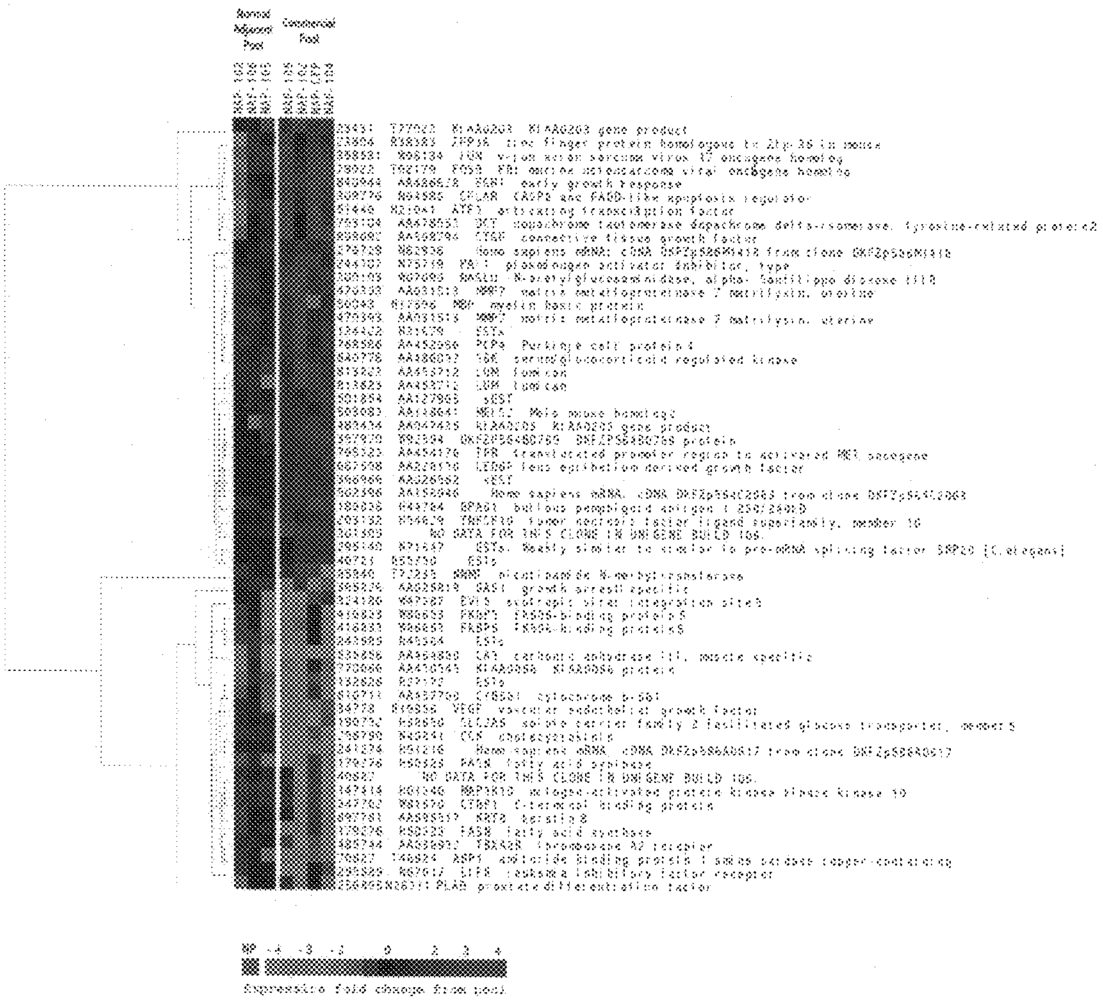
FIG. 5 shows a comparison of gene expression profiles for normal adjacent prostate tissue and normal prostate tissue reference.

A direct comparison between the NAP and CP pool was also made and notable gene expression differences were readily apparent. FIG. 5 shows a comparison between the NAP and CP pools. Table 7 shows a table of the associated data for FIG. 5 (See description of Table 3). The same convention for representing changes in transcript levels was used as in FIG. 1. The cluster was obtained by selecting for genes with at least a 2.5-fold variation in any two of the samples of each class, namely the normal tissues versus the NAP pool and normal tissue versus the CP pool at a 50% filter. Of the genes analyzed 59 were selected with this criteria. Genes that were found to be up-regulated in the NAP pool in comparison with CP pool included connective tissue growth factor, EGR-1 (Early Growth Response 1), matrilysin (MMP7), CFLAR/1-FLICE (caspase 8 and FADD-like apoptosis regulator), lumican, serum glucocorticoid regulated kinase, lens epithelium derived growth factor, PAI1 (plasminogen activator inhibitor type 1), JUN and FOS B, among others. Vascular endothelial growth factor (VEGF), growth arrest specific (GAS1), cholecystokinin (CCK), amiloride binding protein (ABP1) were among the down-regulated genes in the normal adjacent prostate pool when compared to the commercial pool. The present invention is not limited to a particular mechanism. Indeed, an understanding of the mechanism is not necessary to practice the present invention. Nonetheless, it is contemplated that the gene expression differences between normal prostate adjacent to PCA (NAP) and normal prostate tissue from individuals without prostate pathology (CP) may be attributable to a "field effect" induced by PCA itself.

Example 3

Northern Blot Analysis

Thirty micrograms of total RNA was resolved by denaturing formaldehyde agarose gel and transferred onto Hybond membrane (Amersham) by a capillary transfer set up. Hybridizations were performed by the method described by Church and Gilbert, 1984. Signal was visualized and quantitated by phosphorimager. For relative fold estimation, the ratio between the signals obtained from hepsin and GAPDH probes was calculated.

Selected genes identified by microarray analysis were corroborated by Northern analysis. For example, hevin, 4½ LIM domain protein and gelsolin were shown to be 3.2-, 3.2- and 1.9-fold down-regulated, respectively by microarray and 8.8-, 4.5-, and 3.5-fold down-regulated by Northern analysis. Similarly, hepsin was 4.3-fold up-regulated by microarray and 11.3-fold up-regulated by Northern analysis (FIG. 3*a*). As hepsin is a cell-surface serine protease with transcript expression precisely restricted to localized and metastatic PCA, its expression was examined in more detail at the protein level (See Example 4 below).

Example 4

Tissue Analysis

This example describes the analysis of protein expression in normal and cancerous prostate tissues.

A. Tissue Microarray Construction.

Kononen et al. have described a method for evaluating tumor tissues in large numbers on a single glass slide (Kononen et al., Nat. Med., 4:844 [1998]). These high-density tissue microarrays allow for analysis of up to 1,000 tissue samples on a single slide. These slides can be evaluated by routine light microscopy on hematoxylin and eosin (H&E) prepared and immunohistochemically stained slides. Thus, candidate cancer biomarkers, identified by gene expression methodologies, can be evaluated at the protein level over a large number of clinically stratified tumor specimens.

Prostate tissues used in microarray analysis included 4 BPH, 8 NAP, 1 commercial pool of normal prostate tissue (from 19 individuals), 1 prostatitis, 11 localized PCA, and 7 metastatic PCA specimens. High-density tissue microarrays (TMA) were assembled using a manual tissue puncher/array (Beecher Instruments, Silver Springs, Md.) as previously described (Kononen et al., Nat. Med., 4:844 [1998]; Perrone et al., J. Natl. Cancer Inst., 92:937 [2000]). The instrument consists of thin-walled stainless steel needles with an inner diameter of approximately 600 μm and stylet used to transfer and empty the needle contents. The assembly is held in an X-Y position guide that is manually adjusted by digital micrometers. Small biopsies are retrieved from selected regions of donor tissue and are precisely arrayed in a new paraffin block. Tissue cores were 0.6 mm in diameter and ranged in length from 1.0 mm to 3.0 mm depending on the depth of tissue in the donor block. Multiple replicate core samples of normal, HGPIN, and PCA were acquired from each tissue block of each case. Cores were inserted into a 45×20×12 mm recipient bock and spaced at a distance of 0.8 mm apart. Prostate tumor grading was performed using the system described by Gleason (Gleason, Cancer Chemother Rep., 50:125 [1966]). Pathologic stages for the radical prostatectomies were determined using the TNM staging system (Schroder et al., Prostate Suppl., 4:129 [1992]). Surgical margins were assessed separately and are not included in tumor staging.

B. Immunohistochemistry

TMA sections were cut at five-micron thick intervals for immunohistochemistry. Initial sections were stained for hematoxylin and eosin to verify histology. TMA slides prepared from formalin-fixed paraffin embedded tissue were heated for 0.5-1 hours at 600 centigrade. All slides were placed in 10 millimolar citrate buffer (pH 6.0) and microwaved for 5 minutes. Standard biotin-avidin complex immunohistochemistry was performed. The affinity purified polyclonal Rabbit antibody against hHepsin was used at a 1:40 dilution (original concentration 0.2 mg/ml) for this study. Immunostaining intensity was scored by a dedicated genitourinary pathologist as absent, weak, moderate, or strong. Scoring was performed using a telepathology system in a blinded fashion without knowledge of overall Gleason score (e.g., tumor grade), tumor size, or clinical outcome (Perrone et al., supra). A total of 738 tissue samples from benign (n=205), high-grade PIN (n=38), localized prostate cancer (n=335) and hormone refractory prostate cancer (n=160) were examined.

Similarly, pim-1 was analyzed using two TMA blocks from a total of 810 PCA samples from 135 patients. Six PCA samples were evaluated from each case and a median score was calculated. In addition, a small number of samples with benign prostatic tissues (e.g., benign epithelium and atrophy) and HG-PIN were examined. Immunohistochemistry was performed as above, using a rabbit polyclonal antibody against the N-terminus of pim-1 (Santa Cruz Biotechnology) at a 1:100 dilution. Pim-1 demonstrated cytoplasmic staining and was graded as either negative, weak, moderate, or strong. All samples were reviewed blinded with respect to all related pathology and clinical data.

C. Statistical Methods

A nonparametric ANOVA test (Mann-Whitney [two categories]) was employed to evaluate whether the prostate samples expressed hepsin and pim-1 at different levels based on various parameters (tissue type, Gleason score, and tumor size). Kaplan-Meier analysis was used to estimate the cumulative percentage of PSA free progression ("survival"). The log-rank test was employed to assess the differences in disease free progression hepsin immunostaining. Cox proportional-hazard regression was used for multivariate analysis. Commercial software from SPSS (Chicago, Ill.) was used for this study.

D. Results

1. Hepsin

Figure 3:
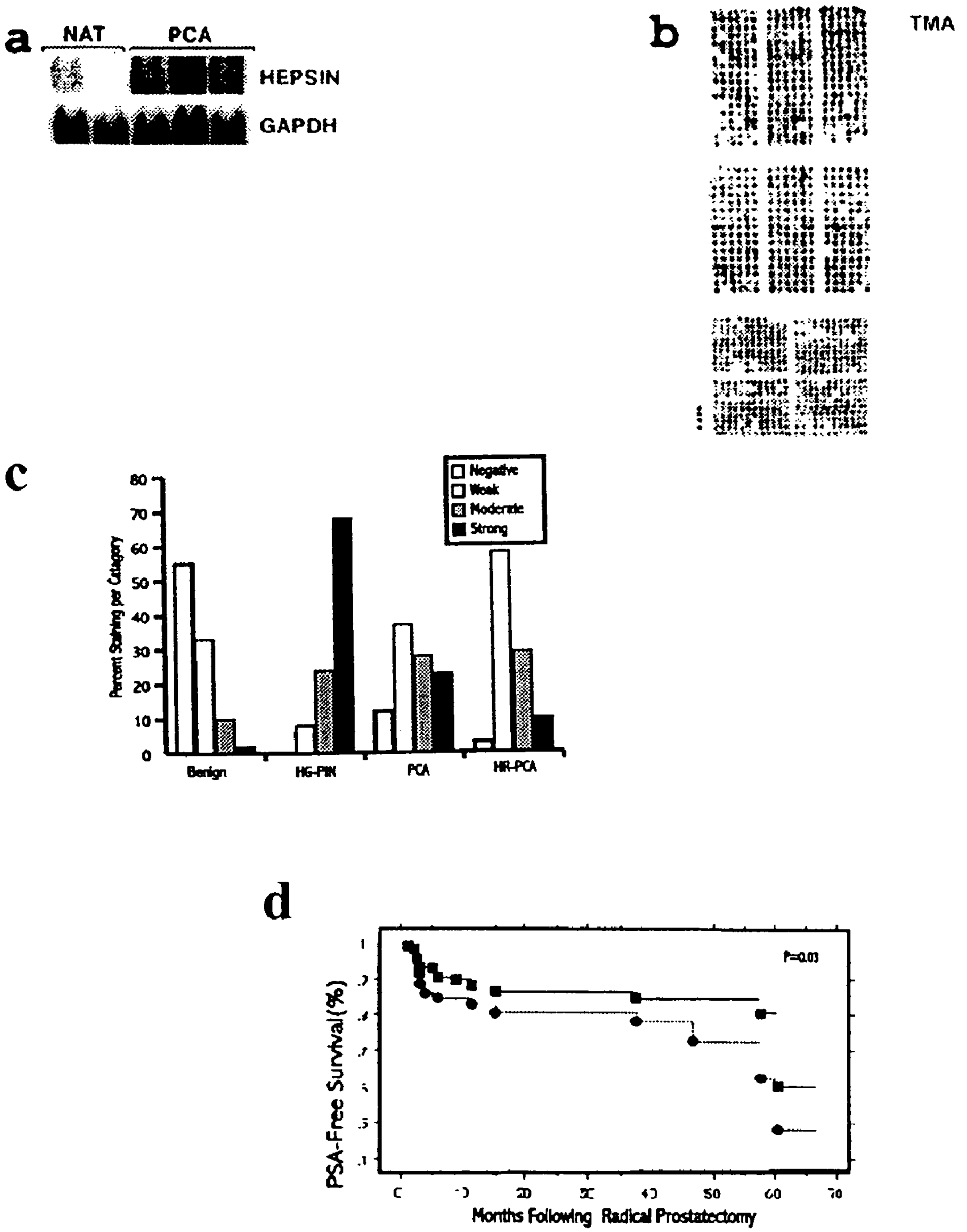
FIG. 3 shows the expression of hepsin in prostate cancer samples as determined by Northern blot analysis and immunohistochemistry.

Microarrays used in this study are shown in FIG. 3*b*. Over 700 benign and malignant prostate tissues were immunohistochemically profiled on tissue microarrays (FIG. 3*c-e*) using an affinity-purified hepsin-peptide antibody (Tsuji et al., J. Biol. Chem., 266:16948 [1991]). FIG. 3 shows the overexpression of Hepsin, a transmembrane serine protease, in prostate cancer. FIG. 3*a* shows a Northern blot analysis of human hepsin (top) and normalization with GAPDH (bottom). NAT indicates normal adjacent prostate tissue and PCA indicates prostate cancer. FIG. 3*b* shows tissue microarrays used for hepsin analysis. Staining was done with hemotoxylin and eosin to verify histology.

Immunohistochemical stains demonstrated absent or weak staining of benign prostate (c1), strong staining in localized prostate cancer (c2-6), and strong staining in a high-grade prostate tumor (magnification 100× was used for all images, samples measure 0.6 mm in diameter). Benign prostate glands demonstrate weak expression in the secretory, luminal cells and strong basal cell staining. In areas where prostate cancer and benign prostate glands are seen, significant hepsin staining differences are observed. Infiltrating prostate cancers (d3-4) demonstrate strong hepsin protein expression. Magnification for all images was 400×. FIG. 3*c* shows a histogram of hepsin protein expression by tissue type. Benign prostate hyperplasia (BPH). High-grade intraepithelial neoplasia (HG-PIN). Localized prostate cancer (PCA). Hormone-refractory prostate cancer (MET). Relative strength of hepsin staining was qualitatively assessed and categorized. Percentage of hepsin staining per category is shown on the y-axis. FIG. 3*d* shows Kaplan Meier Analysis. PSA-free survival was stratified by level of hepsin protein expression into two categories absent/low expression (circles) versus moderate/strong expression (squares).

Internal controls showed that liver tissue, as previously described, stained strongly for hepsin. Overall, hepsin exhibited predominantly membrane staining and was preferentially expressed in neoplastic prostate over benign prostate (Mann-Whitney test, $p<0.0001$). Importantly, the precursor lesion of PCA, HG-PIN, had the strongest expression of hepsin, and almost never had absent staining (Mann-Whitney, $p<0.0001$). Most cases of low or absent hepsin staining were seen in benign prostate specimens. In addition, hormone refractory metastatic cancers were intermediate in staining intensity between localized prostate tumors and benign prostate.

Men who develop elevated PSA levels following radical prostatectomy are at a high risk to develop distant metastases and die due to prostate cancer (Pound et al., JAMA, 281:1591 [1999]. Therefore, to assess the usefulness of hepsin as a potential PCA biomarker, PSA failure was defined as a PSA elevation of greater than 0.2 ng/ml following radical prostatectomy. Analysis was performed on 334 localized prostate cancer samples treating each as an independent sample. PSA elevation following radical prostatectomy was significantly associated with absent and low hepsin immunostaining with a 28% (46/119 samples) PSA failure rate, in contrast to 17% (28/141 samples) PSA failure rate for tumors with moderate to strong hepsin expression (FIG. 3*d*, Log Rank test $P=0.03$). Multivariate analysis was performed to examine if these results were independent of Gleason score, a well-established histologic grading system for PCA (Gleason, Hum. Pathol., 23:273 [1992]). Based on the results from fitting a Cox proportional hazards model, there is an association of weak or absent hepsin protein expression in PCA with increased risk of PSA elevation following prostatectomy, similar to high Gleason score (corresponding risk ratios were 2.9 ($p=0.0004$) and 1.65 ($p=0.037$), respectively). Weak or absent hepsin expression was also associated with large prostate cancers; the median tumor dimension for prostate tumors with moderate to strong expression was 1.3 cm but 1.5 cm for tumors with absent or weak staining (Mann-Whitney Rank test, $P=0.043$). Taken together, hepsin protein expression in PCA correlated inversely with measures of patient prognosis.

Hepsin is a 51 kDa transmembrane protein with highest expression in the liver, and like PSA, is a serine protease (Kurachi et al., Methods Enzymol., 244:100 [1994]). The protease domain of hepsin has access to the extracellular space and can potentially activate other proteases or degrade components of extracellular matrix. The function of hepsin is poorly understood. It has been proposed to have a role in controlling cell growth (Torres-Rosado et al., PNAS, 90:7181 [1993], cell morphology, and activating the extrinsic coagulation pathway on the cell surface, leading to thrombin formation (Kazama et al., J. Biol. Chem., 270:66 [1995]). Additionally, hepsin mRNA levels have been shown to be elevated in ovarian carcinomas (Tanimoto et al., Cancer Res., 57:2884 [1997]). The present invention is not limited to a particular mechanism. Indeed, an understanding of the mechanism is not necessary to practice the present invention. Nonetheless, it is contemplated that the high expression of hepsin in HG-PIN, and not benign prostate, suggests that hepsin plays a role in the establishment of PIN or in the transition from HG-PIN to carcinoma. Subsequent decreases in hepsin expression seen in large localized cancers and hormone-refractory cancers suggest a decreased requirement of this protease in later stages of PCA. Alternatively, patients with advanced PCA often develop disseminated intravascular coagulation (DIC) (Riddell et al., J. Nucl. Med., 37:401 [1996]) whereby hepsin may play an important role.

2. pim-1

Tumorigenic growth of the prostate depends on the evasion of normal homeostatic control mechanisms, where cell proliferation exceeds cell death (Bruckheimer and Kyprianou, Cell Tissue Res., 301: 153 [2000]). While it is well known that the oncogene myc is overexpressed in many PCAs (Buttyan et al., prostate 11:327-37 [1987]; Abate-Shen and Shen, supra), the present invention demonstrates that the proto-oncogene pim-1 kinase is similarly up-regulated (cell growth/cell death cluster, FIG. 2). Previous studies suggest that the cooperative interaction between pim-1 and myc may induce lymphoid cell transformation by promoting cell cycle progression and blocking apoptosis (Shirogane, et al., Immunity 11:709 [1999]). The present analysis supports a similar co-transcriptional regulation (or gene amplification) of pim-1 and myc possibly mediating a synergistic oncogenic effect in PCA.

Pim-1 kinase protein expression in PCA was also explored using high-denisty TMAs. FIG. 4 shows the overexpression of pim-1 in prostate cancer. Immunohistochemical stains demonstrated absent or weak staining of benign prostate, and strong cytoplasmic staining in localized prostate cancer. Benign prostate glands demonstrated absent or weak expression in the secretory, luminal cells. Infiltrating prostate cancers demonstrated strong pim-1 protein expression. Magnification for all images 1000×. FIG. 4*a* shows a histogram of pim-1 protein expression by tissue type as assessed from 810 tissue microarray elements. High-grade intraepithelial neoplasia (HG-PIN). Localized prostate cancer (PCA). Relative strength of pim-1 staining is represented in the included legend. The percentage of pim-1 staining per category shown on y-axis. FIG. 4*b* shows Kaplan-Meier analysis demonstrating that patients with PCA that have negative to weak pim-1 expression (bottom line) are at a greater risk of developing PSA-failure following prostatectomy (log rank $p=0.04$). PSA-free survival was stratified by level of pim-1 protein expression into two categories absent/weak expression (bottom line) versus moderate/strong expression (top line).

Pim-1 protein was found to be markedly overexpressed in PCA (FIG. 4). Negative to weak pim-1 protein expression was observed in the majority of benign prostatic epithelial (97%), prostatic atrophy (73%), and high-grade PIN (82%) samples (FIG. 4*a*). In contrast, moderate to strong pim-1 expression was observed in approximately half of the PCA samples (51%) (FIG. 4*a*). Kaplan-Meier analysis for PSA-free survival demonstrated positive extraprostatic extension, seminal vesicle invasion, Gleason score greater than 7 and decreased pim-1 expression to be associated with a higher cumulative rate of PSA failure (FIG. 4*b*). By univariate Cox models, it was found that Pim-1 expression is a strong predictor of PSA recurrence (hazard ratio (HR)=2.1 (95% CI 1.2-3.8, p=0.01)).

Among the variables examined, significant predictors of PSA recurrence were Gleason score (HR=1.8 (95% CI 1.1-3.0), p=0.03), Gleason pattern 4/5 PCA (HR=3.9 (95% CI 1.8-8.3), p<0.001), extraprostatic extension status (HR=2.6 (95% CI 1.6-4.2), p<0.0001), surgical margin status (HR=2.6 (95% CI 1.2-5.6), p=0.01), seminal vesicle status (HR=3.5 (95% CI 2.0-6.2), p<0.0001), the natural log of pre-operative PSA level (HR=2.5 (95% CI 1.6-3.8), p<0.001), HR=2.4, p<0.001), and maximum tumor dimension (HR=2.7 (95% CI 1.6-4.7), p<0.0001). Presence of Gleason pattern 4/5 PCA (HR=3.8 (95% CI 1.4-10.0), p<0.01), Ln(PSA) (HR=2.1 (95% CI 1.1-3.9), p=0.02), and decreased pim-1 protein expression (HR4.5 (95% CI 1.6-15.2), p=0.01) were both found to be significant predictors of PSA recurrence by a multivariate Cox model. Thus, even more so than hepsin, decreased expression of pim-1 kinase in PCA correlated significantly with measures of poor patient outcome.

Pim-1 kinase is a proto-oncogene that is regulated by cytokine receptors (Matikainen et al., Blood 93:1980 [1999]). It was first described as a common site of proviral integration in murine retrovirus-induced T cell lymphomas (Cuypers et al., Cell 37:141 [1984]), and was previously thought to be involved exclusively in hematopoietic malignancies (Breuer et al., Nature 340:61 [1989]). Co-transcriptional regulation of pim-1 and myc was observed in the experiments described herein (FIG. 2 cell growth/cell death cluster). Chronic overexpression of myc in the ventral prostate of transgenic mice induced epithelial abnormalities similar to low-grade PIN, but progression to adenocarcinoma in this model was never observed (Zhang et al., Prostate 43:278 [2000]). The present invention is not limited to any one mechanism. Indeed, an understanding of the mechanism is not necessary to practice the present invention. Nonetheless, it is contemplated that pim-1 overexpression may potentiate myc-induced prostate carcinogenesis.

FIG. 8 provides a schematic overview of representative genes differentially expressed in PCA identified by DNA microarray analysis. Genes are grouped functionally and arrows represent up- or down-regulation in metastatic hormone-refractory PCA (MET) and/or localized PCA (PCA) relative to normal prostate epithelium. See FIG. 2 for gene expression levels.

Example 5

AMACR Expression Analysis

The Example describes the analysis of the gene expression data described in Examples 1-4 above to identify AMACR as being consistently over-expressed in prostate cancer.

A. Tissue Samples

In order to examine the widest range of prostate cancer specimens, clinical samples were taken from the radical prostatectomy series at the University of Michigan and from the Rapid Autopsy Program. Both programs are part of the University of Michigan Prostate Cancer Specialized Program of Research Excellence (S.P.O.R.E.) Tissue Core.

Prostatectomy cases for the tissue microarray (TMA) outcomes array were selected from a cohort of 632 patients, who underwent radical retropubic prostatectomy at the University of Michigan as a monotherapy (i.e., no hormonal or radiation therapy) for clinically localized prostate cancer between the years of 1994 and 1998. Clinical and pathology data for all patients was acquired with approval from the Institutional Review Board at the University of Michigan. Detailed clinical, pathology, and TMA data is maintained on a secure relational database (Manley et al., Am. J. Pathol., 159:837 [2001]).

Processing of the prostate specimens began within approximately 15-20 minutes after surgical resection. The prostates were partially sampled and approximately 50% of the tissue was used for research. This protocol has been evaluated in a formal study to assure that partial sampling does not impair accurate staging and evaluation of the surgical margins (Hollenbeck et al., J. Urol., 164:1583 [2000]). Briefly, alternate sections of the prostate gland were submitted for histologic review. The remaining sections were frozen and stored in the SPORE Tissue Core. These samples were collected only from patients who had signed an IRB-approved informed consent. The samples were snap-frozen in OCT embedding media at −80° C. and stored in a holding area until the pathology report was finalized. These frozen samples were not available to researchers until adequate diagnosis and staging had been performed. The samples used for cDNA expression array analysis and RT-PCR were all evaluated by the study pathologists. All samples were grossly trimmed such that greater than 95% of the sample represented the desired lesion (e.g., prostate cancer, BPH, or benign prostate). Samples with prostate cancer were also assigned a Gleason score based on the sample used for molecular analysis.

In order to study hormone refractory prostate cancer, a Rapid Autopsy Protocol was used, which represents a valuable source of metastatic prostate tumors. Modeled after protocols developed at the University of Washington (Seattle, Wash.) and Johns Hopkins University (Baltimore, Md.), this program allows men with advanced prostate cancer to consent to an autopsy immediately after death. To date, 23 complete autopsies have been performed with a median time of 2 hours from death to autopsy. This procedure has previously been described in detail (Rubin et al., Clin. Cancer Res., 6:1038 [2000]). In brief, patients diagnosed with hormone refractory prostate cancer were asked to take part in a posthumous tissue donor program. The objectives and procedures for tissue donation were explained to the patient. Having agreed to participate in this IRB-approved tumor donor program, permission for autopsy is obtained before the death, with consent provided by the patient, or by next of kin. Hormone refractory primary and metastatic prostate cancer samples were collected using liquid nitrogen. Mirrored samples from the same lesion were placed in 10% buffered formalin. The fixed samples were embedded in paraffin and used for the development of TMAs. As with the prostatectomy samples, the study pathologist reviewed the glass slides, circled areas of viable prostate cancer, while avoiding areas of necrosis, and used these slides as a template for TMA construction.

B. Pathology and Evaluation

Prostates were inked before the assessment of surgical margins. Surgical margins from the apex and base were cut perpendicular to the prostatic urethral axis. The seminal vesicles were cut perpendicular to their entry into the prostate gland and submitted as the seminal vesicle margin. The prostates for this study were all partially embedded, taking alternate full sections from the apex, mid, and base. Detailed prostatectomy pathology reports included the presence or absence of surgical margin involvement by tumor (surgical margin status), the presence of extraprostatic extension, and seminal vesicle invasion. Tumors were staged using the TNM system, which includes extraprostatic extension and seminal vesicle invasion but does not take into account surgical margin status (Bostwick et al., Simin. Urol. Oncol., 17:222 [1999]). Tumors were graded using the Gleason grading system (Gleason, Cancer Chemother. Rep., 50:125 [1966]; Gleason, The Veterans Administration Cooperative Urological Research Group. Histologic Grading and Clinical Staging of Prostate Carcinoma. In: Tannenbaum M, editor. Urologic Pathology: The Prostate. Philadelphia: Lea & Febiger; 1977. p. 171-98).

As preparation for the construction of the TMAs, all glass slides were re-reviewed to identify areas of benign prostate, prostatic atrophy, high-grade prostatic intraepithelial neoplasia, and prostate cancer. To optimize the transfer of these designated tissues to the arrays, area of tumor involvement was encircled on the glass slide template as tightly around each lesion as possible. Areas with infiltrating tumor adjacent to benign glands were avoided.

C. RT-PCR

Total RNA integrity was judged by denaturing-formaldehyde agarose gel electrophoresis. cDNA was prepared using 1 μg of total RNA isolated from prostate tissue specimens. Primers used to amplify specific gene products were: AMACR sense, 5' CGTATGCCCCGCTGAATCTCGTG-3' (SEQ ID NO:100); AMACR antisense, 5'-TGGCCAATCATCCGTGCTCATCTG-3' (SEQ ID NO:101); GAPDH sense, 5'-CGGAGTCAACGGATTTGGTCGTAT-3' (SEQ ID NO:102); and GAPDH antisense, 5'-AGCCTTCTCCATGGTGGTGAAGAC-3' (SEQ ID NO:103). PCR conditions for AMACR and GAPDH comprised 94° C. for 5 min, 28 cycles of 95° C. for 1 min, 60° C. for 1 min (annealing), and 72° C. for 1 min, and a final elongation step of 72° C. for 7 min. PCR reactions used a volume of 50 μl, with 1 unit of Taq DNA polymerase (Gibco BRL). Amplification products (5 μl) were separated by 2% agarose gel electrophoresis and visualized by ultraviolet light.

D. Immunoblot Analysis

Representative prostate tissue specimens were used for Western blot analysis. Tissues were homogenized in NP-40 lysis buffer containing 50 mmol/L Tris-HCl, pH 7.4, 1% Nonidet P-40 (Sigma, St. Louis. MO) and complete protein-ase inhibitor cocktail (Roche, Ind., USA). Fifteen μg of protein extracts were mixed with SDS sample buffer and electrophoresed onto a 10% SDS-polyacrylamide gel under reducing conditions. The separated proteins were transferred onto nitrocellulose membranes (Amersham Pharmacia Biotech, Piscataway, N.J.). The membrane was incubated for 1 hour in blocking buffer (Tris-buffered saline with 0.1% Tween (TBS-T) and 5% nonfat dry milk). The AMACR antibody (Obtained from Dr. R Wanders, University of Amsterdam) was applied at 1:10,000 diluted in blocking buffer overnight at 4° C. After washing three times with TBS-T buffer, the membrane was incubated with horseradish peroxidase-linked donkey anti-rabbit IgG antibody (Amersham Pharmacia Biotech, Piscataway, N.J.) at 1:5000 for 1 hour at room temperature. The signals were visualized with the ECL detection system (Amersham Pharmacia biotech, Piscataway, N.J.) and autoradiography.

For β-tubulin western blots, the AMACR antibody probed membrane was stripped with Western Re-Probe buffer (Geno-tech, St. Louis, Mo.) and blocked in Tris-buffered saline with 0.1% Tween (TBS-T) with 5% nonfat dry milk and incubated with rabbit anti 13-tubulin antibodies (Santa Cruz Biotechnologies, Santa Cruz, Calif.) at 1:500 for two hours. The western blot was then processed as described above.

E. Immunohistochemistry

Standard indirect immunohistochemistry (IHC) was performed to evaluate AMACR protein expression using a polyclonal anti-AMACR antibody. Protein expression was scored as negative (score=1), weak (score 2), moderate (3) and strong (4). In order to evaluate whether AMACR protein expression was associated with prostate cancer proliferation, a subset of samples were evaluated using the monoclonal mouse IgG Mib-1 antibody for Ki-67 (1:150 dilution, Coulter-Immunotech, Miami, Fla.). Microwave pretreatment (30 minutes at 100 C in Tris EDTA Buffer) for antigen retrieval was performed using 3,3' diaminobenzidine tetrahydrocloride as a chromogen. Lymph node tissue with known high Ki-67 positivity was used as a control.

F. Tissue Microarray Construction, Digital Image Capture, and Analysis

Five TMAs were used for this study. Three contained tissue from the prostatectomy series and two contained hormone refractory prostate cancer from the Rapid Autopsy Program. The TMAs were assembled using the manual tissue arrayer (Beecher Instruments, Silver Spring, Md.) as previously described (Kononen et al., Nat. Med., 4:844 [1998]; Perrone et al., J. Natl. Cancer Inst., 92:937 [2000]). Tissue cores from the circled areas (as described above) were targeted for transfer to the recipient array blocks. Five replicate tissue cores were sampled from each of the selected tissue types. The 0.6 mm diameter TMA cores were each spaced at 0.8 mm from core-center to core-center. After construction, 4 μm sections were cut and H&E staining was performed on the initial slide to verify the histology.

TMA H&E images were acquired using the BLISS Imaging System (Bacus Labs, Lombard, Ill.). AMACR protein expression was evaluated in a blinded manner. All images were scored for AMACR protein expression intensity. In addition, all TMA samples were assigned a diagnosis (i.e., benign, atrophy, high-grade prostatic intraepithelial neoplasia, and prostate cancer). This is recommended because the targeted tissues may not be what were actually transferred. Therefore, verification was performed at each step. TMA slides were evaluated for proliferation index using a CAS200 Cell Analysis System (Bacus Labs). Selected areas were evaluated under the 40× objective. Measurements were recorded as the percentage of total nuclear area that was positively stained. All positive nuclear staining, regardless of the intensity, was measured. Sites for analysis were selected to minimize the presence of stromal and basal cells; only tumor epithelium was evaluated. Specimens were evaluated for Ki-67 expression as previously described (Perrone et al., J. Natl. Cancer Inst. 92:937 [2000]). Each measurement was based on approximately 50-100 epithelial nuclei. Due to the fixed size of TMA samples, 5 repeat non-overlapping measurement was the maximum attainable.

G. Analysis of Prostate Needle Biopsies

In order to evaluate the usefulness of AMACR expression in diagnostic 18 gauge needle biopsies, 100 consecutive biopsies with prostate cancer or atypia that required further work-up were tested for AMACR expression. All cases were immunostained using two basal cell specific markers (34βE12 and p63) and AMACR. Cases were evaluated for cancer sensitivity and specificity. Twenty-six of these cases were seen in consultation with a pathologist and were considered diagnostically difficult, requiring expert review and additional characterization.

H. Results

Figure 11:
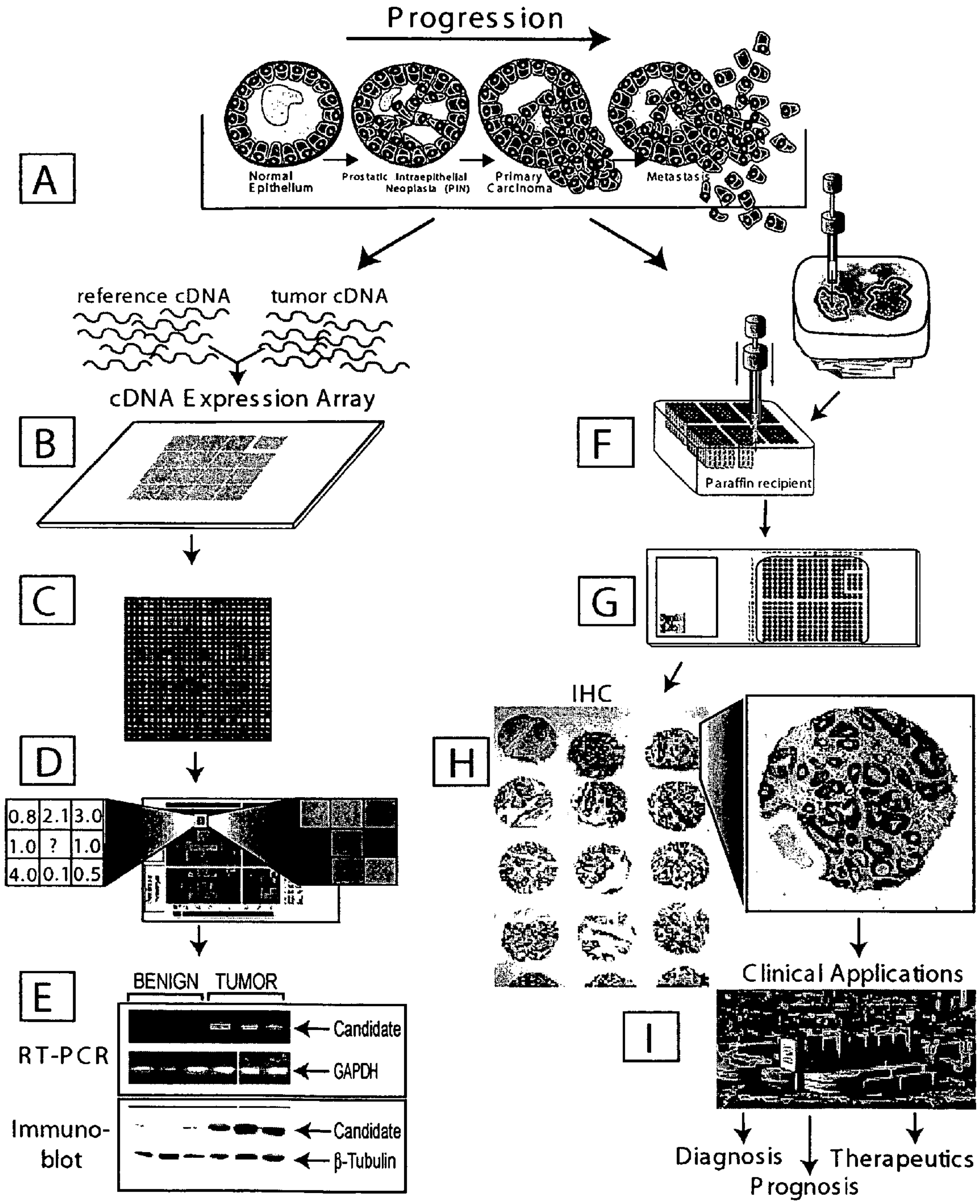
FIG. 11 an overview of the discovery and characterization of AMACR in prostate cancer utilized in some embodiments of the present invention.

FIG. 11 shows a schematic of the DNA and tissue microarray paradigm that lead to the discovery and characterization of AMACR in prostate cancer. A) Prostate cancer progression as adapted from Abate-Shen and Shen, (Genes Dev., 14:2410 [2000]). Distinct molecular changes occur at each stage of prostate cancer progression that can be studied using DNA microarray or "chip" technology. B) cDNA generated from tumor (prostate cancer) and reference (benign prostate tissue) samples is labeled with distinguishable fluorescent dyes and interrogated with a DNA microarray that can monitor thousands of genes in one experiment. C) After hybridization, the DNA microarray is analyzed using a scanner and fluorescence ratios determined for each gene (in this case prostate cancer/benign tissue). D) The ratios are deposited into a computer database and subsequently analyzed using various statistical algorithms. One exemplary method of surveying the data (Eisen et al., PNAS 95:14863 [1998]) assigns color intensity to the ratios of gene expression. In this case, shades of red represent genes that are up-regulated in prostate cancer (e.g., a ratio of 4.0) and shades of green represent genes that a down-regulated (e.g., ratio of 0.1). Genes that are unchanged between tumor and benign tissues are represented by a black color and missing elements by a gray color. E) Genes that are identified by DNA microarray can then be validated at the transcript level (e.g., Northern blot, RT-PCR) or at the protein level (e.g., immunoblot). F) Construction of prostate cancer tissue microarrays facilitates the study of hundreds of patients (rather than hundreds of genes). G) Each tissue microarray slide contains hundreds of clinically stratified prostate cancer specimens linked to clinical and pathology databases (not shown). H) Tissue microarray slides can then be analyzed using various molecular or biochemical methods (in this case immunohistochemistry). I) Both DNA and tissue microarray data have clinical applications. Examples include, but are not limited to: 1. using gene expression profiles to predict patient prognosis, 2. identification of clinical markers and 3. development of novel therapeutic targets.

Figure 12:
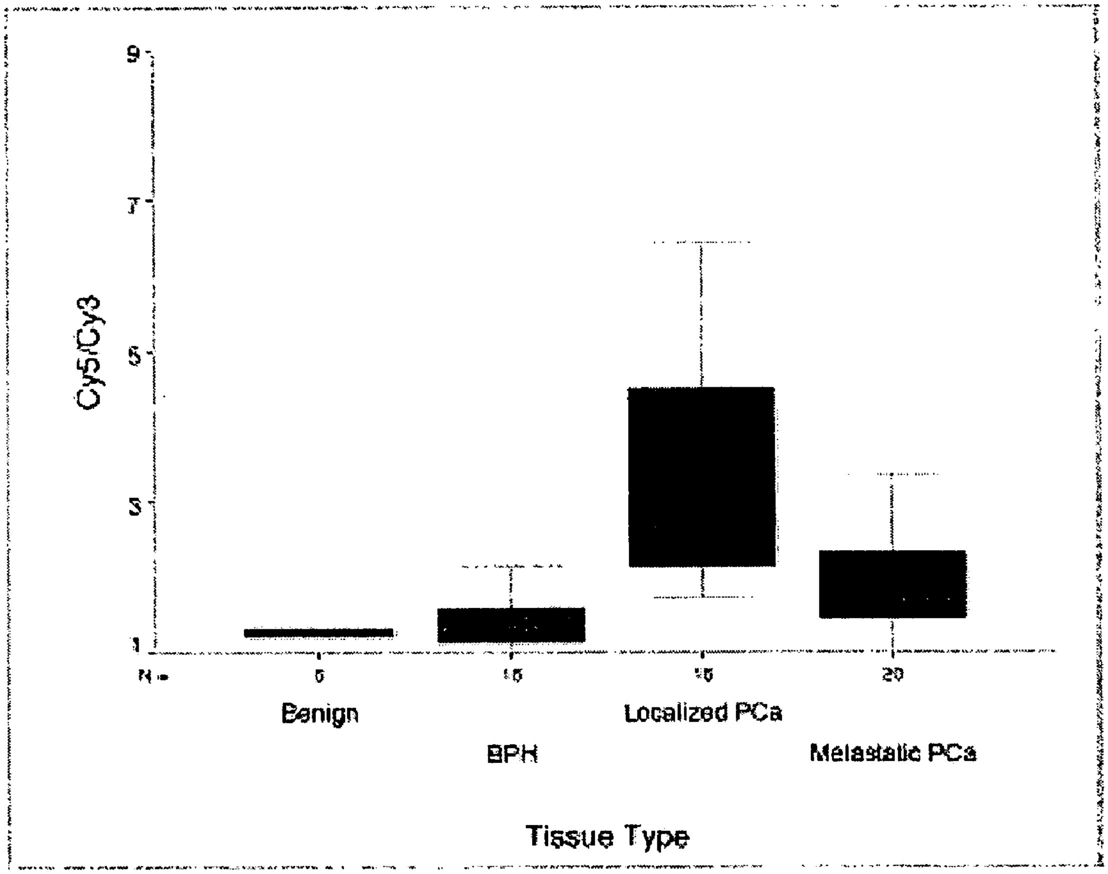
FIG. 12 describes a DNA microanalysis of AMACR expression in prostate cancer.

FIG. 12 summarizes AMACR transcript levels as determined by DNA microarray analysis over 57 prostate cancer specimens. Samples (Dhanasekaran et al., Nature 412: 822 [2001]) were grouped according to tissue type and averaged. The experimental sample was labeled in the Cy5 channel while the reference sample (pool of benign prostate tissue) was labeled in the Cy3 channel. The box-plot demonstrates the range of AMACR expression within each group. Tissues were grouped into the following classes benign (normal adjacent prostate tissue), benign prostatic hyperplasia (BPH), clinically localized prostate cancer, and metastatic prostate cancer. In relation to benign prostate tissues, localized prostate cancer and metastatic prostate cancer were 3.1 (Mann-Whitney test, $p<0.0001$) and 1.67 (Mann-Whitney test, $p<0.004$) fold up-regulated, respectively (represented as Cy5/Cy3 ratios).

DNA microarray results of AMACR mRNA levels were validated using an independent experimental methodology. AMACR-specific primers were generated and RT-PCR performed on the various RNA samples from 28 prostate tissue specimens and 6 prostate cell lines (FIG. 13A). GAPDH served as the loading control. Pool, refers to RNA from normal prostate tissues obtained from a commercial source. NAP, normal adjacent prostate tissue from a patient who has prostate cancer. 3+3, 3+4, 4+4, refers to the major and minor Gleason patterns of the clinically localized prostate cancer (PCA) examined. MET, metastatic prostate cancer. Various prostate cell lines are also examined. RT-PCR without enzyme served as a negative control. An RT-PCR product was clearly observed in the 20 localized prostate cancer samples but not in the benign samples examined. Metastatic prostate cancer and prostate cell lines displayed varying levels of AMACR transcript as compared to localized prostate cancer.

In order to gauge AMACR protein levels, immunoblot analysis was performed on selected prostate tissue extracts (FIG. 13B). β-tubulin served as a control for sample loading. Similar to AMACR transcript, over-expression of AMACR protein was observed in malignant prostate tissue relative to benign prostate tissue.

In order to validate protein expression of AMACR in situ, a separate cohort of prostate samples from those used in the cDNA expression array analysis was used. These prostate samples were taken from the University of Michigan Prostate SPORE Tissue Core and were assembled onto high-density tissue microarrays (schematically illustrated in FIG. 11F-H). Moderate to strong AMACR protein expression was seen in clinically localized prostate cancer samples with predominately cytoplasmic localization. A large contrast in levels of AMACR in malignant epithelia relative to adjacent benign epithelia was seen. Prostatic intraepithelial neoplasia (PIN) and some atrophic lesions, which are thought to be potentially pre-cancerous lesions (Putzi et al., Urology 56:828 [2000]; Shah et al., Am. J. Pathol., 158:1767 [2001]), demonstrated cytoplasmic staining of AMACR. High-grade prostate cancer also demonstrated strong cytoplasmic staining. However, no association was identified with AMACR staining intensity and Gleason (tumor) score. Many of the metastatic prostate cancer samples demonstrated only weak AMACR expression. The metastatic samples showed uniform PSA immunostaining, confirming the immunogenicity of these autopsy samples.

Figure 14:
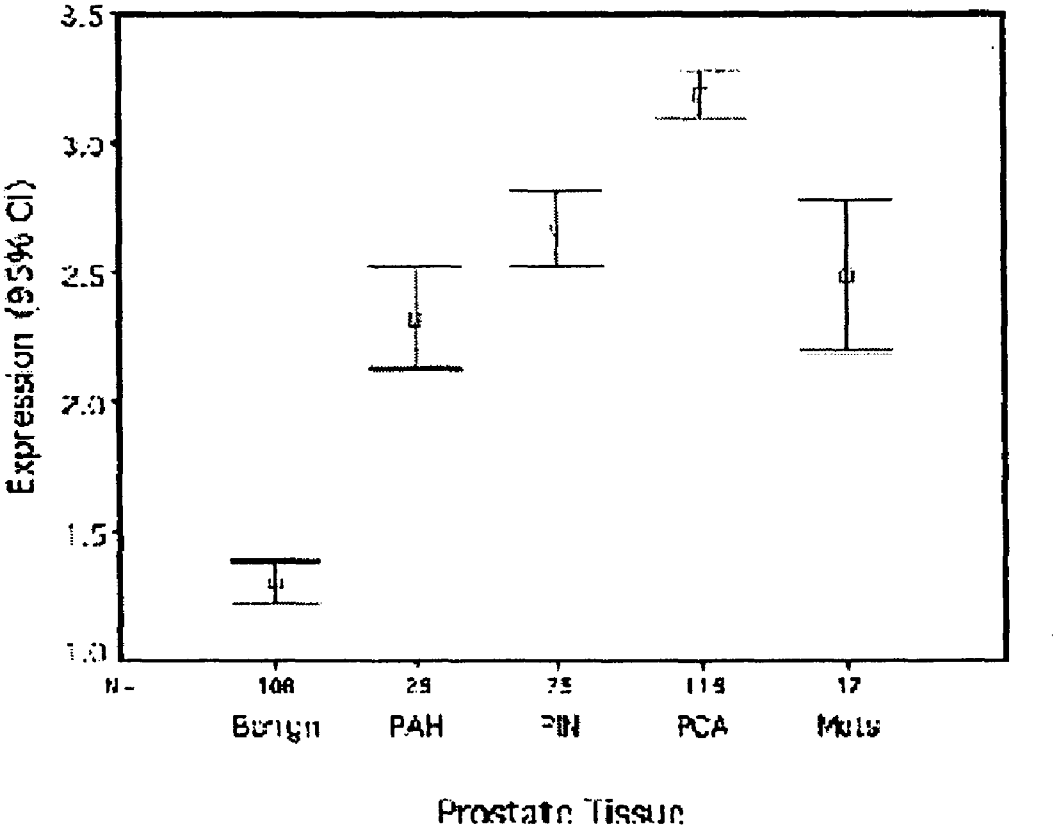
FIG. 14 describes an analysis of AMACR protein expression using prostate cancer tissue microarrays.

In order to assess AMACR protein expression over hundreds of prostate specimens, the tissue microarray data was quantitated. Benign prostate, atrophic prostate, PIN, localized prostate cancer, and metastatic prostate cancer demonstrated mean AMACR protein staining intensity of 1.0 (SE 0), 2.0 (SE 0.1), 2.5 (SE 0.1), 3.0 (SE 0), and 2.5 (SE 0.1), respectively (ANOVA p-value<0.0001). This data is graphically summarized using error bars representing the 95% confidence interval for each tissue category (FIG. 14).

The correlation of AMACR levels with tumor proliferation was next investigated using Ki-67 (Perrone et al., supra). There was no significant association between AMACR expression and Ki-67 expression with a correlation coefficient of 0.13 (p-value=0.22). In addition, no significant associations were identified between AMACR protein expression and pathology parameters such as radical prostatectomy, Gleason score, tumor stage, tumor size (cm), or surgical margin status. AMACR protein levels were next evaluated for association with PSA recurrence following surgery in 120 prostatectomy cases with a median follow-up time of 3 years. No statistically significant association was identified. AMACR demonstrated uniform moderate to strong expression in clinically localized prostate cancer with a high sensitivity for tumor and an equally high specificity. In addition, a preliminary survey of normal tissues including ovary, liver, lymph nodes, spleen, testis, stomach, thyroid, colon, pancreas, cerebrum, and striated muscle revealed significant AMACR protein expression in only normal liver.

The large difference in AMACR protein levels between normal secretory epithelial cells and malignant cells provides a clinical use for testing AMACR expression in prostate needle biopsy specimens. In diagnostically challenging cases, pathologists often employ the basal cell markers 34βE12 (O'Malley et al., Virchows Arch A Patho. Anat. Histopathol., 417:191 [1990]; Wojno et al., Am. J. Surg. Pathol., 19:251 [1995]; Googe et al., Am. J. Clin. Pathol., 107:219 [1997] or p63 (Parson et al., Urology 58:619 [2001]; Signoretti et al., Am. J. Pathol., 157:1769 [2000]), which stain the basal cell layer of benign glands. This second basal cell layer is absent in malignant glands. In many equivocal biopsy specimens, the surgical pathologist must rely on absence of staining to make the final diagnosis of prostate cancer. The clinical utility of AMACR immunostaining on 94 prostate needle biopsies was evaluated. The results are shown in Table 2. The sensitivity and specificity were calculated as 97% and 100%, respectively. These results included 26 cases where the final diagnosis required the use of a basal cell specific immunohistochemical marker (i.e., 34βE12 or p63).

This example demonstrated that AMACR is associated with PCA and that AMACR expression in prostate biopsies is useful for the diagnosis of cancer in inconclusive biopsy samples.

TABLE 2

Clinical utility of Assessing AMACR Protein in Prostate Needle Biopsies (n = 94)

| Sensitivity (TP/(TP + FN)) | Specificity (TN/(TN + FP)) | Positive Predictive Value (TP/(TP + FP)) | Negative Predictive Value (TN/(TN + FN)) |
|---|---|---|---|
| 97% ((68/(2 + 68)) | 100% ((24/(24 + 0)) | 100% ((68/(68 + 0)) | 92% ((24/24 + 2)) |

Example 6

Hormone Regulation of AMACR

This example describes studies that indicate that AMACR expression is hormone independent.

A. Sample Collection, cDNA Array and TMA Construction and Evaluation

Clinical samples were taken from the radical prostatectomy series and from the Rapid Autopsy Program at the University of Michigan. Both are part of the University of Michigan Prostate Cancer Specialized Program of Research Excellence (S.P.O.R.E.). Primary PCA of metastatic cases as well as lymph node metastases were contributed in collaboration from the University of Ulm, Germany. Detailed clinical and expression analysis as well as TMA data was acquired and maintained on a secure relational database according to the Institutional Review Board protocol of both institutions. Tissue procurement for expression analysis on the RNA level is described in the above examples. For the development of TMA, samples were embedded in paraffin. The study pathologist reviewed slides of all cases and circled areas of interest. These slides were used as a template for construction of the six TMAs used in this study. All TMAs were assembled using a manual tissue arrayer (Beecher Instruments, Silver Spring, Md.). At least three tissue cores were sampled from each donor block. Histologic diagnosis of the tissue cores was verified by standard haematoxylin and eosin (H&E) staining of the initial TMA slide. Standard biotin-avidin complex immunohistochemistry (IHC) was performed using a poly-clonal anti-AMACR antibody (Ronald Wanders, University of Amsterdam). Digital images were acquired using the BLISS Imaging System (Bacus Lab, Lombard, Ill.). Staining intensity was scored as negative (score=1), weak (score 2), moderate (3) and strong (4). For exploration of the treatment effect by the means of hormonal withdrawal before radical prostatectomy, standard slides were used for regular H&E staining and consecutive sections for detection of AMACR expression. In order to test AMACR expression in poorly differentiated colon cancers, cases were used from a cohort of well-described colon tumors. In addition to well-differentiated colon cancers, a recently described subset of poorly differentiated colon carcinomas with a distinctive histopathological appearance, termed large cell minimally differentiated carcinomas, was used. These poorly differentiated colon carcinomas had a high frequency of the microsatellite instability phenotype.

B. Cell Culture and Immunoblot Analysis

Prostate cell lines (RWPE-1, LNCaP, PC3 and DU 145) were obtained from the American Tissue Culture Collection. Cells were maintained in RPMI-1640 with 8% decomplemented fetal bovine serum, 0.1% glutamine and 0.1% penicillin and streptomycin (BioWhittaker, Walkersville, Md.). Cells were grown to 75% confluence and then treated for 24 and 48 with the antiandrogen bicalutamide (CASODEX, Zeneca Pharmaceuticals, Plankstadt, Germany) at a final concentration of 20 μM or with methyltrienolone (synthetic androgen (R1881); NEN, Life Science Products, Boston, Mass.) at a final concentration of 1 nM. Cells were harvested and lysed in NP-40 lysis buffer containing 50 mmol/L Tris-HCl, pH 7.4, 1% Nonidet P-40 (Sigma, St. Louis, Mo.) and complete proteinase inhibitor cocktail (Roche, Ind., USA). 15 μg of protein extracts were mixed with SDS sample buffer and electrophoresed onto a 10% SDS-polyacrylamide gel under reducing conditions. After transferring, the membranes (Amersham Pharmacia Biotech, Piscataway, N.J.) were incubated for 1 hour in blocking buffer (Tris-buffered saline with 0.1% Tween and 5% nonfat dry milk). The AMACR antibody was applied at 1:10.000 diluted blocking buffer overnight at 4° C. After three washes with TBS-T buffer, the membrane was incubated with horseradish peroxidase-linked donkey anti-rabbit IgG antibody (Amersham Pharmacia Biotech, Piscataway, N.J.) at 1:5000 for 1 hour at room temperature. The signals were visualized with the ECL detection system (Amersham Pharmacia biotech, Piscataway, N.J.). For β-tubulin blots, membranes were stripped with Western Re-Probe buffer (Geno-tech, St. Louis, Mo.) and blocked in Tris-buffered saline with 0.1% Tween with 5% nonfat dry milk and incubated with rabbit anti β-tubulin antibodies (Santa Cruz Biotechnologies, Santa Cruz, Calif.) at 1:500 for two hours. For PSA expression the membranes were reprobed in the described manner with PSA antibody. (rabbit polyclonal; DAKO Corporation, Carpinteria, Calif.) at 1:1000 dilution and further processed.

C. Statistical Analysis

Primary analysis of the cDNA expression data was done with the Genepix software. Cluster analysis with the program Cluster and generation of figures with TreeView was performed as described above. AMACR protein expression was statistically evaluated using the mean score result for each prostate tissue type (i.e., benign prostate, naive localized or advanced prostate cancer, hormone treated and hormone refractory prostate cancer). To test for significant differences in AMACR protein expression between all tissue types, a one-way ANOVA test was performed. To determine differences between all pairs, a post-hoc analysis using the Scheffe method was applied as described above. For comparison of naive primaries to their corresponding lymph node metastases with respect to AMACR protein expression, a non parametric analysis (Mann Whitney test) was performed. To compare AMACR expression intensity to the scored hormonal effect of the pretreated localized prostate cancer cases the Mantel-Haenszel Chi-Square test was applied. AMACR expression scores are presented in a graphical format using error-bars with 95% confidence intervals. P-values <0.05 were considered statistically significant.

D. Results

Figure 15:
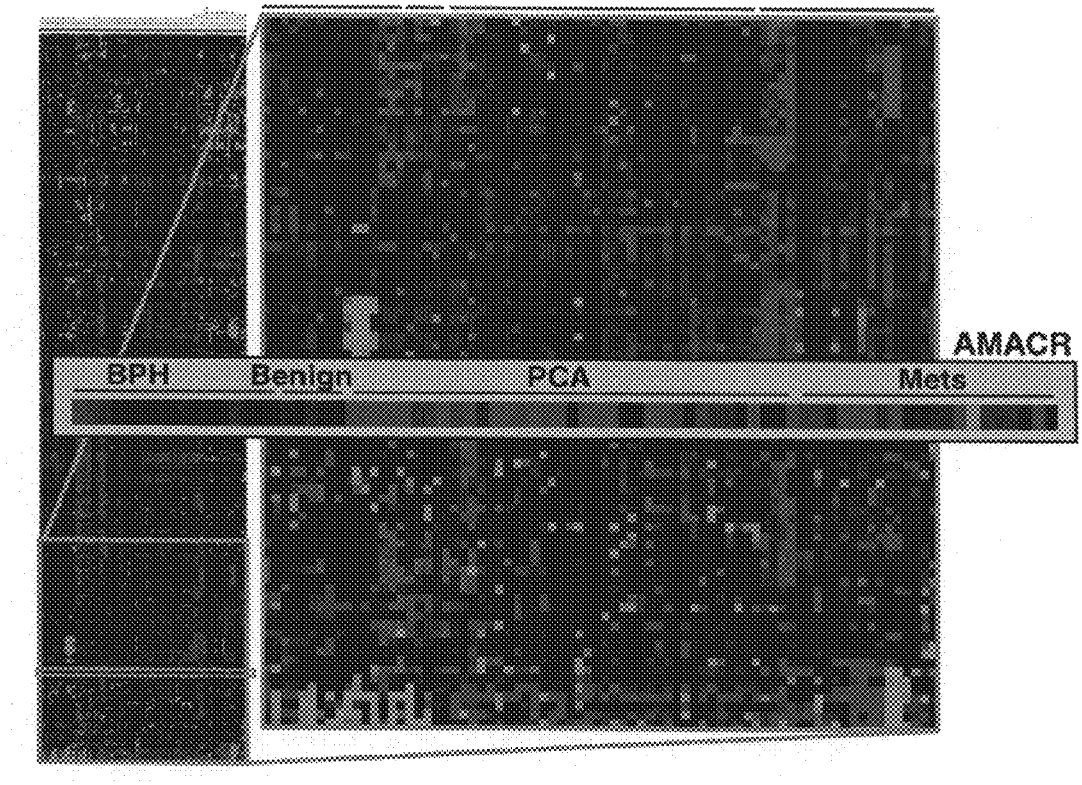
FIG. 15 shows relative gene expression of AMACR in several samples.

Hierarchical clustering of 76 prostate tissues including benign, BPH, localized PCA and metastatic PCA and filtering for only those genes with a 1.5 fold expression difference or greater, clustered the samples into histologically distinct groups as described above. As demonstrated by a TreeView presentation of this data (FIG. 15), AMACR was one of several genes that demonstrated over expression at the cDNA level of PCA samples with respect to benign pooled prostate tissue. The highest level of over expression by cDNA analysis was in the clinically localized PCA cases.

Figure 16:
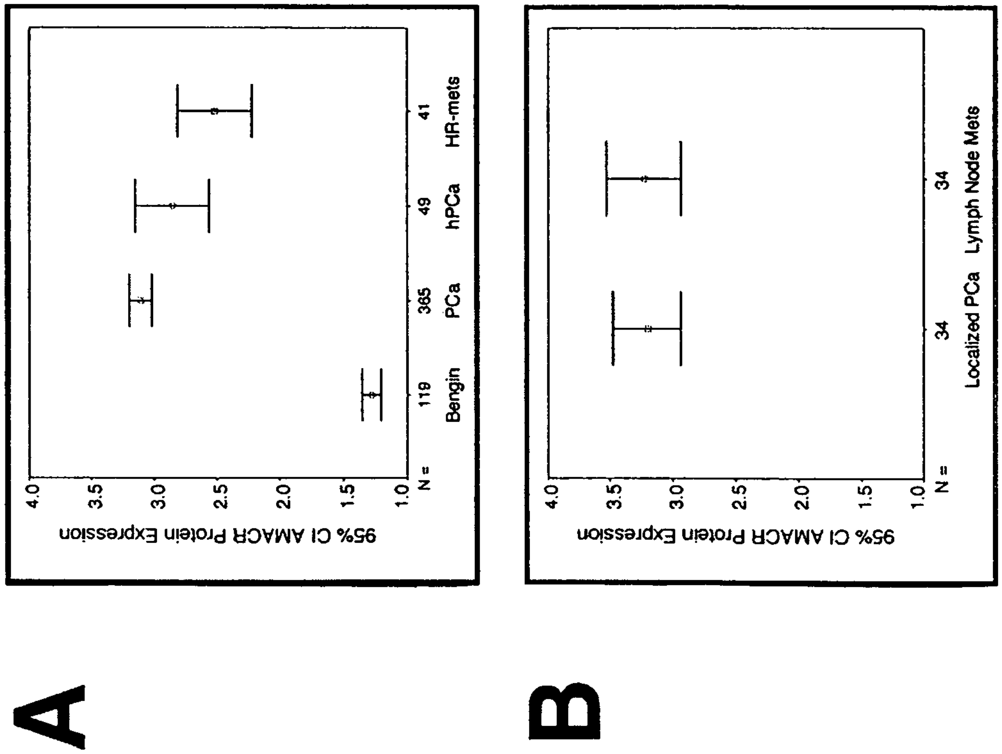
FIG. 16 shows AMACR protein expression PCA.

In order to further investigate the role of AMACR protein expression in samples with variable differentiation and exposure to anti-androgen treatment, several TMAs with a wide range of PCA were constructed: a total of 119 benign prostate samples, 365 primary hormone naive PCA samples, 37 naive prostate cancer lymph node metastases, and 41 hormone refractory metastatic PCA samples were evaluated. An additional 49 hormone treated primary prostate cancers (including 22 on standard slides) were examined for histologic changes associated with anti-androgen treatment and AMACR protein expression. The mean AMACR protein expression levels for each tissue category is presented in FIG. 16. Benign prostate, naive primary prostate cancer, hormone treated primary cancer, and hormone refractory metastatic tissue had a mean staining intensity of 1.28 (Standard Error SE 0.038, 95% Confidence Intervals CI 1.20-1.35), 3.11 (SE 0.046, CI 3.02-3.20), 2.86 (SE 0.15, CI 2.56-3.15) and 2.52 (SE 0.15, CI 2.22-2.28), respectively). One-way ANOVA analysis revealed a p-value of <0.0001. To specifically examine the difference between different tissue types, a post-hoc pair-wise comparison was performed. Clinically localized PCA demonstrated a significantly stronger AMACR protein expression as compared to benign prostate tissue (post-hoc analysis using Scheffe method, mean difference=1.83, p<0.0001, CI 1.53-2.13). A significant decrease in AMACR protein expression was observed in the metastatic hormone refractory PCA samples with respect to clinically localized PCA (0.59, p=0.002, CI 0.15-1.03). Hormone treated primaries had a mean AMACR expression of 2.86, which was between the expression levels of naive primaries (3.11) and hormone refractory cases (2.52) (post-hoc analysis using Scheffe method, p=0.51, CI −0.66-0.16 and p=0.56, CI −0.23-0.91). There was no significant difference in AMACR expression in the 37 naive primary prostate samples and lymph node metastases derived from the same patient (Mann Whitney test, p=0.8). In other words, matched primaries and lymph node metastases showed similar AMACR expression pattern.

Figure 17:
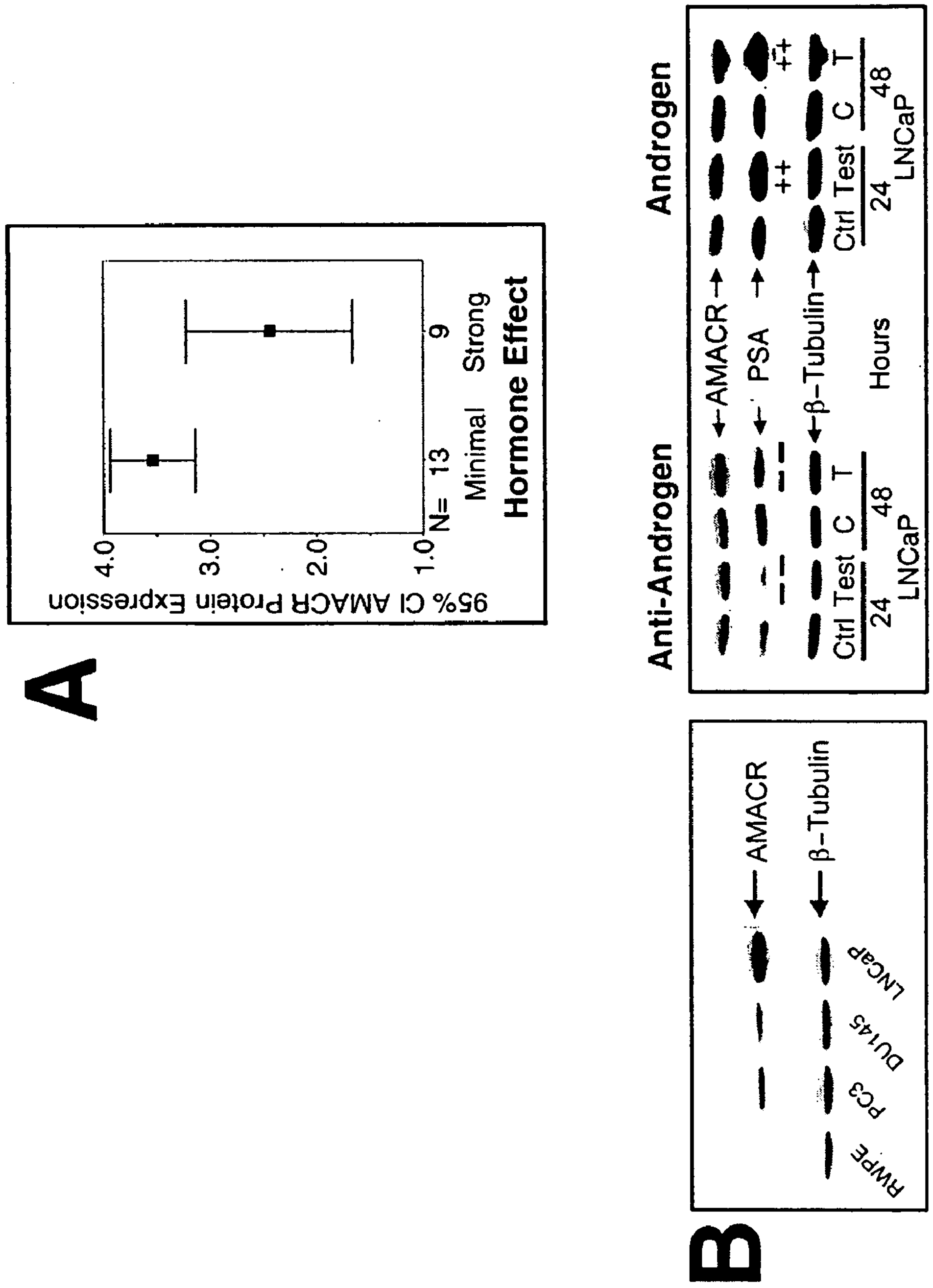
FIG. 17 shows the hormonal effect on AMACR expression.

A subset of 22 PCA cases in which the patients received variable amount and types of anti-androgen treatment prior to surgery was examined. These cases were evaluated blindly with respect to treatment protocol for histological evidence of hormone treatment (H&E slide) and AMACR protein expression. The hormonal effect visible on the H&E slides was classified from 1 to 4 with 1 representing "no effect" and 4 showing a "very strong effect". 13 cases demonstrated either no or moderate hormonal effect, and 9 cases had a very strong hormonal effect. Statistical analysis revealed a significant difference between these two groups with respect to AMACR expression intensity (FIG. 17, Mantel-Haenszel Chi-Square, p=0.009). FIG. 17 presents an example of a PCA case treated prior to surgery with anti-androgens that has a strong hormonal effect appreciated on H&E and decreased AMACR protein expression (FIG. 17A). In this dataset there was neither a correlation between treatment duration nor treatment type (monotherapy or complete hormonal withdrawal for hormone deprivation) and AMACR expression.

For further exploration of the hormonal effect on AMACR expression, primary cell culture experiments and Western blot analysis were performed. As demonstrated in FIG. 17 Panel B, LNCaP cells, derived from a metastatic lesion but considered hormone responsive, showed a higher baseline AMACR expression as compared to PC3 and DU-145 cells, which are both hormone independent cell lines derived from metastatic lesions. A benign cell line, RWPE-1 (Bello et al., Carcinogenesis 18:1215 [1997]), showed near absent AMACR expression, which is consistent with the in situ protein expression data. To simulate an anti-androgen treatment, the hormone responsive cell line LNCaP was treated with bicalutamide in a final concentration of 20 μM for a time period of 24 and 48 hours. AMACR expression in cell lysates of LNCaP cells did not change at either time point when exposed to anti-androgen therapy. Under the same conditions, PSA, a gene known to be regulated by the androgen receptor, showed decreased protein expression. In addition, when LNCaP cells were exposed to a synthetic androgen R1881, no increase in AMACR expression was observed (FIG. 17, Panel B). Therefore, these cell culture experiments provide evidence that AMACR expression is not regulated by the androgen pathway.

The present invention is not limited to a particular mechanism. Indeed, an understanding of the mechanism is not necessary to practice the present invention. Nonetheless, it is contemplated that another explanation for these observations was that AMACR over expression occurred in PCA, but as these tumors became poorly differentiated, as in the hormone refractory PCA, AMACR expression was down regulated either directly or indirectly due to the process of de-differentiation. To elucidate this potential correlation colon cancer samples were examined for AMACR expression (See Example 7). AMACR protein expression is also observed in some other tumor types, with the highest overall expression in colorectal cancers. Colorectal cancers are not known to be regulated by androgens and were therefore used as a control to test this hypothesis. Four well differentiated and seven anaplastic colon cancer samples were chosen. The poorly differentiated tumors have distinct molecular alterations distinguishing them from the common well to moderately differentiated colorectal tumors (Hinoi et al., Am. J. Pathol. 159:2239 [2001]). Strong AMACR protein expression in a moderately differentiated colon cancer was observed. This tumor still forms well defined glandular structures. The surrounding benign colonic tissue does not express AMACR. The anaplastic colon cancers demonstrated weak AMACR protein expression. Primarily data revealed positive AMACR expression in 4/4 well differentiated cases but only 4/7 anaplastic colonic cancers. Three of the anaplastic colon cancers had weak to moderate expression. Metastatic hormone refractory PCA demonstrated weak AMACR protein expression in tissue microarrays.

Example 7

AMACR Expression in a Variety of Cancers

A. Analysis of Online EST and SAGE Database

The National Cancer Institute Cancer Genome Anatomy Project (CGAP) has several gene expression databases available online for comparing gene expression across multiple samples (See the Internet Web site of the National Cancer Institute). Both EST and SAGE databases offer Virtual Northern blots, which allow users to visualize and compare the expression level of a particular gene among multiple samples. The SAGE database includes over 5 million tags from 112 libraries of multiple benign and malignant tissues.

B. Selection of Study Cases

A total of 96 cases of cancers from different sites were selected for construction of a multi-tumor tissue microarray. The tissue microarray was constructed to perform a wide survey of multiple common tumor types. A minimum of three tissue cores (0.6 mm in diameter) was taken for each case. Tumors surveyed included colorectal adenocarcinoma (n=15 cases), renal cell carcinoma (6), prostatic adenocarcinoma (6), urothelial carcinoma (4), cervical squamous cell carcinoma (6), lung non-small cell carcinoma (4), lymphoma (15), melanoma (9) and several other cancer types. Normal adjacent tissue was taken when available. The prostate tissue microarray was constructed from selected patients who underwent radical prostatectomies as monotherapy for clinically localized prostate cancer. This tissue microarray contained a spectrum of prostatic tissue including prostatic atrophy, high-grade prostatic intraepithelial neoplasia (PIN), and clinically localized prostate cancer. In addition, standard slides were used to confirm results for colon cancer. Twenty-four cases of colorectal adenocarcinoma (16 well to moderately differentiated carcinoma and 8 large cell minimally differentiated carcinoma) and 8 endoscopically derived colorectal adenomas were selected for immunostaining for AMACR. For breast carcinoma, a TMA of 52 cases of invasive ductal carcinoma was used. Specimens were collected and analyzed in accordance with the Institutional Review Board guidelines.

C. Immunohistochemistry

Standard avidin-biotin complex immunohistochemistry was used. Pre-treatment was performed by steaming the slides for 10 minutes in sodium citrate buffer in a microwave oven. The slides were then incubated sequentially with primary antibody (1:2000 dilution, polyclonal rabbit anti-AMACR antibody), biotinylated secondary antibody, avidin-biotin complex and chromogenic substrate 3,3'-diaminobenzidine. Slides were evaluated for adequacy using a standard bright field microscope. Digital images were then acquired using the BLISS Imaging System (Bacus Lab, Lombard, Ill.) and evaluated by two pathologists. Protein expression was scored as negative, weak stain (faint cytoplasmic stain or granular apical staining), moderate (diffuse granular cytoplasmic stain) and strong (diffuse intense cytoplasmic stain). Only moderate and strong staining was considered as positive staining.

D. Laser Capture Microdissection

Sections of 2 radical prostatectomy samples were frozen in OCT in accordance with an Institutional Review Board protocol. Frozen sections (5 μm thick) were fixed in 70% alcohol for 10 minutes and then stained in hemotoxylin and eosin. Prostate cancer and benign prostate glands were dissected on a μCUT laser capture microdissector (MMI GmbH, Heidelberg, Germany). Approximately 6000 cells were harvested. Total RNA was isolated using Qiagen micro-isolation kit (Qiagen, San Diego, Calif.). Reverse transcription was performed using both oligo dT and random hexamer primers. Primers used to amplify specific gene products were: AMACR sense, 5'-CGTATGCCCCGCTGAATCTCGTG-3' (SEQ ID NO:104); AMACR antisense, 5'-TGGCCAATCATCCGTGCTCATCTG-3' (SEQ ID NO:105); GAPDH sense, 5'AGCCTTCTCCATGGTGGTGAAGAC-3' (SEQ ID NO:106); and GAPDH antisense, 5'-AGCCTTCTCCATGGTGGTGAAGAC-3' (SEQ ID NO:107). PCR conditions for AMACR and GAPDH were: heat denaturation at 94° C. for 5 min, cycles of 94° C. for 1 min, 60° C. for 1 min, and 72° C. for 1 min (32 cycles for GAPDH, 40 cycles for AMACR), and a final extension step at 72° C. for 5 min. PCR products were then separated on 2% agarose gel and visualized by UV illumination.

E. Results

Using the Virtual Northern tool from the online CGAP program, AMACR expression was surveyed in two databases, EST and SAGE libraries. AMACR was found to be expressed in a wide range of tissues, including central and peripheral nervous system, colon, kidney, breast, pancreas, prostate and blood. Compared to their normal counterparts, a number of cancers have elevated AMACR expression, including tumors arising in bone marrow, breast, colon, genitourinary system, lung, lymph node, nervous system, pancreas, prostate, soft tissue and uterus.

Figure 18:
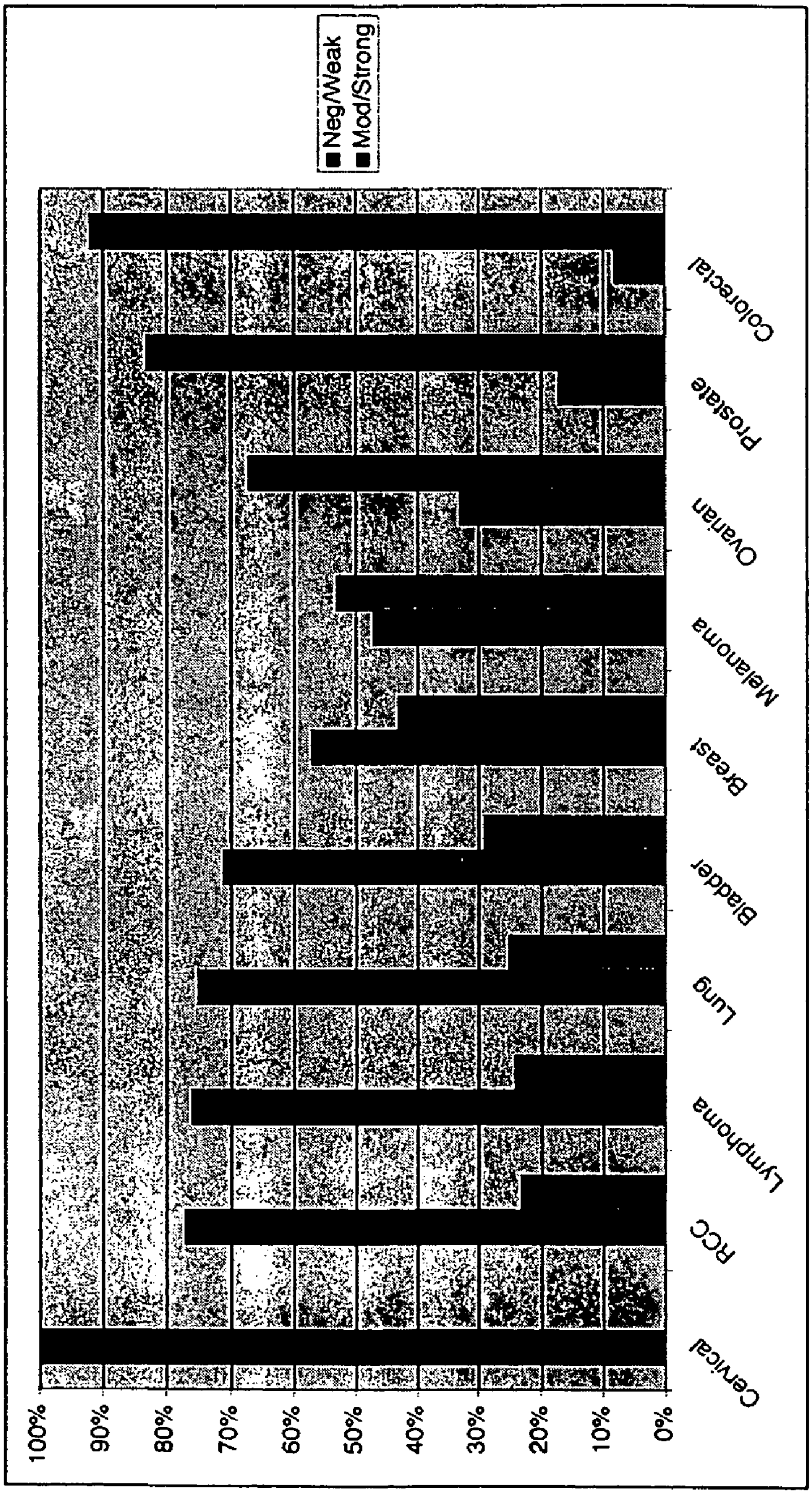
FIG. 18 shows AMACR over-expression in multiple tumors. AMACR protein expression was evaluated by immunohistochemistry on a multi-tumor and a breast cancer tissue microarray. Percentage of cases with positive staining (moderate and strong staining intensity) is summarized on the Y-axis. The left bar represents negative or weak staining and the right bar represents moderate or strong staining.

To confirm the gene expression data, AMACR immunohistochemistry was performed on a multi-tumor tissue array that included some of the most common cancers from multiple sites. AMACR protein level was increased in many cancers, including colorectal, prostate, ovarian, lung cancers, lymphoma and melanoma (FIG. 18). In particular, AMACR over-expression was observed in 92% and 83% of colorectal and prostate cancer, respectively. Using a breast cancer tissue microarray, it was found that AMACR over-expression was present in 44% of invasive ductal carcinomas. AMACR over expression was not observed in female cervical squamous cell carcinoma (6 cases).

Figure 19:
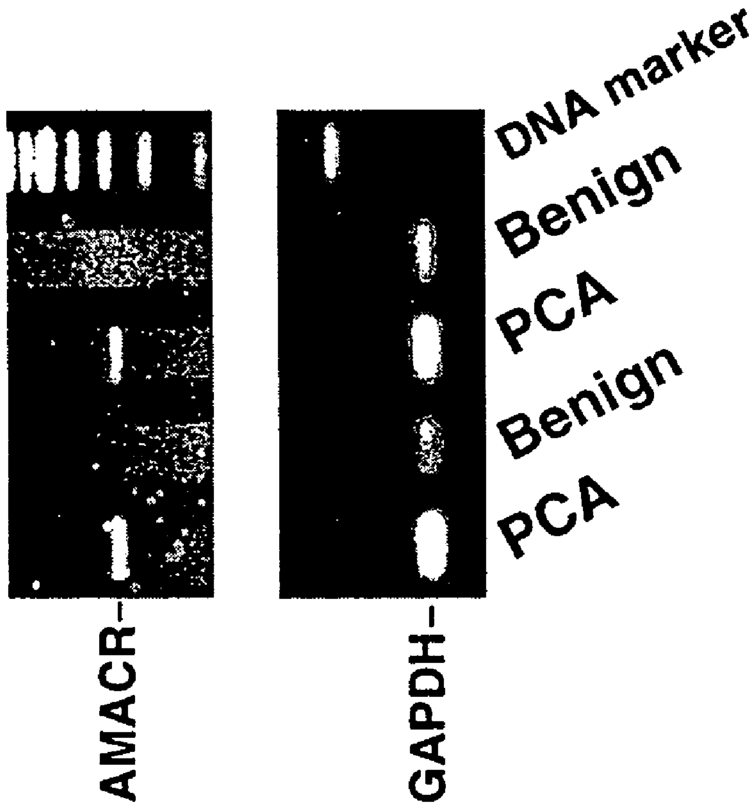
FIG. 19 shows the results of laser capture microdissection (LCM) and RT-PCR amplification of AMACR in prostate cancer. LCM was used to isolate pure prostate cancer and benign glands and AMACR gene expression was characterized by RT-PCR in 2 radical prostatectomies. A constitutively expressed gene, GAPDH, was used as quantitative control of input mRNA. AMACR expression is barely detectable in benign glands, and is elevated in prostate cancer.

To further characterize AMACR expression in a spectrum of proliferative prostate lesions, a prostate tissue microarray, which included prostate cancer, high grade PIN and atrophic glands, was utilized. Positive AMACR staining (moderate and strong staining) was observed in 83% and 64% of clinically localized prostate cancer and high-grade PIN, respectively. Focal AMACR expression was observed in 36% of the atrophic lesions and in rare morphologically benign glands. To confirm that AMACR protein over-expression was the result of increased gene transcription, laser capture microdissection was used to isolate cancerous and benign prostatic glands. RT-PCR was performed to assess the AMACR mRNA expression. Benign glands had very low baseline expression (FIG. 19). In contrast, prostate cancer had much higher mRNA level, confirming that increased AMACR gene transcription leads to elevated protein over expression in prostate cancer.

AMACR expression was studied in 24 colorectal adenocarcinomas, including 16 well to moderately differentiated, and 8 poorly differentiated large cell adenocarcinomas. Overall, 83% (20/24) demonstrated positive AMACR protein expression. All (16/16, 100%) cases of well to moderately differentiated carcinoma had positive staining, compared to 64% (5/8) of poorly differentiated carcinoma. AMACR expression was examined in 8 colorectal adenoma biopsies obtained by colonoscopy. Moderate staining was present in 6 (75%) cases. Compared with well-differentiated adenocarcinomas, adenomas usually showed more focal (10-60% of cells) and less intense staining.

Example 8

Characterization of EZH2 expression in Prostate Cancer

A. SAM Analysis

SAM analysis was performed by comparing gene expression profiles of 7 metastatic prostate cancer samples against 10 clinically localized prostate cancer samples. Data was normalized per array by multiplication by a factor to adjust the aggregate ratio of medians to one, then log base 2 transformed and median centered. This normalized data was divided into two groups for comparison using a two-class, unpaired t-test. Critical values for the analysis include: Iterations=500, Random Number Seed 1234567, a fold change cutoff of 1.5 and a delta cutoff of 0.985, resulting in a final largest median False Discovery Rate of 0.898% for the 535 genes selected as significant (55 relatively up and 480 relatively down regulated between MET and PCA). These 535 genes were analyzed using Cluster (Eisen et al., PNAS 95:14863 [1998]) implementing average linkage hierarchical clustering of genes. The output was visualized by Treeview (Eisen et al., [1998], supra).

B. RT-PCR

Reverse transcription and PCR amplification were performed with 1 μg total RNA isolated from the indicated prostate tissues and cell lines. Human EZH2 forward (5'-GCCAGACTGGGAAGAAATCTG-3' (SEQ ID NO:108)), reverse (5'-TGTGCTGGAAAATCCAAGTCA-3' (SEQ ID NO:109)) and GAPDH sense (5'-CGGAGTCAACGGATTTGGTCGTAT-3' (SEQ ID NO:110)), antisense 5'-AGCCTTCTCCATGGTGGTGAAGAC-3' (SEQ ID NO:111)) primers were used. The amplified DNA was resolved on agarose gels and visualized with ethidium bromide.

C. Immunoblot Analysis

Prostate tissue extracts were separated by SDS-PAGE and blotted onto nitrocellulose membranes. Anti-EZH2 (Sewalt et al., Mol. Cell. Biol. 18:3586 [1998]), anti-EED (Sewalt et al., supra), and polyclonal anti-tubulin (Santa Cruz biotechnology) antibodies were used at 1:1000 dilution for immunoblot analysis. The primary antibodies were detected using horseradish peroxidase-conjugated secondary antibodies and visualized by enhanced chemiluminescence as described by the manufacturer (Amersham-Pharmacia).

D. Tissue Microarray Analysis

Clinically stratified prostate cancer tissue microarrays used in this study have been described previously (See above examples). Tissues utilized were from the radical prostatectomy series at the University of Michigan and from the Rapid Autopsy Program, which are both part of University of Michigan Prostate Cancer Specialized Program of Research Excellence (S.P.O.R.E.) Tissue Core. Institutional Review Board approval was obtained to procure and analyze the tissues used in this study.

EZH-2 protein expression was evaluated on a wide range of prostate tissue to determine the intensity and extent in situ. Immunohistochemistry was performed on three tissue microarrays (TMA) containing samples of benign prostate, prostatic atrophy, high-grade prostatic intraepithelial neoplasia (PIN), clinically localized prostate cancer (PCA), and metastatic hormone refractory prostate cancer (HR-METSs). Standard biotin-avidin complex immunohistochemistry (IHC) was performed to evaluate EZH2 protein expression using a polyclonal anti-EZH2 antibody. Protein expression was scored as negative (score=1), weak (score 2), moderate (3) and strong (4).

Approximately 700 TMA samples (0.6 mm diameter) were evaluated for this study (3-4 tissue cores per case). The TMAs were assembled using a manual tissue arrayer (Beecher Instruments, Silver Spring, Md.) as previously described (See above examples). Four replicate tissue cores were sampled from each of the selected tissue types. After construction, 4 μm sections were cut and hematoxylin and eosin staining was performed on the initial slide to verify the histologic diagnosis. TMA hematoxylin and eosin images were acquired using the BLISS Imaging System (Bacus Lab, Lombard, Ill.). EZH2 protein expression was evaluated in a blinded manner by the study pathologist using a validated web-based tool (Manley et al., Am. J. Pathol. 159:837 [2001]; Bova et al., Hum. Pathol. 32:417 [2001]) and the median value of all measurements from a single patient were used for subsequent analysis.

E. Clinical Outcomes Analysis

To assess individual variables for risk of recurrence, Kaplan-Meier survival analysis was performed and a univariate Cox proportional hazards model was generated. PSA-recurrence was defined as 0.2 ng/ml following radical prostatectomy. Covariates included Gleason sum, preoperative PSA, maximum tumor dimension, tumor stage, and surgical margin status. To assess the influence of several variables simultaneously including EZH2 protein expression, a final multivariate Cox proportional hazards model of statistically significant covariates was generated. Statistical significance in univariate and multivariate Cox models were determined by Wald's test. A p-value <0.05 was considered statistically significant.

F. EZH2 Constructs

Myc-tagged EZH2-pCMV was used. The Myc-EZH2 fragment was released with BamHI/XhoI double digest and was sub-cloned into the mammalian expression vector pCDNA3 (Invitrogen). An EZH2-ER in-frame fusion expression construct was generated by replacing the FADD fragment released by Kpn I/Not I double digest of the FADD-ER construct (originally derived from Myc-ER (Littlewood et al., Nuc. Acids. Res. 23:1686 [1995]) with the PCR amplified human EZH2 devoid of its stop codon. The EZH2.5ET mutant DNA was amplified using the primers 5'GGGGTACCATGGGCGGCCGCGAACAAAAGTTGATT 3' (SEQ ID NO:112) and 5'GGGGAATTCTCATGCCAGCAATAGATGCTTTTT3' (SEQ ID NO:113) and subsequently sub-cloned into pCDNA3 utilizing the in built KpnI/EcoRI sites. Expression of these constructs was verified by immunoblot analysis of the expressed proteins using either anti-Myc HRP (Roche, Inc) or anti-EZH2 antibodies.

G. RNA Interference 21-nucleotide sense and antisense RNA oligonucleotides were chemically synthesized (Dharmacon Research Inc.) and annealed to form duplexes. The siRNA employed in the study were targeted to the region corresponding from 85 to 106 of the reported human EZH2 (NM004456). Control siRNA duplexes targeted luciferase, lamin and AMACR (NM014324). The human transformed prostate cell line RWPE (Webber et al., Carcinogenesis 18:1225 [1997]) and PC3 were plated at $2\times10^5$ cells per well in a 12 well plate (for immunoblot analysis, cell counts, and fluorescence activated cell sorting (FACS) analysis) and $1.5\times10^4$ cell per well in a 96 well plate (for WST-1 proliferation assays). Twelve hours after plating, the cells were transfected with 60 picomoles of siRNA duplex, sense or antisense oligonucleotides (targeting EZH2) using oligofectamine (Invitrogen). A second identical transfection was performed 24 hours later. Forty-eight hours after the first transfection, the cells were lysed for immunoblot analysis and trypsinized for cell number estimation or FACS analysis. Cell viability was assessed 60 hours after the initial transfection.

H. Cell Proliferation Assays

Cell proliferation was determined with the colorimetric assay of cell viability, based on the cleavage of tetrazolium salt WST-1 by mitochondrial dehydrogenases as per manufacturers instructions (Roche, Inc.). The absorbance of the formazan dye formed, which directly correlates with the number of metabolically active cells in the culture, was measured at 450 nm (Bio-Tek instruments), an hour after the addition of the reagent. Cell counts were estimated by trypsinizing cells and analysis by coulter cell counter.

I. Flow Cytometric Analysis

Trypsinized cells were washed with phosphate buffered saline (PBS) and cell number was determined by using a coulter cell counter. For FACS analysis, the washed cells were fixed in 70% ethanol overnight. Before staining with propidium iodide, the cells were washed again with PBS and analyzed by flow cytometry (Becton Dickinson).

J. Microarray Analysis of EZH2 Transfected Cells

Initial testing of this transient transfection/transcriptome analysis system demonstrated that transient overexpression of TNFR1 (p55), a receptor for tumor necrosis factor, induced similar expression profiles as was observed with incubation of cells with TNF (Kumar-Smith et al., J. Biol. Chem. 24:24 [2001]). Other molecules have been similarly tested with this approach. Cells were transfected with different EZH2 constructs and transfection efficiency was monitored by beta-galactosidase assay and was approximately 30-50%. EZH2.5ET mutant expressing samples were compared to EZH2 expressing samples using the SAM analysis package (Tusher et al., PNAS 98:5116 [2001]). Data was pre-processed by multiplication by a normalization factor to adjust the aggregate ratio of medians to one, log base 2 transformed and median centered each array, individually. This pre-processed data was divided into 2 groups for comparison using a two-class, unpaired t-test. Critical values for the analysis include: iterations=5000, (720 at convergence) random Number Seed 1234567, a fold change of 1.5 and a delta cutoff of 0.45205, resulting in a final largest median False Discovery Rate of 0.45% for the 161 genes selected as significant. These 161 genes were supplemented by the values for EZH2 and then analyzed using Cluster implementing average linkage hierarchical clustering of genes. The output was visualized in Treeview. Selected genes identified as being repressed by EZH2 (e.g., EPC and cdc27) were re-sequenced to confirm identity.

The molecular identity of a cell is determined by the genes it expresses (and represses). Embryogenesis and cell differentiation intimately depend upon keeping certain genes "on" and other genes "off". When the transcriptional "memory" of a cell is perturbed this can lead to severe developmental defects (Jacobs et al., Semin. Cell Dev. Biol. 10:227 [1999]; Francis et al., Nat. Rev. Mol. Cell. Biol. 2:409 [2001]). Lack of differentiation, or anaplasia, is a hallmark of cancer, which results from normal cells "forgetting" their cellular identity. Thus, it is not surprising that dysregulation of the transcriptional maintenance system can lead to malignancy (Francis et al., supra; Jabobs et al., Nature 397:164 [1999]; Beuchle et al., Development 128:993 [2001]).

Studies in *Drosophila melanogaster* have been instrumental in the understanding of the proteins involved in transcriptional maintenance (Beuchle et al., [[2001], supra; Strutt et al., Mol. Cell. Biol. 17:6773 [1997]; Tie et al., Development 128:275 [2001]). Two groups of proteins have been implicated in the maintenance of homeotic gene expression and include polycomb (PcG) and trithorax (trxG) group proteins (Mahmoudi et al., Oncogene 20:3055 [2001]; Lajeunesse et al., Development 122:2189 [1996]). PcG proteins act in large complexes and are thought to repress gene expression, while trxG proteins are operationally defined as antagonists of PcG proteins and thus activate gene expression (Francis et al., Nat. Rev. Mol. Cell. Biol. 2:409 [2001]; Mahmoudi et al., supra). There are at least twenty PcG and trxG proteins in *Drosophila*, and many have mammalian counterparts. In human malignancies, PcG and trxG proteins have primarily been found to be dysregulated in cells of hematopoietic origin (Yu et al., Nature 378:505 [1995]; Raaphorst et al., Am. J. Pathol., 157:709 [2000]; van Lohuizzen et al., Cell 65:737 [1991). EZH2 is the human homolog of the *Drosophila* protein Enhancer of Zeste (E(z)) ((Laible et al., Embo. J. 16:3219 [1997]), for which genetic data defines as a PcG protein with additional trxG properties (LaJeunesse et al., supra). E(z) and EZH2 share homology in four regions including domain I, domain II, a cysteine-rich amino acid stretch, and a C-terminal SET domain (Laible et al., supra). The SET domain is a highly conserved domain found in chromatin-associated regulators of gene expression often modulating cell growth pathways (Jenuwein et al., Cell. Mol. Life Sci. 54:80 [1998]). EZH2 is thought to function in a PcG protein complex made up of EED, YY1 and HDAC2 (Satijn et al., Biochim. Biophys. Acta. 1447:1 [1999]). Disruption of the EZH2 gene in mice causes embryonic lethality suggesting a crucial role in development (O'Carroll et al., Mol. Cell. Biol. 21:4330 [2001]).

Figure 20:
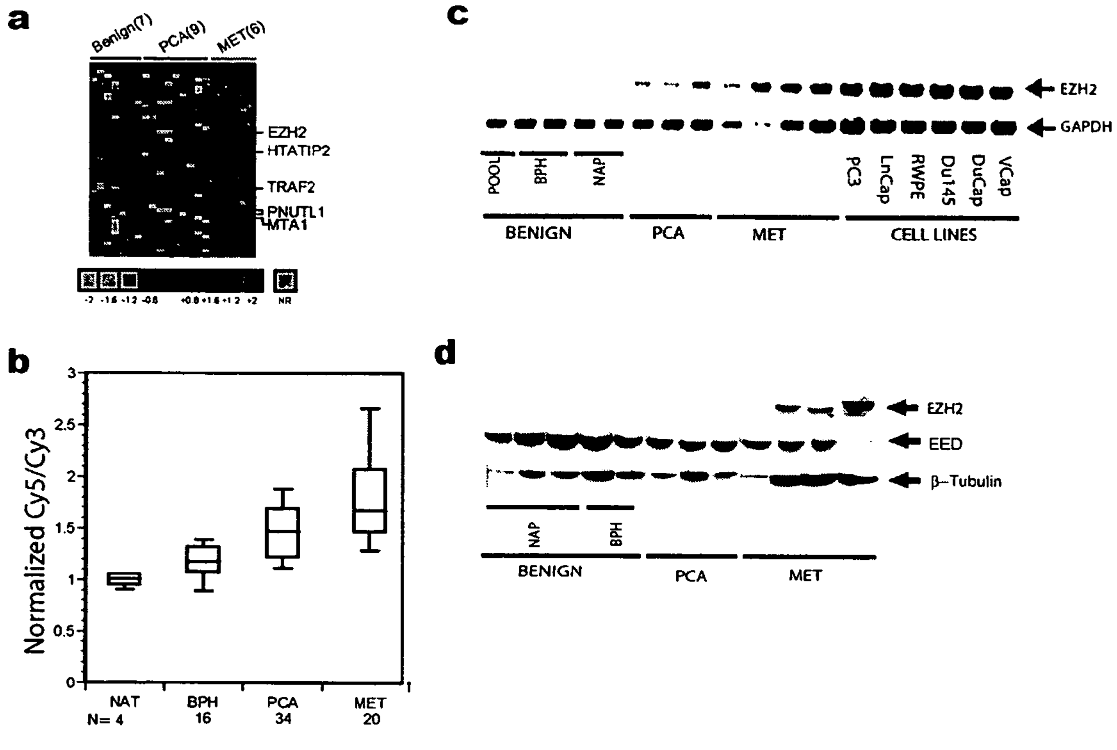
FIG. 20 describes the identification and validation of EZH2 over-expression in metastatic prostate cancer.

In previous studies (See e.g., Example 1), the gene at the top of the "list" of genes significantly up-regulated in metastatic prostate cancer was EZH2, which had a d-score (Tusher et al. PNAS 98:5116 [2001]) of 4.58 and a gene-specific FDR of 0.0012 (also called a "q-value" which is analogous to p-values, but adapted to multiple inference scenarios. FIG. 20*a* displays the 55 up-regulated genes identified by this approach. FIG. 20*b* summarizes the gene expression of EZH2 in 74 prostate tissue specimens analyzed on DNA microarrays made up of 10 K elements. The EZH2 transcript was significantly increased in metastatic prostate cancer with respect to clinically localized prostate cancer (Mann-Whitney test, p=0.001) and benign prostate (p=0.0001).

As independent experimental validation of DNA microarray results, RT-PCR was performed on 18 prostate samples and cell lines. As expected, EZH2 mRNA transcript levels were elevated in malignant prostate samples relative to benign (FIG. 20*c*). To determine whether EZH2 is up-regulated at the protein level in metastatic prostate cancer, tissue extracts were examined by immunoblotting. In the samples examined by immunoblot analysis, EZH2 protein was markedly elevated in metastatic prostate cancer relative to localized prostate cancer or benign prostate (FIG. 20*d*).

Figure 21:
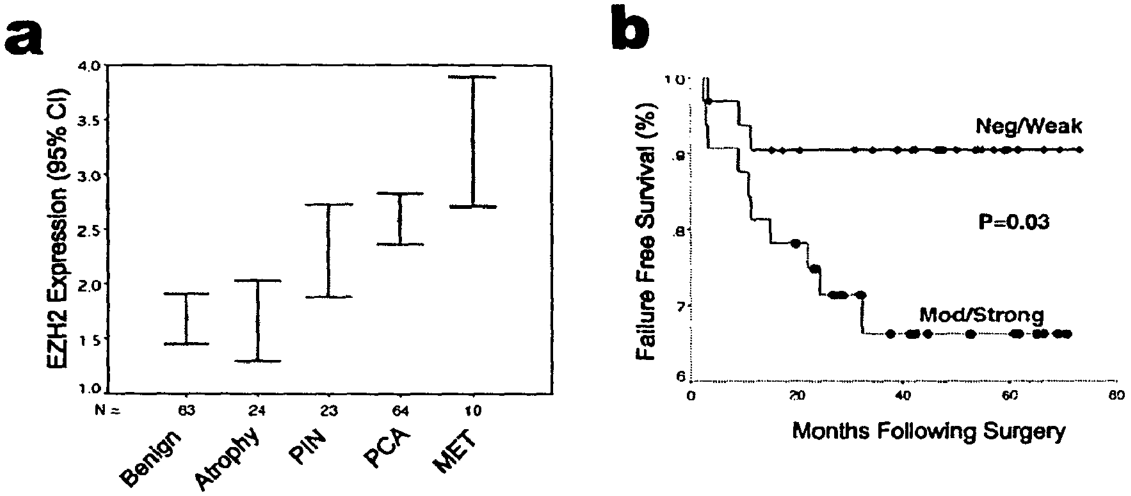
FIG. 21 shows that EZH2 protein levels correlate with the lethal progression and aggressiveness of prostate cancer.

Importantly, EED, a PcG protein that forms a complex with EZH2 (vanLohuizen et al., supra; Sewalt et al., supra), along with an un-related protein, β-tubulin, did not exhibit similar protein dysregulation. EZH2 protein expression was evaluated on a wide range of prostate tissues (over 700 tissue microarray elements) to determine the intensity and extent of expression in situ (FIG. 21 *a,b*). When highly expressed, EZH2 expression was primarily observed in the nucleus as suggested previously (Raaphorst et al., supra). The staining intensity was increased from benign, prostatic atrophy, prostatic intraepithelial neoplasia (PIN), to clinically localized prostate cancer with median staining intensity of 1.7 (standard error [SE], 0.1; 95% confidence interval [CI], 1.5-1.9), 1.7 (SE, 0.2; 95% CI, 1.3-2.0), 2.3 (SE, 0.2; 95% CI, 1.9-2.7), and 2.6 (SE, 0.1; 95% CI, 2.4-2.8), respectively (FIG. 24*b*). The strongest EZH2 protein expression was observed in hormone-refractory metastatic prostate cancer with a median staining intensity of 3.3 (SE, 0.3; 95% CI, 2.7-3.9). There was a statistically significant difference in EZH2 staining intensity between benign prostate tissue and localized prostate cancer (ANOVA post-hoc analysis mean difference 0.9, $p<0.0001$). Although metastatic prostate cancer had a higher mean expression level than localized prostate cancer, the difference did not reach statistical significance (ANOVA post-hoc analysis mean difference 0.7, $p=0.3$). These findings suggest that as prostate neoplasia progresses there was a trend towards increased EZH2 protein expression, mimicking that seen by DNA expression array analysis. The present invention is not limited to a particular mechanism. Indeed, an understanding of the mechanism is not necessary to practice the present invention. Nonetheless, it is contemplated that this observation suggests that EZH2 levels may indicate how aggressive an individual's prostate cancer is given that the highest level of expression was observed in hormone-refractory, metastatic prostate cancer. Therefore, to test this hypothesis, the utility of EZH2 protein levels to predict clinical outcome in men treated with surgery for clinically localized prostate cancer was examined.

Two hundred and twenty-five (225) specimens from sixty-four patients (3-4 replicate samples per patient) with clinical follow up were interrogated on a single tissue microarray. These men had a median age of 61 years (range 43-76 years) and a 7.3 ng/ml median pre-operative serum prostate specific antigen (PSA) (range 0.8-21.0 ng/ml). Pathologic examination of their prostatectomy specimens indicated that 77% had organ-confined disease (pT2 stage) and 72% had negative surgical margins. The patient demographics and tumor stages were representative of the over 1500 radical prostatectomy patients. In order to test the utility of EZH2 as a potential tissue biomarker for prostate cancer, the clinical outcome of these 64 cases was examined, taking into account clinical and pathological parameters. Clinical failure was defined as either a 0.2 ng/ml PSA elevation or disease recurrence following prostatectomy (e.g., development of metastatic disease). By Kaplan-Meier analysis (FIG. 21*c*), EZH2 staining intensity of 3 and greater was significantly associated with clinical failure in 31% (10/32) of patients in contrast to 9% (3/32) of patients with an EZH2 protein levels below 3 (log rank $p=0.03$). There was no significant correlation between EZH2 levels and Gleason score (<7 versus=7), tumor stage (pT2 versus pT3), or surgical margin status (negative versus positive). There was a significant ($p=0.048$) albeit weak (Pearson coefficient=0.33) correlation between EZH2 protein levels and proliferation index in situ as assessed by Ki-67 labeling index. Multivariable Cox-Hazards regression analysis revealed that EZH2 protein expression (=3 versus <3) was the best predictor of clinical outcome with a recurrence ratio of 4.6 (95% CI 1.2-17.1, $p=0.02$), which was significantly better than surgical margin status, maximum tumor dimension, Gleason score, and pre-operative PSA. Thus, monitoring EZH2 protein levels in prostate specimens may provide additional prognostic information not discernible with current clinical and pathology parameters alone.

Figure 22:
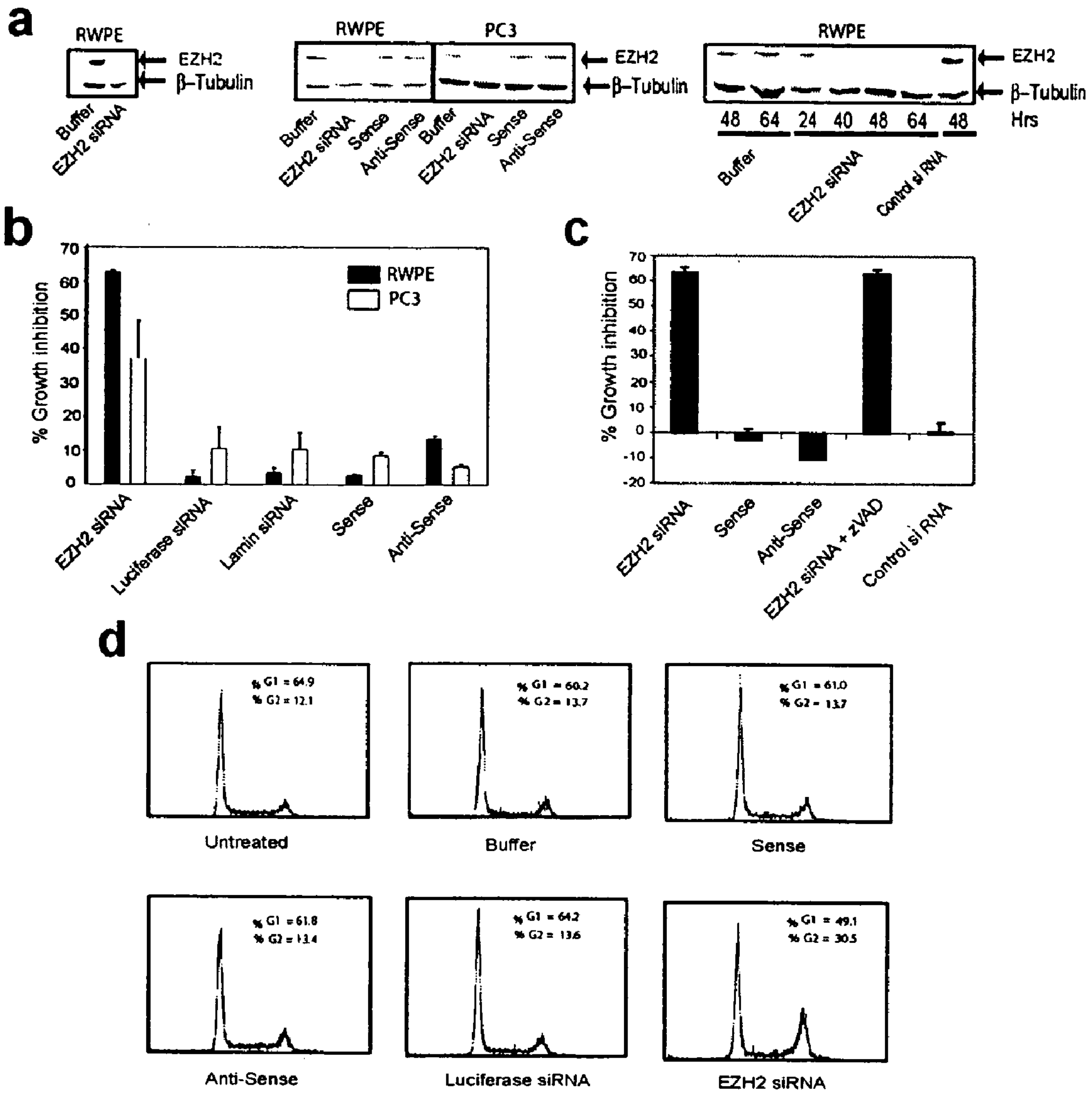
FIG. 22 shows the role of EZH2 in prostate cell proliferation.

To shed light into the functional role of EZH2 in prostate cancer progression, EZH2 expression in transformed prostate cells in vitro was disrupted using RNA interference. T. Tuschl and colleagues recently reported that duplexes of 21-nucleotide RNA (siRNAs) mediate RNA interference in cultured mammalian cells in a gene-specific fashion (Elbashir et al., Nature 411:494 [2001]). RNA interference has been used effectively in insect cell lines to "knock-down" the expression of specific proteins, owing to sequence-specific, double stranded-RNA mediated RNA degradation (Hammond et al., Nature 404:293 [2000]). siRNAs are potent mediators of gene silencing, several orders of magnitude more potent than conventional antisense or ribozyme approaches (Macejak et al., Hepatology 31:769 [2000]). Thus, a 21-nucleotide stretch of the EZH2 molecule was targeted using criteria provided by Elbashir et al. (supra), and RNA oligonucleotides were synthesized commercially. After the RNA oligos were annealed to form siRNA duplexes, they were tested on the transformed androgen-responsive prostate cell line RWPE (Webber et al., Carcinogenesis 18:1225 [1997]; Bello et al., Carcinogenesis 18:1215 [1997]) as well as the metastatic prostate cancer cell line PC3. Forty-eight hours after transfection with siRNA duplexes, the levels of endogenous EZH2 protein were quntitated. When EZH2 protein was specifically down-regulated in prostate cell lines, the levels of the un-related control protein, β-tubulin, remained unchanged (FIG. 22*a*). The sense or anti-sense oligonucleotides comprising the EZH2 duplex, as well as un-related siRNA duplexes, did not affect EZH2 protein levels (FIG. 22*a*, middle and right panels), verifying the specificity of the siRNA approach in both prostate cell lines.

The phenotype of EZH2 "knock-down" prostate cells was next examined. By phase contrast microscopy, it was observed that siRNA directed against EZH2 markedly inhibited cell number/confluency relative to buffer control. Cell counts taken 48 hrs after transfection with siRNA showed a 62% inhibition of RWPE cell growth mediated by the EZH2 siRNA duplex, which is in contrast to the corresponding sense and anti-sense EZH2 oligonucleotides or control duplexes (targeting luciferase and lamin) which exhibited minimal inhibition (FIG. 22*b*). The prostate cancer cell line, PC3, demonstrated a similar growth inhibition mediated by EZH2 siRNA, suggesting that the findings are not a peculiarity of the RWPE cell line (FIG. 22*b*). Using a commercially available cell proliferation reagent WST-1, which measures mitochondrial dehydrogenase activity, a decrease in cell proliferation mediated by the EZH2 siRNA duplex, but not by un-related duplexes, was observed (FIG. 22*c*). In the time frame considered (48 hrs), RNA interference of EZH2 did not induce apoptosis as assessed by propidium idodide staining of nuclei or PARP cleavage. Consistent with this, the broad-spectrum caspase inhibitor, z-VAD-fink, failed to attenuate EZH2 siRNA induced inhibition of cell proliferation (FIG. 22*c*). Thus, activation of the apoptosis pathway does not account for the decreases in cell number observed by RNA interference of EZH2.

Various PcG Group proteins have been suggested to play a role in cell cycle progression (Jacobs et al., Nature 397:164

[1999]; Visser et al., Br. J. Hematol. 112:950 [2001]; Borck et al. Curr. Opin. Genet. Dev. 11:175 [2001]). Flow cytometric analysis of EZH2 siRNA-treated prostate cells demonstrated cell cycle arrest in the G2/M phase (FIG. 22*d*). Un-related control siRNA duplexes failed to induce a similar cell cycle dysregulation. Few apoptotic cells (sub-G1 cells) were present in any of the experimental samples tested as assessed by flow cytometry (FIG. 22*d*). The present invention is not limited to a particular mechanism. Indeed, an understanding of the mechanism is not necessary to practice the present invention. Nonetheless, it is contemplated that these observations suggest that EZH2 plays a role in prostate cell proliferation by mitigating the G2/M transition.

To further understand the functional role of EZH2 in prostate cells, an epitope-tagged version of wild-type EZH2 and a deletion mutant of EZH2 missing the conserved SET domain in the eukaryotic expression vector pcDNA3 were generated (FIG. 23*a*). An "inducible"-version of EZH2 was also generated by creating a fusion protein with a modified murine estrogen receptor (ER) (FIG. 26*a*) (Littlewood et al., Nuc. Acid. Res. 23:1686 [1995]; Juin et al., Genes Dev. 13:1367 [1999]). EZH2-ER fusion was expressed in cells (FIG. 26*b*) and is inactivated, presumably by sequestration/binding to hsp90 and other proteins (Littlewood et al., supra). Upon treatment of cells with 4-hydroxytamoxifen, hsp90 dissociates from the ER fusion and liberates its activity. Expression of the epitope-tagged EZH2 constructs was confirmed by transfection in 293 (FIG. 23*b*), RWPE and in other mammalian cell lines.

PcG proteins have been proposed to mediate their functions by repression of target genes (Laible et al., supra; Jacobs et al., Semin Cell Dev. Biol. 10:227 [1999]). To begin to test this hypothesis, RWPE prostate cells were transiently transfected with wild-type EZH2 and global gene expression alterations were monitored using DNA microarrays. While RNA from the experimental (transfected) cell line was labeled with one fluorescent dye, the paired reference sample was labeled with a second distinguishable fluorescent dye. By making direct comparisons between "gene"-transfected cell lines and control vector-transfected cell lines the molecular differences between the samples were observed. When EZH2 was over-expressed in RWPE cells or SUM149 breast carcinoma cells, there was a consistent repression of a cohort of genes (FIGS. 23*c, d*). This exclusive repression of genes was unique compared to other molecules tested in this system including c-myc and TNFR1, among others. When compared to vector-transfected cells the only gene that was significantly up-regulated in EZH2-transfected cells was EZH2 itself (FIG. 23*c*).

EZH2-mediated transcriptional repression was dependent on an intact SET domain (FIG. 23*c*), as deletion of this domain did not produce a repressive phenotype and in some cases "de-repressed" genes. EZH2 has been shown to interact with histone deacetylase 2 (HDAC2) via the EED protein (van der Vlag et al., Nat. Genet. 23:474 [1999]). In the experiments described above, EZH2-mediated gene silencing was dependent on HDAC activity, as the commonly used HDAC inhibitor, trichostatin A (TSA) completely abrogated the effects of EZH2 (FIG. 23*c*). Thus, EZH2 function requires both an intact SET domain as well as endogenous HDAC activity.

To identify genes that are significantly repressed by EZH2, wild-type EZH2-transfected cells were compared with EZH2 SET-transfected cells. Using this approach, 163 genes were consistently repressed while no genes were activated at an FDR of 0.0045 (FIG. 23*d*). Examination of the significant gene list identified the PcG group protein EPC, which is the human homolog of the *drosophila* protein Enhancer of Polycomb (E(Pc)) as being consistently repressed by EZH2 (FIG. 23*c*). Of the *Drosophila* PcG proteins, E(Pc) and E(z) are related in that they both act as suppressors of variegation (Su(var)) (Sinclair et al., Genetics 148:211 [1998]) and are the only PcG proteins to have yeast homologs, emphasizing the evolutionary conservation of this PcG pair. In addition to EPC, a host of other transcriptional regulators/activators were transcriptionally silenced by EZH2 including MDNA, RNF5, RNF15, ZNF42, ZNF262, ZNFN1A1, RBM5, SPIB, and FOXF2, among others (FIG. 23*c*). MDNA, also known as myeloid cell nuclear differentiation antigen, mediates transcriptional repression by interacting with the transcription factor YY1, which is a PcG homolog of *Drosophila* Pho and shown to be part of the EZH2/EED complex of proteins (Satijin et al., Mol. Cell. Biol. 21:1360 [2001]).

Figure 23:
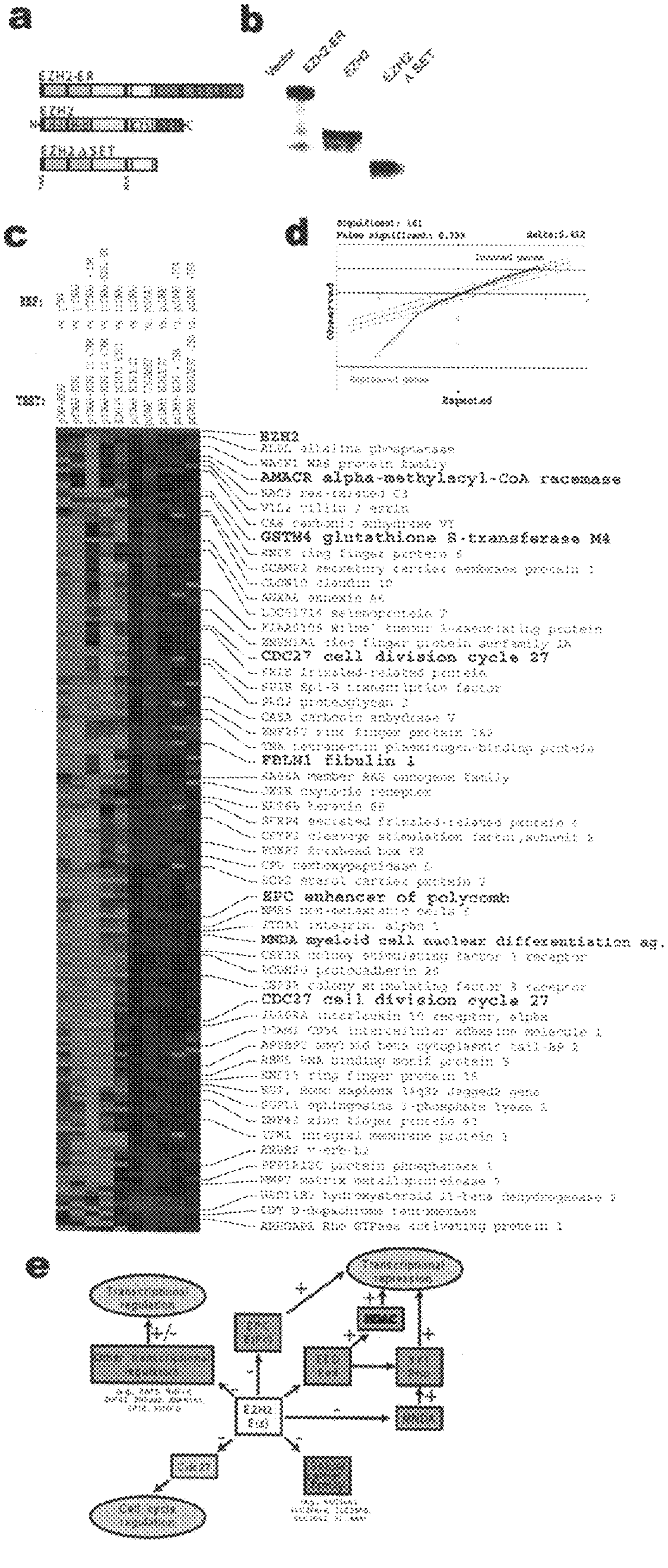
FIG. 23 shows that EZH2 functions as a transcriptional repressor in prostate cells.

In addition to transcriptional repression in prostate cells, the results also support a role for EZH2 in regulating cell growth (FIG. 23). Transcriptional repression of cdc27 (two independent Unigene clones) was also observed. Cdc27 is part of the anaphase-promoting complex (APC) which mediates ubiquitination of cyclin BI, resulting in cyclinB/cdk complex degradation (Jorgensen et al., Mol. Cell. Biol. 18:468 [1998]). Another family of proteins that was repressed when EZH2 was targeted was the solute carriers. At least 5 distinct members were shown to be repressed (i.e., SSLC34A2, SLC25A16, SLC25A6, SLC16A2, and SLC4A3).

Example 9

Expression of AMACR in Serum and Urine

Figure 24:
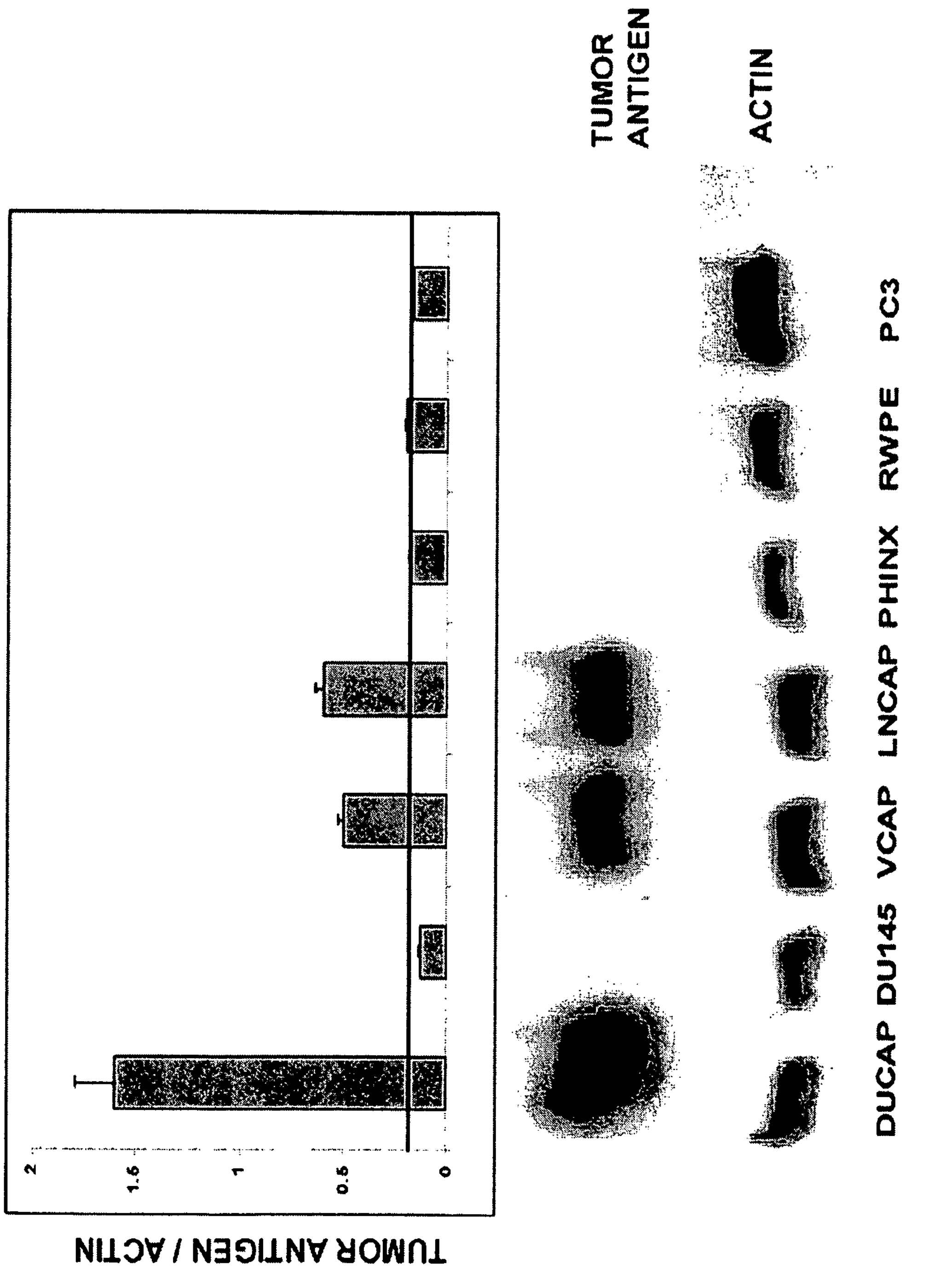
FIG. 24 shows the detection of AMACR in PCA cell lines.

This example describes the expression of AMACR in serum and urine. AMACR was detected by standard immunoblotting and by protein microarray using a polyclonal rabbit anti-AMACR antibody. The results are shown in FIGS. 24-27: FIG. 24 shows the detection of AMACR protein in PCA cell lines by quantitation of microarray data. DUCAP, DU145, and VCAP are prostate cancer cell lines. RWPE is a benign prostate cell line. PHINX is a human embryonic kidney cell line.

Figure 25:
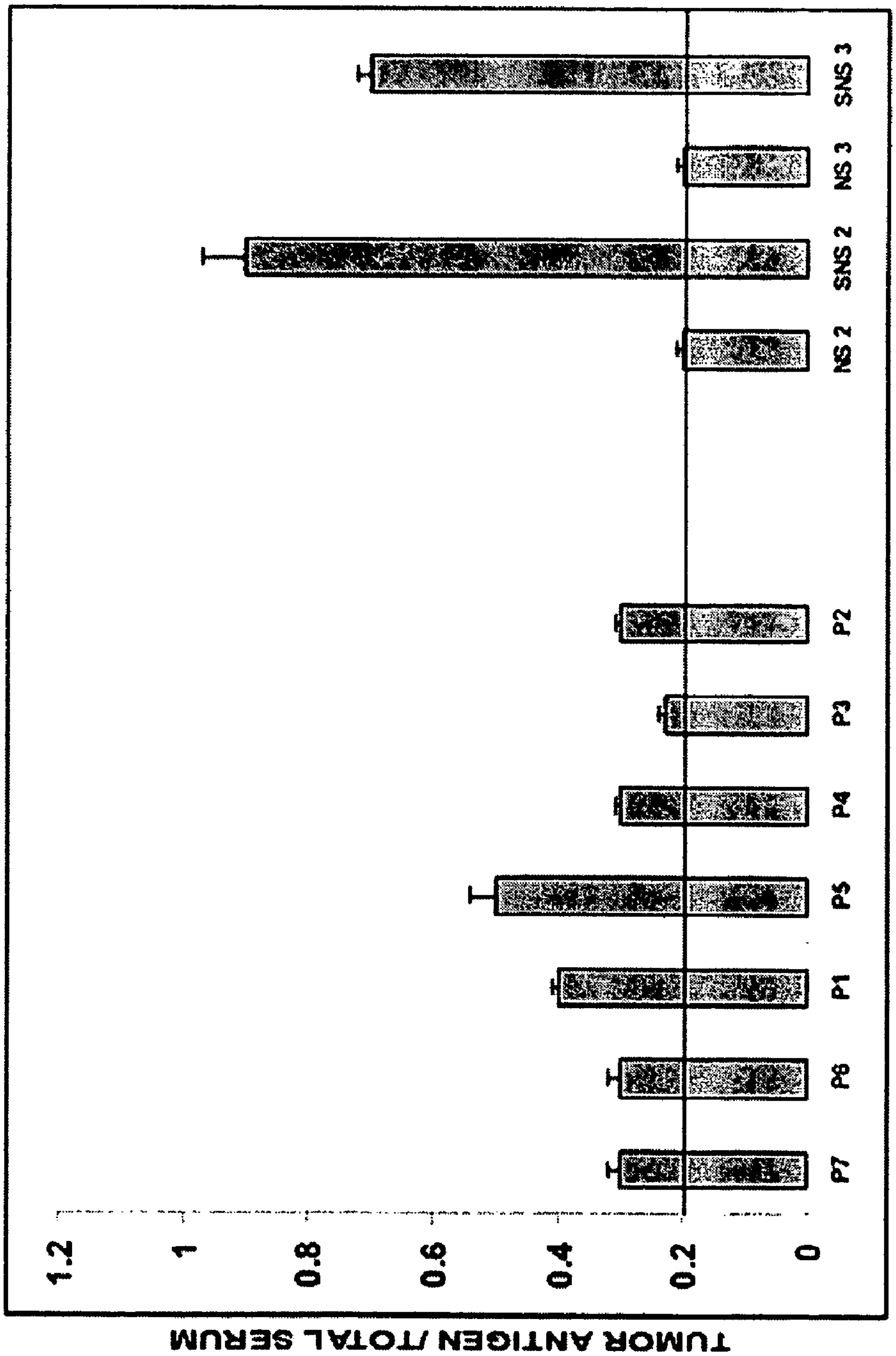
FIG. 25 shows the detection of AMACR protein in serum by quantitation of microarray data.
Figure 26:
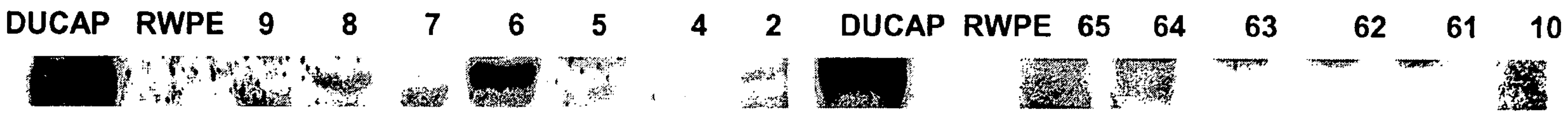
FIG. 26 shows an immunoblot analysis of serum from patients with either negative or positive PSA antigen.
Figure 27:
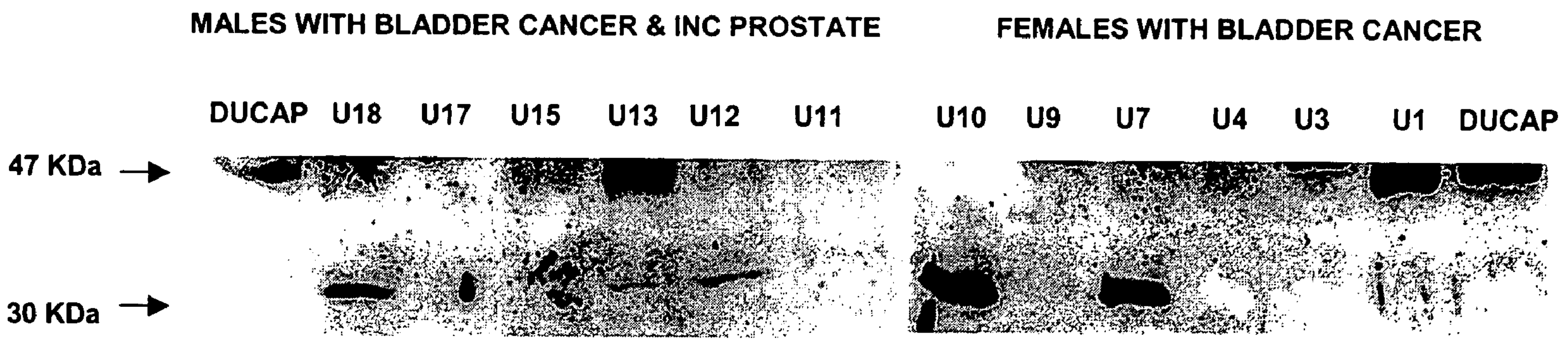
FIG. 27 shows an immunoblot analysis of the presence of AMACR in urine samples from patients with bladder cancer (females) or bladder cancer and increased PSA (males).

FIG. 25 shows the detection of AMACR protein in serum by quantitation of microarray data. P1-P7 represent serum from patients with prostate cancer. NS2 and NS3 represent serum from patients that do not have PCA. SNS2 and SNS3 represent serum from patients that do not have PCA that has been spiked with AMACR protein. FIG. 26 shows an immunoblot analysis of serum from patients with either negative or positive PSA antigen. FIG. 27 shows an immunoblot analysis of the presence of AMACR in urine samples from patients with bladder cancer (females) or bladder cancer and incidental prostate cancer (males). The results demonstrate that AMACR can be detected in the serum and urine of patients with bladder cancer or bladder cancer and prostate cancer.

Example 10

AMACR as a Tumor Antigen

Figure 28:
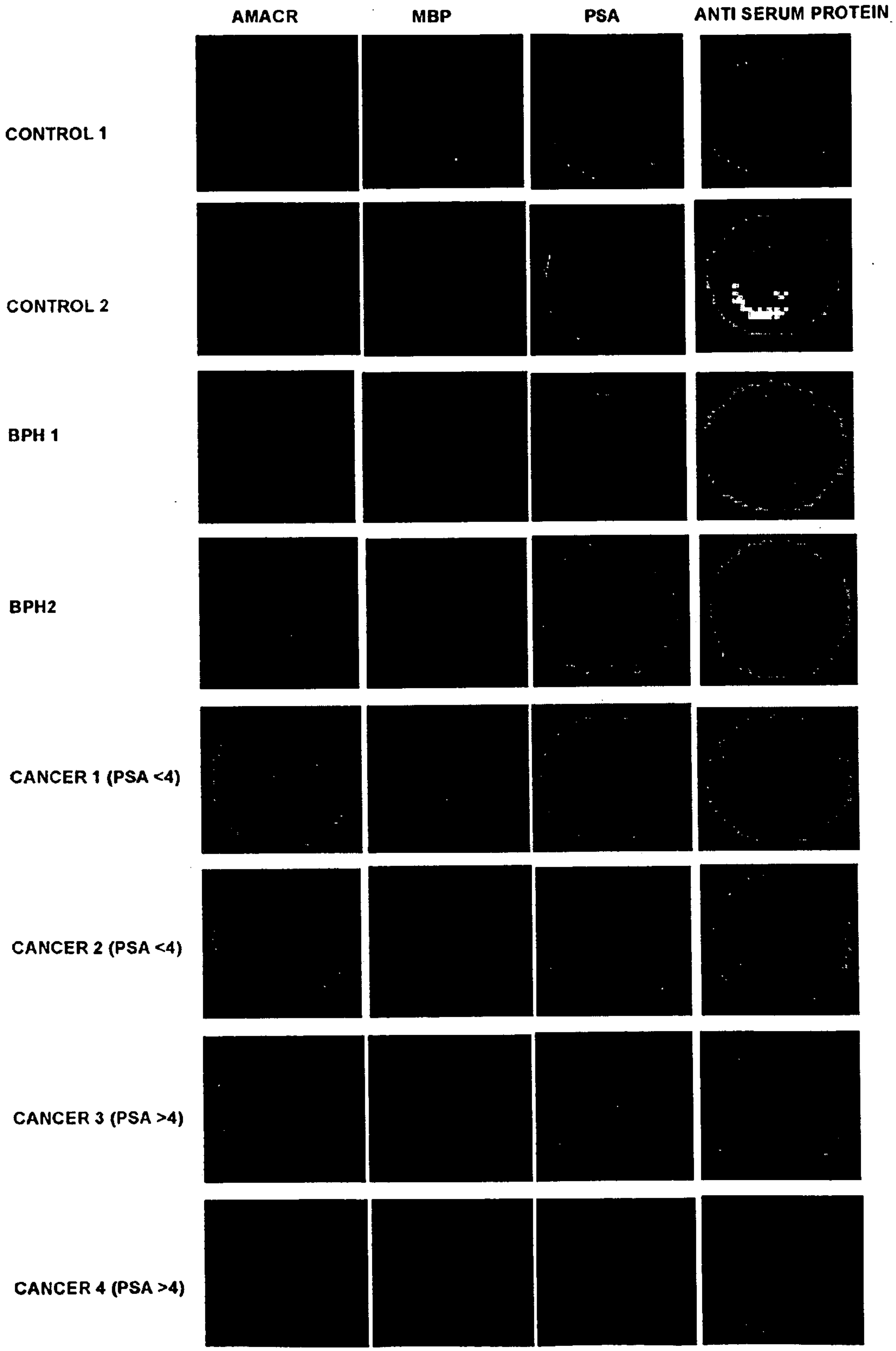
FIG. 28 shows representative data of a humoral response by protein microarray analysis.

This example describes the presence of an immune response against AMACR in serum. FIG. 28 shows representative data of a humoral response by protein microarray analysis. Tumor antigens including AMACR, PSA, CEA, HSPs were spotted onto nitrocellulose coated slides the slides were incubated with sera from different patients to detect a humoral response. The microarray was then washed. A Cy5 labeled goat anti-human IgG was used to detect the humoral response. The slide was then scanned using a microarray scanner (Axon). After data normalization, intensity of spots reflects the presence, absence or strength of humoral response to specific tumor antigen. A specific humoral response to AMACR was detected in cancer patients but not in controls. Cancer refers to sera from prostate cancer patients. BPH refers to sera from patients with benign prostate hyperplasia.

FIG. 29 shows immunoblot analysis of the humoral response to AMACR. FIG. 29A shows an SDS-PAGE gel containing recombinant MBP (control protein=M) and recombinant AMACR-MBP (A) that was run and transferred to nitrocellulose paper. Each strip blot was then incubated with human sera. A humoral response to the AMACR was detected using an HRP-conjugated anti-human antibody. Only AMACR and fragments of AMACR were detected in sera from prostate cancer patients and not in controls. FIG. 29B shows a control experiment whereby the humoral response is blocked with recombinant AMACR (quenched) and thus shows the specificity of the response.

This example demonstrates that AMACR functions as a tumor antigen in human serum of prostate cancer patients. A specific immune response was generated to AMACR in the serum of PCA patients, but not in controls.

Example 11

Expression of GP73 in Prostate Cancer

This example describes the association of GP73 with prostate cancer.

A. Methods

Microarray analysis, RT-PCR, Western blotting, and immunohistochemistry were performed as described in the above examples.

B. Results

Figure 30:
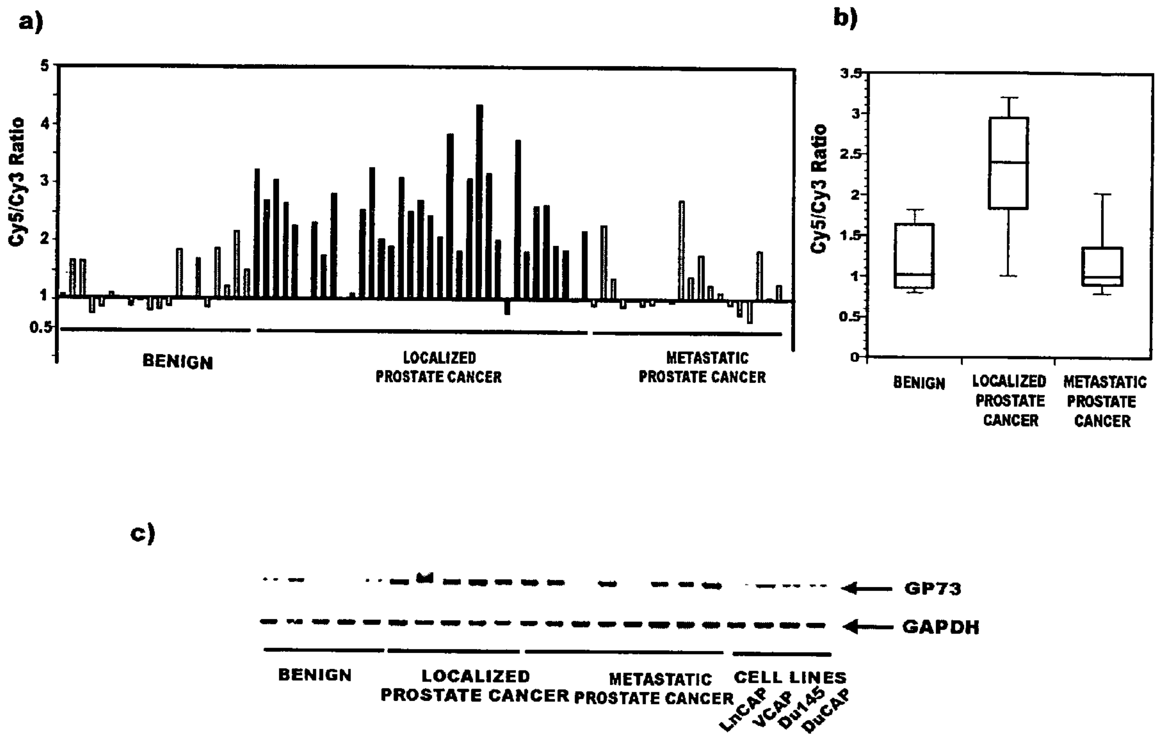
FIG. 30 shows GP73 Transcript levels in prostate cancer. Figures show the level of GP73 in individual samples after microarray analysis. Figures show the result of GP73 transcripts determined by DNA microarray analysis from 76 prostate samples grouped according to sample type and averaged.

FIG. 30 shows GP73 Transcript levels in prostate cancer. FIG. 30*a* shows the level of GP73 in individual samples after microarray analysis. The graph shows the values of Cy5 versus Cy3 ratio wherein the prostate cancer tissue sample RNA were labeled with Cy5 fluorescent dye, while the reference sample (pool of benign tissue RNA) sample was labeled with Cy3 fluorescent dye. A total of 76 individual experiments from different prostate tissue are plotted and they are classified as benign, prostate cancer and metastatic cancer types. FIG. 30*b* shows the result of GP73 transcripts determined by DNA microarray analysis from 76 prostate samples grouped according to sample type and averaged. The experimental samples were labeled with Cy5 fluorescent dye, whereas the reference sample (pool of benign tissue sample) was labeled with Cy3 fluorescent dye. The box plot demonstrates the range of GP73 expression within each group. The middle horizontal bar indicates median values; the upper and lower limits of the boxes, interquartile ranges; and the error bars, 95% confidence intervals. FIG. 30*c* demonstrates that GP73 transcript levels are elevated in prostate cancer. RT-PCR was used to detect GP73 transcript levels in RNA preparations from prostate tissue extracts. GAPDH served as the loading control.

FIG. 31 shows that GP73 protein is upregulated in prostate cancer. FIG. 31*a* shows Western blot analysis of GP73 protein in prostate cancer. Total tissue proteins from benign, cancer and metastatic tissues (10 μg) were analyzed using anti-GP73 antiserum. β-Tubulin serves as control for sample loading. FIG. 31*b* shows an immunoblot analysis of the Golgi resident protein Golgin 97. The Golgin 97 protein levels were analyzed in the prostate tissue sample to indicate the level of Golgi structure in normal and cancerous prostate tissue. β-Tubulin serves as control for sample loading.

Tissue microarray analysis of GP73 protein in normal and cancerous prostate tissue was also performed. GP73 protein expression was analyzed by standard biotin-avidin immunohistochemical analysis using a polyclonal mouse antibody to GP73. Protein expression was evaluated on a wide range of prostate tissue using high-density tissue microarrays. High levels of staining were observed in prostate cancer tissue. Some normal epithelial cells did not stain for GP73 in a sub region of prostate cancer tissue.

Figure 32:
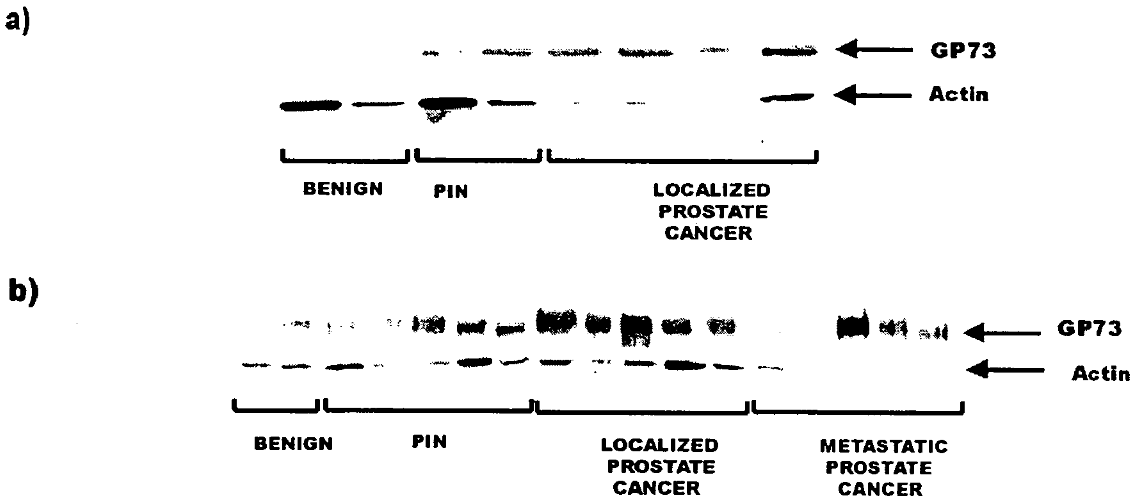
FIG. 32 shows immunoblot analysis of normal and prostate cancer epithelial cells.

FIG. 32 shows immunoblot analysis of normal and prostate cancer epithelial cells. The epithelial cells were isolated from normal prostate tissue and cancer tissue to specifically isolate the protein from epithelial cell for GP73 immunoblot analysis. For this purpose, laser capture microdissected samples were used. Actin western serves as control.

Example 12

Lethal Markers and Targets

This example describes the identification of lethal markers. The markers serve as potential therapeutic targets. Markers were identified by correlating the number of samples with clinical parameters and gene expression. Specifically, the present study identified markers that have an expression profile similar to EZH2, which serves as a prototypic lethal biomarker of prostate cancer. These genes were identified by a scoring system that takes into account whether localized prostate cancer has recurred or not recurred. In addition, genes that have highly correlated expression with EZH2 were identified that may serve as markers to supplement EZH2.

| mean | dev | Total High | 16 bph_count | 13 pca_count | 16 pcau_count | 6 pcar_count | 20 met_count | score | UIQID | NAME |
|---|---|---|---|---|---|---|---|---|---|---|
| −0.024 | 0.3725 | 0.7206 | 0 | 4 | 5 | 6 | 16 | 18 | 5814 | NULL ESTs Hs.30237 |
| −0.306 | 0.1707 | 0.0351 | 0 | 0 | 3 | 3 | 14 | 17 | 2506 | HN1 |
| −0.348 | 0.2394 | 0.1312 | 0 | 2 | 1 | 4 | 14 | 16 | 5112 | CSF2 |
| 0.0623 | 0.1578 | 0.3779 | 0 | 1 | 2 | 3 | 13 | 15 | 6053 | ASNS |
| −0.246 | 0.1689 | 0.0921 | 0 | 2 | 0 | 2 | 15 | 15 | 1520 | NULL ESTs Hs.16304 |
| −0.212 | 0.1386 | 0.0648 | 0 | 2 | 0 | 2 | 15 | 15 | 8273 | PRC1 |
| −0.352 | 0.1458 | −0.06 | 0 | 3 | 7 | 3 | 14 | 14 | 34 | GPAA1 |
| −0.292 | 0.2538 | 0.2153 | 0 | 0 | 1 | 3 | 10 | 13 | 5239 | KIAA1691 |
| −0.141 | 0.1572 | 0.1729 | 0 | 2 | 5 | 3 | 12 | 13 | 8562 | NULL Human clone 23614 |
| −0.21 | 0.1083 | 0.0067 | 0 | 4 | 4 | 2 | 15 | 13 | 3351 | FLJ11715 hypothetical protein |
| −0.22 | 0.1846 | 0.1495 | 0 | 5 | 4 | 5 | 13 | 13 | 2715 | NULL ESTs |

-continued

| mean | dev | Total High | 16 bph_count | 13 pca_count | 16 pcau_count | 6 pcar_count | 20 met_count | score | UIQID | NAME |
|---|---|---|---|---|---|---|---|---|---|---|
| −0.638 | 0.2696 | −0.099 | 1 | 5 | 4 | 3 | 15 | 13 | 9556 | FLJ12443 hypothetical protein |
| −0.142 | 0.1396 | 0.1371 | 0 | 0 | 2 | 2 | 10 | 12 | 1158 | TGFBI |
| −0.124 | 0.1606 | 0.1967 | 0 | 1 | 1 | 3 | 10 | 12 | 5292 | NULL ESTs |
| −0.444 | 0.2474 | 0.0504 | 0 | 1 | 2 | 2 | 11 | 12 | 3689 | NUF2R hypothetical protein |
| −0.205 | 0.2362 | 0.2674 | 0 | 2 | 1 | 2 | 12 | 12 | 1219 | ABCC5 |
| −0.09 | 0.2214 | 0.3526 | 0 | 4 | 2 | 4 | 12 | 12 | 1360 | MEN1 |
| −0.241 | 0.1541 | 0.0673 | 0 | 5 | 3 | 2 | 15 | 12 | 8476 | SARM and HEAT/Armadillo motif |
| −0.874 | 0.3367 | −0.201 | 0 | 1 | 4 | 2 | 10 | 11 | 3747 | H2BFB |
| −0.196 | 0.254 | 0.3122 | 0 | 2 | 1 | 3 | 10 | 11 | 4941 | VAV2 |
| −0.166 | 0.1486 | 0.1307 | 0 | 2 | 4 | 2 | 11 | 11 | 8636 | NULL ESTs Hs.23268 |
| 0.0255 | 0.1542 | 0.3338 | 0 | 3 | 3 | 3 | 11 | 11 | 280 | TOP2A |
| −0.226 | 0.2536 | 0.2812 | 0 | 4 | 3 | 4 | 11 | 11 | 2156 | EZH2 |
| −0.031 | 0.1826 | 0.3346 | 0 | 4 | 4 | 2 | 13 | 11 | 1979 | NULL ESTs Hs.268921 |
| −0.48 | 0.2967 | 0.1131 | 0 | 2 | 0 | 2 | 10 | 10 | 906 | MGC5627 hypothetical protein |
| −0.243 | 0.1421 | 0.0411 | 0 | 2 | 8 | 2 | 10 | 10 | 3728 | NULL ESTs |
| −0.133 | 0.1806 | 0.2279 | 0 | 2 | 2 | 2 | 10 | 10 | 8759 | RAB24 |
| −0.192 | 0.1782 | 0.1645 | 0 | 3 | 2 | 2 | 11 | 10 | 2029 | FLJ12876 hypothetical protein |
| −0.617 | 0 | −0.617 | 0 | 3 | 2 | 2 | 10 | 9 | 3928 | DGKD |
| 0.1079 | 0.1132 | 0.3343 | 0 | 3 | 2 | 2 | 10 | 9 | 5372 | ODF2 |
| −0.288 | 0.1221 | −0.043 | 0 | 4 | 3 | 3 | 10 | 9 | 7193 | KIAA0602 |
| −0.167 | 0.2278 | 0.2883 | 0 | 4 | 2 | 2 | 11 | 9 | 8535 | EHM2 |
| −0.95 | 0.3504 | −0.249 | 0 | 4 | 2 | 2 | 11 | 9 | 9824 | SLC19A1 |
| −0.314 | 0.187 | 0.06 | 1 | 4 | 2 | 2 | 11 | 9 | 9447 | LIG1 |
| 0.1366 | 0.1883 | 0.5132 | 1 | 4 | 3 | 2 | 10 | 8 | 327 | NULL ESTs |
| −0.586 | 0.2952 | 0.0044 | 0 | 5 | 2 | 2 | 11 | 8 | 1269 | DGKZ |

mean: mean expression in BPH
Dev: standard deviation in BPH
High: 2 SD's above the mean (threshold)
Bph: # of BPH samples > thresh
PCA: # of PCA samples > thresh (>1 yr no recur)
Pcau: # of PCA samples > thresh (<1 yr followup)
Pcar: # of PCA samples > thresh (recur)
Met: # of metastatic samples > thresh
Score: = met + pcar − pca
Total: # of samples in category Exemplary lethal markers identified using the above methods include ABCC5 (MDR5). This multi-drug resistance gene actively pumps cyclic nucleotides and other small molecules out of cells. An unrelated study found that this enzyme is potently Inhibited by phosphodiesterase inhibitors, including sildenafil (viagra). The present invention is not limited to a particular mechanism. Indeed, an understanding of the mechanism is not required to practice the present invention. Nonetheless, it is contemplated that sildenafil may be useful in the treatment of aggressive PCA.

Another lethal marker identified is asparagine synthetase (ASNS). Current therapeutics for the inhibition of ASNS include asparaginase, an enzyme that destroys asparagine in the body. It has been shown that cancers expressing the synthetase are resistant. Analogs are being developed to inhibit the synthetase.

Top2A (topoisomerase 2) and the Vav2 Oncogene were also identified using the methods of the present invention. Vav2 is required for cell spreading, but is dependent on src. The present invention is not limited to a particular mechanism. Indeed, an understanding of the mechanism is not required to practice the present invention. Nonetheless, it is contemplated src inhibitors can stop vav2 mediated cell spreading This example describes the identification of cancer markers overexpressed in prostate cancers. The present invention is not limited to a particular mechanism. Indeed, an understanding of the mechanism is not necessary to practice the present invention. Nonetheless, it is contemplated that therapeutic compounds that inhibit these lethal markers are useful in the treatment of prostate cancer.

Example 13

Characterization of Annexin Expression in Prostate Cancer

This Example describes the expression of Annexins in prostate cancer.

A. Materials and Methods

Prostate Sample Collection

Prostate tissues were taken from the radical prostatectomy series and the rapid autopsy program available through the University of Michigan Prostate Cancer Specialized Program of Research Excellence (S.P.O.R.E.) Tissue Core. This program is approved by Institutional Review Board at the University of Michigan.

Hormone naïve, clinically localized PCA samples used for this study were taken from a cohort of men who underwent radical retropubic prostatectomy as a monotherapy (i.e., no hormonal or radiation therapy) for clinically localized PCA between the years 1994 and 1998. Processing of the prostatic tissues started within 20 minutes after surgical resection. The prostates were partially sampled and approximately 50% of the tissue was used for research. This protocol has been evaluated in a formal study to assure that partial sampling does not impair accurate staging and evaluation of the surgical margins (Hollenbeck et al., J. Urol. 164:1583 [2000]). The snap frozen samples used for cDNA expression array analysis were all evaluated by one of the study pathologists. All samples were grossly trimmed to ensure greater than 95% of the sample represented the desired lesion.

Hormone refractory PCA samples were collected from the rapid autopsy program (Rubin et al., [2000], supra). Snap frozen samples were used for cDNA expression array analysis. Mirrored samples from the same lesion were placed in 10% buffered formalin. The fixed samples are embedded in paraffin. As with the prostatectomy samples, the study pathologist reviewed the glass slides, circled areas of viable prostate cancer, avoiding areas of necrosis, and used these slides as a template for tissue microarray construction. In this study, twenty (20) hormone refractory metastatic PCAs were extracted from 15 rapid autopsy cases performed from 1997 to 2000. The patients' ages ranged from 53 to 84 and time from diagnosis to death ranged from 21 to 193 months. All 15 patients died with widely metastatic PCA after extensive treatment, which included antiandrogens and chemotherapy.

Prostatectomy samples were evaluated for the presence or absence of surgical margin involvement by tumor (surgical margin status), the presence of extraprostatic extension, and seminal vesicle invasion. Tumors were staged using the TNM system, which includes extraprostatic extension and seminal vesicle invasion but does not take into account surgical margin status (Bostwick et al., Semin. Urol. Oncol. 17:222 [1999]). Tumors were graded using the Gleason grading system (Gleason, [1966], supra).

Immunohistochemistry

After paraffin removal and hydration, the tissue microarray slides were immersed in 10 mM citrate buffer placed in a pressure cooker chamber and microwaved for 10 minutes for optimal antigen retrieval. Immunostaining was performed using a Dako autostainer (DAKO, Carpinteria, Calif.). The primary antibody was incubated for 45 minutes at room temperature and a secondary biotin-labeled antibody for 30 minutes. Streptavidin-LSA amplification method (DAKO K0679) was carried out for 30 minutes followed by peroxidase/diaminobenzidine substrate/Chromagen. The slides were counterstained with hematoxylin. Polyclonal antibodies directed against the N-terminus of annexin 1 (dilution 1:50), annexin 2 (dilution 1:100), annexin 4 (dilution 1:100), annexin 7 (dilution 1:500), and annexin 11 (dilution 1:100) were obtained from a signal source (Santa Cruz Biotechnology, Santa Cruz, Calif.). Protein expression as determined by two pathologists immunohistochemistry was scored as negative (score=1), weak (score 2), moderate (3) or strong (4), using the system described above.

Tissue Microarray Construction, Digital Image Capture, and Analysis

Tissue microarrays were constructed as previously described to evaluate protein expression in a wide range of samples ranging from benign prostate tissue taken from the prostatectomy samples to hormone refractory PCA. Three tissue microarrays were used for this study consisting of benign prostate, localized PCAs, and hormone refractory PCA. The tissue microarrays were assembled using the manual tissue arrayer (Beecher Instruments, Silver Spring, Md.) as previously described (Kononen et al., [1998], supra; Perrone et al., [2000], supra). Tissue cores from the circled areas of interest were targeted for transfer to the recipient array blocks. The 0.6 mm diameter tissue microarray cores were each spaced at 0.8 mm from core-center to core-center. Tissue microarray images were acquired using the BLISS Imaging System (Bacus Lab, Lombard, Ill.).

Statistical Analyses

To investigate the statistical significance associated with the differential expression of annexins across 4 independent gene expression studies, standard methods (Hedges et al., Statistical Methods for Meta-analysis meta-analysis. Orlando, Academic Press 1985, pp xxii, 369) were used to combine the results. For each of the studies, a t-statistic was computed (with the two groups being benign tissue compared against localized prostate cancer) and the associated p-values were transformed using a negative logarithmic transformation. These numbers were then doubled and added together to arrive at a summary measure of differential gene expression across the three studies. To assess the statistical significance associated with this summary measure, a permutation-based approach was adopted (Hedges et al., supra). Namely, the tissue types were permutated within studies, and the summary measure was computed for the permutated data. A p-value was computed using the permutation distribution of the summary measure. The issue then arises of whether or not the t-statistics from the three studies are comparable.

Annexin protein expression was statistically evaluated using the mean score results from each tissue microarray sample for each prostate tissue type (i.e., benign, localized PCA, and hormone refractory PCA). To determine differences between all pairs (e.g., localized prostate cancer versus benign), an ANOVA with a post-hoc analysis was performed using the Scheffé method (Scheffae et al., supra). The mean expression scores for all examined cases were presented in a graphical format by using error-bars with 95% confidence intervals.

B. Results

Figure 33:
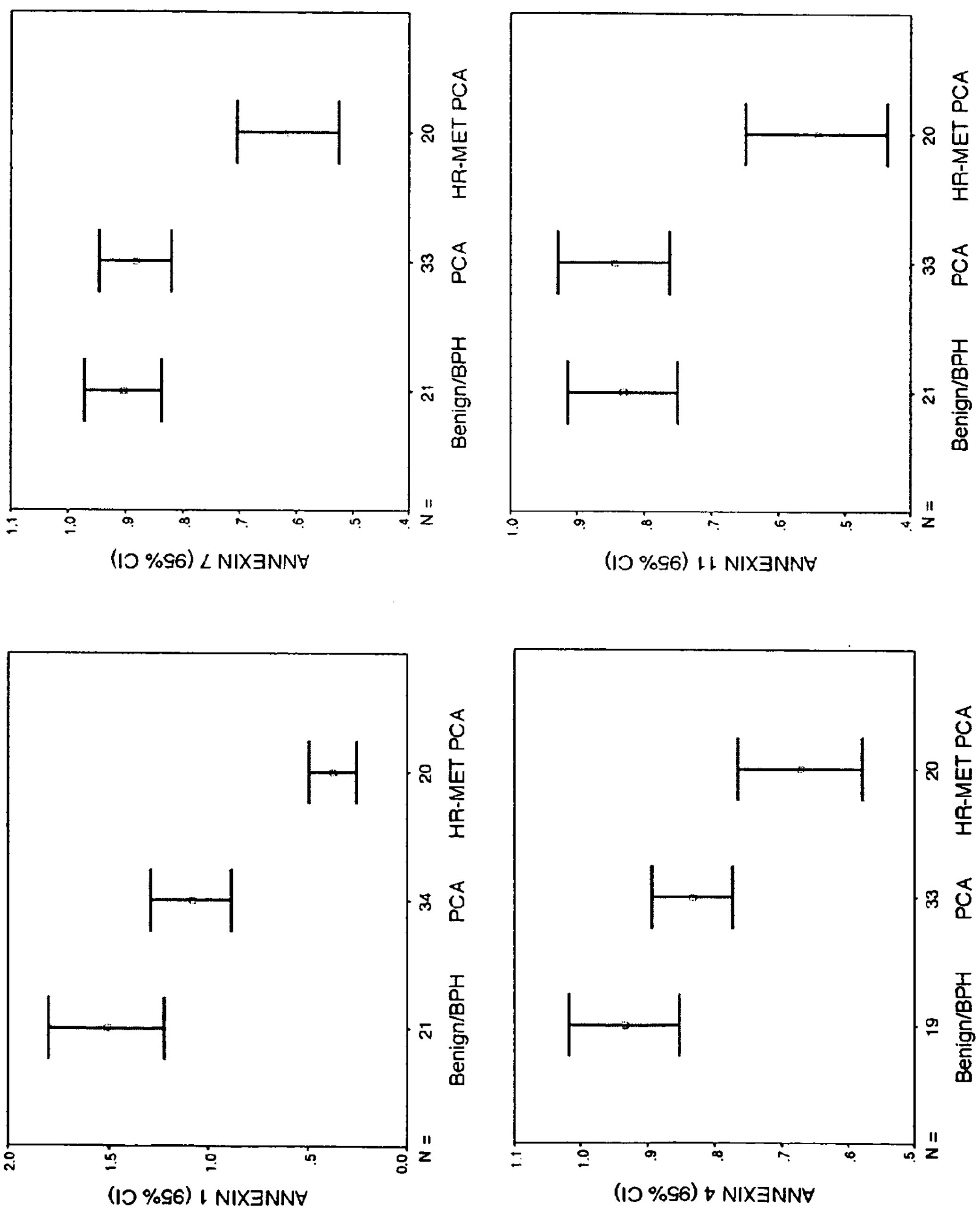
FIG. 33 shows the cDNA expression of select annexin gene family members.

Expression array analysis revealed a significant dysregulation of annexin family members with PCA progression. The cDNA expression of annexins 1, 2, 4, 7 and 11 were significantly decreased in the hormone refractory PCA samples as compared to localized hormone sensitive PCA samples with 2.2, 1.5, 1.3, 1.4 and 1.8 fold decrease, respectively (all p-values <0.01) (Table 8 and FIG. 33). Annexins 1 and 4 showed significant decreases of mRNA expression in localized PCA samples as compared to the benign samples. There were no significant differences between localized hormone naive PCA and the benign samples for annexin 2, 7, and 11. No cDNA dysregulation between the tested prostate samples and annexins 8 and 13 was observed. Annexin 6 demonstrated a slight decrease in cDNA expression between localized PCA and benign samples, which was not statistically significant (Table 8).

Figure 34:
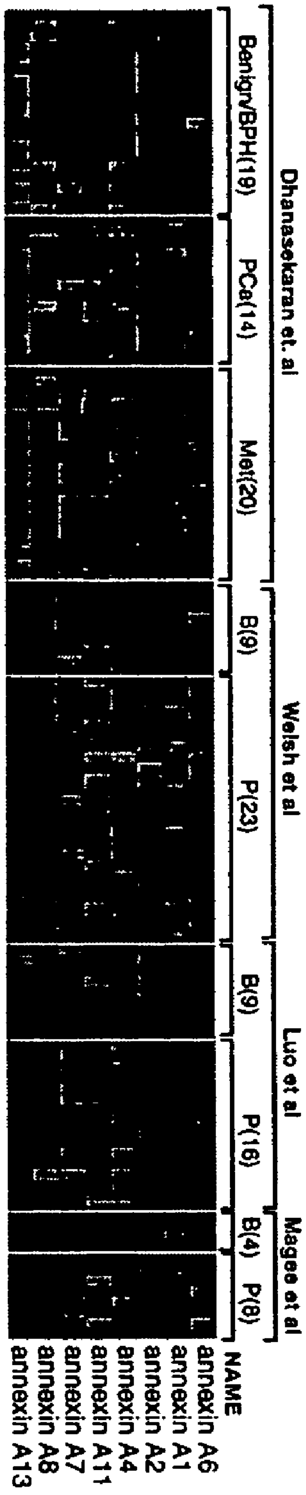
FIG. 34 shows a heat map representation of annexin family gene expression across four prostate cancer profiling studies. Over and under expression at the transcript level are represented by shades of red and green, respectively. Gray shading indicates that insufficient data was available. Each square represents an individual tissue sample.

In order to cross validate the cDNA expression results for these annexin family members, a meta-analysis of gene expression was performed. Annexin family members cDNA expression results were evaluated using a series of data sets (Welsh et al., Cancer Res. 61:5974 [2001]; Luo et al., Cancer Res. 61:4683 [2001]; Magee et al., Cancer Res. 61:5692 [2001]). The analysis evaluated annexins for each of the individual studies as well as performing a summary statistic, taking into account the significance of the gene expression across the 4 studies. The meta-analysis compared differences between clinically localized PCA and benign prostate tissue as not all of the studies had hormone refractory metastatic PCA. The meta-analysis (Table 9 and FIG. 34) demonstrated that annexins 1, 2, 4, and 6 were significantly down regulated across independent studies. Annexin 6 was down regulated to a significant level in 4 of 4 studies. Annexin 1 demonstrated down regulation in 3 of 4 studies. Annexins 2 and 4 were down regulated in 2 studies and overall considered to be significantly under expressed by the meta-analysis. Annexin 7 was not found to be significantly under expressed in any of the 4 studies at the transcript level.

Immunohistochemistry was performed to confirm these results at the protein level (Table 10). By immunohistochemistry, a significant decrease in protein expression for annexins 1, 2, 4, 7 and 11 in hormone refractory PCA samples as compared to localized PCA samples was identified with 2.5 (3.8 vs. 1.5 median expression), 2.4 (4 vs. 1.7 median expression), 3.6 (4 vs. 1.1 median expression) and 3.3 (4 vs. 1.2 median expression) fold decreases, respectively (Kruskal Wallis test, all p-values $p<0.05$). No statistically significant differences were seen between benign and localized PCA samples in any of the annexins tested.

TABLE 8

Gene Expression of Select Annexins.

| | Benign | | BPH[1] | | Loc-PCA[2] | | Met-PCA[3] | | Ratio | p |
|---|---|---|---|---|---|---|---|---|---|---|
| Annexin | Count | Median | Count | Median | Count | Median | Count | Median | PCA/Met | Value* |
| 1 | 5 | 1.56 | 16 | 1.35 | 16 | 0.69 | 20 | 0.31 | 2.23 | <0.001 |
| 2 | 5 | 0.79 | 16 | 0.69 | 16 | 0.74 | 20 | 0.49 | 1.51 | 0.009 |
| 4 | 5 | 0.91 | 16 | 0.97 | 16 | 0.9 | 20 | 0.69 | 1.30 | 0.001 |
| 6 | 5 | 1.2 | 16 | 1.29 | 16 | 1.05 | 20 | 1.15 | 0.91 | 0.377 |
| 7 | 5 | 0.8 | 16 | 0.88 | 16 | 0.88 | 20 | 0.62 | 1.42 | <0.001 |
| 8 | 5 | 1.14 | 16 | 1.06 | 16 | 0.99 | 20 | 1.19 | 0.83 | 0.156 |
| 11 | 5 | 0.99 | 16 | 0.76 | 16 | 0.94 | 20 | 0.52 | 1.81 | <0.001 |
| 13 | 5 | 1.08 | 16 | 1.35 | 16 | 1.03 | 20 | 0.94 | 1.10 | 0.393 |

*Kruskal Wallis Test.
[1]BPH, benign prostatic hyperplasia.
[2]Loc-PCA, localized prostate cancer.
[3]Met-PCA, metastatic hormone refractory prostatic cancer.
Ratio PCA/Met, ratio of expression of localized PCA over hormone refractory PCA.

TABLE 9

Meta-Analysis of cDNA Prostate Gene Expression Studies for Annexin Family Members

| Annexin | Present study | Welsh et al. | Luo et al. | Magee et al. | Summary p-Value |
|---|---|---|---|---|---|
| 6 | 0.024 | 0.0001 | 0.0001 | 0.026 | 0.0001 |
| 1 | 0.0001 | 0.031 | 0.0007 | 0.23 | 0.0001 |
| 2 | NA | 0.0001 | NA | 0.002 | 0.0001 |
| 11 | NA | 0.010 | NA | 0.6 | 0.17 |
| 7 | 0.25 | 0.48 | 0.38 | 0.088 | 0.20 |
| 4 | 0.33 | 0.023 | 0.0093 | 0.58 | 0.011 |
| 13 | 0.177 | NA | 1.00 | NA | 0.48 |
| 8 | 0.79 | NA | 0.104 | NA | 0.29 |

TABLE 10

Tissue Microarray Protein Expression for Annexins by Tissue Type

| | Benign | | Loc-PCA[2] | | Met-PCA[3] | | | |
|---|---|---|---|---|---|---|---|---|
| Annexin | Count | Median | Count | Median | Count | Median | PCA/MET | p-value* |
| 1 | 37 | 2.59 | 360 | 2.45 | 162 | 1.46 | 1.68 | <0.001 |
| 2 | 57 | 3.95 | 82 | 3.62 | 214 | 1.47 | 2.46 | <0.001 |
| 4 | 23 | 3.65 | 357 | 3.96 | 141 | 1.57 | 2.52 | <0.001 |
| 7 | 26 | 3.77 | 350 | 3.97 | 126 | 1.32 | 3.01 | <0.001 |
| 11 | 23 | 4.00 | 360 | 3.99 | 163 | 1.30 | 3.01 | <0.001 |

*Kruskal Wallis Test.
[1]BPH, benign prostatic hyperplasia.
[2]Loc-PCA, localized prostate cancer.
[3]Met-PCA, metastatic hormone refractory prostatic cancer.

Example 14

Association of CtBP with Prostate Cancer

This example describes the expression of C-terminal binding proteins 1 and 2 (CtBP1 and CtBP2) in prostate cancer. Microarray analysis, Western Blots, immunohistochemistry, and statistical analysis were performed as described in the above examples.

Figure 35:
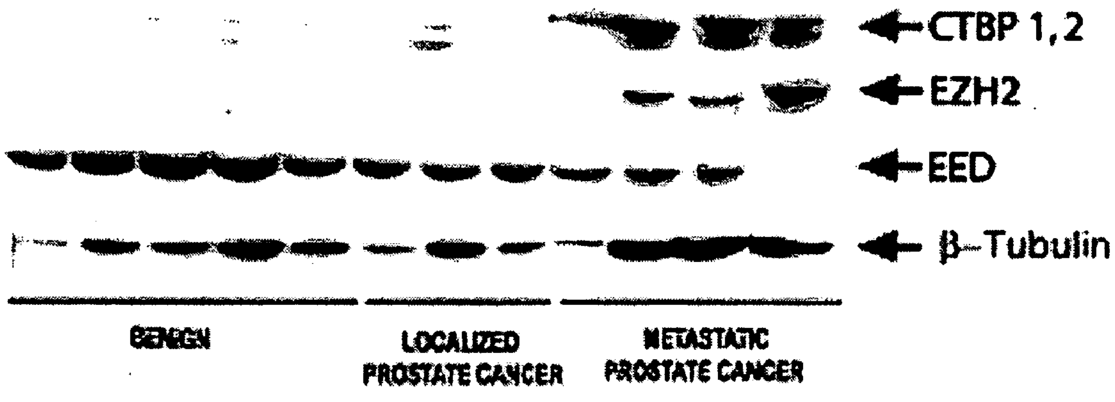
FIG. 35 shows the expression of CtBP proteins in PCA specimens.
Figure 38:
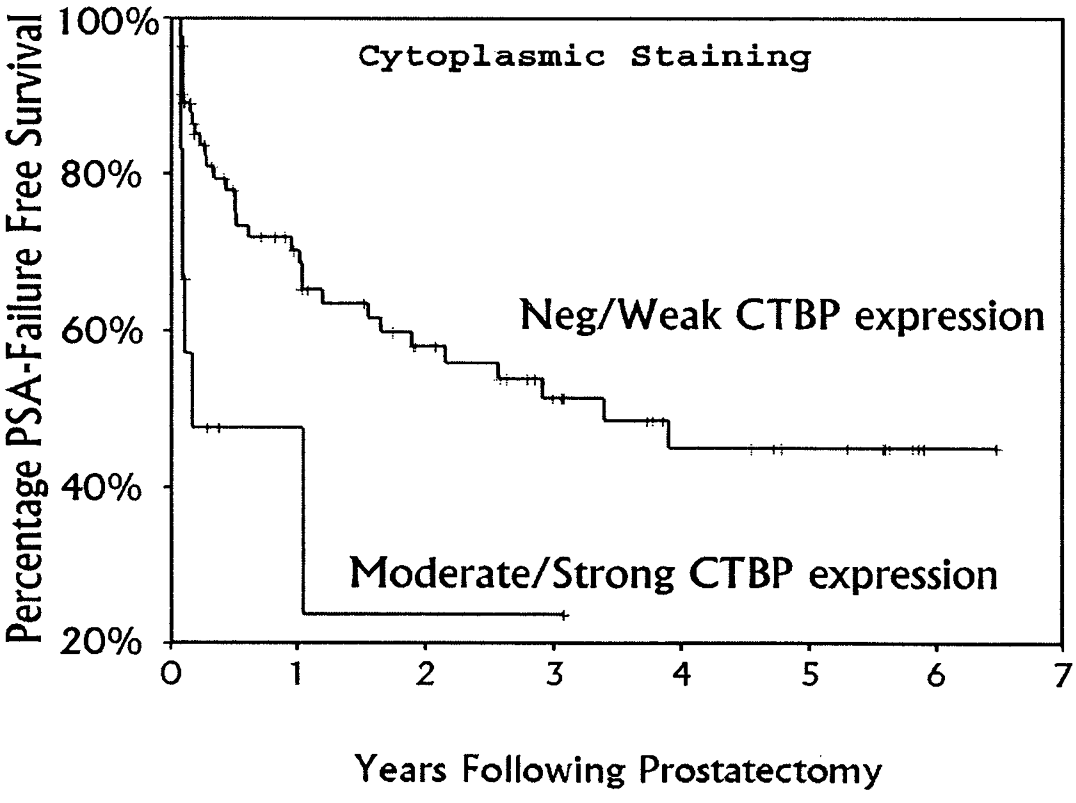
FIG. 38 shows a Kaplan-Meier Analysis of prostate cancer tissue microarray data.

The CtBP transcript was found to be up-regulated in metastatic prostate cancer (FIG. 38). Tissue extracts were used to validate this finding at the protein level using an antibody that recognizes CtBP1 and CtBP2 (Sewalt et al., Mol. Cell. Biol. 19:777 [1999]. The results are shown in FIG. 35. FIG. 35 shows the Expression of CtBP proteins in PCA specimens. Extracts from selected prostate specimens were assessed for expression of CtBP and PcG proteins by immunoblot analysis. Protein level was equalized in each extract before loading and blots were stained with Ponceau S to confirm equal loading. β-tubulin was used as a control protein.

Both CtBPs were over-expressed in metastatic prostate cancer relative to localized prostate cancer and benign tissue. EZH2 protein was also elevated in metastatic prostate cancer relative to localized prostate cancer or benign prostate (FIG. 35). EED, a PcG protein that forms a complex with EZH2, along with an un-related protein, β-tubulin, did not exhibit similar protein dysregulation. Thus, both transcriptional repressors (CtBP and EZH2) are mis-expressed in metastatic prostate cancer.

To determine in situ expression of CtBP, immunohistochemistry of prostate tissue sections were performed using prostate tissue microarrays. Benign prostatic epithelia exhibited exclusively nuclear staining consistent with CtBP's role as a transcriptional repressor. Both clinically localized and metastatic prostate cancer exhibited nuclear staining as well. Most of the metastatic prostate cancer cases and a fraction of the localized prostate cancer cases exhibited distinct cytoplasmic staining of CTBP.

Figure 36:
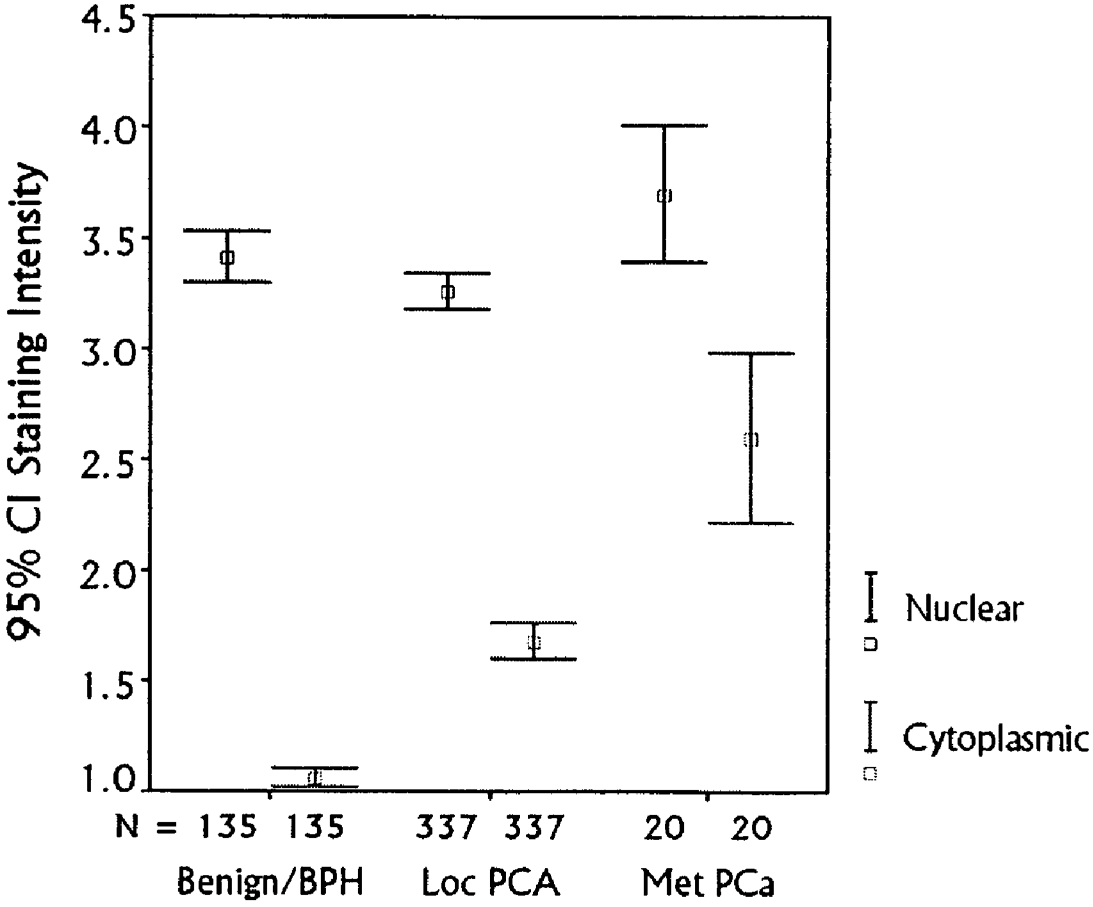
FIG. 36 shows tissue microarray analysis of CtBP in prostate cancer that suggests mis-localization during prostate cancer progression.
Figure 37:
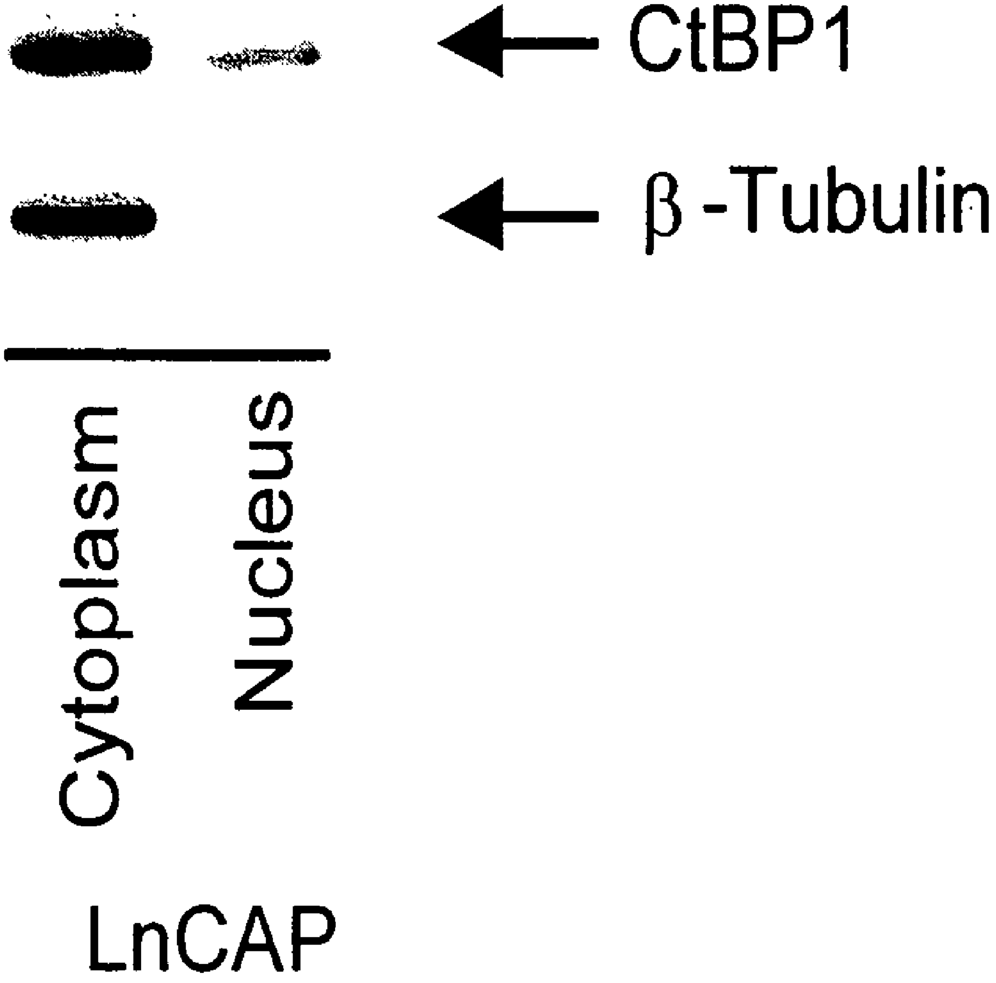
FIG. 37 shows the sub-cellular fractionation of LNCaP cells.

FIG. 36 shows tissue microarray analysis of CtBP in prostate cancer that suggests mis-localization during prostate cancer progression. The mean CtBP protein expression for the indicated prostate tissues and sub-cellular compartment is summarized using error bars with 95% confidence intervals. FIG. 37 shows the sub-cellular fractionation of LNCaP cells. The results show an increased level of CtBP 1 in the cytoplasm relative to the nucleus. CtBP2 is weakly expressed in the cell lines and is not easily apparent. β-tubulin, which is not expressed in the nucleus, is provided as a control. FIG. 38 shows a Kaplan-Meier Analysis of prostate cancer tissue microarray data. The results demonstrate that the presence of cytoplasmic CtBP may be associated with a poorer clinical outcome. The median follow up time for all patients was 1 year (range 2 month to 6.5 years). Over this follow up time, 38% of the patients developed a recurrence or PSA elevation greater than 0.2 ng/ml. Prostate tumors from 97 patients demonstrated near uniform nuclear protein expression for CTBP. Cytoplasmic expression was variable with 85 of 97 cases (88%) demonstrating weak cytoplasmic staining and 12 (12%) with moderate to strong CTBP expression. There was a significant association with increased CTBP cytoplasmic staining intensity and PSA recurrence or presence of recurrent disease following prostatectomy with a relative risk of 1.7 (Cox regression analysis p=0.034). The data presented demonstrates a Kaplan-Meier Analysis of outcome stratified by negative/weak cytoplasmic CTBP staining and moderate/strong staining. CTBP cytoplasmic expression predicted recurrence even when Gleason score was taken into account in a multivariable model, suggesting that CTBP is a prognostic predictor of poor outcome [Gleason relative risk 1.4 (p=0.005) and cCTBP rr 1.6 (p=0.042)].

CtBP has been shown to bind nitric oxide synthase (NOS), which is thought to shift the localization of CtBP from the nuclear compartment to the cytoplasmic compartment (Riefler et al., J. Biol. Chem. 276:48262 [2001]). Weigert and colleagues have proposed a cytoplasmic role for CtBP in the induction of Golgi membrane fission (Weigart et al., Nature 402:429 [1999]). To further support the preliminary immunohistochemical findings, LNCaP (metastatic) prostate cancer cells were fractionated and it was found that CtBP levels were higher in the cytosol relative to the nucleus (FIG. 38).

Example 15

Methods of Characterizing Cancer Markers

This example describes exemplary methods for the characterization of new cancer markers of the present invention. These methods, in combination with the methods described in the above examples, are used to characterized new cancer markers and identify new diagnostic and therapeutic targets.

A. Determination of Quantitative mRNA Transcript Levels of Cancer Markers in Prostate Cancer Specimens In some embodiments, markers revealed to be over or under expressed in cancer microarrays (See e.g., Example 1 for a description of microarrays) are quantitated using real-time PCR (Wurmbach et al., J. Biol. Chem. 276:47195 [2001]).

In preferred embodiments, cDNA from over 100 prostate samples for archived cDNA samples and associated clinical data are available (See Example 1). The level of expression in the microarray is compared to those obtained by real-time PCR. To identify genes with dysregulation of expression, real-time PCR analysis of cDNA generated from laser-capture microdissected prostate cancer epithelia and benign epithelia is performed.

B. Detection of Mis-Localized Transcripts

In some embodiments, in order to determine if a cancer marker normally present in the nucleus of a cell (e.g., a transcriptional repressor) is mis-localized to the cytoplasm (or other mis-locations) in cancer, the expression of the marker is examined in tissue extracts from preferably at least 20 benign prostate samples, 20 prostate cancer specimens, and 20 metastatic prostate specimens. Expression of the marker in benign prostate cell lines (RWPE), primary prostatic epithelial cells (Clonetics, Inc.) and a panel of prostate cancer cells including LNCaP, DU145, PC3, DUCaP, and VCaP cells is also examined. Once overall expression of prostate cell lines and tissues is established, the cellular localization of the marker is determined by 2 methods. In the first method, the cell and tissue extracts are fractionated into a nuclear fraction and a cytosolic fraction (NE-PER, Pierce-Endogen; Orth et al., J. Biol. Chem. 271:16443 [1996]). Quantitated protein is then analyzed by immunoblotting. Relative levels of cytosolic and nuclear cancer marker are determined by densitometry. To verify clean fractionation, antibodies to β-tubulin and PCNA (or lamin A) are used to assess cytosolic and nuclear fractions, respectively.

In the second method, cells are immunostained with antibodies to the cancer marker followed by detection using anti-rabbit FITC secondary antibody. Confocal microscopy (U of M Anatomy and Cell Biology Core Facility) is used to examine in situ localization of the cancer markers.

In some embodiments, mis-localization is further investigated by sequencing the gene in cells containing the mis-located transcript (e.g., metastatic cases) for mutations.

C. Correlation of Cancer Markers with Clinical Outcome

In some preferred embodiments, the association of expression or mis-localization of a cancer marker with clinical outcome is investigated. The ratio of total cancer marker to β-tubulin by immunoblot analysis of prostate cancer tissue extracts is first determined and associated with clinical outcome parameters. For markers suspected of being mis-localized in cancer (e.g., CtBP), the ratio of cytoplasmic marker to nuclear marker is next determined by immunoblot analysis of prostate cancer tissue extracts and associated with clinical outcome parameters. For example, it is contemplated that a high cytoplasmic/nuclear cancer marker ratio may portend a poor clinical outcome. In some embodiments (e.g., where a cancer marker is suspected of being mis-localized), immunohistochemistry of prostate cancer tissue microarrays is used to determine whether the presence of cytoplasmic marker correlates with poor clinical outcome. Tissue microarrays are prepared and performed as described in the above examples.

Briefly, high-density tissue microarrays (TMA) are constructed as previously described (Perrone et al, supra; Kononen et al., supra). Immunostaining intensity is scored by a genitourinary pathologist as absent, weak, moderate, or strong (or alternatively analyzed separately as for cytoplasmic and nuclear staining). Scoring is performed using a telepathology system in a blinded fashion without knowledge of overall Gleason score (e.g., tumor grade), tumor size, or clinical outcome (Perrone et al., supra). Tumor samples are derived from patients with clinically localized, advanced hormone refractory prostate cancer and naïve metastatic PCA. Cases of clinically localized prostate cancer are identified from the University of Michigan Prostate S.P.O.R.E. Tumor Bank. All patients were operated on between 1993 and 1998 for clinically localized prostate cancer as determined by preoperative PSA, digital-rectal examination, and prostate needle biopsy. All tissues used are collected with institutional review board approval. The advanced prostate tumors are collected from a series of 23 rapid autopsies performed at the University of Michigan on men who died of hormone refractory prostate cancer. The clinical and pathologic findings of these cases have been reported (Rubin et al., [2000], supra).

Statistical analysis of the array data is used to correlate the cancer marker protein measurements on the TMA with clinical outcomes, such as time to PSA recurrence and survival time. This analysis involves survival analysis methods for correlating the measurements with these censored response times. Kaplan-Meier curves are plotted for descriptive purposes. Univariate analyses is performed using the Cox model associating the biomarker with the survival time. In addition, multivariate Cox regression analysis is performed to test whether the biomarker adds any prognostic information over and above that available from known prognostic markers (i.e., Gleason score, tumor stage, margin status, PSA level before surgery).

D. RNA Interference

In some embodiments, RNA interference of cancer markers is used to investigate the role of the cancer marker in cell culture and well as for application as a therapeutic cancer treatment (See e.g., Example 8 for an example of RNA interference). 21-nucleotide RNAs (siACE-RNAi) are synthesized through a commercial vendor (Dharmacon Research, Inc.). RNA interference has been used in mammalian cells (Elbashir et al., Nature 411:494 [2001]). Several siRNA duplexes and controls are designed for each marker. The design of the siRNA duplexes uses criteria provided by Elbashir et al. (Elbashir et al., supra) and Dharmacon Research which include: starting approximately 75 bases downstream of the start codon, locating an adenine-adenine dimer, maintaining G/C content around 50%, and performing a BLAST-search against EST databases to ensure that only one gene is targeted. Multiple (e.g., two) siRNA duplexes are designed for each molecule of interest since whether the siRNA duplex is functional is a relatively empirical process. In addition, it is contemplated that using two siRNA duplexes may provide a combined "knock-down" effect. As a control, a "scrambled" siRNA, in which the order of nucleotides is randomized, is designed for each molecule of interest. Oligonucleotides are purchased deprotected and desalted. Upon arrival, the oligonucleotides are annealed to form a duplex using the manufacturer's provided protocol.

To test the efficacy of each siRNA duplex, prostate cell lines (RWPE, DU145, LnCAP, and PC3) are transfected with the OLIGOFECTAMINE reagent as described (Elbashir et al., supra). The cells are assayed for gene silencing 48 hrs post-transfection by immunoblotting with respective antibodies. A number of controls are included: buffer controls, sense siRNA oligo alone, anti-sense siRNA oligo alone, scrambled siRNA duplex, and siRNA duplexes directed against unrelated proteins. If significant silencing is not appreciated after single transfection, sequential transfection is performed and inhibition is monitored at later time points (i.e., 8 days later) as suggested by others (Breiling et al., Nature. 412: 51 [2001]). This may be necessary with proteins that have a long half-life.

In addition to the transient expression of siRNAs, a method for stable expression of siRNAs in mammalian cells is used (Brummelkamp et al., Science 296:550 [2002]). Prostate cancer cell lines are generated that express siRNA targeting cancer markers using the pSUPER system. Scrambled siRNA is used as a control. The cell lines facilitate downstream characterization of cancer markers that may be cumbersome using duplexes transiently. If inhibition of a specific cancer marker is found to be toxic to cells, the pSUPER cassette containing siRNA to the marker is cloned into an inducible vector system (e.g., Tet on/off).

E. Generation of Mutants.

To study the function of cancer markers of the present invention, mutants of cancer markers are generated in eukaryotic expression vectors. myc-epitope tagged versions of cancer marker mutants are generated in both pcDNA3 and pcDNA3-ER (a modified estrogen receptor ligand binding domain). In the case of the ER constructs, the vectors produce an in-frame fusion protein with modified ER, thus generating a post-transcriptionally inducible vector (Littlewood et al., Nucleic Acids Res. 23: 686 [1995]). The ER-ligand domain is mutated and fails to bind endogenous estrogen, yet can be activated by 4-hydroxytamoxifen (Littlewood et al., supra). The ER-fusion proteins are inactivated in the absence of ligand presumably due to binding of proteins such as hsp90. In the presence of exogenously added 4-hydroxytamoxifen, ER-fusions become liberated. By using an inducible vector system, cell lines expressing a "toxic" or growth inhibitory version of a cancer marker can still be isolated.

Various N-terminal and C-terminal deletion mutants are generated that encompass function domains of the cancer marker (e.g., the PXDLS, dehydrogenase, and PDZ binding domains of CtBP; Chinnadurai, Mol Cell. 9: 213 [2002]). It is contemplated that some of the mutant versions of the cancer markers of the present invention act as dominant negative inhibitors of endogenous cancer marker function. Expression of epitope-tagged cancer markers and mutants is assessed by transient transfection of human embryonic kidney cells (using FUGENE) and subsequent Western blotting.

F. Establishing Stable Cell Lines Expressing Cancer Markers And Mutants

In some embodiments, cell lines stably expressing cancer markers of the present invention are generated for use in downstream analysis. FUGENE is used to transiently transfect prostate cell lines (RWPE, DU145, LnCAP, and PC3) with cancer markers and fusions or mutants using the above mentioned vectors and appropriate G418 selection. Prostate cell lines with varied expression levels of endogenous cancer marker protein are used. Both individual clones and pooled populations are derived and expression of cancer markers and mutants assessed by immunoblotting for the epitope tag. By also using an inducible system, clones expressing toxic versions of cancer markers or mutants can be isolated.

G. Cell Proliferation and Apoptosis Studies

In some embodiments, the role of cancer marker expression in prostate cell proliferation is investigated using a multifaceted approach that includes 1. RNA interference, 2. transient transfection of cancer markers and potential dominant negative mutants, and 3. comparing stable transfectants of cancer markers and mutants. The following predictions are tested using these methods: 1. whether inhibition of cancer markers will block cell growth and 2. whether overexpression of cancer markers will enhance cell proliferation.

Cell proliferation is assessed by cell counting (Coulter counter) over a time course in culture by using the WST-1 reagent (Roche, Inc.), which is a non-radioactive alternative to [$^3$H]-thymidine incorporation and analogous to the MTT assay. The rate of incorporation of the DNA labeling dye bromodeoxyuridine (BrdU) will also be measured as described previously (Jacobs et al., Nature. 397:164 [1999]). Potential cell cycle arrest induced by siRNA or dominant negative inhibitors of is determined by conventional flow cytometric methods. By using stable cell lines that "activate" cancer markers and mutants in a 4-hydroxytamoxifen-dependent fashion, cell proliferation and cell cycle alterations are monitored in a highly controlled in vitro system. To confirm that overexpression or inhibition of cancer markers does not activate the apoptosis pathway, several assays are used including propidium iodide staining of nuclei, TUNEL assay and caspase activation.

If a cancer marker is found to be a regulator of cell proliferation in prostate cells, studies are designed to address how components of cell cycle machinery are modulated by the cancer marker. Thus, in order to study cancer marker mediated effects on the cell cycle machinery of prostate cells, cancer marker functions are modulated with the above mentioned tools (i.e., siRNA, dominant negative inhibition, etc.) and the expression levels (transcript and protein) of cyclins (cyclin D1,E,A), cyclins-dependent kinases (cdk2, cdk4, cdk6) and cyclin-dependent kinase inhibitors (p21 CIP1, p27KIP1, p45SKP2, p161NK4) are monitored.

H. Cell Adhesion and Invasion Assays

If a cancer marker is suspected of altering cell adhesion (e.g., the transcriptional repression of an epithelial gene program such as E-cadherin), the methods described above are used to investigate whether over-expression of the cancer marker causes increased or decreased cell adhesion. Adhesion to extracellular matrix components, human bone marrow endothelium (HBME) as well as to human umbilical vein endothelial cells (HUVEC) is tested. Cancer markers are further tested for their ability to modulate invasion of PCA.

Known methods are used in these studies (Cooper et al., Clin. Cancer Res. 6:4839 [2000]). Briefly, snap-apart 96-well tissue culture plates are coated with crude bone and kidney matrices. Plates are incubated overnight at room temperature under sterile conditions and stored at 4° C. until needed. Assay plates are also coated with extracellular matrix components (e.g., human collagen I, human fibronectin, mouse laminin I) and human transferrin at various concentrations according to the manufacturer's instruction (Collaborative Biomedical Products, Bedford, Mass.). Endothelial cells (HBME or HUVEC) are seeded onto bone matrices or plastic substrata at a concentration of 900 cells/μl and grown to confluence. Tumor cells are removed from the flask by a 15-20 minute treatment with 0.5 mM EDTA in Hank's balanced salt solution. Once the EDTA solution is removed, the cells are resuspended in adhesion medium (e.g., minimum essential medium (MEM) with 1% bovine serum albumin (BSA) supplemented with 10 uCi $^{51}$Cr sodium salt (NEN, Boston, Mass.)) for 1 hour at 37° C. Cells are then washed three times in isotope free media and $1\times10^5$ radio-labeled tumor cells are resuspended in adhesion media and layered upon a confluent layer of endothelial cells for 30 min at 37° C. In addition, radiolabeled tumor cells are applied to crude bone matrices. Again, plates are washed three times in phosphate buffered saline and adhesion is determined by counting individual wells on a gamma counter. Cell adhesion is reported relative to the adhesion of controls (PC-3 cells on plastic), which are set to 100.

Cell invasion assays are performed using a classic Boyden chamber assay. Both strategies to inhibit and overexpress cancer markers are evaluated. Previous reports have correlated increased cell migration in a Boyden Chamber system with increased invasive properties in vivo (Klemke et al., J. Cell Biol. 140:61 [1998]. Commercially available 24-well invasion chambers are used (e.g., BD biosciences, Chemicon International).

I. Transcriptional Suppression in Prostate Cancer Cells

In some embodiments, the effect of cancer markers on gene silencing in prostate cells is assessed. Gene silencing is assayed in several ways. First, gene expression alterations induced by transient transfection of cancer markers and mutants in prostate cell lines (RWPE, DU145, LnCAP, and PC3) is assayed using FUGENE. Twelve to 48 hours after transfection, cells are harvested and a portion is processed to confirm expression of the transfectants by immunoblotting. Using vector-transfected cells as a reference sample, total RNA from transfected cells is then assessed on 20K cDNA microarrays.

In addition to transient transfections, stable cell lines overexpressing cancer markers and cancer marker mutants are generated. Patterns of gene expression from cancer marker and cancer marker mutant expressing cell lines are compared to vector-matched controls in order to identify a gene or group genes that is repressed by a given cancer marker. The present invention is not limited to a particular mechanism. Indeed, and understanding of the mechanism is not necessary to practice the present invention. Nonetheless, it is contemplated that genes identified as repressed by a given cancer marker will be increased (de-repressed) upon knock-down of the cancer marker (e.g., by siRNA inhibition).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A method for identifying an increased risk of prostate specific antigen failure in a subject, comprising:

a) providing a post-surgical prostate tumor sample from a subject; and b) detecting the level of hepsin expression in said sample; and c) identifying an increased risk of prostate specific antigen failure when said level of expression of hepsin is decreased relative to the level of expression in subjects not at risk of prostate specific antigen failure or absent, wherein said prostate specific antigen failure is defined as a PSA value of greater than 0.2 ng/ml.

2. The method of claim 1, wherein said detecting the level of hepsin expression comprises detecting the level of hepsin mRNA.

3. The method of claim 2, wherein said detecting the level of hepsin mRNA comprises exposing said hepsin mRNA to a nucleic acid probe complementary to said hepsin mRNA.

4. The method of claim 1, wherein said subject comprises a human subject.

* * * * *